US012752128B2

(12) United States Patent
Broach et al.

(10) Patent No.: US 12,752,128 B2
(45) Date of Patent: Oct. 6, 2026

(54) IDENTIFICATION AND PREVENTION OF MYOPIA

(71) Applicant: NeuroRays, LLC, Atlanta, GA (US)

(72) Inventors: Anita Broach, Christiansburg, VA (US); Ronald Blum, Atlanta, GA (US)

(73) Assignee: NeuroRays, LLC, Atlanta, GA (US)

( * ) Notice: Subject to any disclaimer, the term of this patent is extended or adjusted under 35 U.S.C. 154(b) by 0 days.

(21) Appl. No.: 19/228,317

(22) Filed: Jun. 4, 2025

(65) Prior Publication Data

US 2025/0295935 A1 Sep. 25, 2025

Related U.S. Application Data

(63) Continuation-in-part of application No. 19/030,018, filed on Jan. 17, 2025, which is a continuation-in-part of application No. 18/959,511, filed on Nov. 25, 2024, now Pat. No. 12,337,191, and a continuation-in-part of application No. 18/951,274, filed on Nov. 18, 2024, now Pat. No. 12,616,849, and a continuation-in-part of application No. 18/928,126, filed on Oct. 27, 2024, now Pat. No. 12,472,377, and a continuation-in-part of application No. 18/914,202, filed on Oct. 13, 2024, and a continuation-in-part of application No. 18/827,786, filed on Sep. 8, 2024, now Pat. No. 12,409,338, and a continuation-in-part (Continued)

(51) Int. Cl.
*A61N 5/06* (2006.01)

(52) U.S. Cl.
CPC ............. *A61N 5/0622* (2013.01); *A61N 5/06* (2013.01); *A61N 2005/063* (2013.01); *A61N 2005/0648* (2013.01); *A61N 2005/0661* (2013.01); *A61N 2005/0662* (2013.01)

(58) Field of Classification Search
CPC .................... A61N 5/0622; A61N 5/06; A61N 2005/0661; A61N 2005/063; A61N 2005/0648; A61N 2005/0662; A61N 2005/0642; A61N 5/0613; A61N 2005/0626; A61N 5/0618; A61N 2005/0663; A61N 2005/0667; A61F 2009/00863
See application file for complete search history.

(56) References Cited

U.S. PATENT DOCUMENTS

| | | |
|---|---|---|
| 3,826,751 A | 7/1974 | Laliberte |
| 5,083,858 A | 1/1992 | Girerd |

(Continued)

FOREIGN PATENT DOCUMENTS

| | | |
|---|---|---|
| CN | 103926710 A | 7/2014 |
| CN | 111938911 A | 11/2020 |

(Continued)

OTHER PUBLICATIONS

Application No. PCT/US2025/032265, International Search Report and Written Opinion dated Aug. 21, 2025.

(Continued)

*Primary Examiner* — Niketa Patel
*Assistant Examiner* — Sebastian X Lukjan
(74) *Attorney, Agent, or Firm* — Woods Rogers Vandeventer Black PLC; Nathan A. Evans

(57) ABSTRACT

A system for providing ocular photo-bio-stimulation to an eye of a subject.

26 Claims, 121 Drawing Sheets

Related U.S. Application Data of application No. 18/827,782, filed on Sep. 8, 2024, now Pat. No. 12,409,337.

(60) Provisional application No. 63/816,756, filed on Jun. 3, 2025, provisional application No. 63/812,791, filed on May 27, 2025, provisional application No. 63/800,627, filed on May 6, 2025, provisional application No. 63/792,814, filed on Apr. 22, 2025, provisional application No. 63/791,207, filed on Apr. 18, 2025, provisional application No. 63/783,745, filed on Apr. 4, 2025, provisional application No. 63/780,692, filed on Mar. 31, 2025, provisional application No. 63/777,920, filed on Mar. 26, 2025, provisional application No. 63/773,005, filed on Mar. 17, 2025, provisional application No. 63/769,313, filed on Mar. 10, 2025, provisional application No. 63/759,378, filed on Feb. 17, 2025, provisional application No. 63/755,470, filed on Feb. 7, 2025, provisional application No. 63/740,226, filed on Dec. 30, 2024, provisional application No. 63/735,232, filed on Dec. 17, 2024, provisional application No. 63/729,431, filed on Dec. 8, 2024, provisional application No. 63/697,560, filed on Sep. 22, 2024, provisional application No. 63/684,509, filed on Aug. 19, 2024, provisional application No. 63/676,855, filed on Jul. 29, 2024, provisional application No. 63/674,219, filed on Jul. 22, 2024, provisional application No. 63/673,746, filed on Jul. 21, 2024, provisional application No. 63/671,237, filed on Jul. 14, 2024, provisional application No. 63/654,566, filed on May 31, 2024, provisional application No. 63/648,098, filed on May 15, 2024, provisional application No. 63/639,892, filed on Apr. 29, 2024, provisional application No. 63/569,005, filed on Mar. 22, 2024, provisional application No. 63/561,266, filed on Mar. 4, 2024, provisional application No. 63/553,693, filed on Feb. 15, 2024, provisional application No. 63/553,226, filed on Feb. 14, 2024, provisional application No. 63/550,852, filed on Feb. 7, 2024, provisional application No. 63/627,703, filed on Jan. 31, 2024, provisional application No. 63/623,253, filed on Jan. 20, 2024, provisional application No. 63/617,363, filed on Jan. 3, 2024, provisional application No. 63/609,306, filed on Dec. 12, 2023, provisional application No. 63/603,258, filed on Nov. 28, 2023, provisional application No. 63/600,139, filed on Nov. 17, 2023, provisional application No. 63/548,204, filed on Nov. 12, 2023, provisional application No. 63/546,848, filed on Nov. 1, 2023, provisional application No. 63/541,243, filed on Sep. 28, 2023, provisional application No. 63/540,090, filed on Sep. 24, 2023, provisional application No. 63/537,021, filed on Sep. 7, 2023.

(56) References Cited

U.S. PATENT DOCUMENTS

| | | | | |
|---|---|---|---|---|
| 5,243,460 | A | 9/1993 | Kornberg | |
| 5,838,419 | A | 11/1998 | Holland | |
| 5,923,398 | A | 7/1999 | Goldman | |
| 6,350,275 | B1 | 2/2002 | Vreman et al. | |
| 8,469,512 | B2 | 6/2013 | Croft et al. | |
| 8,833,937 | B2 | 9/2014 | Shehadeh et al. | |
| 8,911,082 | B2 | 12/2014 | Ambler | |
| 9,028,064 | B2 | 5/2015 | Harris | |
| 9,138,595 | B2 | 9/2015 | Savage et al. | |
| 9,720,228 | B2 | 8/2017 | Harrison et al. | |
| 9,885,884 | B2 | 2/2018 | Drobe | |
| 10,073,283 | B2 | 9/2018 | Legerton | |
| 10,152,906 | B2 | 12/2018 | Gutierrez | |
| 10,219,944 | B2 | 3/2019 | Tedford et al. | |
| 10,386,654 | B2 | 8/2019 | Marshall et al. | |
| 10,444,505 | B2 | 10/2019 | Rousseau et al. | |
| 10,884,246 | B2 | 1/2021 | Blum et al. | |
| 10,884,264 | B2 | 1/2021 | Hones et al. | |
| 10,895,735 | B1 | 1/2021 | Feinbloom et al. | |
| 10,942,373 | B2 | 3/2021 | Barrau et al. | |
| 11,029,540 | B2 | 6/2021 | To et al. | |
| 11,048,103 | B2 | 6/2021 | Saylor et al. | |
| 11,061,255 | B2 | 7/2021 | Lau et al. | |
| 11,065,468 | B2 | 7/2021 | Barrau et al. | |
| 11,086,145 | B2 | 8/2021 | Flinders | |
| 11,099,408 | B2 | 8/2021 | McCabe et al. | |
| 11,131,869 | B2 | 9/2021 | Marshall et al. | |
| 11,420,072 | B2 | 8/2022 | He et al. | |
| 11,446,514 | B2 | 9/2022 | Bahmani et al. | |
| 11,701,315 | B2 | 7/2023 | Ishak et al. | |
| 11,711,600 | B2 | 7/2023 | Han et al. | |
| 11,774,784 | B2 | 10/2023 | Barrau et al. | |
| 12,055,797 | B2 | 8/2024 | Newman et al. | |
| 12,336,937 | B2 | 6/2025 | Tedford et al. | |
| 2002/0198577 | A1 | 12/2002 | Jaillet | |
| 2010/0033830 | A1 | 2/2010 | Yung | |
| 2010/0103371 | A1 | 4/2010 | Sarver et al. | |
| 2010/0152849 | A1 | 6/2010 | Degenaar et al. | |
| 2012/0200823 | A1 | 8/2012 | Bandhauer et al. | |
| 2013/0211178 | A1 | 8/2013 | Brigatti et al. | |
| 2014/0176898 | A1 | 6/2014 | Yi et al. | |
| 2014/0247423 | A1 | 9/2014 | Drobe | |
| 2015/0088231 | A1 | 3/2015 | Rubinfeld et al. | |
| 2015/0142086 | A1 | 5/2015 | Narita | |
| 2015/0234207 | A1 | 8/2015 | Koifman | |
| 2016/0022225 | A1 | 1/2016 | Palmer et al. | |
| 2016/0067086 | A1 | 3/2016 | Tedford et al. | |
| 2016/0216537 | A1 | 7/2016 | Drobe | |
| 2016/0270656 | A1* | 9/2016 | Samec | A61B 5/398 |
| 2016/0361437 | A1 | 12/2016 | Lucas et al. | |
| 2017/0299898 | A1 | 10/2017 | Gallina et al. | |
| 2018/0017814 | A1* | 1/2018 | Tuan | A61B 3/107 |
| 2018/0035101 | A1 | 2/2018 | Osterhout | |
| 2019/0204624 | A1 | 7/2019 | Barrau et al. | |
| 2019/0212581 | A1 | 7/2019 | Scherlen et al. | |
| 2019/0258086 | A1 | 8/2019 | Barrau et al. | |
| 2019/0328577 | A1* | 10/2019 | Luttrull | A61N 5/0603 |
| 2019/0355287 | A1* | 11/2019 | Lemoff | G02B 27/0172 |
| 2020/0108272 | A1* | 4/2020 | Bahmani | A61N 5/0622 |
| 2021/0031051 | A1* | 2/2021 | Kubota | G02B 27/30 |
| 2021/0157172 | A1 | 5/2021 | Barrau et al. | |
| 2021/0382325 | A1 | 12/2021 | Kubota et al. | |
| 2022/0016023 | A1* | 1/2022 | Zhou | A61P 27/02 |
| 2022/0047887 | A1 | 2/2022 | Honold et al. | |
| 2022/0057651 | A1 | 2/2022 | Segre et al. | |
| 2022/0062634 | A1 | 3/2022 | Masko et al. | |
| 2022/0082860 | A1 | 3/2022 | Guillot et al. | |
| 2022/0111228 | A1 | 4/2022 | Schoutens | |
| 2022/0187628 | A1 | 6/2022 | Valentine et al. | |
| 2022/0233878 | A1 | 7/2022 | Lee et al. | |
| 2022/0252904 | A1 | 8/2022 | Hones, Jr. et al. | |
| 2022/0397774 | A1 | 12/2022 | Barrau et al. | |
| 2022/0413318 | A1 | 12/2022 | Kubota et al. | |
| 2023/0020468 | A1 | 1/2023 | Kubota et al. | |
| 2023/0132952 | A1 | 5/2023 | Youngblood et al. | |
| 2023/0204982 | A1 | 6/2023 | Boyles | |
| 2023/0248937 | A1 | 8/2023 | Blair et al. | |
| 2023/0248993 | A1 | 8/2023 | Bahmani et al. | |
| 2023/0359045 | A1 | 11/2023 | Samec et al. | |
| 2023/0389161 | A1 | 11/2023 | Coleman | |
| 2024/0036357 | A1 | 2/2024 | Schianchi et al. | |
| 2024/0272454 | A1 | 8/2024 | Zheleznyak et al. | |
| 2024/0359031 | A1 | 10/2024 | Marshall et al. | |

(56) References Cited

U.S. PATENT DOCUMENTS

FOREIGN PATENT DOCUMENTS

| | | | | |
|---|---|---|---|---|
| CN | 212973238 | U | 4/2021 | |
| EP | 2772794 | A1 | 9/2014 | |
| EP | 3528036 | A1 | 8/2019 | |
| EP | 3528037 | A1 | 8/2019 | |
| EP | 4248925 | A2 | 9/2023 | |
| EP | 4296762 | A1 | 12/2023 | |
| KR | 20130006766 | U | 11/2013 | |
| KR | 102195466 | B1 | 12/2020 | |
| KR | 102436963 | B1 | 8/2022 | |
| WO | WO-2019109125 | A1 * | 6/2019 | ........... A61F 9/0079 |
| WO | 2021105979 | A1 | 6/2021 | |
| WO | 2021116449 | A1 | 6/2021 | |
| WO | 2021252319 | A1 | 12/2021 | |
| WO | 2022094678 | A1 | 5/2022 | |
| WO | 2022187279 | A1 | 9/2022 | |
| WO | 2022219441 | A1 | 10/2022 | |
| WO | 2022258572 | A1 | 12/2022 | |
| WO | 2023186146 | A1 | 10/2023 | |
| WO | 2024094884 | A1 | 5/2024 | |

OTHER PUBLICATIONS

Akerman, D., Predicting the Onset of Myopia in Children, Review of Myopia Management, Jul. 15, 2024, https://reviewofmm.com/predicting-the-onset-of-myopia-in-children/, downloaded May 30, 2025.

Application No. PCT/US2024/045750, International Search Report and Written Opinion dated Dec. 16, 2024.

Application No. PCT/US2024/045751, International Search Report and Written Opinion dated Dec. 16, 2024.

Application No. PCT/US2024/051175, International Search Report and Written Opinion dated Nov. 25, 2024.

Application No. PCT/US2024/053151, International Search Report and Written Opinion dated Jan. 2, 2025.

Application No. PCT/US2024/056407, International Search Report and Written Opinion dated Jan. 17, 2025.

Application No. PCT/US2024/057354, International Search Report and Written Opinion dated Feb. 3, 2025.

Application No. PCT/US2025/012142, International Search Report and Written Opinion dated Mar. 5, 2025.

Capovilla, G.; Effectiveness of a particular blue lens on photoparoxysmal response in photosensitive epileptic patients; Ital J. Neurol Sci (1999) 20:161-166.

Cardinal Intellectual Property Patent Search Report dated Nov. 4, 2024.

Chakraborty, R., et al.; Axial length reduction and choroidal thickening with short-term exposure to cyan light in human subjects; Ophthalmic Physiol Opt. 2024;00:1-19. https://doi.org/10.1111/opo.13390.

Liu, Z., et al., The Effects of Repeated Low-Level Red-Light Therapy on the Structure and Vasculature of the Choroid and Retina in Children with Premyopia, Ophthalmol Ther 13:739-759 (2024), https://doi.org/10.1007/s40123-023-00875-x, downloaded Jun. 6, 2025 from https://link.springer.com/article/10.1007/s40123-023-00875-x.

Lumivision & Wellbeing: Myproclear webpage; https://url.us.m.mimecastprotect.com/s/PULWCBB8KLtRPYm8SzfGf2jbnq?domain=lumi-visionandwellbeing.co.uk/; downloaded May 19, 2025.

Mutti, D., et al., Predicting the onset of myopia in children by age, sex, ethnicity: Results from the CLEERE Study, Optom Vis Sci. Apr. 1, 2024;101(4):179-186, https://pmc.ncbi.nlm.nih.gov/articles/PMC11060695/, downloaded May 30, 2025.

National Academies of Sciences, Engineering, and Medicine. 2024. Myopia: Causes, Prevention, and Treatment of an Increasingly Common Disease. Washington, DC: The National Academies Press. https://doi.org/10.17226/27734.

Visible Bandpass Filters; Optical Filter Shop; retrieved at https://opticalfiltershop.com/product-category/bandpass-filter/visible-bandpass-filters-390nm-to-750nm/?srsltid=AfmBOoq17fx_K3qa6-4IEMggf0z4wh0-EXqLU41U1dkCunEvOlyDQzcw on Nov. 8, 2024.

Www.dopavision.com/product/, visited Sep. 11, 2024.

* cited by examiner

EYE ANATOMY (PHOTORECEPTORS)

SERATONIN/DOPAMINE

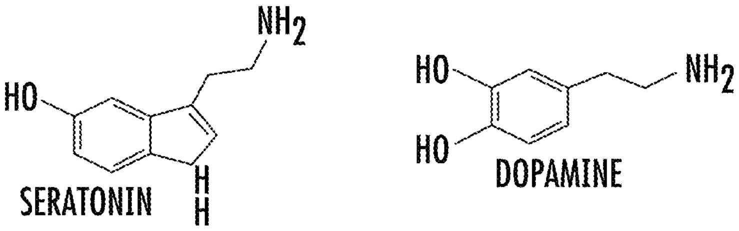

| SERATONIN | DOPAMINE |
|---|---|
| AN INHIBITORY NEUROTRANSMITTER | AN EXCITATORY NEUROTRANSMITTER |
| REGULATE MOOD | REGULATE MOTIVATION |
| ASSOCIATE WITH FEELINGS OF HAPPINESS, FOCUS, AND CALM | ASSOCIATE WITH FEELINGS OF REWARDS, MOTIVATION, AND BEING PRODUCTIVE |
| CONTRIBUTES TO SLEEP AND DIGESTION | IMPORTANT FOR NORMAL MOVEMENT AND BALANCE |
| DEFICIENCY IS LINKED WITH SENSITIVITY TO PAIN, AGGRESSIVENESS, ANXIETY, AND DEPRESSION. | DEFICIENCY IS LINKED WITH SENSITIVITY TO MEMORY LOSS, LOW SEX DRIVE, POOR DIGESTION, AND POOR COGNITION. |

FIG. 10

INVENTIVE EMBODIMENT TO PREVENT, SLOW, OR STOP MYOPIA PROGRESSION

OCULAR PHOTO-BIO-STIMULATION STEERING WHEEL

OCULAR PHOTO-BIO-STIMULATION ELECTRONIC EYEWEAR INSERTS
— FITS BEHIND LENSES OR IN PLACE OF LENSES

OCULAR PHOTO-BIO-STIMULATION ELECTRONIC EYEWEAR INSERTS
—FITS BEHIND LENSES OR IN PLACE OF LENSES

ROLLABLE OCULAR PHOTO-BIO-STIMULATION DISPOSABLE FILTERED OPTICS

OCULAR PHOTO-BIO-STIMULATION FILTERED EYEWEAR WITH SIDE LIGHT PROTECTOR

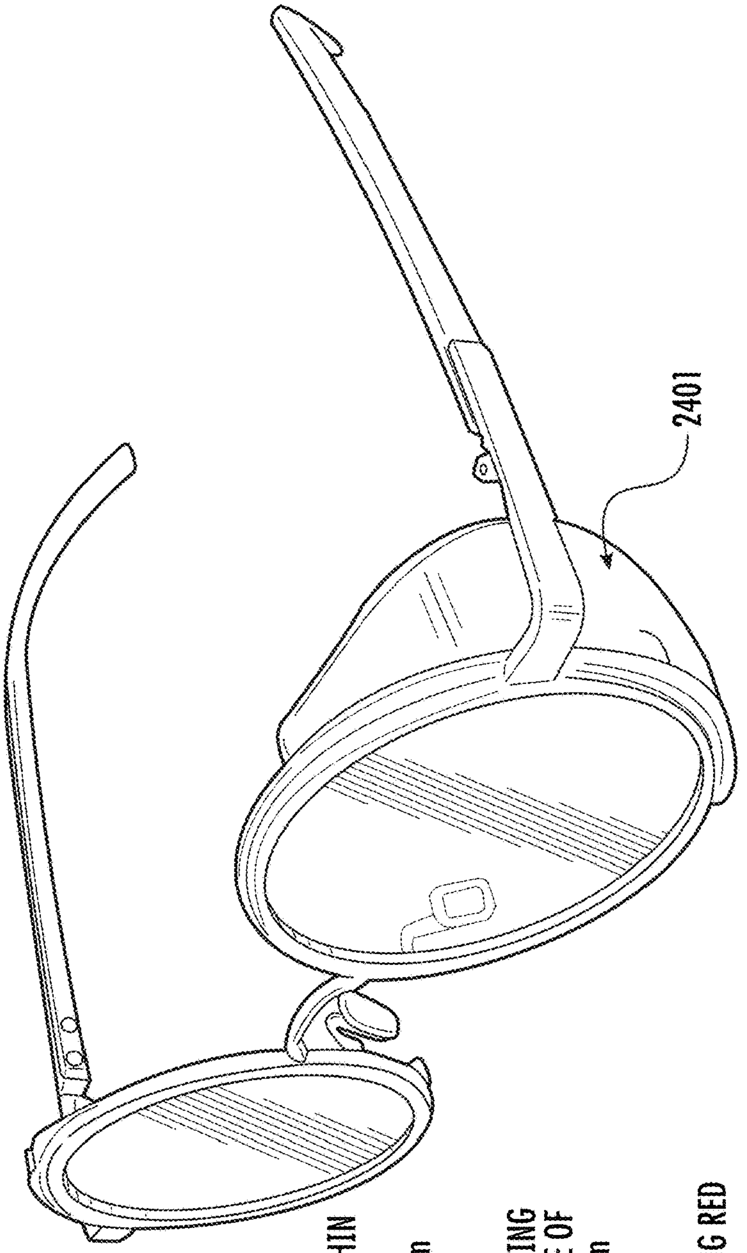

COMPRISES FILTERED OPTIC TRANSMITTING BLUE WAVELENGTHS WITHIN THE RANGE OF 450nm – 500nm, OR 460nm +/-20nm, OR 480nm +/- 30nm

OR

COMPRISES A FILTERED OPTIC TRANSMITTING GREEN WAVELENGTHS WITHIN THE RANGE OF 520nm +/- 10nm OR 530nm +/- 20nm

OR

COMPRISES A FILTERED OPTIC TRANSMITTING RED WAVELENGTHS WITHIN THE RANGE OF 660nm +/- 20nm, OR 630nm +/- 30nm

FIG. 24

OCULAR PHOTO-BIO-STIMULATION FILTERED FIT-OVER EYEWEAR

A PHOTO-BIO-STIMULATION LENS CAN FILTER AND PREDOMINANTLY TRANSMIT LIGHT WAVELENGTHS WITHIN THE RANGE OF LIGHT WAVELENGTHS OF ONE OR MORE OF THE FOLLOWING, 450nm – 500nm, 470nm +/- 20nm, 480nm +/- 30nm, OR 530nm +/- 10nm, 530nm +/- 15nm, 530nm +/- 20nm, 510nm TO 550nm, OR 630nm +/-20nm, 650nm +/- 30nm, OR 600nm – 700nm WHILE AT THE SAME TIME FILTERING AND BLOCKING WAVELENGTHS WITHIN THE RANGE OF LIGHT WAVELENGTHS OF ONE OR MORE OF; 449nm – 421nm AND 419nm – 400nm.

A PHOTO-BIO-STIMULATION LENS CAN FILTER AND PREDOMINANTLY TRANSMIT LIGHT WAVELENGTHS WITHIN THE RANGE OF LIGHT WAVELENGTHS OF ONE OR MORE OF THE FOLLOWING, 450NM – 500NM, 470NM +/- 20NM, 480NM +/- 30NM, OR 530NM +/- 10NM, 530NM +/- 15NM, 530NM +/- 20NM, 510NM TO 550NM, OR 630NM +/-20NM, 650NM +/- 30NM, OR 600NM – 700NM WHILE AT THE SAME TIME FILTERING AND BLOCKING WAVELENGTHS WITHIN THE RANGE OF LIGHT WAVELENGTHS OF ONE OR MORE OF; 449NM – 421NM AND 419NM – 400NM.

FILTERED LENS OR OPTIC WITH DEFOCUS

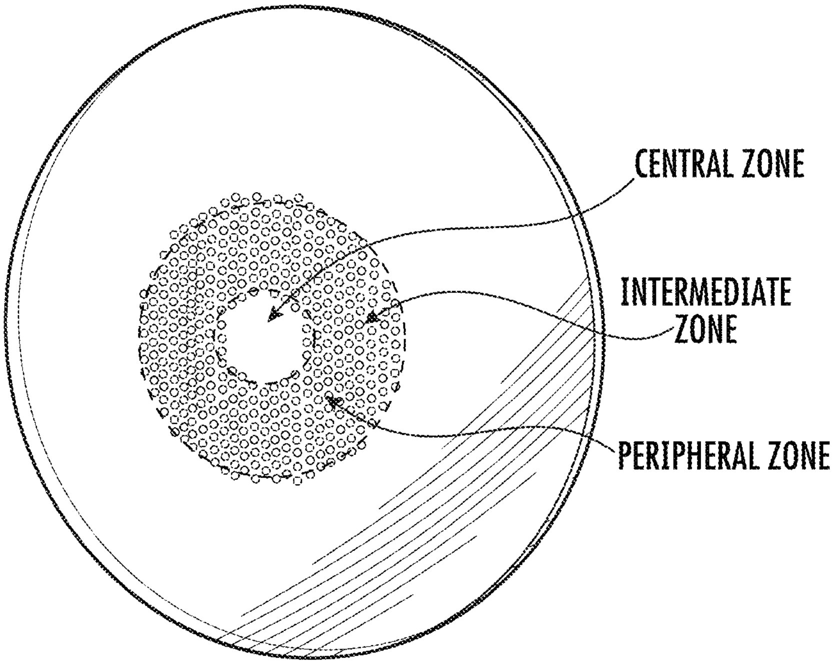

A PHOTO-BIO-STIMULATION LENS CAN FILTER AND PREDOMINANTLY TRANSMIT LIGHT WAVELENGTHS WITHIN THE RANGE OF LIGHT WAVELENGTHS OF ONE OR MORE OF THE FOLLOWING, 450NM – 500NM, 470NM +/- 20NM, 480NM +/- 30NM, OR 530NM +/- 10NM, 530NM +/- 15NM, 530NM +/- 20NM, 510NM TO 550NM, OR 630NM +/-20NM, 650NM +/- 30NM, OR 600NM – 700NM WHILE AT THE SAME TIME FILTERING AND BLOCKING WAVELENGTHS WITHIN THE RANGE OF LIGHT WAVELENGTHS OF ONE OR MORE OF; 449NM – 421NM AND 419NM – 400NM.

FIG. 29

FILTERED LENS OR OPTIC
WITH DEFOCUS

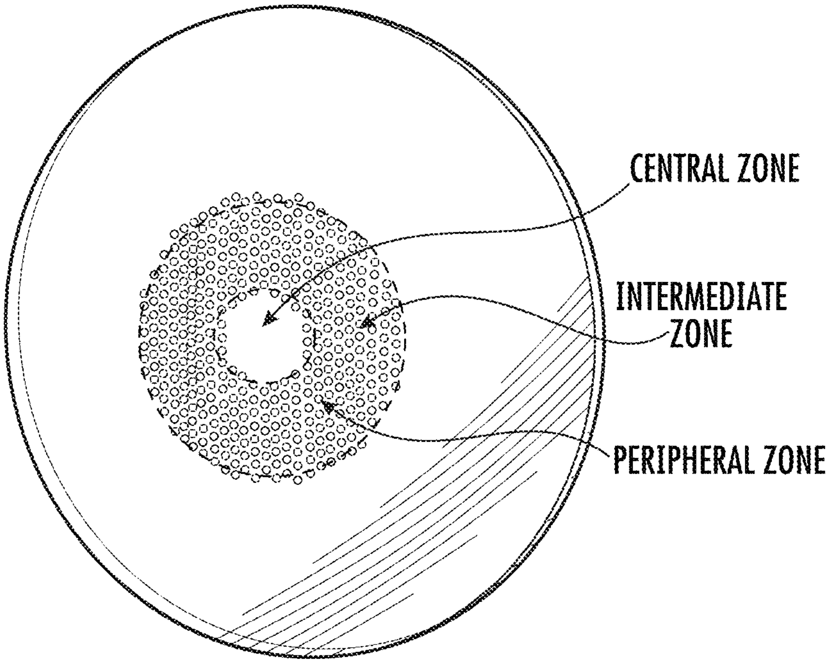

A PHOTO-BIO-STIMULATION LENS CAN FILTER AND PREDOMINANTLY TRANSMIT LIGHT WAVELENGTHS WITHIN THE RANGE OF LIGHT WAVELENGTHS OF ONE OR MORE OF THE FOLLOWING, 450NM – 500NM, 470NM +/- 20NM, 480NM +/- 30NM, OR 530NM +/- 10NM, 530NM +/- 15NM, 530NM +/- 20NM, 510NM TO 550NM, OR 630NM +/-20NM, 650NM +/- 30NM, OR 600NM – 700NM WHILE AT THE SAME TIME FILTERING AND BLOCKING WAVELENGTHS WITHIN THE RANGE OF LIGHT WAVELENGTHS OF ONE OR MORE OF; 449NM – 421NM AND 419NM – 400NM.

FIG. 30

CHROMATIC ABERRATION
FOCUSED LENS

*LENSLETS AND MORE MINUS OR LESS PLUS LENS POWER IN INTERMEDIATE ZONE "TOGETHER" PRODUCES MORE MINUS OR LESS PLUS COMPARED TO CENTRAL ZONE. PERIPHERAL TO THE INTERMEDIATE ZONE THE LENS POWER CONTRIBUTES MORE MINUS OR LESS PLUS COMPARED TO THE CENTRAL ZONE.

SUNGLASS CATEGORIES
| CATEGORY | VLT RANGE | DESCRIPTION | USE | DAY DRIVING | NIGHT DRIVING |
|---|---|---|---|---|---|
| 0 | 100% - 80% | VERY LOW REDUCTION OF VISIBLE LIGHT |  | ✓ | ✓ |
| 1 | 80% - 43% | LIMITED REDUCTION OF VISIBLE LIGHT |  | ✓ | X |
| 2 | 43% - 18% | MEDIUM REDUCTION OF VISIBLE LIGHT |  | ✓ | X |
| 3 | 18% - 8% | HIGH REDUCTION OF VISIBLE LIGHT | 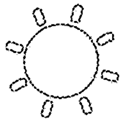 | ✓ | X |
| 4 | 8% - 3% | VERY HIGH REDUCTION OF VISIBLE LIGHT | 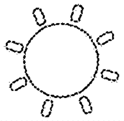 | X | X |
FIG. 44

WITHOUT INVENTIVE EMBODIMENT

RIGHT RETINA

AVERAGE RETINA IS ~30MM – 40MM IN DIAMETER

DETAILS OF THE INVENTION

RETINA OF HUMAN EYE

AUGMENTED OR MIXED REALITY OCULAR PHOTO-BIO-STIMULATION

| CONVENTIONAL SUNGLASSES COMPARISON TO INVENTIVE EMBODIMENT | OVERALL VISIBLE LIGHT TRANSMISSION % | LIGHT TRANSMISSION % BETWEEN 450nm & 510nm (DOPAMINE STIMULATED) | LIGHT TRANSMISSION % OF INVENTIVE EMBODIMENT THAT STIMULATES DOPAMINE PRODUCTION VS CONVENTIONAL SUNGLASSES |
|---|---|---|---|
| INVENTIVE EMBODIMENT = I.E. | 18.2% | 50.5% | INVENTIVE EMBODIMENT = I.E. |
| 1) SUNGLASS GREY | 20.5% | 12.3% | I.E.= 410% GREATER |
| 2) SUNGLASS BLUE | 35.1% | 23.9% | I.E.= 211% GREATER |
| 3) SUNGLASS BLUISH GREY | 15.8% | 17.9% | I.E.= 280% GREATER |
| 4) SUNGLASS MIRRORED | 19.3% | 09.2% | I.E.= 550% GREATER |
| 5) SUNGLASS REDISH BROWN | 15.0% | ~09.0% | I.E.= 561% GREATER |
| 6) SUNGLASS PLASTIC GREY #3 | 15.0% | ~12.3% | I.E.= 411% GREATER |
| 7) SUNGLASS BROWN | 12.0% | ~10.0% | I.E.= 505% GREATER |
| 8) SUNGLASS BROWN POLARIZED | 11.5% | ~05.0% | I.E.= 1,010% GREATER |
| 9) PHOTOCHROMIC BROWN ACTIVATED | 12.0% | ~14.0% | I.E.= 360% GREATER |
| 10) PHOTOCHROMIC GREY ACTIVATED | 14.0% | ~18.0% | I.E.= 280% GREATER |

FIG. 68

| CONVENTIONAL SUNGLASSES COMPARISON TO INVENTIVE EMBODIMENT | LIGHT TRANSMISSION % BETWEEN 450nm & 510nm (DOPAMINE PRODUCED) | ASSUME SUNLIGHT INTENSITY OF 20,000 LUX (INTENSITY GENERATING DOPAMINE) | ASSUME SUNLIGHT IS 12:00NOON & EMBODIMENT'S TRANSMISSION OF BLUE WAVELENGTHS 450nm - 510nm MAKE UP 15% OF VISIBLE SPECTRUM | ASSUME SAME SUN LIGHT, BUT ONLY 465nm - 495nm IS TRANSMITTED. THEN ONLY 7.5% WOULD REACH RETINA |
|---|---|---|---|---|
| INVENTIVE EMBODIMENT = I.E. | 50.5% | 6,060 LUX | 1,515 LUX | 757.5 LUX |
| 1) SUNGLASS GREY | 12.3% | 1,476 LUX | 369 LUX | 184.5 LUX |
| 2) SUNGLASS BLUE | 23.9% | 2,868 LUX | 171 LUX | 358.5 LUX |
| 3) SUNGLASS BLUISH GREY | 17.9% | 2,148 LUX | 537 LUX | 268.5 LUX |
| 4) SUNGLASS MIRRORED | 09.2% | 1,104 LUX | 276 LUX | 138 LUX |
| 5) SUNGLASS RED BROWN | ~09.0% | 1,080 LUX | 270 LUX | 135 LUX |
| 6) SUNGLASS GREY #3 | ~12.3% | 1,476 LUX | 369 LUX | 184.5 LUX |
| 7) SUNGLASS BROWN | ~10.0% | 1,200 LUX | 300 LUX | 150 LUX |
| 8) SUNGLASS BROWN POLARIZED | ~05.0% | 600 LUX | 150 LUX | 75 LUX |
| 9) PHOTOCHROMIC BROWN | ~14.0% | 1,680 LUX | 420 LUX | 210 LUX |
| 10) PHOTOCHROMIC GREY | ~18.0% | 2,160 LUX | 540 LUX | 270 LUX |

FIG. 69

MIDDAY
450nm - 510nm

AFTERNOON
450nm - 510nm

SUNSET
450nm - 510nm

| GOOD SUN LIGHT<br>500 LUX TRANSMITTED BY SUNGLASSES NEEDED FOR DOPAMINE PRODUCTION<br>ACCOUNTS FOR LENS DISTANCE TO RETINA AND ATTENUATION BY EYE TISSUES | OVERALL VISIBLE LIGHT TRANSMISSION (VLT) | LIGHT TRANSMISSION WITHIN THE RANGE OF 450nm & 510nm | ASSUME SUNLIGHT OF 20,000 LUX<br>---------<br>MORNING<br>~30% OR 6,000 BLUE LIGHT LUX | ASSUME SUNLIGHT OF 50,000 LUX<br>---------<br>NOON<br>~20% OR 10,000 BLUE LIGHT LUX | ASSUME SUNLIGHT OF 30,000 LUX<br>---------<br>AFTERNOON<br>~10% OR 3,000 BLUE LIGHT LUX | ASSUME SUNLIGHT OF 20,000 LUX<br>---------<br>SUNSET<br>~5% OR 1,000 BLUE LIGHT LUX |
|---|---|---|---|---|---|---|
| INVENTIVE EMBODIMENT | 18.2% | 50.5% | 3030 LUX | 5050 LUX | 1515 LUX | 505 LUX |
| SUNGLASS GREY | 20.5% | 12.3% | 738 LUX | 1230 LUX | 369 LUX | 123 LUX |
| SUNGLASS BLUE | 35.1% | 23.9% | 1434 LUX | 2390 LUX | 717 LUX | 239 LUX |
| SUNGLASS BLUISH GREY | 15.8% | 17.9% | 1074 LUX | 1790 LUX | 537 LUX | 179 LUX |
| SUNGLASS MIRRORED | 19.3% | 09.2% | 552 LUX | 920 LUX | 276 LUX | 92 LUX |
| SUNGLASS RED BROWN | 15.0% | ~09.0% | 540 LUX | 900 LUX | 270 LUX | 90 LUX |
| SUNGLASS GREY #3 | 15.0% | ~12.3% | 738 LUX | 1230 LUX | 369 LUX | 123 LUX |
| SUNGLASS BROWN | 12.0% | ~10.0% | 600 LUX | 1000 LUX | 300 LUX | 100 LUX |
| SUNGLASS BROWN POLARIZED | 11.5% | ~05.0% | 300 LUX | 500 LUX | 150 LUX | 50 LUX |
| PHOTOCHROMIC BRN ACTIVATED | 12.0% | ~14.0% | 840 LUX | 1400 LUX | 420 LUX | 140 LUX |
| PHOTOCHROMIC GREY ACTIVATED | 14.0% | ~18.0% | 1080 LUX | 1800 LUX | 540 LUX | 180 LUX |

FIG. 74

| SHADED SUN LIGHT<br>500 LUX TRANSMITTED BY SUNGLASSES NEEDED FOR DOPAMINE PRODUCTION<br>ACCOUNTS FOR LENS DISTANCE TO RETINA AND ATTENUATION BY EYE TISSUES | OVERALL VISIBLE LIGHT TRANSMISSION (VLT) | LIGHT TRANSMISSION WITHIN THE RANGE OF 450nm & 510nm | SUNLIGHT TRANSLUCENT SHADE 1 (8200 LUX) | SUNLIGHT TRANSLUCENT SHADE 2 (4200 LUX) | SUNLIGHT BIG TREE SHADE (1600 LUX) | SUNLIGHT BETWEEN 3 BUILDINGS (1000 LUX) |
|---|---|---|---|---|---|---|
| INVENTIVE EMBODIMENT | 18.2% | 50.5% | 4141 LUX | 2121 LUX | 808 LUX | 505 LUX |
| SUNGLASS GREY | 20.5% | 12.3% | 1009 LUX | 517 LUX | 197 LUX | 123 LUX |
| SUNGLASS BLUE | 35.1% | 23.9% | 1960 LUX | 1004 LUX | 382 LUX | 239 LUX |
| SUNGLASS BLUISH GREY | 15.8% | 17.9% | 1468 LUX | 752 LUX | 286 LUX | 179 LUX |
| SUNGLASS MIRRORED | 19.3% | 09.2% | 754 LUX | 386 LUX | 147 LUX | 92 LUX |
| SUNGLASS RED BROWN | 15.0% | ~09.0% | 738 LUX | 378 LUX | 144 LUX | 90 LUX |
| SUNGLASS GREY #3 | 15.0% | ~12.3% | 1009 LUX | 517 LUX | 197 LUX | 123 LUX |
| SUNGLASS BROWN | 12.0% | ~10.0% | 820 LUX | 420 LUX | 160 LUX | 100 LUX |
| SUNGLASS BROWN POLARIZED | 11.5% | ~05.0% | 410 LUX | 210 LUX | 80 LUX | 50 LUX |
| PHOTOCHROMIC BRN ACTIVATED | 12.0% | ~14.0% | 1148 LUX | 588 LUX | 224 LUX | 140 LUX |
| PHOTOCHROMIC GREY ACTIVATED | 14.0% | ~18.0% | 1476 LUX | 756 LUX | 288 LUX | 180 LUX |

FIG. 75

SUNGLASS CATEGORIES
| CATEGORY | VLT RANGE | DESCRIPTION | USE | DAY DRIVING | NIGHT DRIVING |
|---|---|---|---|---|---|
| 0 | 100% - 80% | VERY LOW REDUCTION OF VISIBLE LIGHT |  | ✓ | ✓ |
| 1 | 80% - 43% | LIMITED REDUCTION OF VISIBLE LIGHT |  | ✓ | X |
| 2 | 43% - 18% | MEDIUM REDUCTION OF VISIBLE LIGHT |  | ✓ | X |
| 3 | 18% - 8% | HIGH REDUCTION OF VISIBLE LIGHT | 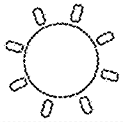 | ✓ | X |
| 4 | 8% - 3% | VERY HIGH REDUCTION OF VISIBLE LIGHT | 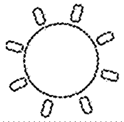 | X | X |
FIG. 76

OCULAR PHOTO-BIO-STIMULATION

IPHONE 2024 NIGHT MODE OFF

THE COMBINATION OF THE ABOVE CAN BE USED TO STIMULATE THE PRODUCTION OF DOPAMINE IN THE EYE AND / OR BRAIN OF THE USER. THE BRIGHTNESS LEVEL IN LUX SHOULD BE TURNED UP TO DISPLAY TO 1,000 LUX OR GREATER BRIGHTNESS INTENSITY OF 2,000 LUX.

CELL PHONE, TABLET, LAPTOP, DESKTOP, COMPUTERIZED ELECTRONIC DISPLAY WITH APP

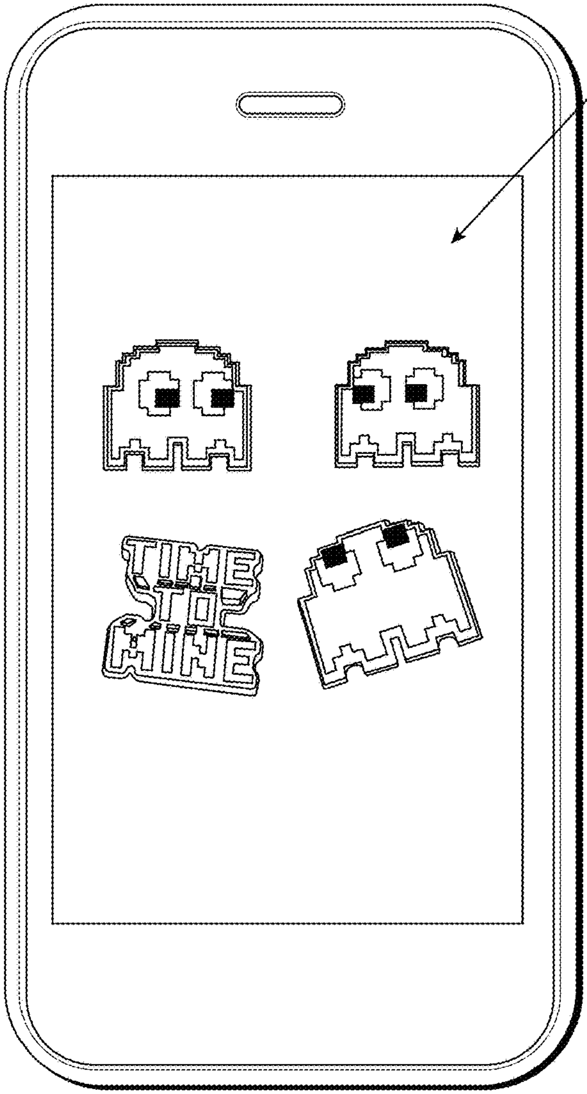

MOSTLY WHITE LIGHT MADE UP OF THE FOLLOWING LIGHT WAVELENGTHS

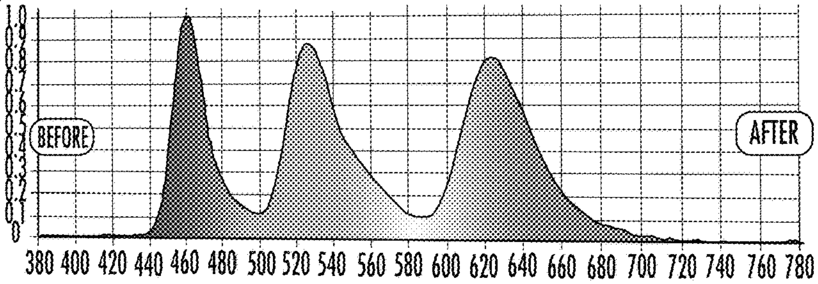

THE APP PERMITS USERS WHO ARE DISTANCE SEPARATED AND BEING TREATED WITH OCULAR PHOTO-BIO-STIMULATION TO COMPETE OR PLAY GAMES WITH ONE ANOTHER OR WITHIN USER GROUPS THAT COMPETE WHILE RECEIVING THEIR OCULAR PHOTO BIO-STIMULATION TREATMENT. SUCH COMPETITION OR GAME PLAY CAN BE WIRELESS. THE USERS CAN BE LOCATED, BY WAY OF EXAMPLE ONLY, IN DIFFERENT HOUSES OR CITIES

FIG. 93

IDENTIFICATION AND PREVENTION OF MYOPIA

CROSS-REFERENCE TO RELATED APPLICATIONS

The present application relies on the disclosures of and claims priority to and the benefit of the filing dates of the following U.S. patent applications:

The present application relies on the disclosures of and claims priority to and the benefit of the filing dates of the following U.S. patent applications:

U.S. Appl. No. 63/755,470, filed Feb. 7, 2025, titled Ocular Photo-Bio-Stimulation Updated U.S. Appl. No. 63/759,378, filed Feb. 17, 2025, titled Enhanced Ocular Photo-Bio-Stimulation U.S. Appl. No. 63/769,313, filed Mar. 10, 2025, Fabrication of Myopia Control Lenses U.S. Appl. No. 63/773,005, filed Mar. 17, 2025, titled Myopia Control Medicine and Additive Component U.S. Appl. No. 63/777,920, filed Mar. 26, 2025, titled Electronic Myopia Control Eyewear U.S. Appl. No. 63/780,692, filed Mar. 31, 2025, titled General Blue Light Embodiments Provisional U.S. Appl. No. 63/783,745, filed Apr. 4, 2025, titled General Blue Light Embodiments Provisional U.S. Appl. No. 63/791,207, filed Apr. 18, 2025, titled Blue Light and Red-Light Ocular Neuro Therapy U.S. Appl. No. 63/792,814, filed Apr. 22, 2025, titled Ocular Light Therapy U.S. Appl. No. 63/800,627, filed May 6, 2025, titled Color Balancing to Pass ISO and ANSI Traffic Signal Testing U.S. Appl. No. 63/812,791, filed May 27, 2025, titled Ocular Photo-Bio-Stimulation Fixation Target For Protecting the Fovea and/or Macula U.S. Appl. No. 63/816,756, filed Jun. 3, 2025, titled A Highly Efficient and Sustained Approach for Myopia Control Based on Myopia Control Lenses and Ocular Light Therapy Continuation of U.S. application Ser. No. 19/030,018, filed Jan. 17, 2025, titled Ocular Photo-Bio-Stimulation, which claims priority to and the benefit of the filing dates of:

U.S. Appl. No. 63/623,253, filed Jan. 20, 2024, titled Neuro-Light Therapy Further Optimized U.S. Appl. No. 63/627,703, filed Jan. 31, 2024, titled Neuro-Light Optogenetic Therapy U.S. Appl. No. 63/550,852, filed Feb. 7, 2024, titled Enhanced Neuro-Light Optogenetic Therapy U.S. Appl. No. 63/553,226, filed Feb. 14, 2024, titled Neuro-Light Optogenetic Therapy Enhanced U.S. Appl. No. 63/553,693, filed Feb. 15, 2024, titled Enhanced Neuro-Light Optogenetic Therapy U.S. Appl. No. 63/561,266, filed Mar. 4, 2024, titled Ocular Neuro-Light Therapy U.S. Appl. No. 63/569,005, filed Mar. 22, 2024, titled Ocular Neuro-Light Therapy Improved U.S. Appl. No. 63/639,892, filed Apr. 29, 2024, titled Ocular Optogenetic Neuro Therapy U.S. Appl. No. 63/648,098, filed May 15, 2024, titled Ocular Optogenetic Therapy U.S. Appl. No. 63/654,566, filed May 31, 2024, titled Optogenetic Lens Designs U.S. Appl. No. 63/671,237, filed Jul. 14, 2024, titled XR Optogenetic Stimulation of the Human Eye and Sunglasses Allowing Dopamine Production U.S. Appl. No. 63/673,746, filed Jul. 21, 2024, titled Enhanced XR Optogenetic Stimulation of the Human Eye and Sunglasses Allowing Dopamine Production U.S. Appl. No. 63/674,219, filed Jul. 22, 2024, titled Advanced XR Optogenetic Stimulation of the Human Eye and Sunglasses Allowing Dopamine Production U.S. Appl. No. 63/676,855, filed Jul. 29, 2024, titled XR Optogenetic Stimulation U.S. Appl. No. 63/684,509, filed Aug. 19, 2024, titled Refined Optogenetic Lens Designs U.S. application Ser. No. 18/827,782, filed Sep. 8, 2024, titled Ocular Photo-Bio-Stimulation Optics U.S. application Ser. No. 18/827,786, filed Sep. 8, 2024, titled Ocular Photo-Bio-Stimulation Optics U.S. Appl. No. 63/697,560, filed Sep. 22, 2024, titled Filtering Eyewear and Optics for Ocular Photo-Bio-Stimulation U.S. application Ser. No. 18/914,202, filed Oct. 13, 2024, titled Filtering Eyewear and Optics for Ocular Photo-Bio-Stimulation U.S. application Ser. No. 18/928,126, filed Oct. 27, 2024, titled Filtering Eyewear and Optics for Ocular Photo-Bio-Stimulation U.S. application Ser. No. 18/951,274, filed Nov. 18, 2024, titled Sunglass Lens and Sunglass Optics for Ocular Photo-Bio-Stimulation U.S. application Ser. No. 18/959,511, filed Nov. 25, 2024, titled Color Balanced Sunglass Lens for Ocular Photo-Bio-Stimulation U.S. Appl. No. 63/729,431, filed Dec. 8, 2024, titled Balancing Transmitted Color for Sunglasses that Increase Dopamine Production in the Eye and Possibly the Brain While Passing the ISO and/or ANSI Traffic Signal Testing U.S. Appl. No. 63/735,232, filed Dec. 17, 2024, titled Ocular Photo-Bio-Stimulation Miscellaneous U.S. Appl. No. 63/740,226, filed Dec. 30, 2024, titled Updated Provisional Ocular Photo-Bio-Stimulation Miscellaneous U.S. application Ser. Nos. 18/827,782, and 18/827,786 rely on the disclosures of and claim priority to and the benefit of the filing dates of U.S. Appl. No. 63/537,021, filed Sep. 7, 2023, titled Device Providing Blue Light for Alertness and Red Light for Calming, U.S. Appl. No. 63/540,090, filed Sep. 24, 2023, titled Enhanced Device Providing Blue Light for Alertness and Red Light for Calming, and U.S. Appl. No. 63/541,243, filed Sep. 28, 2023, titled Device Providing Blue Light Alertness and/or Red Light Calming, U.S. Appl. No. 63/546,848, filed Nov. 1, 2023, titled Improved Eyewear or Optic Providing Blue Light Alertness, Myopia Control, Green Light Pain Relief, and Red-Light Calming, U.S. Appl. No. 63/548,204, filed Nov. 12, 2023, titled Neuro-Light Therapy, U.S. Appl. No. 63/600,139, filed Nov. 17, 2023, titled Enhanced Neuro-Light Therapy., U.S. Appl. No. 63/603,258, filed Nov. 28, 2023, titled Optimized Neuro-Light Therapy, U.S. Appl. No. 63/609,306, filed Dec. 12, 2023, titled Neuro-Light Therapy Improved, and U.S. Appl. No. 63/617,363, filed Jan. 3, 2024, titled Neuro-Light Therapy Optimized.

The disclosures of those applications are hereby incorporated by reference herein in their entireties.

Guide:

For the purpose of assisting in navigating this comprehensive patent application, the following main sections with page numbers are provided. It is important to note that due to common, supportive, and overlapping teachings, while the patent application is divided into sections, certain teachings are taught in multiple sections.

Background of the Invention
Summary of Invention
Definitions
Ocular Photo-Bio-Stimulation with Inventive Embodiments
Ocular Photo-Bio-Stimulation Cell Phone Case
Ocular Photo-Bio-Stimulation Electronic Display Screen with Controllable Lighted Border
Ocular Photo-Bio-Stimulation Electronic Display Screen with Fixed Lighted Border Edge
Ocular Photo-Bio-Stimulation Steering Wheel, dashboard, or instrument panel of a Vehicle.
Eyewear and Optics for Providing Ocular Photo-Bio-Stimulation
Lenses or Optics Comprising a Defocus Zone for Ocular Photo-Bio-Stimulation Therapy
Chromatic Aberration Focused Lens for Ocular Photo-Bio-Stimulation
Sunglass Lens or Sunglass Optic or Filtered lens or Filtered optic that Provides Ocular Photo-Bio-Stimulation
XR Devices for Ocular Photo-Bio-Stimulation
A System and App for a Computerized Device Comprising an Ocular Photo-Bio-Stimulation Light Source
Claims

BACKGROUND OF THE INVENTION

Field of the Invention

The current invention relates, in part, to ocular photo-bio-stimulation therapy, a biological technique to control or influence the activity of neurons or other cell types in, on or about the eye with light. As used herein ocular photo-bio-stimulation is an umbrella category of which photobiomodulation, optogenetics and phototherapy are forms thereof. The current invention relates, in part, to photobiomodulation therapy, which includes the utilization of non-ionizing electromagnetic energy to trigger photochemical changes within cellular structures. The current invention relates, in part, to optogenetics. Optogenetics is a biological technique to control the activity of neurons or other cell types with light. The current invention relates, in part, to phototherapy, also known as light therapy or bright light therapy, which is a treatment that uses controlled exposure to artificial or natural light to treat medical conditions.

A description of the anatomy of the eye will help understand the invention described herein.

The Eye's Retinal Layer

In reference to FIG. 1, retinal cones are photoreceptor cells in the retina that give humans color vision and help them see fine details. They are cone-shaped, with a pointed tip at the top and a circular bottom, and are concentrated in the center of the retina, in an area called the macula, the center of which is called the fovea. There are ~6M cones.

In further reference to FIG. 1, retinal Rods make up more than 95% of the photoreceptors. There are ~125M rods, and they pool signals to provide high sensitivity for dark-adapted vision, say starlight, which appears monochromatic. A lack of color vision is the hallmark of rod-mediated vision. Rods are absent within 350 μm of the fovea but reach a peak density in an annular region at about 20 degrees eccentricity.

In further reference to FIG. 7, rhodopsin is the opsin of the rod cells in the retina and a light-sensitive receptor protein that triggers visual phototransduction in rods.

In further reference to FIG. 1, intrinsically photosensitive retinal ganglion cells (ipRGCs), also called photosensitive retinal ganglion cells that contain melanopsin (ipRGC) or called (mRGcs), are retinal ganglion cells (RGCs), which are neurons in the retina that transmit visual information from the eye to the brain. They are located near the inner surface (the ganglion cell layer) of the retina of the eye. It receives visual information from photoreceptors via two intermediate neuron types: bipolar cells and amacrine cells. Retinal ganglion cells collectively transmit image-forming and non-image forming visual information from the retina to several regions in the thalamus, hypothalamus, and mesencephalon, or midbrain. There are about 1.2 to 1.5 million retinal ganglion cells in the human retina. The melanopsin-containing retinal ganglion cells (mRGCs) represent only between 0.3% and 0.8% of the total ganglion cells of the retina.

In further reference to FIG. 7, melanopsin, a G family coupled receptor, is found within the ganglion cell layer in the retina and plays an important role in non-image-forming visual functions, including hormone secretion, entrainment of circadian rhythms, cognitive and affective processes.

In further reference to FIG. 9, melatonin is a natural hormone that is mainly produced by your pineal gland in your brain. It plays a role in managing your sleep wake cycle and circadian rhythm.

In further reference to FIG. 1, Amacrine cells are nerve cells in the vertebrate retina that act as interneurons, or local circuit neurons, to connect two projection neurons. They are located in the inner nuclear layer of the retina and are the first neurons in the visual system to fire action potentials. Amacrine cells are named for their presumed lack of an axon. They come in many shapes and sizes and are synaptically active in the inner plexiform layer (IPL).

In further reference to FIG. 1, dopaminergic amacrine cells (DACs) serve as the sole source of retinal dopamine, and dopamine release in the retina follows a circadian rhythm and is modulated by light exposure. Dopaminergic amacrine cells (DACs) make up less than 1% of all amacrine cells in the retina. DACs are the main source of dopamine in the retina and are one of the rarest cell types in the retina, with a density of about 10-100 per mm. DACs are the first retinal neurons to be identified neurochemically. They have long primary dendrites, a sparse dendritic arbor, and an axon that usually emerges from the soma or primary dendrite. Their dendritic fields are irregular, often elongated or asymmetric.

In further reference to FIG. 1, the optic nerve head (optic disk) is composed of neural, vascular, and connective tissues. The convergence of axons of retinal ganglion cells (RG) at the optic disc creates the neuroretinal rim that surrounds the cup, a central shallow depression in the optic disc.

In further reference to FIG. 2, the macula is a small, round area in the center of the retina, the light-sensitive layer of tissue at the back of the eye. It is about 5 millimeters across and a quarter of a millimeter thick, and is responsible for central vision, color vision, and fine detail. The macula is the part of the retina used when looking directly at objects, such as when reading or recognizing faces at a distance.

In further reference to FIG. 2, the fovea centralis, or fovea, is a small depression within the neurosensory retina where visual acuity is the highest. The fovea itself is the central portion of the macula, which is responsible for central vision.

In reference to FIG. 1, retinal rods & cones are photoreceptors in the retina that detect light and convert it into signals that the brain can use for vision.

In reference to FIG. 4, it shows the eyes retina diameter and retinal zones of the retina relative to the center of the fovea: posterior zone (or central zone) (radius<10 mm), midperiphery zone (radius=10-15 mm), and far-periphery zone (radius>15 mm.

In reference to FIG. 5, it shows pupil size relative to ambient light, by way of example only, a pupil size can be 3.5 mm at 550 lux, 4.2 mm at 350 lux, 5.2 mm at 150 lux, 5.03 mm at 40 lux, and 5.4 mm at 2 lux.

In reference to FIG. 11, myopia (nearsightedness or shortsightedness), is a common eye disease that causes light rays to bend and focus in front of the retina instead of on it. This makes distant objects appear blurry, while nearby objects appear normal. There is a silent epidemic of myopia in the world. It is forecasted that by 2050 approximately 50% of the world's population will be myopic. The number of myopes forecasted is approximately 5 billion. Hyperopia (farsightedness) is a common vision condition in which you can see distant objects clearly, but objects nearby may be blurry. With hyperopia the eye focus of the light rays is behind the retina. Astigmatism is a common eye problem that occurs when the cornea or lens of the eye is an abnormal shape, causing light to bend differently as it enters the eye. This refractive error results in distorted or blurred vision at any distance and can make it difficult to see fine details. Presbyopia is a refractive error that causes the eye to lose its ability to focus on close objects as it ages. It is also known as age-related farsightedness. Presbyopia occurs when the eye's lens loses its elasticity and can no longer focus light correctly on the retina. This makes it harder to read, thread a needle, or do other close-up tasks. Symptoms include blurry close-up vision, eyestrain, headaches, difficulty focusing on crafts and hobbies, and needing brighter lighting for clearer near vision. Dry macular degeneration (AMD) is a common eye disorder that affects the macula, the part of the retina that gives the eye clear vision. It is a chronic condition that usually develops in both eyes and is caused by a metabolic disorder, genetics, and environmental factors. As people age, the macula thins and the light-sensitive cells in it slowly break down, causing blurred or reduced central vision. AMD is referred to as age related macular degeneration and as such begins centrally within the macular area of the retina. Diabetic retinopathy (DR) is a chronic eye condition that occurs when high blood sugar from diabetes damages the retina's blood vessels. The damaged blood vessels can swell, leak, or bleed, which can lead to blurry vision, dark areas, and difficulty seeing colors. This usually begins peripheral to the macular area of the retina. Retinitis pigmentosa (RP) is a rare genetic disorder that affects the retina, the light-sensitive part of the eye at the back. RP causes the retina's photoreceptor cells to gradually break down over time, leading to vision loss. Symptoms often start in childhood or adolescence and include night blindness and peripheral vision loss. This may begin in the far and mid periphery of the retina and progresses centrally from the peripheral retina.

In reference to FIG. 6, the visible light wavelength spectrum is the segment of the electromagnetic spectrum that the human eye can view. More simply, this range of wavelengths is called visible light. Typically, the human eye can detect wavelengths from 380 to 700 nanometers.

In reference to FIG. 7, light sensitivity spectrum for melanopsin, rhodopsin is shown. Regarding the spectral sensitivity of human vision, the maximum spectral sensitivity of the human eye under daylight conditions is ~555 nm (yellow/green arrowhead), while at night the peak shifts to ~507 nm (green arrowhead), near the peak of rhodopsin (dashed blue-green line with a peak at 505 nm). Circadian photoreception mediated by melanopsin-expressing, intrinsically photosensitive ganglion cells integrate light information, but is most sensitive to a distinct blue portion of the spectrum (dashed blue line). The human retina also contains macular xanthophylls (X), yellow pigments found to be composed of two chromatographically separable components (i) lutein and (ii) zeaxanthin, whose absorption spectrum is a broad band (~100 nm width) with a spectral center between the short and medium-long wavelength photoreceptor pigments of the retina (peak ~460 nm). Rhodopsin, a visual pigment found in photoreceptor rods, has a peak sensitivity to blue-green light at around 500 nanometers (nm). This means that rhodopsin absorbs green-blue light most strongly, which gives it a reddish-purple appearance. The peak for melanopsin is ~480 nm. In addition, between 25 and 33% of all light entering the eye is absorbed by pigment granules in the RPE and the choroid. The naturally occurring pigment melanin, contained within pigment granules in the RPE and the choroid, and to a lesser extent hemoglobin in red blood cells, absorbs excess and scattered light to improve visual acuity. This serves to protect photoreceptors from photic injury and is thought to function as a quencher of free radicals and suppressor of photosensitized molecules.

In reference to FIG. 8, longitudinal chromatic aberration (LCA) is a lens's inability to focus on different color wavelengths in the same focal plane. It occurs when different wavelengths of light disperse from a lens at different points along the optical axis, creating a circle of confusion. This results in unintentional color fringes, even in the center of an image, and colored areas where not all three colors are in focus. The eye's natural longitudinal chromatic aberration (LCA) is an optical imperfection in the human eye that causes images projected onto the retina to blur. It occurs because the eye's refractive index varies with wavelength, causing the eye's focal power to change by almost 2 diopters (D) across the visible spectrum. This chromatic difference of focus causes short wavelengths to focus in front of long wavelengths, which is known as LCA. Optical lens material's longitudinal chromatic aberration (LCA) decreases as Abbe number increases. Abbe number is a measure of how much light a lens disperses, and lenses with higher Abbe numbers disperse less light and produce less chromatic aberration. Chromatic aberration is inversely proportional to the Abbe number, meaning that as Abbe number decreases, chromatic aberration increases.

In reference to FIG. 9, Brain—melatonin, serotonin, dopamine, studies show that dopamine production and release increases with light and decreases with darkness, while melatonin does the opposite. Seasonal Affective Disorder (SAD) is a type of depression that occurs in a seasonal pattern, often during the fall and winter months when there is less sunlight.

In reference to FIG. 10, serotonin and dopamine are neurotransmitters that act as chemical messengers between nerve cells in the brain and other parts of the body. They are often called "happy hormones" because they both play a role in positive mood and emotion. Brain Serotonin (5-HT) is a chemical messenger that the body produces naturally and acts as a neurotransmitter and hormone. It is involved in many physiological functions, including the central nervous system: mood, memory, anger, fear, appetite, stress, addiction, sexual pleasure, sleep, pain perception, and central respiratory drive and pupil dilation. Serotonin is a chemical messenger that affects wellbeing and happiness. Many anti-depressants increase serotonin levels in the brain. Serotonin is found in the eye, where it acts as a neuromodulator in the retina and is present in human tears. Eye serotonin is found in the A17 cell, where it co-exists with GABA. Serotonin receptor signaling pathways are specific to the retina, and activating these receptors can help prevent photoreceptor degeneration. Serotonin is also involved in retinal physiology, physiopathology, and photoreceptor survival. Sunlight entering the eyes can stimulate the retina, which then signals the brain to produce serotonin. Brain dopamine is a chemical messenger in the brain that helps nerve cells communicate with each other. It is produced in the brain and acts on cells in other parts of the brain. Dopamine plays a role in many body functions, including motivation, pleasure, movement, memory, and mood. Dopamine is known as the feel-good hormone. Dopamine levels that are too high or too low can be associated with diseases like Parkinson's disease, restless legs syndrome, and attention deficit hyperactivity disorder (ADHD). Low dopamine levels can also lead to symptoms like anxiety, sadness, difficulty sleeping, and low sex drive. Eye dopamine (DA) is a neurotransmitter in the retina that plays a role in visual signaling, development, and refractive development. It is found in the retinas of all vertebrates, including humans, and is released from dopaminergic amacrine cells in the retina's inner plexiform layer. DA levels are dependent on light and retinal image contrast. Attention-deficit/hyperactivity disorder (ADHD) is one of the most common and most studied neurodevelopmental disorders in children. "Neuro" means nerves in cases. Scientists have discovered there are differences in the brain, nerve networks and neurotransmitters of people with ADHD. ADHD is a long-term (chronic) brain condition that causes executive dysfunction, which means it disrupts a person's ability to manage their own emotions, thoughts and actions. ADHD makes it difficult for people to: manage their behavior, pay attention, control overactivity, regulate their mood, stay organized, concentrate, and/or follow directions and sit still. Kids usually receive a diagnosis during childhood and the condition often lasts into adulthood. However, effective treatment is available. Left untreated, ADHD can cause serious, lifelong complications. According to the Centers for Disease Control and Prevention, almost 11% of U.S. children between the ages of 2 and 17 have received an ADHD diagnosis representing an estimated 6 million children ages 3 to 17 years. Worldwide, 7.2% of children have received an ADHD diagnosis. It is estimated that adult ADHD affects more than 8 million adults (or up to 5% of Americans). Many medical conditions are linked to low levels of dopamine including attention deficit hyperactivity disorder (ADHD), Parkinson's disease, Alzheimer's, restless legs syndrome, depression, schizophrenia, brain fog, mood swings, chronic fatigue and muscle spasms. Low levels of serotonin may be associated with many health conditions including depression and other mood problems such as anxiety, sleep problems, digestive problems, suicidal behavior, obsessive-compulsive disorder, post-traumatic stress disorder and panic disorders.

Exposure to blue light wavelengths stimulates the body's production of serotonin and dopamine, both in the eye and possibly the brain. Also, very bright intense red light has been found to stimulate serotonin and dopamine. Serotonin is an inhibitory neurotransmitter that affects mood, appetite, sleep, temperature regulation, and some social behavior. 95% of the body's serotonin is generated in the intestine. Dopamine is an excitatory neurotransmitter that regulates motivation. A low dopamine level can contribute to ADHD, as well as memory loss, low sex drive, poor digestion, muscle spasms, restless legs syndrome, Parkinson's Disease, poor cognition, as well as an increase in myopia. Dopamine is produced in serval areas of the brain. Some dopamine is generated in the retina of the eye by the rods and/or ganglion cells more so than the cones.

Norepinephrine, also called noradrenaline, is both a neurotransmitter and a hormone. As a neurotransmitter, it's a chemical messenger that helps transmit nerve signals across nerve endings to another nerve cell, muscle cell or gland cell. It regulates arousal and attention. Norepinephrine helps regulate arousal, attention, cognitive function, and stress reaction. Dopamine is converted into norepinephrine in the body.

Research findings suggest that green light wavelengths can alleviate or reduce pain by stimulating cone cells, which then initiate a signaling pathway that results in the activation of opioid receptors in the DRN. It is believed that green lighting can stimulate the release of endogenous endorphins and stimulate the cannabinoid system which results in improved moods and higher pain tolerance. By way of example, it is thought that green light can reduce the pain associated with migraines and other types of pain.

The "ISO sunglass traffic light test" refers to a standardized procedure outlined in the ISO 12312-1, which measures how well a pair of sunglasses allows a wearer to distinguish between traffic light colors, ensuring they meet safety requirements for driving by not significantly altering the visibility of red, yellow, and green lights: essentially testing the sunglasses' ability to accurately transmit the necessary wavelengths of light for traffic signal perception. Key points about the ISO sunglass traffic light test include: The test is based on the ISO 12312-1 standard, which covers requirements for general use sunglasses, including those worn while driving. The test assesses the "luminous transmittance" of the sunglasses at specific wavelengths corresponding to red, yellow, and green light, ensuring a sufficient level of light passes through the lenses to accurately perceive traffic signals. The ANSI sunglass traffic light test is of a similar type test. It is critical for a sunglass lens/optic/eyewear to pass such testing to show that, when worn by a wearer/user, they are safe to drive when wearing and driving. Thus, the appropriate color balance of light being transmitted to the eye through the sunglass lens is critical for safe driving.

Description of Related Art

While ocular photo-bio-stimulations have been tested before, a need for improvement exists within the art. For example, U.S. Pat. No. 10,444,505 B2 teaches a head mounted display comprising a light emitting source and an optical waveguide adapted to collect light emitting from the light emitting source and to guide the collected light to the eye. U.S. Pat. No. 10,444,505 B2 further teaches the use of blue green wavelengths of light within the range of 460 nm and 520 nm directly targeting intrinsically photosensitive retinal ganglion cells (ipRGC), more specifically the melanopsin-ganglion cells, and indirectly targeting rods. However, U.S. Pat. No. 10,444,505 B2 does not teach a means for maximizing the number or ganglion cells and rods stimulated. The larger number of melanopsin ganglion cells and rods that are stimulated the greater the physiological response. This prior art is silent as to how to stimulate certain areas of the mid peripheral and far peripheral retina that are not normally stimulated when light is shined into an eye. The teachings included herein will show that an estimated 20%-30% of each eye's retina is not normally stimulated when looking straight ahead. U.S. Pat. No. 5,923,398 teaches off axis photon stimulation of a person's eye, provided by a light field which provides biological or psychological benefits. This art teaches embedded or fixed light delivery elements such as fiber optic members that deliver off axis stimulation to peripheral areas of the retina. The cosmetics of the device leave much to be desired. Furthermore, anyone looking at an individual wearing such a device would look bizarre as the wearer's eye lids, and eyes, would appear lighted. Both U.S. Pat. Nos. 10,444,505 B2 and 5,923,398 teach the use of eye tracking for the purpose of identifying the location of the pupil of the eye. Thus, there is a need for a simplified and more cosmetically desirable way to provide photo-bio-stimulation to the eye or eyes of a user. The inventive embodiments taught herein solve that need. The invention disclosed herein teaches various embodiments of electronic displays, optics, lenses, extended reality and modified extended reality that are not taught by any known art.

U.S. Pat. No. 3,826,751 teaches a selective optical filter having a transmittance of wavelengths in the wavelength range between 625 nm and 875 nm, which is manageable from zero up to any desired value, while reducing the near infrared transmittance. Materials are shown that can be used for sunglasses. Subsequent, external dying (with methods known in the art) can be used to lower the transmission of the shorter wavelength portion of the visible spectrum. Various light curves showing different light wavelength spectrums are shown. U.S. Pat. No. 3,826,751 is silent regarding amount of light intensity (lux) (or lumens) being transmitted from the sunglass lens to stimulate dopamine in the eye of the wearer, and silent as to the light intensity (lux) that strikes the retina of the eye of the wearer. The patent is silent as to time of day when worn, silent regarding color balance transmission, and silent regarding the proper color balance of light wavelengths transmitted to the eye needed to pass the ANSI or ISO traffic light/signal test. The current invention is an improvement over that technology.

U.S. Pat. No. 5,083,858 teaches the design of a tinted lens that filters and transmits light that approximates the absorption curve for rhodopsin. However, U.S. Pat. No. 5,083,858 does not teach a tinted lens that transmits filtered light that approximates the absorption curve for melanopsin. Further, U.S. Pat. No. 5,083,858 does not teach a filtered lens capable of reducing the overall visible light transmission below 40% or 30% while approximating the absorption curve of rhodopsin, among other differences. U.S. Pat. No. 5,083,858 is silent regarding amount of light intensity (lux) (or lumens) being transmitted from the sunglass lens to stimulate dopamine in the eye of the wearer, and silent as to the light intensity (lux) that strikes the retina of the eye of the wearer. The patent is silent as to time of day when worn, silent regarding color balance transmission, and silent regarding the proper color balance of light wavelengths transmitted to the eye needed to pass the ANSI or ISO traffic light/signal test. The current invention is an improvement over that technology.

U.S. Pat. No. 11,086,145 B2 teaches additional examples of tinted filtered lenses that have a light transmission peak of 465 nm or 495 nn and also have a light transmission range within the wavelength range of 400 nm-490 nm of 70% and outside of 400 nm-490 nm being less than 70%. Once again, U.S. Pat. No. 11,086,145 B2 does not teach filtered tinted lenses having the overall visible light transmission being less than 40% or 30%, among other differences. The current invention is an improvement over that technology. U.S. Pat. No. 11,086,145 B2 teaches light intensity (lux) leaving the sunglass lens of at least 200 lux (but not the lumens) and limits the light intensity lux to no more than 300 lux. It is also silent as to the light intensity (lux) that strikes the retina of the eye of the wearer. The patent is silent as to time of day when worn, silent regarding color balance transmission, and silent regarding the proper color balance of light wavelengths transmitted to the eye needed to pass the ANSI or ISO traffic light/signal test. The current invention is an improvement over that technology.

EP 3,528,036 A1 teaches tinted filtered lenses that have an absorption spectrum that approximates the absorption curve of melanopsin, while also showing other tinted lenses that predate EP 3,528,036. However, the overall visible light transmission is not less 40% or less, or 30% or less, among other differences with the current invention. EP 3,528,036 is silent regarding amount of light intensity (lux) (or lumens) transmitted from the sunglass lens to stimulate dopamine in the eye of the wearer, and silent as to the light intensity (lux) that strikes the retina of the eye of the wearer. The patent is silent as to time of day when worn, silent regarding color balance transmission, and silent regarding the proper color balance of light wavelengths transmitted to the eye needed to pass the ANSI or ISO traffic light/signal test. The current invention is an improvement over that technology. The current invention is an improvement over that technology.

U.S. Publication No. 2024/0036357 A1 teaches a photochromatic lens that in an activated state is that of a photochromic sunglass having overall visible light transmission between 40% and 55%, with the light transmission within the range of 450 nm and 510 nm being less than 50%. FIG. 3 of U.S. 2024/0036357 lays out the light transmission by nanometer and when calculated teaches an overall visible transmission of 42.13%. FIGS. 3 and 4 show that the overall visible light transmission would be greater and not less than 42.13%. FIGS. 1, 2 and 3 of 2024/0036357 A1 show that the light transmission within the range of 450 nm and 510 nm is always less than 50%. U.S. Publication No. 2024/0036357 is silent regarding amount of light intensity (lux) (or lumens) being transmitted from the sunglass lens so to stimulate dopamine in the eye of the wearer, and silent as to the light intensity (lux) that strikes the retina of the eye of the wearer. The patent application is silent as to time of day when worn, silent regarding color balance transmission, and silent regarding the proper color balance of light wavelengths transmitted to the eye needed to pass the ANSI or ISO traffic light/signal test. The current invention is an improvement over that technology.

U.S. Pat. No. 11,065,468 teaches a wide range of wavelengths falling within the range of 450 nm-530 nm, 460 nm-560 nm, and preferably 480 nm-520 nm. U.S. Pat. No. 11,065,468 teaches a light transmission within the range of 480 nm-510 nm of 50% or more. Further, this art teaches overall visual transmission of 18%-43%, 8%-17%, and 3%-8%. U.S. Pat. No. 11,065,468 is silent regarding amount of light intensity (lux) (or lumens) being transmitted from the sunglass lens, and silent as to the light intensity (lux) that strikes the retina of the eye of the wearer. The patent is silent as to time of day when worn, silent regarding color balance transmission, and silent regarding the proper color balance of light wavelengths transmitted to the eye needed to pass the ANSI or ISO traffic light/signal test. The current invention is an improvement over that technology.

U.S. Publication No. 2022/0397774 A1 teaches a transmitted 30 nanometer, limited, light wavelength range of 465 nm-495 nm, which is less than 50% of the absorption curve of melanopsins or rhodopsin. U.S. Publication No. 2022/0397774 A1 does, within the limited/narrow 30 nanometer light wavelength range, show the ability for the tinted filtered lens to transmit over 32% of light within 465 nm and 495 nm, and also for the tinted filtered lens to have an overall visible transmission of 18% or less. However, the light transmission performance of the tinted lens of U.S. Publication No. 2022/0397774 A1, within the wavelength range of 465 nm and 495 nm and the overall visible transmission percentage of the tinted lens, is due to utilizing such a narrow 30 nanometer wavelength range within 465 nm and 495 nm. The limited 30 nanometer wavelength range, while advantageous for achieving less than an 18% overall visible light transmission of the tinted lens, significantly limits the ability of the tinted lens to transmit sunlight blue light intensity (lux) from sunrise to sunset, as well as the amount of blue light intensity (lux) that is transmitted through the tinted lens. This is due to the fact that as the sun moves in the sky throughout the day, the percentage of blue light wavelengths in sunlight reduces from morning until night. Thus, if the lens only transmits blue light within a limited wavelength range of 465 nm-495 nm, as opposed to a broader wavelength range of 450 nm to 510 nm, the amount of blue light intensity (lux) will be significantly reduced as sunlight moves from sunrise, to morning, to midday, to afternoon, to sunset (see FIGS. 70-73). U.S. Publication No. 2022/0397774 A1 is silent regarding amount of light intensity (lux) (or lumens) being transmitted from the sunglass lens to stimulate dopamine in the eye of the wearer, and silent as to the light intensity (lux) that strikes the retina of the eye of the wearer. The patent application is silent as to time of day when worn, silent regarding color balance transmission, and silent regarding the proper color balance of light wavelengths transmitted to the eye needed to pass the ANSI or ISO traffic light/signal test. The current invention is an improvement over that technology. The current invention is an improvement over that technology

SUMMARY OF THE INVENTION

Embodiments disclosed herein can provide ocular photo-bio-stimulation through light stimulation of specific wavelengths to the eye's retina, and, in some embodiments, to the entire eye's retina, the retina peripheral to the fovea, and/or the retina peripheral to the macula. In certain embodiments, the light stimulation is targeted at or to the rods. In other embodiments, the light stimulation is targeted at or to the ganglion cells. In still other embodiments, it is targeted at or to the rods and the ganglion cells. When ganglion cells are mentioned herein, the ganglion cells targeted or stimulated are the melanopsin containing ganglion cells (ipRGCs) or can also be called mRGCs.

According to embodiments of the current invention described herein, for the purpose of stimulating dopamine production in the eye and/or brain of the user/wearer, and for the amount of dopamine produced and for longevity of dopamine to remain active, the brighter the light intensity (lux) delivered to the eye's retina through a tinted filtered lens throughout the day, the better the dopamine outcome for the user/wearer. Various embodiments of a sunglass lens taught herein take in to account: time of day, the amount of sunlight lux striking the sunglass lens, the amount of light intensity (lux) leaving the sunglass lens transmitted within a specified range of light wavelengths needed to stimulate dopamine in an eye of the user/wearer, the overall visible light transmission of the sunglass lens, the percentage of light transmission within a defined range of light wavelengths that cover the majority of the absorption curves of melanopsin and rhodopsin as well as certain of the cone opsins, the width of a range of wavelengths of light within the range of 450 nm-520 nm, the color balance of light wavelengths needed to be transferred from the sunglass lens to the eye of the wearer, and the ability of the sunglass lens to pass the ISO and/or ANSI traffic light test. As can be understood, embodiments taught herein must balance numerous components that contribute to the ability of the sunglass lens to cause the production of dopamine or increase the production of dopamine in the eye's retina of the wearer of the sunglass lens, while also providing the appropriate level of clear distance and/or (near) vision clarity for the wearer of the sunglass lens, and further provides the appropriate color balance of light wavelengths transmitted from the sunglass lens to the eye of the wearer of the sunglass lens, so that either the wearer of the sunglass lens subjective measurements or the sunglass lens by way of objective measurements can pass the ISO and/or ANSI traffic light test.

Embodiments herein teach the stimulation of the rods and/or ipRGCs with specific light wavelengths. The retina of the human eye contains 100+M rods, 1M ganglion cells but fewer than 7,000 ipRGCs which are the ganglion cells that contain melanopsin. ipRGCs are less sensitive to photic stimulation and their response kinetics are slow compared to that of rods and cones. Response latency is inversely related to stimulus intensity and under dim light conditions ipRGCs can take many seconds to reach a peak response; the response may also persist for minutes after stimulus termination. However, ipRGCs are similar to rods and cones in that they show adaptation by adjusting their sensitivity according to lighting conditions. While slow to respond to dim light conditions, ipRGCs appear capable of responding to the capture of a single photon of light. It has been estimated that the membrane density of melanopsin is about a thousand times lower than that of photopigments in the outer segments of rod and cone photoreceptors; this relatively low density may account for the poor absorption rate of ipRGCs. The capture of a single photon in an ipRGC generates a large and prolonged membrane current, greater than that recorded in rod photoreceptors but also 20-fold slower.

In aspects, embodiments disclosed herein teach stimulating both the rods and ipRGC. Several embodiments teach exciting both rods and ipRGC with ocular photo-bio-stimulation light. The rods become excited first and then the ipRGC, in cases. The rods outnumber the ipRGC and thus provide a significant amount of initial stimulation and response, however the stimulation effect of the ipRGC outlives that of the rods and thus the long term stimulation effect can be due to that of the ipRGC being stimulated.

Melanopsin photopigment expressed in intrinsically photosensitive retinal ganglion cells (ipRGCs) plays a crucial role in the adaptation of mammals to their ambient light environment through non-image-forming (NIF) visual responses. ipRGCs are structurally and functionally distinct from classical rod/cone photoreceptors and have unique properties including single-photon response, long response latency, photon integration over time, and slow deactivation.

The efficiency of melanopsin is comparable to that of rod and cone. ipRGCs, however, lack specialized photopigment-concentrating organelles (such a rod/cone outer segments) to maximize the probability of photon capture. As a result, the probability of absorbing a photo by ipRGCs is greater than 1 million times lower than in rods or cones for a given area of photo stimulation. Consequently, even though the ipRGC phototransduction cascade has high amplification, melanopsin photoreception is much less sensitive than that of rods and cones. Once the threshold for melanopsin activation has been reached, however, the intrinsic light response scales with stimulus intensity over several decimal orders and is remarkably persistent, being sustained over long durations of constant illumination.

Many of the embodiments herein teach a wide wavelength range within that of 450 nm-520 nm for ocular photo-bio-stimulation. The wider range can provide light wavelengths needed to activate different photoreceptors in the retina, e.g., most of the ipRGCs and rods, in addition to partially excite the S- and M-cones, all implicated to have different and important functions due to the visual and non-visual effects of the light striking them.

As the time of the ocular photo-bio-stimulation lasts, the retina becomes less sensitive and the excitation of the retina moves from a first highest sensitivity at 510 nm to a lower sensitivity at 480 nm, in aspects. By way of example only; 1 second of exposure at 510, then 10 seconds of exposure at 500 nm and then 100 seconds of exposure at 460 nm. Thus, the longer the exposure from the ocular photo-bio-stimulation light source, the light wavelengths that provide maximum stimulation of the retina change over time.

The wide range of light wavelengths that overlap melanopsin and rhodopsin absorption curves allow for more light of different spectral quality to the eye and these different (more) wavelengths cause the eye to enable different physiological functions, all contributing towards better eye health, brain/cognitive health, or overall health, by way of example.

Cyan light (blue green) wavelengths (~495 nm-520 nm) have been found to contribute more towards increasing choroidal thickness which is an important parameter in treating/stopping myopia.

Blue light wavelengths (~450 nm-495 nm or ~450 nm-500 nm) are helpful for the eye, by way of reducing the eye's axial length, another important factor when treating myopia and stopping its progression. Also, blue light increases one's alertness, improves cognitive function and other beneficial neurological functions. This occurs due to the stimulation of or one or more of dopamine, serotonin or norepinephrine in the brain.

Blue light (~465 nm-495 nm) has been found to be good for non-visual pupillary reflex, i.e., keeping the pupil constricted or small, thus, to maximize clear vision, while looking through a tinted sunglass lens.

Moreover, more blue light is needed to maintain a healthy circadian rhythm in the lens' wearer.

Embodiments disclosed herein that are directed to increasing dopamine in an individual's eye's retina or one or more of dopamine, serotonin or norepinephrine in the brain of the individual whose eye was stimulated attempt to use wavelength ranges that cover the peak sensitivities for melanopsin (480 nm) and also for rhodopsin (500 nm). Given that rhodopsin of Rods is 20 times faster to react than melanopsin of ipRGCs, but that melanopsin has much longer reactive staying power than the reaction of rhodopsin, combined with the fact that rods are 10+ times the number of ipRGCs, is the reason various embodiments disclosed herein use light wavelengths within the light wavelength ranges of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm. The lower level of 480 nm+/−30 nm is to capture direct stimulation of melanopsin by ipRGCs and indirect stimulation of melanopsin by rods.

In certain embodiments when generating dopamine in the eye (or one or more of dopamine, serotonin or norepinephrine in the brain) via the eye light, the invention utilizes light wavelengths that strike the eye's retina which fall within the wavelength range of the following at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, which would include blue, bluish green and green wavelengths. These light wavelength ranges can be generated by light emitters, filtered optics or filtered lenses.

FIG. 77 presents the light transmission spectrum of the inventive embodiment filtered lens or filtered optic, or sunglass lens or sunglass optic, overlapped with the light absorption spectra of two photoreceptors: ipRGCs (containing melanopsin) and rods (containing rhodopsin) photoreceptors. The light passing through the inventive embodiment lens, in particular, the light between the light wavelength range of 450 nm and 510 nm, transmitted towards the eye of the wearer will stimulate/activate the melanopsin and/or the rhodopsin in the ipRGC and rods photoreceptors, respectively.

The brighter the ocular photo-bio-stimulation light, the higher intensity this light is, and, in aspects, the best case for generating dopamine. It has been found that a minimum light intensity of 400 lux striking eye's retina, within the wavelength range of 450 nm-520 nm, is required to effectively generate dopamine in the eye's retina and/or one or more of dopamine, serotonin or norepinephrine in the brain. When taking into consideration that the eye's tissues (depending upon age) absorb or attenuate up to 60% of blue light (e.g., 25% for a 9 year old, 50% for a 25 year old, 60% for a 60 year old), and further that eyewear and sunglasses sit approximately 13 mm from the cornea of the eye, in many, but not all, embodiments taught herein, it is believed the various inventive embodiments disclosed herein will allow one or more of 400 lux or more, 450 lux or more, or 500 lux or more, light to be transmitted from the lens or eyewear (within the wavelength range of 450 nm to 510 nm) for what is needed to stimulate dopamine production in the eye of the wearer/user of lens/eyewear designed to stimulate dopamine production in the eye and/or the brain. The amount of the ocular photo-bio-stimulation light intensity of lux required at the ocular photo-bio-stimulation light source needed to achieve the desired physiological response of the patient or subject can be one or more of: 250 lux or more, 500 lux or more, 1,000 lux or more, 2,000 lux or more, and so on. The ocular photo-bio-stimulation light intensity can be expressed in lumens given off by the ocular photo-bio-stimulation light source. When considering the light radiating in a cone light manner from the ocular photo-bio-stimulation light source to strike the eye and face of the user or subject, the number of lumens given off from the ocular photo-bio-stimulation light source can be one of 10 lumens or more, 25 lumens or more, 50 lumens or more, 100 lumens or more, 200 lumens or more, and so on. The exact amount of lux or lumens needed to be radiated from the ocular photo-bio-stimulation light source can depend upon various attenuation factors, each causing attenuation of the light intensity as it travels from the ocular photo-bio-stimulation light source to strike the retina of the eye of the patient or subject. In embodiments disclosed herein the desired physiological response of the patient or subject is the increased production or the production of dopamine in the patient or subject's eye's retina. To achieve the production of dopamine in most, but not all, embodiments, the desire is to have enough light intensity given off from the ocular photo-bio-stimulation light source so that when taking all attenuation into account a minimum of 350 lux or more, or 400 lux or more, by way of example, strikes the retina of the patient or subject's eye. In certain other embodiments the desired physiological response of the patient or subject is one or more of, the production of either dopamine, serotonin or another hormone in the brain that acts like dopamine or serotonin. To achieve the production of or one or more of dopamine, serotonin or norepinephrine in the brain that acts in a similar way, in most, but not all, embodiments, the desire is to have enough light intensity given off from the ocular photo-bio-stimulation light source so that when taking all attenuation into account a minimum of one or more of: 350 lux or more, or 400 lux or more, or 500 lux or more, strikes the retina of the patient or subject's eye.

It has been reported that higher intensity of light (brighter light) is needed to affect the generation of retinal dopamine and improve the brain function with regards to cognitive functions, alertness, mood, and reduce sleepiness. It has been reported that under photopic conditions more retinal dopamine is generated. ipRGCs and rods have been implicated as being responsible for the retinal dopamine generation. It is noteworthy that rod photoreceptors have recently been found to be active under sustained bright light conditions, which is contrary to the conventional thinking that rods respond only under scotopic conditions.

Inventive embodiments taught herein teach a filtered lens or filter optic, or sunglass lens or sunglass optic, comprising a light transmission curve that approximates (by way of coverage) most of, or a vast majority of, or all of, the light absorption curve of melanopsin and also, in aspects, approximating over 75% or more of the light absorption curve of rhodopsin. In certain embodiments the light transmission curve of the filtered lens or filtered optic, or the sunglass lens or sunglass optic, can approximate (by way of covering) all of the light absorption curves of melanopsin and rhodopsin. As used herein the word coverage means having one light transmission curve overlayed over a light absorption curve and seeing or measuring the extent of how the light transmission curve covers the light absorption curve, or that of the absorption spectra within the absorption curve spectra. And in certain cases, it can also be the reverse of having the light absorption curve overlayed over that of the light transmission curve.

In embodiments of the filtered lens or filtered optic, or sunglass lens or sunglass optic, they can comprise light transmission within the wavelength range of 450 nm-510 nm of 50% or greater, while maintaining an overall visible light transmission through the filtered lens or filtered optic, or sunglass lens or sunglass optic, of 40% or less or 30% or less. This balance of having a high transmission within the wide wavelength range of 450 nm-510 nm or even 450 nm-520 nm, while providing overall visible light transmission so to qualify as a class 2 or class 3 sunglass lens or sunglass optic, and at the same time providing UV and HEV protection, is one of the strong inventive attributes of the embodiments described herein. This is needed in order to provide light intensity of 400 lux or greater of the blue light wavelengths to stimulate the production of dopamine in the eye and/or brain of the wearer while wearing category 2 and category 3 sunglasses throughout most, if not all, daylight hours in the sun.

The narrow wavelength range of only 30 nanometers, as seen in some existing sunglass eyewear, significantly reduces the amount of blue light that is transmitted to the eye of the wearer for producing dopamine, as the sunlight color changes from majority blue in the morning to majority red in the late afternoon. The inventive embodiments described herein can have greater than 30 nanometers of wavelength range within the wavelength range of 450 nm-510 nm or 450 nm-520 nm (thus up to 60 nanometers to 70 nanometers), which can provide far more blue light lux throughout the day in sunlight for the production of dopamine while at the same time allowing for a darkened sunglass having an overall visible light transmission of 30% or less. Thus, in embodiments, the current invention can qualify as either a category 2, or category 3, sunglass lens.

As the day proceeds from dawn to noon to dusk, the predominant sunlight colors move from the majority of blue in the morning to the majority of red in the afternoon. (See, FIGS. 70-73.) In the morning, blue light represents approximately 30% or more of the visible spectrum. In midday, blue light represents approximately 20% of the visible spectrum. In the afternoon, blue light represents approximately 10% of the visible spectrum, and at sunset blue light represents approximately 5% or less. Thus, as the day proceeds from morning to noon to afternoon to sunset, it becomes more difficult for a filtered lens or filtered optic or a sunglass lens or sunglass optic to transmit blue light within the wavelength range of 450 nm-510 nm to stimulate dopamine in the eye and/or one or more of dopamine, serotonin or norepinephrine in the brain (see FIG. 74). This occurs because as the day progresses the blue component of sunlight decreases. The narrower the wavelength range of the tinted lens or optic that transmits the blue light, such as that of 30 nanometers within 465 nm-495 nm (see, e.g., U.S. US2022/0397774 A1), the less light intensity (lux) of the required blue light wavelengths is transmitted and available to stimulate dopamine throughout the day, compared to anything greater than 30 nm, such as 60 or 70 nanometers taught with the inventive embodiments described herein. As discussed, this is due to the level of blue light in sunlight that changes from a high in the morning to a low at sunset.

Conventional sunglasses transmit low amounts of blue light and thus as the day progresses most conventional sunglasses actually in the afternoon inhibit the production of dopamine in the eye and/or one or more of dopamine, serotonin or norepinephrine in the brain, while in all cases all known conventional sunglasses dramatically reduce the light intensity lux needed for the production of dopamine in the eye and/or one or more of dopamine, serotonin or norepinephrine in the brain of the user/wearer as the day proceeds from morning to sunset, with afternoon and sunset being the worst. Certain conventional sunglasses actually inhibit the production of dopamine in the eye and/or one or more of dopamine, serotonin or norepinephrine in the brain from the time they are worn by a wearer. In most cases, the vast majority of the time conventional sunglasses are worn, they reduce the amount or production of dopamine in the eye and/or the brain.

The most popular sunglass categories are those of class 2 and class 3. Certain of the embodiments disclosed herein qualify as being class 2 or class 3 sunglasses (see, FIG. 76). However, unlike conventional sunglasses (which cannot perform in the manner according to the current invention), certain of the inventive filtered lens or filtered optic embodiments, or sunglass lens or sunglass optic embodiments, taught herein can transmit 400 lux or more within the wavelength range of 450 nm-510 nm from morning until midafternoon, or even in certain embodiments taught herein, from sunrise to sunset (see, e.g., FIG. 74).

Thus, there is a pressing need for a filtered lens or filtered optic or sunglass lens or sunglass optic that transmits a meaningful/safe/effective amount of blue light within a range that stimulates and/or excites melanopsin and/or rhodopsin, while at the same time protecting the eye from sunlight. This will allow the eye to produce dopamine and possibly cause the production of dopamine and serotonin in the brain throughout the day, while at the same time protecting the eye from the sun.

A filtered lens or filtered optic, or sunglass lens or sunglass embodiment, taught herein, can transmit light within the wavelength range of 450 nm to 510 nm, thus stimulating melanopsin and/or rhodopsin the eye's retina. In embodiments, the lens or optic transmits blue light such that it covers the full light absorption curve of melanopsin, or the vast majority of the light absorption curve of melanopsins, and 75% or more of the light absorption curve for rhodopsin. These embodiments have benefits in stimulating the production of dopamine in the eye and/or the brain of the user/wearer over conventional sunglasses.

By way of example only, if the sunlight intensity is, by way of example only, 20,000 lux during midday, the embodiment of a filtered lens or filtered optic, or sunglass lens or sunglass optic, taught herein can, by way of example only, have a light transmission of 50.5% within the range of 450 nm-510 nm and would transmit 20% of the visible spectrum due to midday sunlight. Therefore, if the filtered lens or filtered optic embodiment has an overall visible transmission of 50.5% and transmits 20% of the light intensity from the sun due to it being midday, the transmitted light intensity would be 20,000 lux×50.5%×20% for a total of 2,020 Lux. In certain other embodiments of the invention, a light transmission range can be within 450 nm-520 nm, and in still other embodiments of the invention the light transmission range can be within 440 nm-510 nm, or 440 nm-520 nm. By increasing the wavelength range it is possible to cover the changing color of sunlight as the day progresses from sunrise to sunset, thus optimizing the transmission of blue wavelengths of light that can stimulate/excite melanopsin and rhodopsin.

Embodiments allowing filtered transmitted blue light wavelength ranges being either between 450 nm-510 nm or 440 nm-510 nm or 440 nm-520 nm, have to do with limiting the amount of HEV (High Energy Violet) light on one end of the range and the level of green light wavelengths on the other end of the wavelength range. In still another embodiment, the filtered lens or filtered optic, or sunglass lens or sunglass optic, comprises a transmission curve or spectra that includes the absorption peaks of melanopsin of approximately at around 480 nm and rhodopsin at approximately around 500 nm, while also protecting the eye of the wearer from UV wavelengths at 400 nm or below and reducing HEV light wavelengths from 400 nm to 440 nm to being at a transmission peak height of 40% or less or 30% or less.

In another embodiment, the sun light intensity, by way of example only, is 20,000 lux during midday (blue light being 20% of sunlight during midday) and the filtered lens or filtered optic or sunglass lens or sunglass embodiment, by way of example only, has a light transmission of 50.5% but within a much more limited wavelength range of 465 nm to 495 nm (which does not cover the full absorption spectrum of melanopsin and rhodopsin), but rather half (or less than half) of the absorption spectrum, wherein the transmitted light intensity would be 20,000 lux×50.5%×20% still obtaining a total of 2,020 lux "midday." However, as the day proceeds to "midafternoon," and the blue color of the sunlight reduces and becomes more red, embodiments having the limited light transmission spectrum from 465 nm to 495 nm will provide less blue light intensity needed to produce or stimulate dopamine in the eye and/or the brain of the user/wearer when compared to embodiments having a light transmission wavelength range from 450 nm-510 nm, that cover the vast majority of the absorption spectrum of melanopsin and 75% or more of rhodopsin. To further emphasize this point, later in the "late afternoon" as the blue light of sunlight decreases even further, this difference in the amount of light intensity lux providing dopamine production or stimulation between an embodiment having light transmission within the range of 465 nm to 495 nm compared to an embodiment having light transmission within the rage of 450 nm-510 nm, will become even more pronounced in favor of the embodiment having light transmission within the range of 450 nm-510 nm, in aspects. By way of example, it is estimated that in the morning approximately 30% of blue light from the sun is located within 450 nm-510 nm, by noon approximately 20% of blue light from the sun is within 450 nm-510 nm, by midafternoon approximately 10% is within 450 nm-510 nm, and by sunset less than approximately 5% within 450 nm-510 nm.

As used herein, in embodiments when light wavelengths are generated by way of filtered optics or filtered lenses, the peak spectral curve of the wavelength range that strike the eye's retina fall within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In certain embodiments disclosed herein, when a filtered optic or filtered lens is used, the overall light transmission through the filtered optic or filtered lens can be 50% or less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

In certain embodiments disclosed herein, when a filtered optic or filtered lens is used, the overall light transmission through the filtered optic or filtered lens can be 40% or less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

In certain embodiments disclosed herein, when a filtered optic or filtered lens is used, the overall light transmission through the filtered optic or filtered lens can be 30% or less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens. In other embodiments the pupil of the eye remains constricted due to a higher percentage of blue light wavelengths being transmitted. Still in other embodiments taught herein the pupil is tricked by way of a modulation of the light source thus permitting blue light wavelengths to strike the retina before the pupil constricts. This then can be repeated over and over again.

As used herein, in embodiments when light wavelengths are generated by way of a light emitter(s) if in a dark room with no ambient lighting the wavelength range that strikes the eye's retina fall within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

As used herein, in embodiments when light wavelengths are generated by a light emitter(s) if ambient lighting is present (including that of artificial light or sun light) the blended light wavelengths of the light emitter(s) and also the ambient light comprises wavelengths of light that strike the eye's retina falling within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

It should be understood that when interpreting embodiments utilized herein unless total darkness is specified, it should be assumed that there is ambient light and thus the light wavelengths striking the retina are blended by the light from the light emitter and the ambient light. The same is true with a filtered optic or filtered lens. In most but not all cases the filtered optic or filtered lens is located 12+mm from the eye of the wearer unless the filtered optic or filtered lens is that of a contact lens or intraocular lens. An exception to this interpretation would be that of the use of a virtual reality device or a modified reality device whereby the device is sealed from ambient light.

In still other embodiments, a light wavelength(s) from either a filtered optic, filtered lens, light emitter(s), and/or light emitter(s), combined with ambient light that strikes the retina of the eye, are selected so that the radiation peak of these wavelengths falls between the peak melanopsin sensitivity (480 nm, and rhodopsin sensitivity (500 nm)). Thus, the spectral curve peak of these wavelengths falls within the range of 480 nm and 500 nn. In these embodiments this occurs whether the wavelengths were generated by a filtered optic, filtered lens, light emitter, and/or light emitter, combined with ambient light.

In still other embodiments, the light stimulation is targeted at or to the cones, rods and ganglion cells. In certain embodiments the objective of ocular photo-bio-stimulation is to increase dopamine within the eye. In certain embodiments the objective of ocular photo-bio-stimulation is to increase dopamine within the eye's retina. When increasing dopamine in the eye and/or retina, ocular photo-bio-stimulation blue light or blue green light having wavelengths within the range of 450 nm to 510 nm can be used, or, for increasing dopamine in the eye and/or retina, ocular photo-bio-stimulation red light wavelengths of 650 nm+/−30 nm or 700 nm+/−30 nm can be utilized. In certain embodiments the objective of ocular photo-bio-stimulation is to increase dopamine within the eye's retina and the brain. In still other embodiments the objective of ocular photo-bio-stimulation is to reduce pain. In still other embodiments the objective of ocular photo-bio-stimulation is to reduce the severity of a headache. When reducing pain by ocular photo-bio-stimulation, green light having wavelengths within the range of 530 nm+/−20 nm can be utilized. In still other embodiments the use of light wavelengths in the range of 650 nm+/−30 nm or 700 nm+/−30 nm can improve mitochondria function and/or reduce age related inflammation in the eye of the user. In other embodiments the objective is to improve mitochondria function and/or reduce age related inflammation in the eye's retina of the user.

In still other embodiments, the objective of ocular photo-bio-stimulation is to increase the number or healthy mitochondria present within the ocular photo-bio-stimulation, the area of the retina in which the ocular photo-bio-stimulation has targeted. When increasing healthy mitochondria by way of ocular photo-bio-stimulation, red light having wavelengths within the range of one of 650 m to 700 nm, 650 nm+/−30 nm, 700 nm+/−30 nm, or 830 nm+/−30 nm, can be utilized. Such ocular photo-bio-stimulation, according to the present invention, increases retinal mitochondrial function and attenuates oxidative stress thus increasing the number of healthy mitochondria within the area of the retina being treated. This can be important for treating, by way of example only, diabetic retinopathy, macular degeneration, and/or retinitis pigmentosa.

In still other embodiments, the objective of ocular photo-bio-stimulation is to increase the alertness of the individual being treated with ocular photo-bio-stimulation. When increasing alertness by way of ocular photo-bio-stimulation, blue light having wavelengths within the range of 450 nm to 510 nm can be utilized. In still other embodiments the objective of ocular photo-bio-stimulation is to increase the slowing down, to slow the progressing of, or to stop myopia of the individual being treated with ocular photo-bio-stimulation. When slowing down or stopping myopia by way of ocular photo-bio-stimulation, blue light having wavelengths within the range of 450 nm to 510 nm, or red light within the wavelength range of 650 nm+/−30 nm or 700 nm+/−30 nm can be utilized. Such ocular photo-bio-stimulation wavelengths can be applied to a large portion of the eye's retina to stimulate the ipRGC ganglion cells and/or rods, or to the ganglion axons of the optic nerve head for the purposes of generating increased retinal dopamine.

In still other embodiments, the objective of ocular photo-bio-stimulation is to treat or correct a neurological abnormality of the individual being treated with the ocular photo-bio-stimulation. When correcting a neurological abnormality by way of ocular photo-bio-stimulation, blue light having wavelengths within the range of 450 nm to 510 nm can be utilized. Neurological abnormalities that may be treatable by ocular photo-bio-stimulation are by way of example only: Alzheimer's, cognitive disorders, ADD, ADHD, depression, anxiety, and/or Parkinson's disorder.

In still other embodiments the objective of ocular photo-bio-stimulation is to prevent myopia from occurring with the individual being treated with the ocular photo-bio-stimulation. In still other embodiments the objective of ocular photo-bio-stimulation is to treat or correct an ocular abnormality of the individual being treated with ocular photo-bio-stimulation. When correcting an ocular abnormality, the use of the appropriate light wavelengths must be employed when treating with ocular photo-bio-stimulation. Ocular abnormalities that may be treatable by ocular photo-bio-stimulation are by way of example only: myopia, AMD, dry AMD, diabetic retinopathy, retinal degenerative disease, glaucoma, optic neuropathy, cataract, and/or meibomian gland disfunction leading to dry eye.

For all embodiments provided herein for providing ocular photo-bio-stimulation, light wavelengths predominantly fall within the wavelength range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, which can be utilized in addition to what is stated within the embodiment description. The desired wavelength band of the above will depend upon the type of ocular photo-bio-stimulation that is desired to produce the desired physiological response. Thus, for any embodiment disclosed within this invention disclosure, any of the above ranges of wavelengths can be applied over and beyond what may be stated.

In certain other embodiments which reduce any visual unpleasantness from flicker for the driver or user, the ocular photo-bio-modulation light source can be modulated light wavelength ranges between blue (450 nm-495 nm) and bluish green/cyan (495 nm-520 nm).

In still other embodiments which reduce any visual unpleasantness from flicker, the ocular photo-bio-modulation light source can be modulated within light wavelength ranges between blue (450 nm-495 nm) and green (495 nm-570 nm).

In certain embodiments the light can be flickered or modulated when providing ocular photo-bio-stimulation therapy to the eye's retina. In other embodiments the light is devoid of a flicker. For embodiments that stimulate the production of dopamine in the eye's retina or an increase in the production of dopamine, the ocular photo-bio-light source can flicker or be modulated at a rate of 1 Hz-15 Hz. In certain embodiments the range is between 10 Hz to 12 Hz.

In certain embodiments the light can be flickered or modulated when providing ocular photo-bio-stimulation therapy to the brain. In other embodiments the light is devoid of a flicker.

For embodiments that stimulate the production of dopamine in the brain or an increase in the production of dopamine in the brain, the ocular photo-bio-light source can flicker or be modulated at a rate of 40 Hz+/−20 Hz. In certain embodiments the range is between 40 Hz-65 Hz.

In certain embodiments that cause the brain to increase alertness, the ocular photo-bio-light source can be flickered or modulated at a rate of 40 Hz+/−10 Hz.

In certain embodiments that cause the brain to increase cognitive ability, the ocular photo-bio-light source can be flickered or modulated at a rate of 40 Hz+/−10 Hz.

For embodiments that stimulate the production of serotonin in the brain or an increase in the production of serotonin in the brain, the ocular photo-bio-light source can flicker or be modulated at a rate of 3 Hz-20 Hz. In certain embodiments the range is between 5 Hz+/−10 Hz.

For embodiments that stimulate the production of norepinephrine in the brain or an increase in the production of norepinephrine in the brain, the ocular photo-bio-light source can flicker or be modulated at a rate of 3 Hz-10 Hz.

In embodiments, a second eyewear to be worn by a wearer, wherein the second eyewear when worn is in optical communication with a first eyewear worn by a wearer, wherein the second eyewear comprises a filtered lens or filtered optic, wherein the filtered lens or filtered optic of the second eyewear predominantly transmits light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10n, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, to an eye of the wearer, wherein the first eyewear comprises a first eyewear lens for optically correcting the distance vision of the wearer, and wherein the filtered lens or filtered optic of the second eyewear is distinct from first eyewear lens.

Embodiments include the overall transmission of the first and second eyewear filtered lens or filtered optic that cause the pupil of the eye of the wearer to constrict or remain smaller in size compared to when wearing conventional sunglasses where the pupil of the eye will enlarge in size. However, in certain embodiments, it is more important to provide more ocular photo-bio-stimulation as opposed to maximum vision clarity. In these embodiments, it is necessary to trick the wearer's retinal neurological feedback that causes the pupil to constrict while still providing blue light within the range of 450 nm-530 nm, preferably 480 nm+/−20 nm to strike the wearer's/user's retina. This can occur when, for example, utilizing an XR eyewear approach that comprises modulating the image being seen by the wearer of the XR eyewear; the image modulating between, by way of example only, black and blue, thus causing the pupil of the eye to enlarge and then constrict and enlarge and then constrict. By example only, as soon as the pupil enlarges exposing the retina to blue light thus causing the pupil to constrict, then as soon as the pupil constricts exposing the retina to black light (or a black image) causing the pupil to enlarge and so on. The transmission of light wavelengths is within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, providing ocular photo-bio-modulation to the retina of the eye of the wearer.

However, in most cases when the eye's retina is exposed to blue light within the range of 450 nm to 530 nm, preferably 480 nm+/−20 nm, the pupil of the eye constricts or remains constricted. The constriction of the pupil when viewing through a filtered optic or filtered lens allows for the user/wearer of the filtered lens/optic to have improved or maximum vison clarity. However, in certain embodiments it is more important to provide ocular photo-bio-stimulation as opposed to maximum vision clarity. In these embodiments it is necessary to trick the wearer's retinal neurological feedback that causes the pupil to constrict while still providing blue light within the range of 450 nm-530 nm, preferably 480 nm+/−20 nm to strike the wearer's/user's retina.

Various embodiments taught herein take in to account: time of day, the amount of sunlight lux striking the sunglass lens, the amount of light intensity (lux) leaving the sunglass lens transmitted within a specified range of light wavelengths needed to stimulate dopamine in an eye of the user/wearer, the overall visible light transmission of the sunglass lens, the percentage of light transmission within a defined range of light wavelengths that cover the majority of the absorption curves of melanopsin and rhodopsin as well as certain of the cone opsins, the width of a range of wavelengths of light within the range of 450 nm-520 nm, the color balance of light wavelengths needed to be transferred from the sunglass lens to the eye of the wearer, and the ability of the sunglass lens to pass the ISO and/or ANSI traffic light or signal test. Embodiments taught herein must balance numerous components that contribute to the ability of the sunglass lens to cause the production of dopamine or increase the production of dopamine in the eye's retina of the wearer of the sunglass lens, or cause the production or increase the production of one or more of dopamine, serotonin, norepinephrine in the brain, while also providing the appropriate level of clear distance and/or near vision clarity for the wearer of the sunglass lens. And the invention can further provide the appropriate color balance of light wavelengths transmitted from the sunglass lens to the eye of the wearer of the sunglass lens, so that either the wearer of the sunglass lens by way of subjective measurements or the sunglass lens by way of objective measurements can pass the ISO and/or ANSI traffic light test.

An embodiment can be that of a filtered lens or filtered optic or sunglass lens or sunglass optic that transmits a higher percentage of blue light and bluish green light wavelengths within the wavelength range of one or more of 480 nm+/−30 nm or 530 nm+/−20 nm, than a lens or optic comprises an average visible light transmission percentage within the range of 380 nm-780 nm and passes the ISO 12312-1 sunglass traffic light/signal test.

In embodiments, biofeedback can be utilized to confirm that one or more of, increased dopamine, serotonin, or norepinephrine, is being produced within the brain of a patient having ocular photo-bio-stimulation therapy. Such biofeedback can be comparing one or more of: increased blink rate of the eye(s) of the patient being treated, increased diameter of pupil(s) of the patient being treated, and/or increased heart rate of the patient being treated to that of a base line for the same activity prior to the ocular photo-bio-stimulation therapy.

In embodiments, one or more of a timer, geolocation, an alarm (such as by way of example only, sound, vibration, light, or image), and/or wireless or wired communication to notify a remote third party, can be incorporated or associated with eyewear providing ocular photo-bio-stimulation therapy.

BRIEF DESCRIPTION OF THE DRAWINGS

The accompanying drawings illustrate certain aspects of some of the embodiments of the present invention and should not be used to limit or define the invention. Together with the written description the drawings serve to explain certain principles of the invention.

FIG. 10 shows background information for purposes of explaining the invention herein.

FIG. 24 shows an embodiment of the current invention as described herein.

FIG. 29 shows an embodiment of the current invention as described herein.

FIG. 30 shows an embodiment of the current invention as described herein.

FIG. 44 shows categories of sunglasses.

FIG. 68 is a chart showing improvements provided by the current invention over conventional eyewear.

FIG. 69 shows sunlight spectrum at a point of time during the day.

FIG. 74 is a chart showing improvements provided by the current invention over conventional eyewear.

FIG. 75 is a chart showing improvements provided by the current invention over conventional eyewear.

FIG. 76 shows sunglass categories.

FIG. 93 shows that a computer application can be used to manage the device. In aspects, children (or people of any age) in different locations can compete with one another with games while receiving ocular photo-bio-stimulation light therapy. In aspects, as the eye follows the animated image around the display, blue light within the range of 450 nm to 520 nm strike different regions of the eye's retina. This photo-therapy can be performed monocularly or binocularly. The affect can be seen, by way of example, in the inset graph.

DETAILED DESCRIPTION OF THE INVENTION

Figure 1:
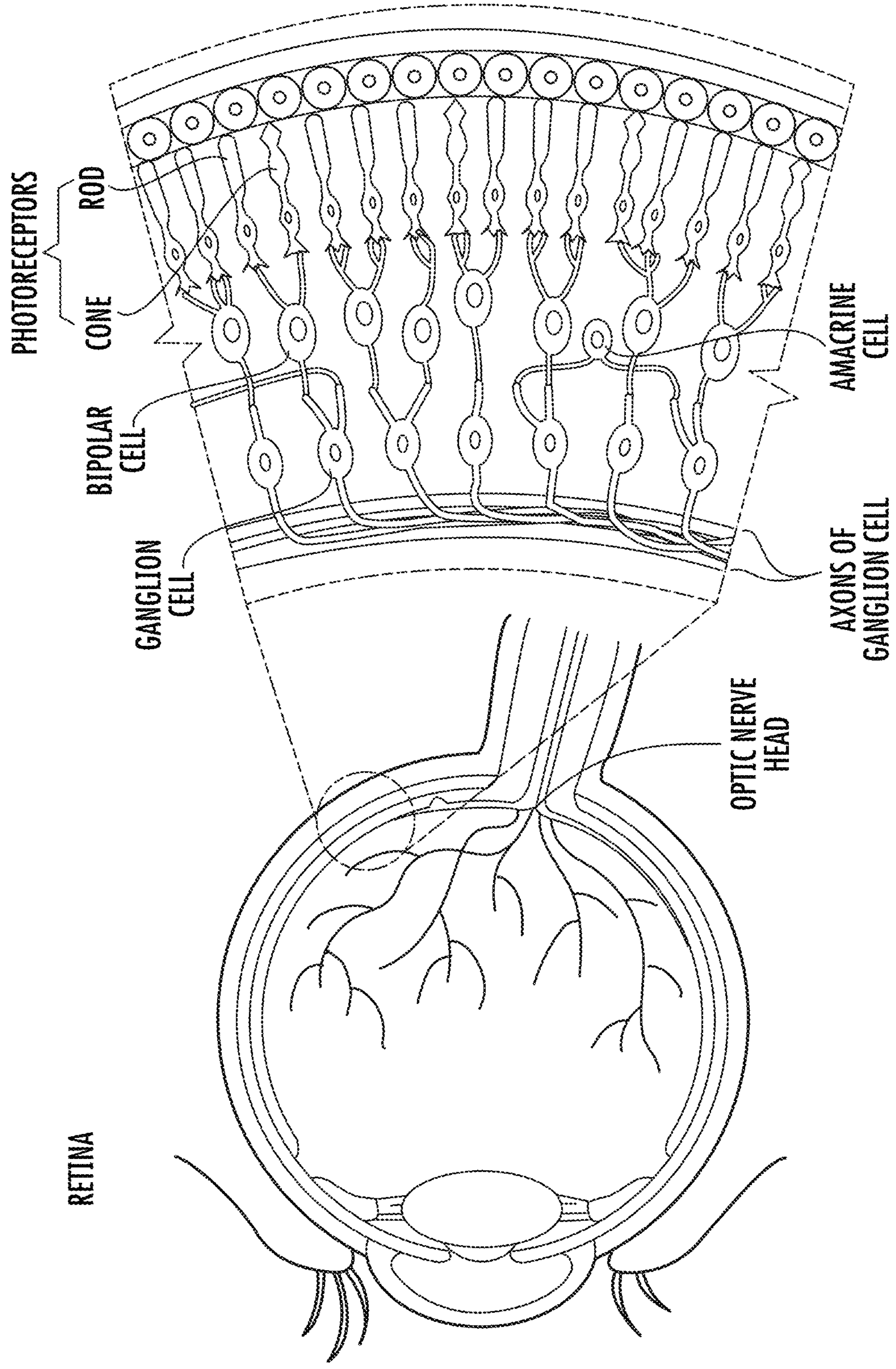
FIG. 1 shows background information for purposes of explaining the invention herein.
Figure 2:
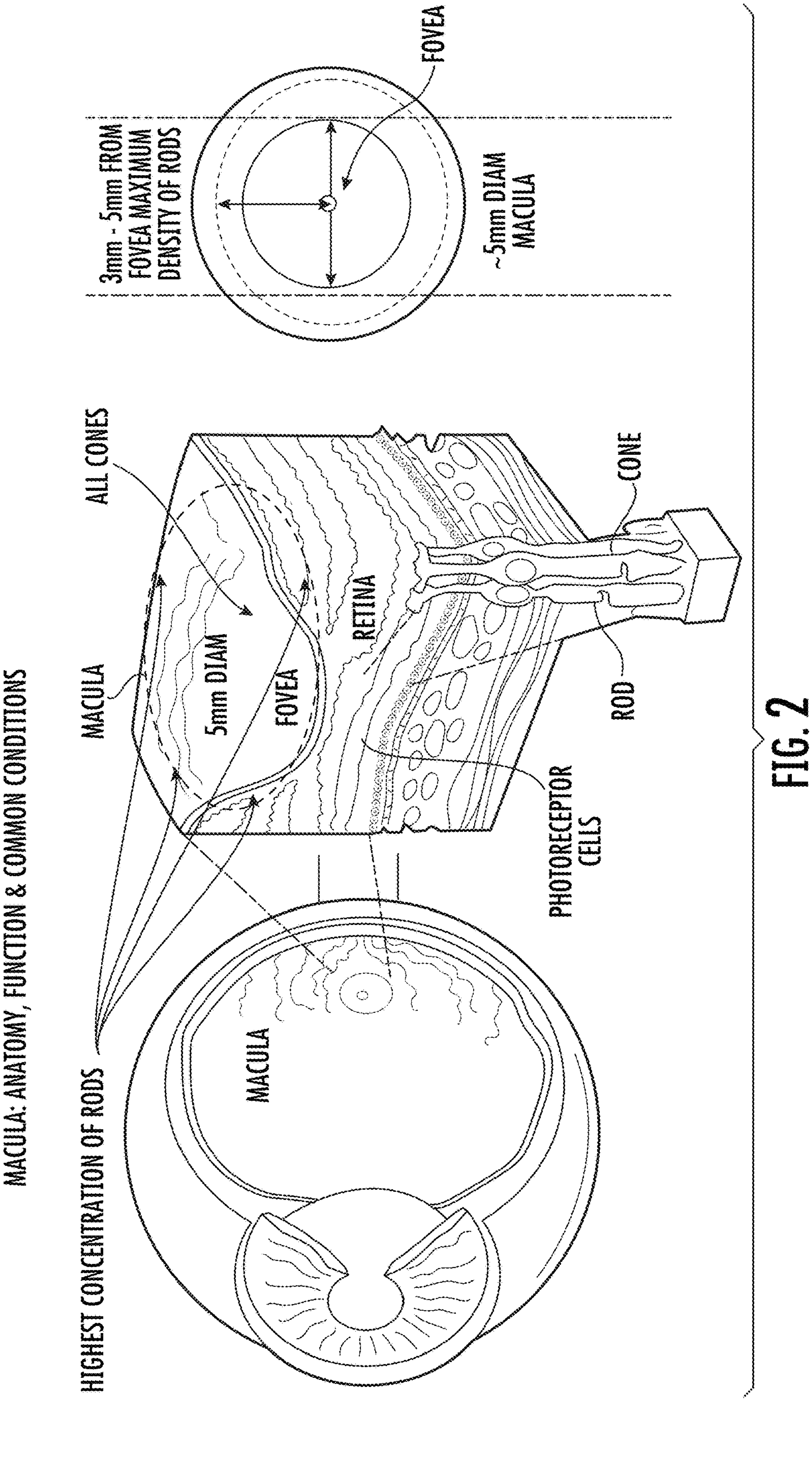
FIG. 2 shows background information for purposes of explaining the invention herein.
Figure 3:
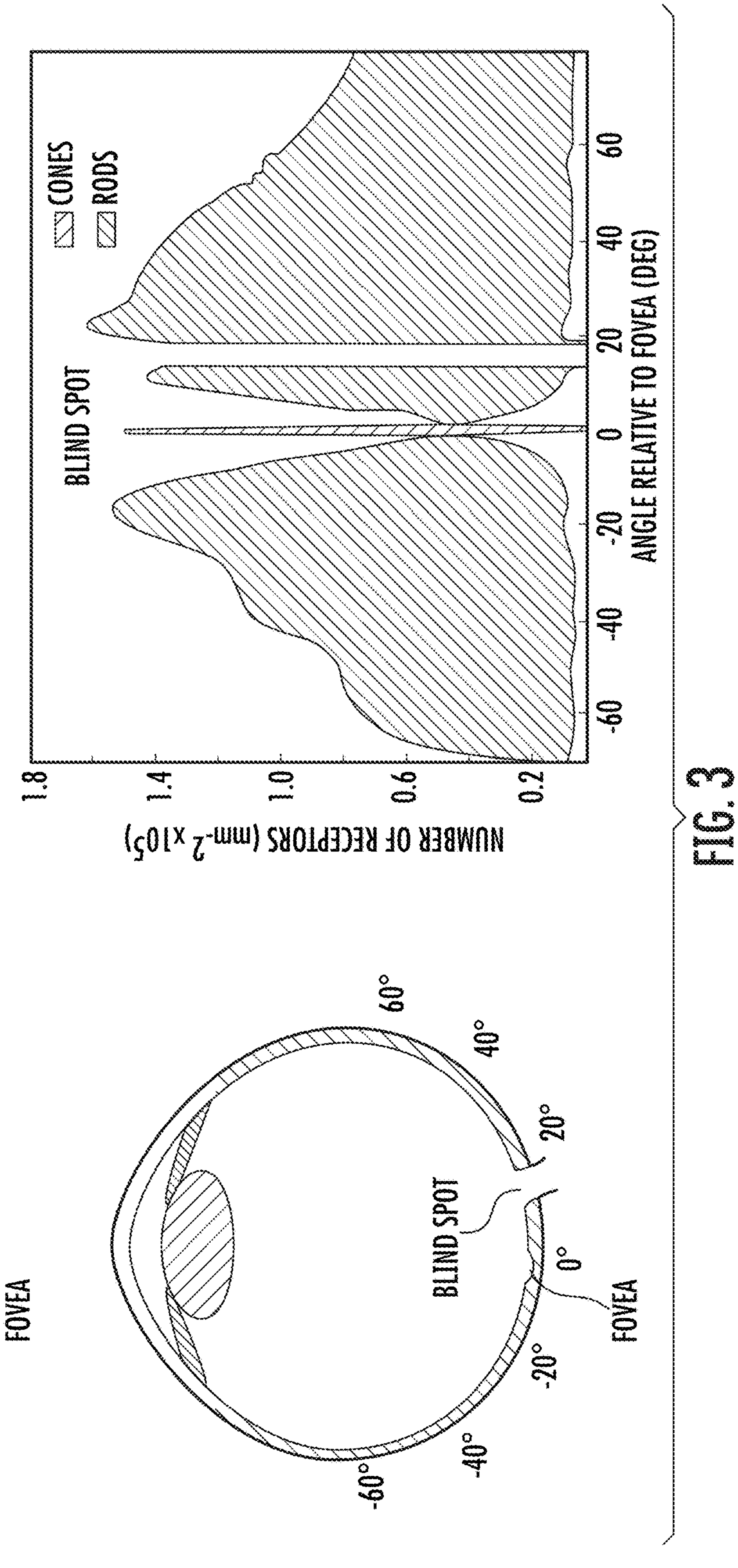
FIG. 3 shows background information for purposes of explaining the invention herein.
Figure 4:
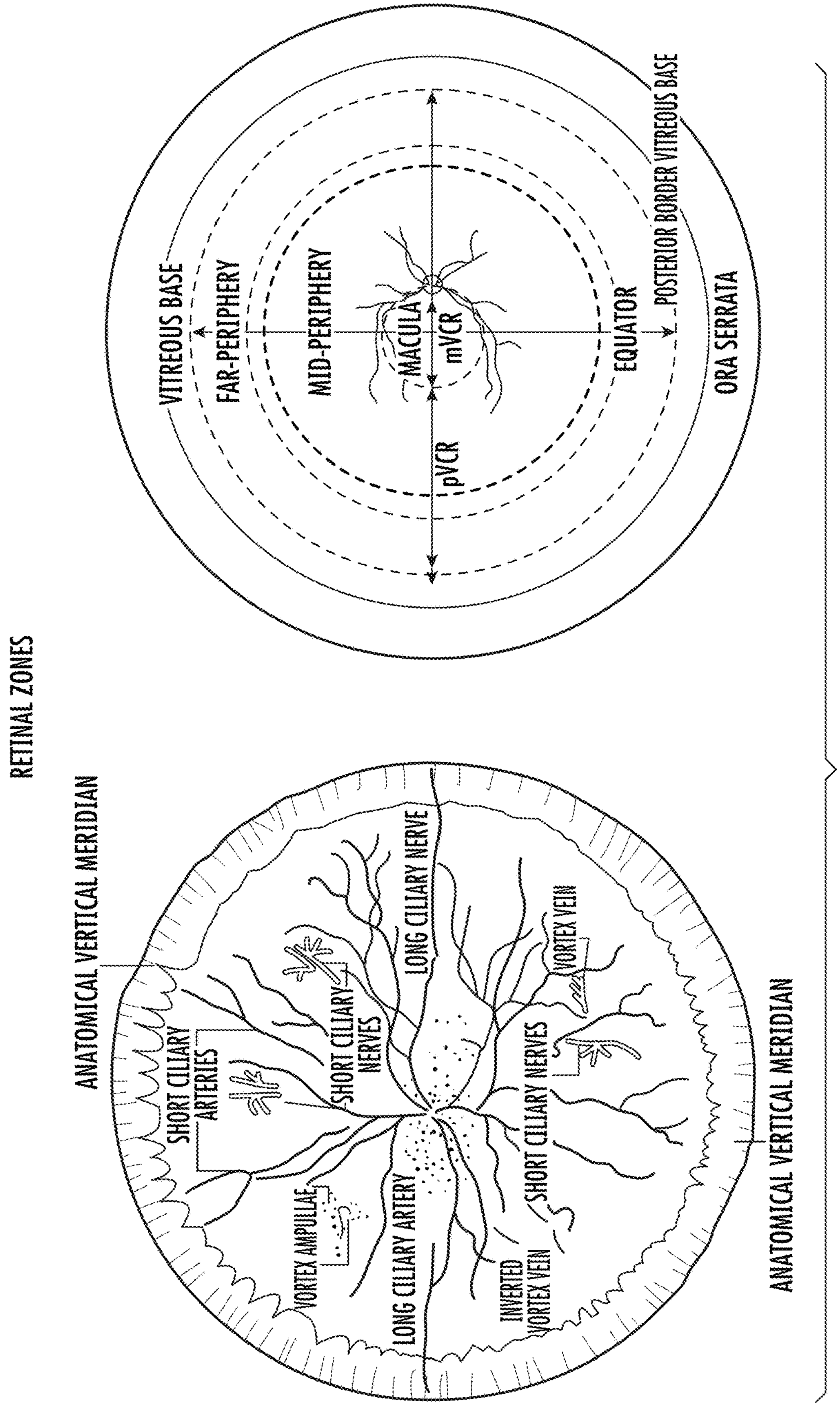
FIG. 4 shows background information for purposes of explaining the invention herein.
Figure 5:
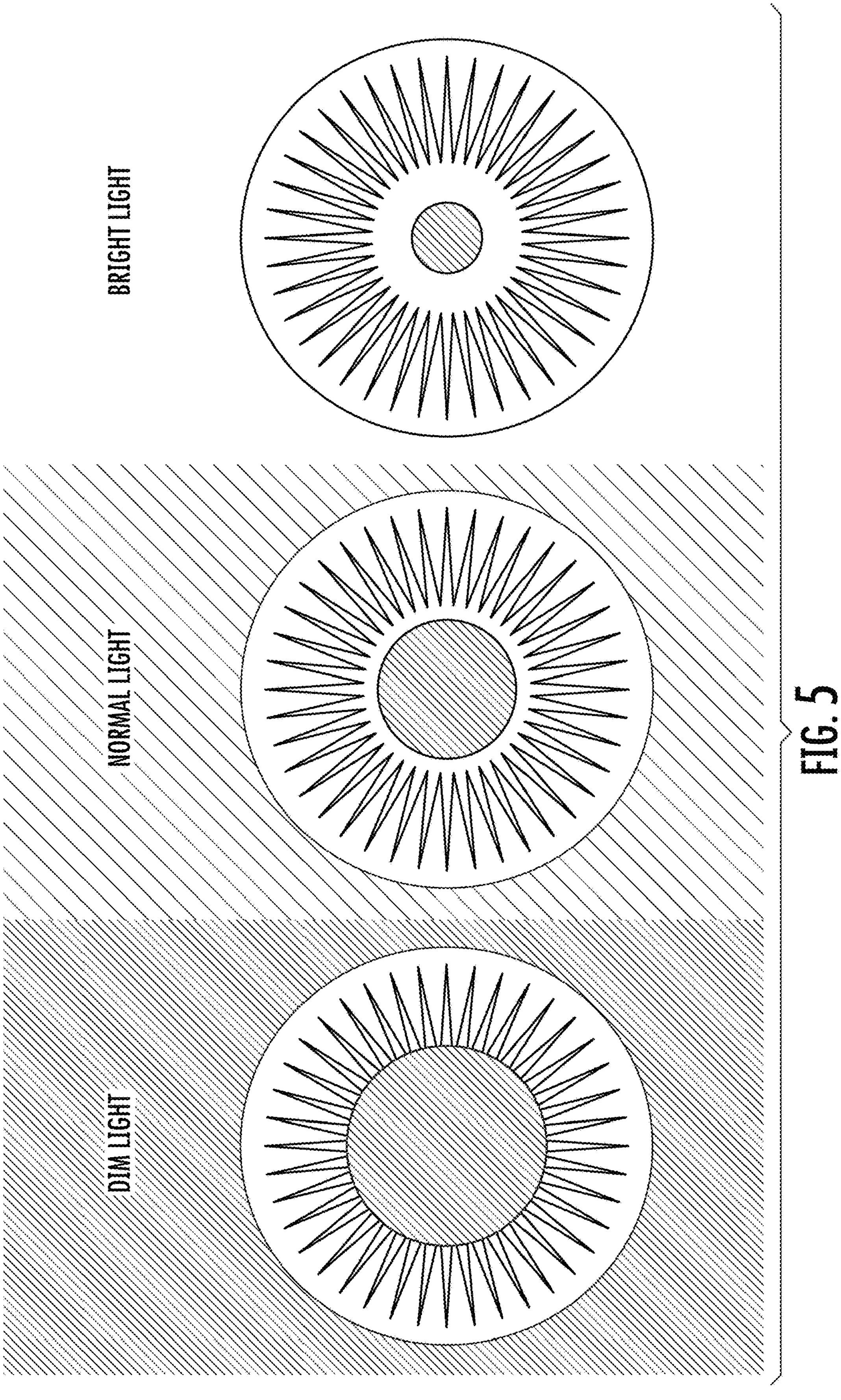
FIG. 5 shows background information for purposes of explaining the invention herein.
Figure 6:
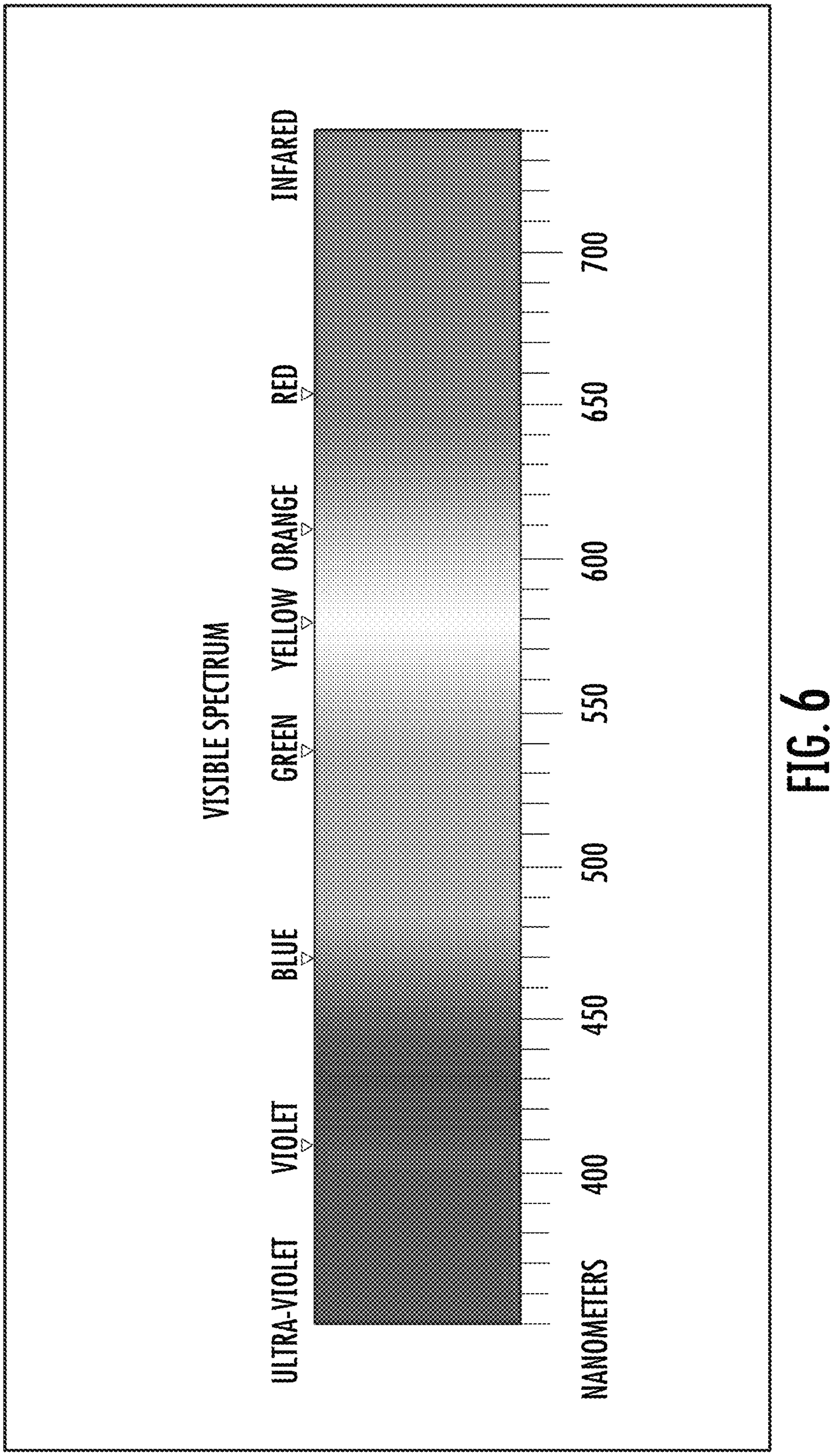
FIG. 6 shows background information for purposes of explaining the invention herein.
Figure 7:
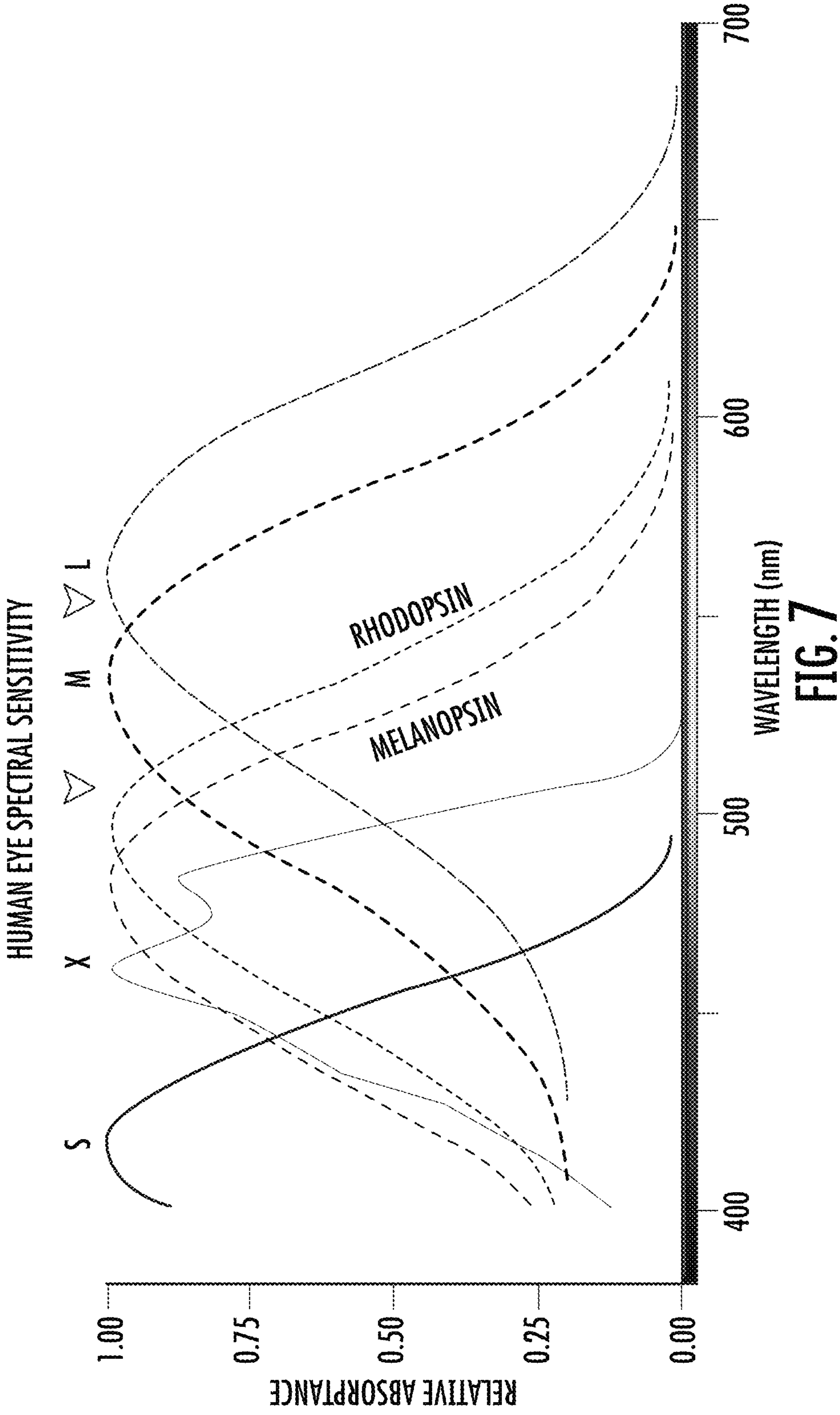
FIG. 7 shows background information for purposes of explaining the invention herein.
Figure 8:
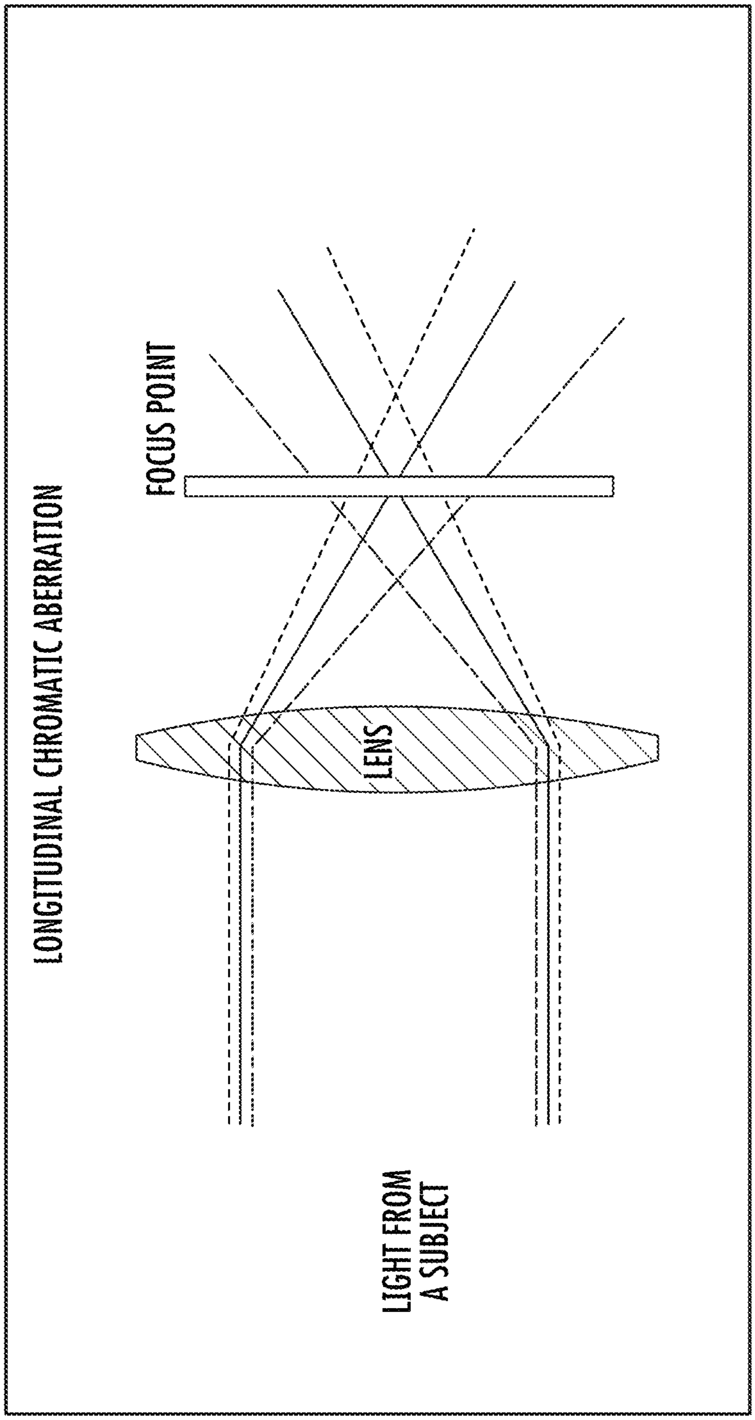
FIG. 8 shows background information for purposes of explaining the invention herein.
Figure 9:
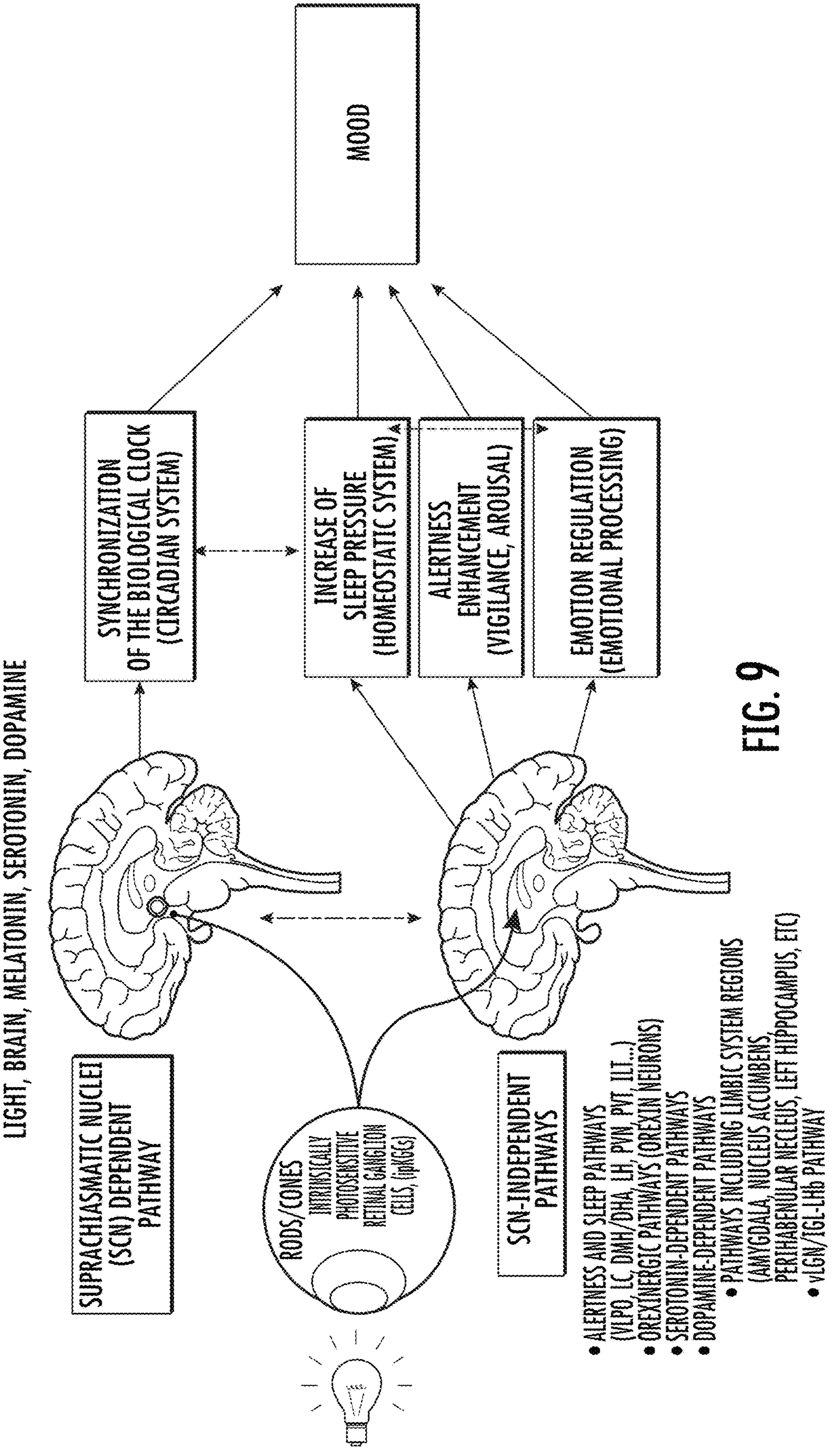
FIG. 9 shows background information for purposes of explaining the invention herein.
Figure 11:
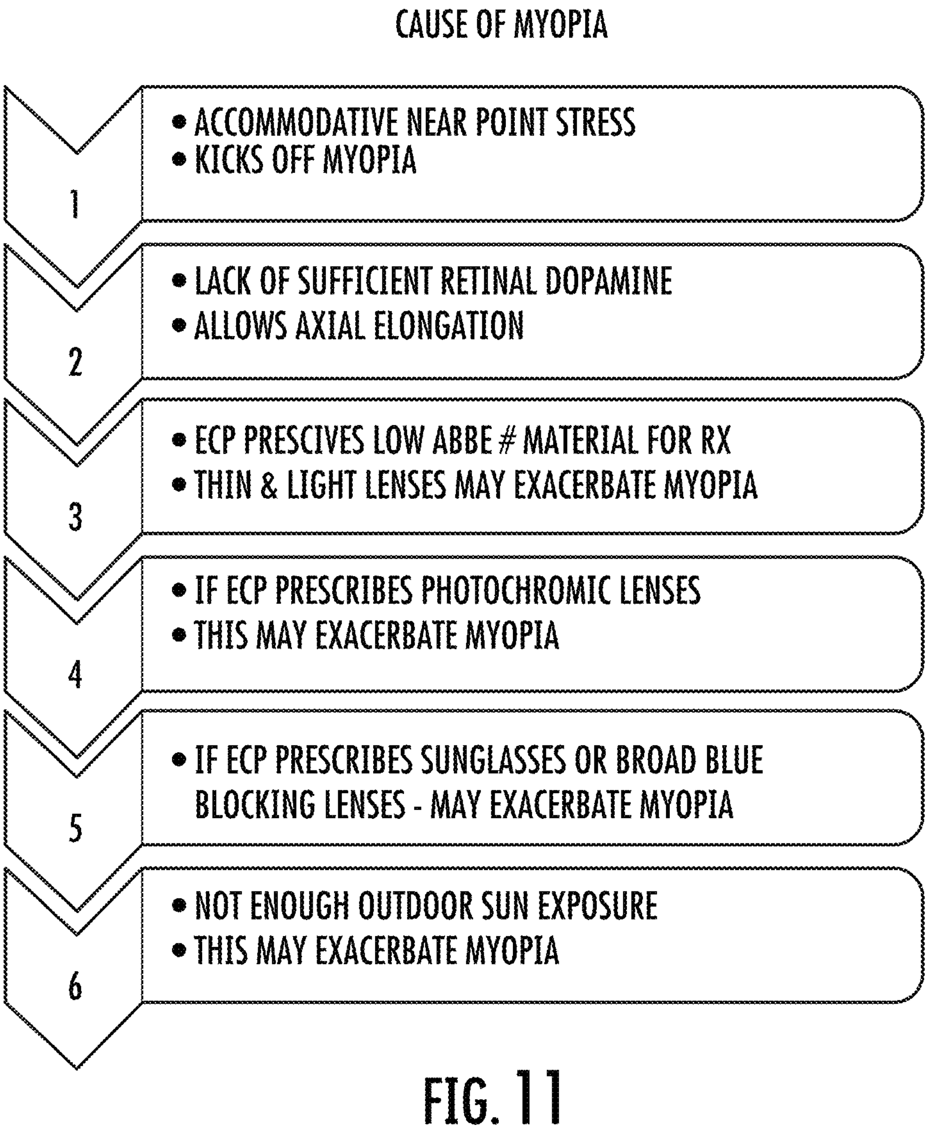
FIG. 11 shows background information for purposes of explaining the invention herein.

Definitions:

As used herein, ambient light can be that of indoor artificial light or sunlight. Ambient light as used herein can be that which would be in addition to that of a light emitter.

As used herein, ECP stands for Eye Care Professional.

As used herein, ocular photo-bio-stimulation is an umbrella term. Ocular photo-bio-stimulation is a biological non-invasive technique of using light to stimulate a neuron(s) or other cells within, on, or about the eye for the purpose of generating a physiological response within the human body. Such stimulation can directly or indirectly amount to stimulation or inhibition of a biological, neurological or chemical process within the human body.

As used herein optogenetic therapy is broadly defined as a form of photo-bio-stimulation.

As used herein, photo-bio-modulation is broadly defined as a form of photo-bio-stimulation.

As used herein, painting the retina, is defined as causing a light that is providing ocular photo-bio-stimulation of the retina to project its wavelengths of light onto the retina of an eye in such a manner that the light paints, covers, or affects, different portions or different neurons of the retina with light wavelengths as the light moves relative to the retina or the retina moves relative to the light.

As used herein, the visible light spectrum is as follows: Visible Light Spectrum (electromagnetic radiation spectrum) can be divided by color: blue/violet (400 nm-450 nm), blue (450 nm-495), bluish green (495-520 nm), green (521 nm-556 nm), yellow (556 nm-590 nm), orange (590 nm-625 nm), and/or red (625 nm-700 nm). However, in a general sense as used herein blue can be from 400 nm-520 nm.

As used herein, Blue light wavelengths are considered from 400 nm-500 nm, with bluish green being between, 490 nm and 520 nm, with 450 nm to 495 nm being bright blue.

As used herein, Cyan light wavelengths are considered to be bluish green and between 495 nm and 520 nm.

As used herein HEV stands for high energy violet light. The HEV light within the range of 400 nm-440 nm can be harmful to the retina of the eye, and more specifically 410 nm-430 nm appears to be the most harmful.

As used herein, UV light, which stands for ultraviolet light has wavelengths which are less than 400 nm in wavelength or said another way 399 nm or less.

As used herein, BVA stands for the level of vision when considering the best visual correction of a patient's distance vision needs. For example, that of 20/25, 20/20, or 20/15.

As used herein, a wavelength within the range of, by way of example only, 480 nm+/−30 nm means any single wavelength or wavelengths found within the range of 480 nm+/−30 nm.

As used herein, a wavelength within the range of by way of example only, 530 nm+/−20 nm means any single wavelength or wavelengths found within the range of 530 nm+/−30 nm.

As used herein, a wavelength within the range of by way of example only, 650 nm+/−30 nm means any single wavelength or wavelengths found within the range of 650 nm+/−30 nm.

As used herein, a wavelength band or wavelengths band, means one or more wavelengths of light within a certain range.

As used herein, predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, to the eye(s) of the wearer, means at least one of the preceding ranges of wavelengths includes the predominant (or most) light wavelengths within that wavelength range transmitted to the eye(s) of the wearer.

As used herein, when referring to wavelengths within the range of X, this is meant to convey that any two or more wavelengths that are within the given range of wavelengths are predominantly or solely emitted or transmitted wavelengths (within the light wavelength range given) for the optic, filter, lens, and/or system, when discussing lighting or transmission. In certain cases, the word predominantly may be omitted, however in all cases the word predominantly should be read in to express the meaning.

As used herein a wavelength band is a band of light wavelengths that run concurrent with a beginning wavelength and ending wavelength.

As used herein, a transmission peak is the peak light wavelength or wavelengths having the highest light transmission that fall within a band of light wavelengths. A transmission peak can be that of a curve or a plateau.

As used herein an image can be generated by light or by the absence of light when surrounded by a lighted image (in the case of a black image). A black image can also be generated by the colors of: blue, magenta, and yellow.

As used herein, a light emitter can be any a component that converts an electrical signal into a light signal. Light emitters can be, for example only, LEDs, OLEDs, TOLEDs. micro-OLEDs, micro-LEDs, micro-ileds, iLEDs, quantum dots, florescent lights, incandescent lights, and/or the sun.

As used herein, a light source can be any artificial light source that comprises a light emitter or light emitters or a light source can be that of the sun.

As used herein, an electronic display screen can be that of any electronic display screen. By way of example only, cell phone display screen, tablet display screen, laptop computer display screen, desktop computer display screen, or television display screen.

As used herein, an optical filter is any device or material that changes the spectral distribution of a light beam spectrally selectively or non-selectively.

As used herein, an optic is a material that transmits light. An optic can be part of an optical system. However, a lens can also be an optic. As used herein, an optic can be any kind of optic. Furthermore, a lens can be an optic, or an optic can be a lens.

As used herein, a lens is an optic that focuses or defocuses light. A lens is a transmissive optical device that focuses or disperses a light beam by means of refraction. As used herein, a lens can be any kind of lens. Furthermore, a lens can be of any optical power including plano, unless that an optical power is specified in the disclosure.

As used herein, optical power can be any optical power of a lens or optic including plano optical power. It is common in the optical industry to refer to lens having no optical power as plano optical power. A lens with optical power (other than that of plano optical power) can refract and focus light to that of a focal point.

As used herein, plano optical power means the lens or optic comprises no optical power. When an eye doctor prescribes for a patient a lens comprising no optical power the eye doctor prescribes plano. While the lens may be of a plano optical power (meaning no optical power) the lens in most cases (by way of example only) can comprise a lens structure, diameter, curvature, thickness and ultraviolet protection for the wearer eyes.

As used herein, more minus or less plus optical power can be expressed when comparing the sphere and cylinder optical power of two different lens zones' optical powers, or by way of comparing the spherical equivalent of the two different lens zones' optical powers. The same can be true when comparing two different lenses' or optics' optical powers.

As used herein, an eyeglass lens can include or be a transparent optical component designed to enhance visual clarity and provide corrective vision for individuals with refractive errors, such as myopia, hyperopia, astigmatism, or presbyopia. It can be made from various materials, including glass and plastic, and may incorporate special features such as coatings for anti-reflective properties, ultraviolet ("UV") protection, or light filtration. Eyeglass lenses can be customized to fit a wide range of frame styles and can also include specialized lenses for conditions like photophobia or low vision, catering to diverse visual needs and preferences.

As used herein, the Abbe value, also known as the V-number or constringence, is a numerical value that measures how much light disperses into individual wavelengths as it passes through a transparent material.

As used herein, eyewear means any device used on, in, or about the eye that transmits or directs light into the eye of the wearer of such eyewear. By way of example only, one of: spectacles, sunglasses, disposable eyewear, goggles, dress eyewear, safety eyewear, sports eyewear, clip on eyewear, fit over eyewear, magnetic attachable eyewear, military eyewear, smart eyewear, XR eyewear, AR eyewear, VR eyewear, MR eyewear, modified reality eyewear, contact lens, intra-ocular lenses, corneal implant, lens or lenses that are housed, supported, attached to eyewear or a frame worn around the eye or eyes of the wearer.

As used herein, optical finishing can be the application of any finish, coating, tinting, to a lens. Such a coating can be by way of example only, hard scratch resistant coat, antireflection coat, spin coat, dip coat, vacuum deposition coat, surface cast.

As used herein a semi-finished lens blank is a lens blank that has one of its surfaces polished.

As used herein a finished lens blank is a lens blank that has both of its surfaces polished and further that optical power can be measured.

As used herein, a filtered optic, is an optic or lens that comprises one or more filters or is in optical alignment with one or more filters. Such filters can be by way of example only one or more of, interference filter, bandpass filter, absorption filter, notch filter, selective wavelength(s) filter, and/or neutral density filter.

As used herein, a filtered lens is a lens or optic that comprises one or more filters or is in optical alignment with one or more filters. Such filters can be by way of example only one or more of, interference filter, bandpass filter, absorption filter, notch filter, selective wavelength(s) filter, and/or neutral density filter.

As used herein, optical alignment means that two optics (such as, two optics, two lenses, and/or one optic and one lens) are aligned so that a light ray can pass through each of the two optics.

As used herein, chromatic aberration is aberration caused by the differences in refraction of the colored rays of the spectrum.

As used herein, longitudinal chromatic aberration (LCA) is a lens's inability to properly focus different color wavelengths in the same focal plane.

As used herein, the central retina (macula) is a circular area of the retina that is about 5 mm-6 millimeters in diameter with the fovea in the center, which is a small area in the center of the retina. The retina is between 30 mm to 40 mm in diameter.

As used herein, the peripheral retina is any area of the retina that is outside of the central retina.

As used herein, the midperipheral retina is located between the far peripheral retina and the central retina.

As used herein the far peripheral retina is located between the ora serrata and the mid periphery of the retina.

As used herein, a biomarker (short for biological marker) is an objective measure that captures what is happening in a cell or an organism at a given moment As used herein, a physiological response is a bodily response that can be the result of direct or indirect neural simulation. The physiological response can be immediate or delayed. By way of example only, slowing myopia may result from stimulating retinal rods and/or ganglion cells with an ocular photo-bio-stimulation light comprising blue light wavelengths within the range of 480 nm+/−30 nm. The immediate response, in aspects, can be the increase of dopamine in the eye produced by the amacrine cells, while the delayed response could, for example, be that of slowing myopia. For the purposes of this invention disclosure, both the increasing dopamine and slowing of myopia would be considered physiological responses. Another example would be stimulating dopamine and/or serotonin in the brain.

As used herein, intrinsically photosensitive retinal ganglion cells (ipRGCs), also called photosensitive retinal ganglion cells (pRGC) are ganglion cells containing melanopsin and are a type of neuron in the retina of the human eye.

As used herein, melanopsin-containing retinal ganglion cells (mRGCs) are specialized ganglion cells that contain melanopsin and are a type of neuron in the retina of the human eye.

As used herein, scotopic light is a type of light that is used to describe vision in dim or dark conditions, also known as scotopic vision or night vision. Scotopic light can be below 0.4 lux.

As used herein, mesopic light or mesopic vision, sometimes also called twilight vision, is a combination of photopic and scotopic vision under low-light (but not necessarily dark) conditions. An example of mesopic light is low light level light provided by public lighting of 0.4 lux up to 10 lux (about 0.6 cd/m2).

As used herein, photopic light, also known as daytime vision, is the visual perception that occurs when the eyes are light-adapted and there is enough brightness. A candle at 1 meter distance gives 1 photopic lux of light. Typical room illumination is in the order of 300-500 lux, whereas outdoor light varies from 1,500 lux on a cloudy day to 100,000 lux on a sunny day.

As used herein, light intensity or luminous intensity is measured in lumens per square foot (footcandles) or lumens per square meter (lux). Lumens measure the intensity of light emitted by a luminaire, while lux is a measurement of the light that is achieved and perceived. Lux, in some cases, is a more important measurement because it relates brightness to distance from the light source.

As used herein, light transmission is the percentage of all visible light transmission through a lens or optic within a range of wavelengths less than that of the visible spectrum.

As used herein, overall visible light transmission means the same visible light transmission or VLT and is expressed as a percentage. Further, it includes all visible light wavelengths transmitted through a lens or optic.

As used herein, the transmission of light wavelengths (within a range of given wavelengths) is the transmission percentage measured within a given range of light wavelengths through a lens or optic of the overall visible light that is transmitted through the lens or optic. By way of example only, if the overall transmission of visible light through the lens or optic was 2,000 lux and only 1,000 lux of light was transmitted through and measured within 480 nm+/−30 nm, then the transmission percentage through the wavelength range of 480 nm+/−30 nm would be 50%.

As used here in light transmission curve spectra, light transmission curve spectrum, is a light curve that is charted/plotted by light transmission percentages for various wavelengths of light.

As used here in light absorption curve spectra, light absorption curve spectrum, is a light curve that is charted/plotted by light absorption percentages for various wavelengths of light.

As used herein within a range of wavelengths or within a wavelength range means one or more wavelengths within the given range.

As used herein, dopamine deficiency disorders are any disorder caused by a lack of the appropriate amount of dopamine. Low levels of dopamine can affect both physical and mental health.

As used herein, serotonin deficiency disorders are any disorder caused by a lack of the appropriate amount of serotonin. Low levels of serotonin can affect one's mental, behavioral, and emotional health.

As used herein, Extended Reality (XR) is an umbrella term to refer to augmented reality (AR), virtual reality (VR), mixed reality (MR), modified reality (MoR), and combinations thereof. The technology is intended to combine or mirror the physical world with a "digital world" able to interact with it, giving users an immersive experience by being in a virtual or augmented environment.

Virtual Reality (VR) is a computer-generated environment with scenes and objects that appear to be real, making the user feel they are immersed in their surroundings. This environment is perceived through a device known as a Virtual Reality headset or helmet.

Mixed Reality (MR) combines Augmented Reality (AR) and Virtual Reality (VR). While AR overlays digital content onto the real world, and VR immerses the user in a completely virtual environment, MR blends these two, creating interactive environments where physical and digital objects coexist and interact.

Augmented reality (AR) is an interactive experience that visually combines the real world and computer-generated 3 D content.

The distinctions between VR and AR come down to the devices they require and the experience itself: AR uses a real-world setting while VR is completely virtual.

As used herein, Modified Reality is a modified version of extended reality which results in any deviation from Augmented Reality, Mixed Reality, or Virtual Reality, where a portion of one, two or more lighted images are seen with an eye or eyes of a user merged or intertwined or overlapped. Such modified reality can be a modified form of augmented reality, virtual reality or mixed reality.

As used herein, a near eye display is an electronic display that is within 30 mm or less (in most cases 20 mm or less) of the cornea of the eye of the user. A near eye display can comprise or be aligned and in optical communication with a micro-lens array. The use of a micro-lens array allows for the user to see a clear virtual image from said near eye display. However, in certain cases the near eye display is used to provide defocused light and in these cases a micro-lens array is not utilized.

As used herein, a see-through near eye display is an electronic near eye display that the eye of the user can see a real image by looking through. In most cases, the use of a micro-lens array allows for the user to see a clear virtual image from said near eye display. However, a micro-lens array can be fabricated to defocus light or diffuse light.

As used herein, a non-see-though near eye display is an electronic near eye display that the eye of the user cannot see a real image through. In most cases the use of a micro-lens array allows for the user to see a clear virtual image from said near eye display. However, a micro-lens array can be fabricated to defocus light or diffuse light.

As used herein, an eyewear apparatus includes any device or apparatus described herein that filters, treats, changes, enhances, diffuses, focuses, defocuses, transmits, generates, or otherwise is capable of producing or affecting light in such a way that the light can be used for ocular photo-bio-stimulation purposes.

As used herein, a micro-lens array is a structure made up of many small lenses, or microlenses, that are arranged in a patterned manner. A micro-lens array can comprise hundreds, thousands or millions of micro-lenses. A micro-lens array as used herein can be for one or more of, providing focused light, defocused light, diffused light, and/or filtered light.

As used herein, a chromatic aberration focused lens or optic can be that of a peripheral refocused chromatic aberration lens or optic. A chromatic aberration focused lens is a lens or optic where a portion or all of the lens peripheral to the central zone of the lens, focuses one or more of the chromatic aberration wavelength bands (blue, green, red) farther away from the lens or optic. Said another way, while the central zone maintains its normal focus of chromatic aberration wavelength bands, the chromatic aberration wavelength bands peripheral to the central zone focuses farther from the lens or optic than those of the central zone.

As used herein defocused light can be that of one or more of: light that focuses in front of the retinal, behind the retina, is scattered light, and/or dispersed or diffused light.

As used herein when discussing enlarging the pupil diameter it is meant to enlarge the pupil diameter relative to what the pupil diameter would have been if all light (without being filtered or blocked) was permitted to strike the retina of the wearer/user's eye(s).

As used herein, a vehicle can be that of any vehicle. By way of example only, a vehicle can be an airplane, car, truck, bus, trolley, ship, train, subway, or tram.

As used herein, the frame of an electronic display can be the other edge or a frame that goes around the outer edge of the display.

As used herein, programable means software, memory, or an electrical component that was one or more of, programed during the fabrication of the device, can be programmed after fabrication, can be programed after fabrication remotely, and/or can be programed by the consumer after purchase.

As used herein, a vehicle means any type of vehicle. By way of example only, an automobile, a car, a truck, a bus, a ship, a boat, an airplane, a trolley, a train, a tram, a spaceship, a motorcycle, etc.

The "ISO 12312-1 sunglass traffic signal test also referred to here within as the ISO 12312-1 sunglass traffic light/signal test" refers to a standardized test procedure within the ISO 12312-1 standard, which evaluates the ability of sunglasses to transmit light from traffic signals adequately, ensuring drivers can clearly distinguish between red, yellow, and green lights while wearing them; this test primarily measures the "relative visual attenuation quotient (Q factor)" of the sunglasses across different light wavelengths corresponding to traffic signal colors.

All embodiments disclosed herein, when appropriate, can utilize one or more of the following: bandpass filter, notch filter, selective filter, absorption filter, interference filter, neutral density filter, coating, and/or dye, to achieve the desired wavelength transmission results. When more than one filter is used, it can be referred to herein as a hybrid filter. In certain embodiments a film or optic comprising the appropriate filter can be applied over or in front of an electronic display or optic to allow for the desired wavelengths of light to be transmitted. The film or optic comprising the filter can be attachable and removable from the display screen or built into the screen (or optic).

Myopia, Prevention and Control:

According to the current invention, it is believed that juvenile-onset myopia (nearsightedness) occurs due to accommodative near point stress that generates a force causing an increase in the axial length of the eye. The resulting axial elongation occurs when the eye's ocular structure is unable to provide an offsetting force equal to or larger than that of the force causing axial elongation. The weakness of the opposing ocular structural is due to a deficiency of dopamine present in the retina.

Figure 12:
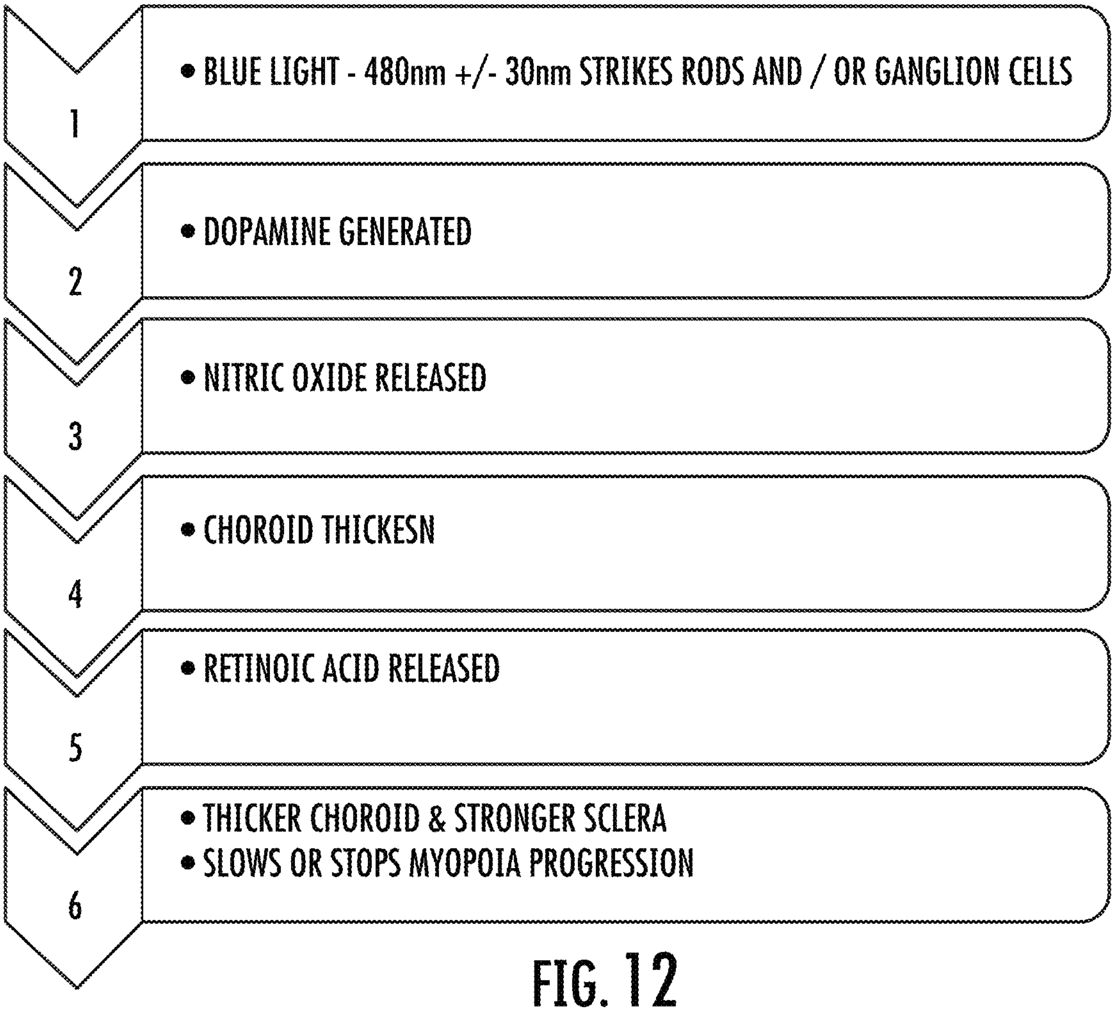
FIG. 12 shows an embodiment of the current invention as described herein.

In reference to FIG. 12, ample retinal dopamine is required to increase choroid thickness and maintain a healthy sclera, both of which generate an offsetting force of resistance to axial elongation of the eye. Thus, the following embodiment provides for the prevention of myopia or slowing or stopping myopia progression.

An embodiment of the invention is that of identifying children susceptible to myopia and treating them before their myopia develops. A diagnostic test can be performed to determine the level of dopamine in the eye or eyes of a child. By way of example only an ERG (electroretinogram) test can be performed at an early age, (for example) 6 years and older. When such a test is performed one can identify if a child has a dopamine deficiency disorder. Following this, a refractive examination can be performed, whether subjective or objective, using a retinoscope, automatic refractor, or phoropter. Accordingly, the results can be used to identify those children who have 0.75 D of hyperopia or less of hyperopia. Such children would include emmetropes. The result of these two tests (electroretinogram and refraction) can then identify which children are susceptible to becoming myopic. In certain cases an additional test for contrast sensitivity can be performed. Low contrast sensitivity can be an indication of a dopamine deficiency. Upon identifying a child that is susceptible of becoming myopic, one can begin treatment for ocular dopamine generation. Such means of treatment are identified in this invention disclosure. By improving the level of dopamine in the retina of the child's eye, one can offset the development of ocular axial elongation (or myopia).

Said another way, an embodiment for the prevention of myopia is:

1) Identify those children 6 years old or older (or even younger) who have low levels of dopamine in their retina;
2) Test those children to identify their BVA (best distance visual acuity) refractive status; and
3) If the refractive status of the child is +0.75 D or less hyperopia and their ocular dopamine test indicates low dopamine, begin therapy to increase retinal dopamine.

For those children who already have myopia it is important to stop or slow the progression of myopia as the child ages. Thus, it is important to increase the level of retinal dopamine in those children. Embodiments for increasing dopamine in the eye's retina are disclosed herein.

An embodiment of the current invention can be that of a device that is capable of determining a level of dopamine in the eye's retina of a patient, while also determining a refractive status of the eye. By way of example only, such a device can measure if the patient's eye comprises dopamine at a level that meets or exceeds "X", wherein X represents the level of dopamine deficiency, and also measure if the same eye comprises a refractive status that is less than "Y" diopters of hyperopia or is emmetropia or myopic. Another example would be that such a device can measure if the patient's eye comprises dopamine at a level that meets or exceeds "X", wherein X represents the level of dopamine deficiency, and also measure if the same eye comprises a best distance refractive correction that measures +0.75 D or less of hyperopia.

An embodiment can be an instrument for identifying a child or young adult that is susceptible to developing myopia, wherein the child or young adult is 25 years or younger, wherein the instrument determines if the child or young adult's eye comprises dopamine at a level that meets or exceeds "X", wherein X represents the level of dopamine deficiency, and wherein the instrument can also determine if the same eye's distance refractive correction (being that of the best distance correction optical power) is that of +0.75 D or less.

An embodiment can be an instrument for identifying a child or young adult that is susceptible for developing myopia, wherein the child or young adult is 25 years or younger, wherein the instrument determines if the child or young adult's eye comprises dopamine at a level that meets or exceeds "X", wherein X represents the level of dopamine deficiency, and wherein the instrument can also measure if the same eye's refractive correction, being that of the best distance correction optical power, is that of a spherical equivalent that is +0.75 D or less hyperopic.

Such a device could determine both the level of dopamine in the retina or eye and the refractive status simultaneously or in succession. Such a device could be one of, handheld, a tabletop instrument, attachable to a slit lamp bio microscope, or attachable to a phoropter stand. By way of example only, such a device could be a combination ERG instrument and an autorefractor.

An embodiment can be that of an instrument for identifying a child or young adult that is susceptible for developing myopia, wherein the child or young adult is 25 years or younger, wherein the instrument determines if the child or young adult's eye comprises dopamine at a level that exceeds "X", wherein X represents the level of dopamine deficiency, and wherein the instrument can also determine if the same eye's distance refractive correction (being that of the best distance correction optical power) is that of +0.75 D or less.

In determining if the child or an adult's eye has a dopamine deficiency, the following tests can be performed by:

A. ERG (more specifically measuring the B Wave Amplitude of an ERG)
B. Measuring contrast sensitivity An embodiment can be that of an instrument for treating myopia progression, wherein the instrument can determine a level of dopamine in the eye, wherein the instrument can also determine if the eye's refraction requires an increase in minus optical power. Such an instrument can be that of an electroretinogram (ERG). Such an instrument can be handheld, or table mounted. For testing children, the use of a handheld ERG instrument that uses electrodes connected to the skin of the patient is recommended as opposed to corneal electrodes. By measuring the B wave amplitude, it is possible to determine a level of dopamine in the retina of the eye. A reduction in the B wave amplitude can indicate a dopamine deficiency. In certain cases, the testing of the child's contrast sensitivity can also give an indication of a dopamine deficiency. Poor contrast sensitivity can be such an indication. The instrument further comprises the ability to provide ocular photo-bio-stimulation. Artificial intelligence (AI) can be incorporated into such an instrument to further help with optimizing such a diagnosis and treatment.

The following is a listing of diagnostic testing and providing myopia control light therapy, and such an instrument embodiment could comprise:

a. ERG (more specifically measuring the B Wave Amplitude of an ERG)
b. Measuring contrast sensitivity
c. Measuring Refractive Error
d. Measuring or checking the scleral thickness
e. Measuring or documenting the eye's axial length or elongation, and/or
f. Treating with providing ocular photo-bio-stimulation In certain embodiments the diagnostic and myopia control therapy instrument can comprise a combination handheld or table mounted instrument that comprises three or more of the following:

a. ERG testing (for measuring the B wave amplitude)
b. Optical biometer (for measuring the axial length of the eye)
c. Auto-refractor (for measuring the refractive error of the eye)
d. Contrast sensitivity tester (for measuring the contrast sensitivity of the eye)
e. Measurement of scleral thickness of the eye
f. Ocular photo-bio-stimulation (for providing light therapy to increase dopamine production in the retina)
g. AI (Artificial Intelligence)
h. ML (Machine Learning)

In certain embodiments the diagnostic and myopia control therapy instrument can comprise a combination handheld or table mounted instrument that comprises four or more of the following:

a. ERG testing (for measuring the B wave amplitude)
b. Optical biometer (for measuring the axial length of the eye)
c. Auto-refractor (for measuring the refractive error of the eye)
d. Contrast sensitivity tester (for measuring the contrast sensitivity of the eye)
e. Measurement of scleral thickness of the eye
f. Ocular photo-bio-stimulation (for providing light therapy to increase dopamine production in the retina)
g. AI (Artificial Intelligence)
h. ML (Machine Learning)

In certain embodiments the diagnostic and myopia control therapy instrument can comprise a combination handheld or table mounted instrument that comprises five or more, six or more, seven or more, or eight or more of the following:

a. ERG testing (for measuring the B wave amplitude)
b. Optical biometer (for measuring the axial length of the eye)
c. Auto-refractor (for measuring the refractive error of the eye)
d. Contrast sensitivity tester (for measuring the contrast sensitivity of the eye)
e. Measurement of scleral thickness of the eye
f. Ocular photo-bio-stimulation (for providing light therapy to increase dopamine production in the retina)
g. AI (Artificial Intelligence)
h. ML (Machine Learning)

An embodiment can be that of an instrument for treating myopia progression, wherein the instrument can determine a level of dopamine in the eye, wherein the instrument can also determine if the eye's refraction requires an increase in minus optical power. Such an instrument can be that of an electroretinogram (ERG). Such an instrument can be handheld, or table mounted. For testing children, the use of a handheld ERG instrument that uses electrodes connected to the skin of the patient is recommended as opposed to corneal electrodes. By measuring the B wave amplitude, it is possible to determine a level of dopamine in the retina of the eye. A reduction in the B wave amplitude can indicate a dopamine deficiency. In certain cases the testing of the child's contrast sensitivity can also give an indication of a dopamine deficiency. Poor contrast sensitivity can be such an indication. Artificial intelligence (AI) can be incorporated into such an instrument to further help with optimizing such a diagnosis and treatment.

An embodiment can be that of an instrument for preventing or treating myopia, wherein the instrument can determine a level of dopamine in the eye's retina, wherein the instrument can also determine if the eye's best distance refraction is +0.75 D or less of plus optical power or if the eye requires an increase in minus optical power to maintain its best corrected distance vision. Artificial intelligence (AI) can be incorporated into such an instrument to further help with optimizing such diagnosis and treatment.

An embodiment can be that of an instrument for preventing or treating myopia, wherein the instrument can determine a level of dopamine in a patient's eye's retina, wherein the instrument can also determine the optical power required to achieve for the same eye of the patient its best distance vision correction or best distance visual acuity. Artificial intelligence (AI) can be incorporated into such an instrument to further help with optimizing such a diagnosis and treatment.

An embodiment can be that of an instrument for preventing and/or treating myopia, wherein the instrument can determine a level of dopamine in a patient's eye's retina, wherein the instrument can also determine the optical power required to achieve for the same eye of the patient its best distance vision correction or best distance visual acuity, and wherein the instrument can apply photo-bio-stimulation. Artificial intelligence (AI) can be incorporated into such an instrument to further help with optimizing such diagnosis and treatment.

As disclosed herein, a means for determining an indication of the level of dopamine in the retina of the eye of a patient one or more of the following can be measured; the B wave amplitude of an electroretinogram, the thickness of the choroid and/or sclera. Such thickness can be measured (by way of example only) by a Cirrus HD-OCT 5000. A contrast sensitivity test that indicates low contrast sensitivity can also indicate a dopamine deficiency. Artificial intelligence (AI) can be incorporated into such an instrument to further help with optimizing such diagnosis and treatment.

An embodiment for slowing or preventing myopia can comprise modulation of the image or light source. Such modulation can be within the range of 5 Hz-15 Hz, 10 Hz to 20 Hz, or 40 Hz+/−20 Hz.

An embodiment can comprise a light source or light emitter having a light intensity of at least one of: 300 lux or greater, 500 lux or greater, 1,000 lux or greater, or 5,000 lux or greater. An embodiment can comprise light that strikes the eye of the user or wearer of at least one of: 300 Lux or greater, 500 lux or greater, 1,000 lux or greater, or 5,000 lux or greater.

An embodiment can comprise an ocular-photo-bio-stimulation time of 1 minute to 5 minutes, 5 minutes to 30 minutes, or one hour or less. With certain embodiments of eyewear disclosed herein such an ocular-photo-bio-stimulation time can be that of normal daily wear of the eyewear.

Another embodiment of the invention can be a diagnostic test to determine the thickness of the choroid and/or scleral thickness of the eye or eyes of a child. By way of example only an OCT test can be performed at an early age, (for example) 6 years and older. When such a test is performed one can identify if a child has a dopamine deficiency disorder by way of measuring the choroidal and/or scleral thickness and/or testing the child's contrast sensitivity. Following this, a refractive examination can be performed, whether subjective or objective, using a retinoscope, automatic refractor, or phoropter. Accordingly, the results can be used to identify those children who have 0.75 D of hyperopia or less hyperopia. Such children would include emmetropes. The result of these two tests (electroretinogram and refraction) can then identify which children are susceptible to becoming myopic. Upon identifying a child that is susceptible to becoming myopic, one can begin treatment for ocular dopamine generation. Such means of treatment are identified in this invention disclosure. By utilizing ocular photo-bio-stimulation therapy one can stimulate dopamine production in the retina of the eye or eyes, also increase the thickness of the choroid and or sclera of the child's eye(s), thus offsetting the development of ocular axial elongation (or myopia). A further indication of increased dopamine production can be by way of measuring an increase in the child's contrast sensitivity. And an additional indication of increased dopamine production can be by way of performing and ERG test whereby the ERG test indicates an increase in the B wave amplitude. Artificial intelligence (AI) can be incorporated into such a diagnostic test to further help with optimizing such diagnosis and treatment.

Said another way, an embodiment for the prevention of myopia is:

4) Identify those children 6 years old or older (or even younger) who have low levels of dopamine in their retina.
5) Test those children to identify their BVA (best distance visual acuity) refractive status; and 6) If the refractive status of the child is +0.75 D or less hyperopia and their choroidal and/or scleral thickness indicates a low dopamine level, begin therapy to increase retinal dopamine and choroidal and/or scleral thickness.

For those children who already have myopia it is important to stop or slow the progression of myopia as the child ages. Thus, it is important to increase the level of retinal dopamine in those children. Embodiments for increasing dopamine in the eye's retina are disclosed Ocular Photo-Bio-Stimulation with Inventive Embodiments Embodiments disclosed herein can provide ocular photo-bio-stimulation through light stimulation of specific wavelengths to the eye's retina, and, in some embodiments, to the entire eye's retina, the retina peripheral to the fovea, and/or the retina peripheral to the macula. In certain embodiments, the light stimulation is targeted at or to the rods. In other embodiments, the light stimulation is targeted at or to the ganglion cells. In still other embodiments, it is targeted at or to the rods and the ganglion cells. When ganglion cells are mentioned herein, the ganglion cells targeted or stimulated are the melanopsin containing ganglion cells (ipRGCs) or can also be called mRGCs.

Embodiments herein teach the stimulation of the rods and/or ipRGCs with specific light wavelengths. The retina of the human eye contains 100+M rods, 1M ganglion cells but fewer than 7,000 ipRGCs which are the ganglion cells that contain melanopsin. ipRGCs are less sensitive to photic stimulation and their response kinetics are slow compared to that of rods and cones. Response latency is inversely related to stimulus intensity and under dim light conditions ipRGCs can take many seconds to reach a peak response; the response may also persist for minutes after stimulus termination. However, ipRGCs are similar to rods and cones in that they show adaptation by adjusting their sensitivity according to lighting conditions. While slow to respond to dim light conditions, ipRGCs appear capable of responding to the capture of a single photon of light. It has been estimated that the membrane density of melanopsin is about a thousand times lower than that of photopigments in the outer segments of rod and cone photoreceptors; this relatively low density may account for the poor absorption rate of ipRGCs. The capture of a single photon in an ipRGC generates a large and prolonged membrane current, greater than that recorded in rod photoreceptors but also 20-fold slower.

In still other embodiments, the light stimulation is targeted at or to the cones, rods and ganglion cells. In certain embodiments the objective of ocular photo-bio-stimulation is to increase dopamine within the eye. In certain embodiments the objective of ocular photo-bio-stimulation is to increase dopamine within the eye's retina. When increasing dopamine in the eye and/or retina, ocular photo-bio-stimulation blue light having wavelengths within the range of 450 nm to 510 nm can be used, or, for increasing dopamine in the eye and/or retina, ocular photo-bio-stimulation red light wavelengths of 650 nm+/−30 nm can be utilized. In certain embodiments the objective of ocular photo-bio-stimulation is to increase dopamine within the eye's retina and the brain. In still other embodiments the objective of ocular photo-bio-stimulation is to reduce pain. In still other embodiments the objective of ocular photo-bio-stimulation is to reduce the severity of a headache. When reducing pain by ocular photo-bio-stimulation, green light having wavelengths within the range of 530 nm+/−20 nm can be utilized. In still other embodiments the use of light wavelengths in the range of 650 nm+/−30 nm can improve mitochondria function and/or reduce age related inflammation in the eye of the user. In other embodiments the objective is to improve mitochondria function and/or reduce age related inflammation in the eye's retina of the user.

In still other embodiments, the objective of ocular photo-bio-stimulation is to increase the number or healthy mitochondria present within the ocular photo-bio-stimulation, the area of the retina in which the ocular photo-bio-stimulation has targeted. When increasing healthy mitochondria by way of ocular photo-bio-stimulation, red light having wavelengths within the range of one of 650 m to 700 nm, 650 nm+/−30 nm, 700 nm+/−30 nm or 830 nm+/−30 nm, can be utilized. Such ocular photo-bio-stimulation, according to the present invention, increases retinal mitochondrial function and attenuates oxidative stress thus increasing the number of healthy mitochondria within the area of the retina being treated. This can be important for treating, by way of example only, diabetic retinopathy, macular degeneration, and/or retinitis pigmentosa.

For most if not all embodiments provided herein for providing ocular photo-bio-stimulation, light wavelengths predominantly fall within one of the wavelength ranges of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, and can be utilized in addition to what is stated within the embodiments. The exact wavelength band of the above will depend upon the type of ocular photo-bio-stimulation that is desired to produce the desired physiological response. Biofeedback or diagnostics involving one or more of, pupil size increase, lid blink rate increase, heart rate increase, or blood oxygen level increase, can be an indication of increased production or stimulation of dopamine or norepinephrine in the brain and in some cases serotonin. An increase in contrast sensitivity, B wave amplitude of an ERG, scleral thickening, and/or slowing of axial length eye growth, can indicate an increase in the production of dopamine in the retina.

Embodiments when light wavelengths are generated by way of filtered optics or filtered lenses, the peak spectral curve of the wavelength range that strike the eye's retina falls within the wavelength range of one: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

Embodiments providing ocular photo-bio-stimulation can filter or block damaging high energy blue light, UV, and reduce bright light visual discomfort.

Melanopsin photopigment expressed in intrinsically photosensitive retinal ganglion cells (ipRGCs) plays a crucial role in the adaptation of mammals to their ambient light environment through non-image-forming (NIF) visual responses. ipRGCs are structurally and functionally distinct from classical rod/cone photoreceptors and have unique properties including single-photon response, long response latency, photon integration over time, and slow deactivation.

Embodiments disclosed herein that are directed to increasing dopamine in an individual's eye's retina or dopamine in the brain of the individual whose eye was stimulated, attempt to use wavelength ranges that cover the peak sensitivities for melanopsin (480 nm) and also for rhodopsin (500 nm). Given that rhodopsin of Rods is 20 times faster to react than melanopsin of ipRGCs, but that melanopsin has much longer reactive staying power than the reaction of rhodopsin, combined with the fact that rods are 10+ times the number of ipRGCs, is the reason various embodiments disclosed herein use light wavelengths within the light wavelength ranges of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, and/or 700 nm+/−30 nm. The lower level of 480 nm+/−30 nm is to capture direct stimulation of melanopsin by ipRGCs and indirect stimulation of melanopsin by Rods.

In certain embodiments, when generating dopamine in the eye or the brain via the eye light, the invention utilizes light wavelengths that strike the eye's retina, which fall within at least one of the wavelength ranges of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm which would include blue, bluish green and green wavelengths. These light wavelength ranges can be generated by light emitters, filtered optics or filtered lenses.

In embodiments when light wavelengths are generated by way of filtered optics or filtered lenses, the transmission peak of the wavelength range that strike the eye's retina fall within one of the wavelength ranges of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In embodiments when light wavelengths are generated by way of a light emitter(s) if in a dark room with no ambient lighting, the wavelength range that strike the eye's retina fall within at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In embodiments when light wavelengths are generated by a light emitter(s) if ambient lighting is present (including that of artificial light or sun light) the blended light wavelengths of the light emitter(s) and also the ambient light comprises wavelengths of light that strike the eye's retina fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

It should be understood that when interpreting the embodiments utilized herein unless total darkness is specified, it should be assumed that there is ambient light and thus the light wavelengths striking the retina are blended by the light from the light emitter and the ambient light. The same is true with a filtered optic or filtered lens. In most but not all cases the filtered optic or filtered lens is located 12+mm from the eye of the wearer unless the filtered optic or filtered lens is that of a contact lens or intraocular lens. An exception to this interpretation would be that of the use of a virtual reality device or a modified reality device whereby the device is sealed or mostly sealed from ambient light.

Examples only of light emitters that emit light wavelengths which significantly excite melanopsin and rhodopsin in the retina of the human eye can be, by way of example only, Green LED light, Blue LED light, Cold White LED light, and/or Sunlight.

In still other embodiments, light wavelength from either a filtered optic, filtered lens, and/or light emitter(s), that strikes the retina of the eye are selected so that the radiation peak of these wavelengths falls between the peak melanopsin sensitivity (480 nm, and rhodopsin sensitivity (500 nm)). Thus, the transmission peak of these wavelengths falls within the range of 480 nm and 500 nm.

In certain embodiments when a filtered optic or filtered lens is used, the overall light transmission through the filtered optic or filtered lens can be 50% or less, 40% or less, or 30% or less, while the light transmission within the predominant transmitted filtered wavelength range being transmitted to the eye can be 50% or more. In certain cases, the pupil of the eye enlarges when looking through the filtered optic or filtered lens and constricts when not looking through the filtered optic or filtered lens.

In still other embodiments, the objective of ocular photo-bio-stimulation is to increase the alertness of the individual being treated with ocular photo-bio-stimulation. When increasing alertness by way of ocular photo-bio-stimulation, blue light having wavelengths within the range of 450 nm to 510 nm can be utilized. In still other embodiments the objective of ocular photo-bio-stimulation is to increase the slowing down, to slow the progressing of, or to stop myopia of the individual being treated with ocular photo-bio-stimulation. When slowing down or stopping myopia by way of ocular photo-bio-stimulation, blue light having wavelengths within the range of 450 nm to 510 nm, or red light within the wavelength range of 650 nm+/−30 nm or 700 nm+/−30 nm, can be utilized. Such ocular photo-bio-stimulation wavelengths can be applied to a large portion of the eye's retina to stimulate the ipRGC ganglion cells and/or rods, or to the ganglion axons of the optic nerve head for the purposes of generating increased retinal dopamine.

In still other embodiments, the objective of ocular photo-bio-stimulation is to treat or correct a neurological abnormality of the individual being treated with the ocular photo-bio-stimulation. When correcting a neurological abnormality by way of ocular photo-bio-stimulation, blue light having wavelengths within the range of 450 nm to 510 nm can be utilized. Neurological abnormalities that may be treatable by ocular photo-bio-stimulation are by way of example only: Alzheimer's, cognitive disorders, ADD, ADHD, depression, anxiety, and/or Parkinson's disorder.

In still other embodiments the objective of ocular photo-bio-stimulation is to prevent myopia from occurring with the individual being treated with the ocular photo-bio-stimulation. In still other embodiments the objective of ocular photo-bio-stimulation is to treat or correct an ocular abnormality of the individual being treated with ocular photo-bio-stimulation. When correcting an ocular abnormality, the use of the appropriate light wavelengths must be employed when treating with ocular photo-bio-stimulation. Ocular abnormalities that may be treatable by ocular photo-bio-stimulation are by way of example only: myopia, AMD, dry AMD, diabetic retinopathy, retinal degenerative disease, glaucoma, optic neuropathy, cataract, and/or meibomian gland disfunction leading to dry eye.

In embodiments, biofeedback can be utilized to confirm that increased dopamine and/or serotonin is being produced within the brain of a patient having ocular photo-bio-stimulation therapy. Such biofeedback can be comparing one or more of: increased blink rate of the eye(s) of the patient being treated, increased diameter of pupil(s) of the patient being treated, increased heart rate, and/or increased body temperature of the wearer of the patient being treated comparted to that of a base line for the same activity prior to the ocular photo-bio-stimulation therapy.

An embodiment for ocular photo-bio-stimulation can comprise modulation of the image or light source. Such modulation can be within the range of 5 Hz-15 Hz, 10 Hz to 20 Hz, or 40 Hz+/−20 Hz.

An embodiment can comprise a light source or light emitter having a light intensity of at least one of: 300 lux or greater, 400 lux or greater, 500 lux or greater, 1,000 lux or greater, or 5,000 lux or greater, or 10,000 lux or greater. As used herein, the sun is considered to be a light emitter. As used herein, various electronic devices or components, chemical-based devices or components, or electro-chemical devices or components that emit light are considered light emitters. As used herein, sunlight and artificial light each qualify as ambient light.

An embodiment can comprise an ocular-photo-bio-stimulation time of 1 minute to 5 minutes, 5 minutes to 30 minutes, or one hour or less. With certain embodiments of eyewear disclosed herein such an ocular-photo-bio-stimulation time can be that of normal daily wear of the eyewear. It has been found that the longer the ocular photo-bio-stimulation the eye becomes more sensitive to lower wavelengths of light, thus there is a shift in retinal sensitivity. It appears the retina becomes less sensitive and thus there is a shift in the direction towards melanopsin absorption curves from that of rhodopsin absorption curves. By way of example only, with one second of light stimulation the retina (which includes melanopsin, rhodopsin, and the cones opsins) is most sensitive at 510 nm, for 10 seconds of continuous light stimulation the retina becomes most sensitive at 500 nm, and for 100 seconds of continuous light stimulation the retina becomes most sensitive at 480 nm. Age also affects the melanopsin absorption curves; at age 20 the peak sensitivity of melanopsin is 488 nm and by age 80 the peak sensitivity if 503 nm. So, while time of stimulation shifts the retinal sensitivity to the left and lower wavelengths, age shifts the sensitivity of melanopsin to the right.

Biofeedback or diagnostics involving one or more of, pupil size increase, lid blink rate increase, heart rate increase, and/or blood oxygen level increase, can be an indication of increased production or stimulation of dopamine or norepinephrine in the brain and in some cases-serotonin. An increase in contrast sensitivity, B wave amplitude of an ERG, scleral thickening, and/or slowing of axial length eye growth, can indicate an increase in the production of dopamine in the retina.

An embodiment can be that of a filtered lens or filtered optic or sunglass lens or sunglass optic that transmits a higher percentage of blue light and bluish green light wavelengths within the wavelength range of one or more of 480 nm+/−30 nm or 530 nm+/−20 nm than the lens or optic comprises an average visible light transmission percentage within the range of 380 nm-780 nm and passes the ISO 12312-1 sunglass traffic light/signal test.

An embodiment can be that of a filtered lens or filtered optic or sunglass lens or sunglass optic that transmits a higher percentage of blue light and bluish green light wavelengths within the wavelength range of one or more of 480 nm+/−30 nm or 530 nm+/−20 nm than the lens or optic comprises an average visible light transmission percentage within the range of 380 nm-780 nm to qualify for category 2 or category 3 sunglasses and further passes the ISO 12312-1 sunglass traffic light/signal test.

An embodiment can be a filtered lens or filtered optic or sunglass lens or sunglass optic that transmits 40% or greater percentage of blue light and bluish green light wavelengths within the wavelength range of one or more of 480 nm+/−30 nm or 530 nm+/−20 nm than the lens or optic comprises an average visible light transmission percentage within the range of 380 nm-780 nm to qualify for category 2 or category 3 sunglasses and further passes the ISO 12312-1 sunglass traffic light/signal test.

An embodiment can be a filtered lens or filtered optic or sunglass lens or sunglass optic that transmits 40% or greater percentage of blue light and bluish green light wavelengths within the wavelength range of one or more of 480 nm+/−30 nm or 530 nm+/−20 nm than the lens or optic comprises an average visible light transmission percentage within the range of 380 nm-780 nm to qualify for category 3 sunglasses and further passes the ISO 12312-1 sunglass traffic light/signal test.

Figure 13:
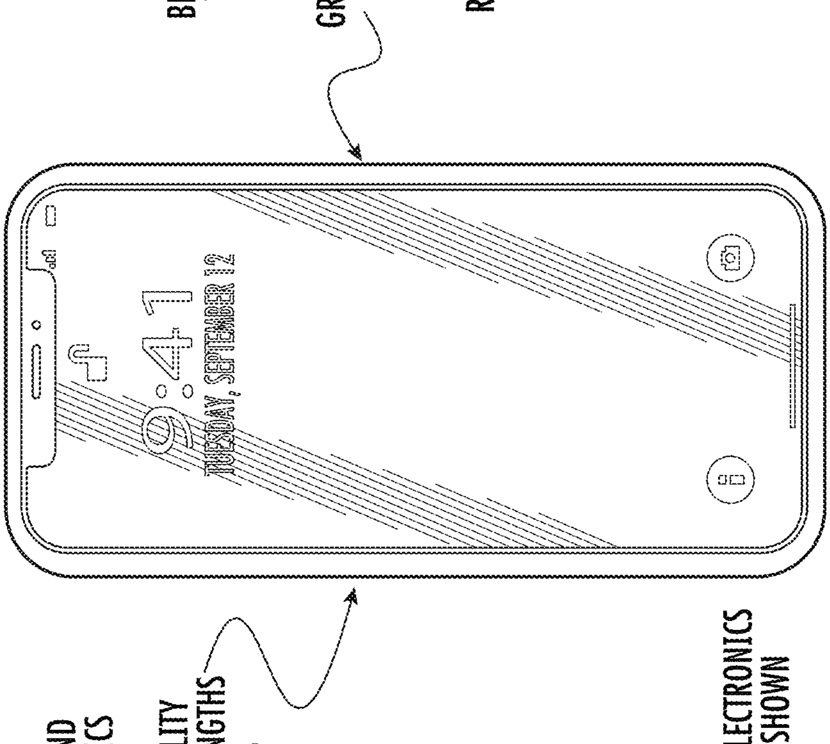
FIG. 13 shows an embodiment of the current invention as described herein.

Electronic Devices for Ocular Photo-Bio-Modulation or Ocular Photo-Bio-Stimulation Ocular Photo-Bio-Stimulation Cell Phone Case FIG. 13 shows an embodiment of the current invention. It shows a cell phone case, which can comprise, among other things, enabling electronics and a blue lighted border that circumvents all or part of the cell phone. The lighted border of the cell phone case can be programmed for one or more light intensity, wavelength, modulation or flicker, start time, and/or end time. The cell phone case can comprise a sensor to measure the distance from a user to the case and the light intensity can be automatically or manually adjusted to provide that appropriate level of light intensity required for the ocular photo-bio-stimulation therapy.

In certain embodiments the cell phone case comprises its own ocular photo-bio-stimulation light source. In other embodiments the cell phone or cell phone case can utilize the light given off by the flashlight of the cell phone. When the cell phone case utilizes the flashlight of the cell phone, the cell phone can comprise light pipes or waveguides. In certain embodiments the inside of the cell phone case is comprised of highly reflective material. The cell phone case can fit around part or all of the cell phone in such a manner whereby there is a space formed between the wall of the cell phone case and the side or sides of the cell phone that extends partially around or fully around the cell phone. Ocular photo-bio-stimulation light can be radiated from the light emitter or emitters through this space.

In certain other embodiments the ocular photo-bio-stimulation light is emitted forward through the front thickness of one or more walls of the cell phone case. In still other embodiments the ocular photo-bio-stimulation light is emitted through the back of the cell phone case. In these embodiments the subject or patient must turn the cell phone case around when receiving ocular photo-bio-stimulation therapy.

In embodiments, the electronic display screen or the housing device which houses the electronic display screen can identify the distance from the eye of the user and can automatically adjust the intensity of the blue, green, or red-light border to be appropriate for such a distance. In a certain embodiment the electronic display screen or the housing of the electronic display screen can comprise a distance sensor and optionally facial recognition. In addition, the border light intensity can be adjusted automatically or manually depending upon the ambient lighting available in the room or space.

The lighted border can comprise wavelengths within the range of one or more of: 441 nm or greater, 460 nm+/−20 nm, 470 nm+/−20 nm, 460 nm-520 nm, or 480 nm+/−30 nm. The ocular photo-bio-stimulation effect targeted can be one or more of (by way of example only), increased dopamine in the eye; the prevention of, slowing down of, or stopping of myopia; increasing dopamine in the brain; increasing alertness; and/or reducing depression severity.

In certain embodiments a lighted border can comprise wavelengths of light within the range of 440 nm to 700 nm. The lighted border can be a white lighted border. The white light can comprise peaks of light wavelengths of: 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted border can provide ocular photo-bio-stimulation. The light intensity of lux given off from the lighted border can be 500 lux or more, 1,000 lux or more, 2,000 lux or more, and so on. When considering the light radiating in a cone light manner from the lighted border to strike the eye and face of the user or subject, the number of lumens given off from the lighted border can be 25 lumens or more, 50 lumens or more, 100 lumens or more, 200 lumens or more, and so on.

In certain embodiments an electronic display can comprise wavelengths of light within the range of 440 nm to 700 nm. The lighted border can be a white lighted border. The white light can comprise peaks of light wavelengths of 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted electronic display can provide ocular photo-bio-stimulation. The lighted border can comprise wavelengths of light within the range of 440 nm to 700 nm. The lighted border can be a white lighted border. The white light can comprise peaks of light wavelengths of 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted border can provide ocular photo-bio-stimulation. The light intensity of lux given off from the lighted border can be 500 lux or more, 1,000 lux or more, 2,000 lux or more, and so on. When considering the light radiating in a cone light manner from the lighted border to strike the eye and face of the user or subject, the number of lumens given off from the lighted border can be 25 lumens or more, 50 lumens or more, 100 lumens or more, 200 lumens or more, and so on.

In certain embodiments an ocular photo-bio-stimulation light source can comprise wavelengths of light within the range of 440 nm to 700 nm. The lighted border can be a white lighted border. The white light can comprise peaks of light wavelengths of; 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted ocular photo-bio-stimulation light source can provide ocular photo-bio-stimulation. The light intensity of lux given off from the ocular photo-bio-stimulation light source can be 500 lux or more, 1,000 lux or more, 2,000 lux or more, and so on. When considering the light radiating in a cone light manner from the ocular photo-bio-stimulation light source to strike the eye and face of the user or subject, the number of lumens given off from the ocular photo-bio-stimulation light source can be 25 lumens or more, 50 lumens or more, 100 lumens or more, 200 lumens or more, and so on.

Biofeedback or diagnostics involving one or more of, pupil size increase, lid blink rate increase, heart rate increase, and/or blood oxygen level increase, can be an indication of increase production or stimulation of dopamine or norepinephrine in the brain and in some cases serotonin. An increase in contrast sensitivity, an increase in the B wave amplitude of an ERG, scleral thickening, and/or slowing of axial length eye growth, can indicate an increase in the production of dopamine in the retina.

Embodiments when light wavelengths are generated by way of filtered optics or filtered lenses, the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In certain embodiments when the intensity of light wavelengths is adjusted by way of filtered optics or filtered lenses, the transmission peak of the wavelength range that strikes the eye's retina falls within the wavelength range of 450 nm-520 nm.

Embodiments when light wavelengths are generated by a light emitter(s) if ambient lighting is present (including that of artificial light or sun light) the blended light wavelengths of the light emitter(s) and also the ambient light comprises wavelengths of light that strike the eye's retina falling within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In certain embodiments, when light wavelengths are generated by a light emitter(s), and if ambient lighting is present (including that of artificial light or sun light), the blended light wavelengths of the light emitter(s) and also the ambient light comprises wavelengths of light that strike the eye's retina falling within one of the wavelength ranges of certain embodiments and/or the range of 450 nm-520 nm.

In certain embodiments, the range of wavelength band includes the peaks of the most sensitive spectral points of rhodopsin (500 nm) and melanopsin (480 nm). This way both rhodopsin and melanopsin can be stimulated or excited. By way of example, by utilizing a filtered optic or lens, that predominantly transmits within the wavelength range of at least one of 460 nm-520 nm or 470 nm to 520 nm, or by utilizing a light source or light emitter that predominately transmits within the wavelength range of at least one of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

The light border can have an intensity of 300 lux or greater. The light border can have an intensity of 400 lux or greater. The light border can have an intensity of 1,000 lux or greater. The light border can have an intensity of 5,000 lux or greater. The time of ocular photo-bio-stimulation treatment can be 5 minutes to 10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more.

The amount of required light intensity given off by an ocular photo-bio-stimulation artificial light source (not the sun) is dependent upon the distance of the light source from the eye of the subject receiving ocular photo-bio-stimulation treatment, the age of the subject, and whether or not the subject is wearing a eyeglass that either filters and/or refracts light. In most, but not all cases, for most handheld devices that give off ocular photo-bio-stimulation, the light intensity needs to be 60 lumens of more leaving the ocular photo-bio-stimulation light source. The preference is for 400 lux of ocular photo-bio-stimulation light or more to strike the retina of the eye of the subject for a period of time in order for the subject to have the desired physiological response.

The lighted border can comprise wavelengths within the range of one of: wavelengths of 530 nm+/−10 nm, 530 nm+/−15 nm, 530 nm+/−20 nm, or 500 nm to 550 nm. The ocular photo-bio-stimulation effect targeted can be one or more of (by way of example only), reduced pain severity, reduced frequency of headaches, and/or reduced frequency of migraines.

The same embodiment can be provided for a red-light border within the wavelengths of 630 nm+/−20 nm, 650 nm+/−30 nm, or 650 nm-700 nm or 700 nm+/−30 nm. The ocular photo-bio-stimulation effect targeted can be that of one or more of (by way of example only), increased mitochondrial health or mitochondrial numbers within the retina of the eye for the purposes of reducing the severity or improving a retinal disease/disorder, such as one or more (by way of example only), dry AMD, retinitis pigmentosa, and/or diabetic retinopathy. In certain cases, the red wavelength border light can also treat or help treat dry eye conditions whereby the tear layer evaporates too quickly.

The border of treatment (e.g., blue light treatment) can appear for a certain time interval that can be programed or preset. The intensity of this blue light border can be adjustable or programed to a setting. The intensity can modulate. The intensity can be adjustable or fixed. The light wavelength can be adjusted or fixed. By way of example only, such a border can appear on one's electronic display screen at 7:00 am and remain there until 8:00 am when it will disappear/stop. The blue light can cause the user of the electronic display to become more alert. The cell phone case border can act as a design feature allowing for different colored lights that can be programable during the day or at night. In most, but not all, cases, the lighted border is in the front periphery (that faces the user) of the cell phone case that surrounds the cell phone. The light can modulate or flicker. The light can be programable with regards to one or more of: light intensity, wavelength, modulation or flicker, start time, and/or end time. The light can modulate by way of example only, within the range of 5 Hz to 15 Hz, 10 Hz to 20 Hz, or 40 Hz+/−20 Hz.

In another embodiment a cell phone case comprises the appropriate enabling electronics and comprises a green light border. The green light can be comprised of wavelengths of green light, for example within the range of 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm, 650 nm+/−30 nm, or 700 nm+/−30 nm. The border of green light can appear for a certain time interval that can be programed or preset. The intensity of this green light border can be adjustable or programed to a setting. The intensity can modulate. The intensity can be adjustable or fixed. The light wavelength can be adjusted or fixed. By way of example only, such a border can appear on one's electronic display screen at 7:00 am and remain there until 8:00 am when it will disappear. The green light can cause the user of the electronic display to have, by way of example only, reduced pain. The cell phone case border can act as a design feature allowing for different colored lights that can be programable during the day or at night. In most, but not all cases the lighted board is in the front periphery (that faces the user) of the cell phone case that surrounds the cell phone. The light can modulate or flicker. The light can be programable with regards to one or more of: light intensity, wavelength, modulation or flicker, start time, and/or end time. In certain embodiments a diffuser can be placed over the light emitters. In certain embodiments a filter or filters are used so as to permit a higher concentration of wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, to be transmitted from the light source.

In another embodiment a cell phone case comprises the appropriate enabling electronics and comprises a red-light border. The red light can be comprised of wavelengths of red light, for example only, 660 nm+/−10 nm or 650 nm+/−30 nm. The border of red-light can appear for a certain time interval that can be programed or preset. The intensity of this red-light border can be adjustable or programed to a setting. The intensity can modulate. The light can modulate or flicker. The intensity can be adjustable or fixed. The light wavelength can be adjusted or fixed. By way of example only, such a border can appear at 10:00 pm and be turned off prior to the user when going to sleep. The red light can cause the user of the electronic display to become more relaxed before going to sleep. The cell phone case border can act as a design feature allowing for different colored lights that can be programable during the day or at night. In most, but not all cases the lighted board is in the front periphery (that faces the user) of the cell phone case that surrounds the cell phone. The light can be programable with regards to one or more of: light intensity, wavelength, modulation or flicker, start time, and/or end time.

An embodiment can be that of a phone case that can provide ocular photo-bio-stimulation therapy, wherein a plurality of light emitters encircle part or all of the cell phone screen, wherein the ocular photo-bio-stimulation light emitters provide one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, wherein the plurality of light emitters are controllable, manually or automatically, with regards to one or more of: intensity, on and/or off time, and/or wavelengths band(s), and wherein the intensity of the ocular photo-bio-stimulation light can be automatically adjusted depending upon one or more of: distance from the face of the user or ambient light of the room or space. The ocular photo-bio-stimulation light can comprise a timer to provide the appropriate level of ocular photo-bio-stimulation therapy.

In certain embodiments the color of the ocular photo-bio-stimulation light can be alternated in a sequence. By way of example only green wavelengths, then blue green wavelengths, then blue wavelengths. In other embodiments, green wavelengths, then blue green wavelengths, then blue wavelengths, then white light. This can be done to maximize the stimulation effect of light wavelength versus time on retinal excitation. Said another way, first (for, in aspects, a short period of time) have the green light wavelengths excite the retina, then the bluish green wavelengths, and the longer the time period have the blue light wavelengths excite the retina. Thus, sequencing strong light intensity of green light wavelengths, then bluish green light wavelengths, and then blue light wavelengths, can provide for the maximum retinal stimulation. By way of example only, emit green for 1-5 seconds, emit bluish green for 10-60 seconds, then emit blue for 60 seconds, and so on . . . until the ocular photo-bio-stimulation is ceased.

In certain embodiments the ocular photo-bio-stimulation light can modulate within the range of, one of: 5 Hz to 15 Hz, 10 Hz to 20 Hz, or 40 Hz+/−20 Hz. In other embodiments the ocular photo-bio-stimulation light source cannot modulate and thus has zero Hz. In certain embodiments an invisible white light spectral flickering can occur. In certain embodiments by using blue light within the wavelength range of 480 nm+/−30 nm and modulating at 40 Hz+/−10 Hz, it can result in a significant improvement of one or more of: depression, cognitive ability, alertness, and decision making of the user. However, visually 40 Hz+/−10 Hz can be annoying and distracting for a user. In certain embodiments an invisible spectral flickering can occur. In certain other embodiments which reduces visual unpleasantness for the user, the ocular photo-bio-modulation light source can be modulated within the ranges between blue (450 nm-495 nm) and bluish green/cyan (495 nm-520 nm). In still other embodiments which reduce any visual unpleasantness, the ocular photo-bio-modulation light source can be modulated within the ranges between blue (450 nm-495 nm) and green (495 nm-570 nm). The ocular photo-bio-stimulation light can then stimulate, one or more of dopamine, serotonin, and/or norepinephrine in the brain. In certain embodiments by using blue light within the wavelength range of 480 nm+/−30 nm and modulation or flickering between 5 Hz and 15 Hz, or between 10 Hz and 12 Hz, the invention can be used to stimulate production or increase the production of dopamine in the eye's retina of the user.

Ocular Photo-Bio-Stimulation Electronic Display Screen with Controllable Lighted Border In certain embodiments a lighted border can comprise wavelengths of light within the range of 440 nm to 700 nm. The lighted border can be a white lighted border. The white light can comprise peaks of light wavelengths of; 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted border can provide ocular photo-bio-stimulation. The light intensity of lux given off from the lighted border can be one of, 500 lux or more, 1,000 lux or more, or 2,000 lux or more. When considering the light radiating in a cone light manner from the lighted border to strike the eye and face of the user or subject, the number of lumens given off from the lighted border can be one of, 25 lumens or more, 50 lumens or more, 100 lumens or more, or 200 lumens or more.

In certain embodiments an electronic display can comprise wavelengths of light within the range of 440 nm to 700 nm. The lighted border can be a white lighted border. The white light can comprise peaks of light wavelengths of; 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted electronic display can provide ocular photo-bio-stimulation. The lighted border can comprise wavelengths of light within the range of 440 nm to 700 nm. The lighted border can be a white lighted border. The white light can comprise peaks of light wavelengths of: 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted border can provide ocular photo-bio-stimulation. The light intensity of lux given off from the lighted border can be one of, 500 lux or more, 1,000 lux or more, or 2,000 lux or more. When considering the light radiating in a cone light manner from the lighted border to strike the eye and face of the user or subject, the number of lumens given off from the lighted border can be one of, 25 lumens or more, 50 lumens or more, 100 lumens or more, or 200 lumens or more.

In certain embodiments an ocular photo-bio-stimulation light source can comprise wavelengths of light within the range of 440 nm to 700 nm. The lighted border can be a white lighted border. The white light can comprise peaks of light wavelengths of 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted ocular photo-bio-stimulation light source can provide ocular photo-bio-stimulation. The light intensity of lux given off from the ocular photo-bio-stimulation light source can be one of, 500 lux or more, 1,000 lux or more, or 2,000 lux or more. When considering the light radiating in a cone light manner from the ocular photo-bio-stimulation light source to strike the eye and face of the user or subject, the number of lumens given off from the ocular photo-bio-stimulation light source can be one of, 25 lumens or more, 50 lumens or more, 100 lumens or more, or 200 lumens or more.

Biofeedback or diagnostics involving one or more of, pupil size increase, lid blink rate increase, heart rate increase, and/or blood oxygen level increase, can be an indication of increase production or stimulation of dopamine or norepinephrine in the brain and in some cases serotonin. An increase in contrast sensitivity, B wave amplitude of an ERG, scleral thickening, and/or slowing of axial length eye growth, can indicate an increase in the production of dopamine in the retina.

Figure 14:
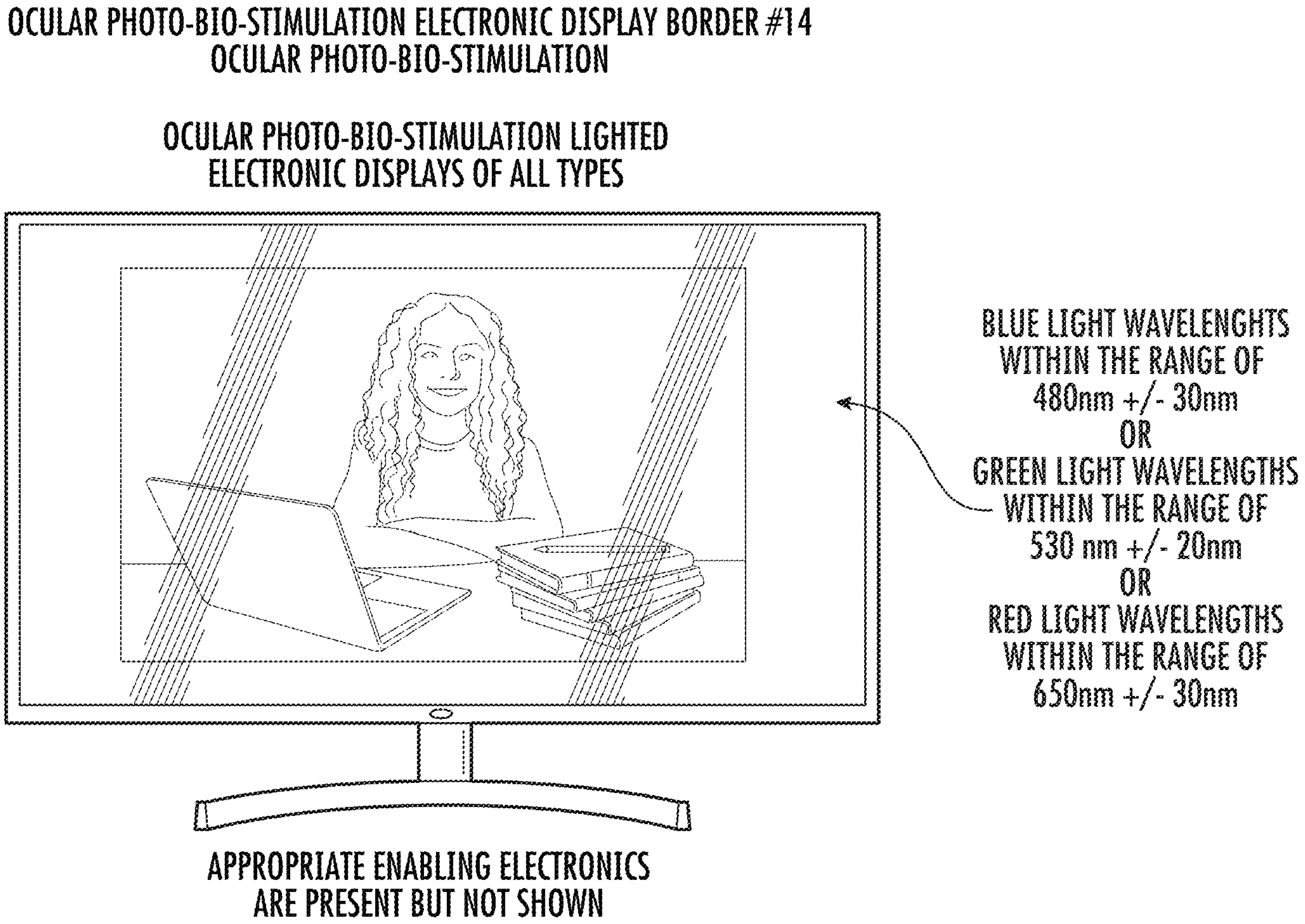
FIG. 14 shows an embodiment of the current invention as described herein.

In reference to FIG. 14, in embodiments, the border of any electronic display provides a lighted ocular photo-bio-stimulation therapy border. Such an electronic display can be, by way of example only, one of cell phone display screen, tablet display screen, laptop computer display screen, desktop computer display screen, or television display screen. By way of example only, in certain embodiments the display can be programed to provide for an outer peripheral zone (the lighted border) that provides ocular photo-bio-stimulation wavelengths of light while the central zone provides visual content, which can be in form or illustrations, letters, numbers or visual images (motion or still). The ocular photo-bio-stimulation border light can be programable with regards to one or more of: light intensity, wavelength, modulation or flicker, start time, and/or end time. The light can modulate by way of example only, within the range of one of 5 Hz to 15 Hz, 10 Hz to 20 Hz, or 40 Hz+/−20 Hz. The display can comprise a sensor to measure the distance from a user to the display and the light intensity can be automatically or manually adjusted to provide that appropriate level of light intensity required for the ocular photo-bio-stimulation therapy.

The light border can have an intensity of 400 lux or greater. The light border can have an intensity of 1,000 lux or greater. The light border can have an intensity of 5,000 lux or greater. The time of ocular photo-bio-stimulation treatment can be 5 minutes-10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more.

In embodiments when light wavelengths are generated by way of filtered optics or filtered lenses, the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In embodiments when light wavelengths are generated by a light emitter(s) if ambient lighting is present (including that of artificial light or sun light), the blended light wavelengths of the light emitter(s) and also the ambient light comprise wavelengths of light that strike the eye's retina, which fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

By way of example only, when the border light is part of the lighted electronic display, the electronic display can be programed for (by way of example only) 8:00 am so that a peripheral lighted border, having a light intensity and light wavelength band, within the electronic display area shows up while the central (non-peripheral border) becomes smaller in overall size. And this lighted border can be programed to turn off at (for example only) 11:00 am so that the central zone which is displaying the content and image(s) for the electronic display increases back to its original size. In this embodiment the electronic display screen or the housing device which houses the electronic display screen can identify the distance from the eye of the user and can automatically adjust the intensity and size and shape of the blue, green, or red-light border to be appropriate for such a distance. In a certain embodiment the electronic display screen or the housing of the electronic display screen comprises a distance sensor and optionally facial recognition. In addition, the border light intensity can be adjusted automatically or manually depending upon the ambient lighting available in the room or space. In certain embodiments a diffuser can be placed over the light emitters. In certain embodiments a filter or filters are used so to permit a higher concentration of wavelengths within the range of one of 480 nm+/−30 nm, 530 nm+/−20 nm, or 650 nm+/−30 nm, to be transmitted from the light source.

The lighted border can comprise wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The ocular photo-bio-stimulation effect targeted can be one or more of (by way of example only), increased dopamine in the eye; prevention of myopia; slowing or stopping myopia; healing myopia; improving myopia diagnosis; increasing one or more of dopamine, serotonin or norepinephrine in the brain; increasing alertness; and/or reducing depression severity.

The lighted border can comprise wavelengths within the range of at least one of: 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The ocular photo-bio-stimulation effect targeted can be one or more of (by way of example only), reduced pain severity, reduced frequency of headaches, and/or reduced frequency of migraines.

The same can be provided for a red-light border within the wavelengths 630 nm+/−20 nm or 650 nm+/−30 nm, or 650 nm-700 nm, or 700 nm+/−30 nm. The ocular photo-bio-stimulation effect targeted can be one or more of (by way of example only), increased mitochondrial health or mitochondrial numbers within the retina of the eye for the purposes of reducing the severity or improving a retinal disease/disorder such as one or more (by way of example only), dry AMD, retinitis pigmentosa, and/or diabetic retinopathy. In certain cases, the red wavelength border light can also be of help with dry eye conditions whereby the tear layer evaporates too quickly by way of stimulating the lids meibomian glands.

In certain embodiments the range of wavelength band includes the peaks of the most sensitive spectral points of rhodopsin (500 nm) and melanopsin (480 nm). This way both rhodopsin and melanopsin can be stimulated or excited. By way of example, by utilizing a filtered optic or lens that predominantly transmits within the wavelength range of at least one of 460 nm-520 nm or 470 nm to 520 nm, or by utilizing a light source or light emitter that predominately transmits within the wavelength range of at least one of 460 nm to 520 nm or 470 nm to 520 nm. This would include blue, bluish green and green wavelengths. This can be most beneficial when stimulating the production of increased dopamine in the retina of an eye. This can be most beneficial when stimulating the production of increased one or more of dopamine, serotonin or norepinephrine, in the brain by way of stimulating the retina of an eye.

An embodiment can be of an electronic display screen, wherein the electronic display screen comprises a programable ocular photo-bio-stimulation light border within the display screen, wherein the programable ocular photo-bio-stimulation light border provides one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, wherein the plurality of light emitters that generate the programable ocular photo-bio-stimulation light border are controllable, manually or automatically, with regards to one of intensity, on and/or off time, and/or wavelength band, and wherein one of the intensity of the ocular photo-bio-stimulation light border, or size of the ocular photo-bio-stimulation light border can be automatically adjusted depending upon one of distance from the face of the user or ambient light of the room or space. Further the programable border can be of any shape and can partially or fully surround a central area of the electronic display. The ocular photo-bio-stimulation light can comprise a timer to provide the appropriate level of ocular photo-bio-stimulation therapy.

Another embodiment can be that of an lighted electronic display screen frame, wherein the electronic display screen frame comprises an ocular photo-bio-stimulation light border around the display screen, wherein the programable ocular photo-bio-stimulation light border provides one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, wherein the plurality of light emitters that generate the programable ocular photo-bio-stimulation light border are controllable, manually or automatically, with regards to one or more of intensity, on and/or off time, and/or wavelength band, and wherein the intensity of the ocular photo-bio-stimulation light border is automatically adjusted depending upon one of distance from the face of the user or ambient light of the room or space. Further the programable border can be of any shape and can partially or fully surround a central area of the electronic display. The ocular photo-bio-stimulation light border can be one or more of, attachable to the display screen frame, attachable and detachable to the display screen frame, or built into and integral with the display screen frame.

The light border can have an intensity of 300 lux or greater. The light border can have an intensity of 400 lux or greater. The light can have an intensity of 1,000 lux or greater. The light can have an intensity of 5,000 lux or greater. The time of ocular photo-bio-stimulation treatment can be 5 minutes-10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more.

Ocular Photo-Bio-Stimulation Electronic Display Screen with Fixed Lighted Border Edge In certain embodiments a lighted border can comprise wavelengths of light within the range of 440 nm to 700 nm. The lighted border can be a white lighted border. The white light can comprise peaks of light wavelengths of; 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted border can provide ocular photo-bio-stimulation. The light intensity of lux given off from the ocular photo-bio-stimulation light source can be one of, 500 lux or more, 1,000 lux or more, or 2,000 lux or more. When considering the light radiating in a cone light manner from the ocular photo-bio-stimulation light source to strike the eye and face of the user or subject, the number of lumens given off from the ocular photo-bio-stimulation light source can be one of, 25 lumens or more, 50 lumens or more, 100 lumens or more, or 200 lumens or more.

In certain embodiments an electronic display can comprise wavelengths of light within the range of 440 nm to 700 nm. The lighted border can be a white lighted border. The white light can comprise peaks of light wavelengths of; 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted electronic display can provide ocular photo-bio-stimulation. The light intensity of lux given off from the ocular photo-bio-stimulation light source can be one of, 500 lux or more, 1,000 lux or more, or 2,000 lux or more. When considering the light radiating in a cone light manner from the ocular photo-bio-stimulation light source to strike the eye and face of the user or subject, the number of lumens given off from the ocular photo-bio-stimulation light source can be one of, 25 lumens or more, 50 lumens or more, 100 lumens or more, or 200 lumens or more.

In certain embodiments an ocular photo-bio-stimulation light source can comprise wavelengths of light within the range of 440 nm to 700 nm. The lighted border can be a white lighted border. The white light can comprise peaks of light wavelengths of, 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted ocular photo-bio-stimulation light source can provide ocular photo-bio-stimulation. The light intensity of lux given off from the ocular photo-bio-stimulation light source can be one of, 500 lux or more, 1,000 lux or more, or 2,000 lux or more. When considering the light radiating in a cone light manner from the ocular photo-bio-stimulation light source to strike the eye and face of the user or subject, the number of lumens given off from the ocular photo-bio-stimulation light source can be one of, 25 lumens or more, 50 lumens or more, 100 lumens or more, or 200 lumens or more.

Figure 15:
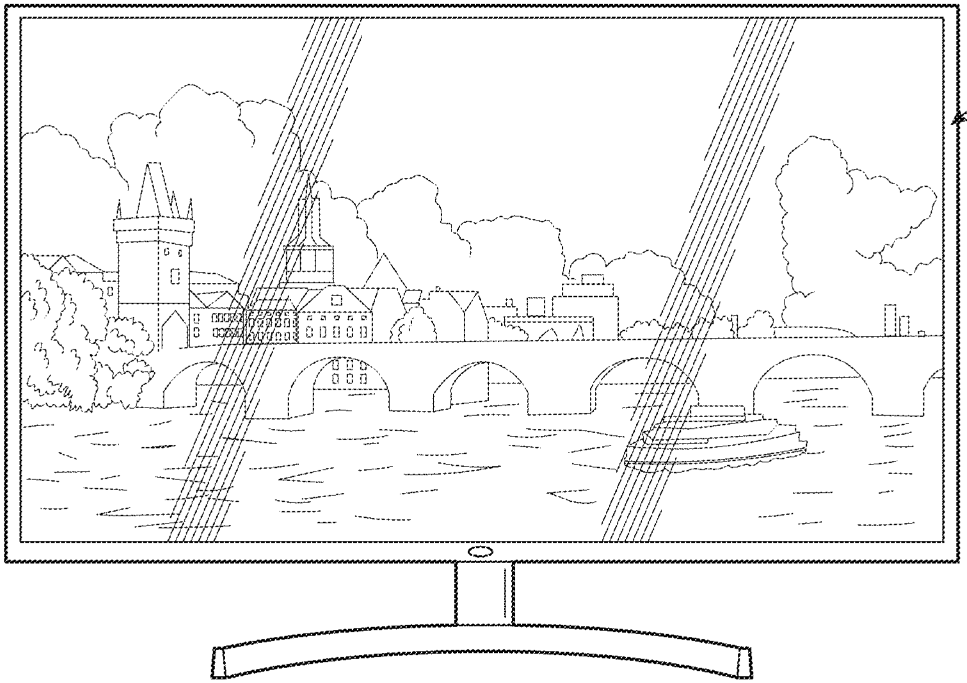
FIG. 15 shows an embodiment of the current invention as described herein.

In reference to FIG. 15, in certain embodiments, the border of any electronic display provides a lighted ocular photo-bio-stimulation therapy border. The embodiment can be a normal viewing screen with programable content that can be shrunk down to allow for an ocular photo-bio-stimulation border to be provided. By way of example only, an embodiment can be a blue light border comprising light wavelengths within the wavelength range of 480 nm+/−30 nm, with the media content being displayed centrally. Said another way the blue light border was fully or partially around the central media that was being displayed. The lighting provided can be automatic and timed to occur for certain periods of usage time or manually set by the user. It can be programed to provide desired light wavelength and intensity for providing ocular photo-bio-stimulation therapy. Such an electronic display can be, by way of example only, a cell phone display screen, tablet display screen, laptop computer display screen, desktop computer display screen, or television display screen. Such a lighted border can be that of a lighted frame itself that houses the display, or a light that attaches to the display screen's outer frame. The photo-bio-stimulation border light can be programable with regards to one or more of: light intensity, wavelength, modulation or flicker, start time, and/or end time. If the border light is fixed to the frame of the electronic display or built into the frame of the electronic display, the size of the border light will be of a fixed size. The ocular photo-bio-stimulation light can comprise a timer to provide the appropriate time for photo-bio-stimulation therapy In embodiments when light wavelengths are generated by way of filtered optics or filtered lenses, the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In embodiments when light wavelengths are generated by a light emitter(s) if ambient lighting is present (including that of artificial light or sun light), the blended light wavelengths of the light emitter(s) and also the ambient light comprise wavelengths of light that strike the eye's retina, which fall within the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm.

For the purposes of this disclosure, the frame of the display screen can be the outer edge or a frame that goes around the outer edge. In certain embodiments a diffuser can be placed over the light emitters. In certain embodiments a filter or filters are used so to permit a higher concentration of wavelengths within the range of one of 480 nm+/−30 nm, 530 nm+/−20 nm, or 650 nm+/−30 nm, to be transmitted from the light source. The photo-bio-stimulation light can modulate. The photo-bio-stimulation light can be comprised of a plurality of light emitters.

The lighted border can comprise wavelengths within the range of at least one of: 441 nm or greater, or 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm. The ocular photo-bio-stimulation effect targeted can be one or more of (by way of example only), increased dopamine in the eye, prevention of myopia, slowing or stopping myopia, increasing dopamine in the brain, increasing alertness, and/or reducing depression severity.

The lighted border can comprise wavelengths within the range of at least one of: 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. The ocular photo-bio-stimulation effect targeted can be one or more of (by way of example only), reduced pain severity, reduced frequency of headaches, and/or reduced frequency of migraines.

The same can be provided for a red-light border within the wavelengths 630 nm+/−20 nm or 650 nm+/−30 nm, or 650 nm-700 nm. The ocular photo-bio-stimulation effect targeted can be one or more of (by way of example only), increased mitochondrial health or mitochondrial numbers within the retina of the eye for the purposes of reducing the severity or improving a retinal disease/disorder such as one or more (by way of example only), dry AMD, retinitis pigmentosa, and/or diabetic retinopathy. In certain cases, the red wavelength border light can also be of help with dry eye conditions whereby the tear layer evaporates too quickly.

In certain embodiments the range of wavelength band includes the peaks of the most sensitive spectral points of rhodopsin (500 nm) and melanopsin (480 nm). This way both rhodopsin and melanopsin can be stimulated or excited. By way of example, by utilizing a filtered optic or lens, that predominantly transmits within the wavelength range of 460 nm-520 nm or 470 nm to 520 nm, or by utilizing a light source or light emitter that predominately transmits within the wavelength range of 460 nm to 520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

In embodiments, to stimulate the production of serotonin and/or dopamine in the brain, light wavelengths within the range of 700 nm+/−30 nm can be utilized. Wavelengths of 710 nm LED light has been shown to not have any detrimental effect on dopamine neurons in substantia nigra of the brain.

By way of example only, utilizing a 2024 iPhone 16 the following would apply in determining the border size needed to stimulate dopamine in the eye of the user and/or one or more of dopamine, serotonin or norepinephrine in the brain. This assumes the iPhone is held 11 inches from the eye of a 12-year-old user, that the user is wearing clear glasses (no filter), and that the user's eye is attenuating the blue light at a rate of 30% before striking the child's retina, and upon striking the retina of the child's eye the light does so with an intensity of 400 lux. The iPhone 16 maximum brightness of white light is 2,000 nits, thus 186 lumens. The size of iPhone 16 pro screen measures 66 mm×144 mm or 9,504 square mm. That is ~0.02 lumens per square mm. Therefore, if 60 lumens of light intensity are needed to impart 400 lux or more on the retina of an eye. The need is for a minimum of 3,000 square mm of lumens coming off of the cell phone display. Therefore, to have a peripheral zone of the cell phone display, around text messages of 8 mm×144 mm×2 or two sides of screen=2,304 square mm (vertically) and 8 mm×(66 m-16 mm or 50 mm)×2 for two sides of screen=800 mm (horizontally). The total square mm of a peripheral zone around the cell phone display of an iPhone 16 that is approximately 8 mm wide would equal approximately 3,104 square mm. Thus, having an 8 mm peripheral border of white light around the image or text on an iPhone 16 would appear to be sufficient for providing 60+ lumens of light, in this particular example only. That would leave 66 mm-16 mm or 50 mm by 144 m-16 mm or 128 mm. Thus, the screen size would be 50 mm×128 mm for text, email, or games when the border appeared to provide light therapy.

The time of stimulation of the retina can affect the retina sensitivity (which includes melanopsin, rhodopsin, and cones' opsin). The longer the time of ocular photo-bio-stimulation exposure the less sensitive the retina, which causes a shift of sensitivity to lower light wavelengths of light. By way of example, 1 second of exposure is most sensitive by the retina at 510 nm; 10 seconds of exposure at 500 nm; and/or 100 seconds of exposure at 480 nm. In certain embodiments the color of the ocular photo-bio-stimulation light can be alternated in a sequence. By way of example only green wavelengths, then blue green wavelengths, then blue wavelengths. In other embodiments, green wavelengths, then blue green wavelengths, then blue wavelengths, then white light. This can be done to maximize the stimulation effect of light wavelength versus time on retinal excitation. Said another way, first (for a short period of time) have the green light wavelengths excite the retina, then the bluish green wavelengths, and the longer the time period have the blue light wavelengths excite the retina. Thus, sequencing strong light intensity of green light wavelengths, then bluish green light wavelengths, and then blue light wavelengths provides for the maximum retinal stimulation. By way of example only, green for 1-5 seconds, bluish green for 10-60 seconds, then blue for 60 seconds, and so on, until the ocular photo-bio-stimulation is ceased. While time of stimulation shifts the retinal sensitivity to the left and lower wavelengths, age shifts the sensitivity of melanopsin to the right.

In certain embodiments, the ocular photo-bio-stimulation light can modulate within the range of at least one of: 5 Hz to 15 Hz, 10 Hz to 20 Hz, and/or 40 Hz+/−20 Hz. In other embodiments the ocular photo-bio-stimulation light source cannot modulate and thus has zero Hz. In certain embodiments an invisible white light spectral flickering can occur. In certain embodiments by using blue light within the wavelength range of 480 nm+/−30 nm and modulating at 40 Hz+/−10 Hz, the invention can result in a significant improvement in the subject's improving one or more of: depression, cognitive ability, alertness, and decision making. However, visually 40 Hz+/−10 Hz can be annoying and distracting for a user. In certain embodiments an invisible spectral flickering can occur. In certain other embodiments which reduce visual unpleasantness for the driver or user, the ocular photo-bio-modulation light source can be modulated within the ranges between blue (450 nm-495 nm) and bluish green/cyan (495 nm-520 nm). In still other embodiments which reduce visual unpleasantness, the ocular photo-bio-modulation light source can be modulated within the ranges between blue (450 nm-495 nm) and green (495 nm-570 nm). The ocular photo-bio-stimulation light can then stimulate, one or more of dopamine, serotonin, and/or norepinephrine in the brain. In certain embodiments by using blue light within the wavelength range of 480 nm+/−30 nm and modulation or flickering between 5 Hz and 15 Hz, or between 10 Hz and 12 Hz, the invention can be used to stimulate production or increase the production of dopamine in the eye's retina of the user.

Ocular Photo-Bio-Stimulation Steering Wheel, dashboard, or instrument panel of a Vehicle.

Ocular photo-bio-stimulation while driving, flying, or navigating a vehicle on land, sea, or air, can be used to increase alertness, improve cognitive ability, and speed decision-making. Ocular photo-bio-stimulation has been shown to increase one or more of dopamine, serotonin or norepinephrine in the brain. Biofeedback involving one or more of, pupil size increase, lid blink increase, heart rate increase, and/or blood oxygen level increase, can be an indication of increased production or stimulation of dopamine or norepinephrine in the brain and in some cases serotonin.

The amount of required light intensity given off by an ocular photo-bio-stimulation artificial light source (not the sun) is dependent upon the distance of the light source from the eye of the subject receiving ocular photo-bio-stimulation treatment, the age of the subject, and whether or not the subject is wearing an eyeglass that either filters or refracts light. In most, but not all cases, for light sources that give off ocular photo-bio-stimulation which are 12 inches away from the eye of the subject, the light intensity needs to be at least one of: 60 lumens of more, 80 lumens or more, or 100 lumens or more, leaving the ocular photo-bio-stimulation light source. By way of example only, if the ocular photo-bio-stimulation light source is located on or in the steering wheel, the number of lumens required of the light source would be less than if the ocular photo-bio-stimulation light source was located on or in the dashboard. The preference is for 400 lux of ocular photo-bio-stimulation light or more to strike the retina of the eye of the subject for a period of time in order for the subject to have the desired physiological response.

Additionally, in certain embodiments, the ocular photo-bio-stimulation light can modulate within the range of at least one of: 5 Hz to 15 Hz, 10 Hz to 20 Hz, or 40 Hz+/−20 Hz. In other embodiments the light cannot modulate and thus has Zero Hz. By using blue light within the wavelength range of 480 nm+/−30 nm and modulating at 40 Hz+/−10 Hz, the invention can result in a significant improvement in one or more of the subject's mood, cognitive ability, alertness, and decision making. However, visually 40 Hz+/−10 Hz can be annoying and distracting for a user or driver. In certain embodiments an invisible spectral flickering can occur. In certain other embodiments which reduces visual unpleasantness for the driver or user, the ocular photo-bio-modulation light source can be modulated within the ranges between blue (450 nm-495 nm) and bluish green/cyan (495 nm-520 nm). In still other embodiments which reduce visual unpleasantness, the ocular photo-bio-modulation light source can be modulated within the ranges between blue (450 nm-495 nm) and green (495 nm-570 nm). The ocular photo-bio-stimulation light can stimulate, one or more of dopamine, serotonin, or norepinephrine in the brain.

In still other embodiments when the ocular photo-bio-stimulation light source comes on it remains with a lower level of modulation (including zero modulation), however the steering wheel can vibrate at a modulation rate of 40 Hz+/−10 Hz during the time of which ocular photo-bio-stimulation is occurring. The ocular photo-bio-stimulation light and vibration can then stimulate one or more of dopamine, or serotonin, norepinephrine in the brain. In certain embodiments the grip portion of the steering wheel is what vibrates, and in other embodiments the hub and the grip section vibrate. In other embodiments the steering wheel and the seat vibrate at 40 Hz+/−10 Hz. In still other embodiments only the steering wheel vibrates at a modulation rate of 40 Hz+/−10 Hz without any ocular photo-bio-modulation for the purposes of one or more of, improving mood, increasing alertness, increasing cognitive ability, and speeding decision-making. And in still other embodiments the steering wheel and the seat vibrate at 40 Hz+/−10 Hz without any ocular photo-bio-stimulation.

In still other embodiments when the ocular photo-bio-stimulation light source comes on it remains with a lower level of modulation (including zero modulation), however the driver's seat can vibrate at a modulation rate of 40 Hz+/−10 Hz during the time of which ocular photo-bio-stimulation is occurring. The ocular photo-bio-stimulation light and vibration can then stimulate, one or more of dopamine, serotonin, or norepinephrine in the brain. In certain embodiments the bottom of the seat (which the driver sits on) is what vibrates, and in other embodiments the bottom of the seat (which the driver sits on) and the seat back section vibrate. In other embodiments the driver's seat vibrates, and the ocular photo-bio-stimulation occurs at 40 Hz+/−10 Hz. In still other embodiments only the driver's seat vibrates at a modulation rate of 40 Hz+/−10 Hz without any ocular photo-bio-modulation for the purposes of one or more of increasing alertness, increasing cognitive ability, and speeding decision-making. And in still other embodiments the driver's seat and the steering wheel vibrate at 40 Hz+/−10 Hz without any ocular photo-bio-stimulation.

In certain embodiments an ocular photo-bio-stimulation light source can comprise wavelengths of light within the range of 440 nm to 700 nm. The white light can comprise peaks of light wavelengths of; 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted ocular photo-bio-stimulation light source can provide ocular photo-bio-stimulation. The light intensity of lux given off from the ocular photo-bio-stimulation light source can be one of, 500 lux or more, 1,000 lux or more, or 2,000 lux or more. When considering the light radiating in a cone light manner from the ocular photo-bio-stimulation light source to strike the eye and face of the user or subject, the number of lumens given off from the ocular photo-bio-stimulation light source can be one of, 50 lumens or more, 100 lumens or more, or 200 lumens or more. The light emitter(s) can be covered by a diffuser. The light emitters can be without a diffuser.

Figure 16:
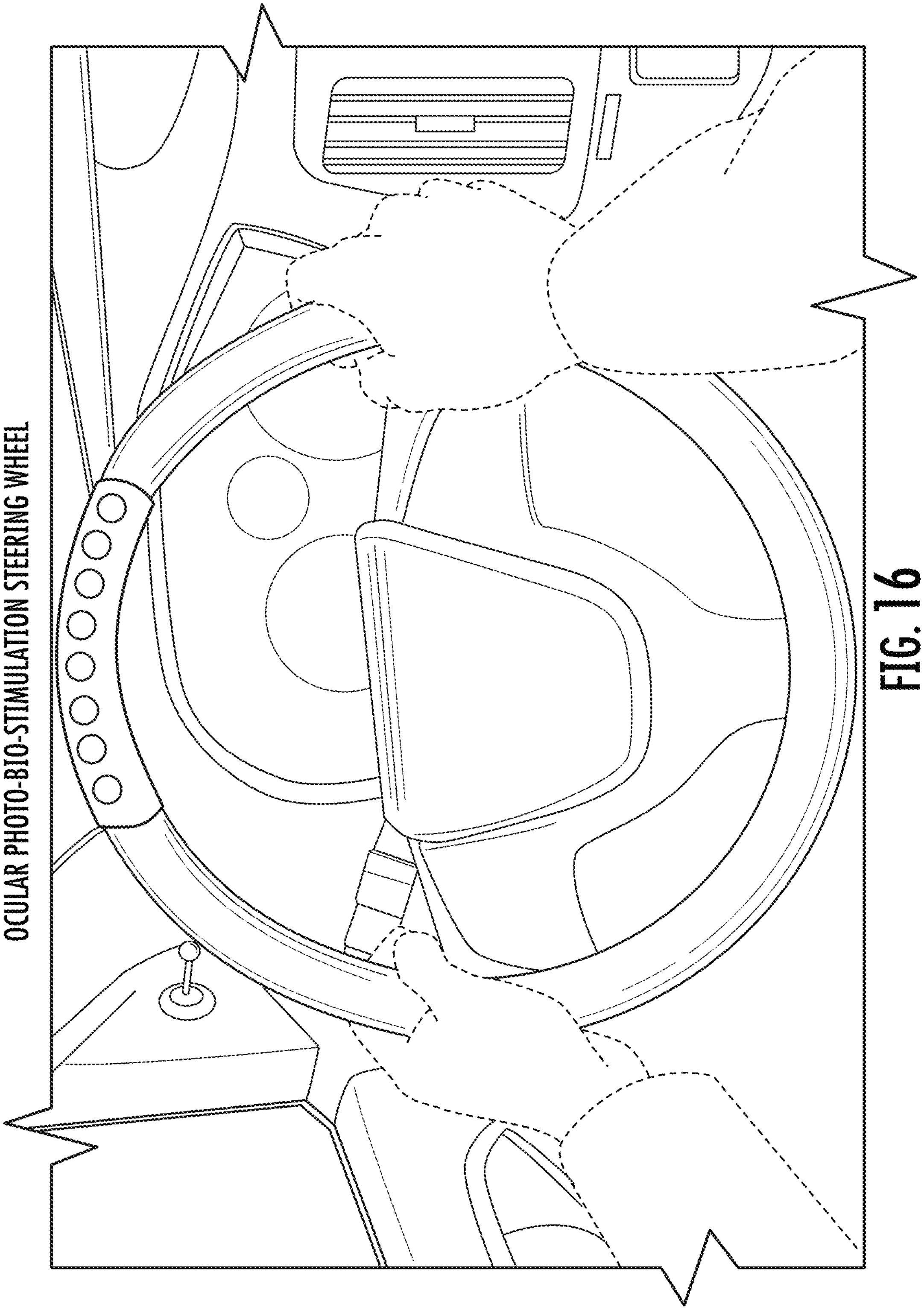
FIG. 16 shows an embodiment of the current invention as described herein, with the invention shown at the top of the steering wheel.

In reference to FIG. 16, embodiments include an ocular photo-bio-stimulation approach that can be implemented to keep a driver of a vehicle alert when driving day or night. The embodiment can be that of a system that comprises an ocular photo-bio-stimulation light source, a steering wheel or a portion of a steering wheel, one or more sensors, electronics, and optional artificial intelligence (AI). In certain other embodiments the system can also include vibration of the steering wheel, use of the radio, and an optional personal assistant.

An ocular photo-bio-stimulation light source can be attached to or incorporated with a portion of the steering wheel having wavelengths of light within the wavelength range of one or more of, 480 nm+/−30 nm (blue and blue green), 530 nm+/−20 nm (green), and/or 650 nm+/−30 nm (red). The ocular photo-bio-stimulation light source can provide a light intensity of 250 lux or more, 500 lux or more, 1,000 lux or more, or 2,000 lux or more. The ocular photo-bio-stimulation light source can provide a light intensity of 50 lumens or more, 100 lumens or more, 250 lumens or more, or 500 lumens or more. The light striking the retina of the eye of the driver can be 300 lux or more, 400 lux or more, or 500 lux or more. Ocular photo-bio-stimulation has been shown to stimulate one or more of dopamine, serotonin or norepinephrine in the brain.

The ocular photo-bio-stimulation light source can be attachable, detachable, or permanently built into a steering wheel. The ocular photo-bio-stimulation light source can be built into the rim or grip section of a steering wheel. The ocular photo-bio-stimulation light source can be attached to the rim or grip section of a steering wheel. The ocular photo-bio-stimulation light source can be built into a portion of the central or hub portion of a steering wheel. The ocular photo-bio-stimulation light source can be attached to the central or hub portion of a steering wheel. The ocular photo-bio-stimulation light source can be built into a portion of the dashboard of a vehicle. The ocular photo-bio-stimulation light source can be attached to portion of the dashboard of a vehicle. The system can comprise its own power source. The system can utilize the electrical power of the automobile.

The ocular photo-bio-stimulation light source or its light emitter(s) can be manually or automatically adjustable so as to be pointed or angled upward such that an imaginary straight line can be drawn from the center of a light emitter directly entering the pupil of the driver's eye. It is important that the light rays from ocular photo-bio-stimulation light source are not blocked by the upper lids of the driver.

The ocular photo-bio-stimulation light source can be programed to come on after a timed period of driving. It can be timed to remain on for a timed period. The control can be automatic or manual. The light can be modulated or flicker when being used if desired. The ocular photo-bio-stimulation effect targeted is, in aspects, increased alertness of the driver, improved cognitive ability, faster decision making and faster reaction time. The ocular photo-bio-stimulation light source can comprise a sensor to measure the distance from a user to the ocular photo-bio-stimulation light source and the light intensity can be automatically or manually adjusted to provide that appropriate level of light intensity required for the ocular photo-bio-stimulation effect based upon at any given time the distance of the driver's eyes from the ocular photo-bio-stimulation light source.

The steering wheel can comprise sensors to determine if the driver is becoming less alert. The dashboard can comprise sensors to determine if the driver is becoming less alert. The automobile or vehicle can comprise sensors to determine if the driver is becoming less alert. Should the sensors detect that the driver is becoming less alert or falling asleep, the sensors can cause the ocular photo-bio-stimulation light source to automatically turn on or change. In some embodiments the sensors can also cause the steering wheel to vibrate. In still other embodiments the sensors can also cause the horn to sound.

In still other embodiments the sensors can also cause a personal assistant to orally by way of the radio, in aspects, to wake up and/or pull over. In certain embodiments facial recognition within the automobile or vehicle can learn and identify the driver's identity and sense the amount of drive time when the specific driver becomes less alert. Thus, in this embodiment, the automobile or vehicle will know in advance certain driving habits of the driver and will then turn on and off the ocular photo-bio-stimulation light source in accordance with those learned driving habits or experiences of the driver. Artificial intelligence (AI) and ML can be incorporated within the embodiment to optimize the desired physiological effect for the driver.

Biofeedback or diagnostics involving one or more of, pupil size increase, lid blink rate increase, heart rate increase, and/or blood oxygen level increase, can be an indication of increase production or stimulation of dopamine or norepinephrine in the brain and in some cases serotonin. An increase in contrast sensitivity, B wave amplitude of an ERG, scleral thickening, and/or slowing of axial length eye growth indicates an increase in the production of dopamine in the retina.

Such an ocular photo-bio-stimulation approach can be that of utilizing a blue, bluish green, or green light emitter(s), having one or more blue wavelengths within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. Such a light can be built into, by way of example only, the steering wheel or steering device of the vehicle. In certain other cases it can be built into the dashboard or instrument panel of the vehicle, such as directly in front of the steering wheel. In embodiments a sensor can identify the distance from the eye of the user and can automatically adjust the intensity of the blue light to be appropriate for such a distance.

In embodiments when light wavelengths are generated by way of filtered optics or filtered lenses, the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In embodiments when light wavelengths are generated by a light emitter(s) if ambient lighting is present (including that of artificial light or sun light), the blended light wavelengths of the light emitter(s) and also the ambient light comprises wavelengths of light that strike the eye's retina fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

In addition, the blue light intensity can be automatically or manually adjusted depending upon the ambient lighting available within the vehicle (or outside the vehicle). Further, the time for the lighted ocular photo-bio-stimulation stimulation can be set manually or automatically for the driver of the car. In certain embodiments facial recognition can be utilized. By way of example only, the blue light can be programmed to turn on after a driver has driven for one hour and can remain on for 30 minutes. It further can be programmed (by way of example only) to come on every hour and off every hour. The light can also be programmed to modulate or flicker. In addition, vibration and or sound can be programmed to occur at certain intervals when the blue light is either on or off. The light can be further programmed to turn on if the car senses the driver is not alert. In certain embodiments a diffuser can be placed over the light emitters. In certain embodiments a filter or filters are used to permit a higher concentration of wavelengths within the range of 480 nm+/−30 nm to be transmitted from the light source. Artificial intelligence (AI) and ML can be incorporated within the embodiment to optimize the desired physiological effect for the driver.

The light can have an intensity of 300 lux or greater. The light can have an intensity of 400 lux or greater. The light can have an intensity of 1,000 lux or greater. The light can have an intensity of 5,000 lux or greater. The time of ocular photo-bio-stimulation treatment can be 5 minutes-10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more. The light can modulate. The light can flicker. The light can modulate within the range of one of 5 Hz to 15 Hz, 10 Hz to 20 Hz, or 40 Hz+/−20 Hz.

An embodiment can be that of an ocular photo-bio-stimulation light within a vehicle, wherein the ocular photo-bio-stimulation light provides blue wavelengths of light predominantly within the wavelength range of 480 nm+/−30 nm, and wherein one of, the intensity of the ocular photo-bio-stimulation light, or the size or location of the ocular photo-bio-stimulation light, is automatically adjusted depending upon one of distance from the face of the user or ambient light of the vehicle (and/or outside the vehicle). The ocular photo-bio-stimulation light can comprise a timer to provide the appropriate level of ocular photo-bio-stimulation therapy.

An embodiment of the invention which can be utilized to improve the alertness of any pilot, driver, or steerer of a vehicle, and can be a system that employs blue, bluish green or green light of the wavelengths predominantly within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm, and wherein the blue light strikes the retina of the eye(s) of the pilot, driver, or steerer of the vehicle, is hereby disclosed. Such a vehicle can be that of any vehicle, for example only, car, automobile, truck, bus, subway, trolley, tram, train, aircraft, spaceship, boat, ocean liner, cargo ship, or ship. The blue light can be releasably attachable and detachable to the steering wheel or integrated into the steering wheel. The blue light can paint the retinas of the wearer's eyes as the steering wheel is rotated or turned while driving. The blue light can be releasably attachable and detachable to the dashboard or integrated into the dashboard. The blue light emitter can be any light emitter that emits blue light predominantly within the wavelength range of 450 nm to 510 nm or 480 nm+/−30 nm. The blue lights can be programed to turn on automatically when the pilot, driver, or steerer of the vehicle shows signs of fatigue. The blue lights can be turned on manually when the pilot, driver, or steerer of the vehicle feels signs of fatigue. The blue lights can be modulated to turn on for X period of time and turn off for Y period of time. The lights can be set to turn on for, by way of example, only 2 minutes every 2 hours of driving time and then turned off until it is time for them to be turned on. This timing sequence can be set manually by the driver or automatically programmed. The intensity of the blue lights can become brighter during daytime and less bright during nighttime. The lights can be controlled by a dimmer or programed to maintain a certain intensity depending upon ambient light in the vehicle. The blue lights can be manually adjusted towards the eyes of pilot, driver, or steerer of the vehicle. Artificial intelligence (AI) can be incorporated within the embodiment to optimize the desired physiological effect for the driver.

While the above discusses using blue light predominantly within the wavelength range of 450 nm-510 nm, red light within the wavelength range of 650 nm+/−30 nm or 700 nm+/−30 nm can be used in place of the blue light, or a combination of blue light and red-light wavelengths predominantly within the range of 450 nm-510 nm and of 650 nm+/−30 nm can be utilized. This is due to the fact that the light wavelengths predominantly within the ranges of 450 nm-500 nm, of 650 nm-700 nm, or of 700 nm+/−30 nm, produce dopamine and increase alertness. In certain cases, for morning hours the blue light of wavelengths predominantly within the range of 450 nm to 500 nm are used and for afternoon hours red light predominantly within the wavelength ranges of 620 nm-700 nm or of 700 nm+/−30 nm are used.

The steering wheel can comprise one or more pressure sensor(s) such that when the pilot, driver, or steerer feels tired or desires to manually set such a hand pressure sensitive system, it can be set to the pressure threshold as desired by the pilot, driver, or steerer. So long as the pilot, driver, or steerer exerts the set hand pressure, the system (within certain limits) will function as if it is dormant, however, should the pressure become relaxed, and an established relaxed pressure threshold become met, an alert system within the car can cause the driver to become more awake or alert. Such a system can use, by way of example only, sound, light, electrical shock, and/or vibration to increase the alertness of the pilot, driver, or steerer. In certain embodiments for use with blue lighting of the wavelengths within the range of 450 nm-510 nm for a vehicle as disclosed above, or for the steering wheel pressure system disclosed, a vision system can also be utilized to further identify the lack of alertness on the part of the pilot, driver, or steerer. In certain other embodiments for use with red lighting of the wavelengths within the range of 650 nm+/−30 nm for a vehicle as disclosed herein, or for the steering wheel pressure system disclosed, a vision system can also be utilized to further identify the lack of alertness on the part of the pilot, driver, or steerer. Artificial intelligence (AI) can be incorporated within the embodiment to optimize the desired physiological effect for the driver.

Ocular Photo-Bio-Stimulation Light, Lamp or Light Box.

In certain embodiments an ocular photo-bio-stimulation light source can comprise wavelengths of light within the range of 440 nm to 700 nm. The lighted border can be a white lighted border. The white light can comprise peaks of light wavelengths of 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted ocular photo-bio-stimulation light source can provide ocular photo-bio-stimulation. The light intensity of lux given off from the ocular photo-bio-stimulation light source can be one of, 500 lux or more, 1,000 lux or more, 2,000 lux or more, 5,000 lux or more, or 10,000 lux or more. When considering the light radiating in a cone light manner from the ocular photo-bio-stimulation light source to strike the eye and face of the user or subject, the number of lumens given off from the ocular photo-bio-stimulation light source can be one of, 10 lumens or more, 25 lumens or more, 50 lumens or more, 100 lumens or more, or 200 lumens or more.

Figure 17:
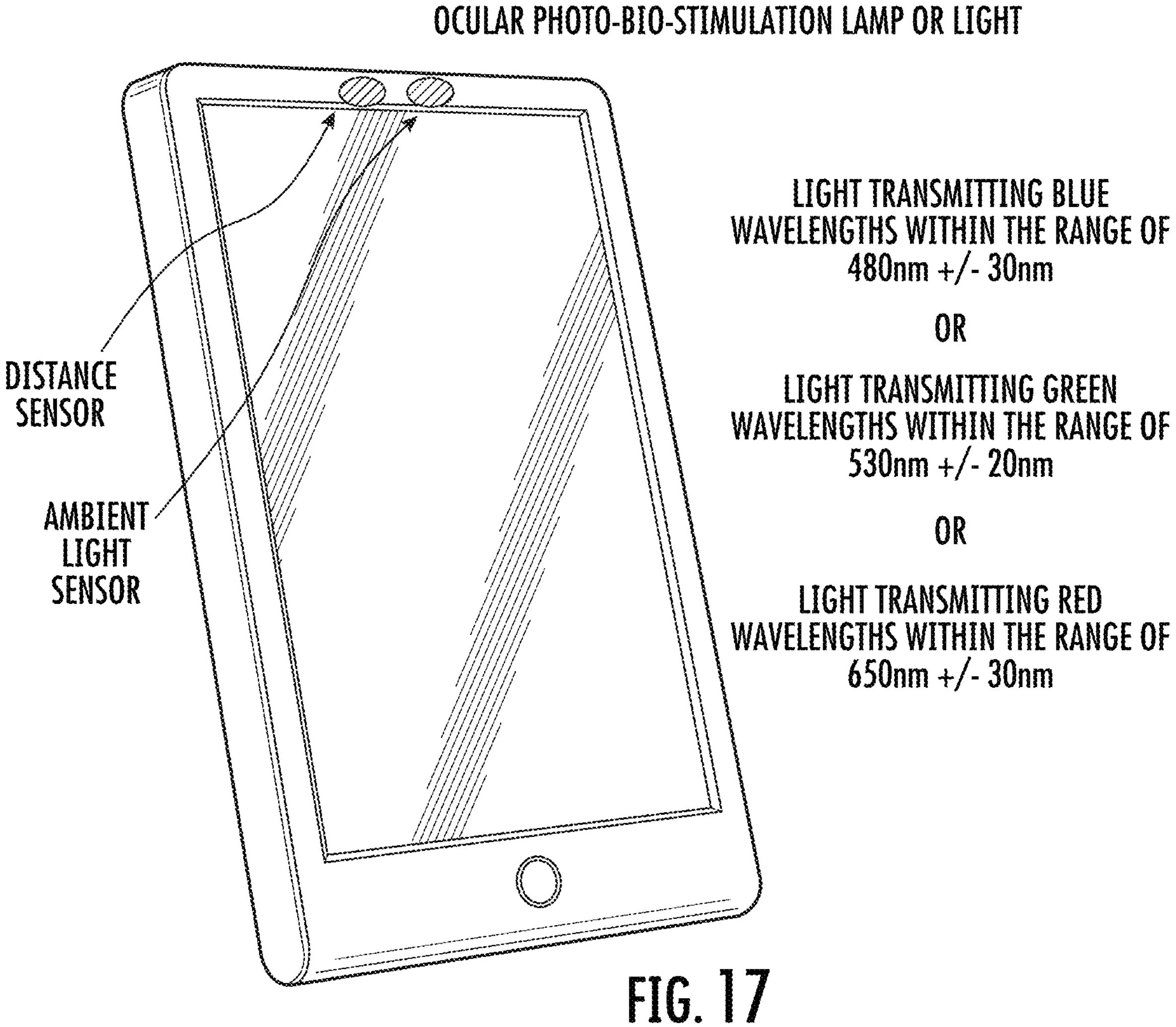
FIG. 17 shows an embodiment of the current invention as described herein.
Figure 18:
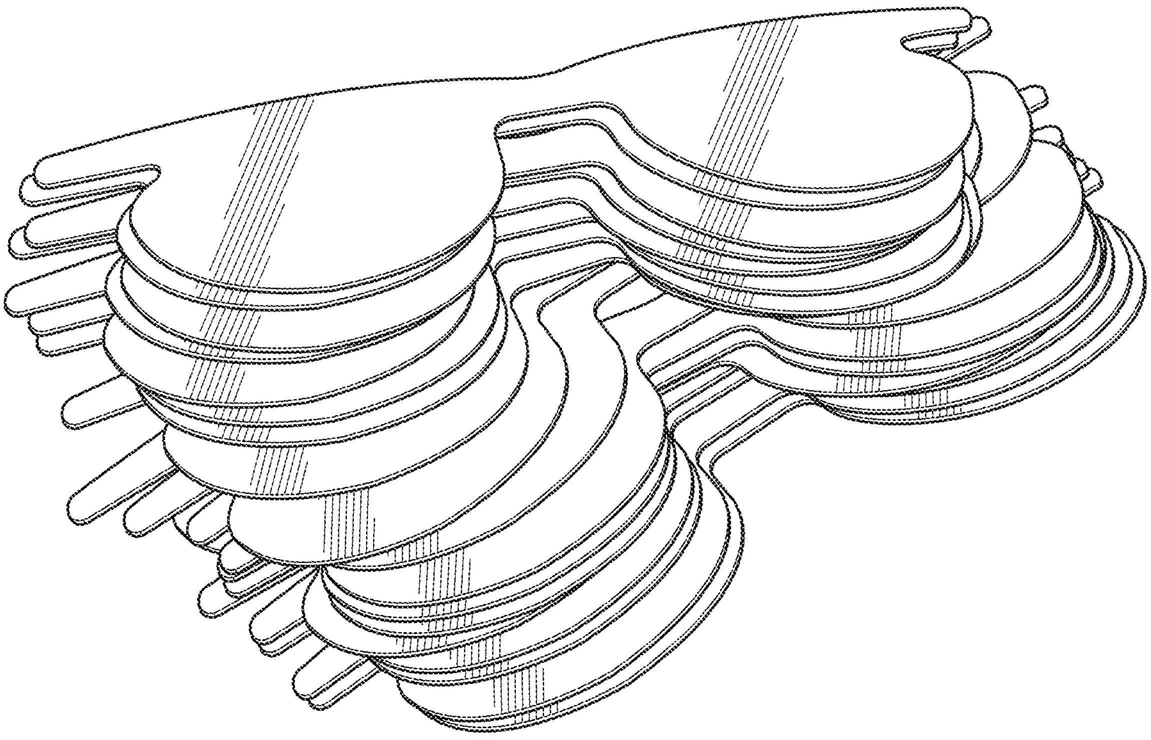
FIG. 18 shows an embodiment of the current invention as described herein.
Figure 19A:
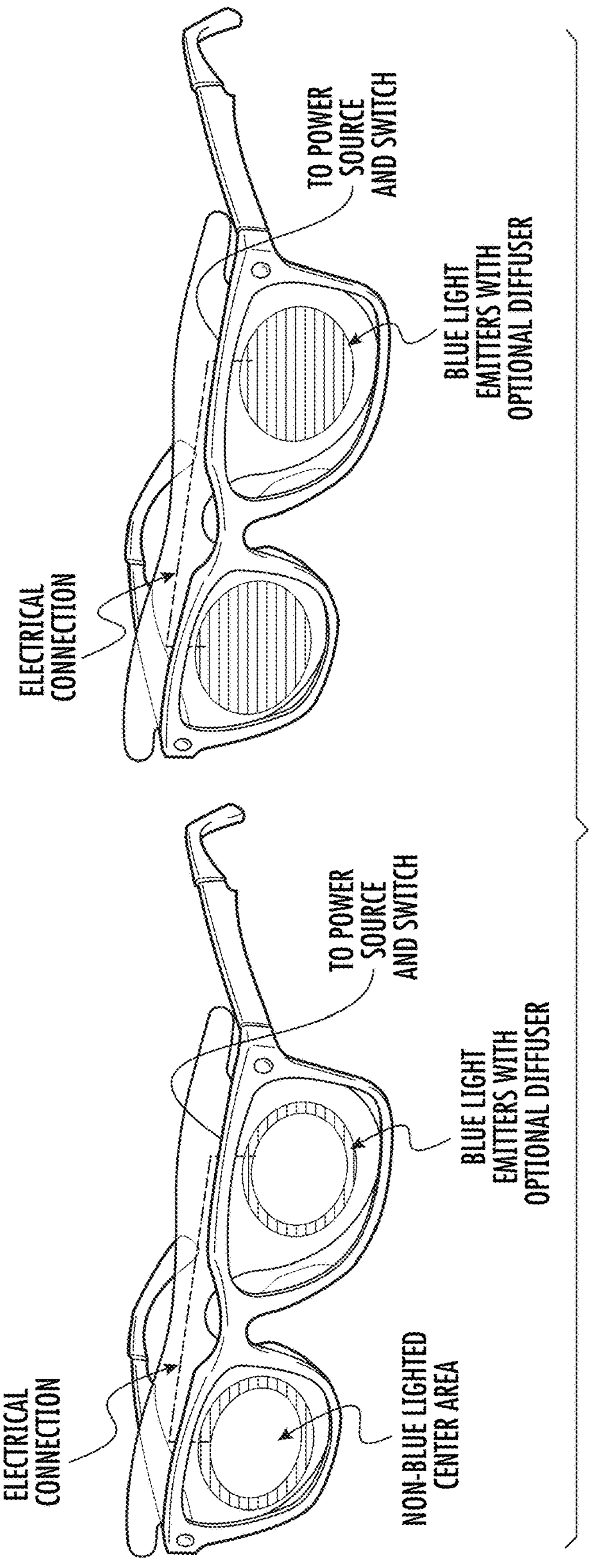
FIG. 19A-F shows an embodiment of the current invention as described herein.
Figure 19B:
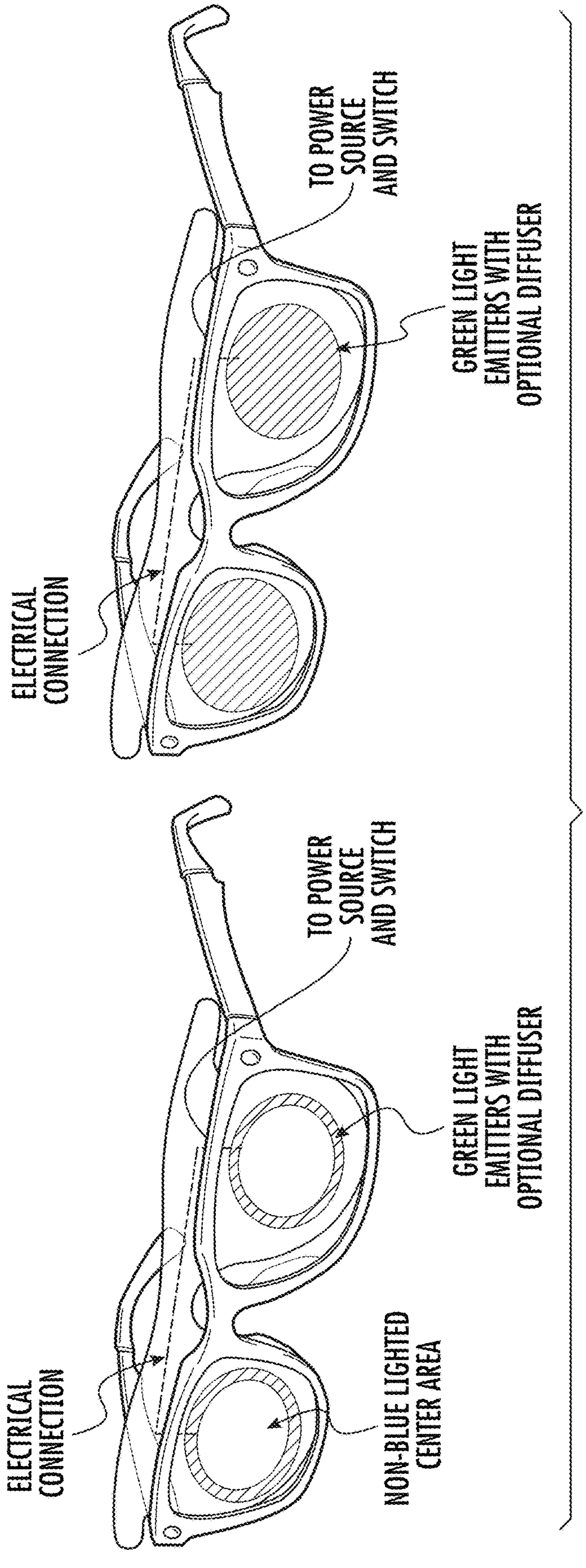
Figure 19C:
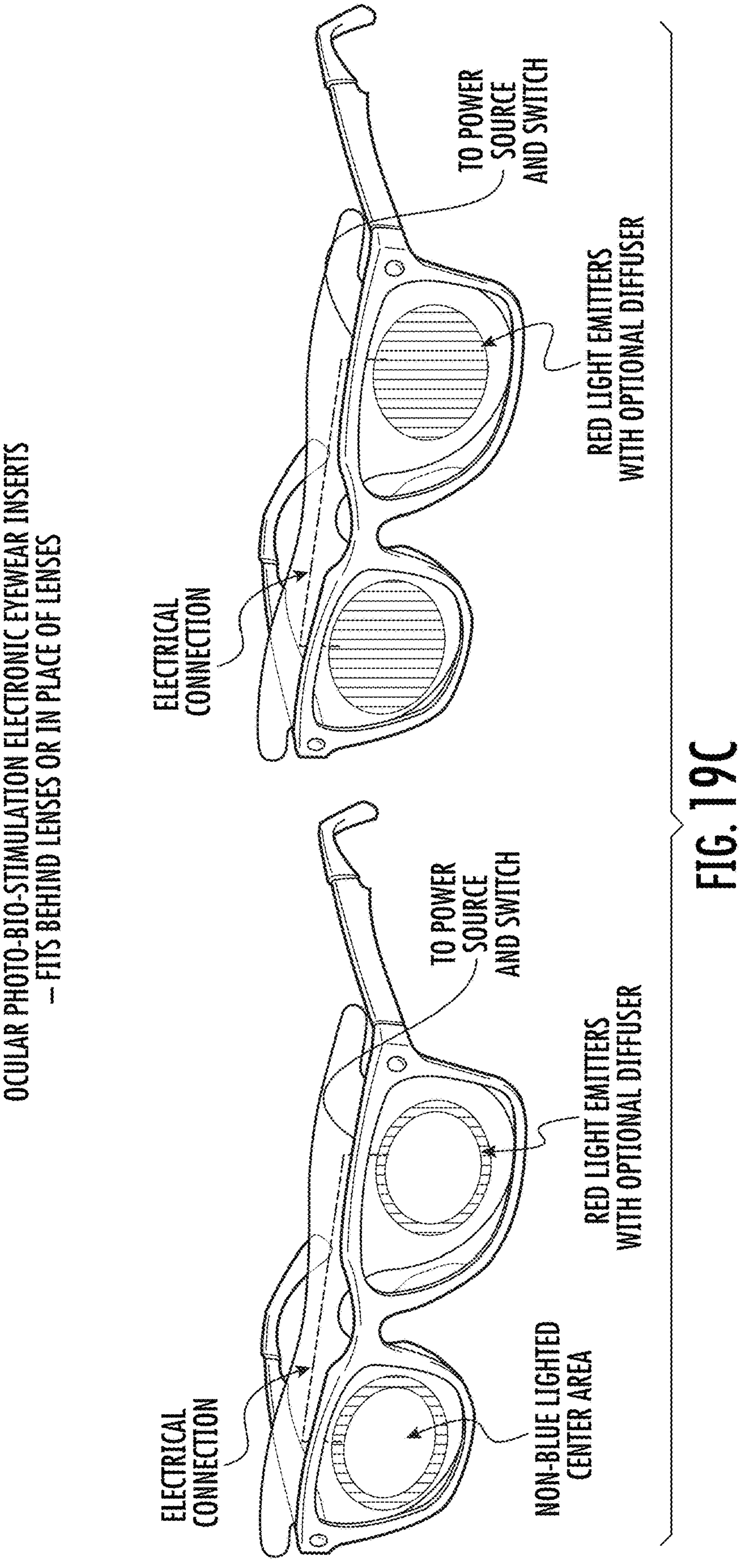
Figure 19D:
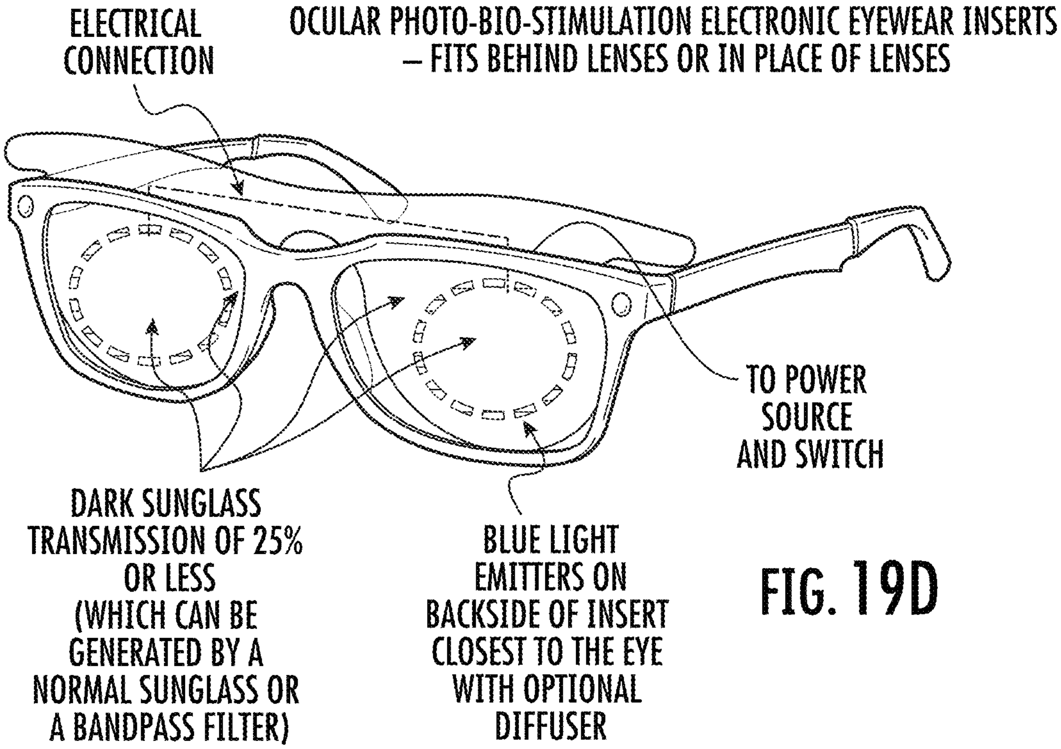
Figure 19E:
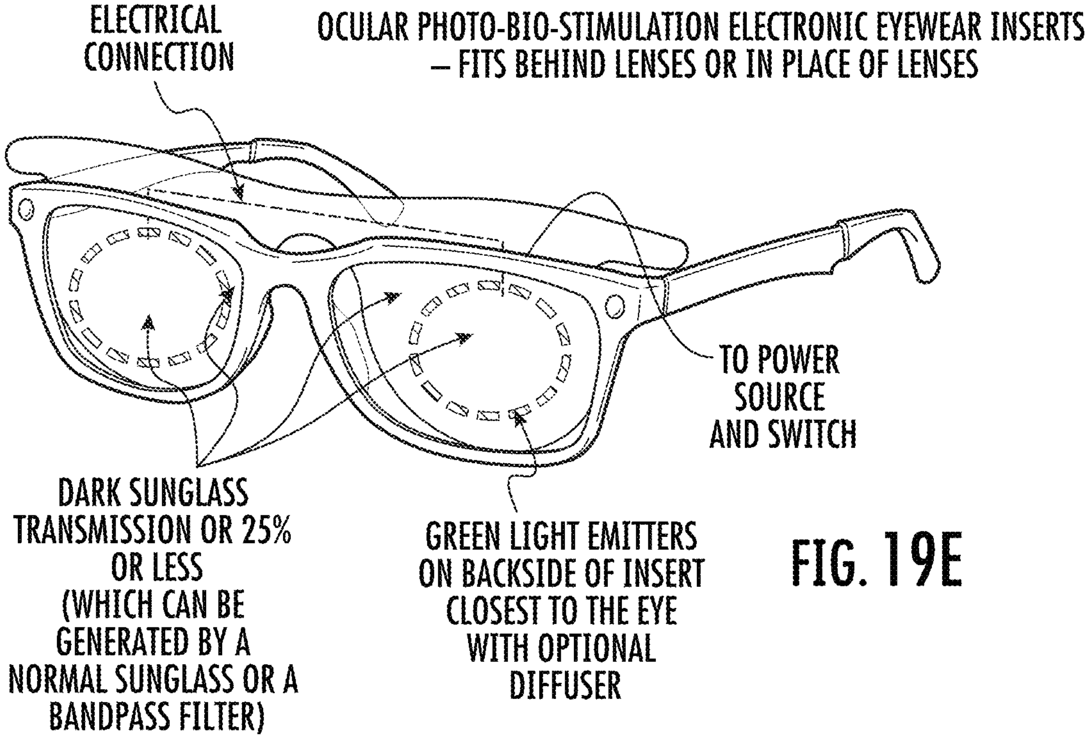
Figure 19F:
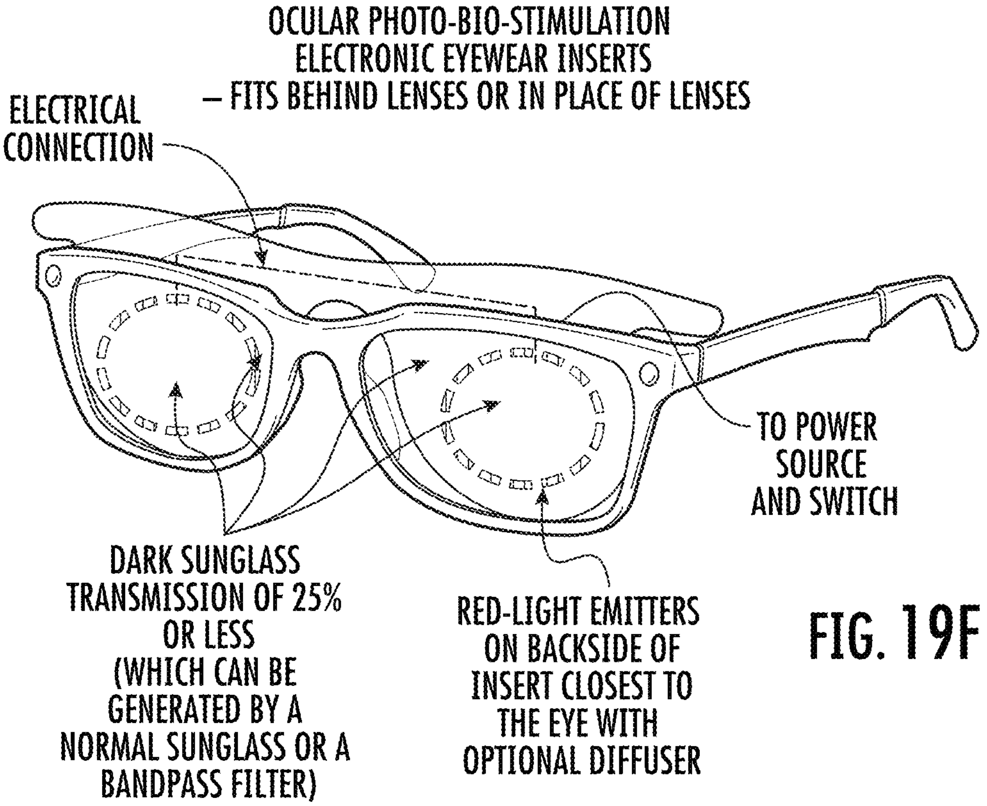

In reference to FIG. 17, embodiments include an ocular photo-bio-stimulation therapy lamp, wherein the ocular photo-bio-stimulation therapy lamp comprises an ocular photo-bio-stimulation light(s), wherein the lamp can be programable, wherein the lamp can provide one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, wherein one or a plurality of light emitters that generate the programable ocular photo-bio-stimulation light or lamp can be controllable, manually or automatically, with regards to one or more of intensity, on and/or off time, and/or wavelength band, and wherein the intensity of the ocular photo-bio-stimulation therapy lamp's light or lamp can be automatically adjusted depending on distance from the face of the user or ambient light of the room or space. The light or lamp can comprise a distance sensor. The ocular photo-bio-stimulation light or lamp can be comprised of one light emitter or a plurality of light emitters. The ocular photo-bio-stimulation light source can increase the production of dopamine in the eye and/or one or more of dopamine, serotonin or norepinephrine in the brain.

Embodiments when light wavelengths are generated by way of filtered optics or filtered lenses the transmission peak of the wavelength range that strike the eye's retina falls within the wavelength range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In embodiments when light wavelengths are generated by a light emitter(s) if ambient lighting is present (including that of artificial light or sun light), the blended light wavelengths of the light emitter(s) and also the ambient light comprises wavelengths of light that strike the eye's retina fall within wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens, which predominantly transmits within the wavelength range of at least one of 460 nm-520 nm or 470 nm to 520 nm, and/or by utilizing a light source or light emitter that predominately transmits within the wavelength range of at least one of 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of or increasing one or more of dopamine, serotonin or norepinephrine in the brain, by way of stimulating the retina of an eye.

The light or lamp can have an intensity of 300 lux or greater. The light or lamp can have an intensity of 400 lux or greater. The light can have an intensity of 1,000 lux or greater. The light can have an intensity of 5,000 lux or greater. The time of ocular photo-bio-stimulation treatment can be 1 minute-5 minutes, 5 minutes-10 minutes. The time of ocular photo-bio-stimulation treatment can be 10 minutes to 30 minutes. The time of ocular photo-bio-stimulation treatment can be 30 minutes to 1 hour. The time of ocular photo-bio-stimulation treatment can be 30 minutes or more. The light can flicker. The light can modulate. The light can modulate, by way of example only, within the range of one of 5 Hz and 15 Hz, 10 Hz to 20 Hz, or 40 Hz+/−20 Hz. In certain embodiments the light source has zero Hz (no modulation).

In embodiments, the ocular photo-bio-stimulation light or lamp can identify the distance from the eye of the user and can automatically adjust the intensity of the blue, green, or red-light to be appropriate for such a distance. In a certain embodiment the ocular photo-bio-stimulation light or lamp comprises a distance sensor and optionally facial recognition. In addition, the light intensity can be adjusted automatically or manually depending upon the ambient lighting available in the room or space. In certain embodiments a diffuser can be placed over the light emitters. In certain embodiments a filter or filters are used so as to permit a higher concentration of wavelengths within the range of at least one of: 480 nm+/−30 nm, 480 nm+/−20 nm, 500 nm+/−30 nm, 500 nm+/−20 nm, 510 nm+/−30 nm, 510 nm+/−20 nm, 530 nm+/−20 nm, 650 nm+/−30 nm 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to be transmitted from the light source. The ocular photo-bio-stimulation light or lamp can modulate or flicker. The ocular photo-bio-stimulation light or lamp can comprise a timer to provide the appropriate level of ocular photo-bio-stimulation therapy.

The ocular photo-bio-stimulation light or lamp can comprise wavelengths within the range of 441 nm or greater, or 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The ocular photo-bio-stimulation effect targeted can be one or more of (by way of example only), increased dopamine in the eye, prevention of myopia, slowing or stopping myopia, increasing or one or more of dopamine, serotonin or norepinephrine in the brain, increasing alertness, and/or reducing depression severity.

The ocular photo-bio-stimulation light or lamp can comprise wavelengths within the range of 530 nm+/−10 nm, or 530 nm+/−15 nm, or 530 nm+/−20 nm, or 500 nm to 550 nm. The ocular photo-bio-stimulation effect targeted can be one or more of (by way of example only), reduced pain severity, reduced frequency of headaches, and/or reduced frequency of migraines.

The ocular photo-bio-stimulation light or lamp can comprise wavelengths within the range of 630 nm+/−20 nm or 650 nm+/−30 nm, or 650 nm-700n or 700 nm+/−30 nm. The ocular photo-bio-stimulation effect targeted can be one or more of (by way of example only), increased mitochondrial health or mitochondrial numbers within the retina of the eye for the purposes of reducing the severity or improving a retinal disease/disorder such as one or more (by way of example only), dry AMD, retinitis pigmentosa, and/or diabetic retinopathy. In certain cases, the ocular photo-bio-stimulation light or lamp can also be of help with dry eye conditions whereby the tear layer evaporates-too quickly.

In certain embodiments the ocular photo-bio-stimulation light can modulate within the range of, one of: 5 Hz to 15 Hz, 10 Hz to 20 Hz, or 40 Hz+/−20 Hz. In other embodiments the ocular photo-bio-stimulation light source cannot modulate and thus has zero Hz. In certain embodiments an invisible white light spectral flickering can occur. In certain embodiments by using blue light within the wavelength range of 480 nm+/−30 nm and modulating at 40 Hz+/−10 Hz, the invention can result in a significant improvement of one or more of: depression, cognitive ability, alertness, and decision making of the user. However, visually 40 Hz+/−10 Hz can be annoying and distracting for a user. In certain embodiments an invisible spectral flickering can occur. In certain other embodiments which reduce visual unpleasantness for the user the ocular photo-bio-modulation light source can be modulated within the ranges between blue (450 nm-495 nm) and bluish green/cyan (495 nm-520 nm). In still other embodiments which reduce visual unpleasantness the ocular photo-bio-modulation light source can be modulated within the ranges between blue (450 nm-495 nm) and green (495 nm-570 nm). The ocular photo-bio-stimulation light can then stimulate, one or more of dopamine, serotonin, or norepinephrine in the brain. In certain embodiments by using blue light within the wavelength range of 480 nm+/−30 nm and modulation or flickering between 5 Hz and 15 Hz, or between 10 Hz and 12 Hz, the invention can be used to stimulate production or increase the production of dopamine in the eye's retina of the user.

Eyewear and Optics for Providing Ocular Photo-Bio-Stimulation

In certain embodiments, an ocular photo-bio-stimulation light source can comprise wavelengths of light within the range of 440 nm to 700 nm. The lighted border can be a white lighted border. The white light can comprise peaks of light wavelengths of 460 nm+/−10 nm, 525 nm+/−10 nm, and/or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted ocular photo-bio-stimulation light source can provide ocular photo-bio-stimulation. The light intensity of lux given off from the ocular photo-bio-stimulation light source can be one of, 250 lux or more, 500 lux or more, 1,000 lux or more, or 2,000 lux or more. When considering the light radiating in a cone light manner from the ocular photo-bio-stimulation light source to strike the eye and face of the user or subject, the number of lumens given off from the ocular photo-bio-stimulation light source can be one of, 10 lumens or more, 25 lumens or more 50 lumens or more, or 100 lumens or more.

Eyewear embodiments for ocular photo-bio-stimulation can comprise a lens or optic that permits a wearer to view an image, wherein certain light wavelengths that pass from the eyewear or the optic stimulates dopamine or serotonin of the wearer, wherein certain of the light wavelengths are of the blue light, and wherein the highest concentration of blue, bluish green, or green light, that reach the eye of the wearer falls within the wavelengths range of 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm, and wherein light wavelengths are filtered or blocked so to cause the overall light transmission of the lens or optic to be less than 50%. Blue, bluish green, green light radiation wavelengths can be within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm, and can increase alertness and concentration, by way of example, upon waking in the morning or during the day when tired and less alert. This occurs by way of increasing dopamine production. In other embodiments wavelengths within the range of 650 nm+/−30 nm or 650 nm-700 nm, or 700 nm+/−30 nm, can be used. It is further known that low levels of dopamine can be associated, by way of example only, with ADHD, myopia and Parkinson disease. The ocular photo-bio-stimulation light source can increase the production of dopamine in the eye and/or one or more of dopamine, serotonin or norepinephrine in the brain.

Embodiments providing ocular photo-bio-stimulation can filter or block damaging high energy blue light, UV, and reduce bright light visual discomfort.

Embodiments when light wavelengths are generated by way of filtered optics or filtered lenses the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

Embodiments when light wavelengths are generated by a light emitter(s) if ambient lighting is present (including that of artificial light or sun light) the blended light wavelengths of the light emitter(s) and also the ambient light comprises wavelengths of light that strike the eye's retina fall within one of the wavelength ranges of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In other embodiments for ocular photo-bio-stimulation, the eyewear or optic can comprise green light within the range of 480 nm+/−30 nm, 450 nm-520 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. Green light wavelengths can, in aspects, reduce the sensation of pain. In still other embodiments the eyewear or an optic can comprise red light within the range of 660 nm+/−20 nm, 650 nm+/−30 nm, or 600 nm to 700 nm. Red light wavelengths within the range of 660 nm+/−20 nm, 600 nm to 700 nm, or 700 nm+/−30 nm, can be soothing, calming and relaxing to the brain, thereby assisting with (by way of example) going to sleep. The eyewear and/or optic can be any type of eyewear or optic known to one of ordinary skill in the art. The eyewear and/or optic can be disposable. The eyewear and/or optic can be an insert that can be inserted or attached to existing eyewear. In most, but not all cases, the insert is positioned behind the corrective eyeglass lenses and is supported by the eye glass frame (see FIGS. 18, 19A, 19B, 19C, 19E, and 19F). The eyewear and/or optic can be a component that is removable or permanently attached to existing eyewear. As used herein an optic can be a lens. A lens can be an optic. A lens or optic can comprise optical power. A lens or optic can comprise no optical power. As used herein an optic can be any item that transmits light, such as a lens, flat sheet of transparent plastic or glass, film, light diffuser, window, etc., as would be understood by one of ordinary skill in the art.

The optic can comprise a single bandpass filter to provide for the transmission of the desired light wavelengths. The optic can comprise a double bandpass filter to provide for the transmission of the desired light wavelengths. The level of transmission of light to the eye's retina used in the various embodiments disclosed herein can be provided at one of scotopic, mesopic, and/or photopic light levels. In embodiments the light level is above 400 lux and is in the higher end of mesopic and most of the time photopic.

In embodiments, ambient light can be filtered or engineered by the design of the optic or lens to spread or focus over the retina, including that of the optic nerve head. In certain embodiments the blue wavelength band of chromatic aberration is engineered by way of the optic design or optic power to focus on or within the retina peripheral to the macula. The optic can be an ophthalmic lens. The optic can be a thin plastic or glass section or part having no optical power that transmits light. An optic can be a window. An optic can be a light diffuser. An optic can be a film. The optic can comprise optical power. The optic can comprise prescription optical power. The optic can comprise no optical power. The optic can be a spectacle lens. The optic can be a contact lens. The optic can be an intra ocular lens.

In some embodiments the highest concentration of blue light radiation or blue wavelengths falls within the range of 460 nm+/−20 nm or 470 nm+/−20 nm or 480 nm+/−30 nm or 450 nm-520 nm. In some embodiments the highest concentration of blue light radiation or blue wavelengths falls within 460 nm+/−35 nm. In some embodiments the highest concentration of blue light radiation or blue wavelengths falls within the range of 460 nm+/−20 nm. In some embodiments the highest concentration of blue light radiation falls within the range of 470 nm+/−15 nm. In some embodiments the highest concentration of blue light radiation or blue wavelengths falls within the range of 470 nm+/−20 rim. In some embodiments the highest concentration of blue light radiation or blue wavelengths falls within the range of 470 nm+/−25 nm. In some embodiments the highest concentration of blue light radiation falls within the range of 480 nm+/−10 nm. In some embodiments the highest concentration of blue light radiation falls within the range of 480 nm+/−15 nm. In some embodiments the highest concentration of blue light radiation or blue wavelengths falls within the range of 480 nm+/−20 nm. In some embodiments the highest concentration of blue light radiation or blue wavelengths falls within the range of 480 nm+/−30 nm. In some embodiments the highest concentration of blue light radiation or blue wavelengths falls above 449 nm. In some embodiments the highest concentration of blue light radiation or blue wavelengths falls above 454 nm. In some embodiments the highest concentration of blue light radiation or blue wavelengths falls above 459 nm.

The eyewear or optic can cause the wearer to be, by way of example only, more alert and/or have better concentration. In aspects, light wavelengths within the range 460 nm+/−10 nm or 470 nm+/−20 nm, more specifically within the range of 480 nm+/−30 nm, are known to produce dopamine within the human eyes' retina and brain. In other embodiments wavelengths within the range of 650 nm-700 nm can be used to increase alertness by increasing dopamine production. Light wavelengths within the wavelength range of 480 nm+/−30 nm and 650 nm+/−30 nm can excite the melanopsin containing ipRGC and/or rods so as to cause an increase in dopamine and/or serotonin production in the retina of an eye. Light wavelengths within the wavelength range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, can excite the melanopsin containing ipRGC and/or rods so as to cause an increase in dopamine and/or serotonin production in the eye, eye's retina, and/or one or more of dopamine, serotonin or norepinephrine in the brain.

In some embodiments, blue light wavelengths below 450 nm are blocked or filtered. In certain embodiments the blue light wavelengths below 450 nm and above 490 nm are blocked or filtered. In certain embodiments all light wavelengths below 450 nm and above 490 nm are blocked or filtered. In certain embodiments the blue light wavelengths below 450 nm and above 480 nm are blocked or filtered. In certain embodiments all light wavelengths below 450 nm and above 480 nm are blocked or filtered. In certain embodiments all light wavelengths below 450 nm and above 510 nm are blocked or filtered. As used herein a filter is intended to filter light and affect the transmission thereof. In embodiments, a filter can affect/block or reduce the transmission of certain ranges of light wavelengths. In certain embodiments the filter blocks and/or filters certain light wavelengths while transmitting others.

The optic can be an ophthalmic lens. The optic can be a thin plastic, film, or glass section or part having non-optical power that transmits light. An optic can be a light diffuser. The optic can be antireflection coated. The optic can be slightly tinted. The optic can be without a color or tint. The optic can be mostly clear of color. The optic can be scratch resistant coated. The optic can be surface treated like any ophthalmic lens. In certain embodiments the optic can be an electrochromic lens.

In certain embodiments the lens or optic can be a chromatic aberration focused lens. The design can include one or more of refractive or diffractive, or a combination of refractive and diffractive. An example of a refractive/diffractive design is one of a lens or optic that comprises a central optic zone having refractive curves (comprising a spherical power or plano/no power) and a zone that is outside of the central zone that comprises Fresnel optical prismatic elements. In other embodiments the lens can be completely a Fresnel diffractive lens in the central zone and the peripheral zone. The peripheral zone can be of an optical power that is more minus or less plus optical power than the central zone. By way of example only, the central zone can be plano and the peripheral zone can be within the range of −0.75 D to −5.00 D or in certain embodiments having an optical power within the range of −1.00 D-−2.00 D. Such a lens or optic can be worn or utilized when providing ocular photo-bio-stimulation therapy to an eye. This lens or optic can be worn in addition to the wearer's conventional eyeglasses when the ocular photo-bio-stimulation therapy is being provided or applied. And it can be removed for normal daily use when the ocular photo-bio-stimulation therapy is no longer being provided or applied. In certain embodiments it is worn in front of and in optical communication with the wearer's conventional eyeglasses. In other embodiments it is worn behind but in optical communication with the wearer's conventional eyeglasses.

In certain embodiments, the lens or optic can be of a design that can include one or more of refractive, or diffractive, or a combination of refractive and diffractive. An example of a refractive/diffractive design is one of a lens or optic that comprises a central optic zone having refractive curves (comprising a spherical power or plano/no power) and a zone that is outside of the central zone that comprises Fresnel optical prismatic elements. In other embodiments the lens can be completely a Fresnel diffractive lens in the central zone and the peripheral zone. The peripheral zone can be of an optical power that is more plus or less minus optical power than the central zone. By way of example only, the central zone can be plano and the peripheral zone can be within the range of +0.75 D to +5.00 D or in certain embodiments having an optical power within the range of +1.00 D to +2.00 D. Such a lens or optic can be worn or utilized when providing ocular photo-bio-stimulation therapy to an eye. This lens or optic can be worn in addition to the wearer's conventional eyeglasses when the ocular photo-bio-stimulation therapy is being provided or applied. And it can be removed for normal daily use when the ocular photo-bio-stimulation therapy is no longer being provided or applied. In certain embodiments it is worn in front of and in optical communication with the wearer's conventional eyeglasses. In other embodiments it is worn behind but in optical communication with the wearer's conventional eyeglasses.

Eyewear can be of any type of eyewear worn around or in the eye. Eyewear as used herein can comprise any eyewear, by way of example only: spectacles, sunglasses, disposable eyewear, goggles, dress eyewear, safety eyewear, sports eyewear, clip-on eyewear, fit-over eyewear, military eyewear, smart eyewear, XR eyewear, AR eyewear, VR eyewear, MR eyewear, contact lens, intra-ocular lenses, or corneal implant. When required the eyewear can comprise a power source and the appropriate electronics needed. Non-prescription can mean non optical power. Plano means no optical power. Optical power can mean all optical powers. The optic can be made of plastic or glass. The use of the word filter means in most cases reducing, but not fully eliminating. However, in some cases, filtering can mean eliminating. The use of the word blocking means eliminating. Diffusing means to spread out. Defocus means not focusing on the retina of the eye of the user. The eyewear or optic can comprise one or more of: a notch filter, bandpass filter, selective blue light filter, absorptive filter, interference filter, a plurality of filters, or a combination of any one or more.

A bandpass filter can be a type of interference filter. An interference filter can be a bandpass filter. The filter can be used in association with one or more lenses, lens blank, optic, and/or optical blank. The filter can be in optical communication with one or more of: a lens, lens blank, optic, optical blank, or another filter. The filter can be applied to one or more of: the concave surface, convex surface, or buried or embedded within the lens, lens blank, optic, or optical blank. The filter can be separated and/or distance separated and in optical communication with one or more of: the lens, lens blank, optic, and/or optical blank. A filter can be used in combination with another filter. A filter can be used in optical communication with a distance separated filter.

A filtered optic or filtered lens can be that of an optic or lens that comprises one or more of: an interference filter, bandpass filter, neutral density filter, notch filter, absorption filter, absorber(s), dyes, and/or selective blue light filter.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 40% of less or 30% or less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

The eyewear or optic can comprise one or more of blue light emitter(s), green light emitter(s), and/or red-light emitter(s). Examples of light emitters can be, by way of example only, LEDs, OLEDs, micro-OLEDs, micro-LEDs, quantum dots, iLEDs, fluorescent, incandescent, and/or the sun. As used herein a light emitter and be any light source that gives off light radiation. By way of example only: an LED, OLEDs, micro-OLED, micro-LED, quantum dots, diode, or the sun. In certain embodiments a light ring is utilized to minimize pupil constriction. This occurs as the eye being treated can fixate on a distant object through the center of the light ring while the light of the light ring is stimulating the photoreceptors of the eye. This further allows for providing light exposure to the peripheral retina of the eye. When an electrical light emitter is utilized, the light can flicker. The light can modulate. The light can modulate within the modulation range of 5 Hz and 15 Hz. Depending upon the type of light source, the light intensity utilized can be 300 lux or greater, 400 lux or greater, 1000 lux or greater, or 10,000 lux or greater.

In certain embodiments, eyewear can comprise blue or red-light emitters facing towards the eye of the wearer, facing inward and reflecting off the optic supported by the eyewear, and/or facing towards the wearer's pupil(s). In other embodiments a band of blue, green, or red-light wavelengths can be varied in intensification of light radiation. The highest concentration of blue, green, or red-light radiation being transmitted can be varied in terms of light radiation. The blue, bluish green or green light emitters can comprise a wavelength within 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. The blue light emitters can comprise a wavelength greater than 449 nm but less than 510 nm. The eyewear or optic can comprise a diffuser for the purposes of diffusing light. The green light emitters can comprise wavelengths within the range of 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. The redlight emitters can comprise wavelengths within the range of 630 nm+/−20 nm, 650 nm+/−30 nm, or 600 nm to 700 nm, or 700 nm+/−30 nm. In embodiments disclosed herein, the light emitters can (optionally) be pulsed or modulated on and off to permit the pupil of the wearer/user to open more (enlarge) before it reduces in diameter. In cases, by using red light, the pupils of the eye will constrict less. Also, by causing the eye to focus on a distant object as opposed to a near object, the pupil of the eye will constrict less. In embodiments disclosed herein, a filter can be utilized to reduce the transmission of non-essential light wavelengths so as to cause the pupil diameter to enlarge compared to what the diameter would have been if all the light was permitted to enter the eye.

Embodiments when light wavelengths are generated by way of filtered optics or filtered lenses the transmission peak of the wavelength range that strike the eye's retina falls within the wavelength range of at least one of: 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In embodiments when light wavelengths are generated by a light emitter(s) if ambient lighting is present (including that of artificial light or sun light), the blended light wavelengths of the light emitter(s) and also the ambient light comprises wavelengths of light that strike the eye's retina can fall within one of the wavelength ranges of at least one of: 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm or by utilizing a light source or light emitter that predominately transmits within the wavelength range of 460 nm-520 nm, 470 nm to 520 nm, or 480 nm+/−30 nm. This would include blue, bluish green and green wavelengths. This can be most beneficial when stimulating the production of increased dopamine in the retina of an eye. This can be most beneficial when stimulating the production of one or more of dopamine, serotonin or norepinephrine in the brain by way of stimulating the retina of an eye.

In embodiments, the blue or green or red-light emitters can be located around the periphery of a clear or lightly tinted optic permitting the center of the optic to be free of most, but not all, blue or green or red light. In embodiments the blue or green or red-light light emitters can be located around the periphery of a clear or lightly tinted optic permitting the center of the optic to be free of all blue or green or red-light light. The blue or green or red-light light emitters can be located around the backside of the eye-wire of an eyeglass frame closest to the eye of the wearer, thereby permitting the center of the optic to be free of most, but not all, blue or green or red-light light. The blue or green or red-light light emitters can be covered by a diffuser.

The emitted light wavelengths can strike or mostly strike the non-macular area of the retina, while mostly visible light wavelengths that pass through the center of the optic can strike or mostly strike the macular area of the retina. The optic can be tinted, by way of example only, blue, and blue light emitters can shine through the blue tinted optic. The wavelengths range being transmitted to the eye of the wearer can be within the range of 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The blue, bluish green, or green light emitters can excite one or more of, the retinal cones, rods and melanopsin containing ipRGCs. In a preferred case the blue light emitters excite the rods and melanopsin containing ganglion cells. The green light emitters can excite one or more of, the macula cones, retinal rods and melanopsin containing ipRGCs. Certain green light emitters within the wavelength range 500 nm and 530 nm can excite rhodopsin and melanopsin. Certain green light emitters within the wavelength range 500 nm and 530 nm can increase dopamine in the eye. Certain green light emitters within the wavelength range 500 nm and 530 nm can increase dopamine in the brain. The red-light emitters can excite one or more of, the macula cones, retinal rods and melanopsin containing ipRGCs. Certain blue light wavelengths increase alertness, focus, and cause the generation of dopamine in the eye and the brain. Certain blue light wavelengths can slow or stop myopia progression. Certain blue light wavelengths can prevent myopia from occurring in the first place. Certain green light wavelengths decrease pain. Certain red-light wavelengths increase calmness and relaxation. Certain red-light wavelengths increase dopamine production and increase alertness. Certain red-light wavelengths of 650 nm+/−30 nm or 700 nm+/−30 nm can improve the health of mitochondria.

In certain embodiments the range of wavelength band includes the peaks of the most sensitive points from rhodopsin (500 nm) and melanopsin (480 nm). This way both rhodopsin and melanopsin can be stimulated or excited. By way of example, the range of 460 nm-520 nm or 470 nm-520 nm, or 480 nm-520 nm, can be used. This would include blue, bluish green and green wavelengths.

The intensity of the light intensity of the ocular photo-bio-stimulation light can be in certain cases, by way of example only, 300 lux or greater. In other cases, by way of example it is less than 500 lux. In still other cases it can be greater than 500 lux. In still other cases it can be 1,000 lux or greater. In certain cases, by way of example, the time of light exposure is within the range of 1-5 minutes. In other cases, by way of example, it is 10 minutes or less. In still other cases, by way of example, it is greater than 10 minutes.

In embodiments for eyewear, the light emitter can have blue light wavelengths within the range of 460 nm+/−20 nm or 470 nm+/−20 nm or 450 nm to 510 nm and can be blended with white light such as providing a blue wavelength enhanced or enriched by or with white light. By way of example only, certain fluorescent light that provides indoor warm white lighting can provide blue light wavelengths within the range of 460 nm+/−20 nm or 470 nm+/−20 nm or 450 nm to 510 nm. In examples a white florescent light can be used with a blue light emitter. In other examples, certain incandescent light that provides indoor lighting can also provide blue light wavelengths within the range of 460 nm+/−20 nm or 470 nm+/−20 nm or 450 nm to 510 nm. In other examples, certain incandescent light that florescent light that provides indoor lighting can be used with an LED having blue light wavelengths within the range of 460 nm+/−20 nm or 470 nm+/−20 nm or 450 nm to 510 nm. And in still other embodiments, by way of example only, a white LED can be provided in combination with a blue LED having wavelengths within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, or 495 nm+/−30 nm. And in still other embodiments, by way of example only, a white light emitter can be provided in combination with a blue light emitter having wavelengths within the range of 460 nm+/−20 nm or 470 nm+/−20 nm or 450 nm to 510 nm. And in still other embodiments, by way of example only, a blue LED can provide a level of blue light within the wavelength range of 460 nm+/−20 nm or 470 nm+/−20 nm or 450 nm to 510 nm. The ocular photo-bio-stimulation light source can increase the production of dopamine in the eye and/or one or more of dopamine, serotonin or norepinephrine in the brain.

In embodiments for eyewear, the light emitter can have green wavelengths within the range of 500 nm-520 nm, 510 nm to 540 nm, or 530 nm+/−20 nm, and be blended with white light such as providing a green wavelength enhanced or enriched by or with white light. By way of example only, certain fluorescent light that provides indoor warm white lighting can also provide green wavelengths within the range of 500 nm to 540 nm. In examples a white florescent light can be used with a green light emitter. In other examples, certain incandescent light that provides indoor lighting can also provide green light wavelengths within the range 510 nm to 540 nm. In other examples, certain incandescent light that florescent light that provides indoor lighting can be used with by way of example, an LED having green light wavelengths within the range of 500 nm-520 nm, 520 nm+/−10 nm, 530 nm+/−20 nm, or 510 nm to 540 nm. And in still other embodiments, by way of example only, a white LED can be provided in combination with a green LED having wavelengths within the range of 530 nm+/−20 nm, 530 nm+/−20 nm, or 510 nm to 540 nm. And in still other embodiments, by way of example only, a white light emitter can be provided in combination with a green light emitter having wavelengths within the range of 500 nm+/−10 nm, 520 nm+/−10 nm, 530 nm+/−20 nm, or 510 nm to 540 nm.

In embodiments for eyewear, the light emitter can have red wavelengths within the range of 630 nm+/−20 nm, 650 nm+/−30 nm, or 600 nm to 700 nm, and be blended with white light such to provide a red wavelength enhanced or enriched white light. By way of example only, certain fluorescent light that provides indoor warm white lighting can also provide red wavelengths within the range of range of 630 nm+/−20 nm, 650 nm+/−30n, or 600 nm to 700 nm. In examples a white florescent light can be used with a red-light emitter. In other examples, certain incandescent light that provides indoor lighting can also provide red-light wavelengths within the range of 630 nm+/−20 nm, 650 nm+/−30 nm, or 600 nm to 700 nm. In other examples, certain incandescent light that florescent light that provides indoor lighting can be used with an LED having red-light wavelengths within the range of range of 660 nm+/−20 nm, 650 nm+/−30 nm, or 600 nm to 700 nm. And in still other embodiments, by way of example only, a white LED can be provided in combination with a red LED having wavelengths within the range of range of 630 nm+/−20 nm, 650 nm+/−30 nm, or 600 nm to 700 nm. And in still other embodiments, by way of example only, a white light emitter can be provided in combination with a red-light emitter having wavelengths within the range of range of 630 nm+/−20 nm, 650 nm+/−30 nm or 600 nm to 700 nm, or 700 nm+/−30 nm.

In embodiments, the blue light emitters can be located around the periphery of a clear or lightly tinted optic permitting the center of the optic to be free of most, but not all, blue light. In embodiments the blue light emitters can be located around the periphery of a clear or lightly tinted optic permitting the center of the optic to be free of all blue light. The blue light emitters can be located around the backside of the eye-wire of an eyeglass frame closest to the eye of the wearer permitting the center of the optic to be free of most, but not all, blue light. The blue light emitters can be covered by a diffuser. The blue light wavelengths can strike or mostly strike the non-macular area of the retina, while mostly visible light wavelengths that pass through the center of the optic can strike or mostly strike the macular area of the retina. The optic can be tinted blue and blue light emitters can shine through the tinted optic. The optic can be tinted blue and blue light emitters can reflect off the surface of the optic. The optic can be tinted blue and white light emitters can shine through the blue tinted optic. In certain embodiments the blue light emitters which are located on the backside of the eyewear can be pointed towards the pupil of the eye of the wearer. In other embodiments the blue light emitters are perpendicular to the backside of the eyewear and can point towards the face of the wearer.

In embodiments the green light emitters can be located around the periphery of a clear or lightly tinted optic permitting the center of the optic to be free of most, but not all, green light. In embodiments the green light emitters can be located around the periphery of a clear or lightly tinted optic permitting the center of the optic to be free of all green light. The green light emitters can be located around the backside of the eye-wire of an eyeglass frame closest to the eye of the wearer permitting the center of the optic to be free of most, but not all, green light. The green light emitters can be covered by a diffuser. The green light wavelengths can strike or mostly strike the macular and non-macular area of the retina, while mostly visible light wavelengths that pass through the center of the optic can strike or mostly strike the macular area of the retina. The optic can be tinted green and green light emitters can shine through the green tinted optic. The optic can be tinted green and green light emitters can reflect off one of the surfaces of the optic. The optic can be tinted green and white light emitters can shine through the green tinted optic. In certain embodiments the green light emitters which are located on the backside of the eyewear can be pointed towards the pupil of the eye of the wearer. In other embodiments the green light emitters are perpendicular to the backside of the eyewear and can point towards the face of the wearer.

In embodiments, the red-light emitters can be located around the periphery of a clear or lightly tinted optic permitting the center of the optic to be free of most, but not all, red light. In embodiments the red-light emitters can be located around the periphery of a clear or lightly tinted optic permitting the center of the optic to be free of all red light. The red-light emitters can be located around the backside of the eye-wire of an eyeglass frame closest to the eye of the wearer permitting the center of the optic to be free of most, but not all, red light. The red-light emitters can be covered by a diffuser. The red-light wavelengths can strike or mostly strike the macular and non-macular area of the retina, while mostly visible light wavelengths that pass through the center of the optic can strike or mostly strike the macular area of the retina. The optic can be tinted red and red-light emitters can shine through the red tinted optic. The optic can be tinted red and red-light emitters can reflect off of one of the surfaces of the optic. The optic can be tinted red and white light emitters can shine through the red tinted optic. In certain embodiments the red-light emitters which are located on the backside of the eyewear can be pointed towards the pupil of the eye of the wearer. In other embodiments the red-light emitters are perpendicular to the backside of the eyewear and can point towards the face of the wearer.

In embodiments, the eyewear houses or supports an optic which can comprise optical power. A defocusing lens can be utilized with the eyewear or optic. Such a defocusing lens can be housed within the eyewear, attached to the eyewear or optic, or worn behind the eyewear or optic. In cases, the defocusing lens is on the backside of a Bandpass Filter between the filter and the eye of the wearer or user. In certain embodiments the eyewear houses or supports an optic which can comprise non-optical power. In certain embodiments the eyewear houses or supports an optic which can comprise an eyeglass prescription. In certain embodiments the eyewear houses or supports an optic which can comprise an eyeglass lens that is non-prescription. In certain embodiments, by way of example, the eyewear can be disposable, comprising a colored optic such that when viewing a bright light source transmits light wavelengths within the range of 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10n, 500 nm+/−20 nm, 500 nm+/−30 nm, or 650 nm+/−30 nm or 700 nm+/−30 nm, to the eye of the wearer. In certain embodiments the eyewear can be disposable, comprising a colored optic such that when viewing a bright light source transmits light wavelengths within the range of 500 nm-520 nm or 530 nm+/−20 nm to the eye of the wearer. In certain embodiments the eyewear can be disposable, comprising a colored optic such that when viewing a distant separated bright light source transmits light wavelengths within the range of 630 nm+/−20 nm, 650 nm+/−30 nm, or 600 nm to 700 nm, or 700 nm+/−30 nm, to the eye of the wearer.

In certain embodiments the eyewear houses or supports an optic that comprises blue light emitters having blue light wavelengths within the range of 441 nm to 500 nm, or 460 nm+/−20 nm or 470 nm+/−20 nm or 480 nm+/−30 nm. In certain embodiments, by way of example only, the eyewear houses or supports an optic that comprises a blue color having blue wavelength within the range of 441 nm to 500 nm, or 460 nm+/−20 nm or 470 nm+/−20 nm or 480 nm+/−30 nm, while, in aspects, filtering or blocking blue light wavelengths of 440 nm or below. In certain embodiments the eyewear houses or supports an optic that comprises a blue color having blue light wavelengths within the range of 441 nm to 500 nm, or 460 nm+/−20 nm or 470 nm+/−20 nm or 480 nm+/−30 nm, and wherein the blue light wavelengths transmitted below 441 nm have been reduced in number or intensity. In still other embodiments a bandpass filter transmits wavelengths within the range of 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. In certain embodiments the eyewear houses or supports an optic that comprises green light emitters having green light wavelengths within the range of 510 nm-540 nm or 530 nm+/−20 nm or 520 nm+/−10 nm. In certain embodiments the eyewear houses or supports an optic that comprises a green color having green light wavelengths within the range of 510 nm-540 nm or 530 nm+/−20 nm.

In some embodiments the eyewear or optic can comprise red-light emitters. In certain other embodiments the eyewear or optic can comprise blue, bluish green, green, and/or red-light emitters. In such cases the light emitters are used for improving, by way of example only, increased alertness and cognitive ability. The light emitters can emit wavelengths within the range of 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The optic can comprise a double bandpass filter that can be used to provide for these ranges of transmission.

The eyewear can comprise blue or red light provided by an electronic display, and wherein the electronic display is located within an optic, in front of an optic, behind an optic, on the surface of an optic, on the eyewear and transmitted or projected to an optic, and/or on the eyewear and transmitted or projected to or on the human eye(s). Such an electronic display used with eyewear can be for XR (extended reality), VR (virtual reality), AR (augmented reality), MR (mixed reality), Modified Reality and in some cases just to provide blue, or green, or red-light to or from an optic. The red-light can be of a red-light within the wavelength range of 660 nm+/−30 nm or 650 nm+/−30 nm or 660 nm+/−20 nm. The blue light can have wavelengths within the range of 441 nm to 500 nm, or 460 nm+/−20 nm or 470 nm+/−20 nm or 480 nm+/−30 nm, while if needed filtering or blocking within the range of 420 nm+/−20 nm. The green light can have wavelengths within the range of 510 nm-540 nm or 530 nm+/−20 nm. The red-light wavelengths can be within the range of 630 nm+/−20 nm, or 650 nm+/−30 nm, or 660 nm+/−30 nm, or 600 nm to 700 nm, or 700 nm+/−30 nm. A plurality of light emitters can be utilized to provide one or more of the preceding wavelength bands.

In certain embodiments the eyewear or optic can comprise white light emitters that shine on a blue colored lens or optic, or a green colored lens or optic, or a red colored lens or optic. Examples of light emitters can be, by way of example only: LEDs, OLEDs, micro-OLEDs, micro-LEDs, iLEDs, and/or quantum dots. A plurality of light emitters can be utilized. A clip-on optic or flip-up or down optic can attach to the eyewear (see, FIG. 21A-D). The eyewear can comprise a prescription lens or non-prescription lens. The eyewear can comprise a lens having optical power or having non-optical power (plano power).

In reference to FIG. 19, in embodiments, one or more lens housed or supported by the eyewear can comprise a blue color having blue wavelengths within the range 450 nm to 500 nm or 460 nm+/−20 nm, or 470 nm+/−20 nm, or 480 nm+/−30 nm, and can filter or block blue wavelengths below 450 nm. A lens having a green color can have wavelength transmission within the range of 510 nm-550 nm, or 530 nm+/−20 nm, or 520 nm+/−10 nm. A lens having a red color can have wavelength transmission within the range of 650 nm+/−30 nm, or 660 nm+/−20 nm or 600 nm to 700 nm, or 700 nm+/−30 nm.

In still other embodiments the lens housed by eyewear can be clear of color. The clip-on optic or flip-up or down optic can comprise a prescription lens or non-prescription lens. The housing of the clip-on optic or flip-up and down optic can attach to the eyewear, by way of example only, magnetically, mechanically, and/or by a tension mount. (See, FIGS. 21A-D and FIG. 22.) In certain other embodiments the optic can be attached to the lens housed by the eyewear by way of example only, with magnets, removable adhesive, and/or through static energy.

Other embodiments, by way of example, may include a ring, a band, or a section of blue or green or red-light emitters, which can be adhered to the lens or optic surface, attached to the lens or optic surface, or embedded within the lens or optic surface, wherein the lens or optic is supported or housed by an eyeglass frame or eyewear. In certain other embodiments by way of example only, a ring, band, or a section of blue or green or red-light emitters, can be adhered to the lens or optic surface, attached to the lens or optic surface, or embedded within the lens or optic surface, such that it can be inserted or such that it is supported or stabilized on an eyeglass frame or eyewear. In aspects, the filters and/or emitters and related embodiments can be removeable inserts, such as attached to a lens, attached to eyewear, inserted into a lens, or embedded in a lens. (See, FIG. 19A-F.)

Figure 20A:
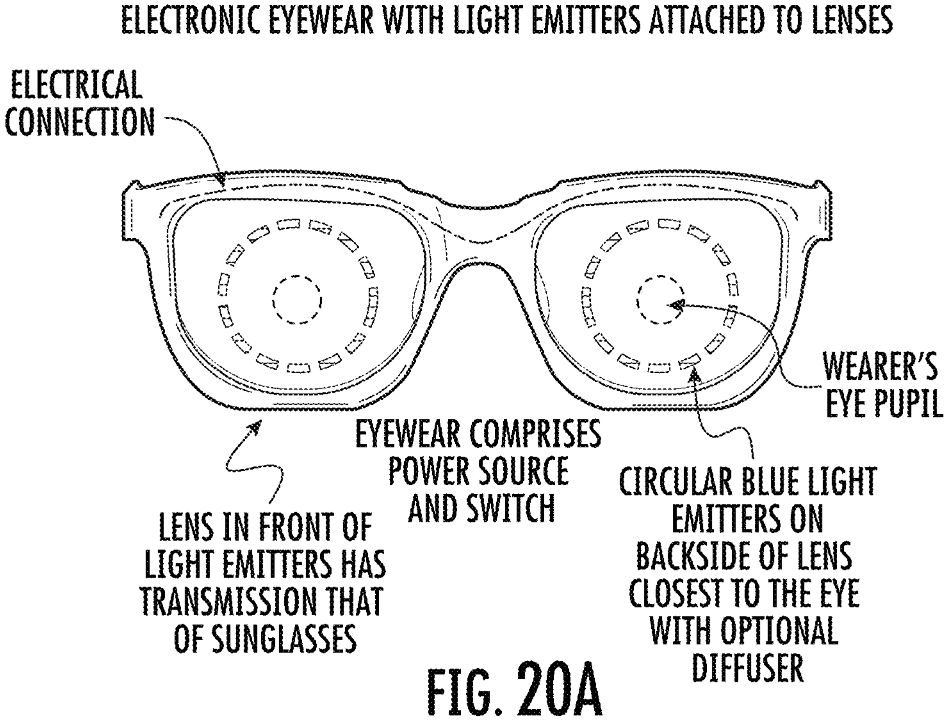
FIG. 20A-C shows an embodiment of the current invention as described herein.
Figure 20B:
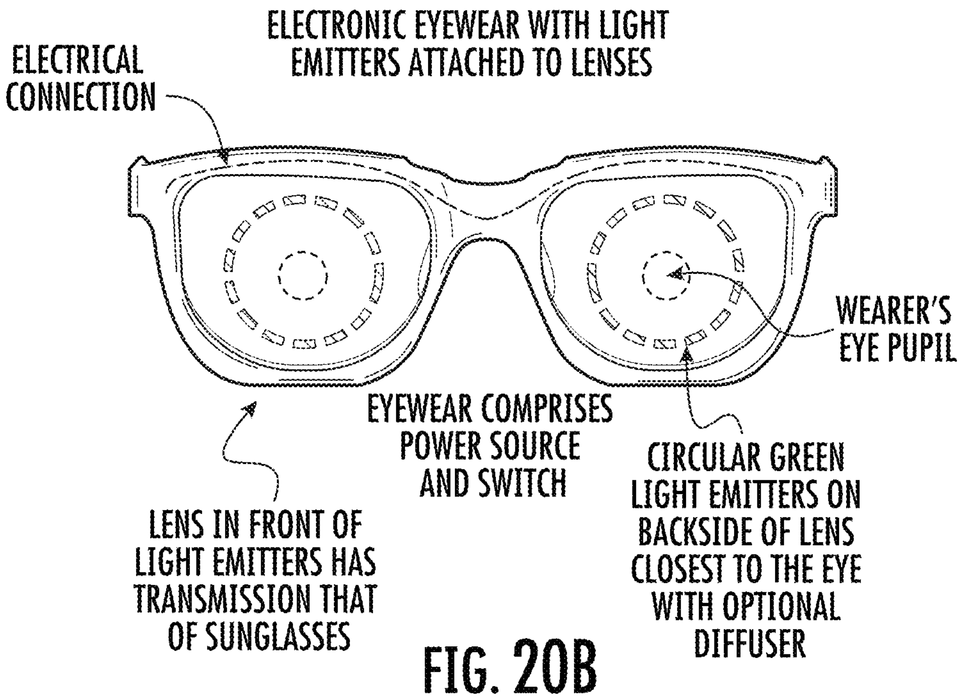
Figure 20C:
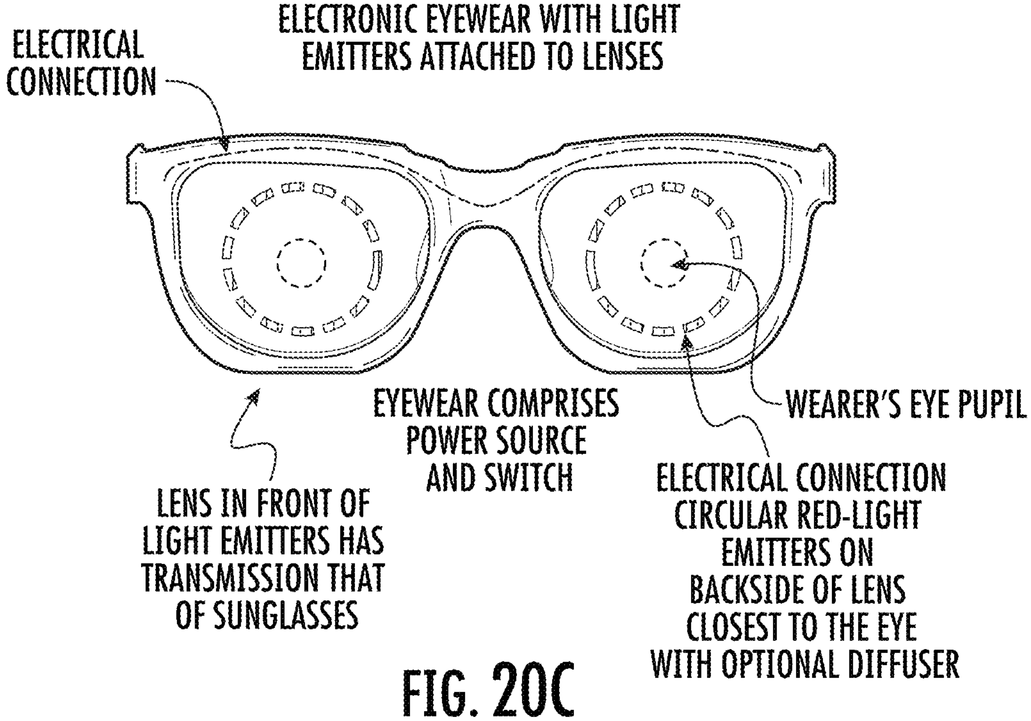

In reference to FIG. 20, in embodiments, the blue, or green, or red-light, or white light emitters, can provide light covering a central portion of the lens or optic. In other cases, the blue, green, or red-light, or white light emitters, can provide light covering a peripheral portion of the lens or optic leaving the center of the lens or optic mostly clear of blue, green, red, or white light. In still other embodiments the blue, green, red or white light emitters can provide light covering a portion of the lens or optic. (See, FIGS. 20A-C.)

In still other embodiments, the blue, or green, or red-light, or white light emitters, can be distance separated from the optic. The light emitters can be covered by a diffuser to spread and soften the light. The light can be directed towards the eye of the wearer. The light can be directed towards the pupils of the eyes of the wearer. In certain embodiments the light source or emitter can modulate for example, within the range of one of 5 Hz-15 Hz, 10 Hz to 20 Hz, or 40 Hz+/−20 Hz. In certain embodiments the light source or emitter can modulate, for example 10 times per second or less. In certain embodiments the light source or emitter can modulate (on and off), for example, 20 times per second or less. In other embodiments the light source or emitter can modulate, for example, 50 times per second or less. And in still other embodiments the light emitter or emitter can modulate, for example, 100 times per second or less. In still other embodiments the light does not modulate or flicker.

In embodiments utilizing blue light as the light source (wavelengths within the range of at least one of 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, or 500 nm+/−20 nm), can be of an intensity of 300 lux or more. In other embodiments the intensity can be of 500 lux or more. In other embodiments the intensity can be of 1,000 lux or more. In certain embodiments utilizing a blue light source, the time of treatment with the light source can be 1 hour or less. In other embodiments the time of treatment can be 30 minutes or less. In still other embodiments it can be 10 minutes or less. And in still other embodiments it can be 5 minutes or less.

In certain embodiments utilizing a green light source (e.g., wavelengths within the range of 530 nm+/−20 nm), the green light source can have an intensity of 250 lux or more. In other embodiments the intensity can be 500 lux or more. In other embodiments the intensity can be 1,000 lux or more. In certain embodiments, when utilizing a green light source, the time of treatment with the light source can be 1 hour or less. In other embodiments the time of treatment can be 30 minutes or less. In still other embodiments it can be 10 minutes or less. And in still other embodiments it can be 5 minutes or less.

In embodiments utilizing a red-light source (wavelengths within the range of 650 nm+/−30 nm or 700 nm+/−30 nm), the red-light source can have an intensity of 400 lux or more. In other embodiments the intensity can be of 500 lux or more. In other embodiments the intensity can be of 1,000 lux or more. In other embodiments the intensity can be of 5,000 lux or more. In certain embodiments utilizing a red-light source the time of treatment with the light source can be 1 hour or less. In other embodiments the time of treatment can be 30 minutes or less. In still other embodiments it can be 10 minutes or less. And in still other embodiments it can be 5 minutes or less. In reference to FIG. 21, an embodiment can include a clip-on optic or flip-up or down optic comprising a lens having optical power or having non-optical power (plano power). In embodiments the clip-on optic or flip-up or down optic can transmit blue wavelengths within the range of 441 nm-500 nm, or 460 nm+/−20 nm, or 470 nm+/−20 nm, or 480 nm+/−30 nm, such as, in cases, using a bandpass filter. (See, e.g., 2101 in FIG. 21*a*.) In still other embodiments the clip-on optic or flip-up or down optic can be clear of color and comprise blue light emitters having blue wavelengths predominately or solely within the range of 441 nm-500 nm, or 460 nm+/−20 nm, or 470 nm+/−20 nm, or 480 nm+/−30 nm, around its periphery of that of the housing that supports the optic. (See, e.g., FIG. 20A-C.) Such a housing can be a frame or an eyewear frame. In certain embodiments the clip-on optic or flip-up or down optic can transmit blue light (e.g., using one or more light emitter 2102) wavelengths within the range of 441 nm-500 nm, or 460 nm+/−20 nm, or 470 nm+/−20 nm, or 480 nm+/−30 nm, and the lens housed by the eyewear can filter or block blue wavelengths 440 nm or below. In certain embodiments the forward optic farthest away from the eye of the wearer can provide or emit a blue color having wavelengths within the range of 441 nm-500 nm, or 460 nm+/−20 nm, or 470 nm+/−20 nm, or 480 nm+/−30 nm. In certain embodiments the forward optic is that of the clip-on or flip down optic and the optic located behind the clip-on or flip down optic is that of the eyewear optic. In certain other embodiments the optic housed in the eyewear can be a stack of two optics with the forward optic comprising a blue color having wavelengths predominately or solely within the range of 441 nm-500 nm, or 460 nm+/−20 nm, or 470 nm+/−20 nm, or 480 nm+/−30 nm, and the optic closest to the eye of the wearer being the optic that either filters or blocks blue light wavelengths. The optic can be a clip on or flip down filter. The filter can be a bandpass filter. The filter can be an interference filter. The filter can be an absorption filter. Any of the clip-on optics or flip-up or down optics can be attachable and detachable to the eyewear, eyewear frame, or optic/lens; in other words, any of the clip-on optics or flip-up or down optics can be attachable and detachable to a frame, or any of the clip-on optics or flip-up or down optics can be integral with or embedded within the frame.

The clip-on optic or flip-up or down optic can comprise a lens having optical power or having non-optical power (plano power). In certain embodiments the clip-on optic or flip-up or down optic can comprise transmission of green light wavelengths predominately or solely within the range of 480 nm+/−30 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. In still other embodiments the clip-on optic or flip-up or down optic can be clear of color and comprise green light emitters having wavelengths within the range of 500 nm-550 nm, or 530 nm+/−20 nm, around its periphery of that of the housing that supports the optic. Such a housing can be a frame or an eyewear frame. In certain embodiments the forward optic furthest away from the eye of the wearer can provide or emit green wavelengths within the range of 480 nm+/−30 nm, 450 nm-520 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, or 500 nm+/−30 nm. In certain embodiments the forward optic is that of the clip-on or flip down optic and the optic located behind the clip-on or flip down optic is that of the eyewear optic comprising an optical power. The optic can be a clip on or flip down filter. The filter can be a bandpass filter. The filter can be an interference filter. The filter can be an absorption filter.

The clip-on optic or flip-up or down optic can comprise a lens having optical power or having non-optical power (plano power). In certain embodiments the clip-on optic or flip-up or down optic can comprise transmission of red-light wavelengths predominately or solely within the range of 630 nm+/−20 nm, 650 nm+/−30 nm, or 600 nm-700 nm. In still other embodiments the clip-on optic or flip-up or down optic can be clear of color and comprise red light emitters having wavelengths within the range of 630 nm+/−20 nm, 650 nm+/−30 nm, or 600 nm-700 nm, or 700 nm+/−30 nm, around its periphery of that of the housing that supports the optic. Such a housing can be a frame or an eyewear frame. In certain embodiments the forward optic farthest away from the eye of the wearer can provide or emit red wavelengths within the range of 630 nm+/−20 nm, 650 nm+/−30 nm, or 600 nm-700 nm, or 700 nm+/−30 nm. In certain embodiments the forward optic is that of the clip-on or flip down optic and the optic located behind the clip-on or flip down optic is that of the eyewear optic comprising an optical power. The optic can be a clip on or flip down filter. The filter can be a bandpass filter. The filter can be an interference filter. The filter can be an absorption filter.

Figure 21A:
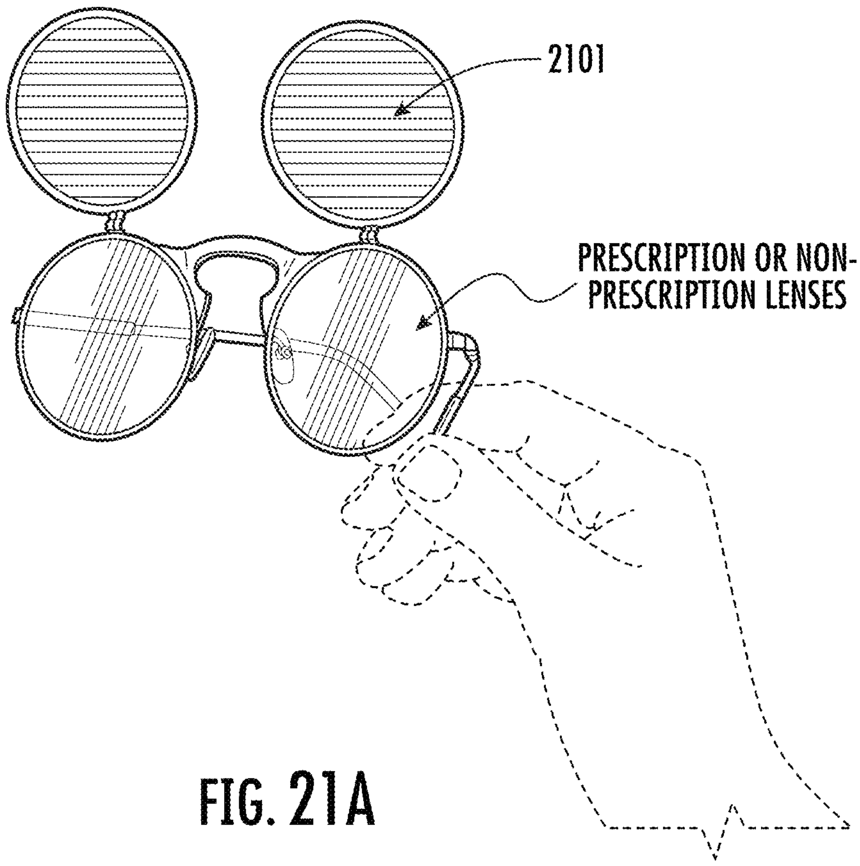
FIG. 21A-D shows an embodiment of the current invention as described herein.
Figure 21B:
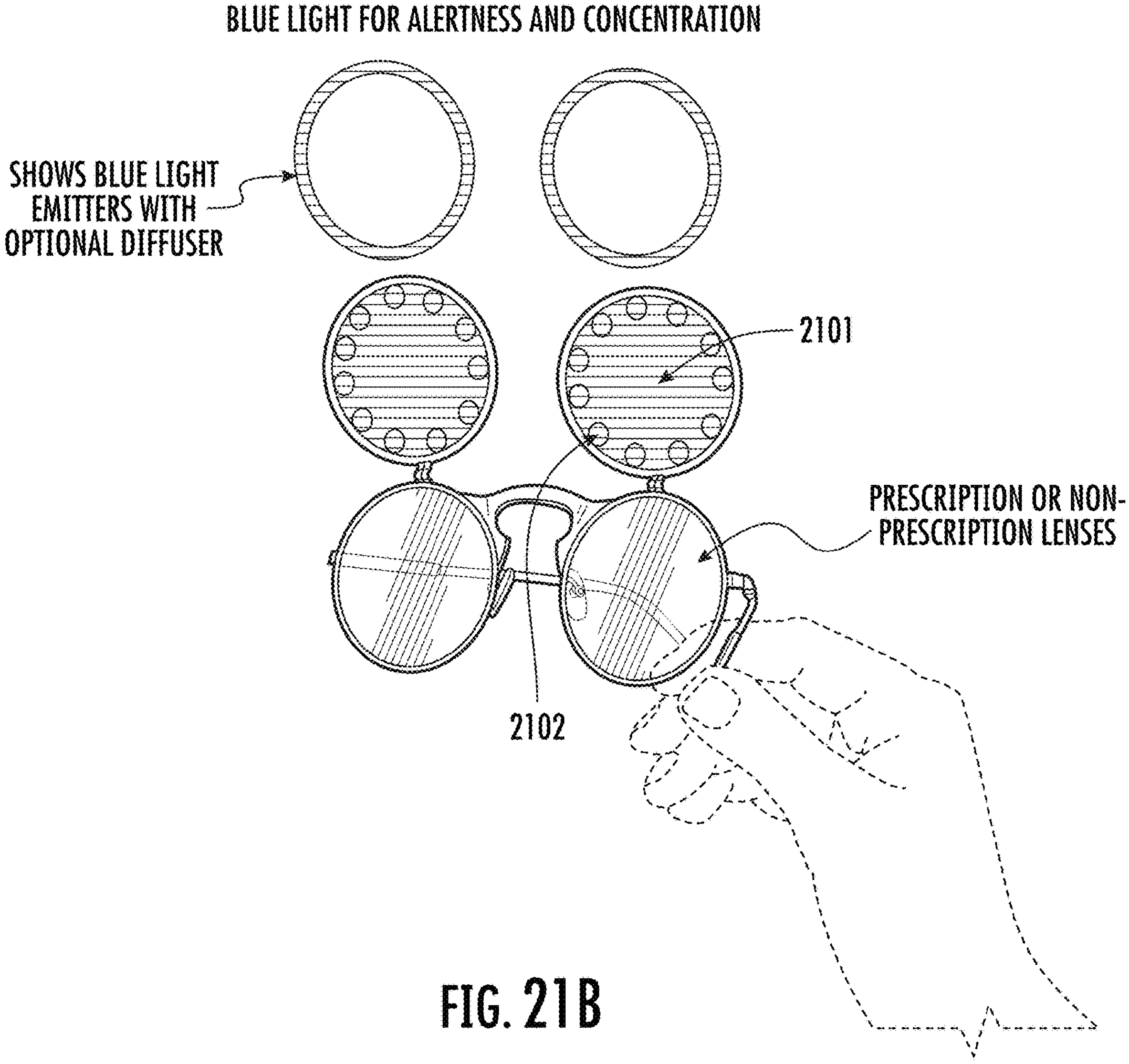
Figure 21C:
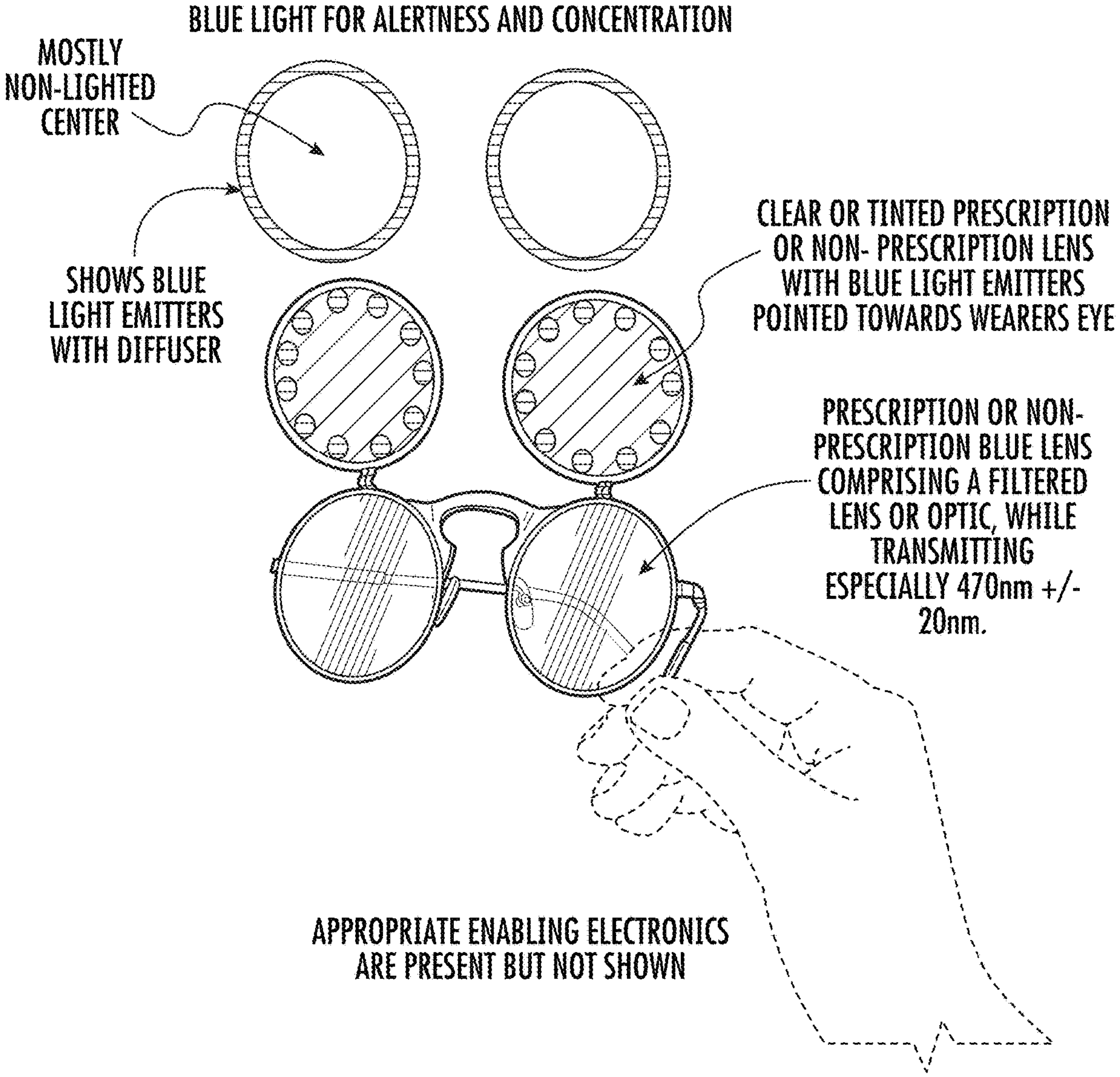
Figure 21D:
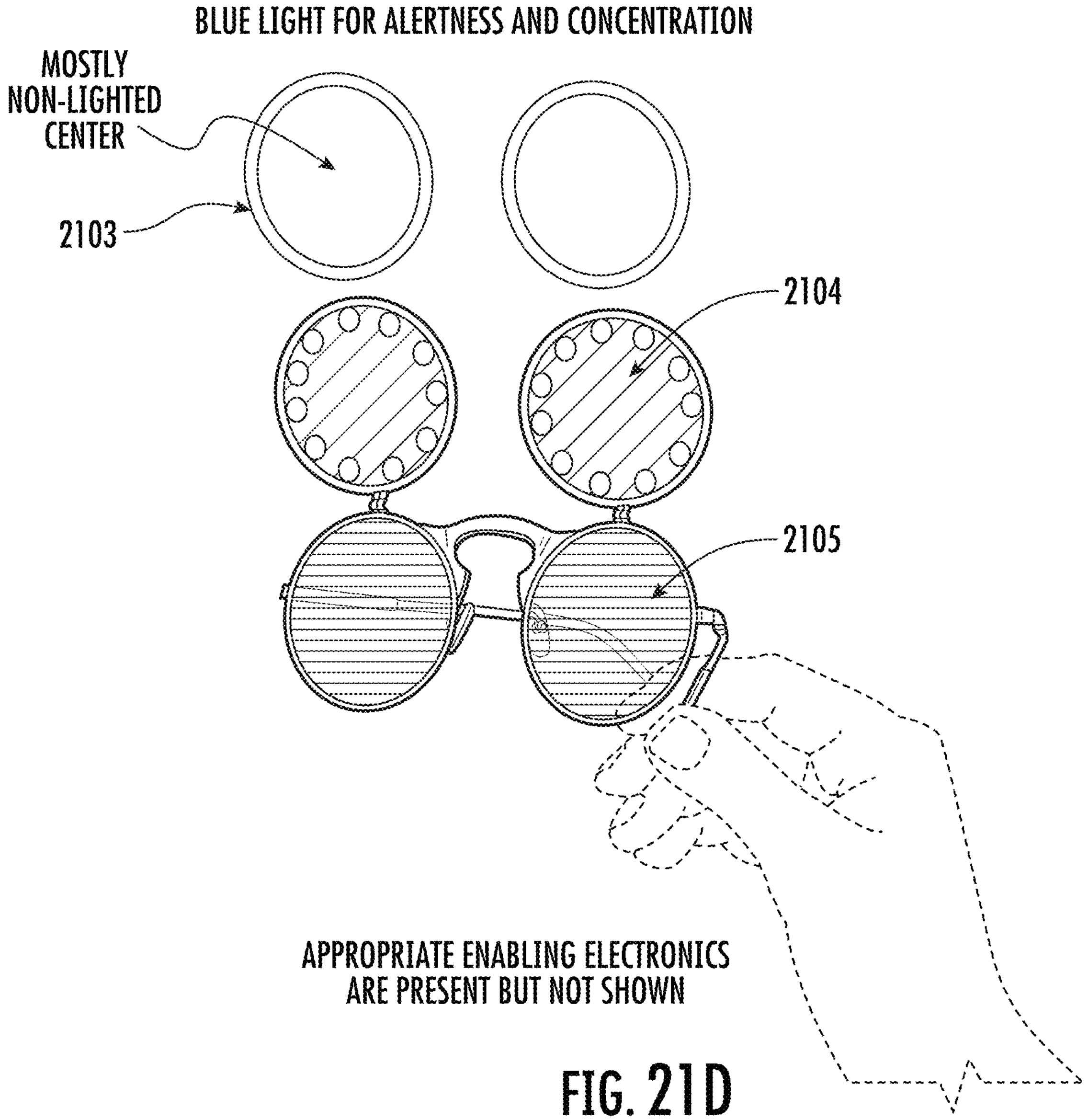

As shown in FIG. 21D, an embodiment can include white light emitters (with or without a diffuser) 2103. The clip-on optic or flip-up or down optic can be prescription, or not. The lenses can be tinted, or not 2104. The lenses can include one or more filter. In embodiments, white LEDs are pointed towards the eye of the wearer, and they can transmit trough a filter 2105 (e.g., blue lens comprising notch filter or bandpass filter while transmitting especially between 480+/−30 nm).

With all embodiments requiring electronics provided herein the appropriate enabling electronics to drive, power, control, modulate, dim or brighten the light emitters are part of or in association with the embodiments even if not identified within the illustrations. With any of the embodiments disclosed herein when appropriate, by way of example only, one or more of a bandpass filter, notch filter, interference filter, dye absorption filter, specialized filter, coating, and/or dye, can be utilized to achieve the desired wavelengths transmission results. In certain embodiments a plurality of filters is used such that each is in optical alignment with the other. The optic can be a clip on or flip down filter. The filter can be a bandpass filter. The filter can be an interference filter. The filter can be an absorption filter.

Figure 22:
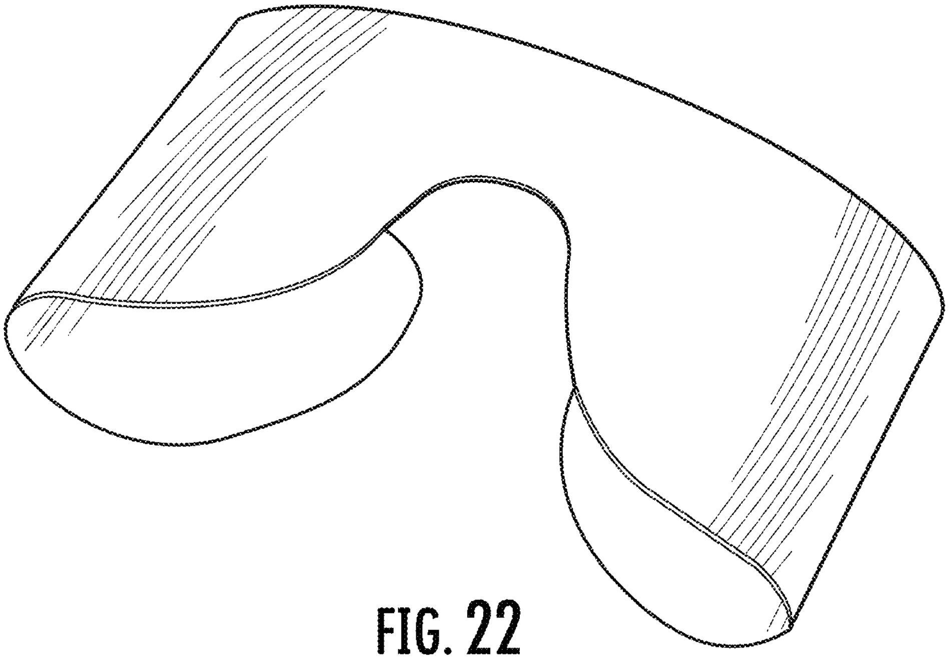
FIG. 22 shows an embodiment of the current invention as described herein.

In reference to FIG. 22, in embodiments, the eyewear and/or optic can be comprised of a non-prescription optic that can by way of example only, one or more of: disposable, repeatably rolled up when not in use and extends back out when in use such that it utilizes pressure to attach to and eyewear frame, rests by way of arms on existing eyewear that is being worn, fits over existing eyewear, and/or clips or snaps on to existing eyewear. The non-prescription eyewear or optic can further be comprised of either a light wavelength filtered material or a light wavelength bandpass material. The eyewear or optic can be largely darkened, only allowing the transmission of 20% or less of the light through. The eyewear or optic can be largely darkened, only allowing the transmission of 15% or less of the light through. The eyewear or optic can be largely darkened, only allowing the transmission of 10% or less of the light through.

Such a transmission will cause the pupil of the eye(s) to enlarge fully or slightly. This increase in the size of the pupil(s) then permits a larger area of the retina to be exposed to the light wavelengths that are being transmitted to the eye(s). In certain cases, light wavelengths within the range of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm are used. In aspects, a defocusing lens can be utilized with the eyewear or optic. Such a defocusing lens can be housed within the eyewear, attached to the eyewear or optic, or worn behind the eyewear or optic. In most, but not all cases, the defocusing lens is on the backside of the bandpass filter between the filter and the eye of the wearer or user.

In reference to FIG. 23, by largely acting as very dark sunglasses, embodiments can cause the pupil to partially or fully enlarge, thus allowing more of the retina to become exposed to the transmitted light wavelengths. This is especially helpful with blue light wavelengths of 460 nm or greater to 480 nm or greater, or 510 nm or less, where the blue light wavelength is intended to cause the wearer to become more alert or focused. This also is the case with red light within the range of 650 nm+/−30 nm or 650 nm-700 nm. The very dark sunglass effect of the eyewear or optic causes the pupil to partially or fully enlarge, which exposes more retinal rods and/or ipRGCs to the blue (or red) light wavelength being transmitted. This in turn increases dopamine production which then assists with making the wearer of the optic or eyewear more alert and focused. In addition, rods and cones are sensitive to green light wavelengths.

Thus, by partially or fully dilating the eye it is possible to expose more of the retinal rods in addition to the cones. When an embodiment comprising a bright light is shined on the retina of a wearer the pupil of the eye constricts and reduces the amount of retina that is stimulated. It is one of the purposes of the invention to stimulate a larger amount of the retina, thus increasing the amount of dopamine produced. This can be accomplished by way of one or more of: defocused light, reducing or eliminating accommodative pupil constriction by fixating on a distant object, utilizing dim light, utilizing red light when possible, and/or utilizing a bandpass filter thus reducing the overall light transmission by way of allowing only the desired light wavelengths to be transmitted. The bandpass filter can be a single bandpass filter or a double bandpass filter. The filter can be a hybrid filter. A bandpass filter can be an interference filter.

Figure 23A:
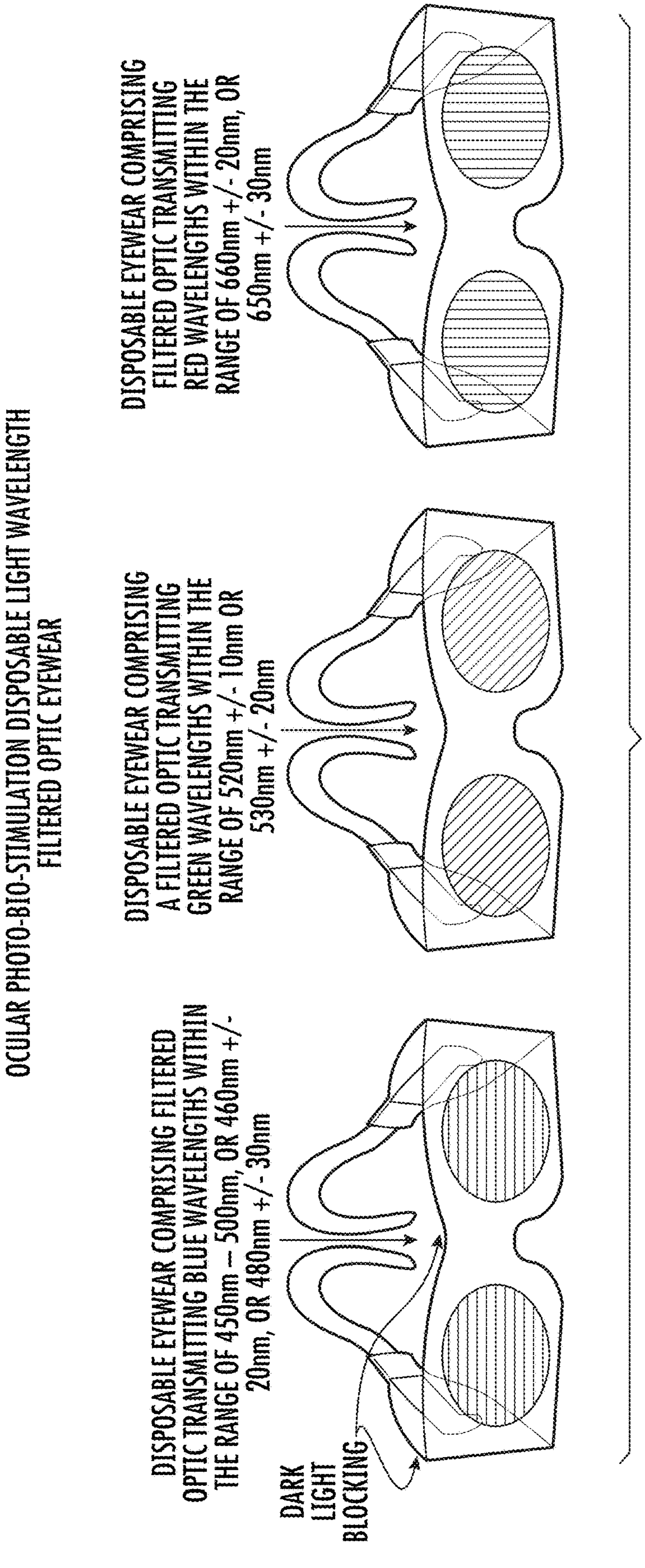
FIG. 23A-B shows an embodiment of the current invention as described herein.
Figure 23B:
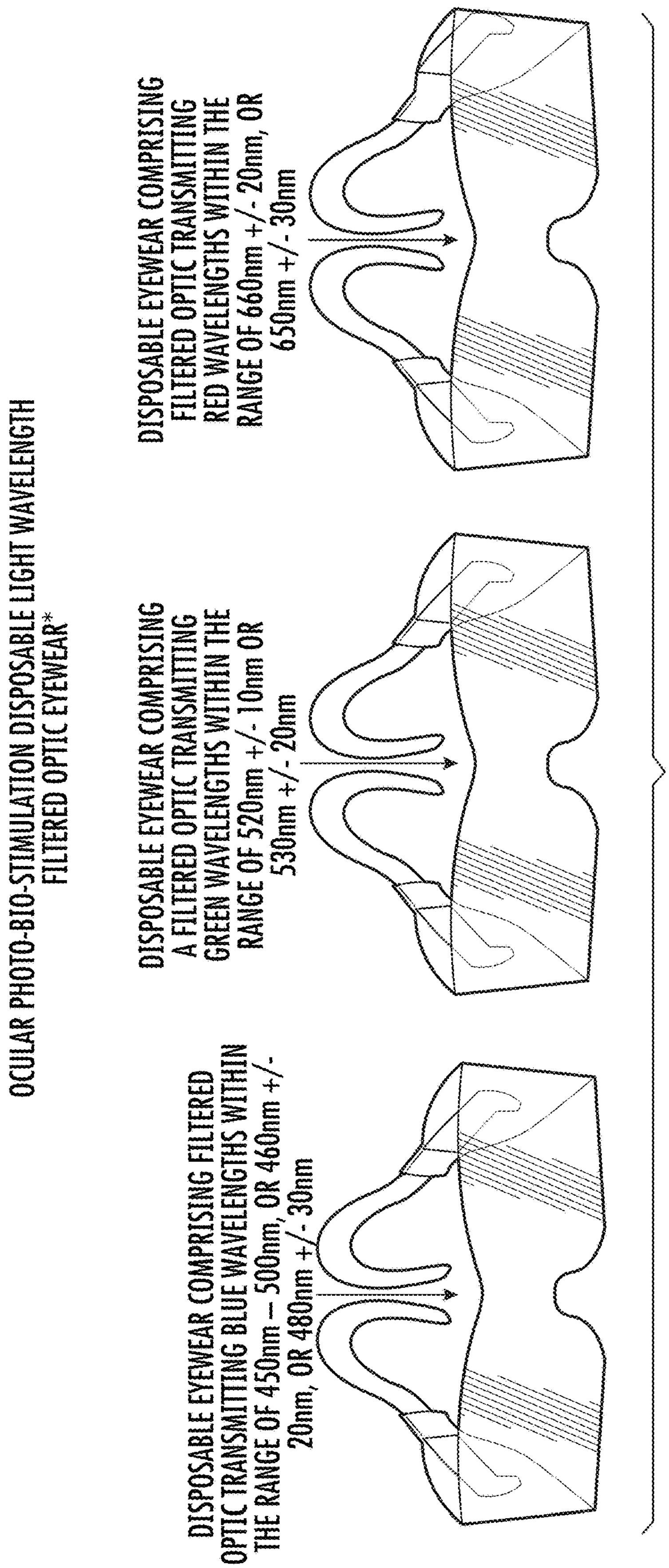

The degree of darkness of the sunglasses or treatment glasses can provide one of or more of: scotopic condition, reduced mesopic conditions, and reduced photopic conditions. FIG. 23A shows examples of ocular photo-bio-stimulation disposable (or non-disposable) light wavelength filtered optic eyewear; the disposable eyewear can be made, by way of example only, a darkly tinted or near opaque colored plastic material having plastic or paper arms that are supported by the wearer's ears, to wear over or around the user's conventional eyeglasses, if needed. The wearer can look at a distance separated bright light source while wearing the disposable eyewear for a time. Such a bright light source can be one of LED, OLED, iLED, quantum dots, fluorescent, incandescent, sun light, laser, plasma display, TV display, tablet display, cell phone display, computer display, or electronic display. A defocusing lens can be utilized with the eyewear or optic. Such a defocusing lens can be housed within the eyewear, attached to the eyewear or optic, or worn behind the eyewear or optic. In most, but not all cases, the defocusing lens is on the backside of the filter between the filter and the eye of the wearer or user. FIG. 23B shows examples of ocular photo-bio-stimulation disposable (or non-disposable) light wavelength filtered optic eyewear; the disposable eyewear can be made, by way of example only, a darkly tinted or near opaque colored plastic material having plastic or paper arms that are supported by the wearer's ears, to wear over or around the user's conventional eyeglasses, if needed. The wearer can look at a distance separated bright light source while wearing the disposable eyewear for a time. Such a bright light source can be one of LED, OLED, iLED, quantum dots, fluorescent, incandescent, sun light, laser, plasma display, TV display, tablet display, cell phone display, computer display, or electronic display. A defocusing lens can be utilized with the eyewear or optic. Such a defocusing lens can be housed within the eyewear, attached to the eyewear or optic, or worn behind the eyewear or optic. In most, but not all cases, the defocusing lens is on the backside of the filter between the filter and the eye of the wearer or user.

If reference to FIG. 24, the embodiment can be eyewear comprising an optic, wherein the eyewear when worn causes the pupil of an eye to enlarge in diameter, wherein the optic transmits light radiation having wavelengths of light within the range of 450 nm and 510 nm and wherein the optic transmits 40% or less of visible light. Eyewear that comprises side shields can be used to assist in blocking light coming in from the periphery. The optic can comprise a filter or filters. The wavelengths of light that can be transmitted, by way of example only, are within the range of 460 nm+/−10 nm or 480 nm+/−30 nm or 450 nm-520 nm. The optic can transmit 30% or less visible light. The optic can transmit 20% or less visible light. The optic can transmit 15% or less of visible light. The optic can transmit 10% or less visible light. The eyewear can be one of: rollable eyewear, clip-on eyewear, disposable eyewear, fit-over eyewear, or flip down or up eyewear. The eyewear can block or filter light from striking the eyes of the wearer by way of the sides and optics of the eyewear. (See, 2401.) The eyewear can block or filters light from striking the eyes of the wearer by way of the optics of the eyewear. The eyewear can comprise wrap around optics. The optics can have no optical power or can be of plano power. The optics can be non-prescription. The optics can comprise optical power. The eyewear can fit over or in front of prescription optics.

In another embodiment eyewear comprises an optic that comprises one or more of a bandpass filter, interference filter, absorption filter, selective wavelengths filter, neutral density filter, and/or notch filter, such that the optic can transmit either light wavelengths within the range of at least one of 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The optic can be used in conjunction with a light source of the appropriate light wavelength and intensity. The eyewear can be one of: rollable eyewear, clip-on eyewear, disposable eyewear, fit-over eyewear, or flip down or up eyewear. The eyewear blocks or filters light from striking the eyes of the wearer by way of the sides and optics of the eyewear. The eyewear blocks or filters light from striking the eyes of the wearer by way of the optics of the eyewear. The eyewear can comprise wrap around optics. The optics can have no optical power or can be of plano power. The optics can be non-prescription. The optics can comprise optical power. The eyewear can fit over or in front of prescription optics. The overall transmission of visible light through the optic of the eyewear can be 40% or less, 30% or less, 20% or less. One or both optic(s) of the eyewear can comprise optical power. One or both optic(s) of the eyewear can comprise no optical power (plano). The optic(s) can be comprised of one or more of: ophthalmic plastic, CR 39, Trivex, mid index, high index ophthalmic materials, polycarbonate, or glass. The higher the index the less longitudinal chromatic aberration. By way of example only, CR39 will have less longitudinal chromatic aberration than polycarbonate. A filter can be added to an optic, in this case a lens or lens blank by way of, imbibed, coated, having an absorptive dye intermixed with the lens matrix material, or surface cast. The filter can be added, by one of: an outer layer, a separate filter that is adjacent to the lens or lens blank, and/or a separate filter that is distance separated but in optical alignment with the lens or lens blank.

When filtered surface casting is utilized, a thin surface cast layer that filters can be placed on the front convex surface of the lens or lens blank. Conventional finishing layers such as, by way of example only, hard scratch resistant coating or an anti-reflective layer or coating can be placed on top of the surface cast layer. For single vision lenses a spherical surface cast layer on the front surface works well with the concave surface providing the astigmatic curve and the curve that causes the spherical power to be what is required. Such a concave surface can be fabricated by way of surfacing or free forming. When fabricating a progressive addition lens, the same surface cast front convex surface can be utilized and the PAL surface can be free formed on the concave surface of the lens, lens blank or semi-finished lens blank.

An embodiment can be that of a filtered lens or filtered optic that comprises a surface cast layer. The surface cast layer can provide all or the majority of the filtering effect. In certain embodiments the lens or lens blank can provide the UV filtering, while the surface cast layer can provide the remainder of the filtering. In an embodiment the surface cast layer comprises two standard dyes, two notch filters, one IR dye, and one UV absorber. In another embodiment the surface cast layer comprises two standard dyes, two notch filters, one IR dye, and the lens or lens blank comprises a UV absorber. In certain other embodiments the filter lens or filtered optic comprises an imbibed filter combined with a surface cast layer comprising a filter. In certain embodiments the filtered lens or filtered optic can comprise a plurality of different filters.

An embodiment can be a surface cast layer that filters such that light transmitted through the layer and measured within the wavelength range of 450 nm-520 nm comprises a 50% or greater transmission, and wherein the overall light visible light transmission through the surface cast layer is 50% or less.

An embodiment can be that of a filtered lens or filtered optic for ocular photo-bio-stimulation that comprises a surface cast layer, whereby the filtered lens or filtered optic comprises an overall visible light transmission of 40% or less and comprises light transmission through the filtered lens or filtered optic and measured within the range of 450 nm-520 nm of 40% or more.

An embodiment can be that of a filtered lens or filtered optic for ocular photo-bio-stimulation that comprises a surface cast layer, whereby the filtered lens or filtered optic comprises an overall visible light transmission of 30% or less and comprises light transmission through the filtered lens or filtered optic and measured within the range of 450 nm-520 nm of 40% or more.

An embodiment can be that of a filtered lens or filtered optic for ocular photo-bio-stimulation that comprises a surface cast layer, whereby the filtered lens or filtered optic comprises an overall visible light transmission of 20% or less and comprises light transmission through the filtered lens or filtered optic and measured within the range of 450 nm-520 nm of 40% or more.

An embodiment can be that of a filtered lens or filtered optic for ocular photo-bio-stimulation that comprises a surface cast layer, whereby the filtered lens or filtered optic comprises an overall visible light transmission of 40% or less and comprises light transmission through the filtered lens or filtered optic and measured within the range of 450 nm-520 nm of 50% or more.

An embodiment can be that of a filtered lens or filtered optic for ocular photo-bio-stimulation that comprises a surface cast layer, whereby the filtered lens or filtered optic comprises an overall visible light transmission of 30% or less and comprises light transmission through the filtered lens or filtered optic and measured within the range of 450 nm-520 nm of 50% or more.

An embodiment can be that of a filtered lens or filtered optic for ocular photo-bio-stimulation that comprises a surface cast layer, whereby the filtered lens or filtered optic comprises an overall visible light transmission of 20% or less and comprises light transmission through the filtered lens or filtered optic and measured within the range of 450 nm-520 nm of 50% or more.

An embodiment can be that of a filtered lens or filtered optic for ocular photo-bio-stimulation that comprises a surface cast layer, whereby the filtered lens or filtered optic comprises an overall visible light transmission of 40% or less and comprises light transmission through the filtered lens or filtered optic and measured within the range of 450 nm-520 nm of 60% or more.

An embodiment can be that of a filtered lens or filtered optic for ocular photo-bio-stimulation that comprises a surface cast layer, whereby the filtered lens or filtered optic comprises an overall visible light transmission of 30% or less and comprises light transmission through the filtered lens or filtered optic and measured within the range of 450 nm-520 nm of 60% or more.

An embodiment can be that of a filtered lens or filtered optic for ocular photo-bio-stimulation that comprises a surface cast layer, whereby the filtered lens or filtered optic comprises an overall visible light transmission of 20% or less and comprises light transmission through the filtered lens or filtered optic and measured within the range of 450 nm-520 nm of 60% or more.

An embodiment can be that of a filtered lens or filtered optic for ocular photo-bio-stimulation, whereby the filtered lens or filtered optic comprises an overall visible light transmission of 40% or less and comprises light transmission through the filtered lens or filtered optic and measured within the range of 450 nm-520 nm of 40% or more.

An embodiment can be that of a filtered lens or filtered optic for ocular photo-bio-stimulation, whereby the filtered lens or filtered optic comprises an overall visible light transmission of 30% or less and comprises light transmission through the filtered lens or filtered optic and measured within the range of 450 nm-520 nm of 40% or more.

An embodiment can be that of a filtered lens or filtered optic for ocular photo-bio-stimulation, whereby the filtered lens or filtered optic comprises an overall visible light transmission of 20% or less and comprises light transmission through the filtered lens or filtered optic and measured within the range of 450 nm-520 nm of 40% or more.

An embodiment can be that of a filtered lens or filtered optic for ocular photo-bio-stimulation, whereby the filtered lens or filtered optic comprises an overall visible light transmission of 40% or less and comprises light transmission through the filtered lens or filtered optic and measured within the range of 450 nm-520 nm of 50% or more.

An embodiment can be that of a filtered lens or filtered optic for ocular photo-bio-stimulation, whereby the filtered lens or filtered optic comprises an overall visible light transmission of 30% or less and comprises light transmission through the filtered lens or filtered optic and measured within the range of 450 nm-520 nm of 50% or more.

An embodiment can be that of a filtered lens or filtered optic for ocular photo-bio-stimulation, whereby the filtered lens or filtered optic comprises an overall visible light transmission of 20% or less and comprises light transmission through the filtered lens or filtered optic and measured within the range of 450 nm-520 nm of 50% or more.

An embodiment can be that of a filtered lens or filtered optic for ocular photo-bio-stimulation, whereby the filtered lens or filtered optic comprises an overall visible light transmission of 40% or less and comprises light transmission through the filtered lens or filtered optic and measured within the range of 450 nm-520 nm of 60% or more.

An embodiment can be that of a filtered lens or filtered optic for ocular photo-bio-stimulation, whereby the filtered lens or filtered optic comprises an overall visible light transmission of 30% or less and comprises light transmission through the filtered lens or filtered optic and measured within the range of 450 nm-520 nm of 60% or more.

An embodiment can be that of a filtered lens or filtered optic for ocular photo-bio-stimulation, whereby the filtered lens or filtered optic comprises an overall visible light transmission of 20% or less and comprises light transmission through the filtered lens or filtered optic and measured within the range of 450 nm-520 nm of 60% or more.

In certain embodiments a filter or filters is/are applied to the convex side of the lens, lens blank, or semi-finished lens blank. In other cases, the filter or filters is/are applied to the concave side of the lens, lens blank, or semi-finished lens blank. In other cases, the filter or filters is/are applied to both sides of the lens, lens blank, or semi-finished lens blank. In still other cases the filter or filters is/are applied to matrix of the lens, lens blank, or semi-finished lens blank. And in still other cases the filter or filters is/are embedded within the lens, lens blank, or semi-finished lens blank. Still in other embodiments the filter or filters is/are separated and placed in optical alignment with the lens, lens blank or semi-finished lens blank.

In certain embodiments a filter or filters transmitting predominantly blue light wavelengths can be utilized in the morning hours and a filter or filters transmitting predominantly red-light wavelengths can be utilized in the afternoon hours. This can be accomplished by having an attachable, detachable front piece comprising or housing the bandpass filter that by way of example only, clips on and off or magnetically attaches to the front or sides of the eyewear, or that attaches by way of pressure on the sides of the eyewear, or that attach mechanically to the eyewear. This allows for swapping the bandpass filters based upon the time of day being used or the filter(s) desired. In this case the prescription optic or nonprescription (plano) optic (which can include defocus or that of a separate defocusing optic) is housed or supported by the base frame to which the detachable front piece is releasably attached.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of, 460 nm-520 nm, 450 nm-520 nm, 470 nm to 520 nm, or 480 nm+/−30 nm, or by utilizing a light source or light emitter that predominately transmits within the wavelength range of at least one of 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

Figure 25A:
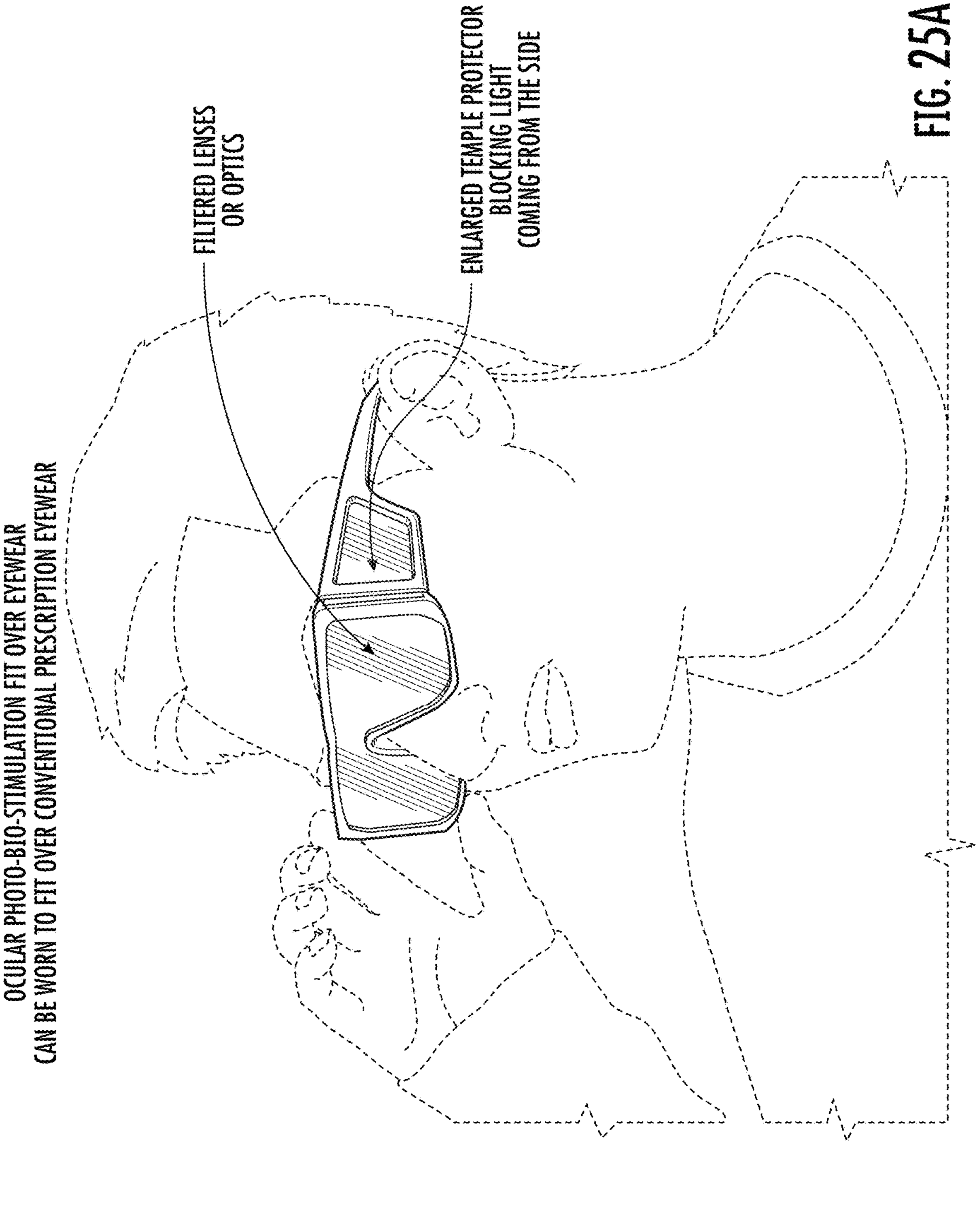
FIG. 25A-C shows an embodiment of the current invention as described herein.
Figure 25B:
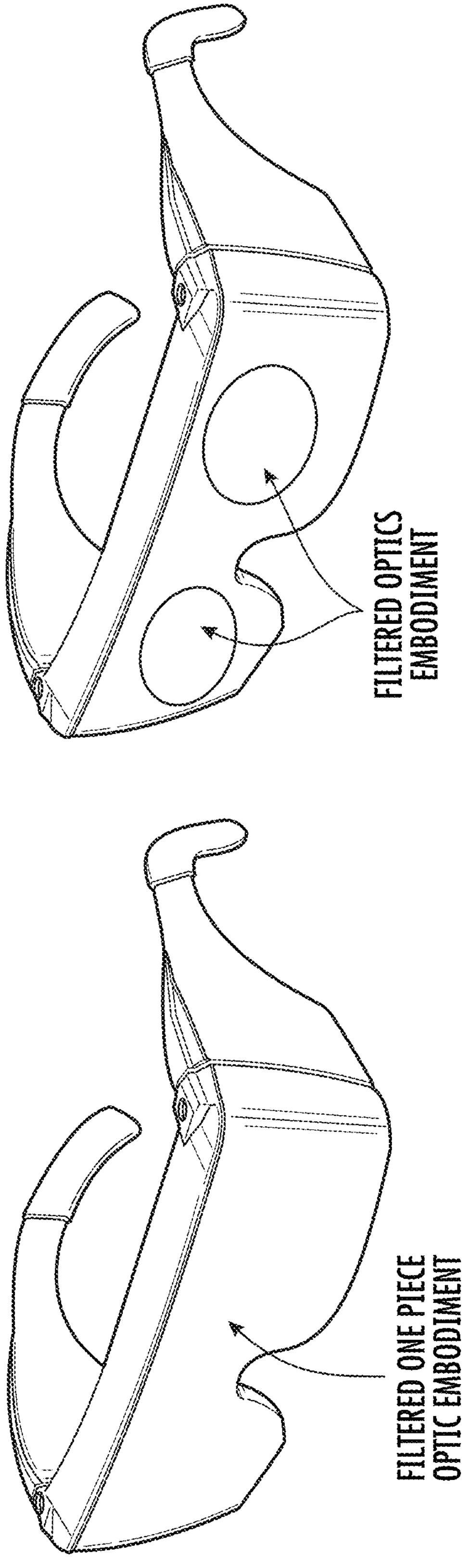
Figure 25C:
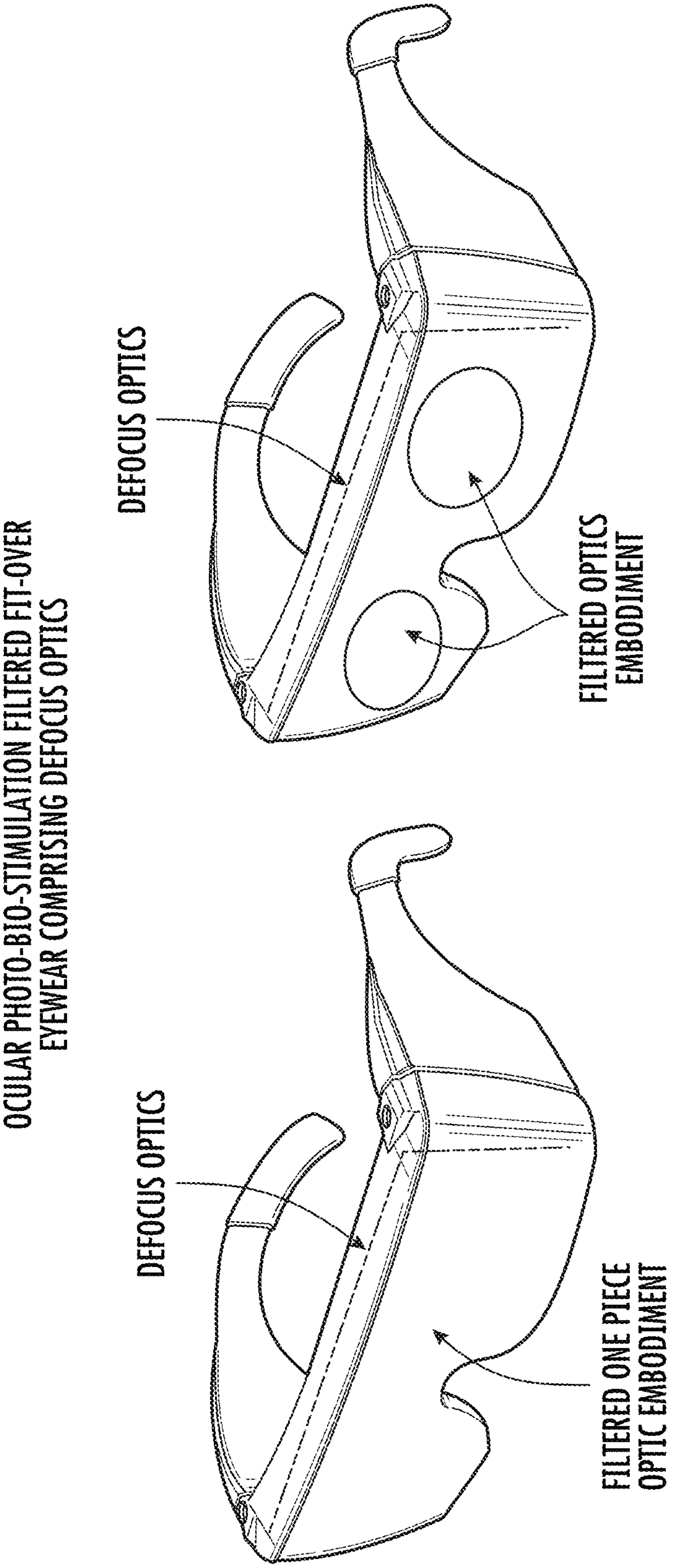

In reference to FIGS. 25*a-c*, an embodiment for ocular photo-bio-stimulation can be fit over eyewear that fits over the wearer's conventional vision correction eyewear. Such an embodiment can comprise:

Lens(es) or optic(s) that transmit predominately wavelengths within the range of, by way of example only, at least one of: 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm, to the retina(s) of the user's eye(s).

Such lens(es) or optic(s) can comprise lens(es) or optic(s) comprising one or more filters, or the one or more filters can be separated and in optical alignment with the lens(es) or optic(s);

Such lens(es) or optic(s) can also comprise a defocusing optic or a light dispersion optic;

Such lens(es) or optic(s) can comprise optical power or no optical power; and/or Optionally, such lens(es) or optic(s) can comprise plus optical power or minus optical power for generating a defocus to enlarge the area of retina stimulated by the desired ocular photo-bio-stimulation therapy light wavelength(s).

Eyewear for ocular photo-bio-stimulation, wherein the eyewear fits over conventional eyewear worn by a wearer (see, e.g., FIGS. 25*a-c*), wherein the fit over eyewear predominantly transmits one or more light wavelengths within the range of at least one of: 450 nm-500 nm, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm, to the eye(s) of the wearer, wherein the fit over eyewear comprises a filter or filters, and wherein the conventional eyewear houses lenses for correcting the distance vision needs of the wearer.

Embodiments of the above inventive optical system as taught herein attempt to keep the user's eye pupil diameter as large as possible during treatment of the eye(s) by one or more of the following: 1) user distance viewing fixation—eliminates accommodative pupil constriction, 2) Lower Level of light intensity being transmitted, 3) utilization of a red wavelength light emitter or emitters), and/or 4) utilization of a red-light filter. While the inventive system will work with a mydriatic pharmaceutical, the inventive embodiments have been designed to work without the use of a mydriatic pharmaceutical, too.

An embodiment can be eyewear that fits over conventional eyewear worn by a wearer, wherein the fit-over eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the user, wherein the fit over eyewear comprises a filter or filters, and wherein the conventional eyewear houses lenses for correcting the distance vision needs of the wearer. The fit-over eyewear can also comprise one or more light emitters.

An embodiment can be eyewear that fits over conventional eyewear worn by a wearer, wherein the fit over eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the user, wherein the fit over eyewear comprises a filter or filters, and wherein the conventional eyewear houses lenses for correcting the distance vision needs of the wearer, and wherein the fit over eyewear comprises a defocusing lens or optic. The fit-over eyewear can also comprise one or more light emitters.

An embodiment can be eyewear that fits over conventional eyewear worn by a wearer, wherein the fit over eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the user, wherein the fit-over eyewear comprises a filter or filters, and wherein the conventional eyewear houses lenses for correcting the distance vision needs of the wearer, and wherein the fit over eyewear comprises a light diffusing lens or optic. The fit-over eyewear can also comprise one or more light emitters.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm, or by utilizing a light source or light emitter that predominately transmits within the wavelength range of 460 nm-520 nm or 470 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye. Wavelengths within the range of 650 nm+/−30 nm or 700 nm+/−30 nm can also be utilized.

An embodiment for ocular photo-bio-stimulation can be by way of example only, one of a clip on, magnetic attachable, or pressure attachable eyewear that is attachable and detachable from the wearer's conventional vision correction eyewear. Such an embodiment can comprise:

Another embodiment includes a second eyewear to be worn by a wearer, wherein the second eyewear when worn is in optical communication with a first eyewear worn by a wearer, wherein the second eyewear comprises a filtered lens or filtered optic, wherein the filtered lens or filtered optic of the second eyewear predominantly transmits at a light wavelength transmission rate of 50% or more within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to an eye of the wearer, wherein the first eyewear comprises a first eyewear lens for optically correcting the distance vision of the wearer, and wherein the filtered lens or filtered optic of the second eyewear is distinct from first eyewear lens and wherein the overall visible light transmission through both the filtered lens or filtered optic and the first lens is 50% or less.

Each filtered lens or filtered optic can be comprised of two or more of: filters, absorbing dyes, light absorbers, or any combination thereof. The filtered lens or filtered optic can comprise one or more of: an interference filter, absorption filter, light absorber, neutral density filter, bandpass filter, notch filter, or selective blue light filter. The filtered lens or filtered optic can comprise two or more of interference filter, absorption filter, neutral density filter, bandpass filter, notch filter, or selective blue light filter. The second eyewear can be releasably attachable to the first eyewear. The second eyewear can be clip on eyewear, magnetic attachable eyewear, pressure mounted eyewear, rollable eyewear, or statically attachable eyewear. The second eyewear can be fit over eyewear which is reusable or disposable. The second eyewear can be disposable eyewear or insert eyewear. The filtered lens or filtered optic can have optical power or be plano (devoid of optical power).

The overall visible light transmission through a filtered lens or filtered optic and the first lens can be 40% or less. The overall visible light transmission through the filtered lens or filtered optic and the first lens can be 30% or less. The filtered lens or filtered optic can comprise a predominant light wavelength transmission that is within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, which can be 40% or greater. The filtered lens or filtered optic can increase choroidal thickness and reduce axial elongation of the wearer's eye. The filtered lens or filtered optic can slow down myopia progression of the wearer's eye. The filtered lens or filtered optic can comprise a peak light transmission spectral curve that falls within at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The first eyewear lens for correcting the distance vision of the wearer can comprise a central zone for correcting the distance vision needs of the wearer and an increased minus optical power zone peripheral to that of the central zone. The first eyewear lens can comprise optical power or optics that provide peripheral vision defocus. The first eyewear lens can comprise an optical power or optics that provide peripheral vision light diffusion or dispersion. The first eyewear lens can comprise optical power or optics that provide a reduction in peripheral vision contrast seen by the eye of a wearer.

The light transmitted by the filtered lens or filtered optic excites rhodopsin in the wearer's eye. The light transmitted by the filtered lens or filtered optic excites melanopsin in the wearer's eye. The light transmitted by the filtered lens or optic can increase dopamine or serotonin in the wearer's eye. The light transmitted by the filtered lens or optic increases dopamine or serotonin in the wearer's brain. The light transmitted by the filtered lens or filtered optic can increase retinal mitochondrial function.

The second eyewear can comprise one or more of timer, alarm, or wireless communication. The second eyewear can comprise a biofeedback component. The wearer's pupil of the second eyewear and the first eyewear can reduce in size absent of wearing the second eyewear and first eyewear when in ambient room light or sunlight. The filtered lens or filtered optic can generate defocused light. The filtered lens or filtered optic can generate dispersed light, diffused light, or light having less image contrast. The filtered lens or filtered optic can transmit the majority of their light wavelengths within a wavelength range to excite melanopsin and rhodopsin.

Lens(es) or optic(s) that transmit predominately wavelengths within the range of, by way of example only, at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, can be transmitted to or painted on the retina(s) of the user's eye(s).

Such lens(es) or optic(s) can comprise lens(es) or optic(s) comprising one or more filters, or the one or more filters can be separated and in optical alignment with the lens(es) or optic(s);

Such lens(es) or optic(s) can also comprise a defocusing optic or a light dispersion optic;

Such lens(es) or optic(s) can comprise optical power or no optical power; and/or Optionally, such lens(es) or optic(s) can comprise plus optical power or minus optical power for generating a defocus to enlarge the area of retina stimulated by the desired ocular photo-bio-stimulation therapy light wavelength(s).

Ocular photo-bio-stimulation embodiments of the above inventive optical system as taught herein attempt to keep the user's eye pupil diameter as large as possible during treatment of the eye(s) by one or more of the following; 1) user distance viewing fixation—eliminates accommodative pupil constriction, 2) Lower Level of light intensity being transmitted, 3) utilization of a red wavelength light emitter or emitters), and/or 4) utilization of a red-light filter. While the inventive system will work with a mydriatic pharmaceutical, the inventive embodiments have been designed to work without the use of a mydriatic pharmaceutical, too.

An embodiment can be that of eyewear that is attachable to conventional eyewear worn by a wearer/user, wherein the attachable eyewear predominantly transmits one or more light wavelengths within the range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the wearer, wherein the fit over eyewear comprises a filter or filters, and wherein the conventional eyewear houses lenses for correcting the distance vision needs of the wearer, and wherein the attachable eyewear comprises a defocusing lens or optic. The attachable eyewear can also comprise one or more light emitters.

As used herein, a light emitter and be any light source that gives off light radiation. By way of example only, one of: LEDs, OLEDs, TOLEDs. micro-OLEDs, micro-LEDs, micro-ileds, iLEDs, quantum dots, florescent lights, incandescent lights, ambient light, and the sun. In certain embodiments a light ring is utilized to minimize pupil constriction. This occurs as the eye being treated can fixate on a distant object through the center of the light ring while the light of the light ring is stimulating the photoreceptors of the eye. This further allows for providing light exposure to the peripheral retina of the eye.

As used herein, a defocusing lens or optic is a lens or optic that causes light to not focus on the retina of the wearer's eye. As used herein, dispersed light can be that of defocused light. In certain embodiments it focuses in front of the retina and in other embodiments it focuses behind the retina. And in still other embodiments it never focuses. In certain embodiments a defocusing lens can be utilized with a filter. In certain embodiments a defocusing lens can comprise a filter. In certain embodiments a defocusing lens can be utilized with a bandpass filter. In certain embodiments a defocusing lens can comprise a bandpass filter. In certain embodiments a defocusing lens can be utilized with an interference filter. In certain embodiments a defocusing lens can comprise an interference filter. In certain embodiments a defocusing lens can be utilized with an absorptive filter. In certain embodiments a defocusing lens can comprise an absorptive filter.

The defocus lens can comprise an optical power that can be one or more of the optical powers within the range of +0.35 D to +5.00 D or −0.35 D to −5.00 D. The defocus lens can comprise an optical power that can be one or more of the optical powers within the range of +0.35 D to +10.00 D or −0.35 D to −10.00 D. The defocusing lens can comprise central defocus. The defocusing lens can comprise peripheral defocus. The defocusing lens can comprise central focus and peripheral defocus. The defocusing lens can comprise defocus for the retina throughout the power of the defocusing lens.

In most, but not all cases, the defocusing lens is located between the filter and the eye of the wearer or user. The defocusing lens can be any optic that defocuses light so that the light after passing through the wearer or user eye's pupil spreads the light rays over a larger area of the retina of the wearer or user's eye as opposed to that of a focusing lens. The defocusing optic can be a minus lens power. The defocusing optic can be a positive lens power. The defocusing optic can be a Fresnel lens. The defocusing optic can be a multifocal lens. The multifocal lens can comprise a plano central zone having no optical power and a peripheral defocusing zone or zones having plus optical power. The multifocal lens can comprise a central zone having optical power that focuses light on the fovea/macular area and a peripheral defocusing zone or zones having plus optical power. The multifocal lens can comprise a central zone of clear vision and a peripheral zone(s) of defocused light. The defocusing optic can be an electronic display. The defocusing optic can be attached to a filter, or distance separated from a filter or a portion of a filter. The multifocal optic can be attached to a filter, or distance separated from a filter or a portion of the filter.

Embodiments when light wavelengths are generated by way of filtered optics or filtered lenses the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

Embodiments when light wavelengths are generated by a light emitter(s) if ambient lighting is present (including that of artificial light or sun light) the blended light wavelengths of the light emitter(s) and also the ambient light comprises wavelengths of light that strike the eye's retina fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

An embodiment is that of eyewear worn by a wearer, wherein the eyewear is attachable to a different set of eyewear, wherein the attachable eyewear predominantly transmits one or more light wavelengths within the range of at least one of: 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the wearer, wherein the eyewear comprises a filter or filters, wherein the eyewear comprises a minus optical power defocusing optic or lens that permits central vision clarity but peripheral defocus, and wherein the peripheral defocus is caused by one of: minus powered lenslets or minus peripheral defocusing power that is peripheral to the central zone of the lens or optic, and wherein the minus optical power defocus is within the range of −0.35 D to −5.00 D.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of 460 nm-520 nm or 470 nm to 520 nm, or by utilizing a light source or light emitter that predominately transmits within the wavelength range of 60 nm-520 nm or 470 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye. However, wavelengths within the range of 650 nm+/−30 nm or 70 nm+/−30 nm can also be utilized.

Another embodiment is that of eyewear worn by a wearer, wherein the eyewear is attachable to a different set of eyewear, wherein the attachable eyewear predominantly transmits one or more light wavelengths within the range of one of: 480 nm+/−30 nm, 530 nm+/−20 nm, or 650 nm+/−30 nm to the eye(s) of the wearer, wherein the eyewear comprises a filter or filters, wherein the eyewear comprises a plus optical power defocusing optic or lens that permits central vision clarity but peripheral defocus, and wherein the peripheral defocus is caused by one of: plus powered lenslets or plus peripheral defocusing power that is peripheral to the central zone of the lens or optic, and wherein the plus optical power defocus is within the range of-+0.35 D-+5.00 D.

Still another embodiment is eyewear worn by a wearer, wherein the eyewear is attachable to a different set of eyewear, wherein the attachable eyewear predominantly transmits one or more light wavelengths within the range of at least one of: 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, to the eye(s) of the wearer, wherein the eyewear comprises a filter or filters, wherein the eyewear comprises a minus defocusing optic or lens that permits central vision clarity but peripheral defocus, and wherein the peripheral defocus is caused by one of: aspheric lenslets or dispersion defocusing power that is peripheral to the central zone of the lens or optic.

In most but not all cases, a filter is located on the front convex surface of the optic. When the optic is devoid of optical power the filter can be on either surface or buried in between either surface. In certain embodiments a lens comprising the desired optical power for correcting the refractive power of the eye of the wearer is located between a filter (which can be on or in an optic) and the front of the eye of the wearer/user. In certain embodiments a lens comprising the desired optical power for correcting the refractive power of the eye of the wearer is attached to a filter (which can be on or in an optic) and the front of the eye of the wearer/user. A filter can be one of deposited, coated, or adhered to a substrate (being an optic) having optical power or no optical power. The substate can be comprised of plastic or glass. The substrate can be a film. In certain cases, the filter or filters can be separated from the optic or lens but aligned to be in optical alignment with the lens or optic.

In certain embodiments the above bandpass filter optic or sunglasses can be utilized without a defocused optic or lens. In certain embodiments the above bandpass filter optic or sunglasses can be utilized in association with a defocused lens. Such a defocused lens can comprise one or more of a central zone of focusing power or no optical power, increasing plus power from the central zone outwards, multiple different plus power zones of optical power, multiple islands of plus optical power, multiple zones of plus defocus optical power, multiple zones of defocus, multiple islands of defocus optical power, and/or multiple zones of defocus. The zones or islands can be of the same plus optical power. The zones or islands can be of different plus optical power. The zones or islands can be of different optical power. The zones or islands can cause different defocus. The zones or islands can increase optical power. The zones or islands can increase in defocus. The zones or islands can decrease in defocus. The zones or islands can decrease in optical power. The zones or islands can remain constant in optical power. The zones or islands can remain constant in defocus. In certain embodiments a central zone can have focus, and the peripheral zones can have defocus.

Such a defocused lens can comprise one or more of a central zone of focusing power or no optical power, increasing minus optical power from the central zone outwards, multiple different plus power zones of optical power, multiple islands of minus optical power, multiple zones of minus defocus optical power, multiple zones of defocus, multiple islands of defocus optical power, and/or multiple zones of defocus. The defocus lens can comprise no optical power. The defocus lens can comprise optical power. The defocus can be caused by one or more of, of a single vision lens, multifocal lens, light scatter material, prism, applicator attached to lens surface, Fresnel optic, holographic optic, micro-lens array, and/or scratched surface of the optic. The defocusing element(s) can be located off center on or in the optic. The defocusing elements can be located centered on or in the optic. The defocusing elements can be located on or in the periphery of the optic. The defocusing elements can be embedded within the optic. The defocusing elements can be attached to the optic. The defocusing element can be attachable and detachable to the optic. The defocusing elements can be located peripheral to a central zone of the optic. When using the term defocusing optic in this disclosure document, it is meant that the light rays do not focus on the retina of the eye(s) of the wearer or user.

The light defocusing optic can comprise one or more of: a positive power convex lens design, negative power concave lens design, spherocylindrical lens design, prismatic lens design, aspheric lens design, Fresnel lens design, micro-lens array design, nano or micro-structure materials, concentric rings, grooves, scratches, and/or surface curves on the convex or concave side of the optic. The nano or micro-structure materials of a different index of refraction from the optic matrix material can be embedded within the optic matrix. The nano or micro-structure materials can be embedded within an optical coating and of a different index of refraction from an optic coating material that is applied to the optic. Such an optical coating can be by way of example only, a hard scratch resistant coating, a cushion coating, and/or a dielectric deposition coating. In certain embodiments the defocusing element is caused by dispersion of light. In such embodiments certain electrochromic optical materials or material properties cause light to disperse into blue, green and red wavelength bundles.

In one embodiment an electrochromic material layer can cause slight dispersion when electricity is applied and when no electricity is applied the electrochromic element returns the lens zone to a clear nondispersive lens zone. This allows for causing, by way of example only, white light to become dispersed when electrical power is applied, thus causing blue wavelengths of light to strike the retina for ocular photo-bio-stimulation light therapy and cease the retinal stimulation when the light therapy is no longer needed, and the electrical power is turned off. The electrochromic lens zone can be in the lens to coincide where light wavelengths can strike an area of the retina having a concentration of rods.

In another embodiment certain electroactive optical materials or material properties cause light to disperse into blue, green and red wavelength bundles. In this embodiment an electroactive liquid crystal layer can cause slight dispersion when electricity is applied and when no electricity is applied the electroactive element returns the lens zone to a clear nondispersive lens zone. This allows for causing when electrical power is applied, by way of example only, white light to become dispersed, thus causing blue wavelengths of light to strike the retina for ocular photo-bio-stimulation light therapy and cease the retinal stimulation when the light therapy is no longer needed, and the electrical power is turned off. The electroactive lens zone can be in the lens to coincide where light wavelengths can strike an area of the retina having a concentration of rods. In still other embodiments a zone comprising a plurality of prismatic surface features can be properly positioned to provide light wavelengths that will strike an area of the retina having a concentration of rods. In each of these embodiments, electrochromic, electroactive, or prismatic, the zone can be located around that of the central zone of the lens and at a location that optimizes dispersed light wavelengths of light striking an area of the retina peripheral to the macula having a high concentration of rods.

In certain embodiments nano or micro-structure particle materials can be used to disperse light. Examples of nano or micro-structure particle materials can be, by way of example only, polycrystalline ceramics like, by example, transparent alumina consisting of birefringent crystals. Additional examples are polystyrene (PS), copolymer polyacrylates (PMMA), polyolefins (PE, PP), titanium dioxide ($TiO2$), Zinc oxide (ZnO), or Zirconium oxide ($ZrO2$). Light passing through a transparent particle with a size comparable to the wavelength of incident light can be refracted or diffracted. Surface scratches or imperfections can cause light scattering. Each of the preceding lens designs, embedded particles in the optic matrix, coatings comprising particles, surface imperfections, surface refractive cures, quantum dots, or particles that fluoresce, can be utilized individually or in any combination to provide defocus. Once again it should be pointed out that the use of defocus as disclosed herein is causing or having the light rays to be defocused on the retina of the wearer or user of the optic. This maximizes the ability of the light wavelengths that strike the retina of the wearer or user of the optic within the wavelengths range of at least one of: 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm or 600 nm-700 nm, or 700 nm+/−30 nm, to be spread out.

In certain embodiments the optic that creates the defocus can be rotated either manually or automatically. When automatically rotated the defocus optic can be rotated by a motor. The rotation can help spread the defocused light wavelengths over the retina painting the retina with the defocused light as the defocused optic is rotated. The optic area of defocus can be from the entire optic. The area of defocus can be from the central zone. The central zone can be 9 mm, 10 mm, or 11 mm in diameter. The defocus can be from the peripheral zone of the optic. The peripheral zone can be any area outside of the central zone. As used herein, defocus means the light rays do not focus to a point on the retina of the eye of the user. In certain embodiments the light rays focus in front of the retina. In other cases, the light rays focus behind the retina. In still other embodiments the light rays are dispersed or scattered.

Any of the eyewear, lamp, electronic display, and/or lighting embodiments disclosed herein, including those comprising a bandpass filter, can also comprise a neutral density filter. By utilizing a neutral density filter in addition to a band pass filter it is possible to adjust the light intensity transmission of the transmitted wavelengths to provide for an enlargement of the pupil(s) of the wearer. The neutral density filter can be separate from the bandpass filter. The neutral density filter can be built into the bandpass filter. The neutral density filter can be attached to the bandpass filter. The neutral density filter can be integral with the bandpass filter. Utilizing a neutral density filter is important when the intensity of the light that is being transmitted by the optic exceeds a threshold where it constricts the pupil of the eye of the wearer or user of the optic. Embodiments disclosed herein prefer for the pupil of the eye to be as large as possible when the desired light wavelengths are being exposed to the retina. In preferred embodiments the pupil(s) of the eye(s) of the wearer or user of the lens or optic would be 3 mm or larger in diameter. In preferred embodiments the pupil(s) of the eye of the wearer or user of the lens or optic would be 4 mm or larger in diameter. In preferred embodiments the pupil(s) of the eye(s) of the wearer or user of the optic would be 5 mm or larger in diameter.

In certain other embodiments, the light source providing wavelengths of light within the range of light wavelengths of 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm or 600 nm-700 nm, or 700 nm+/−30 nm, can be moved relative to one of the eye, cornea, or pupil of the subject whose retina is being exposed to such light wavelengths, or the eye, cornea, or pupil of the subject can be moved relative to the light source. This allows for painting multiple large areas of retina of the subject with the light source. By moving the light source or moving the eyes of the subject the light radiation can intersect the cornea and pupil of the subject at multiple angles thus striking large and/or different areas of the retina as the eye and the light source move relative to one another. Such a device for accomplishing this can be a handheld instrument, tabletop or fixed spaced instrument, virtual reality device, mixed reality device, augmented reality device, eyewear, and/or helmet with a face shield. Ocular photo-bio-stimulation eyewear can be that of wrap around eyewear. Ocular photo-bio stimulation eyewear can comprise side shields for the purposes of blocking peripheral light rays.

A photo-bio-stimulation lens can filter and transmit light wavelengths within the range of light wavelengths of one or more of the following, 480 nm+/−30 nm, 450 nm-520 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm, 419 nm-400 nm, or 399 nm-380 nm.

An embodiment can be that of a wearable eyewear device comprising a filtered lens or filtered optic, wherein the filtered lens or filtered optic provides a light transmission rate of 40% or more, 50% or more, or 60% or more, of ocular photo-bio-stimulation light through and measured within a light wavelength range of at least one of: 480 nm+/−30 nm, 490 nm+/−5 nm, 490 nm+/−10 nm, 450 nm-520 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, to an eye of a wearer of the wearable eyewear device, and wherein the filtered lens or filtered optic further provides an overall visible light transmission rate of 50% or less, 40% or less, or 30% or less.

Another embodiment can be that of a wearable eyewear device comprising a filtered lens or filtered optic, wherein the filtered lens or filtered optic provides a light transmission rate of 40% or more, 50% or more, or 60% or more, of ocular photo-bio-stimulation light through and measured within a light wavelength range of at least one of: 480 nm+/−30 nm or 500 nm+/−20 nm to an eye of a wearer of the wearable eyewear device, and wherein the filtered lens or filtered optic further provides an overall visible light transmission rate of 50% or less, 40% or less, or 30% or less.

By way of example only, if 2,000 lux is considered to be the overall visible transmission through the filtered lens or optic, and the light intensity is 1,000 lux that passes through and measured within the filtered wavelength range of 480 nm+/−30 nm, then the light transmission through and measured within the wavelength range of 480 nm+/−30 nm would be 50% of the overall visible light transmission. By way of another example only, if 1,200 lux is considered to be the overall visible transmission through the filtered lens or optic, and the light intensity is 400 lux through and measured within the filtered wavelength range of 480 nm+/−30 nm, then the light transmission through and measured within the wavelength range of 480 nm+/−30 nm would be ~33% of the total overall visible light transmission. And still by way of another example only, if 1,200 lux is considered to be the overall visible transmission through the filtered lens or optic, and the combined light intensity is 400 lux through and measured within the filtered wavelength ranges of 480 nm+/−30 nm and also that of 700 nm+/−30 nm, then the light transmission through and measured within the wavelength range of 480 nm+/−30 nm and 700 nm+/−30 nm would be ~33% of the total overall visible light transmission Another embodiment can be that of a wearable eyewear device comprising a filtered lens or filtered optic, wherein the filtered lens or filtered optic provides a light transmission rate of 40% or more, 50% or more, or 60% or more, of ocular photo-bio-stimulation light through and measured within light wavelength ranges of a combination of 450 nm+/−30 nm, 450 nm-520 nm, and/or 580 nm+/−20 nm, to an eye of a wearer of the wearable eyewear device, and wherein the filtered lens or filtered optic further provides an overall visible light transmission rate of 50% or less, 40% or less, or 30% or less. Such a lens can be designed to have a greenish color.

Another embodiment can be that of a wearable eyewear device comprising a filtered lens or filtered optic, wherein the filtered lens or filtered optic provides a light transmission rate of 40% or more, 50% or more, or 60% or more, of ocular photo-bio-stimulation light through and measured within light wavelength ranges of a combination of 450 nm+/−30 nm, 450 nm-520 nm, and/or 600 nm+/−30 nm, to an eye of a wearer of the wearable eyewear device, and wherein the filtered lens or filtered optic further provides an overall visible light transmission rate of 50% or less, 40% or less, or 30% or less. Such a lens can be designed to have a reddish-brown color.

Another embodiment can be that of a wearable eyewear device comprising a filtered lens or filtered optic, wherein the filtered lens or filtered optic provides a light transmission rate of 40% or more, 50% or more, or 60% or more, of ocular photo-bio-stimulation light through and measured within light wavelength ranges of a combination of 450 nm+/−30 nm, 450 nm-520 nm, and/or 700 nm+/−30 nm, to an eye of a wearer of the wearable eyewear device, and wherein the filtered lens or filtered optic further provides an overall visible light transmission rate of 50% or less, 40% or less, or 30% or less. Such a lens can be designed to have a purplish color.

Another embodiment can be that of a wearable eyewear device comprising a filtered lens or filtered optic, wherein the filtered lens or filtered optic provides a light transmission rate of 40% or more, 50% or more, or 60% or more, of ocular photo-bio-stimulation light through and measured within light wavelength ranges of a combination of 450 nm+/−30 nm, 450 nm-520 nm, 550 nm+/−30 nm, and/or 650 nm+/−30 nm, to an eye of a wearer of the wearable eyewear device, and wherein the filtered lens or filtered optic further provides an overall visible light transmission rate of 50% or less, 40% or less, or 30% or less. Such a lens can be designed to have one of a bluish color, bluish-green color, reddish-brown color, and/or bluish grey color.

Another embodiment can be that of a wearable eyewear device comprising a filtered lens or filtered optic, wherein the filtered lens or filtered optic provides a light transmission rate of 50% or more or 60% or more of ocular photo-bio-stimulation light through and measured within a light wavelength range of 650 nm+/−30 nm to an eye of a wearer of the wearable eyewear device, and wherein the filtered lens or filtered optic further provides an overall visible light transmission rate of 50% or less, 40% or less, or 30% or less.

Another embodiment can be that of a wearable eyewear device comprising a filtered lens or filtered optic, wherein the filtered lens or filtered optic provides a light transmission rate of 50% or more or 60% or more of ocular photo-bio-stimulation light through and measured within a light wavelength range of 700 nm+/−30 nm to an eye of a wearer of the wearable eyewear device, and wherein the filtered lens or filtered optic further provides an overall visible light transmission rate of 50% or less, 40% or less, or 30% or less.

Ocular photo-bio-stimulation light can be transmitted by the filtered lens or filtered optic and increase the production of dopamine or serotonin in an eye and/or a brain of the wearer of the wearable eyewear device. The wearable eyewear device can be utilized on its own for daily wear, or wherein the wearable device fits over, behind, or around, a second eyewear frame or a lens of the second eyewear frame, or wherein the wearable eyewear device is supported by or releasably attachable to the second eyewear frame or the lens of the second eyewear frame.

The filtered lens or filtered optic can comprise two or more of: a filter, a filtered wafer, a surface cast filtered layer, an absorbing dye, a light absorber, or any combinations thereof. The filtered lens or filtered optic can comprise two or more of: an interference filter, an absorption filter, a light absorber, dye, a neutral density filter, a bandpass filter, a notch filter, or a selective blue light filter. The wearable eyewear device is one of: fit-over eyewear, disposable eyewear, clip-on eyewear, magnetically attachable eyewear, pressure-mounted eyewear, rollable eyewear, statically attachable eyewear, or eyewear. The wearable eyewear device can be dress glasses or sunglasses.

The filtered lens or filtered optic can comprise optical power or can be plano (devoid of optical power). The overall visible light transmission through the filtered lens or filtered optic and an eyeglass lens is 40% or less or 30% or less. The wearable eyewear device can be utilized in association with a light source, wherein the light source has an intensity of 2,000 lux or greater, and wherein a transmission intensity of light is within a wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, or wherein a light intensity of light within one of the wavelength ranges passing through a last surface of the filtered lens or filtered optic closest to an eye of the wearer is 300 lux or greater.

The ocular photo-bio-stimulation light transmitted through the filtered lens or filtered optic can increase choroidal thickness and/or reduce axial elongation of an eye of the wearer of the wearable eyewear device. The ocular photo-bio-stimulation light transmitted through the filtered lens or filtered optic can slow down myopia progression of an eye of the wearer of the wearable eyewear device.

The eyeglass lens of a second eyewear frame can comprise a central zone for correcting distance vision of the wearer of the wearable eyewear device, and the eyeglass lens of the second eyewear frame comprises an increased minus optical power zone peripheral to that of the central zone. The eyeglass lens of a second eyewear frame can comprise optical power, optics that provide peripheral vision defocus, or both. The eyeglass lens of a second eyewear frame can comprise one or more of: optical power, optics that provide peripheral vision light diffusion or dispersion, or both. The eyeglass lens of the second eyewear frame can comprise one or more of: optical power, optics that provide a reduction in peripheral vision contrast, or both.

The ocular photo-bio-stimulation light transmitted through the filtered lens or filtered optic can excite rhodopsin an eye of the wearer of the wearable eyewear device. The ocular photo-bio-stimulation light filtered that is transmitted through the filtered lens or filtered optic can excite melanopsin in an eye of the wearer of the wearable eyewear device. The ocular photo-bio-stimulation light transmitted through the filtered lens or filtered optic can increase retinal mitochondrial function in the wearer of the wearable eyewear device. The wearable eyewear device can comprise one or more of: a timer, an alarm, or a wireless communication component. The wearable eyewear device can comprise a biofeedback component. The filtered lens or filtered optic can cause a pupil of an eye of the wearer of the wearable eyewear device to increase in size when the wearable eyewear device is worn in ambient room light, sunlight, or both.

The filtered lens or filtered optic: defocuses light, disperses light, diffuses light, allows transmission of light having less or decreased image contrast, or combinations thereof. The filtered lens or filtered optic can comprise an imbibed tint or dye. The filtered lens or filtered optic can comprise a deposition coating or spin coating. The filtered lens or filtered optic can be a single vision lens or single vision optic. The filtered lens or filtered optic can comprise a surface cast layer that filters light. The surface cast layer can comprise one or more of a filter, dye, absorber, coating. The filtered lens or filtered optic can comprise a plurality of one or more of, dyes, filters, absorbers, coatings.

The filtered lens or filtered optic can comprise a progressive addition lens topography. The eyeglass lens of the second eyewear frame can comprise single vision lens. The eyeglass lens of the second eyewear frame can comprise a progressive addition lens topography. The wearable eyewear device can be one of spectacle eyewear, XR eyewear, a contact lens, an intraocular lens, or a corneal implant. The eyeglass lens of the second eyewear frame can comprise optical power, and the filtered lens or filtered optic of the wearable eyewear device can comprise a plano optical power.

Lenses or Optics Comprising a Defocus Zone for Ocular Photo-Bio-Stimulation Therapy In certain embodiments, myopia control lenses can be utilized in combination with ocular photo-bio-stimulation therapy. Such ocular photo-bio-stimulation can be with light wavelengths within the range of at least one of: 480 nm+/−30 nm, 530 nm+/−20 nm, and/or 650 nm+/−30 nm. Such ocular photo-bio-stimulation therapy can be applied while the subject or patient is wearing their myopia control lenses. This causes the light from the ocular photo-bio-stimulation light source to be spread across the eye's retina of the subject or patient wearing the myopia control lens or lenses, stimulating the production of retinal dopamine. The ocular photo-bio-stimulation therapy can be applied or provided to the subject or patient once or multiple times per day for, for example, 5 minutes or less per session, 10 minutes or less per session, 20 minutes or less per session, 60 minutes or less per session, 120 minutes or less per session, and other variations.

Embodiments can be that of a filtered lens or a clear lens, either of which comprises a zone of defocus. The defocus can be in the form of optical defocus or defocus caused by light scatter or dispersion. With a filtered lens, the filtering effect and the defocus zone both provide for the desired photo-bio-stimulation effect. With a non-filtered lens (e.g., a clear lens) the defocus zone provides for the desired photo-bio-stimulation effect. Defocus can be utilized to cause light wavelengths to spread across the peripheral retina of the wearer/user. The peripheral retina is the retina peripheral to the central region of the retina, which is that of the macula. As used herein, defocus can be one or more of: optical defocus, light scattering, and/or light dispersion.

An embodiment is a lens that can be that of a filtered lens. The filtered lens can predominantly transmit light wavelengths predominantly within the range of wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm. The filtered lens can comprise a central zone and a defocus zone can be positioned peripheral to the central zone.

The defocus zone can begin at the junction of the outer central zone periphery and the start of a zone adjacent to the central zone. The defocus zone can be comprised of ringed optical power steps (see, FIG. 26). The defocus zone can be comprised of minus optical power. The defocus zone can be comprised of lenslets (see, FIGS. 27, 28, 29, and 30). The defocus zone can be comprised of light scatter elements. The defocus zone can be comprised of minus optical power being more minus optical power or less plus optical power than the central zone's optical power. The minus of optical power increase over that of the central zone's optical power can be within the range of −0.35 D to −5.00 D. Such a lens can comprise a downward channel or zone of increasing positive optical power offsetting some or all of the added minus power. Such a downward channel can connect to a reading zone of increased positive optical power within the range of +1.00 D to +3.25 D over that of the central zone's optical power.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm, or by utilizing a light source or light emitter that predominately transmits within the wavelength range of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

The lenslets can be comprised of −0.35 D to −5.00 D negative power. The lenslets can be aspheric. The defocus zone can be comprised of a microlens array. The defocus zone can be comprised of optical power steps. The defocus zone can be comprised of light scatter elements. The defocus zone can be comprised of liquid crystal. The liquid crystal can switch on and off by way of an electrical potential change. Such a defocus can be that of either light scatter or a change in the refractive optical power of the lens' defocus zone. The liquid crystal can be switched to increase or decrease optical power. The liquid crystal can be switched to cause light scatter. The liquid crystal can be switched to eliminate most or all of the light scatter or to eliminate any change of optical power. By utilizing a switchable liquid crystal defocus zone, the lens can provide the desired level of ocular photo-bio-stimulation which can then be turned on or off as needed. The ability to electrically switch liquid crystal for that of optical power generation or light scattering is known in the art.

Figure 26:
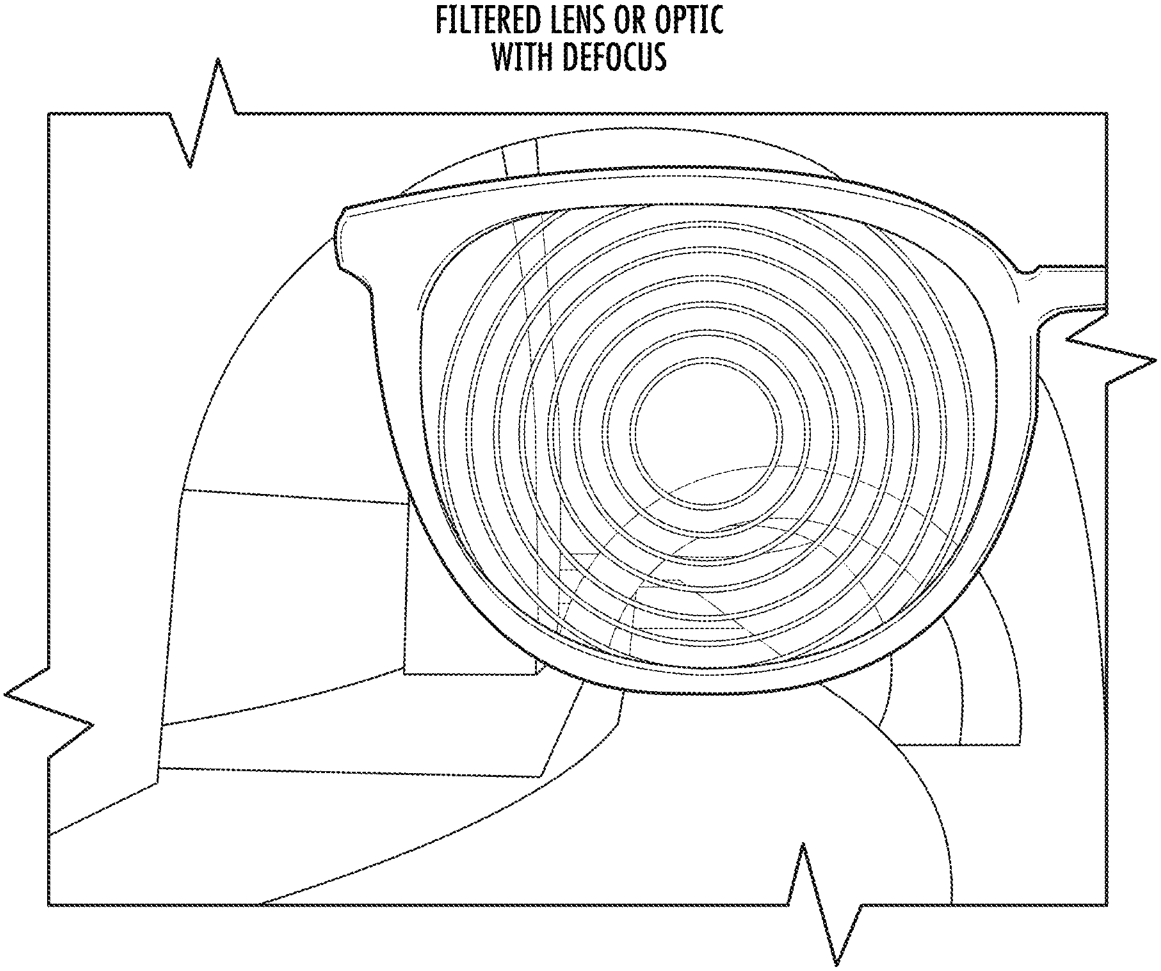
FIG. 26 shows an embodiment of the current invention as described herein.

In reference to FIG. 26, it shows an embodiment of a photo-bio-stimulation filtered defocused lens, which can be a lens that comprises:

- a central zone for correcting distance focus for the wearer and small enough to establish an effective functional zone;
- a selected fill factor to deliver high efficacy while preserving good wearability;
- a central zone of 4 mm-6 mm; and
- added surface power within the range of +0.50 D to +3.50 D or −0.35 D to −5.00 D; and The filtering can predominantly transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

According to the embodiment, a photo-bio-stimulation lens can filter and predominantly transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 40% of less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

In embodiments when a filtered optic or filtered lens is used the overall light transmission through the filtered optic or filtered lens can be 30% of less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm, or by utilizing a light source or light emitter that predominately transmits within the wavelength range of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

Figure 27:
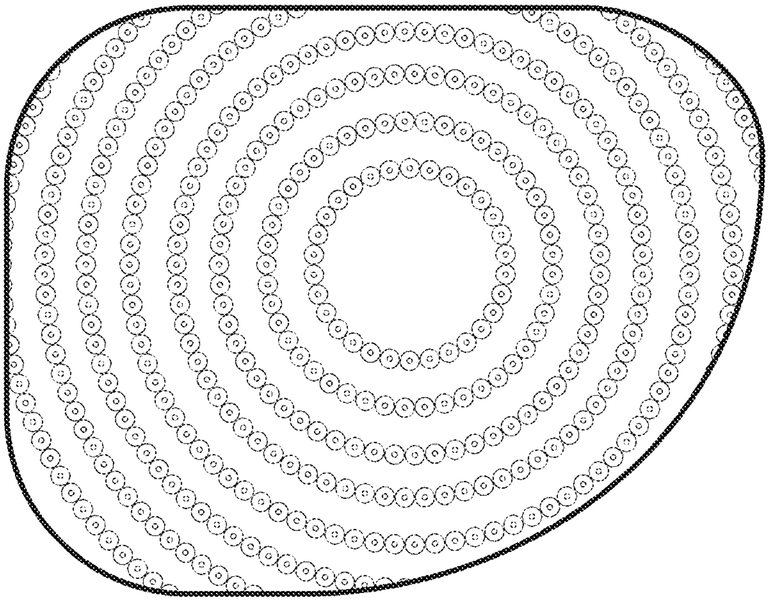
FIG. 27 shows an embodiment of the current invention as described herein.

In reference to FIG. 27, it shows an embodiment of a photo-bio-stimulation filtered defocused lens, which can be a lens that comprises: a spectacle lens for myopia correction and control with Highly Aspherical Lenslet Target (H.A.L.T.) Technology; a central optical zone (9 mm) for correcting distance refractive error of the wearer, with surrounding myopia control zone incorporating 1021 contiguous (touching) highly aspherical lenslets (each 1.12 mmø). Each lenslet does not have a single focal power, instead creating a 'volume of defocus' as a slow-down signal for eye growth. Each of the 11 rings of lenslets features contiguous lenslets of similar asphericity, with successive rings having lenslets with different asphericities. Spaces between the rings of lenslets provide single vision correction. Added optical power peripheral to the central zone being within the range +0.50 D to +3.50 D or −0.35 D to −5.00 D. The filtered lens can transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of 460 nm-520 nm or 470 nm to 520 nm, or by utilizing a light source or light emitter that predominately transmits within the wavelength range of at least one of 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

Figure 28:
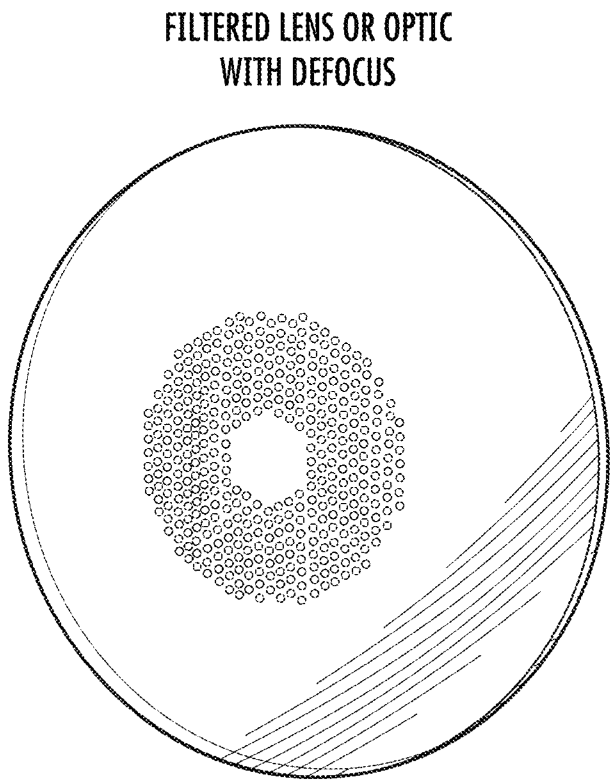
FIG. 28 shows an embodiment of the current invention as described herein.

In reference to FIG. 28, is shows an embodiment of a photo-bio-stimulation filtered defocused lens, which can be a lens that comprises: A spectacle lens for myopia correction and control with Defocus Incorporated Multiple Segments (DIMS) Technology; a central optical zone (9 mmø) for correcting distance refractive error of the wearer, and surrounding treatment zone with honeycomb array of lenslets (each 1.03 mm). The lenslets have a relative positive power within the range of +0.50 D to +3.50 D. The filtered lens can predominantly transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm or 470 nm to 520 nm, or by utilizing a light source or light emitter that predominately transmits within the wavelength range of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

In reference to FIG. 29, it shows an embodiment of a photo-bio-stimulation filtered defocused lens, which can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb array of lenslets (each 1.03 mmø). The lenslets have a relative power within the range of +0.50 D to +3.50 D or −0.35 D to −5.00 D. There are spaces between the lenslets where the single vision correction is accessible. The filtered lens can predominantly transmit light wavelengths within the range of light wavelengths of one or more of the following, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm 421 nm and 419 nm-400 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of 460 nm-520 nm, 470 nm to 520 nm, or 480 nm-520 nm, or by utilizing a light source or light emitter that predominately transmits within the wavelength range of at least one o, 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye. In reference to FIG. 30, it shows an embodiment of a photo-bio-stimulation filtered defocused lens, which can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb micro-lens array of lenslets (each 1.03 mmø). The lenslets have a relative positive power within the range of +0.50 D to +3.50 D or −0.35 D to −5.00 D. There are spaces between the lenslets where the single vision correction is accessible. The filtered lens can predominantly transmit light wavelengths within the range of light wavelengths of one or more of the following 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 600 nm-700 nm, or 700 nm+/−30 nm, while at the same time filtering and blocking wavelengths within the range of light wavelengths of one or more of: 449 nm-421 nm and 419 nm-400 nm.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of one of, 460 nm-520 nm, 470 nm to 520 nm, or 480 nm to 520 nm, or by utilizing a light source or light emitter that predominately transmits within the wavelength range of one of 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

Similarly, another embodiment of the lens can be a non-filtered lens or a clear lens. The lens can comprise a central zone and a defocus zone (see, FIGS. 39, 40, 41, 42, and 43). A defocus zone can be positioned peripheral to the central zone. The defocus zone can begin at the junction of the outer central zone periphery and the start of a zone adjacent to the central zone. The defocus zone can be comprised of lenslets. The defocus zone can be comprised of light scatter elements. The defocus zone can be comprised of minus optical power. The defocus zone can be comprised of minus optical power being more minus optical power or less plus optical power than the central zone's optical power. The minus of optical power increase over that of the central zone's optical power can be within the range of −0.35 D to −5.00 D. Such a lens can comprise a downward channel or zone of increasing positive optical power offsetting some or all of the added minus power. Such a downward channel can connect to a reading zone of increased positive optical power within the range of +1.00 D to +3.25 D over that of the central zone's optical power.

The lenslets can be comprised of −0.35 D to −5.00 D negative power. The lenslets can be aspheric. The defocus zone can be comprised of a microlens array. The defocus zone can be comprised of optical power steps. The defocus zone can be comprised of light scatter elements. The defocus zone can be comprised of liquid crystal. The liquid crystal can switch on and off by way of an electrical potential change. Such a defocus can be that of either light scatter or a change in the refractive optical power of the lens' defocus zone. The liquid crystal can be switched to increase or decrease optical power. The liquid crystal can be switched to cause light scatter. The liquid crystal can be switched to eliminate most or all of the light scatter or to eliminate any change of optical power. By utilizing a switchable liquid crystal defocus zone, the lens can provide the desired level of ocular photo-bio-stimulation which can then be turned on or off as needed.

An embodiment can be that of a lens or optic for ocular photo-bio-stimulation, wherein the lens or optic comprises a central zone and a zone of defocus, wherein the zone of defocus is peripheral to the central zone, wherein the zone of defocus is comprised of liquid crystal, wherein the defocus is one of optical defocus, light scattering, or light dispersion, wherein the liquid crystal can be switched on or off to remove defocus or provide peripheral defocus, and wherein the central zone of the lens remains capable of providing a wearer with clear distance vision. Embodiments when light wavelengths are generated by way of filtered optics or filtered lenses have a the transmission peak of the wavelength range that strike the eye's retina fall within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

Embodiments when light wavelengths are generated by a light emitter(s) if ambient lighting is present (including that of artificial light or sun light) the blended light wavelengths of the light emitter(s) and also the ambient light comprises wavelengths of light that strike the eye's retina fall within one of the wavelength ranges of, 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm.

An embodiment can be that of a lens or optic for ocular photo-bio-stimulation, wherein the lens or optic comprises a central zone and a zone of defocus, wherein the zone of defocus is peripheral to the central zone, wherein the lens or optic is that of a filtered lens or optic, and wherein the lens or optic predominantly transmits light wavelengths within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, so as to strike the retina of an eye. The defocus can be that of either an optical power defocus or light scattering or light dispersion. When lenslets cause an optical power defocus, such lenslets can be of optical power within the optical power range of +0.35 D to +5.00 D or −0.35 D to −5.00 D.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens, that predominantly transmits within the wavelength range of one of 460 nm-520 nm, 470 nm to 520 nm, or 480 to 520 nm, or by utilizing a light source or light emitter that predominately transmits within the wavelength range of one of, 460 nm-520 nm, 470 nm to 520 nm, or 480 nm to 520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

An embodiment can be that of a lens or optic for ocular photo-bio-stimulation, wherein the lens or optic comprises a central zone and a zone of defocus, wherein the zone of defocus is peripheral to the central zone, wherein the lens or optic further comprises an add power zone comprised of an increased positive optical power compared to one of the lens' or optic's peripheral zone or the central zone. The defocus can be that of either an optical power defocus or light scattering or light dispersion. When lenslets cause an optical power defocus, such lenslets can be of optical power within the optical power range of +0.35 D to +5.00 D or −0.35 D to −5.00 D.

Figure 39:
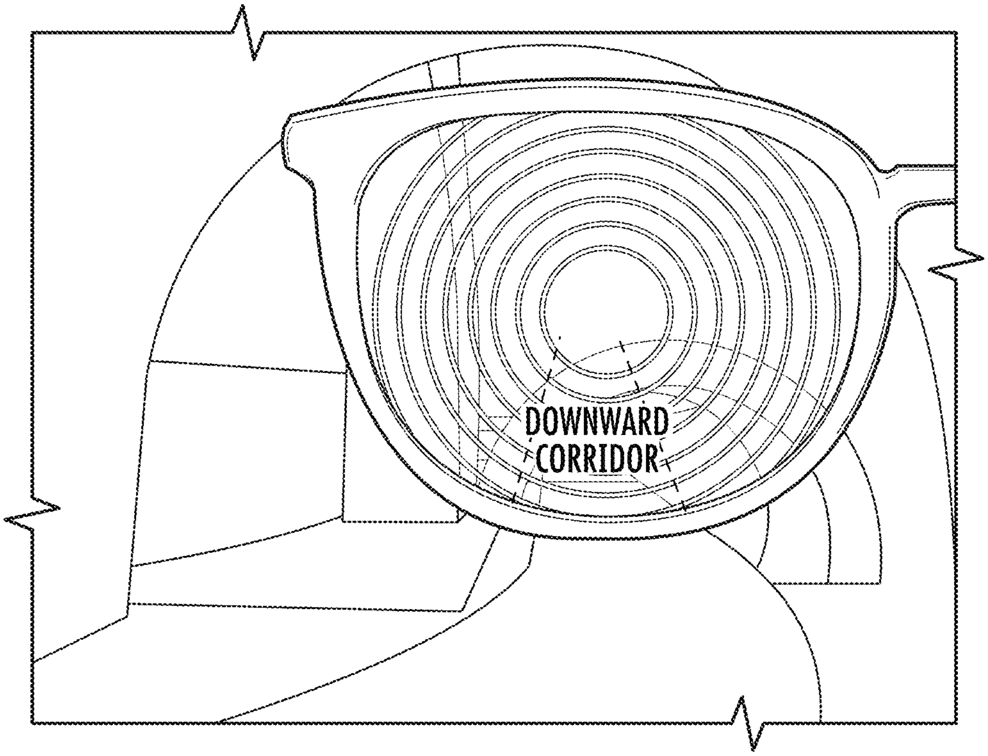
FIG. 39 shows an embodiment of the current invention as described herein.

In reference to FIG. 39, an embodiment of a photo-bio-stimulation filtered defocused lens can be a lens that comprises:

a central zone for correcting distance focus for the wearer and small enough to establish an effective functional zone;

a selected fill factor to deliver high efficacy while preserving good wearability;

a central zone of 4 mm-6 mm; and added Surface power within the range of −0.35 D to −5.00 D.

Figure 40:
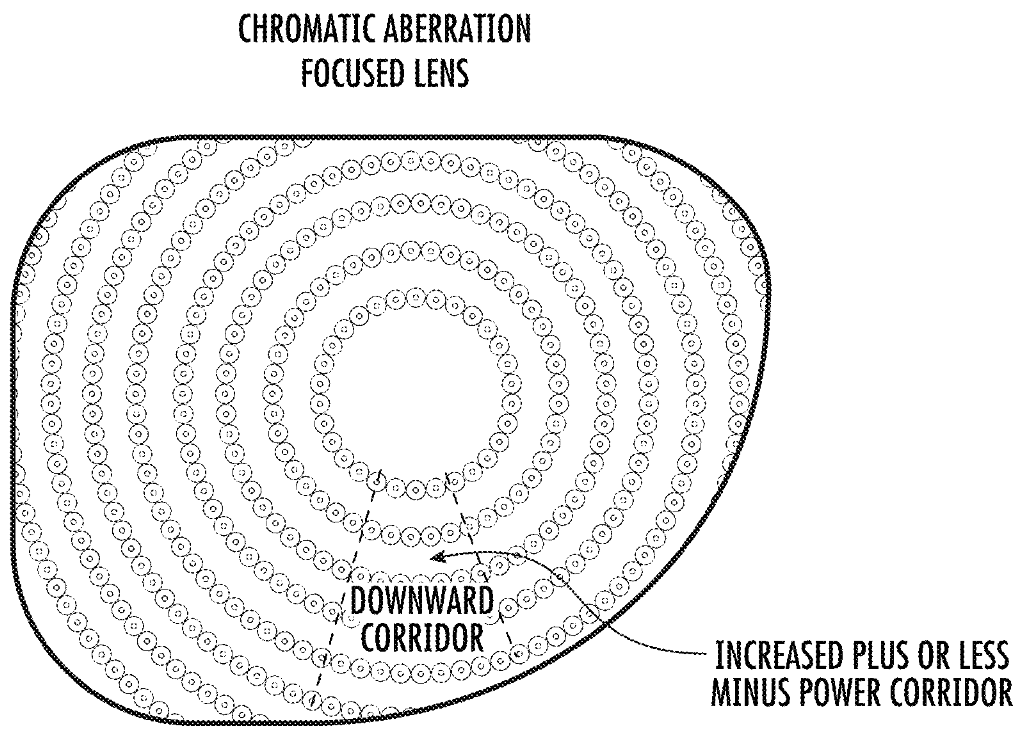
FIG. 40 shows an embodiment of the current invention as described herein.

In reference to FIG. 40, another embodiment of a photo-bio-stimulation filtered defocused lens can be a lens that comprises: a spectacle lens for myopia correction and control with Highly Aspherical Lenslet Target (H.A.L.T.) Technology; a central optical zone (9 mm) for correcting distance refractive error of the wearer, with surrounding myopia control zone incorporating 1021 contiguous (touching) highly aspherical lenslets (each 1.12 mmø). Each lenslet does not have a single focal power, instead creating a 'volume of defocus' as a slow-down signal for eye growth. Each of the 11 rings (or more or less rings) of lenslets features contiguous lenslets of similar asphericity, with successive rings having lenslets with different asphericities. Spaces between the rings of lenslets provide single vision correction. Added optical power peripheral to the central zone being within the range −0.35 D to −5.00 D.

Figure 41:
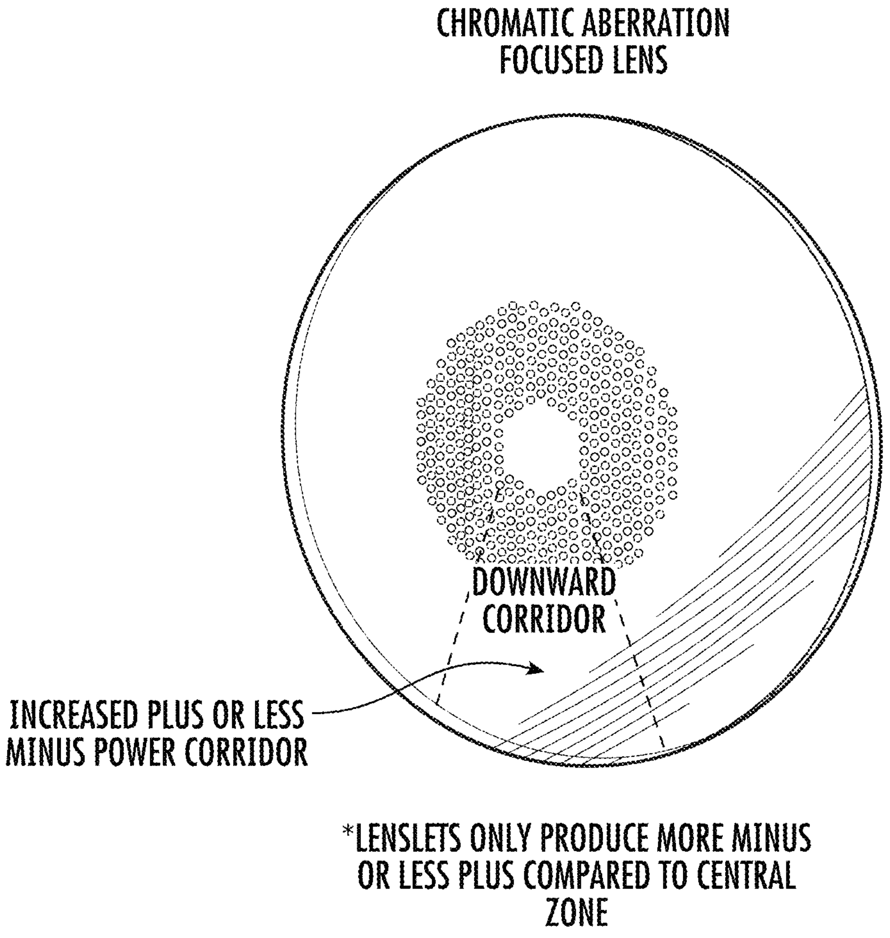
FIG. 41 shows an embodiment of the current invention as described herein.
Figure 42:
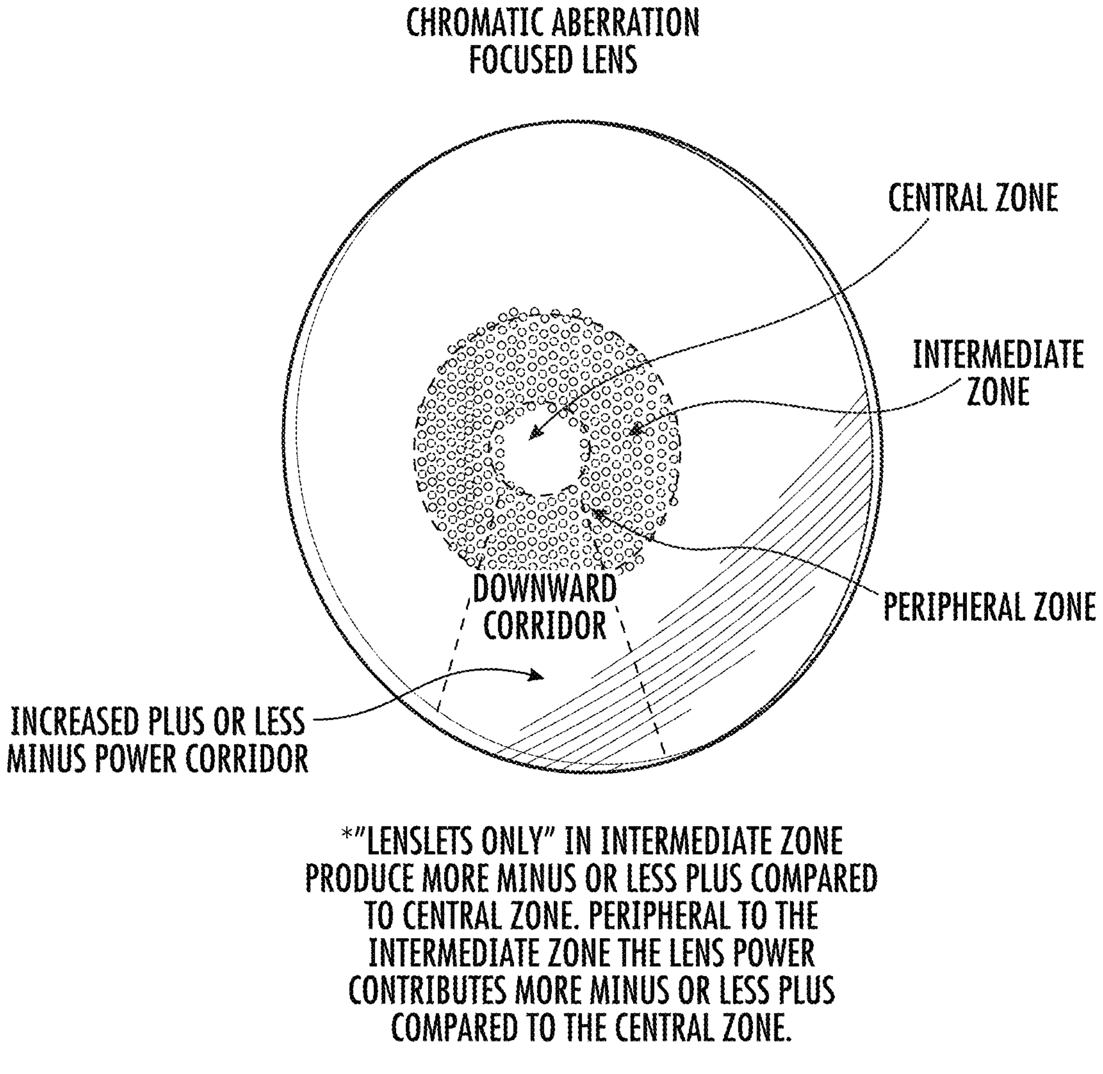
FIG. 42 shows an embodiment of the current invention as described herein.

In reference to FIGS. 41 and 42, still another embodiment of a photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and surrounding treatment zone with honeycomb array of lenslets (each 1.03 mm). The lenslets have a relative positive power within the range of −0.35 D to −5.00 D.

In reference to FIGS. 41 and 42, another embodiment of a photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb array of lenslets (each 1.03 mmø). The lenslets have a relative power within the range of −0.35 D to −5.00 D. There are spaces between the lenslets where the single vision correction is accessible.

Figure 43:
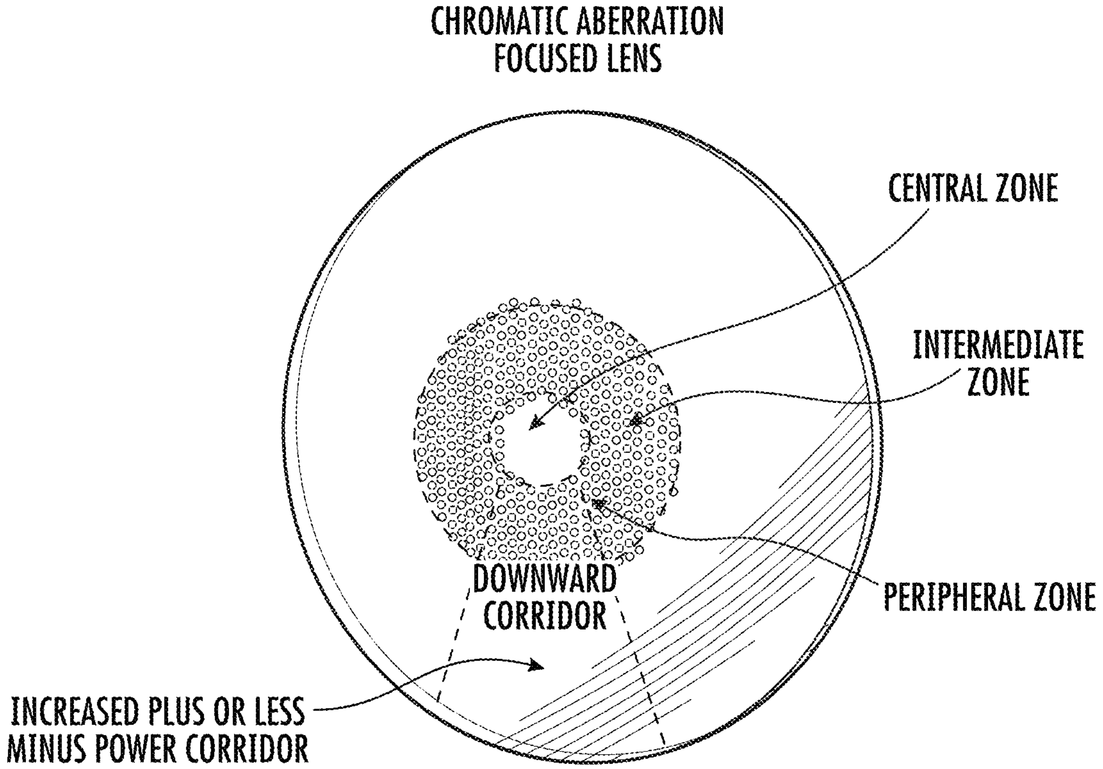
FIG. 43 shows an embodiment of the current invention as described herein.

In reference to FIG. 43, another embodiment of a photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb micro-lens array of lenslets (each 1.03 mm). The lenslets have a relative positive power within the range of −0.35 D to −5.00 D. There are spaces between the lenslets where the single vision correction is accessible. The embodiment further comprises a downward channel of increasing plus optical power or reducing minus optical power.

In certain embodiments myopia control lenses can be utilized in combination with ocular photo-bio-stimulation therapy. Such ocular photo-bio-stimulation can be with light wavelengths within the range of: 480 nm+/−30 nm, 530 nm+/−20 nm, and/or 650 nm+/−30 nm. Such ocular photo-bio-stimulation therapy can be applied while the subject or patient is wearing their myopia control lenses. This causes the light from the ocular photo-bio-stimulation light source to be spread across the eye's retina of the subject or patient wearing the myopia control lens or lenses, stimulating the production of retinal dopamine. The ocular photo-bio-stimulation therapy can be applied or provided to the subject or patient once or multiple times per day.

In certain embodiments the ocular photo-bio-stimulation light can modulate within the range of: 5 Hz to 15 Hz, 10 Hz to 20 Hz, or 40 Hz+/−20 Hz. In other embodiments the ocular photo-bio-stimulation light source cannot modulate and thus has zero Hz. In certain embodiments an invisible white light spectral flickering can occur. In certain embodiments by using blue light within the wavelength range of 480 nm+/−30 nm and modulating at 40 Hz+/−10 Hz can result in a significant improvement of one or more of: depression, cognitive ability, alertness, and decision making of the user. However, visually 40 Hz+/−10 Hz can be annoying and distracting for a user. In certain embodiments an invisible spectral flickering can occur. In certain other embodiments which reduces visual unpleasantness for the user the ocular photo-bio-modulation light source can be modulated within the ranges between blue (450 nm-495 nm) and bluish green/cyan (495 nm-520 nm). In still other embodiments which reduces visual unpleasantness the ocular photo-bio-modulation light source can be modulated within the ranges between blue (450 nm-495 nm) and green (495 nm-570 nm). The ocular photo-bio-stimulation light can then stimulate dopamine, serotonin, or norepinephrine in the brain. In certain embodiments by using blue light within the wavelength range of 480 nm+/−30 nm and modulation or flickering between 5 Hz and 15 Hz, or between 10 Hz and 12 Hz, the invention can be used to stimulate production or increase the production of dopamine in the eye's retina of the user.

Chromatic Aberration Focused Lens for Ocular Photo-Bio-Stimulation

Figure 31:
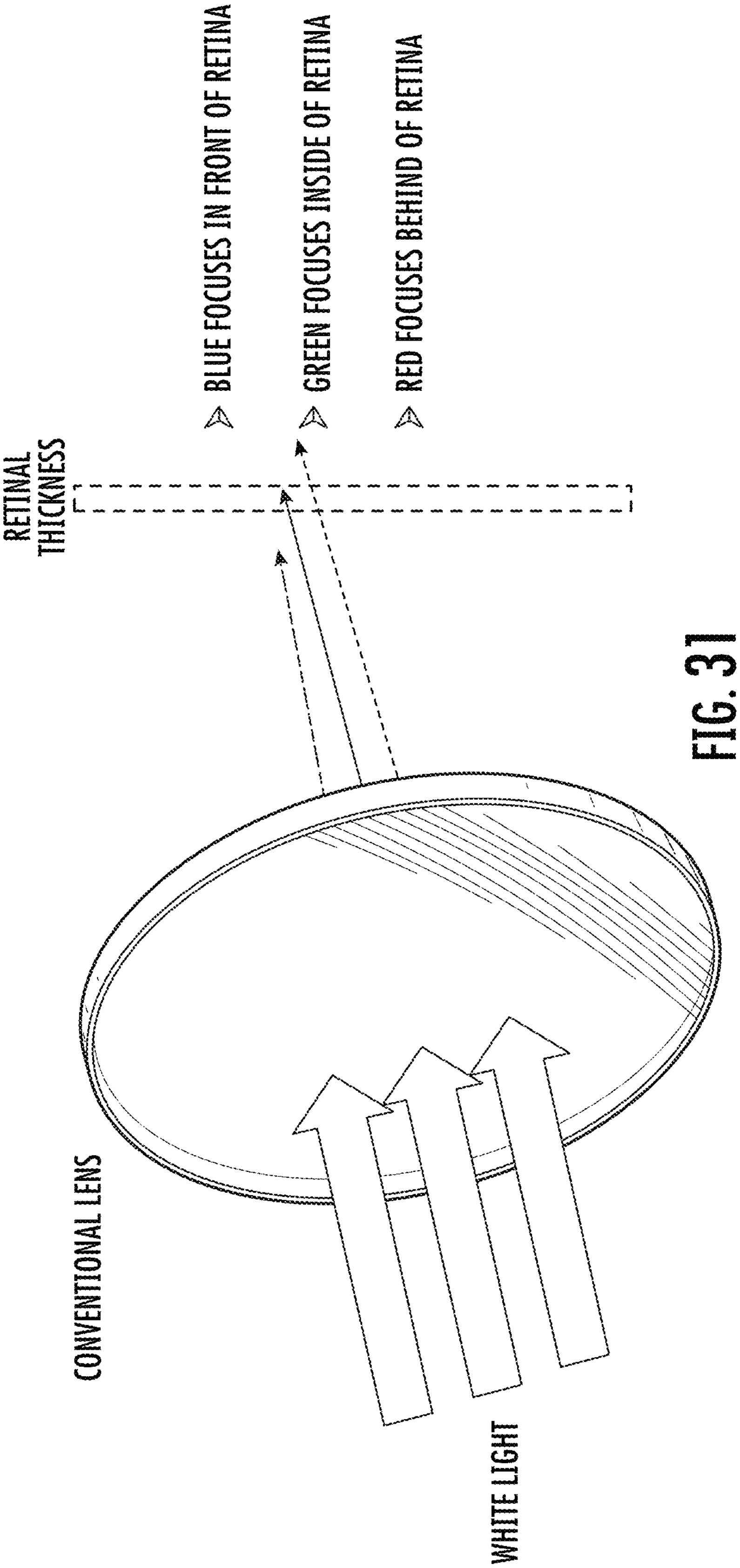
FIG. 31 shows an embodiment of the current invention as described herein.

In reference to FIG. 31, it shows an embodiment of having a conventional lens or optic comprising longitudinal chromatic aberration. The degree of chromatic aberration can be constant unless there is a power change, such as a multifocal. The multifocal area is that of an increase in plus power which pulls the blue wavelength of longitudinal chromatic aberration further in front of the retina. An embodiment of the invention is that of a chromatic aberration focused lens or optic. A chromatic aberration focused lens represents a new category of lenses. A chromatic aberration focused lens or optic for the purposes of this disclosure is a lens that comprises two or more sets of chromatic aberration; the first set of chromatic aberration comprises blue light wavelengths, green light wavelengths and red-light wavelengths, each of the bands of blue, green and red wavelengths are separated from each other after leaving the lens, and wherein the second set of chromatic aberration comprises blue light wavelengths, green light wavelengths and red-light wavelengths, each of the bands of blue, green and red wavelengths are separated from each other after leaving the lens, and wherein the second set of blue, green and red wavelengths of chromatic aberration are positioned farther away from the lens than the first set of blue, green and red wavelengths of chromatic aberration. As used herein, a band represents blue light wavelengths, green light wavelengths, or red-light wavelengths.

Figure 32:
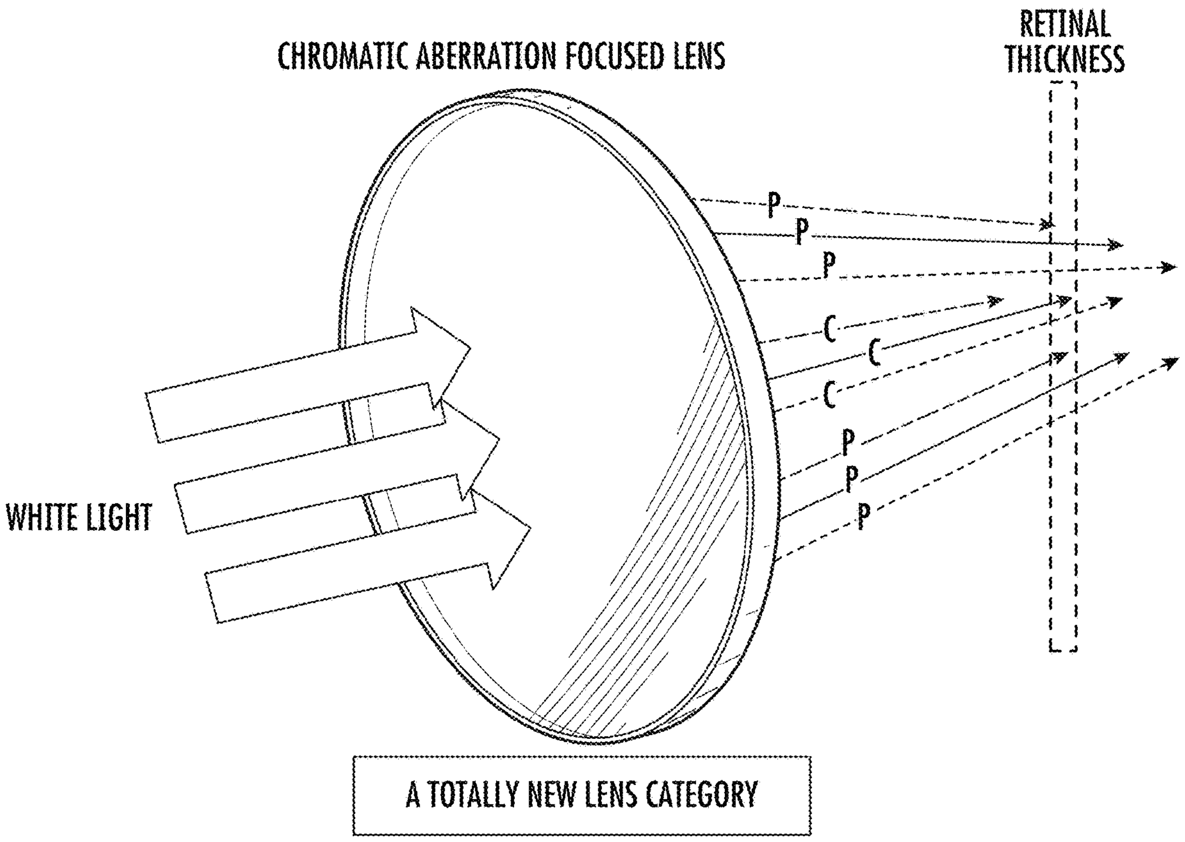
FIG. 32 shows an embodiment of the current invention as described herein.

In reference to FIG. 32, said another way, a chromatic aberration focused lens has two bands of blue wavelengths, two bands of green wavelengths and two bands of red wavelengths, wherein the one set of the blue bands when focusing is farther away from the lens than the other blue band, wherein one set of the green bands when focusing is farther away from the lens than the other green band, wherein one set of the red bands when focusing is farther away from the lens than the other red band. In FIG. 32, "C"

refers to a central lens zone allowing transmission of light wavelengths, and in cases refracting the light wavelengths, so that their focus gives clear distance vision. In FIG. 32, "P" refers to a peripheral lens zone (the area outside of the central lens zone) transmitting light wavelengths that focus farther from the lens due to an increase in minus lens power found outside of the central lens zone of the lens. Said still another way, a chromatic focused lens has two bands of blue wavelengths, two bands of green wavelengths and two bands of red wavelengths, wherein the one set of the blue bands is refracted less upon leaving the lens than the other blue band, wherein one set of the green bands is refracted less upon leaving the lens than the other green band, wherein one set of the red bands is refracted less upon leaving the lens than the other red band. The bands of blue, green and red wavelengths that focus closest to the lens are transmitted by the central zone of the lens. The bands of blue, green and red wavelengths that focus farthest away from the lens are those transmitted by the peripheral zone of the lens. This is accomplished by keeping the central zone's optical power that of the BVA distance correction for the wearer. However, adding minus optical power to the lens outside of the central zone.

This then means that a chromatic aberration focused lens generates a minimum of 6 bands of colored light wavelengths upon light exiting the lens. Thus, a chromatic aberration focused lens comprises a minimum of 6 chromatic aberration produced bands. By utilizing a chromatic focused lens or optic it is possible with a single lens or optic to cause the chromatic aberration to spread its light wavelength bands throughout the thickness of the retina of an eye. The thickness of the retina of an eye range between 250 microns to 300 microns. By way of example only, in certain examples, the first band of blue light wavelengths can be focused just before the surface of the retina, while the second band of blue light wavelengths can be focused within the retina, the first bands of green light wavelengths can be focused within the middle of the retina, while the second bands of green light wavelengths can be focused within the back of the retina, and the first bands of red-light wavelengths can be focused just behind the retina, while the second band of red-light wavelengths can be focused further behind the retina.

In most chromatic aberration focused lenses, the central zone of the lens is optical power corrected for the wearer's best corrected distance vision. Thus, the central zone generates a first set of chromatic aberration bands where the blue light focuses usually in front of the retina and the red light usually behind the retina with the green band within the retina. By utilizing a chromatic aberration focused lens or optic, one of the two or more bands of blue light wavelengths can be caused to focus within the retina closer to the rods as opposed to today's conventional lenses where chromatic aberration causes a proper corrected optical powered lens used to correct one's vision (distance and/or near to 20/20 vision) to have the one blue band of wavelengths from chromatic aberration focus always in front of the retina, thus not focusing close to or on the rods of the retina for the generation of dopamine.

By utilizing a chromatic aberration focused lens or optic it is possible to excite the ganglion cells with blue light, as one of the bands of blue light wavelengths will pass through the ganglion cells as it travels and focuses deeper into the retina closer to the rods. Such a chromatic aberration focused lens or optic can be a single vision lens or optic, multifocal lens or optic, and/or progressive addition lens or optic. A chromatic aberration focused lens can be used for increasing the level of dopamine within the eye and brain of the wearer. By way of example only, a child that is suffering from myopia can wear a chromatic aberration focused lens to reduce the progression of myopia or said another way to reduce the increases in minus optical power of the child's myopia correcting lenses over time. Most individuals who are suffering from dopamine and/or serotonin deficiency can benefit from such a lens type. A chromatic aberration focused lens can be prescribed for all optical powers (plus, minus, cylindrical, including plano/no optical power) required for one or more of: myopes, hyperopes, astigmatism and presbyopia. A chromatic aberration focused lens can be prescribed for myopia, hyperopia, astigmatism, compound astigmatism, emmetropia, and/or presbyopia. A chromatic aberration focused lens can be filtered to transmit mostly wavelengths of light that are within the wavelength range of 480-nm+/−30 nm to further enhance the physiological response of the wearer.

In certain embodiments multiple sets of chromatic aberration bands of blue, green and red wavelengths can be found in the peripheral of the lens due to a plurality of zones of different refractive power. In most cases the first set of chromatic aberration bands is that of axial chromatic aberration, and the second set of chromatic aberration bands is also caused by axial chromatic aberration, and one or both are designed to focus deeper into the retina with the red-light band to focus further behind the retina, the green light band near the back of the retina, thus causing the blue light band to focus within the retina close to the rods. Thus, a chromatic aberration corrected lens allows the central vision of the wearer to remain as it appears with a conventional corrected distance vision lens, and for the peripheral retina (outside of the macular area) to be stimulated by the second set of chromatic aberration bands, wherein the blue band is focused within the retina increasing dopamine and/or serotonin production. In certain embodiments one set of bands of blue, green and red wavelengths, can be generated from the central zone of the lens, and a plurality of bands of blue, green and red wavelengths, can be generated from an area peripheral to the central zone. In still another embodiment, one set of bands of blue, green and red wavelengths, can be generated from the central zone of the lens, and a different set of bands of blue, green and red wavelengths, can be generated from an area peripheral to the central zone.

Another way of thinking about a chromatic aberration focused lens is to consider only the blue band of chromatic aberration. In aspects, there will be two blue bands (of blue wavelengths). One is caused by the chromatic aberration focus from the optical power of the central zone of the lens or optic. A second one is caused by the optical power chromatic aberration focus of an area peripheral to the central zone of the lens or optic. The focus of the first blue band will be focused in front of the retina if the central zone of the lens is providing the wearer with 20/20 distance vision or their corrected distance vision. The focus of the second blue band will be focused further away from the lens deeper into the retina. Because the second band, if generated by an area outside of the central zone of the lens, if thus is focused peripheral to the macular area of the eye, stimulating primary rods and ganglion cells of the wearer (visual clarity from the non-macular area is not of a prime concern). By way of example only, the second blue wave band can be located within the range of 100 microns to 500 microns further from the back of the lens than that of the first blue wave band. Said another way, with a chromatic aberration focused lens the second focused blue band is located between 100 microns to 500 microns from the first focused blue band. In certain embodiments it can be located within the range of 150 microns to 350 microns farther from the back of the lens than that of the first blue wave band. Said another way, in these embodiments, with a chromatic aberration focused lens, the second focused blue band is located between 150 microns to 350 microns from the first focused blue band.

Figure 33:
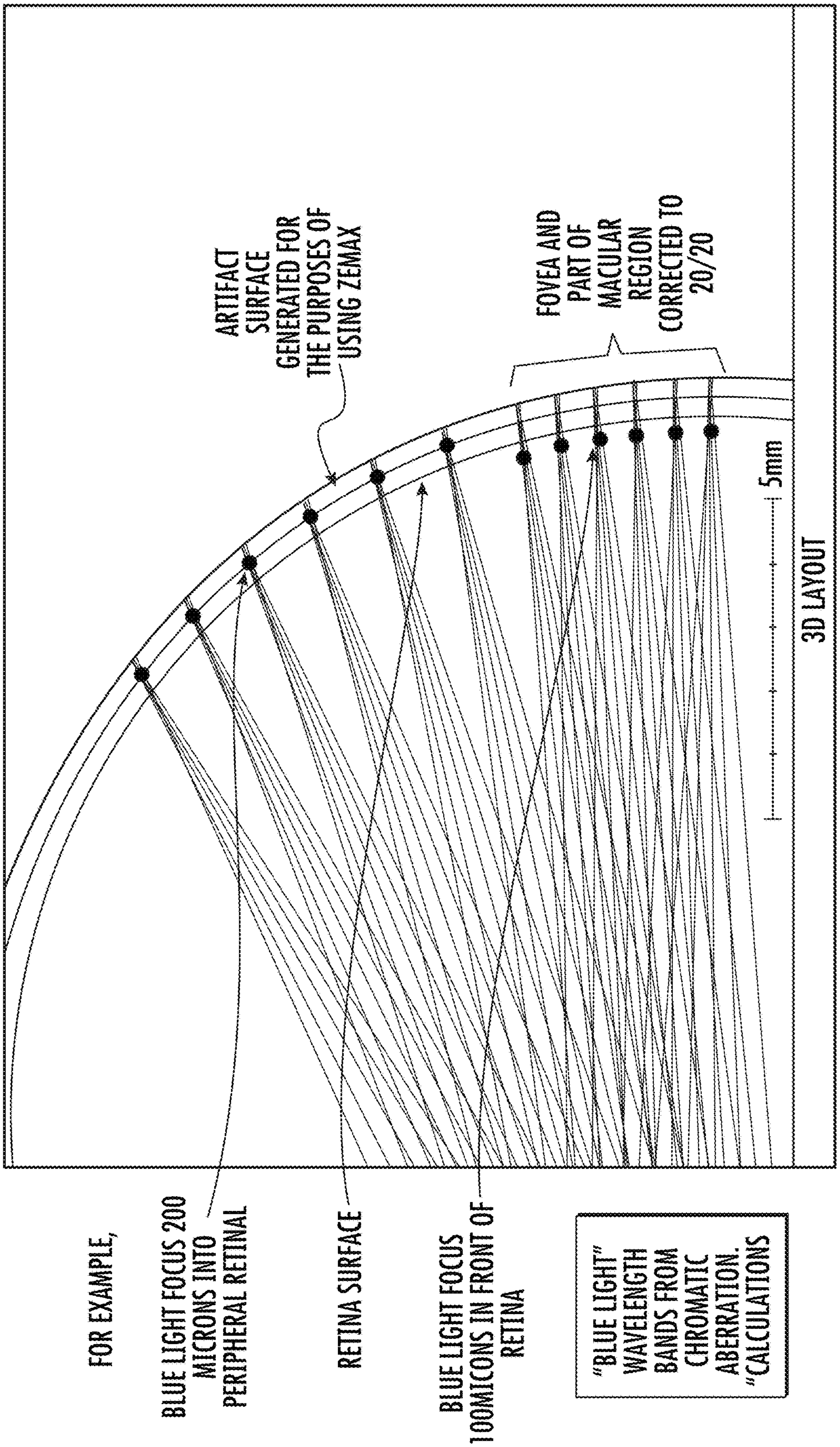
FIG. 33 shows an embodiment of the current invention as described herein.

In reference to FIG. 33, it shows an embodiment of the current invention. In examples, wherein the eye's retina (excluding the foveal area) is within the range of 200 microns to 300 microns thick, the eye's power in diopters may be 1000/16.6=60.24 D. If the focal plane were shifted 0.25 microns back, the device might need a focal length of 16.6+0.25=16.85 mm. And the power in diopters would be 1000/16.85=59.35 D. Thus, a corrector of size 60.24-59.35 D=0.89 D is required in this example. Therefore, for the peripheral area of a lens (outside of the central zone) to cause a second chromatic aberration band of blue light wavelengths to be located within the retina closer to the rods, a minus increase in optical power of approximately −0.90 D more than the optical power found in the central zone of the lens is needed in this example. This is what is needed to correct for the normal/natural longitudinal chromatic aberration of the eye itself.

Another way of understanding this is that the eye's average LCA (longitudinal chromatic aberration) is approximately 1.87 D. That would be from the blue wavelength focus to the red wavelength focus with green approximately within the retina. Thus, to move the blue back to the retina it requires 50% of the 1.87 D in minus optical power. However, when wearing a lens it is necessary to then add the LCA of the lens to the 50% of the 1.87 D. Given that the LCA of the lens will vary by index of refraction and Abbe number and also optical power, it is necessary to calculate the LCA of the lens individually. By way of example only a −2.00 D polycarbonate lens would have 0.034 D LCA. A −4.00 D would have 0.067 D LCA. A −2.00 D CR39 lens would have 0.017 D LCA. And a −4.00 D CR39 would have 0.034 D LCA. However, as with the eye's natural LCA where we divided it by 50% to move the blue back to the retina, the same needs to be done with the lens LCA. Therefore, by way of example only, the LCA adjustment needed to move the blue wavelength focus back from the lens onto or into the retina when including that of the eye's natural LCA, could be approximately 50% of 1.87 D+50% of 0.067 (in the case of a −4.00 D polycarbonate) or 0.935 D+0.335 D for a total of 1.27 D, which needs to be minus power. Therefore, in this particular example 1.27 D of minus optical power or less plus optical power would be required to be added to the optical power outside of the central zone of an aberration correction focused lens.

In certain other embodiments the increase in minus power can range between 0.50 D and 2.00 D (more minus optical power or less plus optical power). In embodiments of a chromatic aberration focused lens in the central zone can comprise an optical power to correct the distance vision requirements of the wearer and the zone peripheral to the central zone can comprise an optical power that is more minus (when the central zone is plano or a minus power) or less plus (when the central zone is of a plus power).

Figure 34:
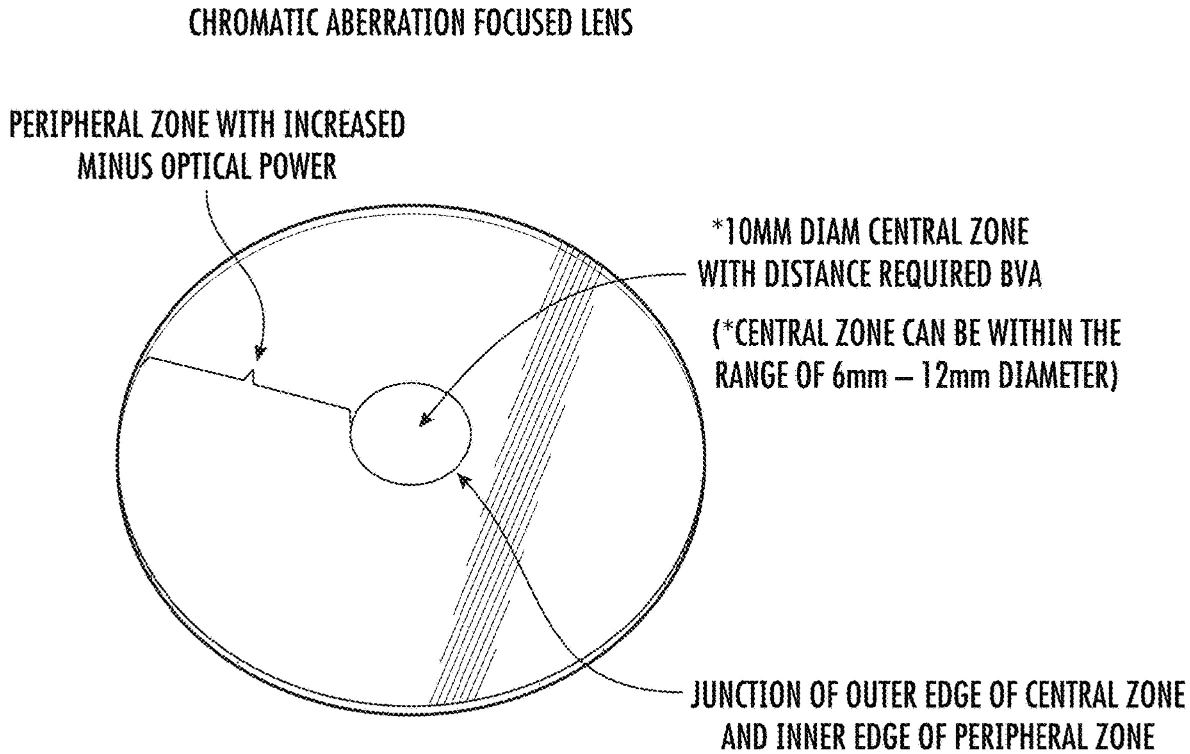
FIG. 34 shows an embodiment of the current invention as described herein.

In reference to FIG. 34, by way of example, the peripheral zone can be of an optical power that is within the range of 0.50 D to 2.00 D more minus (when the central zone is of a minus power) or the peripheral optical power can be within the range of 0.50 D to 2.00 D less plus optical power (when the central zone is of a plus optical power). By way of another example, the peripheral zone can be of an optical power that is within the range of 0.50 D to 1.25 D more minus (when the central zone is plano or minus power), or the peripheral optical power can be within the range of 0.50 D to 1.25 D less plus optical power (when the central zone is of a plus optical power). In certain embodiments the power outside of the central zone can be that a spherical equivalent optical power which is more minus optical power than that of the central zone. In some embodiments the central zone of the lens, by way of example only, can be 10 mm in diameter and there can be an intermediate zone where the optical power of the central zone's optical power changes to that of the peripheral zones increase in minus optical power or less plus optical power. In examples, with this embodiment, one surface of this peripheral zone can be that of a smooth continuous curve. In certain embodiments, the optical power is constant within the tolerance of +/−0.12 D and in other embodiments the optical power can vary. In aspects, the central zone can be of any distance optical power required by an emmetrope, hyperope, myope, astigmat, or any combination thereof. The lens further can comprise an additional positive power for the correction of presbyopia. The additional optical power can be a lined bifocal, trifocal or progressive addition zone. In aspects, a peripheral zone can comprises "increased" Minus Optical Power (or "less" Plus Optical Power) within the range of 0.35 D to 5.00 D compared to that of the Distance Corrected BVA, which is the optical power of the central zone. If the central zone power is plano the peripheral zone would be within the range of −0.50 D and −5.00 D.

Figure 35:
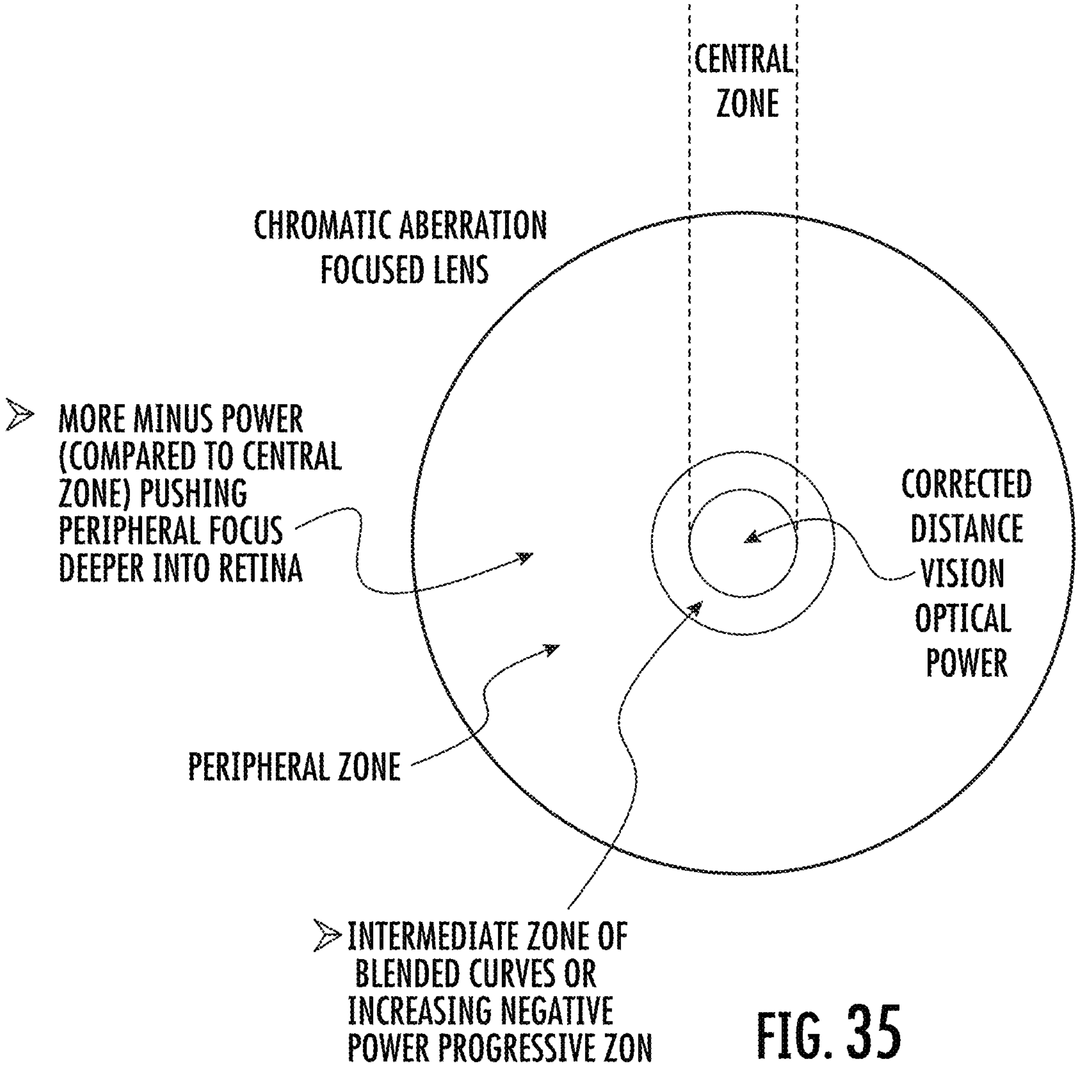
FIG. 35 shows an embodiment of the current invention as described herein.

In reference to FIG. 35, the central zone diameter can be within the range of 5 mm-15 mm, more preferably 6 mm-10 mm. In certain embodiments the intermediate zone can comprise one or more optical power steps. In other embodiments the intermediate zone can comprise one or more continuous curves that alter the optic power as it changes from the central zone's optical power to the peripheral zone's optical power. In still other embodiments the intermediate zone can comprise a blended zone of optical power where the optical power transitions in optical power. In certain other embodiments the intermediate zone can comprise one or more of optical power step(s), continuous curve(s), and/or blended power area(s). In each of these cases the peripheral zone can be of more minus optical power compared to the central zone or less plus optical power compared to the central zone. In still other embodiments the change in optical power can occur over a larger area with a plurality of one or more of, smaller optical power changes in optical steps, continuous curves, or blended regions. In aspects, the lens can have 1.59 refractive index matrix, 30 Abbe, and be of 2.0 mm in thickness.

In embodiments the lower the Abbe number of the lens material the higher the increase in minus optical power in the non-central zone of the lens compared to the central portion. And the higher the Abbe number the lower the increase in minus optical power required in the non-central zone of the lens compared to the central zone of the lens.

In certain embodiments the peripheral thickness (outside of the central zone can increase beyond what it would be in a conventional lens or optic.) This increase in thickness of the lens material can provide for moving the second set of chromatic aberration bands farther away from the lens than those from the central zone of the lens. In still other embodiments, both the peripheral thickness (outside of the central zone can increase beyond what would be in a conventional lens or optic), and the optical power can be increased in minus compared to a central zone of plano or minus optical power, or a less plus compared to a central zone of plus optical power.

In certain embodiments of a chromatic aberration focused lens as described herein, the optical power of the periphery is the same as the optical power of the central zone, but the Abbe number of the periphery can be lower than the Abbe number of the central zone. This can be caused by way of a coating not being present in the central zone, however being present in periphery to the central zone. Such a coating can be, by way of example only, a coating, an AR coating (antireflection coating), or a vacuum deposition coating. When the Abbe of the peripheral zone is of a lower Abbe than the central zone, the chromatic aberration of the peripheral zone can cause the second set of bands of blue light wavelengths (generated by the peripheral zone) to focus deeper into the retina as compared to the first set of blue light bands associated with and generated by the central zone of the lens.

In aspects, a chromatic aberration focused lens can be that of a lens or optic wherein there are 6 chromatic aberration bands, wherein there are two sets of blue wavelength bands, green wavelength bands, and red wavelength bands, wherein a first set of bands is generated from a central zone of a lens, wherein a second set of bands is generated from an area peripheral to the central zone, and/or wherein each band of the second set focuses further from the lens when compared to their counterpart band of the first set. The blue wavelength band of the first set can focus in front of the retina when the optical power of the lens comprises the wearer's distance refractive correction. The blue wavelength band of the second set can focus closer to the rods of the retina compared to the blue wavelength band of the first set. The blue wavelength band of the second set can focus farther away from the lens than the blue wavelength band of the first set. The green wavelength band of the second can focus farther away from the lens than the green wavelength band of the first set. The red wavelength band of the second set can focus farther away from the lens than the red wavelength band of the first set.

The lens can comprise a central zone and a peripheral zone, wherein the surface refractive index of the central zone is higher than the surface refractive index of a peripheral zone. The surface of the peripheral zone can comprise a different coating material as compared to the central zone. Such coating can be by way of example only, an antireflection coating, hard scratch resistant coating, or cushion coating. The lens can comprise a central zone and a peripheral zone, wherein the surface Abbe number of the central zone is higher than the surface Abbe number of a peripheral zone. The surface of the peripheral zone can comprise a different coating material as compared to the central zone. Such coating can be by way of example only, an antireflection coating, hard scratch resistant coating, or cushion coating. The lens can comprise a central zone and a peripheral zone, wherein the optical power of the central zone is of less minus power or more plus power than the optical power of a peripheral zone.

The optical power of a peripheral zone can be within the range of −0.35 D to −2.00 D more minus optical power or less plus optical power when compared to the optical power of the central zone. The optical power of a peripheral zone can be within the range of −0.50 D to −5.00 D more minus optical power or less plus optical power when compared to the optical power of the central zone. The optical power of a peripheral zone can be −1.00 D+/−0.50 D more minus optical power or less plus optical power when compared to the optical power of the central zone. The lens can comprise a central zone, intermediate zone, and peripheral zone. The intermediate zone can comprise a blended region of optical powers or a continuous surface contributing to reducing optical power. The lens can comprise a peripheral zone comprised of zones of lower optical power compared to the central zone of the lens.

The lens can be a single vision, multifocal, or progressive addition lens. The lens can be comprised of any suitable ophthalmic material, by way of example only, CR39, polycarbonate, Trivex, High Index, Cyclic olefin polymers (COP) and cyclic olefin copolymers (COC) that are amorphous, and/or transparent thermoplastics composed of cyclic olefin monomers (norbornene) and linear olefins (e.g. ethene). The lens can be coated, treated, and finished like any other ophthalmic lens. The lens can be first in the form of a semi-finished lens blank before it becomes a lens. The lens can be provided to individuals having one of a dopamine deficiency and/or serotonin deficiency.

An embodiment can be generated by altering the lens focus power between the central zone, an optional intermediate Zone, and a peripheral zone, in such a way that the focus power in the optical intermediate zone and non-optional peripheral zone is more minus focus power or less plus focus power that the central zone. Another embodiment can be generated by altering the index of refraction of the central zone, optional intermediate zone and non-optional peripheral zone. In this case the refractive index would be less in the optional intermediate zone and non-optional peripheral zone of the lens or lens blank as compared to the central zone. And still another embodiment can be caused by a combination of both altering the focal power and the index of refraction. In embodiments, these innovative lens embodiments are comprised of two or more sets of chromatic aberration bands (each comprising blue, green, and red wavelengths of light).

The embodiment can utilize the two or more chromatic aberration sets of bands, so that the first set of chromatic aberration bands is that of a conventional lens with regards to the central area which comprises the distance power focus needed for the wearer of the lens or lens blank. The other chromatic aberration bands which are peripheral to the central set of bands are focused deeper into the retina and/or behind the retina of the eye of the wearer. The retina being 200-300 microns thick. An embodiment can be one of a lens, lens blank, or optic, wherein the lens, lens blank, or optic, which comprise two or more sets of chromatic aberration, wherein one set focuses farther away from the lens, lens blank, or optic than the other set, wherein a first set is caused by an optical power of the lens that provides the proper distance correction for the wearer and a second set that focuses light farther from the lens, lens blank, or optic than the first set.

In embodiments of a chromatic aberration focused lens, the movement of the focus of the second set of chromatic aberration bands farther from the lens than those of the focus of the first set of chromatic aberration bands, can be caused by way of one or more of the following: lower abbe number of the lens peripheral zone compared to the lens central zone, lower refractive index of the lens peripheral zone compared to the lens central zone, increased thickness of the lens peripheral zone compared to the lens central zone, or more minus or less plus optical power of the lens peripheral zone compared to the lens central zone. While all lens materials can be used to fabricate a chromatic aberration focused lens, the lower the abbe number and/or higher index lenses work well in terms of small changes generating larger movement of the focus of the second chromatic aberration bands relative to that of the focus of the first chromatic aberration bands. Thus, while glass or plastic CR39 can be used, polycarbonate or other thin and light high index lenses work well in embodiments. In most embodiments when fabricating (by way of example only), one or more of, free forming, grinding and polishing, casting, molding, stamping, surface casting, and/or coating a chromatic aberration focused lens, once the proper optical power of the central zone of the lens is created so that it delivers the (BVA) best corrected distance vision for the lens (for example, 20/20 distance vision), the optical power of the peripheral zone (compared to the optical power of the central zone) can be of the same increase in minus power or decrease in plus optical power for, by way of example only, all lenses, lens materials, identical lens materials, and/or lens types. Thus, a look up table or software table can be constructed for, by way of example, each lens material or lens type.

In certain embodiments of a chromatic aberration focused lens, the front surface convex curve of the lens is preset when producing a lens blank and the back concave surface is fabricated to provide the proper optical powers. In other embodiments of a chromatic aberration focused lens, the back surface concave curve of the lens is preset when producing a lens blank and the front convex surface is fabricated to provide the proper optical powers. In still other embodiments of a chromatic aberration focused lens, the back surface concave curve of the lens and the front convex surface are fabricated to provide the proper optical powers. In certain embodiments of a chromatic aberration focused lens, the peripheral zone optical power can be an increase in minus optical power compared to the central zone. In other embodiments of a chromatic aberration focused lens, the peripheral zone optical power can be a decrease in plus optical power compared to the central zone. In still other embodiments, the peripheral zone optical power can be that of a spherical equivalent such that it is more minus compared to the central zone optical power when the central zone is plano or minus optical power. In still other embodiments of a chromatic aberration focused lens, the peripheral zone optical power can be that of a spherical equivalent, such that it is less plus compared to the central zone optical power when the central zone is of a plus optical power.

Figure 36:
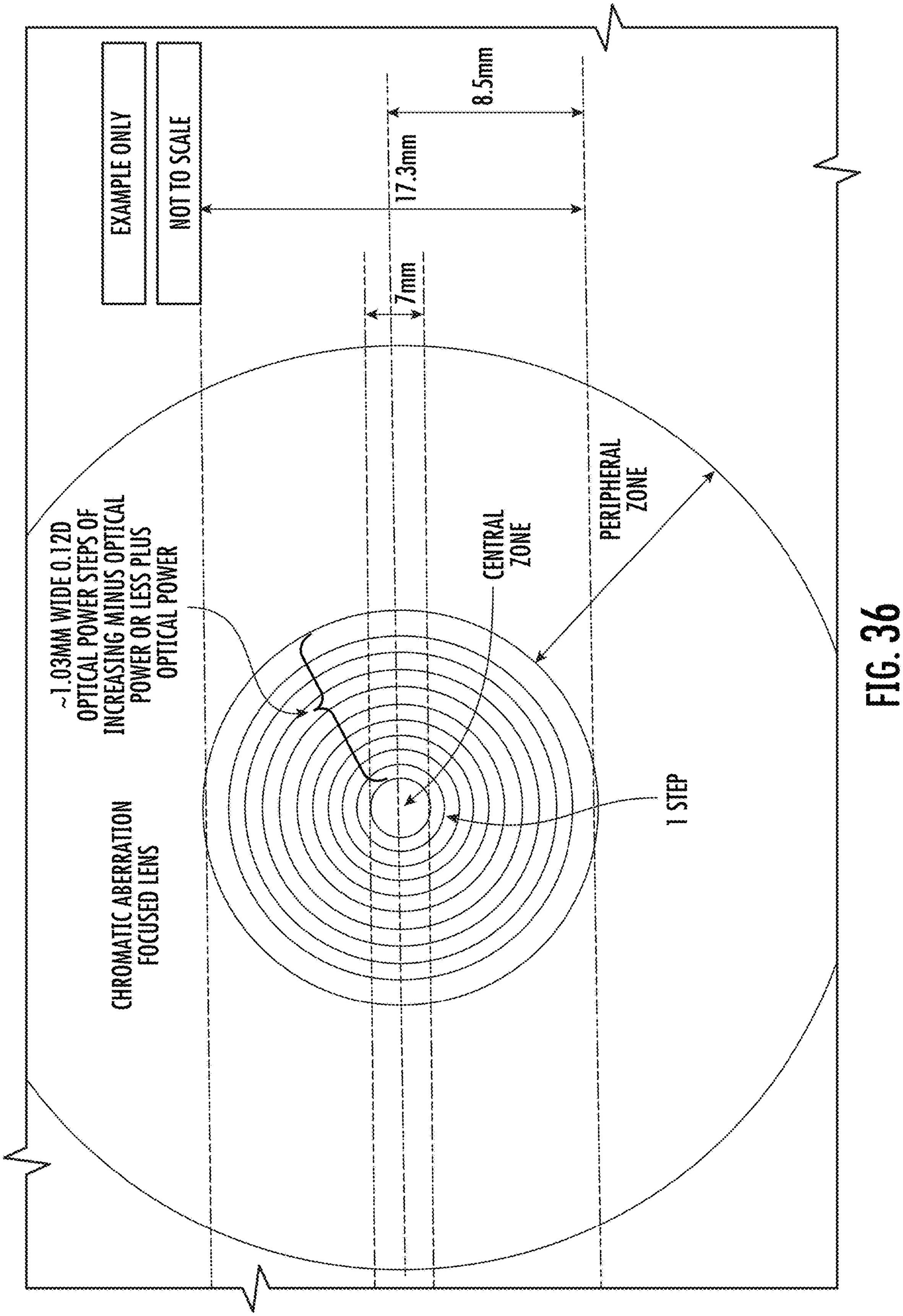
FIG. 36 shows an embodiment of the current invention as described herein.

In reference to FIG. 36, in embodiments of a chromatic aberration focused lens, the central zone can be comprised of a spherical or sphero-cylinder surface curvature causing a spherical or sphero-cylinder optical power, and the peripheral zone can be comprised of a spherical surface curve causing a spherical equivalent optical power. Said another way, a chromatic aberration focused lens that corrects astigmatism of the wearer can comprise an astigmatic correction in the central zone and a spherical equivalent spherical curve (somewhat) in all or part of the peripheral zone. The optical power differential between the central zone, intermediate zone, and peripheral zone can be generated by way of example only, plurality of continuous curvature changes, increasing minus optical progressive curve, a plurality of optical power steps, one optical power step, a micro-lens array, refractive index changes, blended optical power curves or steps, or a combination of any two or more. As shown in FIG. 36, an Intermediate Zone of optical power may comprise 10 Steps of increasing minus optical power or less plus optical power totaling 1.20 D of optical power difference from that of the Central zone. In aspects, optical power in a peripheral zone remains either constant from that of the 1.20 D of increase in minus or reduction of plus optical power, or can further increase in minus, or decrease in plus optical power by way of a continuous surface curvature change. The steps can be on the convex side, and the progressive plus power region on the concave side of the lens or lens blank. The preference is to have one surface on the convex side.

The optical power change from the central zone compared to either the intermediate zone or peripheral zone is of more minus optical power of less plus optical power. When using changes in continuous curvatures, the surface astigmatism generated is moved to the right and left side of the intermediate zone of the lens and superior to the intermediate zone only if needed. In certain embodiments, 50% of the optical power change from the optical power of the central zone is accomplished at the junction of the intermediate zone and the peripheral zone. For the purposes of this disclosure, plano optical power is considered zero optical power, but still can be utilized to denote the optical power of a section or region of the lens or lens blank.

In certain embodiments, a method for determining a preferred or optimal optical power for the central zone is to measure the distance vision refractive error of a patient while utilizing a green bandpass filter (interference filter). This causes focusing only the green wavelength band on the retina. Thus, by optimizing clarity of the green wavelength band to measure the patient's refractive power needs at far, it will establish the best optical power for seeing 20/20 in the distance. Once that is established, the needed increase in minus optical power or decreased plus optical power can be utilized for the peripheral lens area. This needed increase in minus optical power or decreased plus optical power can be a constant depending upon the material type comprised by the chromatic aberration focused lens. By way of example only, polycarbonate with an abbe of 30, a refractive index of 1.59, and a center thickness of 1.5 mm, will provide one constant number of increased minus or decreased plus optical power in the peripheral region of a chromatic aberration focused lens for most if not all optical powers. By way of example only, CR39 with an abbe of 58, a refractive index of 1.49, and a center thickness of 2.0 mm, will provide a different one constant number of increased minus or decreased plus optical power in the peripheral region of a chromatic aberration focused lens for most if not all optical powers.

Such is the case for all other optical materials having known abbe numbers used for fabricating ophthalmic lenses. So once the central zone optical power and the abbe number is known, lookup table (hard copy or electronic software) can be used to calculate the peripheral zone optical power deviation from that of the central zone optical power. In embodiments, the chromatic aberration focused lens can be clear (without a tint). In certain embodiments, the chromatic aberration focused lens can be tinted.

In certain embodiments a secondary attachable/detachable filtered lens, by way of example only, one or more of, a bandpass filter, interference filter, absorption filter, neutral density filter, notch filter, or optic or eyewear (by way of example only, magnetic attachable, pressure attachable, clip on attachable or a fit over optic), can periodically be worn with the chromatic aberration focused lens to further define the wavelengths of light for stimulating the retina of the wearer. By way of example only, a filtered lens such as a bandpass filter (interference filter) transmitting predominantly within the wavelength range of 480 nm+/−30 nm can be worn to further stimulate the rods and ganglion cells to generate dopamine. By way of example only, such a filter can be applied or used for 10 minutes or less in the morning and 10 minutes or less in the early afternoon.

A chromatic aberration focused lens represents a completely new category of lenses that utilize a clear lens' inherent chromatic aberration in a positive way to increase retinal dopamine, thus increasing choroid thickening to neutralize part or all the force responsible for the elongation of the eye that causes myopia. Such a lens can also be worn by patients with other types of dopamine deficiency disorders. Such lenses are taught within this disclosure. In a chromatic aberration focused lens, the longitudinal chromatic aberration found in the central zone of the lens is inherent in the lens required with the proper optical to achieve the wearer's best distance visual acuity. Thus, the central zone of the lens comprises an optical power which provides the wearer with his or her best visual acuity. However, the peripheral zone of the lens which begins at the outer junction with the central zone of the lens comprises additional minus power or less plus power causing the chromatic aberration wavelength bands to be moved farther away from the lens being worn by the wearer of such a lens, or said another way, deeper into or behind the retina of the eye of the wearer.

However, in aspects, peripheral to the central zone, another set of chromatic aberration can be engineered by the lens design to permit the blue wave bands of chromatic aberration to focus on or within the retina peripheral to the macula of the wearer's eye(s). Such lenses can take ambient light, by way of example only, fluorescent light, incandescent light, LED light, or sun light, and cause the blue light band of chromatic aberration generated by the lens to stimulate one or more of the retinal rods and/or ganglion cells to increase dopamine in the retina and in cases the brain. In certain embodiments it is the retinal rods that cause the largest amount of dopamine to be produced. In certain embodiments the desired level of light intensity is 300 lux or greater striking the retina. In other embodiments the desired level of light intensity is 400 lux or greater striking the retina. In other embodiments the desired level of light intensity is 500 lux or greater. In still other embodiments the desired level of light intensity is 1,000 lux or greater.

Another embodiment is that of a darkened, enhanced version of chromatic aberration focused lens that is worn for brief periods of time independent of one's conventional myopic correcting eyewear or as fit over eyewear in addition to one's conventional eyewear. Such an embodiment delivers only the specific wavelengths of light required to produce dopamine in the eye's retina, in aspects. For this reason, this enhanced embodiment can be able to be worn for a little as 5 minutes, 10 minutes, or 15 minutes or less, in the morning and midday to slowdown, and contribute to stopping myopia progression. This enhanced chromatic aberration lens can also be worn by patients with other types of dopamine deficiency disorders.

An embodiment of a chromatic aberration focused lens can be a lens or optic that comprises a central zone of optical power, wherein the central zone's optical power can be of an optical power required to correct an individual's distance refraction needs, wherein the optical power peripheral to a central zone can be of more minus optical power or less plus optical power than the optical power of the central zone, and wherein an outer surface of the zone peripheral to the central zone that comprises the increased minus optical power or reduced plus optical power compared to the central zone can be comprised of a smooth continuous curve.

The increase in minus optical power or reduced plus optical power can be of a difference of an optical power (either positive or negative) of 0.35 D and 5.00 D compared to that of the central zone's optical power. By way of example only, if the central power zone has an optical power of plano, a zone peripheral to the central zone can have an optical power that is within the range of 0.50 D to 5.00 D more minus optical power. Another example would be, if the central power zone had an optical power of −1.00 D a zone peripheral to the central zone could have an optical power of −1.50 D up to −6.00 D. Still another example would be, if the central power zone had an optical power of +1.00 D a zone peripheral to the central zone could have an optical power of +0.50 D up to that of +4.00 D.

The central zone can be comprised of an optical power required by one of an emmetrope, myope, hyperope, astigmat, compound astigmat, and/or presbyope. In addition to the optical powers mentioned herein, the lens or optic can comprise one or more bandpass filter(s), interference filter(s), absorption filter(s), and/or notch filters. The central zone of the lens or optic can be of any optical power including plano. The lens or optic can comprise a near focusing optical power that is applied in the form of a bifocal, trifocal or progressive addition lens. The lens or optic can be sunglass tint, colored tint, or of a clear color. The lens or optic can be finished with any optical coating including that of a hard coat and/or antireflective coating. The lens or optic can have a central zone and a peripheral zone. The lens or optic can comprise a central zone, intermediate zone and a peripheral zone. The lens or optic can comprise multiple intermediate zones of different optical power. The lens or optic can comprise a single change of optical power. The lens or optic can comprise multiple changes of optical power. The change(s) of optical power can be continuous. The change(s) of optical power can be blended. The change(s) of optical power can be immediate. The junction between the central zone and a zone that begins immediately at the junction between such zone and the central zone can be lined due to a sharp optical power change, blended, or continuous with the start of an intermediate zone of that of a peripheral zone (see, FIG. 36).

An embodiment can comprise no blended intermediate zone or a blend at the junction of the outer central zone edge and peripheral zone. In certain embodiments a blended junction or smoothed continuous increased minus powered (or less plus power) junction can be present. In still other embodiments if the central zone is of plus optical power an intermediate power zone can be of less plus power than the central zone's optical power, and the peripheral zone can be of even less optical plus power than the intermediate zone. If the central zone is of minus or plano optical power the intermediate zone can be of increased minus optical power and the peripheral zone can be of a greater amount of minus optical power than that of the intermediate zones minus optical power.

The central zone can be of any distance optical power required by an emmetrope, hyperope, myope, astigmat, or any combination thereof. The lens further can comprise an additional positive power for the correction of presbyopia or to assist with near point accommodative stress. The additional optical power can be a lined bifocal, trifocal or progressive addition zone. Given that the peripheral zone is increasing in minus power this causes additional stress on the near point accommodative system of the wearer, thus depending upon the age of the wearer or the amount of near work that is required of the wearer, for a chromatic aberration lens in certain embodiments additional near point optical power can be required. In certain embodiments the increase in minus power can be generated by curvature on one side of the lens or lens blank, while the near addition optical power (added positive optical power) can be generated on the opposite side of the lens or lens blank. In still other embodiments the increase in minus power and the near addition optical power (added positive optical power) can be generated on the same side of the lens or lens blank while the near addition power can be generated on the opposite side of the lens or lens blank.

This embodiment is also a chromatic aberration focused lens, but in addition to the lens design where the central area focuses the distance BVA of the patient, the lens utilizes a filter or filters, by way of example only: a bandpass filter, interference filter, absorptive filter, notch filter, or a combination of any two or more, to permit the largest concentration of visible wavelengths to be within the wavelength ranges of 450 nm-510 nm or 480 nm+/−30 nm. In certain embodiments, but not all, the central zone is left free of a filter or filters, with the filter being peripheral to the central zone. The lenses can take ambient light, by way of example only, fluorescent light, incandescent light, LED light, or sun light, and cause the light transmitted by the filter to stimulate one or more of the retinal rods and/or ganglion cells to increase dopamine in the retina and in cases the brain. In certain embodiments it is the retinal rods that cause the largest amount of dopamine to be produced. The desired level of light is 300 lux or greater. In other embodiments the desired level of light is 1,000 lux or greater. In still other embodiments the desired level of light is 10,000 lux or greater. With this lens, the filtered passed light wavelengths can be designed to be focused on the retina or in the retina, peripheral to the macula, depending upon the optical power peripheral to the central optic zone of the lens. However, in other embodiments the filter or filters are applied across the lens.

In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of at least one of, 460 nm-520 nm, 470 nm to 520 nm, or 480 nm-520 nm, or by utilizing a light source or light emitter that predominately transmits within the wavelength range of at least one of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

Embodiments when light wavelengths are generated by way of filtered optics or filtered lenses the transmission peak of the wavelength range that strike the eye's retina falls within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In embodiments when light wavelengths are generated by a light emitter(s) if ambient lighting is present (including that of artificial light or sun light), the blended light wavelengths of the light emitter(s) and also the ambient light comprises wavelengths of light that strike the eye's retina, which fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 40% of less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens.

In certain embodiments when a filtered optic or filtered lens is used the overall light transmission through the filtered optic or filtered lens can be 30% of less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens.

An embodiment is that of a lens or optic, wherein the central zone maintains its normal focus of chromatic aberration wavelength bands, wherein one or more of the chromatic aberration wavelength bands that are peripheral to the central zone focuses farther from the lens or optic than those of the central zone, and wherein the lens' or optic's optical power that is peripheral to that of the central zone is within the range of 0.50 D to 5.00 D of increased minus optical power or less plus optical power when compared to the optical power of the central zone of the lens or optic.

Another embodiment is that of a lens or optic, wherein the optical power peripheral to the central zone of the lens or optic is comprised of an increase in minus optical power or a reduction in plus optical power compared to that of the central zone of the lens or optic, and wherein that increase of minus optical power or reduced plus optical power is within the range of 0.50 D to 5.00 D.

Still another embodiment is that of a lens or optic comprising a central zone and a zone or zones peripheral to the central zone, wherein the central zone comprises a diameter within the range of 6 mm to 12 mm, wherein the central zone has an optical power required for the wearer's best distance visual acuity, and wherein the optical power peripheral to the central zone of the lens or optic is comprised of an increase in minus optical power or a reduction in plus optical power compared to that of the central zone of the lens or optic, and wherein that increase of minus optical power or reduced plus optical power is within the range of 0.50 D to 5.00 D.

Figure 37:
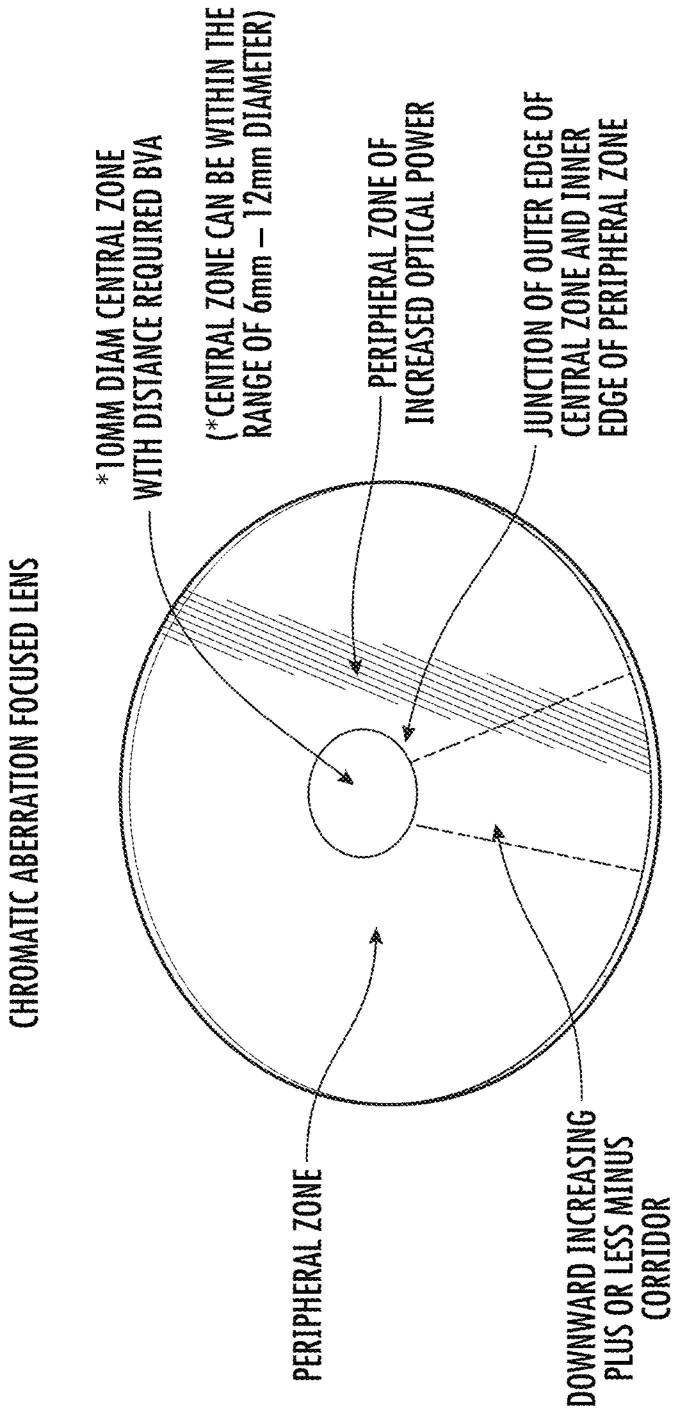
FIG. 37 shows an embodiment of the current invention as described herein.

In reference to FIG. 37, it shows an embodiment of a lens or optic that comprises a central zone of optical power, wherein the optical power peripheral to the central zone is more minus optical power than the optical power of the central zone, wherein the lens or optic comprises a downward directional zone or corridor of optical power that is within 0.50 D of or equal to the central zone's optical power, and wherein the downward corridor of optical power continues in a length of 5 mm or more. The lens or optic can comprise an optical power peripheral to the central zone ranges between −0.50 D to −5.00 D more minus optical power. According to this embodiment, one surface of this peripheral zone is that of a smooth continuous curve. In certain embodiments the optical power is constant within the tolerance of +/−0.25 D and in other embodiments the optical power can vary. In aspects, the peripheral zone comprises "increased" minus optical power (or "less" plus optical power) within the range of 0.35 D to 5.00 D compared to that of the Distance Corrected BVA which is the Optical power of the Central Zone. If the central zone power is plano the peripheral zone would be within the range of −0.50 D and −5.00 D. The central zone can be of any distance optical power required by an emmetrope, hyperope, myope, astigmat or any combination thereof. The lens further can comprise an additional positive power for the correction of presbyopia. The additional optical power can be a lined bifocal, trifocal or progressive addition zone.

The lens or optic can comprise a series of increases of minus optical power steps from the central zone outward. The lens or optic can comprise a series of increases of minus optical power continuous power curves from the central zone outward. The lens or optic can comprise a plurality of minus power lenslets being of more minus power than the central zone outside of the central zone. The lens or optic can comprise a minus power microlens array of more minus power than the central zone outside of the central zone. The lens or optic can comprise a plurality of minus zones having more minus power than the central zone outside of the central zone. The lens or optic can comprise a transition zone of increased optical power between the central zone and a peripheral zone.

The lens or optic can comprise a downward corridor. The downward corridor can be comprised of offsetting positive power. The downward corridor can be positioned below the pupil of the wearer to allow for offsetting all or some of the peripheral minus optical power. The downward corridor can be that of a positive power zone that provides a reduction in the added peripheral minus power of the lens or optic, thus reducing near point accommodative stress of the wearer. The downward corridor can be comprised of increasing positive power compared to that of the peripheral zone's optical power located outside of the downward corridor. The downward corridor can be generated on the front convex surface of the lens. The downward corridor can be generated on the front concave surface of the lens. The lens or optic can comprise surface topography for generating the downward corridor's optical power. Such topography can be located on one side of the lens or optic while the surface topography generating the increasing optical power peripheral to the central zone can be located on the opposite side of the lens or optic.

Figure 38:
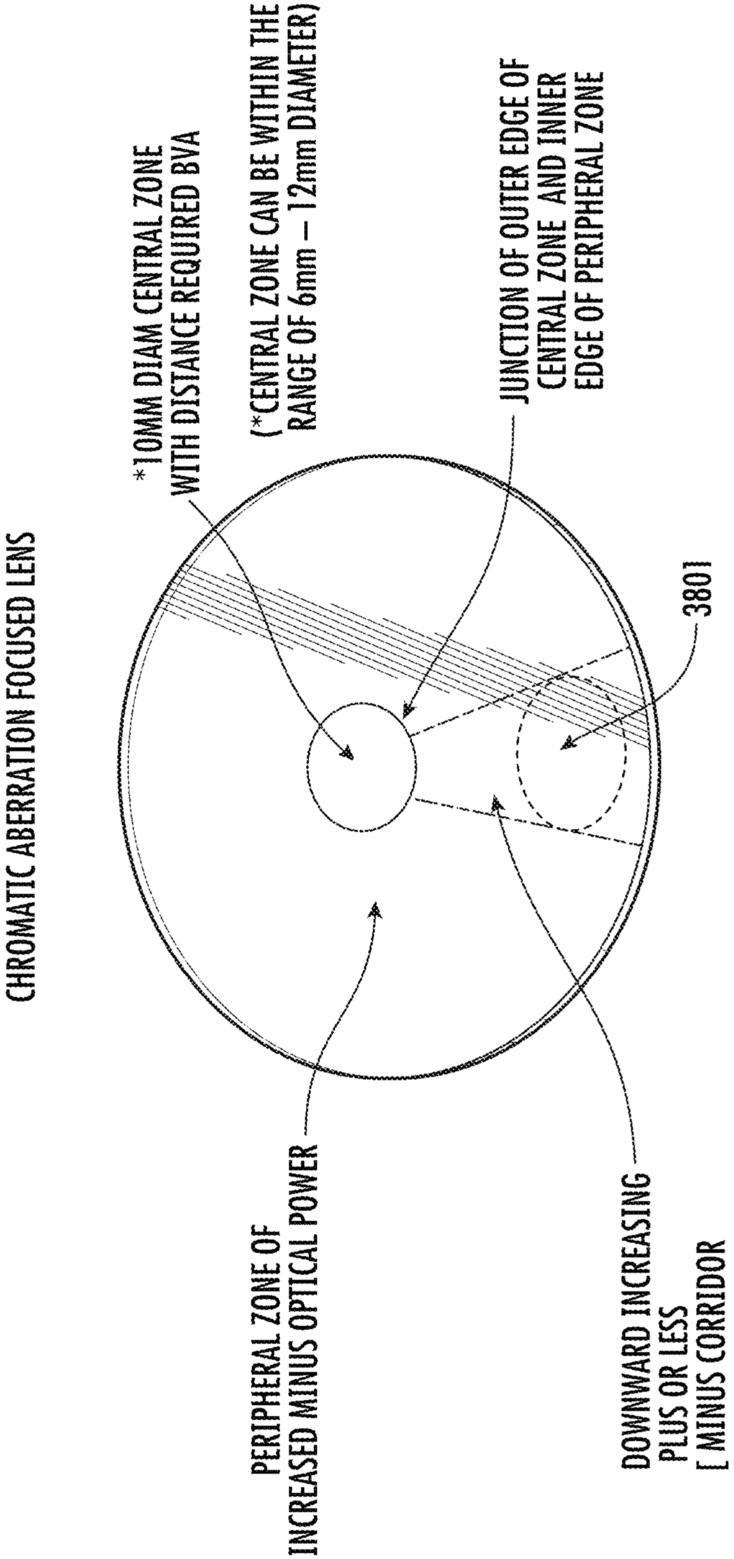
FIG. 38 shows an embodiment of the current invention as described herein.

In reference to FIG. 38, the lens or optic can comprise surface topography for generating the downward corridor's optical power. The lens or optic can comprise surface topography or a zone within in the lens for generating the increasing optical power peripheral to the central zone which can be located on the same side of the lens or optic. The downward corridor can connect to a reading zone. The downward corridor can comprise an optical power equal to that of the central zone. The reading zone can comprise an optical power that is between +0.50 D and +3.25 D of increased plus optical power compared to that of the central zone's optical power. The downward corridor can comprise an optical power that is contributed by both sides of the lens. The downward corridor can comprise a transition of increased added positive optical power. In aspects, one surface of the peripheral zone is that of a smooth continuous curve. In certain embodiments the optical power is constant within the tolerance of +/−0.25 D and in other embodiments the optical power can vary. In aspects, the peripheral zone comprises "increased" Minus Optical Power (or "less" Plus Optical Power) within the range of 0.35 D to 5.00 D compared to that of the Distance Corrected BVA, which is the Optical power of the Central Zone. If the central zone power is plano the peripheral zone would be within the range of −0.50 D and −5.00. The lens further can comprise an additional positive power for the correction of presbyopia 3801. The additional optical power can be a lined bifocal, trifocal or progressive addition zone.

Another embodiment of the lens can be a filtered lens or optic. The filtered lens can comprise one or more of: an interference filter, bandpass filter, absorption filter, notch filter, selective wavelength(s) filter, or neutral density filter. The lens or optic can predominantly transmit wavelengths within the wavelength range of one of: 450 nm-510 nm or 530 nm+/−20 nm or 650 nm+/−30 nm. The filtered lens can comprise a central zone and a defocus zone.

Another embodiment is that of a lens or optic that comprises a central zone of optical power, wherein the central zone's optical power can be of an optical power required to correct an individual's distance refraction needs, wherein the optical power peripheral to a central zone can be of more minus optical power or less plus optical power than the optical power of the central zone, and wherein an outer surface of the zone peripheral to the central zone that comprises the increased minus optical power or reduced plus optical power compared to the central zone is comprised of a smooth continuous curve.

The increase in minus optical power or reduced plus optical power can be of a difference of an optical power (either positive or negative) of 0.35 D and 5.00 D compared to that of the central zone's optical power. By way of example only, if the central power zone has an optical power of plano, a zone peripheral to the central zone can have an optical power that is within the range of 0.35 D to 5.00 D more minus optical power. Another example would be, if the central power zone had an optical power of −1.00 D a zone peripheral to the central zone could have an optical power of −1.35 D up to that of −6.00 D. Still another example would be, if the central power zone had an optical power of +1.00 D a zone peripheral to the central zone could have an optical power of +0.65 D up to that of +4.00 D.

The central zone can be comprised of an optical power required by one of an emmetrope, myope, hyperope, astigmat, compound astigmat, and/or presbyope. In addition to the optical powers mentioned herein, the lens or optic can comprise one or more bandpass filter(s), interference filter(s), absorption filter(s), or notch filters. The central zone of the lens or optic can be of any optical power including plano. The lens or optic can comprise a near focusing optical power that is applied in the form of a bifocal, trifocal or progressive addition lens. The lens or optic can be a sunglass tint, colored tint, or of a clear color. The lens or optic can be finished with any optical coating including that of a hard coat and/or antireflective coating. The lens or optic can have a central zone and a peripheral zone. The lens or optic can comprise a central zone, intermediate zone and a peripheral zone. The lens or optic can comprise multiple intermediate zones of different optical power. The lens or optic can comprise a single change of optical power. The lens or optic can comprise multiple changes of optical power. The change(s) of optical power can be continuous. The change(s) of optical power can be blended. The change(s) of optical power can be immediate.

In another embodiment a chromatic aberration focused lens for photo-bio-stimulation can be fabricated by altering the index of refraction between the central zone and other zones of the lens or lens blank. This can be utilized for altering the lens focus power between the central zone, an optional intermediate zone, and a peripheral zone, in such a way that the focus power in the optical intermediate zone and non-optional peripheral zone is more minus focus power or less plus focus power that the central zone. It can also be generated by altering the index of refraction of the central zone, the optional intermediate zone, and the non-optional peripheral zone. In this case the refractive index would be less in the optional intermediate zone and non-optional peripheral zone of the lens or lens blank as compared to the central zone. And it can be caused by a combination of both altering the focal power and the index of refraction.

In reference to FIG. 39, it shows an embodiment of an ocular photo-bio-stimulation filtered defocused lens can be a lens that comprises: a central zone for correcting distance focus for the wearer and small enough to establish an effective functional zone; a selected or chosen fill factor to deliver high efficacy while preserving good wearability; a central zone of 4 mm-6 mm; and added Surface power within the range of −0.50 D to −5.00 D. In aspects, the fill factor can be of 0.5. In aspects, utilizing this design, the chromatic aberration of outside of the central zone can cause the blue light wavelengths to be focused deeper into the retina, while the central zone's chromatic aberration focuses the blue light wavelengths in front of the retina.

In reference to FIG. 40, it shows an embodiment of an ocular photo-bio-stimulation filtered defocused lens, which can be a lens that comprises: a spectacle lens for myopia correction and control with Highly Aspherical Lenslet Target (H.A.L.T.) Technology; a central optical zone (9 mm) for correcting distance refractive error of the wearer, with surrounding myopia control zone incorporating 1021 contiguous (touching) highly aspherical lenslets (each 1.12 mmø). Each lenslet does not have a single focal power, instead creating a 'volume of defocus' as a slow-down signal for eye growth. Each of the, in aspects, 11 rings of lenslets feature contiguous lenslets of similar asphericity, with successive rings having lenslets with different asphericities. Spaces between the rings of lenslets provide single vision correction. In aspects, added optical power peripheral to the central zone can be within the range of 0.50 D to 5.00 D more minus or less plus. Utilizing this design the chromatic aberration of outside of the central zone causes the blue light wavelengths to be focused deeper into the retina, while the central zone's chromatic aberration focuses thee blue light wavelengths in front of the retina.

In reference to FIG. 41, still Another embodiment of an ocular photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and surrounding treatment zone with honeycomb array of lenslets (each 1.03 mm). In aspects, each lenslet can has a relative negative power within the range of 0.50 D to 5.00 D more minus or less plus. There can be spaces between the lenslets where the single vision correction is accessible. The precise optical power of the lenslets is selected to move the chromatic aberration blue light wavelengths back into the retina. This occurs while the central zone focuses the chromatic aberration blue light wavelengths in front of the retina.

In reference to FIG. 42, another embodiment of an ocular photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb array of lenslets (each 1.03 mmø). The lenslets can have a relative power within the range of −0.50 D to −5.00 D. There can be spaces between the lenslets where the single vision correction is accessible. The precise optical power of the lenslets can be selected to focus the chromatic aberration blue light wavelengths into the retina. This occurs while the central zone focuses the chromatic aberration blue light wavelengths in front of the retina. Outside of the intermediate zone there is a peripheral zone comprised of increased negative power or less plus power compared to the central zone of the lens.

In reference to FIG. 43, another embodiment of an ocular photo-bio-stimulation filtered defocused lens can be a lens that comprises: a spectacle lens for myopia correction and control with Defocus Incorporated Multiple Segments (DIMS) Technology; a central optical zone (9 mmø) for correcting distance refractive error of the wearer, and intermediate treatment zone with honeycomb micro-lens array of lenslets (each 1.03 mmø). Each lenslet can have a relative negative power within the range of 0.50 D to 5.00 D more minus or less plus. There can be spaces between the lenslets where the single vision correction is accessible. In this embodiment the lens power outside of the central zone also increases in minus optical power or less plus optical power. In the intermediate zone the precise combined optical power of the lenslets and the lens power is selected to focus the chromatic aberration blue light wavelengths into the retina. This occurs while the central zone focuses the chromatic aberration blue light wavelengths in front of the retina. Outside of the intermediate zone there is a peripheral zone comprised of increased negative power or less plus power compared to the central zone of the lens.

In order to determine the appropriate amount of added minus optical power to the periphery of a chromatic aberration focused optic that is used for ocular photo-bio-stimulation the use of a duo-chrome test can be helpful. An embodiment can be that of a red-blue vision test, or a green-blue vision test. When refracting a patient for their best corrected distance vision, after determining the appropriate best corrected optical power, have the patient use the distance optical power as a base line. Then while testing the patient monocularly, place a red blue see through duo-chrome in front of the eye. Add minus optical power until the blue side appears to be the best in focus. The optical power that provides the clearest vision when looking through the blue side of the duochrome (when adding minus lenses) should be the point when the blue light wavelengths are focusing on or in the retina. This can also be tested with a green blue duochrome. This test can be performed when looking through a blue tinted optic or lens. This test can also be performed with a blue printed distance eye chart or that of a blue projected eye chart. The amount of increase in minus power that provides the clearest blue image of either the blue duo chrome test or that of a blue eye chart can then be prescribed for the power of the non-central zone (the peripheral zone) of the chromatic aberration focused lens or optic, while measuring and prescribing the optical power required through a clear lens to achieve the BVA distance optical power for that of the central zone of the lens or optic. When testing for the peripheral optical power that will be prescribed (that of the increased minus optical power) the use of the lens material (abbe number) that will be prescribed should be utilized.

An embodiment is that of a look up chart that is calculated in advance. Such an embodiment can show the lens material with the abbe number, the distance optical power for achieving the best corrected distance visual acuity, and/or the increase in minus optical power required to move the blue wavelengths so they will focus on or in the retina for that distance BVA optical power when taking into account the abbe number for the lens material to be used for the lens that will be prescribed. Such a chart can show optical power required for the patient's distance BVA (this being the central zone's optical power) and based upon the lens material to be prescribed (its abbe number), and/or the increased minus optical power over that of the central zone optical power required for the non-central zone. This optical power in the periphery being an increase in minus optical power compared to that of the central zone. Such a look up chart can be a printed chart, manual generated electronic chart, or software automatically generated chart. By way of example only; Distance BVA correction power=−2.00 D/Abee Number 30/non-central (or peripheral) optical power=−3.25 D.

An embodiment can be that of an ocular photo-bio stimulation look up chart for determining the appropriate optical power for the central zone and the peripheral zone of a chromatic aberration focused lens or optic, wherein the look up chart can be one of: printed, manually electronic generated, or automatic software generated, and wherein to determine the optical power of each the central zone and the peripheral zone the user must locate on the chart or enter electronically the wearer's optical power required to provide the wearer with their distance BVA and the material (or Abee #) of which their lens will be made. Once that is filled in electronically the appropriate non-central zone (or peripheral zone) optical power will be expressed. The optical power required for the distance BVA can be expressed as their distance optical power prescription. The optical power required for the distance BVA can be expressed as their distance optical power spherical equivalent.

An embodiment can be a lens or optic comprising a central optical power zone having optical power or plano optical power, and one or more peripheral optical power zones peripheral to the central optical power zone having optical power or plano optical power, wherein the optical power of the central optical power zone substantially corrects or provides for distance vision clarity for a wearer of the lens or optic, wherein the central zone includes a first set of longitudinal chromatic aberration wavelength bands of blue, green, and red, wherein the one or more peripheral optical power zones include a second set of longitudinal chromatic aberration wavelength bands of blue, green, and red, and wherein a focus point of a second blue longitudinal chromatic aberration wavelength band of the second set of longitudinal chromatic aberration wavelength bands is located within a range of 50 microns to 1,000 microns farther away from a back concave side of the lens or optic compared to a focus point of a first blue longitudinal chromatic aberration wavelength band of the first set of longitudinal chromatic aberration wavelength bands. The second blue chromatic aberration wavelength band can focus closer to the retina of an eye of a wearer of the lens or optic than the first blue chromatic aberration wavelength band. The second blue chromatic aberration wavelength band can focus within the retina of a wearer's eye.

One or more peripheral optical power zones of the lens or optic can be within a range of 0.50 D to 5.00 D, more minus or less plus optical power than the optical power of the central optical power zone. When stating that the peripheral power zone is less minus or more plus optical power compared to that of the central zone, that would also be the same for the spherical equivalent optical power.

The central optical power zone of the lens or optic can have a blended abbe number considering the central optical power zone lens material and any coatings thereto, and wherein the central optical power zone's blended abbe number is greater than a blended abbe number of the one or more peripheral optical power zones. The central optical, power zone of the lens or optic can have less thickness than one or more peripheral optical power zones. The light passing through the lens or optic can stimulate the production of dopamine within a retina of the wearer of the lens or optic. The light passing through the lens or optic can stimulate the production of dopamine and/or serotonin within the brain of the wearer of the lens or optic.

The lens or optic can comprise a surface junction between the central optical power zone and the one or more peripheral optical power zones that comprise a smooth surface topography. The surface junction of the lens or optic between the central optical power zone and the one or more peripheral optical power zones can comprise an uneven surface topography. The lens or optic can comprise an optical power junction between the central optical power zone and the one or more peripheral optical power zones that can be a blended optical power junction. The lens or optic can comprise an optical power junction between the central optical power zone and the one or more peripheral optical power zones that can have stepped optical power. The lens or optic can comprise an optical power junction between the central optical power zone and the one or more peripheral optical power zones that can be of a progressive optical power change. The lens or optic can comprise a progressive addition zone. The lens or optic can be a single vision lens or optic. The lens or optic can be multifocal lens or optic.

The lens or optic can filter light such that the lens or optic allows 40% or more light transmission through the lens or optic as measured within the wavelength range of one or more of: 480 nm+/−30 nm, 450 nm to 520 nm, 650 nm+/−30 nm, or 700 nm+/−30 nm. The lens or optic can comprise one or more peripheral optical power zones that comprise dispersive electronically switchable liquid crystal. The lens or optic can comprise one or more peripheral optical power zones that can provide contrast sensitivity reduction. The lens or optic can comprise one or more peripheral optical power zones that can comprise negative optical power defocus. The lens or optic can comprise one or more peripheral optical power zones that can comprise negative optical power defocus including or incorporating multiple segments. The lens or optic can comprise one or more peripheral optical power zones that can comprise negative optical power highly aspheric lenslets. The lens or optic can be devoid of lenslets. The lens or optic can comprise one or more peripheral optical power zones comprise two outer surface curvatures that are continuous with one another.

The lens or optic can comprise an intermediate zone peripheral to the central optical power zone. The lens or optic can comprise an optical power of the intermediate zone that can be more minus or less plus optical power compared to the optical power of the central optical power zone, and wherein the optical power of the intermediate zone can be less minus or more plus optical power compared to the optical power of the one or more peripheral optical power zones. The lens or optic can be a chromatic aberration focused lens or optic. The lens or optic can be a chromatic aberration refocused lens or optic. A chromatic aberration focused lens or optic can mean the same as that of a chromatic aberration refocused lens or optic.

The lens or optic can comprise a central optical power zone that can be within a range of 6 mm-12 mm in diameter. The lens or optic can comprise an optical power junction of (1) the central optical power zone and (2) an intermediate zone or the one or more peripheral optical power zones, that can be located on a convex side of the lens or optic. The lens or optic can comprise an optical power junction of (1) the central optical power zone and (2) an intermediate zone or peripheral zone, that can be located on the back concave side of the lens or optic. The lens or optic can comprise a focus point of the second blue chromatic aberration wavelength band that can be located within a range of 100 microns to 500 microns farther from the back concave side of the lens or optic compared to the focus point of the first blue chromatic aberration wavelength band.

Sunglass Lens or Sunglass Optic or Filtered Lens or Filtered optic that Provides Ocular Photo-Bio-Stimulation An embodiment can be that of a filtered lens or filtered optic or sunglass lens or sunglass optic that transmits a higher percentage of blue light and bluish green light wavelengths within the wavelength range of one or more of 480 nm+/−30 nm or 530 nm+/−20 nm, than the lens or optic comprises an average visible light transmission percentage (VLT) within the range of 380 nm-780 nm and passes the ISO 12312-1 sunglass traffic light/signal test.

An embodiment can be that of a filtered lens or filtered optic or sunglass lens or sunglass optic that transmits a higher percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm to qualify for category 2 or category 3 sunglasses and further passes the ISO 12312-1 sunglass traffic light/signal test.

An embodiment can be a filtered lens or filtered optic or sunglass lens or sunglass optic that transmits 40% or greater percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm to qualify for category 2 or category 3 sunglasses and further passes the ISO 12312-1 sunglass traffic light/signal test.

An embodiment can be a filtered lens or filtered optic or sunglass lens or sunglass optic that transmits 40% or greater percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm to qualify for category 3 sunglasses and further passes the ISO 12312-1 sunglass traffic light/signal test.

An embodiment can be that of a filtered lens or filtered optic or sunglass lens or sunglass optic that transmits a higher percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm and passes the ISO 12312-1 sunglass traffic light/signal test with a red transmittance of 8% or greater, yellow transmittance of 6% or greater, and green transmittance of 6% or greater.

An embodiment can be that of a filtered lens or filtered optic or sunglass lens or sunglass optic that transmits a higher percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm to qualify for category 2 or category 3 sunglasses and further passes the ISO 12312-1 sunglass traffic light/signal test with a red transmittance of 8% or greater, yellow transmittance of 6% or greater, and green transmittance of 6% or greater.

An embodiment can be a filtered lens or filtered optic or sunglass lens or sunglass optic that transmits 40% or greater percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm to qualify for category 2 or category 3 sunglasses and further passes the ISO 12312-1 sunglass traffic light/signal test with a red transmittance of 8% or greater, yellow transmittance of 6% or greater, and green transmittance of 6% or greater.

An embodiment can be a filtered lens or filtered optic or sunglass lens or sunglass optic that transmits 40% or greater percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm to qualify for category 3 sunglasses and further passes the ISO 12312-1 sunglass traffic light/signal test with a red transmittance of 8% or greater, yellow transmittance of 6% or greater, and green transmittance of 6% or greater.

An embodiment can be that of a filtered lens or filtered optic or sunglass lens or sunglass optic that transmits a higher percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm and passes the ANSI sunglass standards for Traffic Signals.

An embodiment can be that of a filtered lens or filtered optic or sunglass lens or sunglass optic that transmits a higher percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm to qualify for category 2 or category 3 sunglasses and further passes ANSI sunglass standards for Traffic Signals.

An embodiment can be a filtered lens or filtered optic or sunglass lens or sunglass optic that transmits 40% or greater percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm to qualify for category 2 or category 3 sunglasses and further passes the ANSI sunglass standards for Traffic Signals.

An embodiment can be a filtered lens or filtered optic or sunglass lens or sunglass optic that transmits 40% or greater percentage of blue light and bluish green light wavelengths within the wavelength range of one or more of 480 nm+/−30 nm or 530 nm+/−20 nm than the lens or optic comprises an average visible light transmission percentage (VLT) within the range of 380 nm-780 nm to qualify for category 3 sunglasses and further passes ANSI sunglass standards for Traffic Signals.

Embodiments when light wavelengths are generated by way of filtered optics or filtered lenses the transmission peak of the wavelength range that strike the eye's retina falls within the wavelength range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In embodiments when light wavelengths are generated by a light emitter(s) if ambient lighting is present (including that of artificial light or sun light,) the blended light wavelengths of the light emitter(s) and also the ambient light comprises wavelengths of light that strike the eye's retina fall within one of the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm or 700 nm+/−30 nm.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens and constricts when looking absent of the filtered optic or filtered lens. However, in cases when the eye's retina is exposed to blue light within the range of 450 nm to 530 nm, preferably 480 nm+/−20 nm, the pupil of the eye constricts or remains constricted. The constriction of the pupil when viewing through a filtered optic or filtered lens allows for the user/wearer of the filtered optic to have maximum vison clarity. However, in certain embodiments it is more important to provide ocular photo-bio-stimulation as opposed to maximum vision clarity. In these embodiments it is necessary to trick the wearer's retinal neurological feedback that causes the pupil to constrict while still providing blue light within the range of 450 nm-530 nm, preferably 480 nm+/−20 nm, to strike the wearer's/user's retina. By way of example only, in certain XR eyewear embodiments, the light source can modulate between (by way of example only, a black image and blue image comprised of light wavelengths within the range of 450 nm-530 nm). When black is visible to the eye of the wearer, the pupil increases in size and then, when the blue wavelengths within the range of 450 nm-530 nm become visible, the pupil constricts.

An embodiment can be an eyewear apparatus worn by a wearer comprising a filtered lens or filtered optic, wherein the filtered lens or filtered optic of the eyewear apparatus transmits light at a light wavelength transmission rate of 50% or more within a light wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, to an eye of the wearer, and wherein the filtered lens or filtered optic of the eyewear apparatus comprises an overall visible light transmission of 40% or less.

In certain embodiments when a filtered optic or filtered lens is used the overall light transmission through the filtered optic or filtered lens can be 40% of less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens. However, in cases when the eye's retina is exposed to blue light within the range of 450 nm to 530 nm, preferably 480 nm+/−20 nm, the pupil of the eye constricts or remains constricted. The constriction of the pupil when viewing through a filtered optic or filtered lens allows for the user/wearer of the filtered optic to have maximum or improved vison clarity. However, in certain embodiments it is more important to provide ocular photo-bio-stimulation as opposed to maximum vision clarity. In these embodiments it is necessary to trick the wearer's retinal neurological feedback that causes the pupil to constrict while still providing blue light within the range of 450 nm-530 nm, preferably 480 nm+/−20 nm to strike the wearer's/user's retina.

In certain embodiments when a filtered optic or filtered lens is used the overall light transmission through the filtered optic or filtered lens can be 30% of less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens. However, in most cases when the eye's retina is exposed to blue light within the range of 450 nm to 530 nm, preferably 480 nm+/−20 nm, the pupil of the eye constricts or remains constricted. The constriction of the pupil when viewing through a filtered optic or filtered lens allows for the user/wearer of the filtered optic to have maximum vison clarity. However, in certain embodiments it is more important to provide ocular photo-bio-stimulation as opposed to maximum vision clarity. In these embodiments it is necessary to trick the wearer's retinal neurological feedback that causes the pupil to constrict while still providing blue light within the range of 450 nm-530 nm, preferably 480 nm+/−20 nm to strike the wearer's/user's retina.

Visible light transmission (VLT) is measured as a percentage of the total visible light that strikes the lenses and is affected by a number of factors such as lens material and thickness, the base lens color, and the coatings applied on top. The VLT percentage tells how much light will reach your eyes. The lower the percentage, the darker your glasses will be.

In reference to FIG. 44, there are 5 sunglass categories of VLT. Sunglasses that fall within categories 2 and 3 are the most popular sunglasses. Category 2 transmits visible light between 18%-43%. Categories, such as categories 3 or 4 filter or block most blue light wavelengths.

Figure 45:
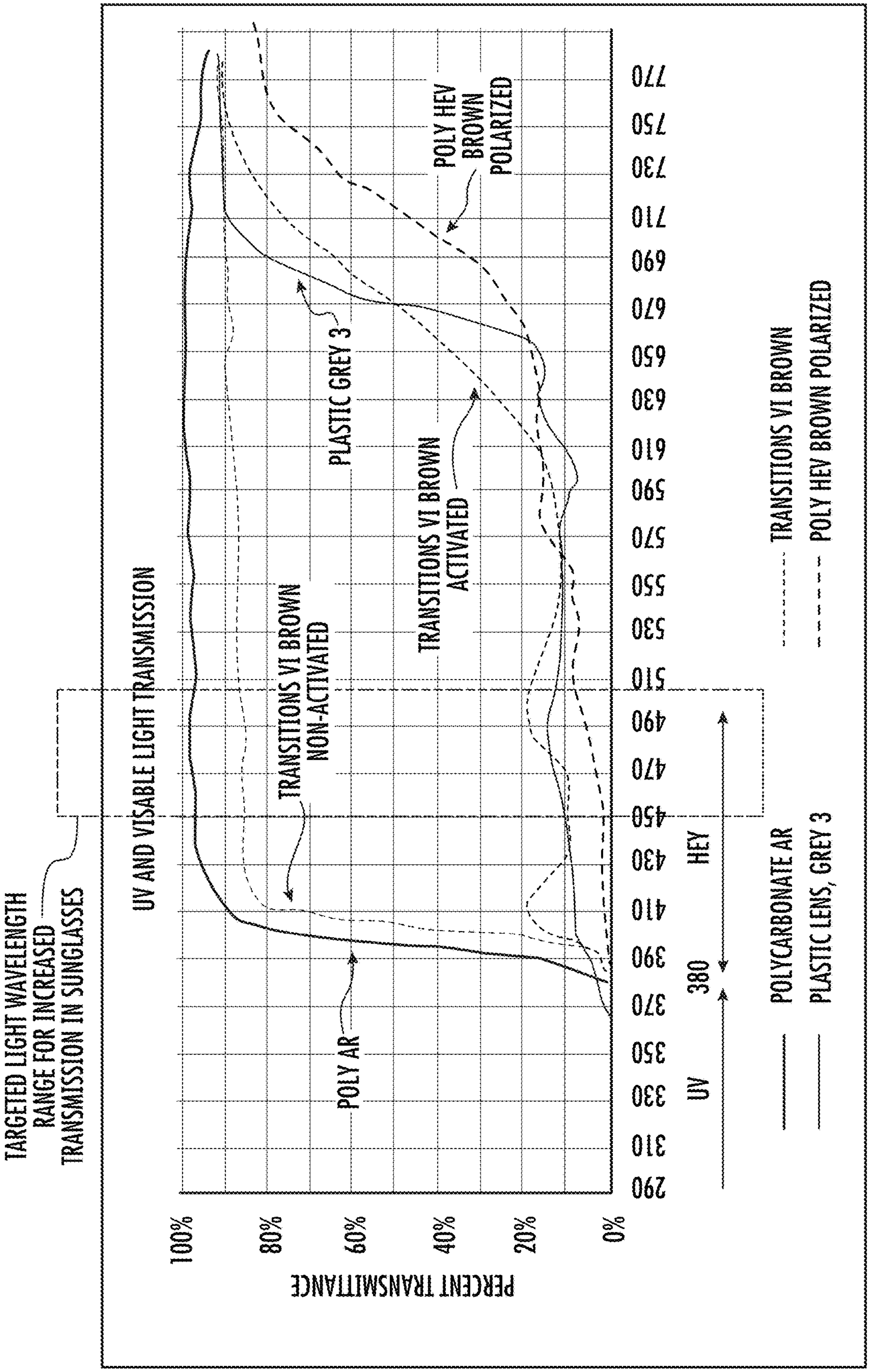
FIG. 45 shows information related to the invention described herein.

In reference to FIG. 45, most sunglass manufacturers lead their marketing by providing information on how much blue light is filtered or blocked with their sunglasses. Unfortunately, sunglasses that fit within categories 3, 4 and 5 provide substantial vision and ocular protection. However, given that they block or filter most blue light and transmit so little, they actually inhibit the production of dopamine in the eye of the wearer and possibly serotonin and dopamine in the brain of the wearer while being worn. This is true of all sunglasses that transmit 43% or less visible light wavelengths including those that are polarized or photochromatic.

Figure 46:
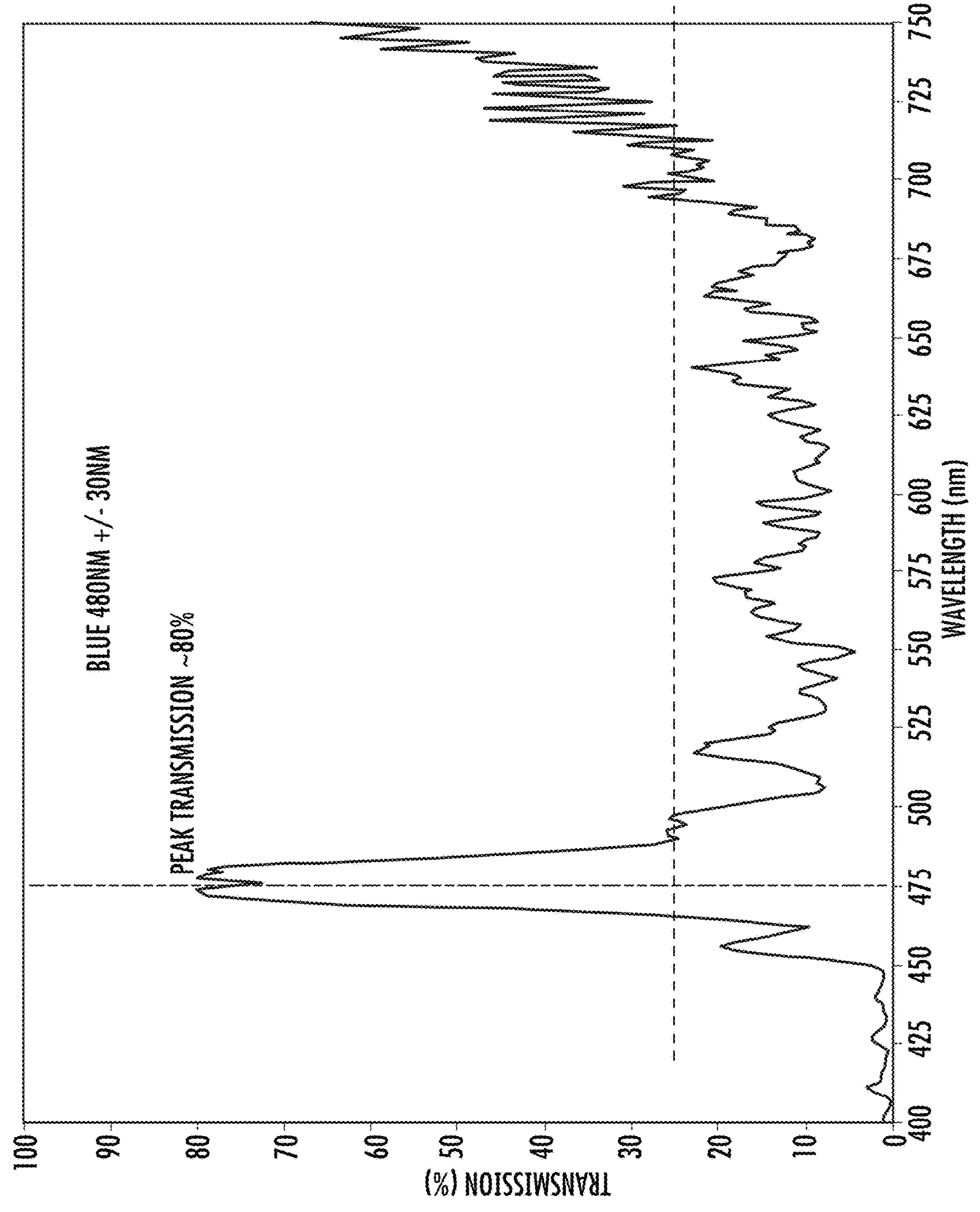
FIG. 46 shows information related to the invention described herein.

In reference to FIG. 46, there is a pressing need for sunglasses having an overall visible light transmission of 40% or less visible light while transmitting 41% or more blue light wavelengths within the range of 480 nm+/−30 nm, and, in addition, that pass color transmission standards/requirements so to be able to permit the wearer to drive and properly identify the colors red and green, by way of example only, on a red light. Sunglasses having a 41% or greater transmission within the wavelength range of 480 nm+/−30 nm would transmit enough of the light wavelengths that are known to stimulate dopamine in the eye's retina and in the brain of the wearer. This then could be most beneficial for individuals suffering from dopamine deficiency disorder.

Figure 47:
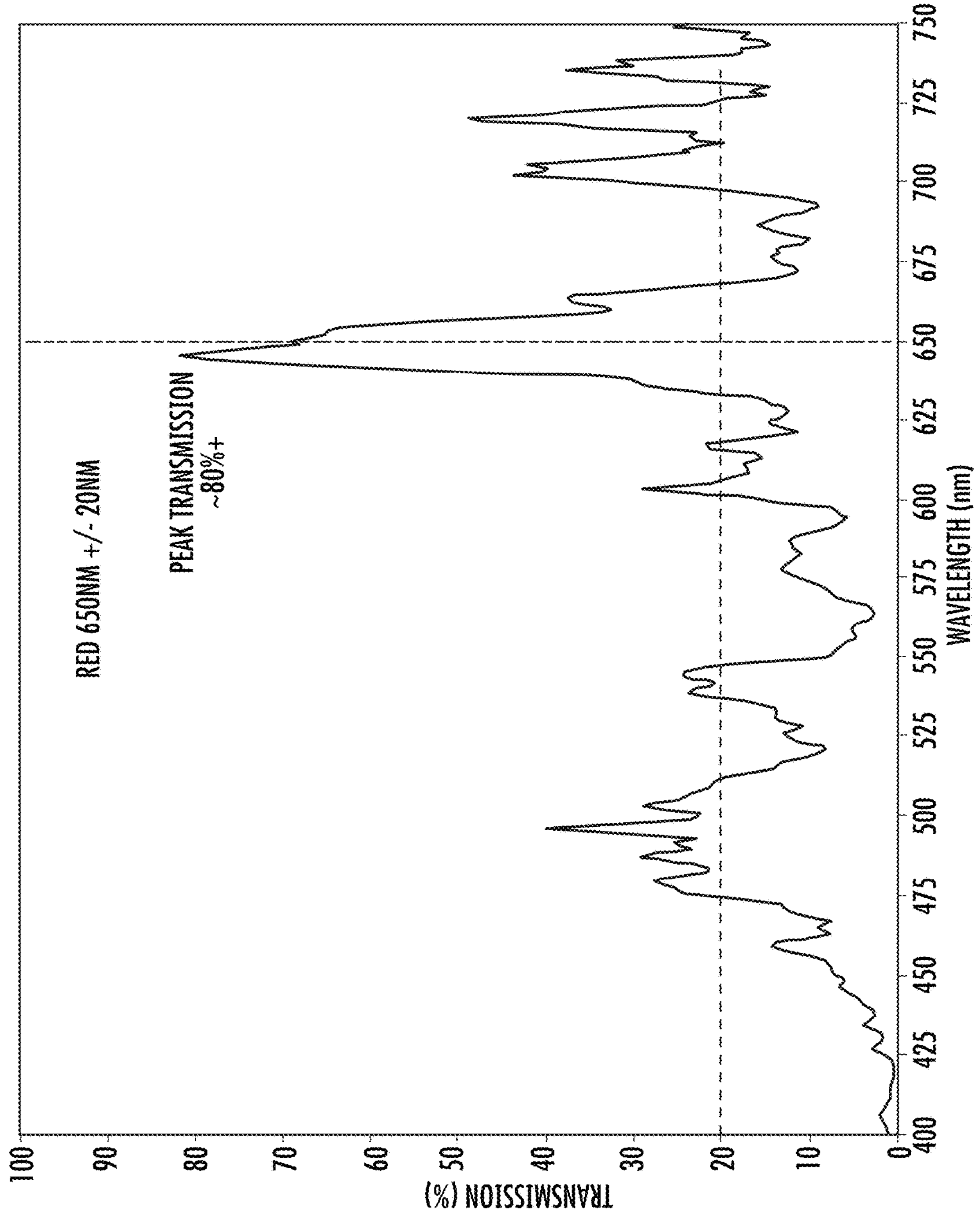
FIG. 47 shows information related to the invention described herein.

In reference to FIG. 47, this shows sunglasses having an overall transmission of 40% or less visible light while transmitting 41% or more red light wavelengths within the range of 650 nm+/−30 nm. In addition, these need to pass color transmission standards/requirements so to be able to permit the wearer to drive and properly identify the colors red and green, by way of example only, on a red light. Sunglasses having a 41% or greater transmission within the wavelength range of 650 nm+/−30 nm would transmit enough of the light wavelengths that are known to stimulate dopamine in the eye's retina and in the brain of the wearer. This then could be most beneficial for individuals suffering from dopamine deficiency disorder.

In certain embodiments a sunglass lens or optic comprises two or more absorptive dyes, wherein one or more of the absorptive dyes filters or blocks light wavelengths within the range of 450 nm downward to 400 nm or lower, and one or more absorptive dyes that filter or block light wavelengths within the range of 490 nn upward to 700 nm or greater, and wherein the light transmission within the range of wavelengths of 450 nm and 490 nm is 40% or more and the overall visible light transmission of the sunglass lens is 30% or less. One or more absorptive dyes can be imbibed into the surface or a surface coating of the lens or optic. One or more absorptive dyes can be coated on one of the surfaces of the lens or optic. One or more absorptive dyes can be imbibed or coated on the convex surface of the lens or optic. One or more absorptive dyes can be imbibed or coated on the concave surface of the lens or optic. One or more dyes can be incorporated within a surface cast layer that is applied or bonded to one or both surfaces of the lens or optic.

In certain embodiments a sunglass lens or optic comprises two or more absorptive dyes, wherein one or more of the absorptive dyes filters or blocks light wavelengths within the range of 440 nm downward to 400 nm or lower, and one or more absorptive dyes filter or block light wavelengths within the range of 500 nn upward to 700 nm or greater, and wherein the light transmission within the range of wavelengths of 440 nm and 510 nm is 40% or more and the overall visible light transmission of the sunglass lens is 30% or less. One or more absorptive dyes can be imbibed into the surface or a surface coating of the lens or optic. One or more absorptive dyes can be coated on one of the surfaces of the lens or optic. One or more absorptive dyes can be imbibed or coated on the convex surface of the lens or optic. One or more absorptive dyes can be imbibed or coated on the concave surface of the lens or optic. One or more dyes can be incorporated within a surface cast layer that is applied or bonded to one or both surfaces of the lens or optic.

In certain embodiments a sunglass lens or optic comprises two or more absorptive dyes, wherein one or more of the absorptive dyes filters or blocks light wavelengths within the range of 450 nm downward to 400 nm or lower, and one or more absorptive dyes filter or block light wavelengths within the range of 490 nn upward to 650 nm or greater, and wherein the light transmission within the range of wavelengths of 450 nm and 510 nm is 40% or more and the overall visible light transmission of the sunglass lens is 30% or less. One or more absorptive dyes can be imbibed into the surface or a surface coating of the lens or optic. One or more absorptive dyes can be coated on one of the surfaces of the lens or optic. One or more absorptive dyes can be imbibed or coated on the convex surface of the lens or optic. One or more absorptive dyes can be imbibed or coated on the concave surface of the lens or optic. One or more dyes can be incorporated within a surface cast layer that is applied or bonded to one or both surfaces of the lens or optic.

In certain embodiments a sunglass lens or optic comprises two or more absorptive dyes, wherein one or more of the absorptive dyes filters or blocks light wavelengths within the range of 440 nm downward to 400 nm or lower, and one or more absorptive dyes filter or block light wavelengths within the range of 500 nn upward to 650 nm or greater, and wherein the light transmission within the range of wavelengths of 440 nm and 510 nm is 40% or more and the overall visible light transmission of the sunglass lens is 30% or less. One or more absorptive dyes can be imbibed into the surface or a surface coating of the lens or optic. One or more absorptive dyes can be coated on one of the surfaces of the lens or optic. One or more absorptive dyes can be imbibed or coated on the convex surface of the lens or optic. One or more absorptive dyes can be imbibed or coated on the concave surface of the lens or optic. One or more dyes can be incorporated within a surface cast layer that is applied or bonded to one or both surfaces of the lens or optic.

In certain embodiments a sunglass lens or optic comprises two or more absorptive dyes, wherein one or more of the absorptive coatings filters or blocks light wavelengths within the range of 450 nm downward to 400 nm or lower, and one or more absorptive coatings filter or block light wavelengths within the range of 490 nn upward to 700 nm or greater, and wherein the light transmission within the range of wavelengths of 450 nm and 490 nm is 40% or more and the overall visible light transmission of the sunglass lens is 30% or less. One or more absorptive coatings can be coated on one of the surfaces of the lens or optic. One or more absorptive coatings can be coated on the convex surface of the lens or optic. One or more absorptive coatings can be coated on the concave surface of the lens or optic. The coating(s) can be coated by vacuum deposition. The coating(s) can be coated by spin coating. The coating(s) can be coated by surface casting. One or more dyes can be incorporated within a surface cast layer that is applied or bonded to one or both surfaces of the lens or optic.

In certain embodiments the dye (or dyes) is/are mixed within the surface cast resin prior to the surface cast resin being cured and bonded to the lens or optic. The surface cast resin can be cured with light. The surface case resin can be cured with light and heat. The surface cast resin can be cured with heat. The surface case layer can be molded. The surface cast layer can be of mostly plano (no optical power). The surface cast layer can be applied to a variety of different ophthalmic materials, by way of example only, CR39, Trivex, polycarbonate, or high index plastics. The surface cast layer can be applied and bonded to the convex surface of an ophthalmic semi-finished lens blank, while the concave surface can be free formed or surfaced. The surface cast layer can be applied and bonded to the convex surface of a lens blank, by way of example only, a single vision lens blank. In certain embodiments when the surface cast layer is applied to the convex surface of a lens or optic the concave surface can be further filtered or tinted by way of imbibing or deposition coating. And still in other embodiments an additional coating or filter can be added on top of the surface cast layer after being applied and bonded to a lens, optic, or semifinished lens blank or lens blank.

In certain embodiments a sunglass lens or optic comprises two or more absorptive coatings, wherein one or more of the absorptive coatings filters or blocks light wavelengths within the range of 450 nm downward to 400 nm or lower, and one or more absorptive coatings filter or block light wavelengths within the range of 500 nn upward to 700 nm or greater, and wherein the light transmission within the range of wavelengths of 450 nm and 510 nm is 40% or more and the overall visible light transmission of the sunglass lens is 30% or less. One or more absorptive coatings can be coated on one of the surfaces of the lens or optic. One or more absorptive coatings can be coated on the convex surface of the lens or optic. One or more absorptive coatings can be coated on the concave surface of the lens or optic. The coating(s) can be coated by vacuum deposition. The coating(s) can be coated by spin coating. The coating(s) can be coated by surface cast coating or molding.

In certain embodiments a sunglass lens or optic comprises two or more absorptive coatings, wherein one or more of the absorptive coatings filters or blocks light wavelengths within the range of 450 nm downward to 400 nm or lower, and one or more absorptive coatings filter or block light wavelengths within the range of 490 nn upward to 650 nm or greater, and wherein the visible light transmission within the range of wavelengths of 450 nm and 510 nm is 40% or more and the overall light transmission of the sunglass lens is 30% or less. One or more absorptive coatings can be coating on one of the surfaces of the lens or optic. One or more absorptive coatings can be coated on the convex surface of the lens or optic. One or more absorptive coatings can be coated on the concave surface of the lens or optic. The coating(s) can be coated by vacuum deposition. The coating(s) can be coated by spin coating. The coating(s) can be coated by surface cast coating or molding.

In certain embodiments a sunglass lens or optic comprises two or more absorptive coatings, wherein one or more of the absorptive coatings filters or blocks light wavelengths within the range of 440 nm downward to 400 nm or lower, and one or more absorptive coatings filter or block light wavelengths within the range of 500 nn upward to 650 nm or greater, and wherein the light transmission within the range of wavelengths of 440 nm and 510 nm is 40% or more and the overall visible light transmission of the sunglass lens is 30% or less. One or more absorptive coatings can be coated on one of the surfaces of the lens or optic. One or more absorptive coatings can be coated on the convex surface of the lens or optic. One or more absorptive coatings can be coated on the concave surface of the lens or optic. The coating(s) can be coated by vacuum deposition. The coating(s) can be coated by spin coating. The coating(s) can be coated by surface cast coating or molding.

In certain embodiments a sunglass lens or optic comprises two or more reflective coatings, wherein one or more of the reflective coatings filters or blocks light wavelengths within the range of 450 nm downward to 400 nm or lower, and one or more reflective coatings filter or block light wavelengths within the range of 490 nn upward to 700 nm or greater, and wherein the light transmission within the range of wavelengths of 450 nm and 510 nm is 40% or more and the overall visible light transmission of the sunglass lens is 30% or less. One or more reflective coatings can be coated on one of the surfaces of the lens or optic. One or more reflective coatings can be coated on the convex surface of the lens or optic. One or more reflective coatings can be coated on the concave surface of the lens or optic. The coating(s) can be coated by vacuum deposition. The coating(s) can be coated by spin coating. The coating(s) can be coated by surface cast coating or molding.

In certain embodiments a sunglass lens or optic comprises two or more reflective coatings, wherein one or more of the reflective coatings filters or blocks light wavelengths within the range of 440 nm downward to 400 nm or lower, and one or more reflective coatings filter or block light wavelengths within the range of 500 nn upward to 700 nm or greater, and wherein the light transmission within the range of wavelengths of 440 nm and 510 nm is 40% or more and the overall visible light transmission of the sunglass lens is 30% or less. One or more reflective coatings can be coated on one of the surfaces of the lens or optic. One or more reflective coatings can be coated on the convex surface of the lens or optic. One or more reflective coatings can be coated on the concave surface of the lens or optic. The coating(s) can be coated by vacuum deposition. The coating(s) can be coated by spin coating. The coating(s) can be coated by surface cast coating or molding.

In certain embodiment a sunglass lens or optic comprises two or more reflective coatings, wherein one or more of the reflective coatings filters or blocks light wavelengths within the range of 450 nm downward to 400 nm or lower, and one or more reflective coatings filter or block light wavelengths within the range of 490 nn upward to 650 nm or greater, and wherein the light transmission within the range of wavelengths of 450 nm and 490 nm is 40% or more and the overall visible light transmission of the sunglass lens is 30% or less. One or more reflective coatings can be coating on one of the surfaces of the lens or optic. One or more reflective coatings can be coated on the convex surface of the lens or optic. One or more reflective coatings can be coated on the concave surface of the lens or optic. The coating(s) can be coated by vacuum deposition. The coating(s) can be coated by spin coating. The coating(s) can be coated by surface cast coating or molding.

In certain embodiments a sunglass lens or optic comprises two or more reflective coatings, wherein one or more of the reflective coatings filters or blocks light wavelengths within the range of 440 nm downward to 400 nm or lower, and one or more reflective coatings filter or block light wavelengths within the range of 500 nn upward to 650 nm or greater, and wherein the light transmission within the range of wavelengths of 440 nm and 510 nm is 40% or more and the overall visible light transmission of the sunglass lens is 30% or less. One or more reflective coatings can be coated on the surface of the lens or optic. One or more reflective coatings can be coated on the convex surface of the lens or optic. One or more reflective coatings can be coated on the concave surface of the lens or optic. The coating(s) can be coated by vacuum deposition. The coating(s) can be coated by spin coating. The coating(s) can be coated by surface casting.

In certain embodiments a sunglass lens or optic comprises two or more reflective, or absorptive coatings and/or absorptive dyes, wherein one or more of the reflective coatings or absorptive coatings and/or absorptive dyes filters or blocks light wavelengths within the range of 450 nm downward to 400 nm or lower, and one or more reflective coatings or absorptive coatings and/or absorptive dyes filter or block light wavelengths within the range of 490 nn upward to 700 nm or greater, and wherein the light transmission within the range of wavelengths of 450 nm and 490 nm is 40% or more and the overall visible light transmission of the sunglass lens is 30% or less. One or more reflective coatings or absorptive coatings and/or absorptive dyes can be coated and/or imbibed on a surface of the lens or optic. One or more reflective coatings or absorptive coatings and/or absorptive dyes can be coated and/or imbibed on the convex surface of the lens or optic. One or more reflective coatings or absorptive coatings and/or absorptive dyes can be coated and/or imbibed on the concave surface of the lens or optic. The coating(s) can be coated by vacuum deposition. The coating(s) can be coated by spin coating. The coating(s) can be coated by surface casting. The dyes (can) can be imbibed by using a heat bath.

In certain embodiments a sunglass lens or optic comprises two or more reflective coatings or absorptive coatings and/or absorptive dyes, wherein one or more of the reflective coatings or absorptive coatings and/or absorptive dyes filters or blocks light wavelengths within the range of 440 nm downward to 400 nm or lower, and one or more reflective coatings or absorptive coatings and/or absorptive dyes filter or block light wavelengths within the range of 500 nn upward to 700 nm or greater, and wherein the light transmission within the range of wavelengths of 440 nm and 510 nm is 40% or more and the overall visible light transmission of the sunglass lens is 30% or less. One or more reflective coatings or absorptive coatings and/or absorptive dyes can be coated on a surface of the lens or optic. One or more reflective coatings or absorptive coatings and/or absorptive dyes can be coated or imbibed on the convex surface of the lens or optic. One or more reflective coatings can be coated or imbibed on the concave surface of the lens or optic. The coating(s) can be coated by vacuum deposition. The coating(s) can be coated by spin coating. The coating(s) can be coated by surface casting. The dyes (can) can be imbibed by use of a heat bath.

In certain embodiments a sunglass lens or optic comprises two or more reflective coatings or absorptive coatings and/or absorptive dyes, wherein one or more of the reflective coatings or absorptive coatings and/or absorptive dyes filters or blocks light wavelengths within the range of 450 nm downward to 400 nm or lower, and one or more reflective coatings or absorptive coatings and/or absorptive dyes filter or block light wavelengths within the range of 490 nn upward to 650 nm or greater, and wherein the light transmission within the range of wavelengths of 450 nm and 490 nm is 40% or more and the overall visible light transmission of the sunglass lens is 30% or less. One or more reflective coatings or absorptive coatings and/or absorptive dyes can be coated or imbibed on a surface of the lens or optic. One or more reflective coatings or absorptive coatings and/or absorptive dyes can be coated or imbibed on the convex surface of the lens or optic. One or more reflective coatings or absorptive coatings and/or absorptive dyes can be coated or imbibed on the concave surface of the lens or optic. The coating(s) can be coated by vacuum deposition. The coating(s) can be coated by spin coating. The coating(s) can be coated by surface casting. The dyes (can) can be imbibed by use of a heat bath.

In certain embodiments a sunglass lens or optic comprises two or more reflective coatings, or absorptive coatings and/or absorptive dyes, wherein one or more of the reflective coatings, or absorptive coatings and/or absorptive dyes, filters or blocks light wavelengths within the range of 440 nm downward to 400 nm or lower, and one or more reflective coatings or absorptive coatings and/or absorptive dyes filter or block light wavelengths within the range of 500 nn upward to 650 nm or greater, and wherein the light transmission within the range of wavelengths of 440 nm and 510 nm is 40% or more and the overall visible light transmission of the sunglass lens is 30% or less. One or more reflective coatings or absorptive coatings and/or absorptive dyes can be coated or imbibed on the surface of the lens or optic. One or more reflective coatings or absorptive coatings and/or absorptive dyes can be coated or imbibed on the convex surface of the lens or optic. One or more reflective coatings or absorptive coatings and/or absorptive dyes can be coated or imbibed on the concave surface of the lens or optic. The coating(s) can be coated by vacuum deposition. The coating(s) can be coated by spin coating. The dyes (can) can be imbibed by use of a heat bath. The coating(s) can be coated by surface cast coating or molding.

An embodiment as described herein is a sunglass lens or optic, wherein the light transmission within the range of wavelengths of 440 nm and 490 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 450 nm and 510 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 460 nm and 500 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 480 nm+/−10 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 480 nm+/−20 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

An embodiment as described herein is a sunglass lens or optic, wherein the light transmission within the range of wavelengths of 480 nm+/−30 nm is 40% or more and the overall visible light transmission of the sunglass lens is 35% or less. The sunglass lens can comprise an absorptive filter. The sunglass lens can comprise one or more reflective filters. The sunglass lens can comprise one or more interference filters. The sunglass lens can comprise one or more neutral density filters.

Ocular photo-bio-stimulation sunglasses can be a sunglass lens or optic, wherein the light transmission within the range of wavelengths of 440 nm and 490 nm is 40% or more and the overall visible light transmission of the sunglass lens is 30% or less. A sunglass lens or optic, wherein the light transmission within the range of wavelengths of 450 nm and 510 nm is 40% or more and the overall visible light transmission of the sunglass lens is 35% or less. A sunglass lens or optic, wherein the light transmission within the range of wavelengths of 460 nm and 510 nm is 40% or more and the overall visible light transmission of the sunglass lens is 35% or less. A sunglass lens or optic, wherein the light transmission within the range of wavelengths of 475 nm+/−20 nm is 40% or more and the overall light visible transmission of the sunglass lens is 35% or less. A sunglass lens or optic, wherein the light transmission within the range of wavelengths of 475 nm+/−30 nm is 40% or more and the overall light visible transmission of the sunglass lens is 35% or less. A sunglass lens or optic, wherein the light transmission within the range of wavelengths of 480 nm+/−30 nm is 40% or more and the overall light visible transmission of the sunglass lens is 35% or less. A sunglass lens or optic, wherein the light transmission within the range of wavelengths of 480 nm+/−30 nm is 40% or more and the overall light visible transmission of the sunglass lens is 30% or less. A sunglass lens or optic, wherein the light transmission within the range of wavelengths of 480 nm+/−30 nm is 40% or more and the wherein the overall light visible transmission of the sunglass lens is 25% or less.

Ocular photo-bio-stimulation sunglasses can be a sunglass lens or optic, wherein the light transmission within the range of wavelengths of 470 nm and 520 nm is 40% or more, and the overall visible light transmission of the sunglass lens is 30% or less. Another embodiment includes a sunglass lens or optic, wherein the light transmission within the range of wavelengths of 480 nm and 520 nm is 40% or more, and the overall visible light transmission of the sunglass lens is 35% or less. Another embodiment is a sunglass lens or optic, wherein the light transmission within the range of wavelengths of 490 nm and 520 nm is 40% or more and the overall visible light transmission of the sunglass lens is 35% or less. Another embodiment is a sunglass lens or optic, wherein the light transmission within the range of wavelengths of 500 nm+/−20 nm is 40% or more and the overall visible light transmission of the sunglass lens is 35% or less. Another embodiment is a sunglass lens or optic, wherein the light transmission within the range of wavelengths of 490 nm+/−30 nm is 40% or more and the overall visible light transmission of the sunglass lens is 35% or less. Another embodiment is a sunglass lens or optic, wherein the light transmission within the range of wavelengths of 480 nm+/−30 nm is 40% or more and the overall light visible transmission of the sunglass lens is 35% or less. Another embodiment is a sunglass lens or optic, wherein the visible light transmission within the range of wavelengths of 470 nm+/−30 nm is 40% or more and the overall visible light transmission of the sunglass lens is 30% or less. Another embodiment is a sunglass lens or optic, wherein the light transmission within the range of wavelengths of 485 nm+/−30 nm is 40% or more and the overall visible light transmission of the sunglass lens is 25% or less.

Ocular photo-bio-stimulation sunglasses can be a sunglass lens or optic, wherein the light transmission within the range of wavelengths of 480 nm+/−30 nm is 40% or more, and the overall visible light transmission of the sunglass lens is 30% or less. Another embodiment includes a sunglass lens or optic, wherein the light transmission within the range of wavelengths of 480 nm+/−30 nm is 40% or more, and the overall visible light transmission of the sunglass lens is 35% or less. Another embodiment is a sunglass lens or optic, wherein the light transmission within the range of wavelengths of 480 nm+/−30 nm is 40% or more and the overall visible light transmission of the sunglass lens is 35% or less. Another embodiment is a sunglass lens or optic, wherein the light transmission within the range of wavelengths of 480 nm+/−30 nm is 40% or more and the overall visible light transmission of the sunglass lens is 35% or less. Another embodiment is a sunglass lens or optic, wherein the light transmission within the range of wavelengths of 480 nm+/−30 nm is 40% or more and the overall visible light transmission of the sunglass lens is 35% or less. Another embodiment is a sunglass lens or optic, wherein the light transmission within the range of wavelengths of 480 nm+/−30 nm is 40% or more and the overall light visible transmission of the sunglass lens is 35% or less. Another embodiment is a sunglass lens or optic, wherein the visible light transmission within the range of wavelengths of 480 nm+/−30 nm is 40% or more and the overall visible light transmission of the sunglass lens is 30% or less. Another embodiment is a sunglass lens or optic, wherein the light transmission within the range of wavelengths of 480 nm+/−30 nm is 40% or more and the overall visible light transmission of the sunglass lens is 25% or less. Another embodiment is a sunglass lens or optic, wherein the light transmission within the range of wavelengths of 480 nm+/−30 nm is 40% or more and the overall visible light transmission of the sunglass lens is 20% or less.

Ocular photo-bio-stimulation sunglasses can be a sunglass lens or optic, wherein the light transmission within the range of wavelengths of 500 nm+/−30 nm is 40% or more, and the overall visible light transmission of the sunglass lens is 30% or less. Another embodiment includes a sunglass lens or optic, wherein the light transmission within the range of wavelengths of 500 nm+/−30 nm is 40% or more, and the overall visible light transmission of the sunglass lens is 35% or less. Another embodiment is a sunglass lens or optic, wherein the light transmission within the range of wavelengths of 500 nm+/−30 nm is 40% or more and the overall visible light transmission of the sunglass lens is 35% or less. Another embodiment is a sunglass lens or optic, wherein the light transmission within the range of wavelengths of 500 nm+/−30 nm is 40% or more and the overall visible light transmission of the sunglass lens is 35% or less. Another embodiment is a sunglass lens or optic, wherein the light transmission within the range of wavelengths of 500 nm+/−30 nm is 40% or more and the overall visible light transmission of the sunglass lens is 35% or less. Another embodiment is a sunglass lens or optic, wherein the light transmission within the range of wavelengths of 500 nm+/−30 nm is 40% or more and the overall light visible transmission of the sunglass lens is 35% or less. Another embodiment is a sunglass lens or optic, wherein the visible light transmission within the range of wavelengths of 500 nm+/−30 nm is 40% or more and the overall visible light transmission of the sunglass lens is 30% or less. Another embodiment is a sunglass lens or optic, wherein the light transmission within the range of wavelengths of 500 nm+/−30 nm is 40% or more and the overall visible light transmission of the sunglass lens is 25% or less. Another embodiment is a sunglass lens or optic, wherein the light transmission within the range of wavelengths of 500 nm+/−30 nm is 40% or more and the overall visible light transmission of the sunglass lens is 20% or less.

Ocular photo-bio-stimulation sunglasses can be a sunglass lens or optic, wherein the light transmission within the range of wavelengths of 650 nm+/−30 nm or 700 nm+/−30 nm is 40% or more, and the overall visible light transmission of the sunglass lens is 30% or less. Another embodiment includes a sunglass lens or optic, wherein the light transmission within the range of wavelengths of 650 nm+/−30 nm or 700 nm+/−30 nm is 40% or more, and the overall visible light transmission of the sunglass lens is 35% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 35% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 35% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 35% or less. Another embodiment is a sunglass lens or optic, wherein the light transmission within the range of wavelengths of 650 nm+/−30 nm or 700 nm+/−30 nm is 40% or more and the overall light visible transmission of the sunglass lens is 35% or less. Another embodiment is a sunglass lens or optic, wherein the visible light transmission within the range of wavelengths of 650 nm+/−30 nm or 700 nm+/−30 nm is 40% or more and the overall visible light transmission of the sunglass lens is 30% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 25% or less. Another embodiment is a sunglass lens or optic, wherein the light transmission within the range of wavelengths of 650 nm+/−30 nm or 700 nm+/−30 nm is 40% or more and the overall visible light transmission of the sunglass lens is 20% or less.

Figure 48:
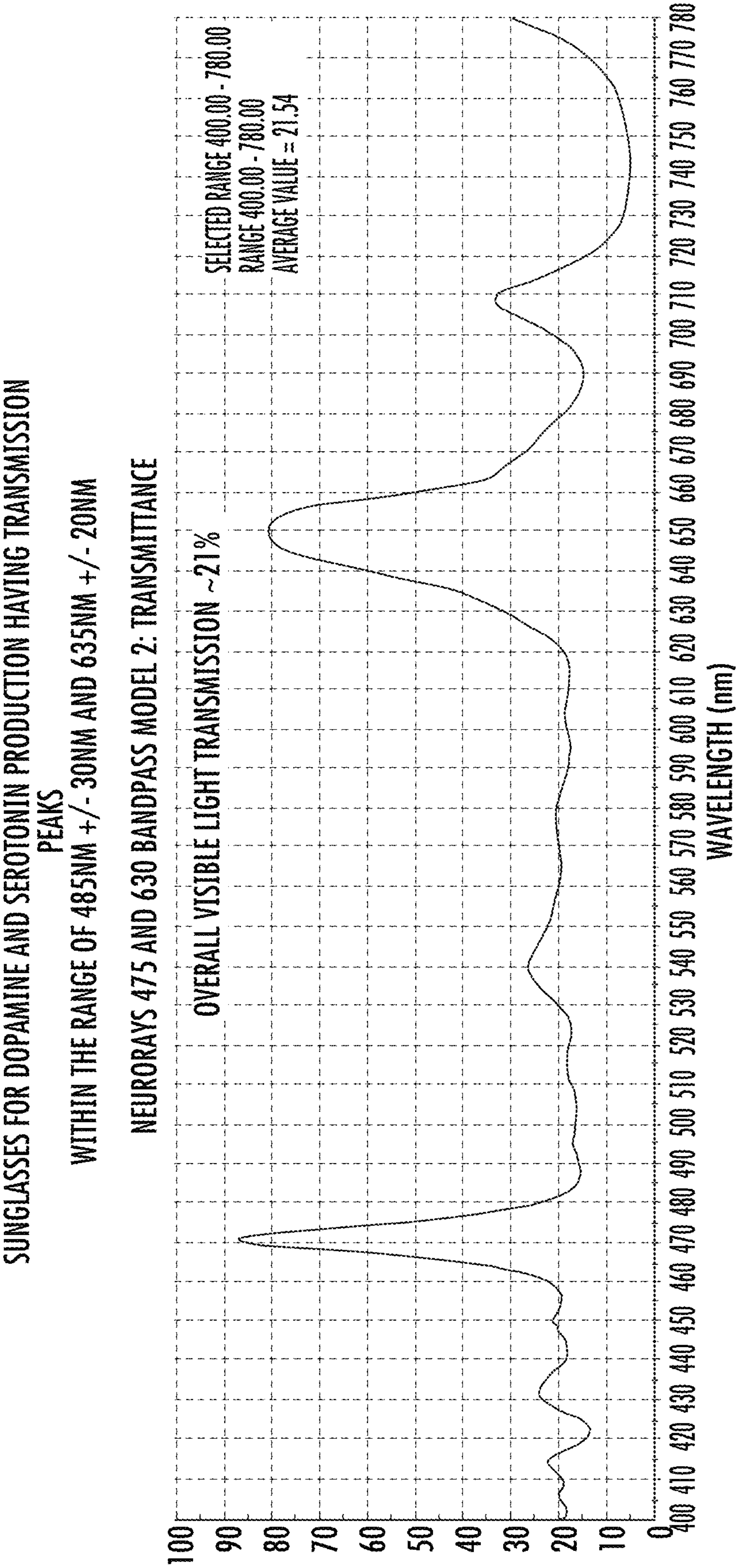
FIG. 48 shows information related to the invention described herein.

In reference to FIG. 48, another embodiment is that of a sunglass lens or optic, wherein the sunglass lens comprises two wavelength peaks of transmission, wherein one wavelength peak of transmission is within the wavelength range of 480 nm+/−30 nm and a second wavelength peak of transmission is within the wavelength range of 650 nm+/−30 nm or 700 nm+/−30 nm, and wherein the light transmission of each peak is 40% or greater and wherein the overall visible light transmission of the sunglass lens is 40% or less. Another embodiment is one wherein one wavelength peak of transmission is within the wavelength range of 480 nm+/−30 nm and a second wavelength peak of transmission is within the wavelength range of 650 nm+/−30 nm or 700 nm+/−30 nm, and wherein the light transmission of each peak is 40% or greater and wherein the overall visible light transmission of the sunglass lens is 30% or less. Another embodiment is wherein one wavelength peak of transmission is within the wavelength range of 480 nm+/−30 nm and a second wavelength peak of transmission is within the wavelength range of 650 nm+/−30 nm or 700 nm+/−30 nm, and wherein the light transmission of each peak is 50% or greater and wherein the overall visible light transmission of the sunglass lens is 40% or less.

Another embodiment is that of a sunglass lens or optic, wherein the sunglass lens or optic comprises a peak of visible wavelength transmission, wherein the visible wavelength peak of transmission is within the wavelength range of 480 nm+/−30 nm, and wherein the transmission peak of the wavelengths within the range of 480 nm+/−30 nm is 40% or greater.

Additional embodiments include: A sunglass lens or sunglass optic, wherein the sunglass lens or sunglass optic provides light transmission of 40% or 50% or more of ocular photo-bio-stimulation light measured within a light wavelength range of 450 nm-510 nm to an eye of a wearer of the sunglass lens or sunglass optic, wherein a light transmission curve spectra of the sunglass lens or sunglass optic when superimposed on a light absorption curve spectra of melanopsin and rhodopsin covers 50% or more or 75% or more of the melanopsin and rhodopsin absorption curve spectra, and wherein an overall visible light transmission of the sunglass lens or sunglass optic is 30% or less. The sunglass lens or sunglass optic can comprise a peak visible light transmission within 540 nm to 750 nmnm that, in aspects, never exceeds 30%.

The sunglass lens or sunglass optic can be supported or housed by at least one of: eyewear, fit over eyewear, disposable eyewear, a helmet, augmented reality, virtual reality, mixed reality, modified reality, contact lens, an intraocular lens, a corneal implant, or sunglasses. The sunglass lens or sunglass optic can transmit light having an intensity of 350 lux or greater. The sunglass lens or sunglass optic can provide ocular photo-bio-stimulation light that includes a wavelength range of 450 nm-510 nm, and wherein the ocular photo-bio-stimulation light including the wavelength range of 450 nm-510 nm stimulates a production of dopamine in the eye of the wearer. The sunglass lens or sunglass optic can provide ocular photo-bio-stimulation light includes a wavelength range of 450 nm-510 nm, and wherein the ocular photo-bio-stimulation light including the wavelength rage of 450 nm-510 nm stimulates a production of dopamine or serotonin in a brain of the wearer.

The sunglass lens or sunglass optic can comprise a surface cast layer that filters light. The sunglass lens or sunglass optic can comprise a lens matrix or optics matrix that filters or blocks ultraviolet light and/or is imbibed with a dye or light absorber. The sunglass lens or sunglass optic can comprise one or more of: an interference filter, an absorption filter, a light absorber, dye, a neutral density filter, a bandpass filter, a notch filter, or a selective blue light filter. The sunglass lens or sunglass optic can comprise an optical power, including plano optical power. The filtered tint of the sunglass lens or sunglass optic can be fixed or constant.

The sunglass lens or sunglass optic can transmit 400 lux or more, or 500 lux or more within a range of 450 nm-510 nm when worn in sunlight throughout a day from morning daylight until early sunset. The sunglass lens or sunglass optic can provide a light transmission of 40% or more of ocular photo-bio-stimulation light measured over a range in excess of 30 nanometers within 450 nm to 510 nm or 450 nm to 520 nm to an eye of a wearer of the sunglass lens or sunglass optic, and the sunglass lens or sunglass optic can further provide an overall visible light transmission percentage of less than 40%. A light transmission curve spectrum of the sunglass lens or sunglass optic within the range of 450 nm-510 nm can overlap with a majority of light absorption curves spectra of melanopsin and rhodopsin.

The sunglass lens or sunglass optic can transmit light through the sunglass lens or sunglass optic within a wavelength range of 450 nm-510 nm having an intensity of 350 lux or greater. The sunglass lens or sunglass optic can comprise light transmission of 40% or more ocular photo-bio-stimulation light within the wavelength range of 450 nm-510 nm stimulates production of dopamine in the eye of the wearer or a brain of the wearer. The sunglass lens or sunglass optic can comprise a surface cast layer that filters light. The sunglass lens or sunglass optic can comprise a lens matrix or optic matrix that filters or blocks ultraviolet light, and/or wherein the sunglass lens or sunglass optic is imbibed with a dye or light absorber. The sunglass lens or sunglass optic can comprise an optical power, including plano optical power. The sunglass lens or sunglass optic can be classified as a category 2 sunglass. The sunglass lens or sunglass optic can be classified as a category 3 sunglass.

The sunglass lens or sunglass optic can provide an overall visible light transmission of 30% or less, wherein the sunglass lens or optic comprises light transmission within a range of 450 nm-510 nm of 50% or greater, wherein when the sunglass lens or sunglass optic when worn by a wearer in sunlight of 20,000 lux or more, the sunglass lens or sunglass optic is capable of transmitting 400 lux or more, or 500 lux or more of light to an eye of the wearer within a range of 450 nm-510 nm from morning until late afternoon. The sunglass lens or sunglass optic can comprise a light transmission curve spectrum of the sunglass lens or sunglass optic within the range of 450 nm-510 nm that overlaps with a majority of light absorption curve spectra of melanopsin and rhodopsin. Light transmitted through the sunglass lens or sunglass optic can have a light intensity of 350 lux or greater after transmission through the sunglass lens or sunglass optic. The sunglass lens or sunglass optic can be classified as category 2 sunglass or category 3 sunglasses. Thus, in embodiments of the current invention, the lens/optic/sunglasses can have overall visible light transmission of 18% or greater, 20% or greater, 30% or greater, and so on, while having a light transmission of 50% or more within the wavelength range of 450 nm to 510 nm. In other embodiments, the visible light transmission can be less than 18% or greater than 5%, while having a light transmission of 40% or more within the wavelength range of 450 nm to 510 nm. Embodiments can transmit a light intensity of 350 lux or greater with in the range of 450 nm to 510 nm.

The sunglass lens or sunglass optic can comprise a surface cast layer that filters light. The sunglass lens or sunglass optic can comprise a lens matrix or optic matrix that filters or blocks ultraviolet light, and/or wherein the sunglass lens or sunglass optic is imbibed with a dye or light absorber. The sunglass lens or sunglass optic can comprise at least one of: an interference filter, an absorption filter, a light absorber, dye, a neutral density filter, a bandpass filter, a notch filter, or a selective blue light filter. The sunglass lens or sunglass optic can comprise an optical power, including plano optical power. The sunglass lens or sunglass optic can comprise a filter tint that is fixed or constant An aspect of the invention includes: a sunglass lens or sunglass optic comprising a filter, wherein the sunglass lens transmits 350 lux or more, 400 lux or more, or 500 lux or more, of light intensity within a range of light wavelengths having a 45% or greater light transmission through the sunglass lens or sunglass optic, wherein the range of light wavelengths cover a majority of absorption curves or spectra of melanopsin and rhodopsin and also partially absorption curves or spectra of at least some opsins of an eye's cones, wherein the sunglass lens provides an overall visible light transmission through the sunglass lens of 3% to 18%, and wherein the sunglass lens provides blended color balance transmission of light wavelengths permitting the sunglass lens to pass the International Organization for Standardization (ISO) and/or American National Standards Institute (ANSI) sunglass traffic light test. An instrument called a spectrophotometer can be used to test a sunglass lens to ensure it can pass the ISO and/or ANSI sunglass traffic light test.

Another embodiment is a sunglass lens or sunglass optic comprises a filter, wherein the sunglass lens transmits 350 lux or more, 400 lux or more, or 500 lux or more, of light intensity within a range of light wavelengths having a 45% or greater light transmission, wherein the range of light wavelengths cover the majority of the absorption curves or spectra of melanopsin and rhodopsin, and partially the absorption curves or spectra of some of the cones' opsins, wherein the sunglass lens comprises an overall visible light transmission through the sunglass lens of 18% to 43%, and wherein the sunglass lens provides blended color balance transmission of light wavelengths permitting the sunglass lens to pass the ISO and/or ANSI sunglass traffic light test.

For either or both of the above two sunglass lens or sunglass optics embodiments, the following may apply:

The sunglass lens can comprise transmitted light intensity and light wavelengths within the light wavelength range that covers the majority of the absorption curves of melanopsin and/or rhodopsin, and partially the absorption curves of some of the cones' opsins, cause the generation of dopamine within the eye of the wearer of the sunglass lens or sunglass optic, or increases the production of dopamine within an eye of the wearer of the sunglass lens. The sunglass lens can comprise a ratio of transmitted light within the range that covers a majority of the absorption curves of melanopsin and rhodopsin compared to that of the overall visible light transmitted by said sunglass lens of 2.0 or greater. The sunglass lens can transmit a range of visible light that covers the majority of the absorption curves of melanopsin and rhodopsin and partially the absorption curves of cones' opsin is within a range 450 nm-530 nm. The range can be 450 nm-520 nm. The range can be 450 nm-510 nm. The range can be 450 nm-500 nm. The range can be 460 nm-500 nm. The sunglass lens can comprise a transmitted color balance of light wavelengths from the sunglass lens that provides for a red traffic signal transmittance of greater than or equal to 8%. The sunglass lens can comprise a transmitted color balance of light wavelengths from the sunglass lens that provides for a yellow traffic signal transmittance of greater than or equal to 9%. The sunglass lens can comprise a transmitted color balance of light wavelengths from the sunglass lens that provides for a green traffic signal transmittance of greater than or equal to 12%. The sunglass lens can transmit 450 lux or more within the wavelength range of 450 nm-520 nm while being worn outdoors in sunlight of 1,000 lux or more during morning until sunset. The sunglass lens can transmit 450 lux or more within the wavelength range of 450 nm-520 nm while being worn outdoors in sunlight of 10,000 lux or more during morning until sunset. The sunglass lens can transmit 450 lux or more within the wavelength range of 450 nm-530 nm while being worn outdoors in sunlight of 1,000 lux or more in an environment of sunshade from morning until sunset. The sunglass lens can comprise a surface cast filtered layer. The surface cast layer can be applied by molding and curing with light and/or heat. The sunglass lens can be plano in optical power and wherein said layer comprises a thickness of 1.0 mm or less, 0.75 mm or less, or 0.50 mm or less. The sunglass lens surface cast filtered layer can comprise one or more of a tint, dye, light or absorber. The sunglass lens can comprise three or more of a tint, dye, absorber, interference filter, bandpass filter, notch filter, neutral density filter, AR coating, and/or scratch resistant coating. The dye(s) or filter can be mixed within the surface cast resin prior to curing and/or bonding. In certain embodiments the dye(s) or filter can be applied after the surface cast layer is molded and cured. Light wavelengths can be transmitted within the range of 450 nm-530 nm by the sunglass lens and can cause the pupil of the wearer to remain constricted while wearing the sunglass lens in sunlight. The sunglass lens can comprise a filter that provides a fixed, constant tint. The sunglass lens can comprise a filter that provides a changeable tint. The changeable tint can be that of a photochromatic tint. The filter can be within the sunglass lens matrix, the filter can be a layer attached to the matrix, the filter can be imbibed into the matrix, the filter can be a surface cast layer affixed, attached, or bonded to the matrix, the filter can be a wafer adhered to the matrix, and/or the filter can be a wafer embedded into the matrix. The sunglass lens can provide ultraviolet light (UV) protection. The sunglass lens can provide high energy blue violet light protection (HEV). In most cases such protection is provided by reducing HEV transmitted light wavelengths within the range of 400 nm-440 nm. The sunglass lens can comprise a back surface anti-reflection coating. The sunglass lens can comprise an anti-reflection coating on both surfaces. The sunglass lens can comprise a scratch resistant coating. The sunglass lens or sunglass optic can be comprised of ophthalmic plastic or glass material. The sunglass lens or sunglass optic can comprise a plano power (no optical power). The sunglass lens or sunglass optic can comprise optical power for correcting the distance and/or near vision needs of a wearer. The sunglass lens or sunglass optic can comprise lenslets. The sunglass lens or sunglass optic can comprise (H.A.L.T) highly aspheric lenslet target technology. The sunglass lens or sunglass optic can comprise (DIMS) defocus incorporated multiple segments technology. The sunglass lens or sunglass optic can comprise a chromatic aberration focused lens technology or a chromatic aberration refocused lens technology. The sunglass lens or sunglass optic can comprise contrast reduction technology. The sunglass lens or sunglass optic can comprise diffusion optics technology. The sunglass lens or sunglass optic can be a myopia control sunglass lens. The sunglass lens or sunglass optic can be housed by any type of eyewear. The sunglass lens or sunglass optic can be inserted into any type of eyewear. The sunglass lens or sunglass optic can be supported by any type of eyewear. The sunglass lens or sunglass optic can be supported by any type of headwear. The sunglass lens or sunglass optic can be incorporated into an XR (extended reality) device. The sunglass lens or sunglass optic can be supported by or inserted into an XR (extended reality) device. The sunglass lens or sunglass optic can be supported by or inserted into XR (extended reality) eyewear. The sunglass lens or sunglass optic can be housed, supported, or incorporated, into disposable or fit over eyewear.

Embodiments of the performance of a sunglass lens take in to account: time of day, the amount of sunlight lux striking the sunglass lens, the amount of light intensity (lux) leaving the sunglass lens transmitted within a specified range of light wavelengths needed to stimulate dopamine in an eye of the user/wearer, the overall visible light transmission of the sunglass lens, the percentage of light transmission within a defined range of light wavelengths that cover the majority of the absorption curves of melanopsin and rhodopsin as well as certain of the cone opsins, the width of a range of wavelengths of light within the range of 450 nm-520 nm, the color balance of light wavelengths needed to be transferred from the sunglass lens to the eye of the wearer, and the ability of the sunglass lens to pass the ISO and/or ANSI traffic light test. Embodiments taught herein can preferably balance numerous components that contribute to the ability of the sunglass lens to cause the production of dopamine or increase the production of dopamine in the eye's retina of the wearer of the sunglass lens, while also providing the appropriate level of clear distance and/or near vision clarity for the wearer of the sunglass lens, and further provide the appropriate color balance of light wavelengths transmitted from the sunglass lens to the eye of the wearer of the sunglass lens, so that either the wearer of the sunglass lens by way of subjective measurements or the sunglass lens by way of objective measurements can pass the ISO and/or ANSI traffic light test.

Various embodiments of a color balanced sunglass lens taught herein consider balancing a plurality of the following in such a manner so to provide a sunglass lens capable of transmitting 50% or more of light within the wavelength range of 450 nm+/−30 nm, having an overall visible light transmission of 43% or less, or 18% or less, and be capable of passing the ISO and/or ANSI traffic signal test. The colored balanced sunglasses can be designed and engineered to consider the 50% or more, 75% or more, or 90% or more of the following:

1) Time of day worn;
2) The amount of sunlight lux striking the sunglass lens;
3) The amount of light intensity (lux) or (lumens) leaving the sunglass lens transmitted within a specified range of light wavelengths needed to stimulate dopamine in an eye of the user/wearer;
4) The overall visible light transmission of the sunglass lens;
5) The percentage of light transmission within a defined range of light wavelengths that cover the majority of the absorption curves of melanopsin and rhodopsin as well as certain of the cone opsins;
6) The width of a range of wavelengths of light within the range of 450 nm-520 nm;
7) The color balance of light wavelengths needed to be transferred from the sunglass lens to the eye of the wearer, and the ability of the sunglass lens to pass the ISO and/or ANSI traffic light test;
8) The % of visible light wavelength transmission of the various colors in order to provide the proper color balance while transmitting a higher level of blue light wavelengths within the range of 480 nm+/−30 nm:
   i. Average red transmission
   ii. Average orange transmission
   iii. Average yellow transmission
   iv. Average green transmission
   v. Average blue transmission
   vi. Average violet transmission.
9) Appropriate level of distance vision clarity; and/or
10) Appropriate level of contrast sensitivity.

In preferred embodiments taught herein, it is preferential to balance numerous components that contribute to the ability of the sunglass lens to cause the production of dopamine or increase the production of dopamine in the eye's retina of the wearer of the sunglass lens, while also providing the appropriate level of clear distance and/or near vision clarity for the wearer of the sunglass lens, and further provide the appropriate color balance of light wavelengths transmitted from the sunglass lens to the eye of the wearer of the sunglass lens, so that either the wearer of the sunglass lens by way of subjective measurements or the sunglass lens by way of objective measurements can pass the ISO and/or ANSI traffic light test.

An embodiment #1 is that of a sunglass lens that provides a transmission of light within the wavelength range of 480 nm+/−30 nm of 50% or greater, wherein the sunglass lens comprises an overall visible wavelength transmission of 43% or less, or 18% or less, and wherein the sunglass lens comprises a color balance transmission of:

8.1% average red transmission+/−3%
12.3% average orange transmission+/−3%
10.2% average yellow transmission+/−3%
29.0% average green transmission+/−3%
51.4% average blue transmission+/−3%
13.5% average violet transmission+/−3%

And wherein the preceding color transmission % falls within a range of +/−2 nm of the following:

- Red: 621-750 nm
- Orange: 591-620 nm
- Yellow: 571-590 nm
- Green: 496-570 nm
- Blue: 451-495 nm
- Violet: 380-450 nm Another embodiment #2 is that of a sunglass lens that provides a transmission of light within the wavelength range of 480 nm+/−30 nm of 50% or greater, wherein the sunglass lens comprises an overall visible wavelength transmission of 43% or less, or 18% or less, and wherein the sunglass lens comprises a color balance transmission of:

- 10.3% average red transmission+/−3%
- 9.2% average orange transmission+/−3%
- 11.1% average yellow transmission+/−3%
- 29.9% average green transmission+/−3%
- 51.7% average blue transmission+/−3%
- 11.0% average violet transmission+/−3%

And wherein the preceding color transmission % falls within a range of +/−2 nm of the following:

- Red: 621-750 nm
- Orange: 591-620 nm
- Yellow: 571-590 nm
- Green: 496-570 nm
- Blue: 451-495 nm
- Violet: 380-450 nm The above two inventive embodiments are just two examples of the invention which comprise color balance transmission such that the sunglass lens passes the ISO and/or ANSI traffic light tests while at the same time providing 50% or greater transmission of light wavelengths within the range of 480 nm+/−30 nm for the purpose of generating dopamine in the eye and possibly the brain, while also transmitting 43% or less visible light or 18% or less visible light. The ISO and/or ANSI traffic light test ensures that the sunglass lens can transmit enough red, yellow and green light wavelengths so that the wearer can recognize the appropriate traffic light color when driving.

In embodiments, the invention utilizes and/or balances a plurality of dyes and at least one absorber. In some embodiments the number of dyes is 3 (three) or more and one or more absorbers. In other embodiments the number of dyes is 5 (five) or more and one or more absorbers. In still other embodiments the number of dyes is 8 (eight) or more and one or more absorbers. In the embodiments the sunglass lens can be AR (anti-reflective) coated on both sides. In other embodiments the sunglass lens is AR coated on the back side only. In still other embodiments the sunglass lens is hard scratch resistant coated, and AR coated.

By way of comparison with conventional sunglasses it is possible to appreciate how different and unique the inventive embodiments are from conventional sunglasses.

Sample Conventional Gray Sunglass Lens

- 52.8% average red transmission versus 8.1% for inventive embodiment #1 or 10.3% for inventive embodiment #2
- 10.0% average orange transmission versus 12.3% for inventive embodiment #1 or 9.2% for inventive embodiment #2
- 9.7% average yellow transmission versus 10.2% for inventive embodiment #1 or 11.1% for inventive embodiment #2
- 12.0% average green transmission versus 29.0% for inventive embodiment #1 or 29.9% for inventive embodiment #2

- 13.6% average blue transmission versus 51.4% for inventive embodiment #1 or 51.7% for inventive embodiment #2
- 5.6% average violet transmission versus 13.5% for inventive embodiment #1 or 11.0% for inventive embodiment #2

Sample Conventional G15 Sunglass lens

- 55.0% average red transmission versus 8.1% for inventive embodiment #1 or 10.3% for inventive embodiment #2
- 11.5% average orange transmission versus 12.3% for inventive embodiment #1 or 9.2% for inventive embodiment #2
- 12.0% average yellow transmission versus 10.2% for inventive embodiment #1 or 11.1% for inventive embodiment #2
- 14.6% average green transmission versus 29.0% for inventive embodiment #1 or 29.9% for inventive embodiment #2
- 13.0% average blue transmission versus 51.4% for inventive embodiment #1 or 51.7% for inventive embodiment #2
- 4.2% average violet transmission versus 13.5% for inventive embodiment #1 or 11.0% for inventive embodiment #2

Sample Conventional Brown Sunglass Lens

- 57.7% average red transmission versus 8.1% for inventive embodiment #1 or 10.3% for inventive embodiment #2
- 15.5% average orange transmission versus 12.3% for inventive embodiment #1 or 9.2% for inventive embodiment #2
- 16.6% average yellow transmission versus 10.2% for inventive embodiment #1 or 11.1% for inventive embodiment #2
- 11.7% average green transmission versus 29.0% for inventive embodiment #1 or 29.9% for inventive embodiment #2
- 6.9% average blue transmission versus 51.4% for inventive embodiment #1 or 51.7% for inventive embodiment #2
- 9.0% average violet transmission versus 13.5% for inventive embodiment #1 or 11.0% for inventive embodiment #2

Another embodiment includes: a color balanced sunglass that transmits 50% or more light wavelengths within the range of 480 nm+/−30 nm and comprises an overall visible light transmission of 20% or less and wherein:

- The average transmittance 400 nm-800 nm (unweighted summation) is 18.6%
- The average transmittance 450 nm-510 nm (unweighted summation) is 51.3%
- The photopic transmittance is 22.4%
- The red traffic signal transmittance is 11.6%
- The yellow traffic signal transmittance is 13.2%
- The green traffic signal transmittance is 29.2%

Another embodiment includes a color balanced sunglass that transmits 50% or more light wavelengths within the range of 480 nm+/−30 nm and comprises an overall visible light transmission of 18% or less, and wherein:

- The average transmittance 400 nm-800 nm (unweighted summation) is 17.7%
- The average transmittance 450 nm-510 nm (unweighted summation) is 50.0%
- The photopic transmittance is 21.3%

In embodiments of the invention:

- Green traffic signal transmittance can be greater than 2× that of yellow traffic signal transmittance;

Green traffic signal transmittance can be greater than 2× that of red traffic signal transmittance; and/or Green traffic signal transmittance can be greater than red traffic signal transmittance+yellow traffic signal transmittance.

In embodiments of the invention the sunglass lens can comprise:

Blue (451 nm-495 nm) average light transmission that can be 2× or greater, or 3× or greater, or 4× or greater than red (621 nm-750 nm) average light transmission; and/or Blue (451 nm-495 nm) average light transmission that can be 2× or greater, or 3× or greater, or 4× or greater than orange (591 nm-620 nm) average light transmission; and/or Blue (451 nm-495 nm) average light transmission that can be 2× or greater, or 3× or greater, or 4× or greater than yellow (621 nm-750 nm) average light transmission; and/or Blue (451 nm-495 nm) average light transmission that can be 2× or greater than green (496 nm-570 nm) average light transmission; and/or Blue (451 nm-495 nm) average light transmission that can be 2× or greater, or 3× or greater, or 4× or greater than violet (380 nm-450 nm) average light transmission.

A color balanced sunglass lens embodiment can be a sunglass lens that passes the ISO and/or ANSI traffic signal tests, and wherein the sunglass lens comprises:

Blue (451 nm-495 nm) wavelength average light transmission that is 2× or greater, or 3× or greater, or 4× or greater than red (621 nm-750 nm) wavelength average light transmission; and/or Blue (451 nm-495 nm) wavelength average light transmission that is 2× or greater, or 3× or greater, or 4× or greater than orange (591 nm-620 nm) wavelength average light transmission; and/or Blue (451 nm-495 nm) wavelength average light transmission that is 2× or greater, or 3× or greater, or 4× or greater than yellow (621 nm-750 nm) wavelength average light transmission; and/or Blue (451 nm-495 nm) wavelength average light transmission that is 2× or greater than green (496 nm-570 nm) wavelength average light transmission; and/or Blue (451 nm-495 nm) wavelength average light transmission that is 2× or greater, or 3× or greater, or 4× or greater than violet (380 nm-450 nm) wavelength average light transmission.

The sunglass lens can comprise an overall visible transmission within the range of 43% and 18%, and wherein the sunglass lens transmits 50% or greater light wavelengths within the range of 480 nm+/−30 nm. The sunglass lens can comprise an overall visible transmission within the range of 18% and 43%, and wherein the sunglass lens transmits 50% or greater light wavelengths within the range of 480 nm+/−30 nm. The sunglass lens can comprise 3 or more dyes and one or more absorber. The sunglass lens can increase the production of dopamine in the eye and/or brain of the wearer.

Another color balanced sunglass lens embodiment can transmit 50% or more light wavelengths within the range of 480 nm+/−30 nm and comprises an overall visible light transmission of 20% or less and wherein the following apply:

The average transmittance 400 nm-800 nm (unweighted summation) is 20% or less;

The average transmittance 450 nm-510 nm (unweighted summation) is 50% or greater;

The photopic transmittance is 25% or less;

The red traffic signal transmittance is 9% or greater;

The yellow traffic signal transmittance is 10% or greater; and

The green traffic signal transmittance is 25% or greater

The color balanced sunglass lens embodiment can also provide:

Green traffic signal transmittance can be greater than 2× that of yellow traffic signal transmittance;

Green traffic signal transmittance can be greater than 2× that of red traffic signal transmittance; and/or Green traffic signal transmittance can be greater than red traffic signal transmission+yellow traffic signal transmittance.

Additionally, the color balanced sunglass lens embodiment can comprise 3 (three) or more dyes and one or more absorber. The color balanced sunglass lens can increase the production of dopamine in the eye and/or brain of the wearer.

Another sunglass lens embodiment can transmit 50% or more light wavelengths within the range of 480 nm+/−30 nm and comprises an overall visible light transmission of 18% or less, and wherein, The average transmittance 400 nm-800 nm (unweighted summation) is 20% or less;

The average transmittance 450 nm-510 nm (unweighted summation) is 50% or greater;

The photopic transmittance is 25% or less;

The red traffic signal transmittance is 9% or greater;

The yellow traffic signal transmittance is 10% or greater; and

The green traffic signal transmittance is 25% or greater.

The sunglass lens embodiment can also provide:

Green traffic signal transmittance can be greater than 2× that of yellow traffic signal transmittance;

Green traffic signal transmittance can be greater than 2× that of red traffic signal transmittance; and/or Green traffic signal transmittance can be greater than red traffic signal transmittance+yellow traffic signal transmittance.

The sunglass lens embodiment can comprise 3 (three) or more dyes and one or more absorber. The sunglass lens embodiment can increase the production of dopamine in the eye and/or brain of the wearer Another embodiment is that of a sunglass lens that provides a transmission of light within the wavelength range of 480 nm+/−30 nm of 50% or greater, wherein the sunglass lens comprises an overall visible wavelength transmission within the range of 43%-18% and wherein the sunglass lens comprises a color balance transmission of:

8.1% average red transmission+/−3%;

12.3% average orange transmission+/−3%;

10.2% average yellow transmission+/−3%;

29.0% average green transmission+/−3%;

51.4% average blue transmission+/−3%;

13.5% average violet transmission+/−3%

And wherein the preceding color transmission % falls within a range of +/−2 nm of the following:

a) Red: 621-750 nm b) Orange: 591-620 nm c) Yellow: 571-590 nm d) Green: 496-570 nm e) Blue: 451-495 nm f) Violet: 380-450 nm The sunglass lens embodiment color balance can comprise 50% or more of the above a-f. The sunglass lens embodiment can pass the ISO and/or ANSI traffic signal test.

The sunglass lens embodiment can comprise 3 (three) or more dyes and one or more absorber. The sunglass lens can increase the production of dopamine in the eye and/or brain of the wearer.

The sunglass lens embodiment can also provide:

Green traffic signal transmittance can be greater than 2× that of yellow traffic signal transmittance;

Green traffic signal transmittance can be greater than 2× that of red traffic signal transmittance; and/or Green traffic signal transmittance can be greater than red traffic signal transmittance+yellow traffic signal transmittance.

Another embodiment is that of a sunglass lens that provides a transmission of light within the wavelength range of 480 nm+/−30 nm of 50% or greater, wherein the sunglass lens comprises an overall visible wavelength transmission within the range of 18%-43% and wherein the sunglass lens comprises a color balance transmission of:

8.1% average red transmission+/−3%
12.3% average orange transmission+/−3%
10.2% average yellow transmission+/−3%
29.0% average green transmission+/−3%
51.4% average blue transmission+/−3%
13.5% average violet transmission+/−3%

And wherein the preceding color transmission % falls within a range of +/−2 nm of the following:

a) Red: 621-750 nm
b) Orange: 591-620 nm
c) Yellow: 571-590 nm
d) Green: 496-570 nm
e) Blue: 451-495 nm
f) Violet: 380-450 nm The sunglass lens embodiment color balance can comprise 50% or more of the above a-f. The sunglass lens embodiment can pass the ISO and/or ANSI traffic signal test. The sunglass lens embodiment can comprise 3 (three) or more dyes and one or more absorber. The sunglass lens can increase the production of dopamine in the eye and/or brain of the wearer.

The sunglass lens embodiment can also provide:

Green traffic signal transmittance can be greater than 2× that of yellow traffic signal transmittance and Green traffic signal transmittance can be greater than 2× that of red traffic signal transmittance and Green traffic signal transmittance can be greater than red traffic signal transmittance+yellow traffic signal transmittance Another embodiment is that of a sunglass lens that provides a transmission of light within the wavelength range of 480 nm+/−30 nm of 50% or greater, wherein the sunglass lens comprises an overall visible wavelength transmission within the range of 43%-18% and wherein the sunglass lens comprises a color balance transmission of:

10.3% average red transmission+/−3%
9.2% average orange transmission+/−3%
11.1% average yellow transmission+/−3%
29.9% average green transmission+/−3%
51.7% average blue transmission+/−3%
11.0% average violet transmission+/−3%

And wherein the preceding color transmission % falls within a range of +/−2 nm of the following:

a) Red: 621-750 nm
b) Orange: 591-620 nm
c) Yellow: 571-590 nm
d) Green: 496-570 nm
e) Blue: 451-495 nm
f) Violet: 380-450 nm The sunglass lens embodiment color balance can comprise 50% or more of the above. The sunglass lens embodiment can pass the ISO and/or ANSI traffic signal test. The sunglass lens embodiment can comprise 3 (three) or more dyes and one or more absorber. The sunglass lens can increase the production of dopamine in the eye and/or brain of the wearer.

The sunglass lens embodiment can also provide:

Green traffic signal transmittance can be greater than 2× that of yellow traffic signal transmittance and Green traffic signal transmittance can be greater than 2× that of red traffic signal transmittance and Green traffic signal transmittance can be greater than red traffic signal transmittance+yellow traffic signal transmittance Another embodiment is that of a sunglass lens that provides a transmission of light within the wavelength range of 480 nm+/−30 nm of 50% or greater, wherein the sunglass lens comprises an overall visible wavelength transmission within the range of 18%-43% and wherein the sunglass lens comprises a color balance transmission of:

1. 10.3% average red transmission+/−3%
2. 9.2% average orange transmission+/−3%
3. 11.1% average yellow transmission+/−3%
4. 29.9% average green transmission+/−3%
5. 51.7% average blue transmission+/−3%
6. 11.0% average violet transmission+/−3%

And wherein the preceding color transmission % falls within a range of +/−2 nm of the following:

a) Red: 621-750 nm
b) Orange: 591-620 nm
c) Yellow: 571-590 nm
d) Green: 496-570 nm
e) Blue: 451-495 nm
f) Violet: 380-450 nm The sunglass lens embodiment color balance can comprise 50% or more of the above a-f. The sunglass lens embodiment can pass the ISO and/or ANSI traffic signal test. The sunglass lens embodiment can comprise 3 (three) or more dyes and one or more absorber. The sunglass lens can increase the production of dopamine in the eye and/or brain of the wearer.

The sunglass lens embodiment can also provide:

1. Green traffic signal transmittance can be greater than 2× that of yellow traffic signal transmittance;
2. Green traffic signal transmittance can be greater than 2× that of red traffic signal transmittance; and/or
3. Green traffic signal transmittance can be greater than red traffic signal transmittance+yellow traffic signal transmittance.

And still another embodiment is that of a sunglass lens that provides a transmission of light within the wavelength range of 480 nm+/−30 nm of 50% or greater, wherein the sunglass lens comprises an overall visible wavelength transmission within the range of 43%-18%, and wherein the sunglass lens comprises a color balance transmission of:

1. Green traffic signal transmittance can be greater than 2× that of yellow traffic signal transmittance;
2. Green traffic signal transmittance can be greater than 2× that of red traffic signal transmittance; and/or
3. Green traffic signal transmittance can be greater than red traffic signal transmittance+yellow traffic signal transmittance.

The sunglass lens embodiment can pass the ISO and/or ANSI traffic signal test. The sunglass lens embodiment can comprise 3 (three) or more dyes and one or more absorber.

The sunglass lens embodiment can increase the production of dopamine in the eye and/or brain of the wearer.

And yet another sunglass lens embodiment can provide a transmission of light within the wavelength range of 480 nm+/−30 nm of 50% or greater, wherein the sunglass lens comprises an overall visible wavelength transmission within the range of 18%-43%, and wherein the sunglass lens comprises a color balance transmission of:

1. Green traffic signal transmittance can be greater than 2× that of yellow traffic signal transmittance;
2. Green traffic signal transmittance can be greater than 2× that of red traffic signal transmittance; and/or
3. Green traffic signal transmittance can be greater than red traffic signal transmittance+yellow traffic signal transmittance.

The sunglass lens embodiment can pass the ISO and/or ANSI traffic signal test. The sunglass lens embodiment can comprise 3 (three) or more dyes and one or more absorber. The sunglass lens embodiment can increase the production of dopamine in the eye and//or one or more of dopamine, serotonin or norepinephrine in the brain of the wearer.

Another embodiment is that of a sunglass lens that provides a transmission of light within the wavelength range of 480 nm+/−30 nm of 50% or greater, wherein the sunglass lens comprises an overall visible wavelength transmission of 30% or less, and wherein the sunglass lens comprises a color balance transmission of blue (451 nm-495 nm) wavelength average light transmission that is 2× or greater than its green (496 nm-570 nm) wavelength average light transmission. The sunglass lens embodiment can pass the ISO and/or ANSI traffic signal test. The sunglass lens embodiment can comprise 3 (three) or more dyes and one or more absorber. The sunglass lens embodiment can comprise a mostly plano power surface cast layer. The sunglass lens embodiment can comprise a chromatic aberration focused lens or chromatic aberration refocused lens. The sunglass lens embodiment can increase the production of dopamine in the eye and/or one or more of dopamine, serotonin or norepinephrine in the brain of the wearer Another sunglass lens embodiment provides a transmission of light within the wavelength range of 480 nm+/−30 nm of 50% or greater, wherein the sunglass lens comprises an overall visible wavelength transmission of 30% or less, and wherein the sunglass lens comprises a color balance transmission of blue (451 nm-495 nm) wavelength average light transmission that is 1.5× or greater than its green (496 nm-570 nm) wavelength average light transmission. The sunglass lens embodiment can pass the ISO and/or ANSI traffic signal test. The sunglass lens embodiment can comprise 3 (three) or more dyes and one or more absorber. The sunglass lens embodiment can comprise a mostly plano power surface cast layer. The sunglass lens embodiment can comprise a chromatic aberration focused lens or chromatic aberration refocused lens. The sunglass lens embodiment can increase the production of dopamine in the eye and/or one or more of dopamine, serotonin or norepinephrine in the brain of the wearer.

Another embodiment can be that of a first sunglass lens that transmits the same or less light than a second sunglass lens, however, the perceived brightness when looking through the first sunglass lens is greater than when looking though the second sunglass lens. Said another way, the embodiment comprises sunglass R and sunglass S, wherein sunglass R comprises an overall visible light transmission of X %, wherein sunglass S that comprises an overall visible light transmission less than X %, and wherein the wearer's perceived light transmission through sunglass S can be greater than the same wearer's perceived light transmission of sunglass R. The overall visible light transmission of sunglass S can be 5% or more less than sunglass R. The wearer's pupil size can be smaller when looking through sunglass S than when looking through sunglass R. Another embodiment is the sunglass R wherein the wearer's pupil size can be larger when looking through sunglass R than sunglass S. The wearer's distance vision can appear clearer to the wearer of sunglass S than sunglass R. The overall visible transmission of sunglass S can be 25% or less. The light transmission percentage of sunglass S can be within a range of wavelengths within 450 nm and 510 nm, and can be greater than sunglass R. The wearer can perceive black and white contrast or color contrast to be greater in sunglass S compared to sunglass R. Sunglass S can pass all tests associated with the ISO or ANSI traffic signal tests, including the daytime chromaticity tests. Sunglass S can be polarized. Sunglass S can be mirrored.

XR Devices for Ocular Photo-Bio-Stimulation

An XR device can be used to provide ocular photo-bio-stimulation to the eye of the wearer. The XR device can receive an electronic download or preloaded with such software that controls or directs the manner in which ocular photo-bio-stimulation of the eye of the wearer is provided. The ocular photo-bio-stimulation can increase the production of dopamine in the eye of the wearer or user of the XR device. The ocular photo-bio-stimulation can increase the production of/or one or more of dopamine, serotonin or norepinephrine in the brain of the wearer or user of the XR device. Biofeedback or diagnostics involving one or more of, pupil size increase, lid blink increase, heart rate increase, and/or blood oxygen level increase can be an indication of increase production or stimulation of dopamine or norepinephrine in the brain and in some cases serotonin. While an increase in contrast sensitivity, B wave amplitude of an ERG, scleral thickening, and/or slowing of axial length eye growth indicates an increase in the production of dopamine in the retina.

The amount of required light intensity given off by an XR eyewear ocular photo-bio-stimulation artificial light source (not the sun) is dependent upon the distance of the light source from the eye of the subject receiving ocular photo-bio-stimulation treatment, the age of the subject, and whether or not the subject is wearing an eyeglass that either filters or refracts light. In most, but not all cases, when wearing XR eyewear with the ocular photo-bio-stimulation light source attached or incorporated therewithin, for the light source that gives off ocular photo-bio-stimulation, the light intensity needs to be 60 lumens or more leaving the ocular photo-bio-stimulation light source. The preference is for 400 lux of ocular photo-bio-stimulation light or more to strike the retina of the eye of the subject for a period of time in order for the subject to have the desired physiological response. The light intensity in lux given off from the XR eyewear ocular photo-bio-stimulation light source can be 250 lux or more, 500 lux or more, 1,000 lux or more, and so on. When considering the light radiating in a cone light manner from the XR eyewear ocular photo-bio-stimulation light source to strike the eye and face of the user or subject, the number of lumens given off from the ocular photo-bio-stimulation light source can be 10 lumens or more, 25 lumens or more, 50 lumens or more, 100 lumens or more, and so on. The light intensity that strikes the retina can be 300 lux or greater, 400 lux or greater, 500 lux or greater, and so on. Artificial intelligence (AI) and ML can be incorporated within the embodiment to optimize the desired physiological effect for the subject or user.

In certain embodiments an ocular photo-bio-stimulation light source can comprise wavelengths of light within the range of 440 nm to 700 nm. The white light can comprise peaks of light wavelengths of; 460 nm+/−10 nm, 525 nm+/−10 nm, or 620 nm+/−10 nm. The transmission peak of 460 nm+/−10 nm can be greater than 80%. The transmission peak of 525 nm+/−10 nm can be greater than 70%. The transmission peak of 620 nm+/−10 nm can be greater than 60%. Such a white lighted ocular photo-bio-stimulation light source can provide ocular photo-bio-stimulation. The light intensity of lux given off from an XR eyewear ocular photo-bio-stimulation light source can be one of, 250 lux or more, 500 lux or more, 1,000 lux or more, and so on. When considering the light radiating in a cone light manner from the ocular photo-bio-stimulation light source to strike the eye and face of the user or subject, the number of lumens given off from the ocular photo-bio-stimulation light source can be 10 lumens or more, 25 lumens or more, 50 lumens or more, 100 lumens or more, and so on. The light intensity that strikes the retina can be 300 lux or greater, 400 lux or greater, 500 lux or greater, and so on. Artificial intelligence (AI) or ML can be incorporated within the embodiment to optimize the desired physiological effect for the subject or user.

In certain embodiments when light wavelengths are generated by way of filtered optics or filtered lenses, the transmission peak of the wavelength range that strike the eye's retina falls within the wavelength range of at least one of: 480 nm+/−30 m, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The light intensity of lux given off from an XR eyewear ocular photo-bio-stimulation light source can be 250 lux or more, 500 lux or more, 1,000 lux or more, and son on. When considering the light radiating in a cone light manner from the ocular photo-bio-stimulation light source to strike the eye and face of the user or subject, the number of lumens given off from the ocular photo-bio-stimulation light source can be 10 lumens or more, 25 lumens or more, 50 lumens or more, 100 lumens or more, and so on. The light intensity that strikes the retina can be 300 lux or greater, 400 lux or greater, 500 lux or greater, and so on.

In certain embodiments when light wavelengths are generated by a light emitter(s) if ambient lighting is present (including that of artificial light or sun light), the blended light wavelengths of the light emitter(s) and also the ambient light comprises wavelengths of light that strike the eye's retina falling within the wavelength ranges of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm.

Figure 49:
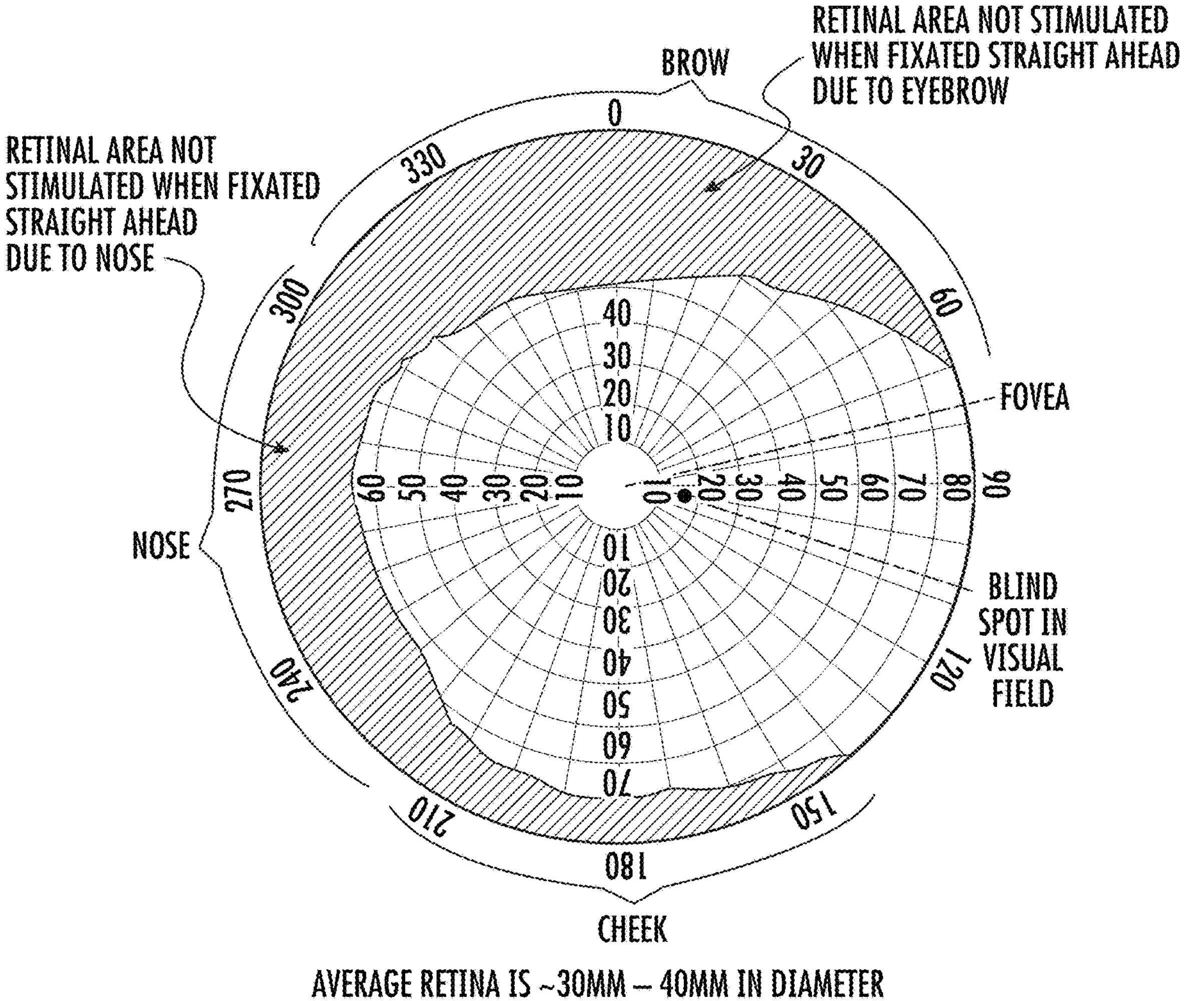
FIG. 49 shows information related to the invention described herein.

In reference to FIG. 49, the retina is comprised of a central zone, mid peripheral zone and a far peripheral zone. Approximately an estimated 20%-30% of each eye's retina is not stimulated by light when looking straight ahead. This is because one's nose and eyebrow interfere with light rays that could stimulate portions of the peripheral retina. Given the more retina of an eye that is stimulated the more robust the ocular photo-bio-stimulation response may be, or the greater efficacy it may have, it is important to apply the ocular photo-bio-stimulation light therapy to as much of the retina as possible. In addition, certain eye diseases, for example only, retinitis pigmentosa, that could be treated with ocular photo-bio-stimulation occur in the far periphery of the retina. There is a need for a way to be able to stimulate and/or treat areas of the retina that under normal circumstances are rarely stimulated with light. The inventive embodiments disclosed herein allow for this to occur.

Figure 50:
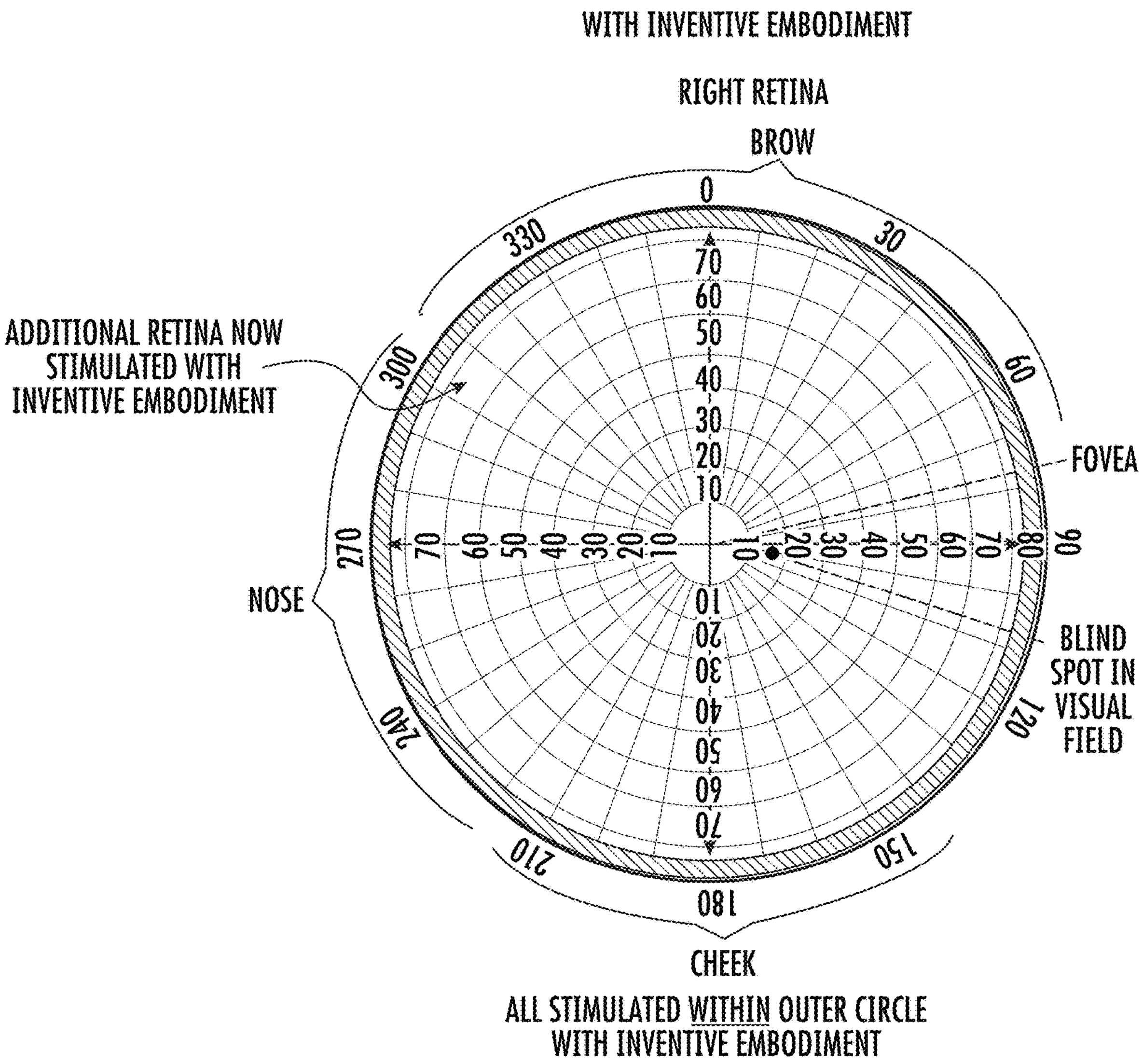
FIG. 50 shows information related to the invention described herein.

In reference to FIG. 50, with XR inventive embodiments disclosed herein it is possible to stimulate areas of the retina of an eye by way of ocular photo-bio-stimulation in such a manner to stimulate the 20%-30% that is normally not stimulated. This is due to the embodiments disclosed herein that cause the painting of all areas of the retina with the desired ocular photo-bio-stimulation wavelengths of light. Such desired wavelengths of light can be, by way of example only, one within the range of wavelengths of at least one of: 480 nm+/−30 nm, 480 nm+/−20 nm, 500 nm+/−30 nm, 500 nm+/−20 nm, 510 nm+/−30 nm, 510 nm+/−20 nm, 530 nm+/−20 nm, or 650 nm+/−30 nm, or 700 nm+/−30 nm. In certain embodiments the range of wavelength band includes the peaks of the most sensitive spectral points of rhodopsin (500 nm) and melanopsin (480 nm). This way both rhodopsin and melanopsin can be stimulated or excited. By way of example, this can be accomplished by utilizing a filtered optic or lens that predominantly transmits within the wavelength range of 460 nm-520 nm, 470 nm to 520 nm, or 480 nm to 520 nm, or by utilizing a light source or light emitter that predominately transmits within the wavelength range of 460 nm-520 nm, 470 nm to 520 nm, or 480 nm-520 nm. This would include blue, bluish green and green wavelengths. This can be most beneficial when stimulating the production of increased dopamine in the retina of an eye. This can be most beneficial when stimulating the production of increased dopamine in a brain by way of stimulating the retina of an eye.

In certain embodiments when a filtered optic or filtered lens is used the overall light transmission through the filtered optic or filtered lens can be 50% of less, while the light transmission within the predominant transmitted filtered wavelength range being transmitted to the eye can be 50% or more. In certain cases, the pupil of the eye enlarges when looking through the filtered optic or filtered lens constricts when looking absent of the filtered optic or filtered lens. However, in most cases when the eye's retina is exposed to blue light within the range of 450 nm to 530 nm, preferably 480 nm+/−20 nm, the pupil of the eye constricts or remains constricted. The constriction of the pupil when viewing through a filtered optic or filtered lens allows for the user/wearer of the filtered optic to have maximum vison clarity. However, in certain embodiments it is more important to provide ocular photo-bio-stimulation as opposed to maximum vision clarity. In these embodiments it is necessary to trick the wearer's retinal neurological feedback that causes the pupil to constrict while still providing blue light within the range of 450 nm-530 nm, preferably 480 nm+/−20 nm, to strike the wearer's/user's retina. By way of example only, in certain XR eyewear embodiments, the light source can modulate between (by way of example only, a black image and blue image comprised of light wavelengths within the range of 450 nm-530 nm). When black is visible to the eye of the wearer the pupil increases in size and then when the blue wavelengths within the range of 450 nm-530 nm become visible, the pupil constricts.

In certain embodiments when a filtered optic or filtered lens is used the overall light transmission through the filtered optic or filtered lens can be 40% of less, while the light transmission within the predominant transmitted filtered wavelength range being transmitted to the eye can be 40% or more. In certain cases, the pupil of the eye enlarges when looking through the filtered optic or filtered lens and constricts when looking absent of the filtered optic or filtered lens. However, in most cases when the eye's retina is exposed to blue light within the range of 450 nm to 530 nm, preferably 480 nm+/−20 nm, the pupil of the eye constricts or remains constricted. The constriction of the pupil when viewing through a filtered optic or filtered lens allows for the user/wearer of the filtered optic to have maximum vison clarity. However, in certain embodiments it is more important to provide ocular photo-bio-stimulation as opposed to maximum vision clarity. In these embodiments it is necessary to trick the wearer's retinal neurological feedback that causes the pupil to constrict while still providing blue light within the range of 450 nm-530 nm, preferably 480 nm+/−20 nm, to strike the wearer's/user's retina.

In certain embodiments when a filtered optic or filtered lens is used the overall light transmission through the filtered optic or filtered lens can be 30% of less, while the light transmission within the predominant transmitted wavelength range being transmitted to the eye can be 40% or more. In certain cases, the pupil of the eye enlarges when looking through the filtered optic or filtered lens and constricts when looking absent of the filtered optic or filtered lens. However, in cases when the eye's retina is exposed to blue light within the range of 450 nm to 530 nm, preferably 480 nm+/−20 nm, the pupil of the eye constricts or remains constricted. The constriction of the pupil when viewing through a filtered optic or filtered lens allows for the user/wearer of the filtered optic to have improved or maximum vison clarity. However, in certain embodiments it is more important to provide ocular photo-bio-stimulation as opposed to maximum vision clarity. In these embodiments it is necessary to trick the wearer's retinal neurological feedback that causes the pupil to constrict while still providing blue light within the range of 450 nm-530 nm, preferably 480 nm+/−20 nm to strike the wearer's/user's retina.

In ocular photo-bio-stimulation embodiments, the virtual image as seen with AR, VR, MR, Modified Reality, and/or XR eyewear as described herein is one or more of a blue light image (with wavelengths within the range of 480 nm+/−30 nm), a green light image (with wavelengths within the range of 530 nm+/−20 nm), and/or a red-light image (with wavelengths within the range of 650 nm+/−30 nm or 700 nm+/−30 nm).

In certain embodiments of VR eyewear, the device embodiment can comprise a filter or a combination of filters for transmitting one or two virtual images. In certain embodiments of AR, MR, VR, Modified Reality, XR eyewear as described herein, they can comprise a filter, or a combination of filters, for transmitting the real image and/or virtual images. The filter or filters can be one or more of a bandpass filter, interference filter, absorptive filter, selective light filter, notch filter, and/or neutral density filter. The filter or filters can transmit light wavelengths, by way of example only, within one or more of the ranges of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. In certain ocular photo-bio-stimulation embodiments of the current invention, the real image that passes through a filter(s) can be of any color, but a color that allows for the user to see the real image comprising wavelengths within the range of 480 nm+/−30 nm in the morning and by switching the filter(s) red wavelengths of 650 nm+/−30 nm in the afternoon. The filter(s) can cause the real image to have a light transmission of 80% or less, 50% or less, or 40% or less. The lower overall visible light transmission through the XR device to the eye, while at the same time transmitting the desired range of wavelengths for ocular photo-bio-stimulation, can enlarge the pupil diameter of the user of the XR device. By way of example only, in certain embodiments a virtual image can be of a black spot that moves around within the virtual image. By way of example only, in certain embodiments the virtual image can be of a black spot that moves around within the real image. By way of example only, in certain embodiments the real image can be of an image that moves around within the virtual image. By way of example only, in certain embodiments the virtual image can be of a colored (which includes black) or white spot that moves around within the real image. In certain other embodiments one virtual image can comprise, by way of example only, a moving black spot that is moving within the perimeter of a second virtual image. In certain other embodiments one virtual image can comprise, by way of example only, a moving black spot that is moving within the perimeter of the same virtual image. In certain embodiments, the virtual image with the moving black spot that moves within the perimeter of the virtual image is part of the same virtual image. Thus, there is only one virtual image. In other embodiments the virtual image with the moving black spot that moves within the perimeter of the virtual image is a separate virtual image that appears within the perimeter but is really an overlapping virtual image. Thus, in this case there would be two virtual images.

Filter(s) can cause the real image to have a light transmission of 50% or less. The filter(s) can cause the real image to have a light transmission of 25% or less. A real image can be an image of a solid color or black. A virtual image can be an image of a color(s) including black. In certain cases, the real image and the virtual image can both be images seen distance separated along the Z axis from the wearer's eye. In cases, the real image is the distance image, and the virtual image is the nearer image, and vice versa. In certain cases of XR, AR, MR, and Modified reality eyewear, the eyes can be fixated on the real image as it moves within the virtual image. In certain cases of XR, AR, MR, Modified reality eyewear, the eyes can be fixated on the real image as it moves within the virtual image.

In certain cases of VR or Modified Reality, the eyes can be fixated on one virtual image as it moves within, around, or in reference to a different virtual image. Still in some cases with Modified Reality, a virtual image can comprise two or more parts with one part moving within the second part. Said another way, one portion of the virtual image can move while the other portion of the same virtual image can be stationary. The eye of a user can fixate on the moving image while the stationary image paints the retina of the eye, or the eye can fixate on the stationary image while the moving image paints the retina of an eye of the user.

In some ocular photo-bio-stimulation embodiments, the eyewear comprises an electronic display attached to the eyewear that projects blue light, or green light, or red-light, through a wave guide to an optic housed within the eyewear. In some embodiments the eyewear comprises an electronic display attached or integrated within a wave guide to an optic housed within the eyewear. In some embodiments the eyewear comprises an electronic display that is attached to or integrated within an optic housed or supported by the eyewear. In some cases, the eyewear houses or supports an optic that incorporates an electronic display and wherein the wearer looks through the electronic display while the electronic display projects blue, or green, or red-light. In various AR, MR, VR, and/or Modified Reality embodiments, a non-see-through near eye display can be utilized to generate a lighted virtual reality image. In some cases, two non-see-through near eye displays are utilized to generate lighted virtual reality images. In some cases, a see-through near eye display can be utilized to generate a lighted virtual reality image. In some cases, two-see-through near eye display can be utilized to generate lighted virtual reality images. In some cases, a non-see-through near eye display optically aligned or in optical communication with a micro-lens array can be is utilized to generate a lighted virtual reality image. In some cases, two non-see-through near eye displays optically aligned or in optical communication with micro-lens arrays are utilized to generate lighted virtual reality images. In some cases, a see-through near eye display optically aligned or in optical communication with a micro-lens array can be utilized to generate a lighted virtual reality image. In certain cases, the micro-lens array can comprise a filtering agent(s). The filtering agent(s) can be coated on to the micro-lens array. The filtering agent(s) can be embedded in the matrix of the microlens array. The filtering agent(s) can be imbibed within the micro-lens array.

In some cases, a see-through near eye display optically aligned or in optical communication with a micro-lens array can be utilized to generate a lighted virtual reality image. In some cases, a see-through near eye display optically aligned or in optical communication with a micro-lens array can be utilized in optical communication with a see-through near eye display to generate a lighted virtual reality image. In some cases, a non-see-through near eye display optically aligned or in optical communication with micro-lens array can be utilized in optical communication (but slightly offset) with a second see-through near eye display to generate a lighted virtual reality image. In some cases, a non-see-through near eye display optically aligned or in optical communication with a micro-lens array can be utilized in optical communication (but slightly offset) with a see-through near eye display that can be aligned with a second micro-lens array to generate a lighted virtual reality image. In some cases, a see-through near eye display optically aligned or in optical communication with a micro-lens array can be in optical communication (but slightly offset) with a second see-through near eye display, which is aligned and in optical communication with a second microlens array, to generate a lighted virtual reality image.

In some cases, a see-through near eye display optically aligned or in optical communication with a micro-lens array can be in optical communication (but slightly offset) with a second see-through near eye display which is aligned and in optical communication with a second microlens array, to generate a lighted virtual reality image while permitting the viewing of a real image through both see-through near eye displays and both microlens arrays.

In some cases, the electronic display provides diffuse blue, green, or red-light all over. In some cases, the electronic display allows the wearer to see an object, image or words, displayed on the display, which is surrounded by blue, or green or red-light, or comprises blue, or green, or red-light peripheral to the object, image, or words being displayed. In certain embodiments, by way of example only, VR (Virtual Reality) or AR (Augmented Reality), or MR (Mixed Reality), or modified reality, the blue, or green, or red light, can be provided in a diffused manner. In other embodiments, especially with VR, AR, MR eyewear, a targeting image or video that caused movement can cause the eyes to gaze while seeing the blue, or green, or red diffused light. In certain embodiments, especially with VR or AR, the blue, or green, or red light, can be provided as the background light, by way of example only, a blue sky or blue ocean, or green grass, or a red sun. By way of example only, a real image can be the object being viewed in the distance and the diffused and/or defocused light can be that of the virtual image. By utilizing this approach, it permits the pupil of the eye to be less constricted.

Figure 51:
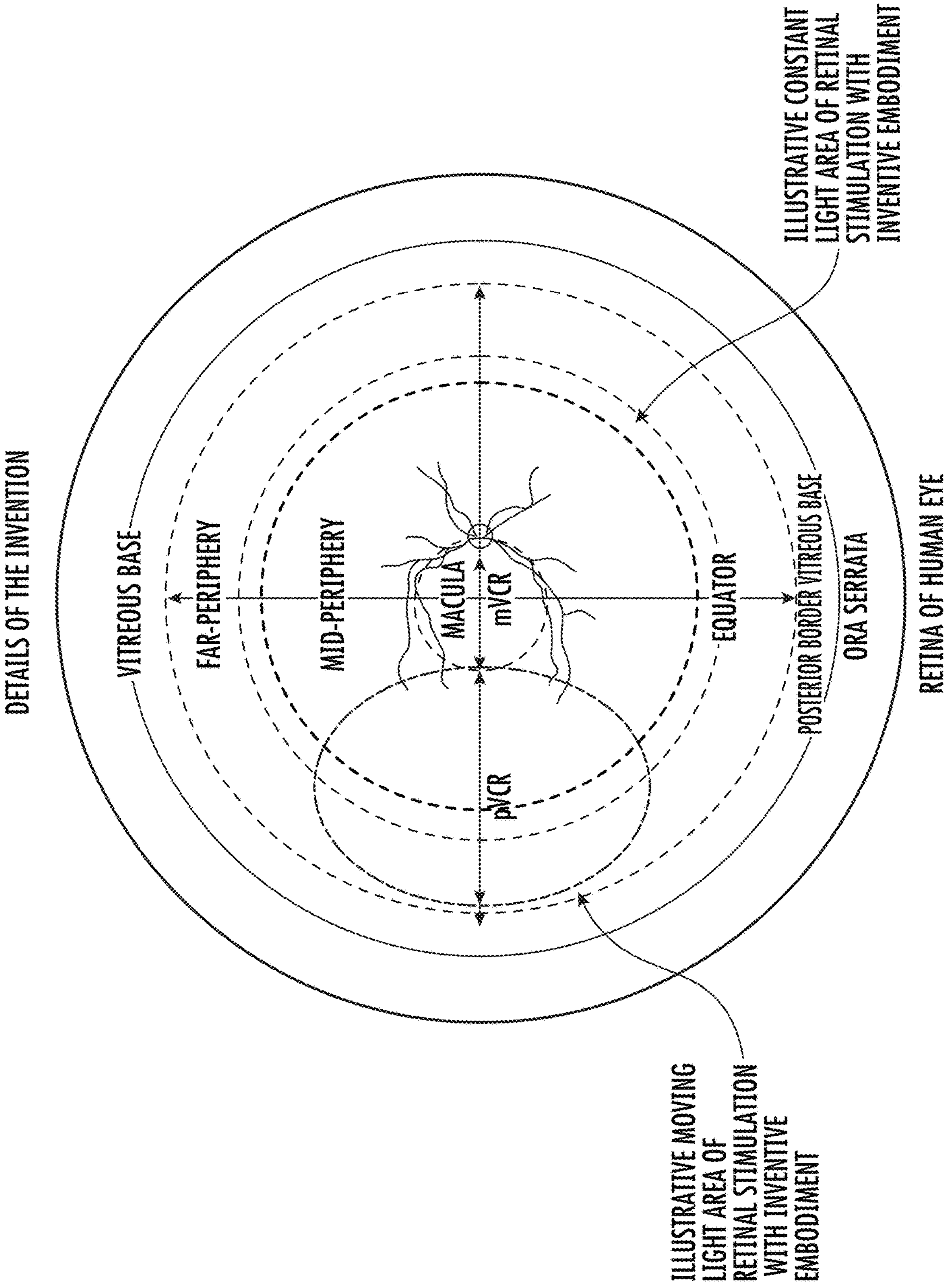
FIG. 51 shows information related to the invention described herein.

In reference to FIG. 51, in most, but not all cases of XR according to the present invention, the image that is stationary is the image or scene that is providing the ocular photo-bio-stimulation to the retina as the eye moves in reference to this stationary image or scene. In most, but not all cases of XR for the invention described herein, the moving image on which the eye is fixated on, is a moving image that focuses on the fovea or macula, while the stationary image or scene is the image that is stimulating the one or more of rods, ganglion cells, or cones of the retina. In addition, generally but not always, the fixated image is smaller than the stationary image that is painting portions of the retina as the eye follows the moving fixated image. For clarity, in most cases the stationary image provides the light of the desired wavelength and intensity for stimulating one or more of the rods, ganglion cells, or cones. The stationary image paints with a band of desired wavelengths of light (by way of example only, 480 nm+/−30 nm or 650 nm+/−30 nm, or 700 nm+/−30 nm) a portion or most of the peripheral retina because the eye is moving relative to the stationary image. In certain cases, both images are moving, however the user fixates on one image as it moves relative to the other. In this case the image that paints with a desired band of light wavelengths the peripheral retina or a portion thereof, is the image that is not fixated by the user's macula, or fovea.

In reference to FIG. 51, by way of example only, for increasing dopamine in the eye's retina as the eye follows the moving image, the fovea or macula will be fixated on that moving image causing the eye to move relative to the stationary image. This allows the light that makes up the stationary image to paint the retina. By way of example only, the stationary image can be a blue image having wavelengths of light within the range of 450 nm-500 nm with over a 300-lux intensity or a red image of 500 lux intensity or greater having wavelengths of light within the range of 650 nm+/−30 nm or 700 nm+/−30 nm, and the moving image can be of any color that stands out against the blue image or red image, including that of black or white. By way of example only, for treating retinitis pigmentosa and increasing the number of healthy mitochondria in the periphery of the eye, the stationary image can be a red image having wavelengths of light within the range of 650 nm-700 nm or near IR of 830 nm+/−30 nm, and the moving image can be of any color that stands out against the red image including that of black or white.

However, by way of another example only, for treating macular degeneration, the fixated moving image or that of a fixated stationary image whereby the fovea and or macula is fixated can be a red image having wavelengths of light within the range of 650 nm-700 nm, 700 nm+/−30 nm, or 830 nm+/−30 nm. In certain embodiments the image that moves and is fixated on by one's fovea can be that of black, dark grey, or red. When using black or dark grey, there is less light stimulation for causing the pupil of the eye of the viewer to constrict fully. Likewise, a red fixation target can allow for the pupil of the eye to be slightly larger. By utilizing the embodiments disclosed herein it is possible to provide ocular photo-bio-stimulation therapy to each of the retina's macula, fovea, optic nerve head, central zone, mid periphery zone, and far periphery zone.

Figure 52:
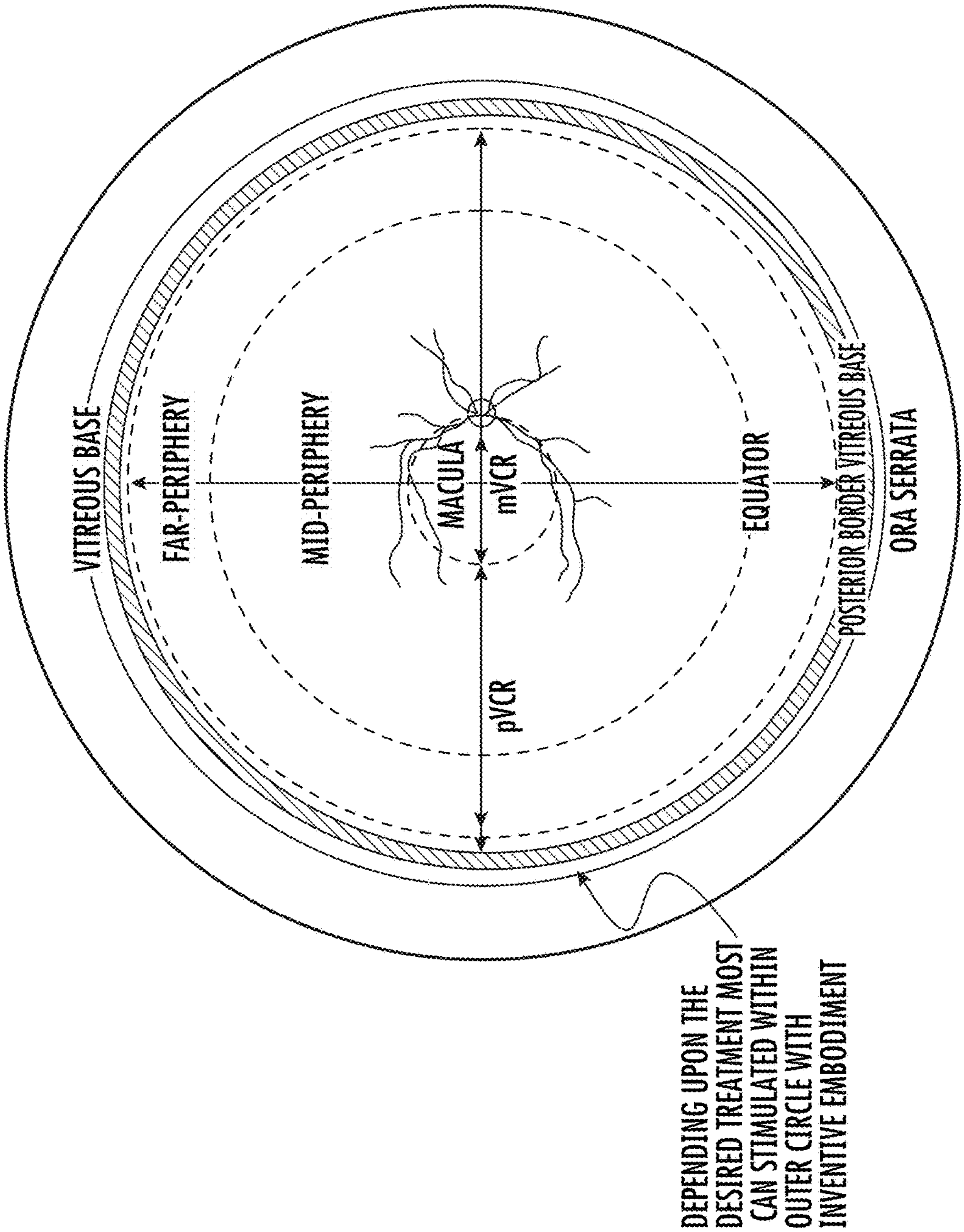
FIG. 52 shows information related to the invention described herein.

In reference to FIG. 52, embodiments of defocused light can be used for generating an image. In certain embodiments focused light can be used for generating an image. In certain embodiments one image can be generated with focused light and the other with defocused light. By using defocused light, it is possible to stimulate more (or a larger area) of the retina at one time with a light stimulus. This is true for a fixed image or an image that is moving relative to a fixed image. Such a defocused image can be generated by a plus lens that focuses in front of the retina or a minus lens that focuses behind the retina. In certain cases, focused light can be used. By way of example, a chromatic aberration focused lens can cause blue light wavelengths to move the focus from in front of the retina of the user's eye, to on or in the retina of the user's eye. In certain cases, a focused lens being of a slight increase in plus power can move the focus of red wavelengths of light from the back of the retina to focusing within the retina.

Embodiments of software that enable the appropriate ocular photo-bio-stimulation for one of a XR, AR, MR, or Modified Reality device, can be available by download to the device. Embodiments envisioned or covered by this invention disclosure can include one or more of the following; 1) appropriate light source(s) that provides wavelengths of light desired for the ocular photo-bio-stimulation 2) the use of light source and one or more filter combinations, 3) a light source or sources of the appropriate intensity to achieve the desired ocular photo-bio-stimulation results, 4) the appropriate timing of the ocular photo-bio-stimulation to achieve the desired results, 5) the appropriate movement of one image relative to another to achieve the desired ocular photo-bio-stimulation results, 6) in the case of treating a fovea and/or macula disorder, the appropriate light source fixation on the fovea and/or macula, 7) the use of defocused or focused light, 8) appropriate optics to achieve the desired outcome from the ocular photo-bio-stimulation, and/or 9) appropriate modulation or flicker of the light source(s) by way of example, 5 Hz-15 Hz, 10 Hz, or 40 Hz, or 40 Hz+/−20 Hz, if such modulation or flicker is desired.

For examples of one of XR, AR, MR, or Modified Reality eyewear devices described herein, the light source that generates ethe real image, virtual image or both, can be generated, by way of example only, by one or more of, LED, OLED, TOLED, iLED, quantum dots, fluorescent, incandescent, sun light, laser, television set, electronic display screen. For a VR, or Modified Reality eyewear device, the light source for either the first virtual image, or the second virtual image, or both, can be, by way of example only, LED, TOLED, OLED, iLED, quantum dots, fluorescent, incandescent, sun light, electronic display screen, and/or laser.

In most embodiments the XR eyewear will comprise one or more ocular photo-bio-stimulation light sources. The light source(s) can be a see-through near eye display or a non-see-through near eye display. Such a display, by way of example only, can be within 100 mm or less of the cornea of the eye of the wearer. In other embodiments such a display can be within 50 mm or less of the cornea of the eye of the wearer. In still other embodiments such a display can be within 15 mm or less of the cornea of the eye of the wearer. The light intensity of lux given off from the XR eyewear ocular photo-bio-stimulation light source can be 250 lux or more, 500 lux or more, 1,000 lux or more, or 2,000 lux or more. When considering the light radiating in a cone light manner from the ocular photo-bio-stimulation light source to strike the eye and face of the user or subject, the number of lumens given off from the ocular photo-bio-stimulation light source can be 10 lumens or more, 25 lumens or more, 50 lumens or more, 100 lumens or more, or 200 lumens or more. The light intensity that strikes the retina can be 300 lux or greater, 400 lux or greater, or 500 lux or greater.

In certain XR embodiments (e.g., AR, MR, VR, and/or Modified Reality), a system for maximizing the stimulation of dopamine and serotonin in the brain of an individual using the system can comprise using a combination of two or more of light, color, sound, aroma, and/or taste. In certain embodiments for stimulating dopamine and/or serotonin, a combination of light and sound are utilized. In certain embodiments for stimulating dopamine and/or serotonin, a combination of light and color are utilized. In certain embodiments for stimulating dopamine and/or serotonin, a combination of light and aroma are utilized. In certain embodiments, for stimulating dopamine and/or serotonin, a combination of light and taste are utilized. In order to detect if the brain is generating an increased level of dopamine and/or serotonin, biofeedback can be sensed or measured. Such sensing can be, by way of example only, sensing or measuring for an increase in the blink rate of the eye of the user of the XR device. Such sensing can be, by way of example only, sensing or measuring for an increase in the pupil diameter of the eye of the user of the XR device The light can comprise wavelengths of light that are predominantly or substantially light wavelengths within the ranges of one or more of: 480 nm+/−30 nm, 530 nm+/−20 nm, and/or 650 nm+/−30 nm. Such a system can comprise any two or more of light, color, sound, aroma, and/or taste. The sound can be, by way of example only, love songs. The aroma can be by, way of example only, cookies being baked. The taste can be, by way of example only, chocolate. In certain embodiments an XR system is utilized. An XR system can be one or more of AR, MR, VR, and/or Modified Reality. An XR system can be utilized on, in, or around the eyes of a wearer or user. The XR system can be one or more of: AR, MR, and/or VR when used in combination with one or more of light, color, sound, aroma, and/or taste. The XR system can comprise or display light. The XR system can display color. The color can be one or more, by way of example only, that of: red, yellow, and/or orange. The XR system can comprise audio. The XR system can comprise an odor emitting component. In certain embodiments smart eyewear can be utilized. Smart eyewear can be used in combination with one or more light, sound, aroma, and/or taste. Smart eyewear can comprise or display light. Smart eyewear can display color. The color can be one or more of, for example only, that of red, yellow, and/or orange. The smart eyewear can comprise audio. Smart eyewear can comprise an odor emitting component.

In certain embodiments an ocular photo-bio-stimulation instrument can be utilized. The instrument can be used in combination with one or more of: light, color, sound, aroma, and/or taste. The instrument can comprise or display light. The instrument can display color. The color can be one of: red, yellow, and/or orange. The instrument can comprise audio. The instrument can comprise an odor emitting component. The light can comprise wavelengths of light that are predominantly or substantially light wavelengths within the ranges of one or more of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. The color can be one or more of, by way of example only, that of red, yellow, and/or orange. The sound can be, by way of example only, love songs. The aroma can be by, way of example only, cookies being baked. The taste can be, by way of example only, chocolate. In certain embodiments an XR helmet or XR eyewear comprising a display can be utilized. The helmet or eyewear comprising a display can be used in combination with one or more of light, color, sound, aroma, and/or taste. The helmet or eyewear comprising a display can comprise or display light. A helmet or eyewear can display color. The color can be one or more of red, yellow, and/or orange. The helmet or eyewear comprising a display can comprise audio aspects. The helmet or eyewear comprising a display can comprise an odor emitting component.

The light can comprise wavelengths of light that are predominantly or substantially light wavelengths within the ranges of one or more of: 480 nm+/−30 nm, 530 nm+/−20 nm, 630 nm+/−20 nm, 650 nm+/−30 nm, and/or 700 nm+/−30 nm. Colors can be one or, by way of example only, that of red, yellow, orange. The sound can be, by way of example only, love songs. In each of these embodiments, the light, or color, or sound, or smell, or a combination thereof, can be modulated within the range of one of, 5 Hz-15 Hz, 10 Hz-20 Hz, 40 Hz+/−10 Hz or 40 Hz+/−20 Hz, by way of example.

In certain ocular photo-bio-stimulation embodiments, an XR device (e.g., AR, MR, VR, or Modified Reality) comprising a display can be used in combination with one or more of light, color, sound, aroma, and/or taste. The XR device comprises a display that can comprise or display light. The XR device can display color. The color can be one of red, yellow, and/or orange. The XR device comprising a display can comprise audio aspects(s). The XR device comprising a display can comprise an odor emitting component. The light can comprise wavelengths of light that are predominantly or substantially light wavelengths within the ranges of one or more of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm. Colors can be one or more of, by way of example only, that of red, yellow, and/or orange. In each of these embodiments the light, or color, or sound, or smell, or a combination thereof, can be modulated within the range of one of 5 Hz-15 Hz, 40 Hz+/−10 Hz or 40 Hz+/−20 Hz, by way of example.

In an embodiment of the invention as described herein, an XR device provides or comprises a first lighted image and a second lighted image, wherein the first lighted image is moved relative to the second lighted image, wherein the first image is generated by a first light source, wherein the second image is generated by a second light source (or absence thereof) forming a black spot, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 630 nm-700 nm, or 650 nm+/−30 nm, or 700 nm+/−30 nm, and wherein the wavelengths of light that fall within the peak transmission band of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 630 nm-700 nm, or 650 nm+/−30 nm, or 700 nm+/−30 nm, paint portions of the retina peripheral to the macula of the user of the XR device as the user views an image with the XR device. The XR device can provide ocular photo-bio-stimulation to the eye or eye's retina. One of the lights can comprise a band of wavelengths of light having a transmission peak of 50% or greater than any other transmission peak of visible light for that light. The first image can move relative to a stationary second image. The second image can move relative to the stationary first image. The first image can move relative to a moving second image. The first image can move relative to a moving second image. The first image and the second image can both move. In certain cases, the virtual image can be black (this can be formed by a combination of colored pixels or the lack of light). In certain cases, both images are virtual images. The black image can be a spot. The black spot can be of any size or shape. The black spot can move within or relative to the real image. The real image can paint the retina as the eye follows the movement of the black spot. When the light source generates a virtual image, the light source can be, by way of example only, that of a non-see-through near eye display comprising light emitters. When the light source generates a virtual image, the light source can be, by way of example only, that of a see-through near eye display comprising light emitters. When the image is that of a real image, the real image can be generated by, by way of example, a light source of one or more of: sun, ambient light, television, or an electronic display of a remote computerized device.

In an embodiment of the invention as described herein, an XR device provides or comprises a first lighted image and a second lighted image, wherein the first image is moved relative to the second image, wherein the first image is generated by a first light source, wherein the second image is generated by a second light source (or absence thereof) forming a black spot, wherein the predominant wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, and wherein the predominant wavelengths of light that fall within the transmission band of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, paint portions of the retina peripheral to the macula of the user of the XR device as the user views an image with the XR device. The XR device can provide ocular photo-bio-stimulation to the eye or eye's retina. One of the light sources can generate a band of wavelengths of light having a transmission of the predominant wavelengths being 50% or greater than any other transmission of visible light for that light. The first image can move relative to a stationary second image. The second image can move relative to the stationary first image. The first image can move relative to a moving second image. The first image can move relative to a moving second image. The first image and the second image can both move. In certain cases, the virtual image can be black (this can be formed by a combination of colored pixels or the lack of light). In certain cases, both images are virtual images. The black image can be a spot. The black spot can be of any size or shape. The black spot can move within or relative to the real image. The real image can paint the retina as the eye follows the movement of the black spot. When the light source generates a virtual image, the light source can be, by way of example only, that of a non-see-through near eye display comprising light emitters.

When the light source generates a virtual image, the light source can be, by way of example only, that of a see-through near eye display comprising light emitters. When the image is that of a real image the real image can be generated by way of example by a light source of one or more of, sun, ambient light, television, or electronic display of a remote computerized device.

Figure 53A:
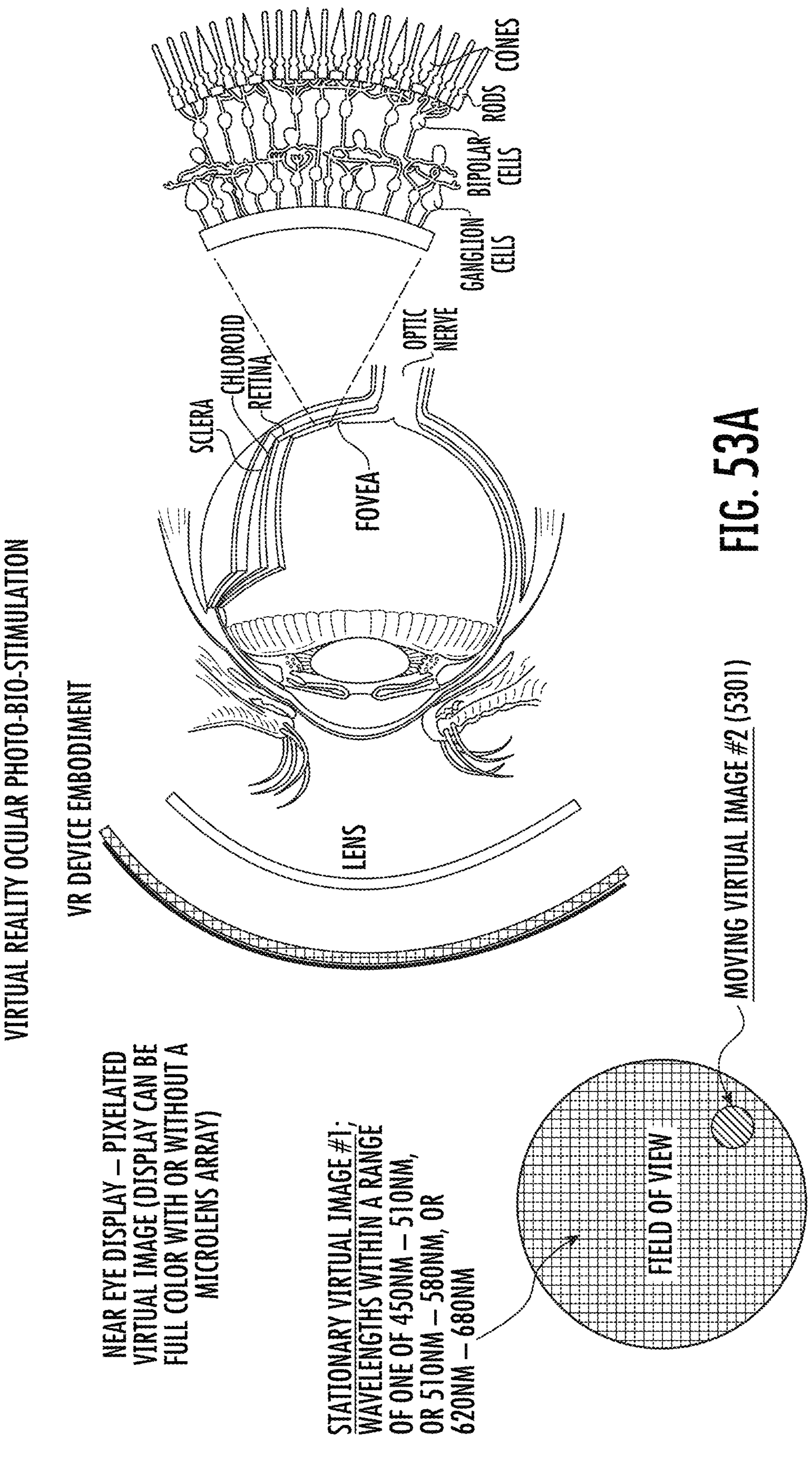
FIG. 53A-D shows an embodiment of the current invention as described herein.
Figure 53B:
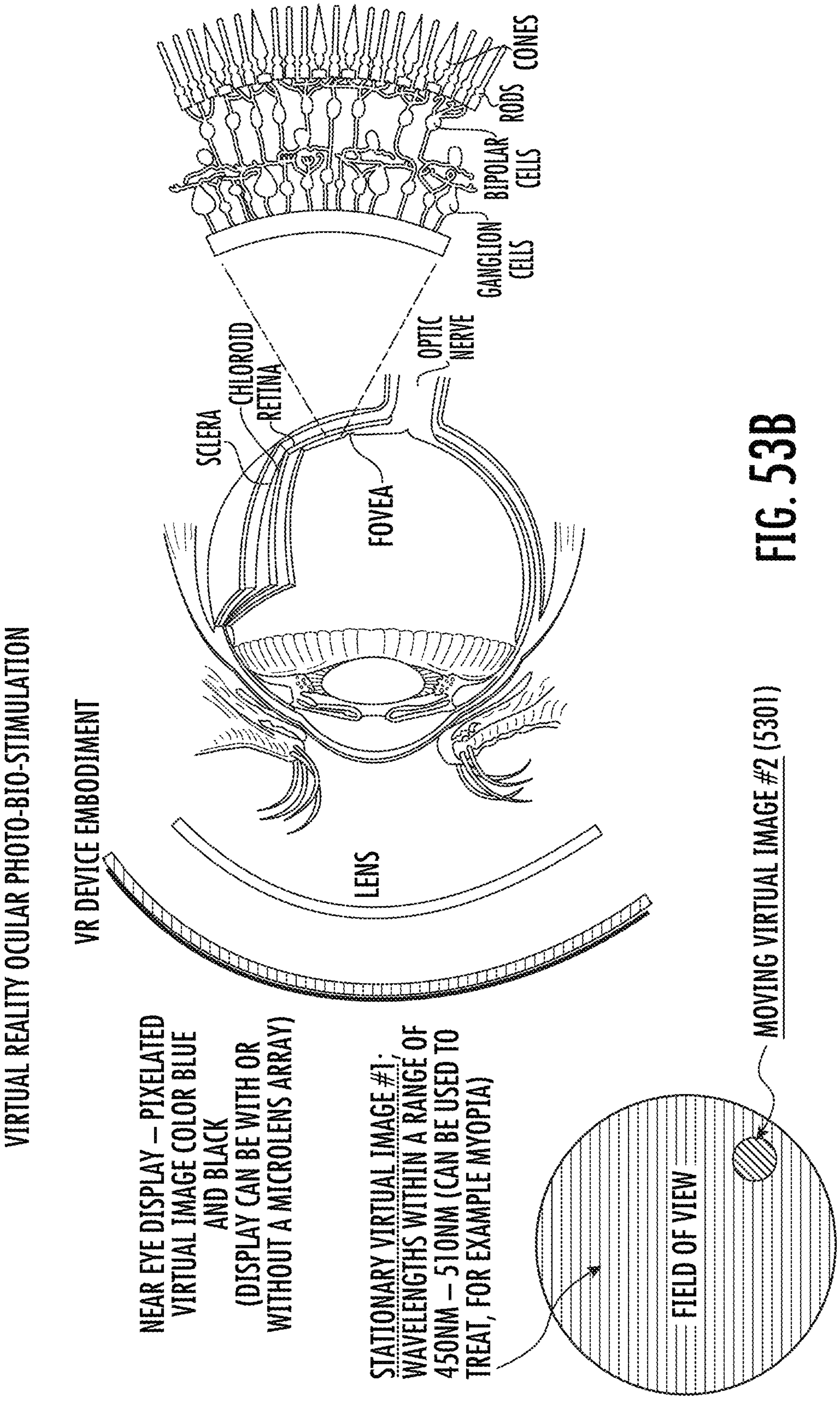
Figure 53C:
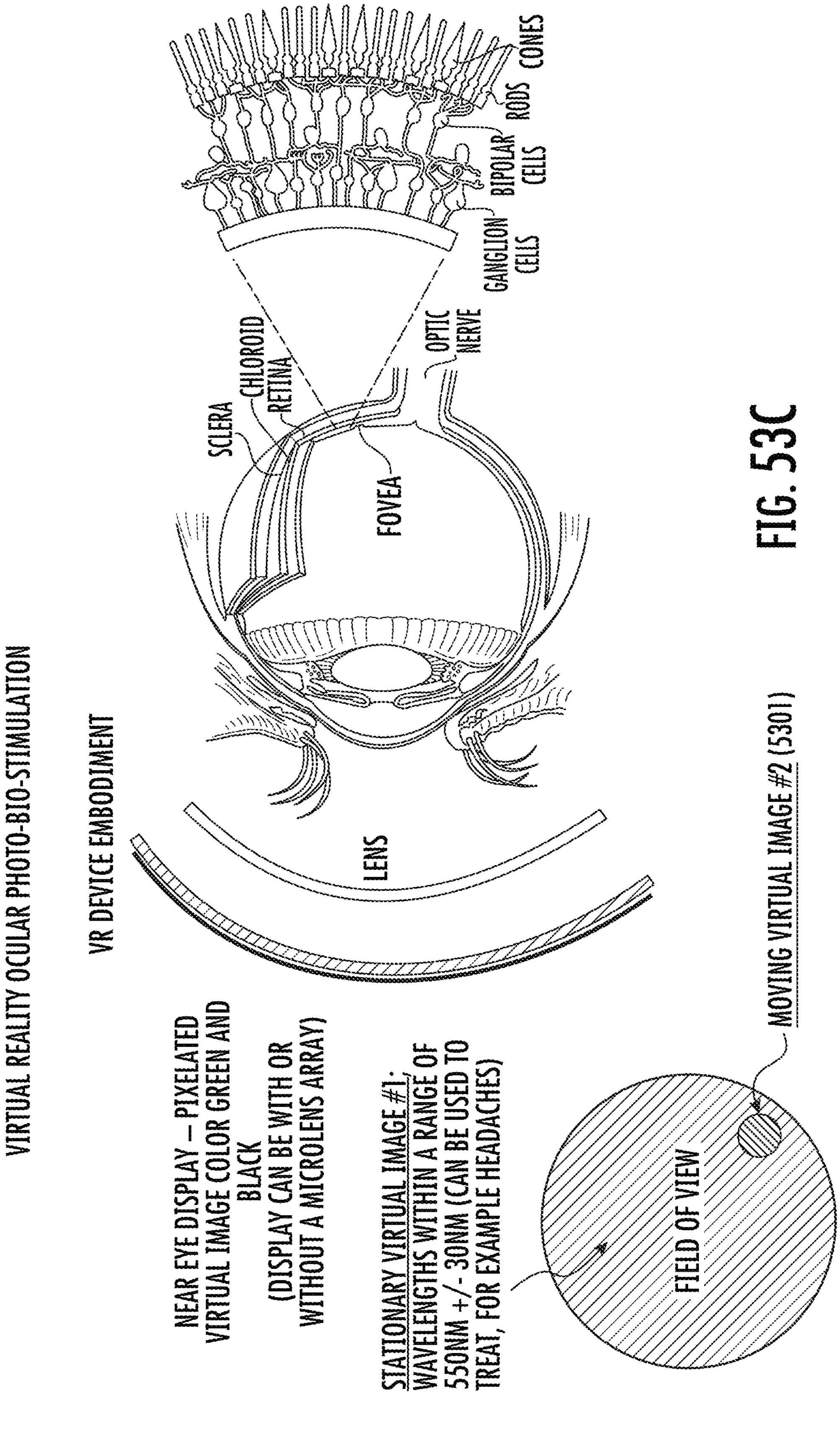
Figure 53D:
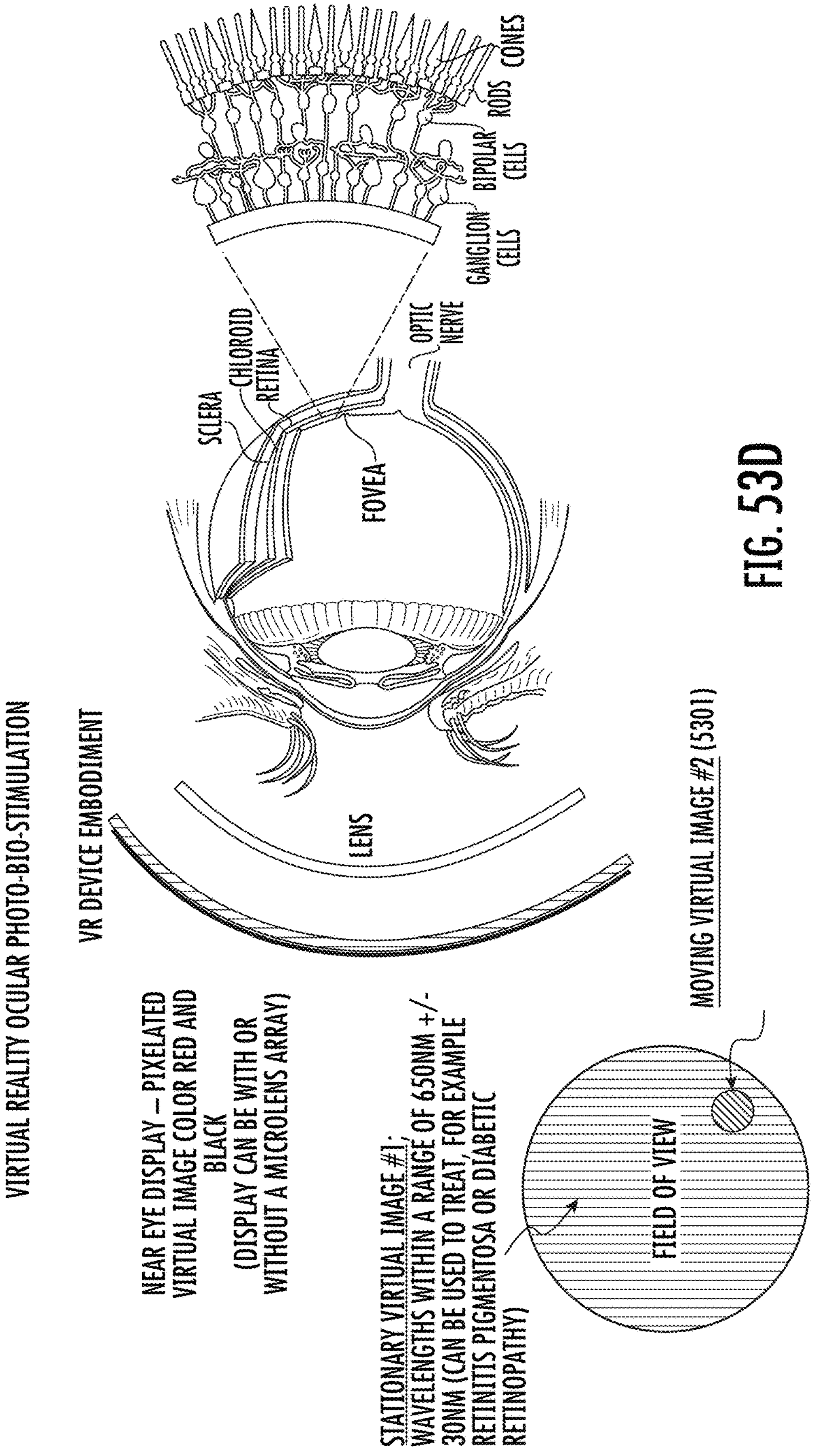

In reference to FIG. 53A, a VR or Modified Reality device can be capable of painting with desired light wavelengths to most of the retina peripheral to the macula or fovea. By way of example, the VR device can provide focused, non-focused, scattered light. Illumination can be within the range of 400 lux to 20,000 lux. Pixels can be comprised by way of example only one of: OLEDs, TOLEDs, microOLEDs, iLeds, Quantum Dots, or LEDs. With respect to the moving virtual image #2 5301, it can be, by way of example only, one of continuous, periodic, intermittent movement from place to place of any desired colored dot including black, grey or white. In aspects, the moving image can be comprised of, by way of example, a combination of colors, lack of light, and/or lack of color. Such ocular photo-bio-stimulation treatment can be done on a monocular basis or a binocular basis.

FIGS. 53, 54, and 55, show how, by way of example only, a non-see-through near eye display or a see-through near eye display can be curved to conform with the eyewear lens(es). Not shown is the curved micro-lens array that can be in alignment with and in optical communication with either the appropriate non-see-though near eye display or a see-through near eye display. By curving a non-see-through near eye display or a see-through near eye display along with a micro-lens array, it is possible to cause light from the pixels of the display to cover or stimulate a larger area of the retina of the eye of the wearer.

In embodiments, the first image can be a real image fixated on by the fovea of the user's eye. The second image can be a virtual image. The second image can paint portions of the far peripheral retina with light. The second image can move relative to a stationary first image. The first image can move relative to a stationary secondary image. The first image can be a virtual image. The second image can be a virtual image. The second image can be a real image fixated on by the fovea of the user's eye. The second image can be a virtual image fixated on by the fovea of the user's eye. The first image can paint portions of the far peripheral retina with light wavelengths.

The moving image (whether a virtual image or a real image) can be by way of example only, one of continuous, periodic, or intermittent movement, from place to place of any desired colored dot (including black, grey, or white). Such ocular photo-bio-stimulation treatment can be done on a monocular basis or a binocular basis.

The image (whether a virtual image or real image) which is painting the retina of an eye can be generated by a light emitter or emitters, by way of example only, having illumination within the range of 400 lux to 20,000 lux. In certain embodiments, when an electronic display is utilized for XR (such as by example only, one of a see-through near eye display, a near eye display, and/or a non-see-through near eye display), the electronic display can be located directly in front of the eye within the line of sight of the eye when the eye is looking straight ahead. In certain embodiments when an electronic display is utilized for XR (such as by example only, one of a see-through near eye display, a near eye display, and/or a non-see-through near eye display), the electronic display can be located in front of the eye but offset with regards to the line of sight of the eye when the eye is looking straight ahead. The electronic display pixels can be comprised of, by way of example only: OLEDs, TOLEDs, micro-OLEDs, iLEDs, Quantum Dots, and/or LEDs. The light can be that of focused, non-focused or scattered light. When an electronic display is remote from the lens or optic or located on the eyewear or the edge of the lens or optic, a waveguide can be utilized to cause the light to be directed into the eye, the electronic display pixels can be, by way of example only: OLEDs, TOLEDs, micro-OLEDs, iLEDs, Quantum Dots, and/or LEDs. The light can be that of focused, non-focused or scattered light. The light emitter or emitters, by way of example only, can have illumination within the range of 400 lux to 20,000 lux.

The XR eyewear can utilize one or more of a near eye display, see-through near eye display, non-see-through near eye display, or waveguide. Any one or more of those will allow for the embodiment of moving a first light that forms an image that is fixed upon by the eye of a user/wearer, while another the light that forms a second image paints the retina. In certain embodiments both images are virtual images. In other embodiments one image (the moving fixated image) is that of a real image and the second image (stationary image) is that of a virtual image. In still other embodiments one image (the moving fixated image) is that of a virtual image and the second image (stationary image) is that of a real image.

The XR device can be a VR or Modified Reality device (see, e.g., FIGS. 53A-D and 54A-B). With the VR device the first image and the second image can be virtual images. In certain cases, one of the virtual images can be black (this can be formed by a combination of colored pixels or the lack of light) The first light can be focused light. The black image can be a spot. The black spot can be of any size or shape. The black spot can move within or relative to the second virtual image. The second virtual image can paint the retina as the eye follows the movement of the black spot. The first light can be focused light. The second light can be defocused light. The first light can be defocused light. The second light can be focused light. The first light can be filtered light. The second light can be filtered light. The light wavelength band of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 700 nm+/−30 nm, or 830 nm+/−30 nm, and it can be generated by way of the use one or more of: an interference filter, absorption filter, neutral density filter, bandpass filter, and/or notch filter.

The image movement can be continuous. The image movement can be intermittent. The image movement can be periodic. The first light can be one of generated by one or more of: LEDs, OLEDs, TOLEDs, micro-OLEDs, micro-LEDs, micro-ileds, iLEDs, quantum dots, florescent lights, incandescent lights, sun, laser, plasma display, TV display, tablet display, cell phone display, computer display, and/or electronic display. The second light can be generated by one or more of: LEDs, OLEDs, TOLEDs, micro-OLEDs, micro-LEDs, micro-ileds, iLEDs, quantum dots, florescent lights, incandescent lights, sun, laser, plasma display, TV display, tablet display, cell phone display, computer display, and/or electronic display.

The first image can modulate within the range of one of: 5 Hz-15 Hz, 10 Hz+20 Hz, 40 Hz+/−10 Hz, or 40 Hz+/−20 Hz. The second image can modulate within the range of: 5 Hz-15 Hz, 10 Hz+20 Hz, 40 Hz+/−10 Hz, or 40 Hz+/−20 Hz. The first light can flicker. The second light can flicker. The first light can have an intensity of 300 lux or greater. The second light can have an intensity of 300 lux or greater. The time of ocular photo-bio-stimulation exposure can be for each treatment session, 5 minutes or less, 15 minutes or less, or 1 hour or less. A filter or filters that block or filter light wavelengths within the wavelength range of 449 nm-380 nm can be utilized.

The light that paints the peripheral retina can target rods. The light that paints the peripheral retina can target ipRGCs (melanopsin containing ganglion cells). The light that paints the peripheral retina can target amacrine cells. The XR device can provide two or more of the following, each chosen with the goal of stimulating dopamine in the human body: light, color, sound, and/or smell. Taste can be added to further stimulate dopamine in the human body.

Another embodiment of the invention is that of an XR device (again, AR, MR, VR, or Modified Reality) comprising a first image and a second image, wherein the first image is generated by a first light, wherein the second image is generated by a second light, wherein one of the lights comprise a band of wavelengths of light having a transmission peak 2× or greater compared to any other transmission peak of visible light for that particular light, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm. 480 nm+/−30 nm, 480 nm+/−20 nm, 500 nm+/−30 nm, 500 nm+/−20 nm, 510 nm+/−30 nm, 510 nm+/−20 nm, 530 nm+/−20 nm, or 650 nm+/−30 nm, or 700 nm+/−30 nm, and wherein the wavelengths of light that fall within the peak transmission band stimulate portions of the retina peripheral to macula of the user of the XR device as the user views an image with the XR device.

The XR device can provide ocular photo-bio-stimulation to the eye's or both eyes' retina. One of the lights can comprise a band of wavelengths of light having a transmission peak of 50% or greater than any other transmission peak of visible light for that light. The first image can move relative to a stationary second image. The second image can move relative to the first image. The first image and the second image can both move.

In reference to FIG. 54, in regards to the XR device, the first image can be a real image fixated on by the fovea of the user's eye. The second image can be a virtual image. The second image can paint portions of the peripheral retina with light. The second image can move relative to a stationary first image. The first image can move relative to a stationary secondary image. The first image can be a virtual image. The second image can be a virtual image. The second image can be a real image fixated on by the fovea of the user's eye. The second image can be a virtual image fixated on by the fovea of the user's eye. The first image can paint portions of the peripheral retina with light wavelengths. The XR device can be a VR device.

With the VR or Modified Reality device the first image and the second image can be virtual images. The first light can be focused light. The second light can be defocused light. The first light can be defocused light. The second light can be focused light. The first light can be filtered light. The second light can be filtered light. The light wavelength band of one of: 480 nm+/−30 nm, 530 nm+/−20 nm, 575 nm+/−30 nm, 630 nm-700 nm, 650 nm+/−30 nm, 700 nm+/−30 nm, or 830 nm+/−30 nm, can be generated by way of the use one or more of: an interference filter, absorption filter, neutral density filter, bandpass filter, and/or notch filter.

Figure 54A:
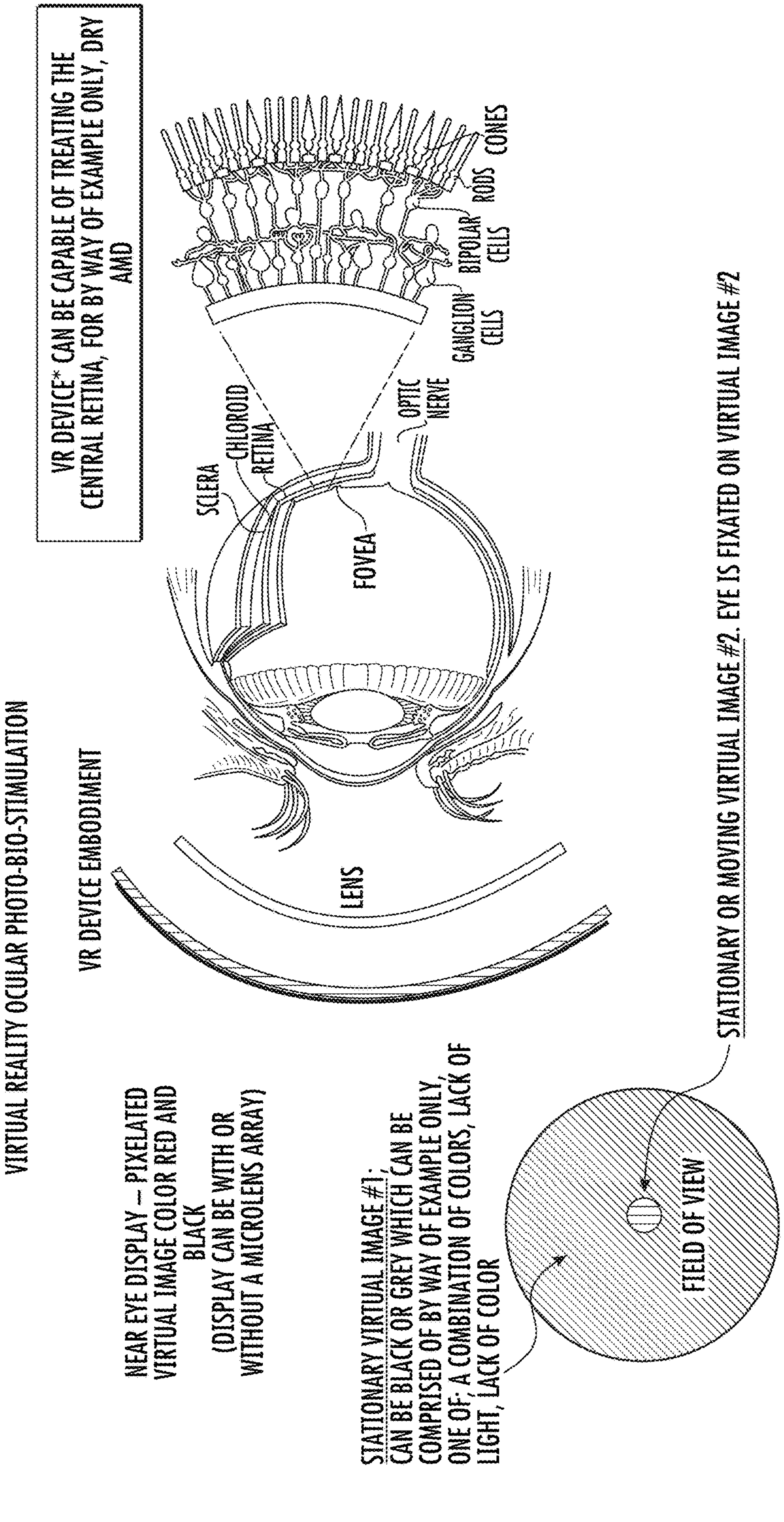
FIG. 54A-B shows an embodiment of the current invention as described herein.

In reference to FIG. 54A, the light wavelengths can be by way of example only within the range of 650 nm+/−30 nm or 620 nm to 700 nm, for treating the macula or fovea for slowing or stopping the progression of dry AMD. Such ocular photo-bio-stimulation treatment in most but not all cases is performed on a monocular basis. In aspects, by way of example, the devices in FIG. 54 can provide focused, non-focused, and/or scattered light. Illumination can be within the range of 400 lux to 20,000 lux. Pixels can be comprised by way of example only one or more of: OLEDs, TOLEDs, microOLEDs, iLeds, Quantum Dots, or LEDs. Real world light can include, by way of example, LED, OLEDs, fluorescent light, incandescent light, ambient sun light, television, electronic display of a remote computerized device, etc.

Figure 54B:
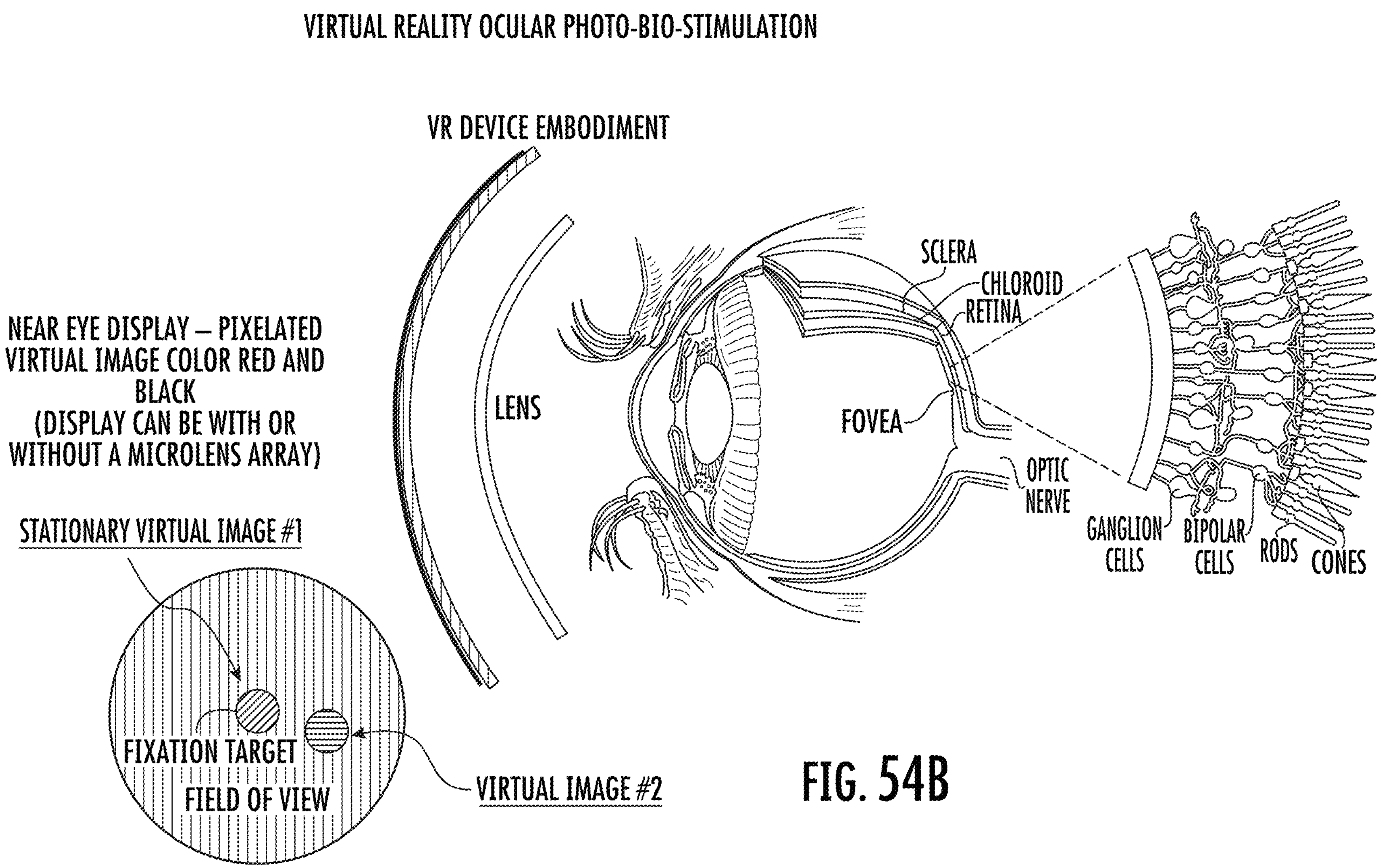

In reference to FIG. 54B, the device can be used to treat the ganglion cells axons of optic nerve head or surrounding ipRGCs. Wavelengths of virtual image #2 can be by way of example only within the range of one of 475 nm+/−30 nm or 650 nm+/−30 nm for treating the optic nerve head to generate retinal dopamine to slow or stop myopia progression. When treating the optic nerve head using ocular photo-bio-stimulation, the eye is to remains centrally fixated on image #1 which can be moving or stationary. Virtual Image #2 is off set from virtual image #1 so that if the wearer fixates on virtual image #1 the optic nerve head is being treated by virtual image #2 or its light. By first turning on and off the pixels that form virtual image #2, it is possible to ensure that the image is aligned and solely targeting the optic nerve head. If when fixating on virtual image #1, it is possible to see virtual image #2, then the alignment is not correct and different pixels can be activated until virtual image #2 is not able to be seen. Such alignment must be done on a monocular basis, in cases. In aspects, a stationary virtual image #1, the image for central fixation, can be comprised of a black dot. The black dot can be comprised of by way of example only, one of; a combination of colors, lack of light, or lack of color (red wavelengths can be within the range of 600 nm-700 nm. Virtual image #2, which treats the optic nerve head with ocular photo-bio-stimulation, can be comprised of light wavelengths within the wavelength range of one of 480 nm+/−30 nm or 650 nm+/−30 nm.

Figure 55A:
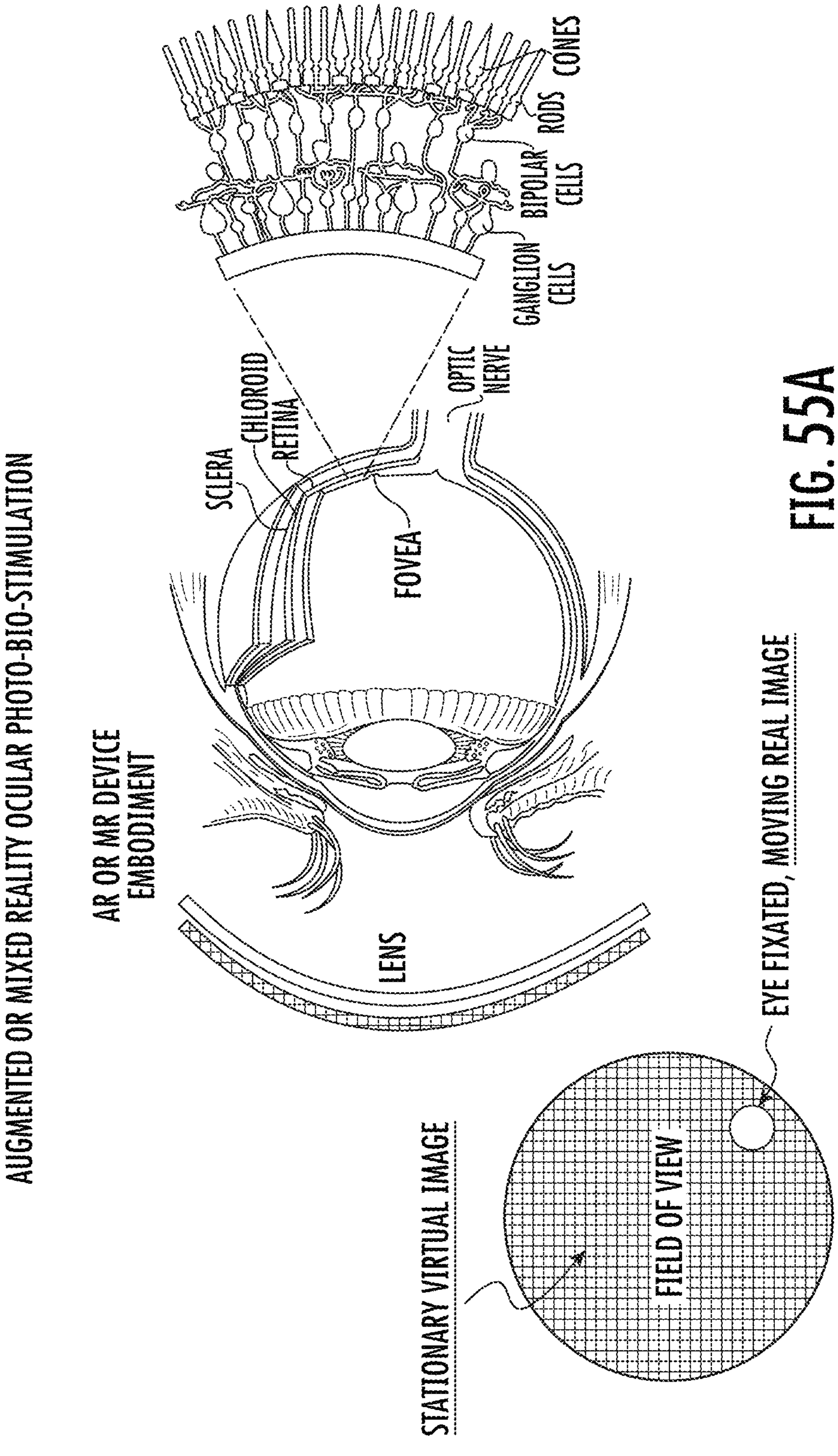
FIG. 55A-I shows an embodiment of the current invention as described herein.

In reference to FIG. 55A, it shows that one of an AR, MR, or Modified Reality ocular photo-bio-stimulation device can be capable of painting with desired light wavelengths most of the retina peripheral to the macula or fovea. In cases, the real-world image can be seen through the virtual image. In aspects, a "see through" near-eye display can be used to generate light, such as a pixelated, full color display, which can be with or without a microlens array. The microlens array can focus the virtual image one of: in front of the retina, in the retina, or behind the retina. In regard to the stationary virtual image, in embodiments, the wavelengths may be within a range of: 450 nm-510 nm, or 520 nm-580 nm, or 620 nm-680 nm. Regarding the moving real image, it can be one of continuous, periodic, and/or intermittent movement from place to place of the real-world image. The movement can be a constant continuous movement or a movement that jumps from one place to another. The image can appear as a moving hole showing a real image or the real world or real-world image within the virtual image. Such ocular photo-bio-stimulation treatment can be performed monocularly or binocularly. In aspects, by way of example, the devices in FIG. 55*a* can provide one of, focused, non-focused, and/or scattered light. The illumination that generates the virtual image can be within the range of 300 lux to 20,000 lux or greater. The pixel light emitters which generate the virtual image can be comprised by way of example only one or more of: OLEDs, TOLEDs, microOLEDs, iLeds, Quantum Dots, or LEDs. The real-world light that generates the real image can include, by way of example, one or more of, remote LED, OLEDs, fluorescent light, incandescent light, ambient sunlight, television, or display of a remote computerized device, which are capable of generating a real image seen at far, etc. The real image movement can be continuous. The image movement can be intermittent. The image movement can be periodic. In aspects, the moving real image will appear as a moving hole filled in with a real distance image. As the eye fixates on the real moving image the virtual image will paint the retina of the user.

Figure 55B:
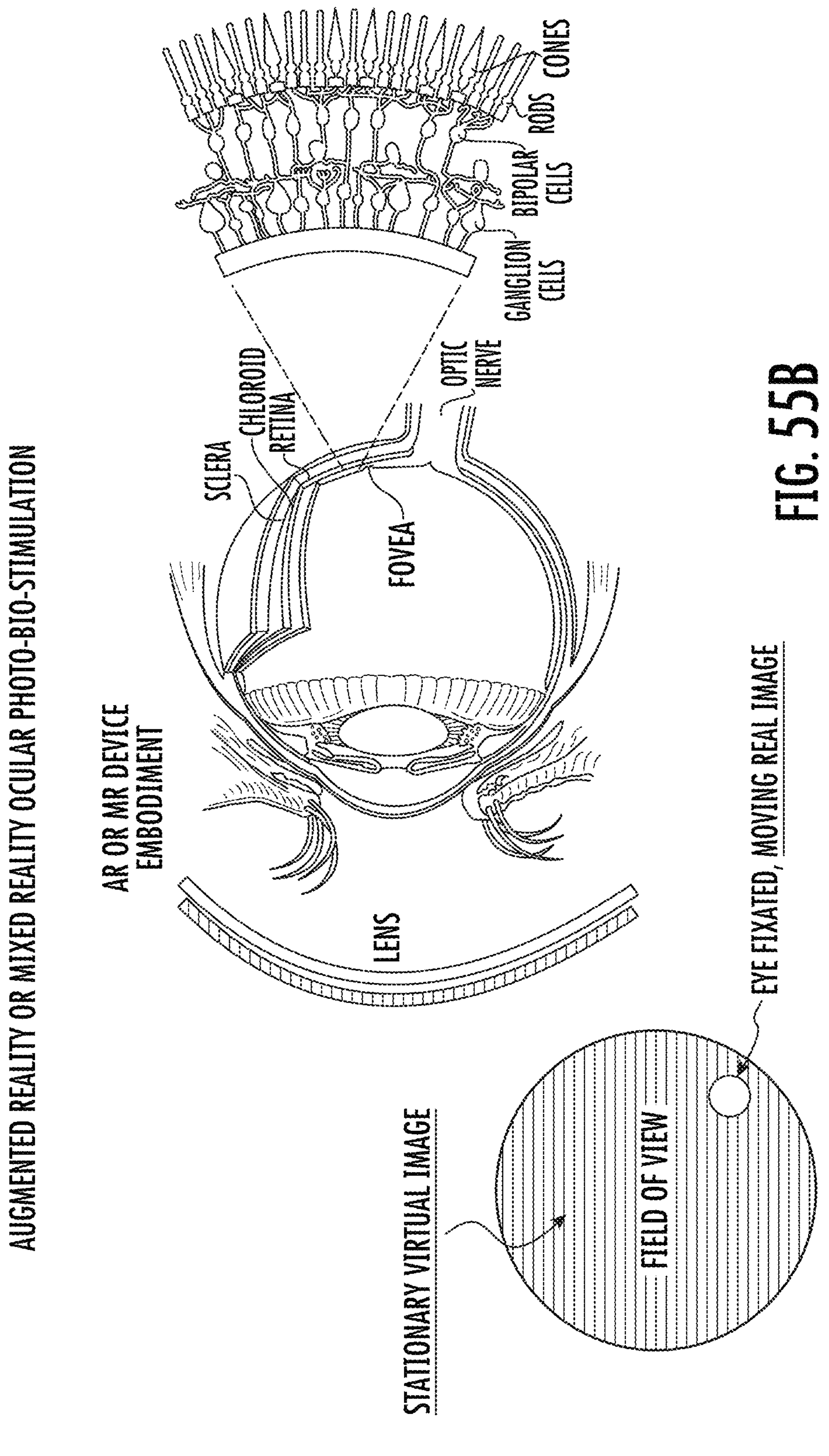

In reference to FIG. 55B, it shows that one of an AR, MR, or Modified Reality ocular photo-bio-stimulation device can be capable of painting with desired light wavelengths most of the retina peripheral to the macula or fovea. In cases, the real-world image can be seen through the virtual image. In aspects, a "see through" near-eye display can be used to generate light, such as a pixelated, blue monochrome, which can be with or without a microlens array. The microlens array can focus the virtual image one of: in front of the retina, in the retina, or behind the retina. A stationary virtual image can include wavelengths within a range of 450 nm-510 nm (can be used to treat, for example, myopia). In cases, the real-world image can be seen through the virtual image. In aspects, the eye fixates on a moving real image, the movement of which can be continuous, periodic, or intermittent movement from place to place of a real-world image. The movement can be a constant continuous movement or a movement that jumps from one place to another. The moving image can appear as a moving hole showing a real image within the virtual image. Such photo-bio-stimulation treatment can be performed monocularly or binocularly.

Figure 55C:
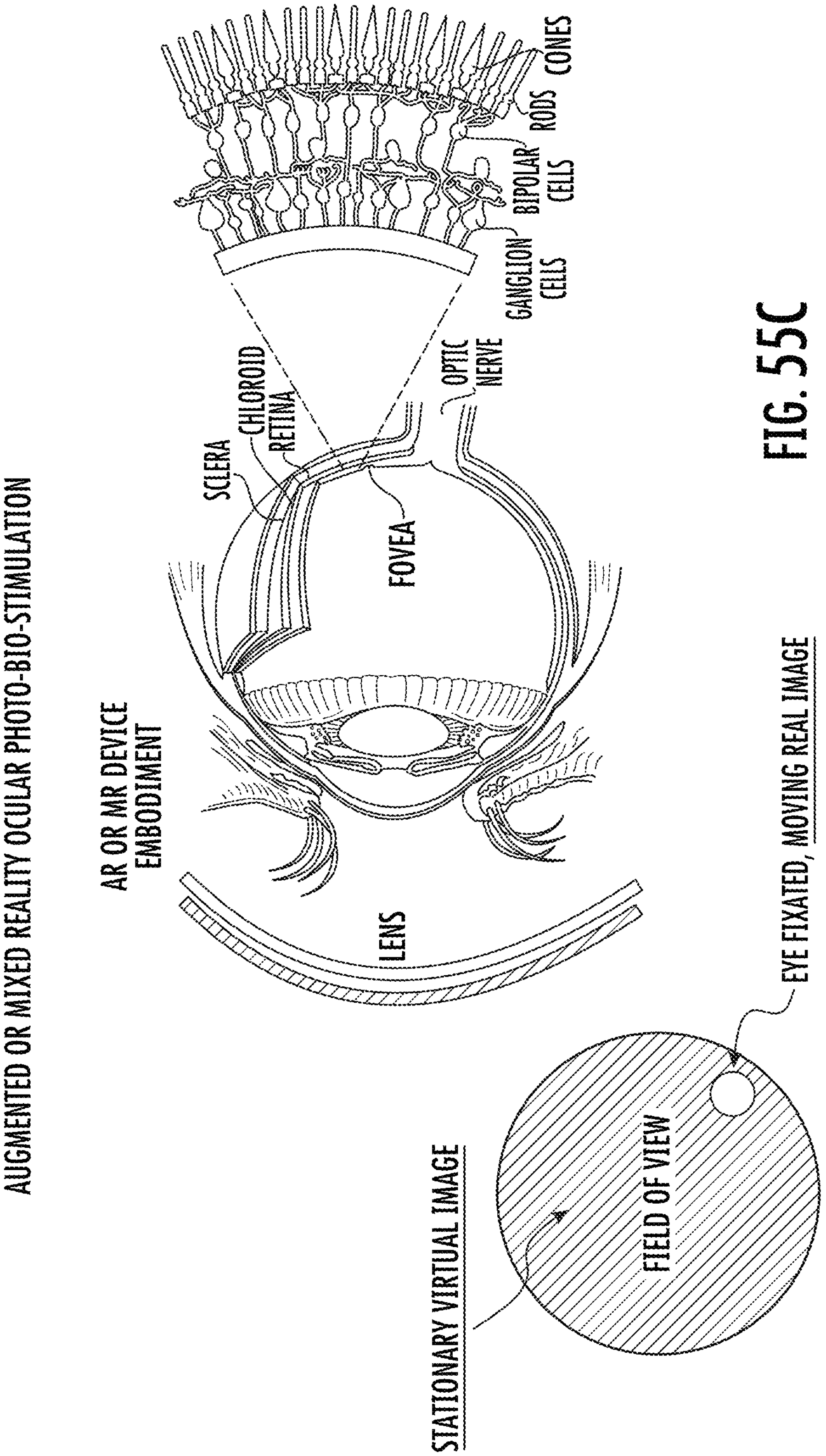

In reference to FIG. 55C, it shows that one of an AR, MR, or Modified Reality ocular photo-bio-stimulation device can be capable of painting with desired light wavelengths most of the retina peripheral to the macula or fovea. In cases, the real-world image can be seen through the virtual image. In aspects, a "see through" near-eye display can be used to generate light, such as a pixelated, green monochrome, which can be with or without a microlens array. The microlens array can focus the virtual image one of: in front of the retina, in the retina, or behind the retina. A stationary virtual image can include wavelengths within a range of 550 nm+/−30 nm (can be used to treat, for example, headaches). In cases, the real-world image can be seen through the virtual image. In aspects, the eye fixates on a moving real image, the movement of which can be continuous, periodic, or intermittent movement from place to place of a real-world image. The movement can be a constant continuous movement or a movement that jumps from one place to another. The moving image can appear as a moving hole showing a real image within the virtual image. Such ocular photo-bio-stimulation treatment can be performed monocularly or binocularly.

Figure 55D:
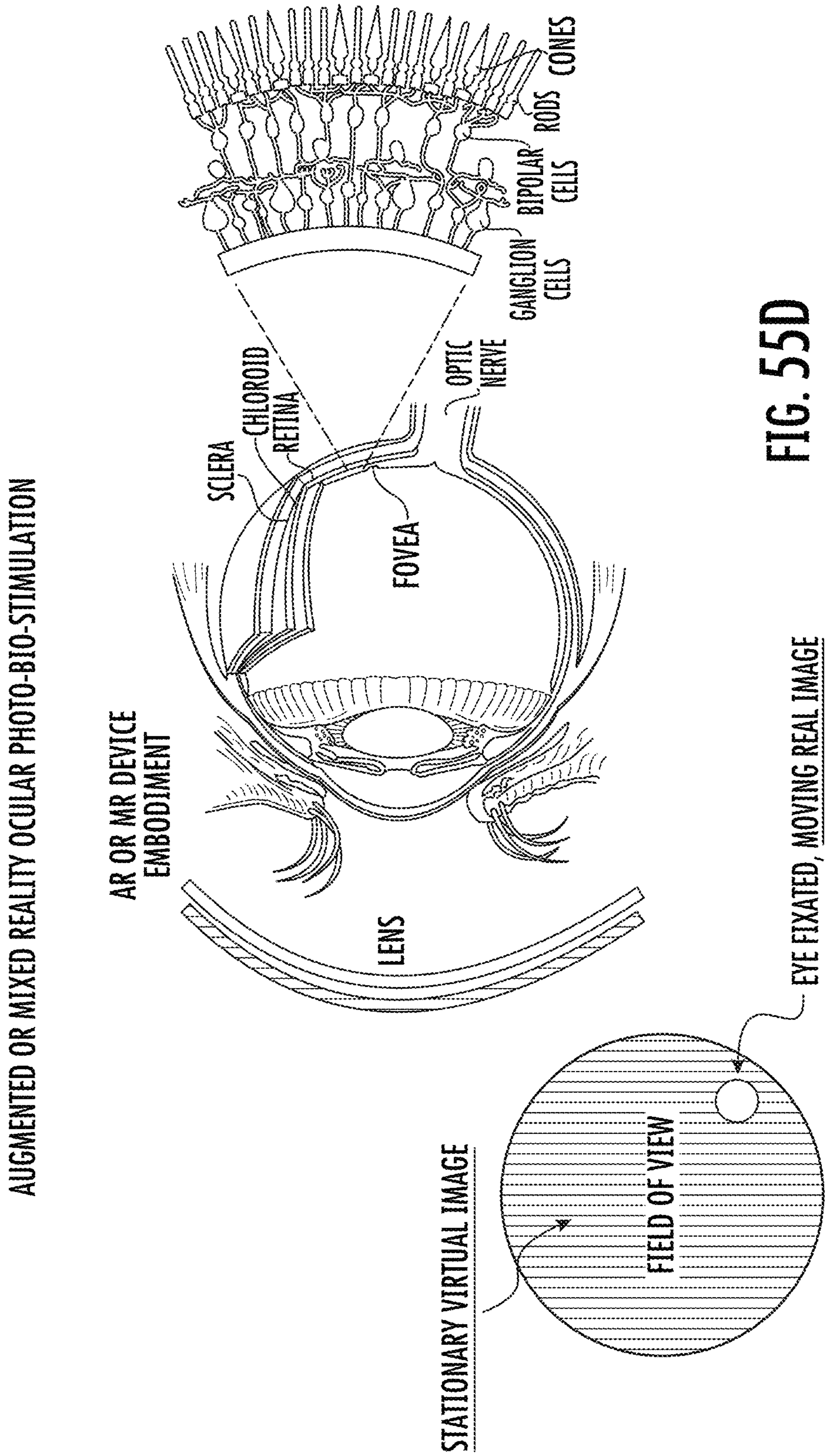

In reference to FIG. 55D, it shows that one of an AR, MR, or Modified Reality ocular photo-bio-stimulation device can be capable of painting with desired light wavelengths most of the retina peripheral to the macula or fovea. In cases, the real-world image can be seen through the virtual image. In aspects, a "see through" near-eye display can be used to generate light, such as a pixelated red monochrome, which can be with or without a microlens array. The microlens array can focus the virtual image one of: in front of the retina, in the retina, or behind the retina. A stationary virtual image can include wavelengths within a range of 650 nm+/−30 nm (can be used to treat, for example, retinitis pigmentosa or diabetic retinopathy). In cases, the real-world image can be seen through the virtual image. In aspects, the eye fixates on a moving real image, the movement of which can be continuous, periodic, or intermittent movement from place to place of a real-world image. The movement can be a constant continuous movement or a movement that jumps from one place to another. The moving image can appear as a moving hole showing a real image within the virtual image. Such photo-bio-stimulation treatment can be performed monocularly or binocularly.

Figure 55E:
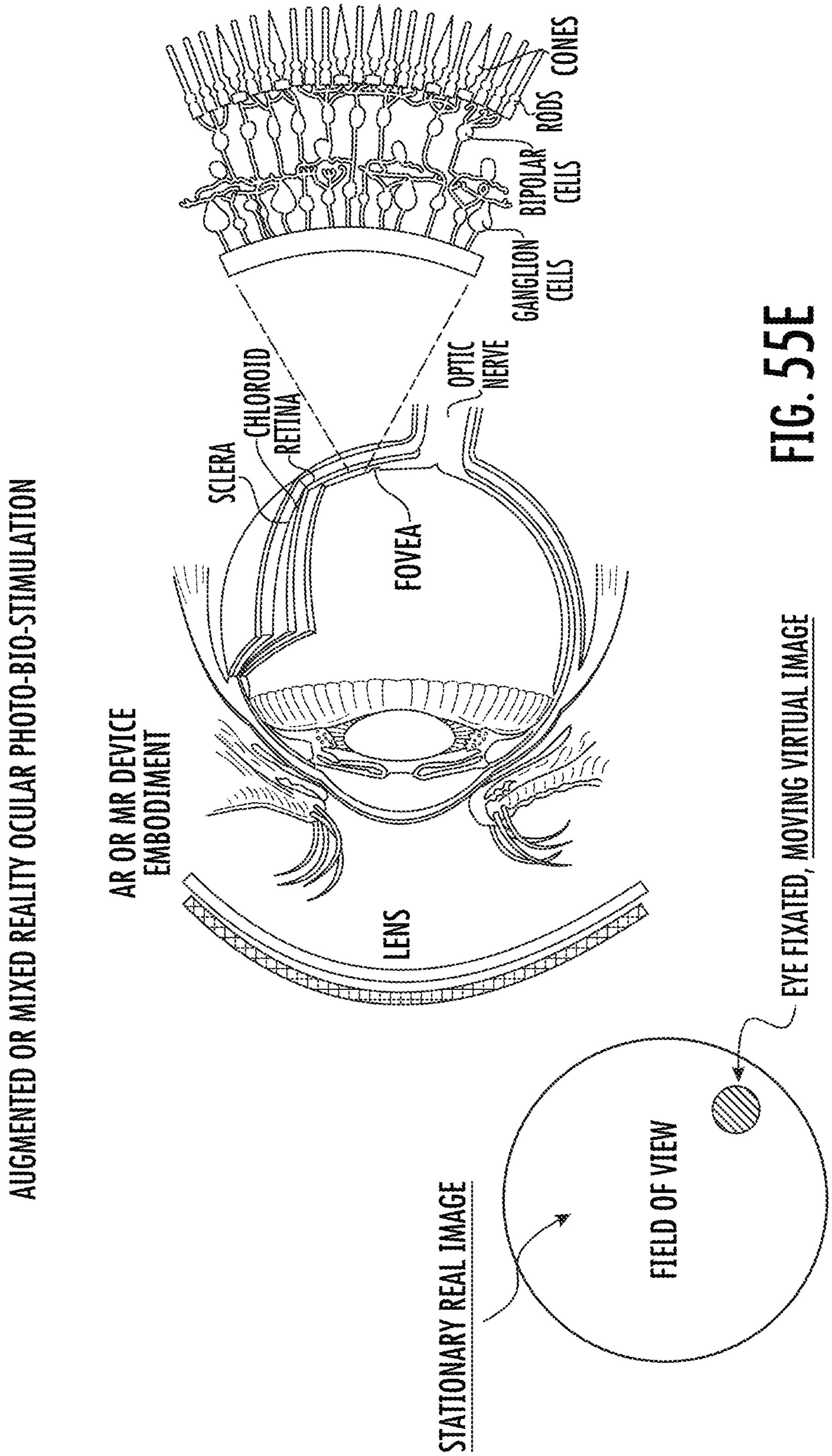

In reference to FIG. 55E, it shows that one of an AR, MR, or Modified Reality ocular photo-bio-stimulation device can be capable of painting with desired light wavelengths most of the retina peripheral to the macula or fovea. In aspects, a "see through" near-eye display can be used to generate light, such as a pixelated, full color display, which can be with or without a microlens array. The microlens array can focus the virtual image one of: in front of the retina, in the retina, or behind the retina. A stationary real image can include, by way of example, light wavelengths within the visible range of 380 nm-700 nm (sunlight). It can be used to treat, for example, myopia. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

Figure 55F:
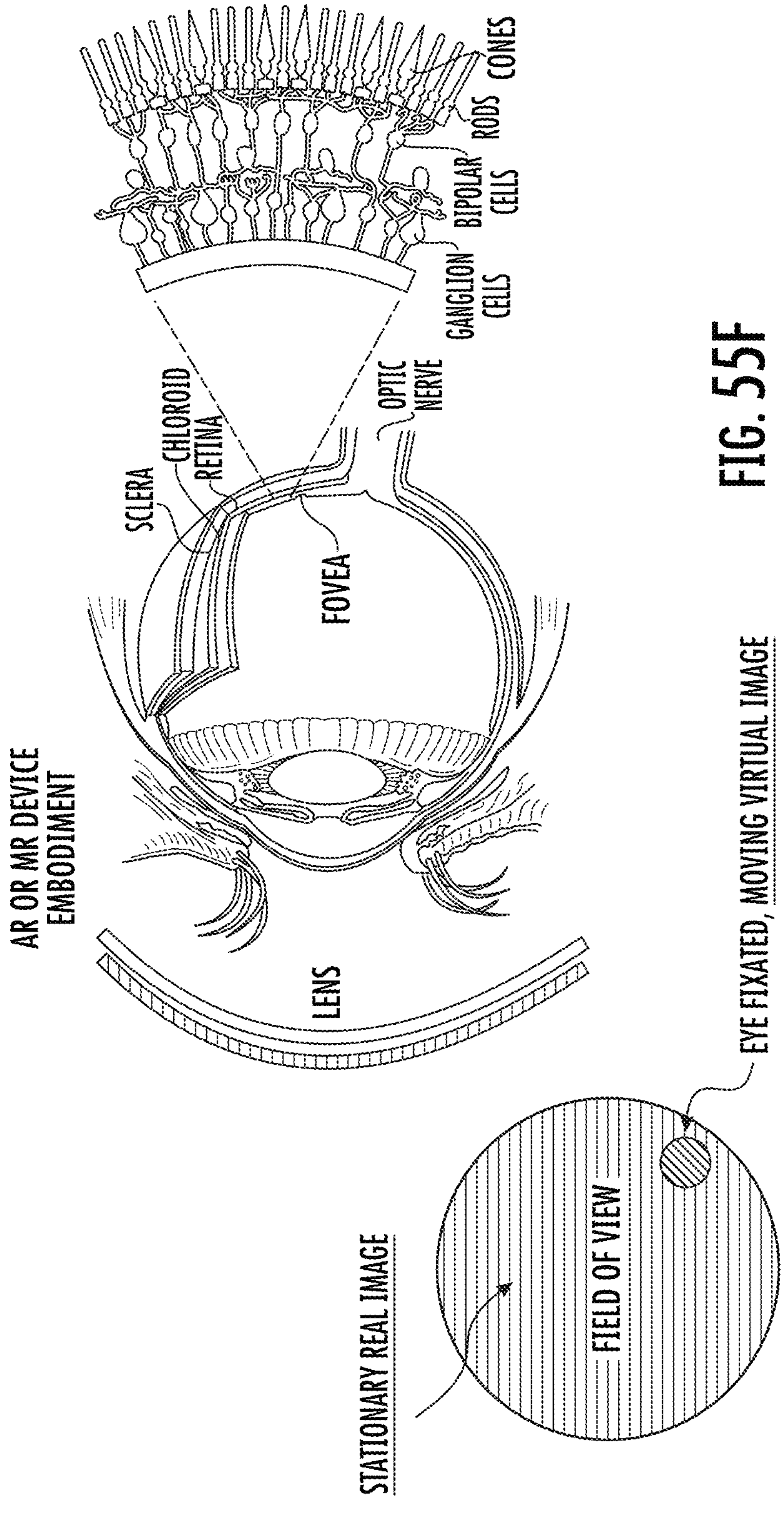

In reference to FIG. 55F, it shows that one of an AR, MR, or Modified Reality ocular photo-bio-stimulation device can be capable of painting with desired light wavelengths most of the retina peripheral to the macula or fovea. In aspects, a "see through" near-eye display can be used with a pixelated black color, which can be with or without a microlens array. The microlens array can focus the virtual image one of: in front of the retina, in the retina, or behind the retina. A real image can use ambient light of the real world that is filtered to allow blue wavelengths to pass. A stationary real image can use a "filtered lens" allowing for wavelengths within the range of 450 nm-510 nm or 475 nm+/−20 nm to strike/paint the retina. It can be used to treat, for example, myopia. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

Figure 55G:
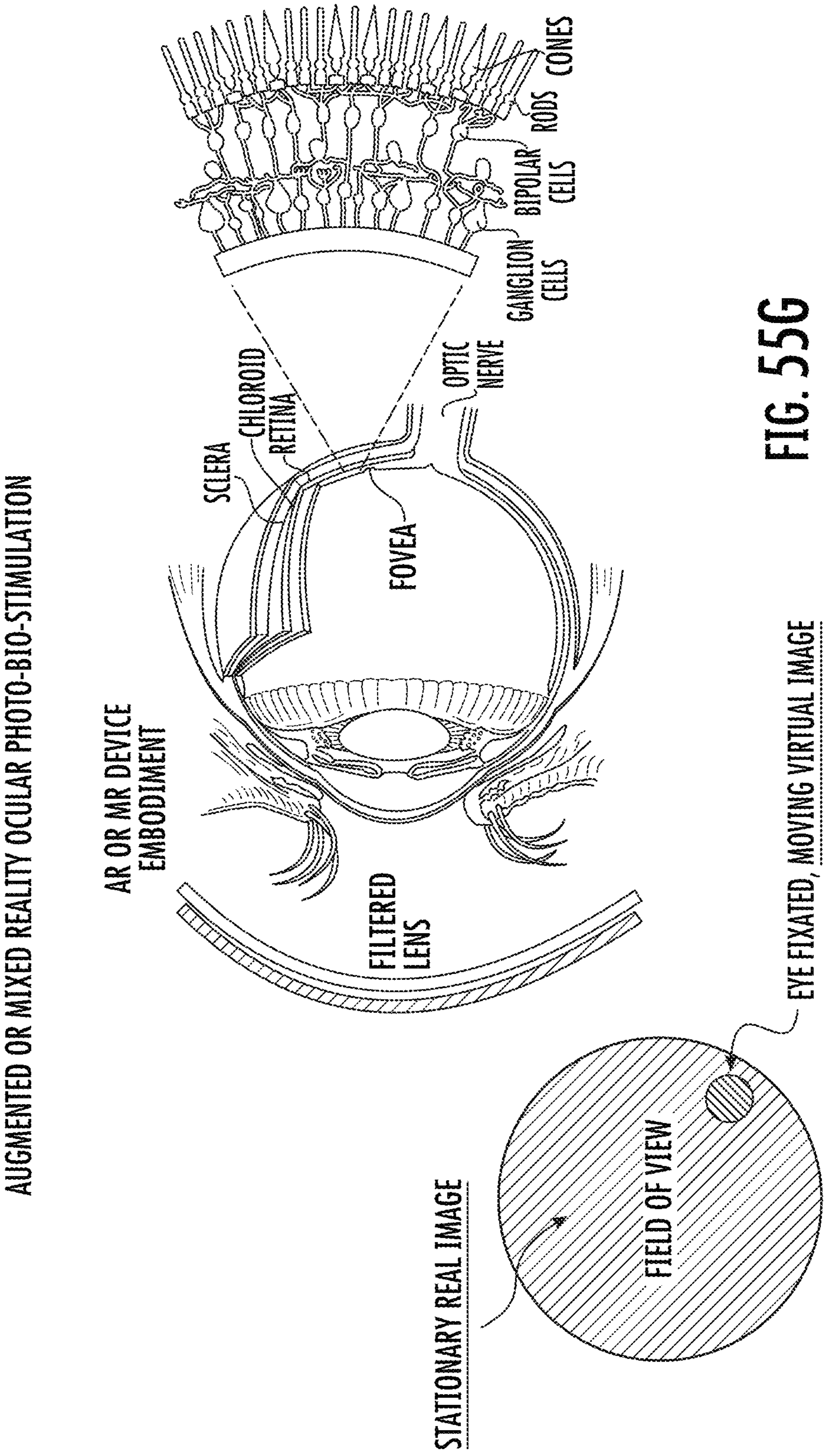

In reference to FIG. 55G, it shows that one of, an AR, MR, Modified Reality ocular photo-bio-stimulation device can be capable of painting with desired light wavelengths most of the retina peripheral to the macula or fovea. In aspects, a "see through" near-eye display can be used with a pixelated black color, which can be with or without a microlens array. The microlens array can focus the virtual image one of: in front of the retina, in the retina, or behind the retina. A real image can use ambient light of the real world that is filtered to allow green wavelengths to pass. A stationary real image can use a "filtered lens" allowing for wavelengths within the range of 550 nm+/−30 nm or 510+/−20 nm to strike/paint the retina. It can be used to treat, for example, headaches. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

Figure 55H:
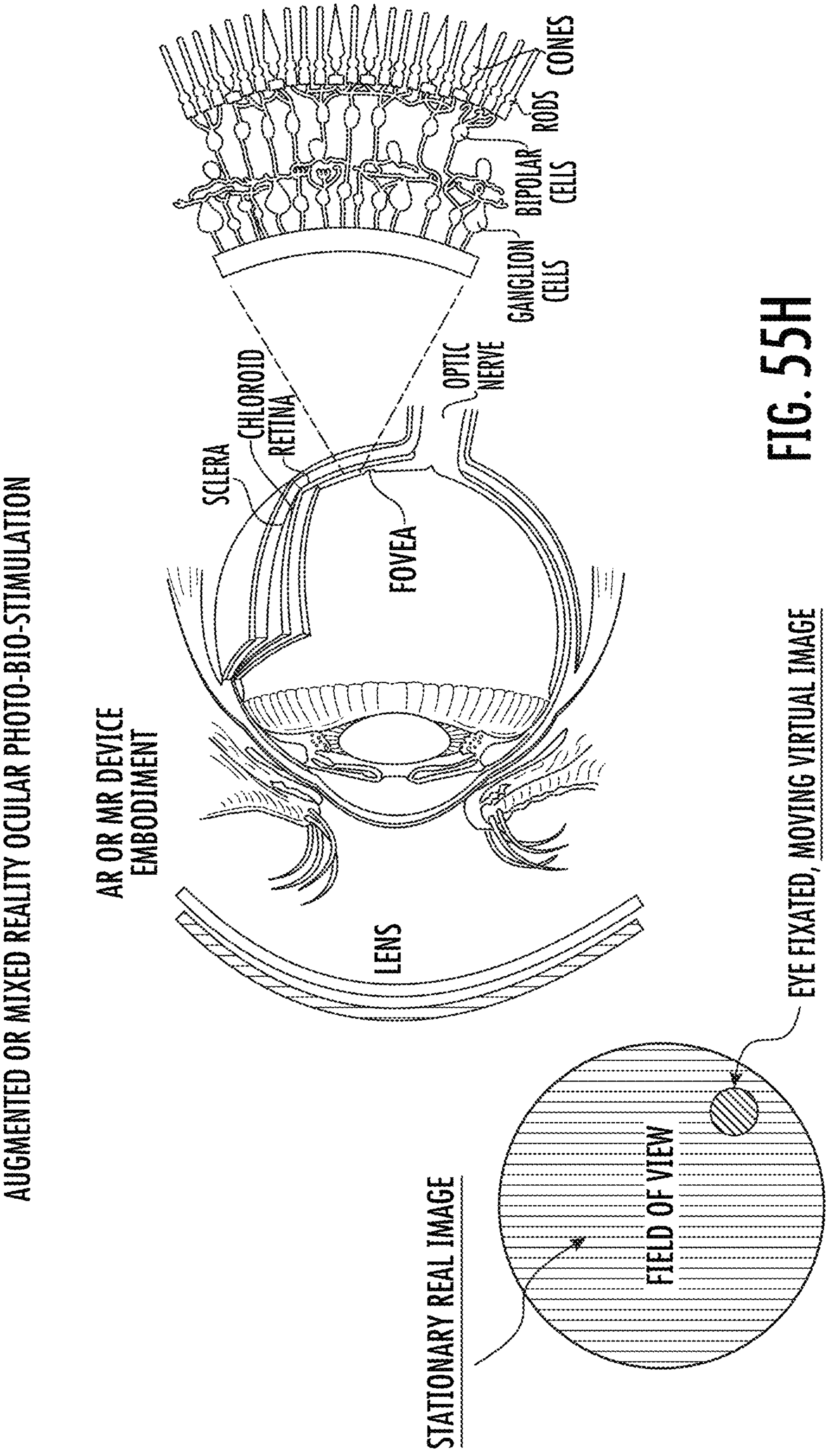

In reference to FIG. 55H, it shows that one of an AR, MR, or Modified Reality ocular photo-bio-stimulation device can be capable of painting with desired light wavelengths most of the retina peripheral to the macula or fovea. In aspects, a "see through" near-eye display can be used with a pixelated black color, which can be with or without a microlens array. The microlens array can focus the virtual image one of: in front of the retina, in the retina, or behind the retina. A real image can use ambient light of the real world that is filtered to allow red wavelengths to pass. A stationary, or 700 nm+/−30 nm, real image can use a "filtered lens" allowing for wavelengths within the range of 650 nm+/−30 nm or 700 nm+/−30 nm to strike/paint the retina. It can be used to treat, for example, retinitis pigmentosa or diabetic retinopathy. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

Figure 55I:
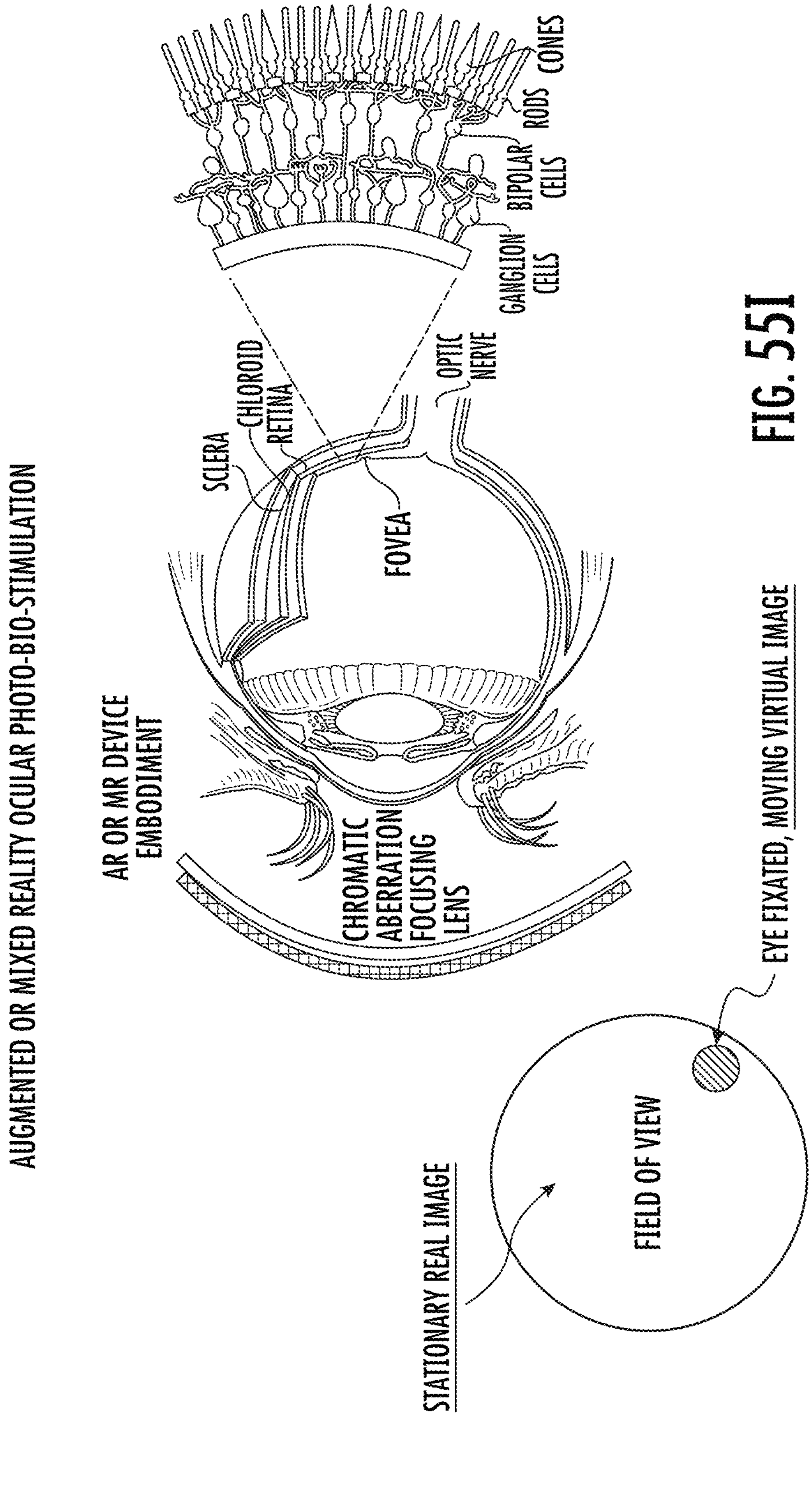

In reference to FIG. 55I, it shows that one of an AR, MR, or Modified Reality ocular photo-bio-stimulation device can be capable of painting with desired light wavelengths most of the retina peripheral to the macula or fovea. In aspects, a "see through" near-eye display can be used with a pixelated black color, which can be with or without a microlens array. The microlens array can focus the virtual image one of: in front of the retina, in the retina, or behind the retina. A real image can use ambient light of the real world that when focused by the lens peripheral to the central zone can cause blue wavelengths to strike/paint the periphery of the retina. In aspects, a stationary real image uses ambient light, such that the chromatic aberration focusing lens causes wavelengths within the range of 450 nm-510 nm or 475 nm+/−20 nm to strike/paint the retina. It can be used to treat, for example, myopia. In aspects, the eye fixates on a moving virtual image, the movement of which can be continuous, periodic, or intermittent movement from place to place of a black or grey dot, which can be comprised of by way of example only: a combination of colors, lack of light, or lack of color. Such ocular photo-bio-stimulation treatment can be performed monocularly or binocularly.

In aspects, the first image can modulate within the range of one of, 5 Hz-15 Hz, 10 Hz+20 Hz, 40 Hz+/−10 Hz, or 40 Hz+/−20 Hz. The second image can modulate within the range one of, 5 Hz-15 Hz, 10 Hz+20 Hz, 40 Hz+/−10 Hz, or 40 Hz+/−20 Hz. The first light can flicker. The second light can flicker. The first light can have an intensity of 400 lux or greater. The second light can have an intensity of 300 lux or greater. The time of ocular photo-bio-stimulation exposure for each treatment session can be 5 minutes or less, 15 minutes or less, or 1 hour or less. The light that paints the peripheral retina can target cones. The light that paints the peripheral retina can target rods. The light that paints the peripheral retina can target ganglion cells. The light that paints the peripheral retina can target melanopsin ganglion cells. The light that paints the peripheral retina can target amacrine cells. The XR device can provide two or more of the following, each chosen with the goal of stimulating dopamine in the human body: light, color, sound, and/or smell. Taste can be added to further stimulate dopamine in the human body.

Still another embodiment of the invention is of an XR device being one of, AR, MR, VR, or Modified Reality, comprising a first image and a second image, wherein the first image is generated by a first light source, wherein the second image is generated by a second light source, wherein one of the lights comprise a band of wavelengths of light having a transmission peak 2× or greater than any other visible light transmitted by the XR device to the eye of the user of the XR device, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm or 630 nm-700 nm, and wherein the wavelengths of light that fall within the peak transmission band stimulate the macula or fovea of the user of the XR device as the user views an image with the XR device. The XR device can provide ocular photo-bio-stimulation of the eye or eyes' retina. One of the lights can comprise a band of wavelengths of light having a transmission peak for the light transmitted to the eye of the user of 50% or greater than any other transmission peak of visible light for that light.

The first image can move relative to a stationary second image. The second image can move relative to the first image. The first image and the second image can both move. The XR device can be one of an AR, MR, or Modified Reality device. The first image can be a real image fixated on by the fovea of the user's eye. The second image can be a virtual image. The second image can paint portions of the peripheral retina with light. The second image can move relative to a stationary first image. The first image can move relative to a stationary secondary image. The first image can be a virtual image. The second image can be a virtual image. The second image can be a real image fixated on by the fovea of the user's eye. The second image can be a virtual image fixated on by the fovea of the user's eye. The first image can paint portions of the peripheral retina with light wavelengths while the second image stimulates the macula or fovea. The first image can paint portions of the peripheral retina with light wavelengths while the eye fixates centrally on the second image. The first image can move. The second image can move. The first image can move relative to the second image. The second image can move relative to the first image. The second image can paint portions of the peripheral retina with light wavelengths while the first image stimulates the macula or fovea. The XR device can be VR or Modified Reality. With the VR device the first image and the second image can be virtual images. The first light can be focused light. The second light can be defocused light. The first light can be defocused light. The second light can be focused light. The first light can be filtered light. The second light can be filtered light.

The light wavelength band can be 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 700 nm+/−30 nm, or 830 nm+/−30 nm, which can be generated by way of one or more of: an interference filter, absorption filter, neutral density filter, bandpass filter, or notch filter. The image movement can be continuous. The image movement can be intermittent. The image movement can be periodic. The first light can be one of: LED, OLED, iLED, quantum dots, fluorescent, incandescent, sun light, laser, plasma display, TV display, tablet display, cell phone display, computer display, or electronic display. The second light can be one of: LED, TOLED, OLED, iLED, quantum dots, fluorescent, incandescent, sunlight, laser, plasma display, TV display, tablet display, cell phone display, computer display, or electronic display.

The first image can modulate within the range of one of, 5 Hz-15 Hz, 10 Hz+20 Hz, 40 Hz+/−10 Hz, or 40 Hz+/−20 Hz. The second image can modulate within the range of one of, 5 Hz-15 Hz, 10 Hz+20 Hz, 40 Hz+/−10 Hz, or 40 Hz+/−20 Hz. The first light can flicker. The second light can flicker. The light that is providing the ocular photo-bio-stimulation treatment or therapy can be 400 lux or more, 700 lux, or more 1000 lux or more, or 5,000 lux or more. The time of ocular photo-bio-stimulation stimulation exposure for each treatment session can be 5 minutes or less, 15 minutes or less, or 1 hour or less. The light that paints the peripheral retina can target rods. The light that paints the peripheral retina can target ganglion cells (ipRGCs). The light that paints the peripheral retina can target amacrine cells. The light that targets the macula or fovea can target mitochondria. The XR device (being one of AR, MR, VR, or Modified Reality device) can provide light within the wavelength range 650 nm+/−30 nm, 700 nm+/−30 nm, or 830 nm+/−30 nm, for increasing the number of healthy mitochondria within the eye. The XR device can provide two or more of the following, each chosen with the goal of stimulating dopamine in the human body: light, color, sound, and/or smell. Taste can be added to further stimulate dopamine in the human body.

Still another embodiment of the invention is of an XR device being one of AR, MR, VR, or Modified Reality, comprising a first image and a second image, wherein the first image is generated by a first light source, wherein the second image is generated by a second light source, wherein one of the lights comprise a band of wavelengths of light having a light transmission peak percentage of light wavelengths transmitted to the eye of a user of the XR device that can be 2× or greater than any other light wavelength transmission peak percentage of visible light wavelengths for that particular light that are transmitted to the eye of a user, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 630 nm-700 nm, or 700 nm+/−30 nm, and wherein the wavelengths of light that fall within the peak transmission percentage wavelength band stimulate the macula or fovea of the user of the XR device as the user views an image with the XR device.

The XR device can provide ocular photo-bio-stimulation to the eye or eye's retina. One of the lights can comprise a band of wavelengths of light having a transmission peak 50% or greater than any other transmission peak of visible light wavelengths for that light. The first image can move relative to a stationary second image. The second image can move relative to the first image. The first image and the second image can both move. The first image can be a real image fixated on by the fovea of the user's eye. The second image can be a virtual image. The second image can paint portions of the peripheral retina with light. The second image can move relative to a stationary first image. The first image can move relative to a stationary secondary image. The first image can be a virtual image. The second image can be a virtual image. The second image can be a real image fixated on by the fovea of the user's eye. The second image can be a virtual image fixated on by the fovea of the user's eye. The first image can paint portions of the peripheral retina with light wavelengths while the second image stimulates the macula or fovea. The second image can paint portions of the peripheral retina with light wavelengths while the first image stimulates the macula or fovea. The first image can paint portions of the peripheral retina with light wavelengths while the eye is fixated on the second image. The second image can paint portions of the peripheral retina with light wavelengths while the eye is fixated on the first image.

The XR device can be a VR or a Modified Reality device. With the VR device the first image and the second image can be virtual images. The first light can be focused light. The second light can be defocused light. The first light can be defocused light. The second light can be focused light. The first light can be filtered light. The second light can be filtered light. The light wavelength band of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, 630 nm-700 nm, 700 nm+/−30 nm or 830 nm+/−30 nm, can be generated by way of the use one or more of an interference filter, absorption filter, neutral density filter, bandpass filter, or notch filter.

The image movement can be continuous. The image movement can be intermittent. The image movement can be periodic. The first light can be LED, OLED, TOLED, iLED, quantum dots, fluorescent, incandescent, sun light, laser, plasma display, TV display, tablet display, cell phone display, computer display, or electronic display. The second light can be LED, OLED, iLED, quantum dots, fluorescent, incandescent, sun light, laser, plasma display, TV display, tablet display, cell phone display, computer display, or electronic display.

The first image can modulate within the range one of, 5 Hz-15 Hz, 10 Hz+20 Hz, 40 Hz+/−10 Hz, or 40 Hz+/−20 Hz. The second image can modulate within the range of one of, 5 Hz-15 Hz, 10 Hz+20 Hz, 40 Hz+/−10 Hz, or 40 Hz+/−20 Hz. The first light can flicker. The second light can flicker. The light that is providing the ocular photo-bio-stimulation treatment or therapy can be 300 lux or more, 700 lux or more, 1000 lux or more, or 5,000 lux or more. The light that paints the peripheral retina can target rods. The light that paints the peripheral retina can target ganglion cells. The light that paints the peripheral retina can target amacrine cells. The light that targets the macula or fovea can target mitochondria. The XR device can provide light within the wavelength range 650 nm+/−30 nm, 700 nm+/−30 nm, or 830 nm+/−30 nm, for increasing the number of healthy mitochondria within the eye.

In still other embodiments of XR for the purposes of treating the fovea or macula, the light used for the treatment can be of a light wavelength not visible to the human eye, such as, by way of example only, 830 nm+/−30 nm. The second image can be that of black or dark grey. By using this combination, it is possible to have the pupil naturally dilate for darkness while the ocular photo-bio-stimulation treatment is taking place. In certain embodiments a mild mydriatic eye drop can be used.

Figure 56:
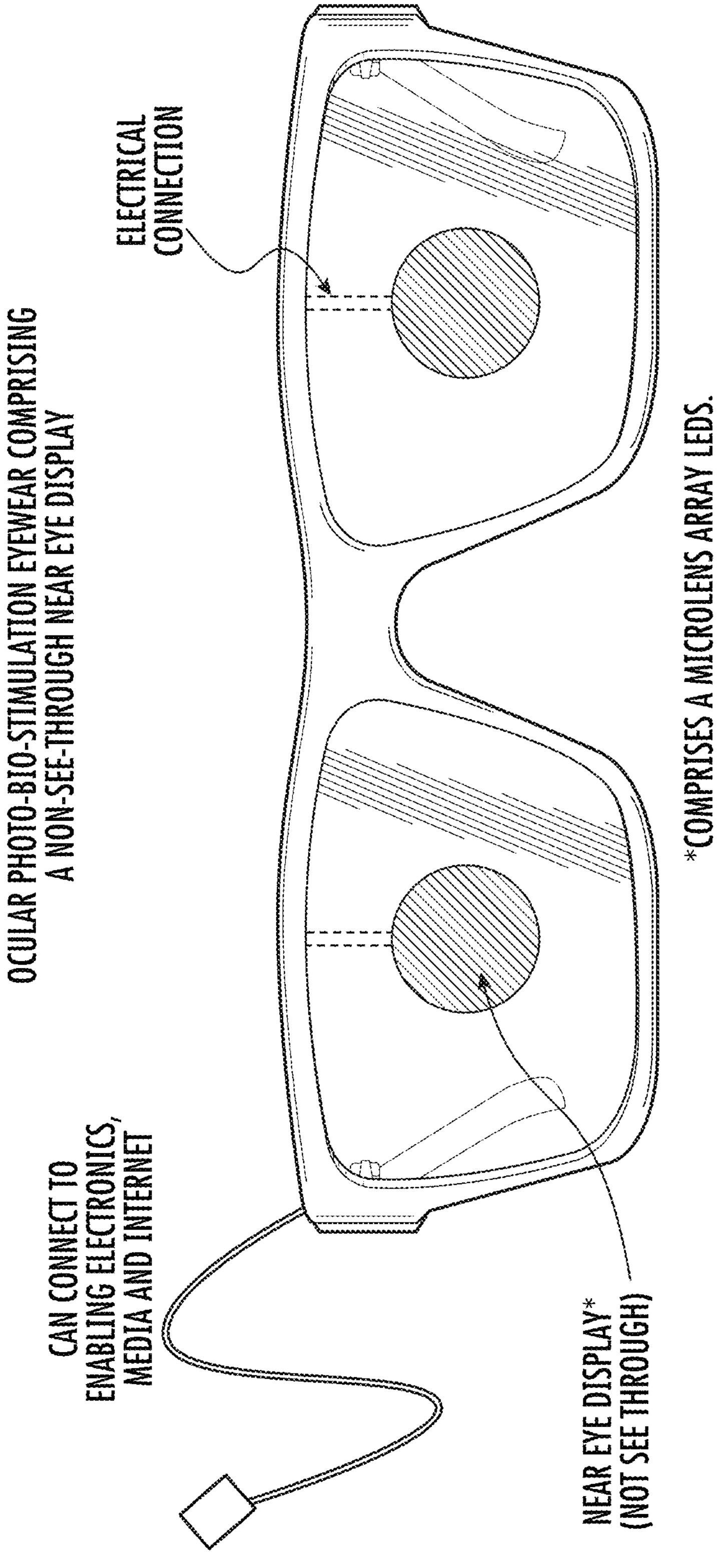
FIG. 56 shows an embodiment of the current invention as described herein.
Figure 57:
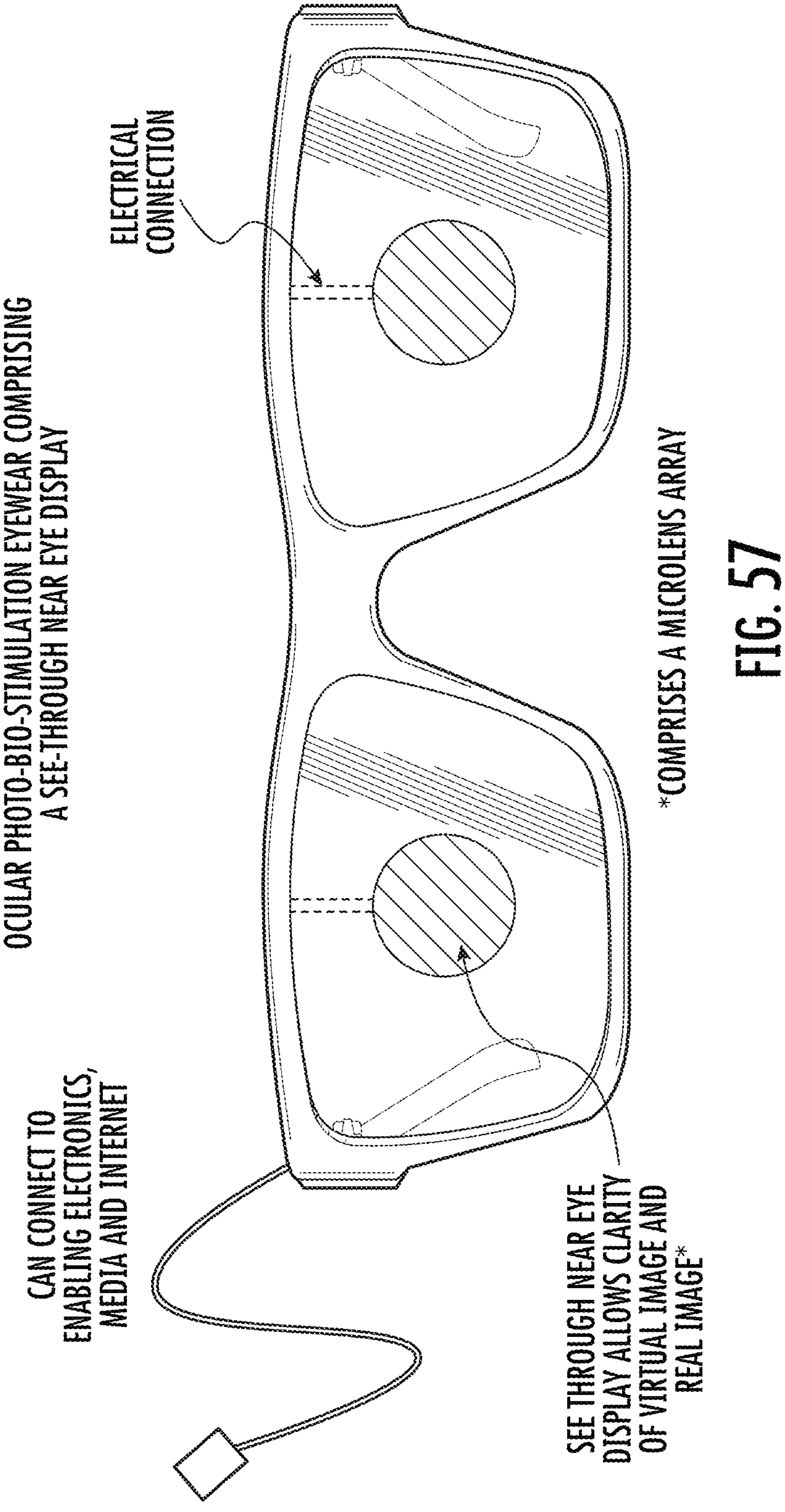
FIG. 57 shows an embodiment of the current invention as described herein.
Figure 58:
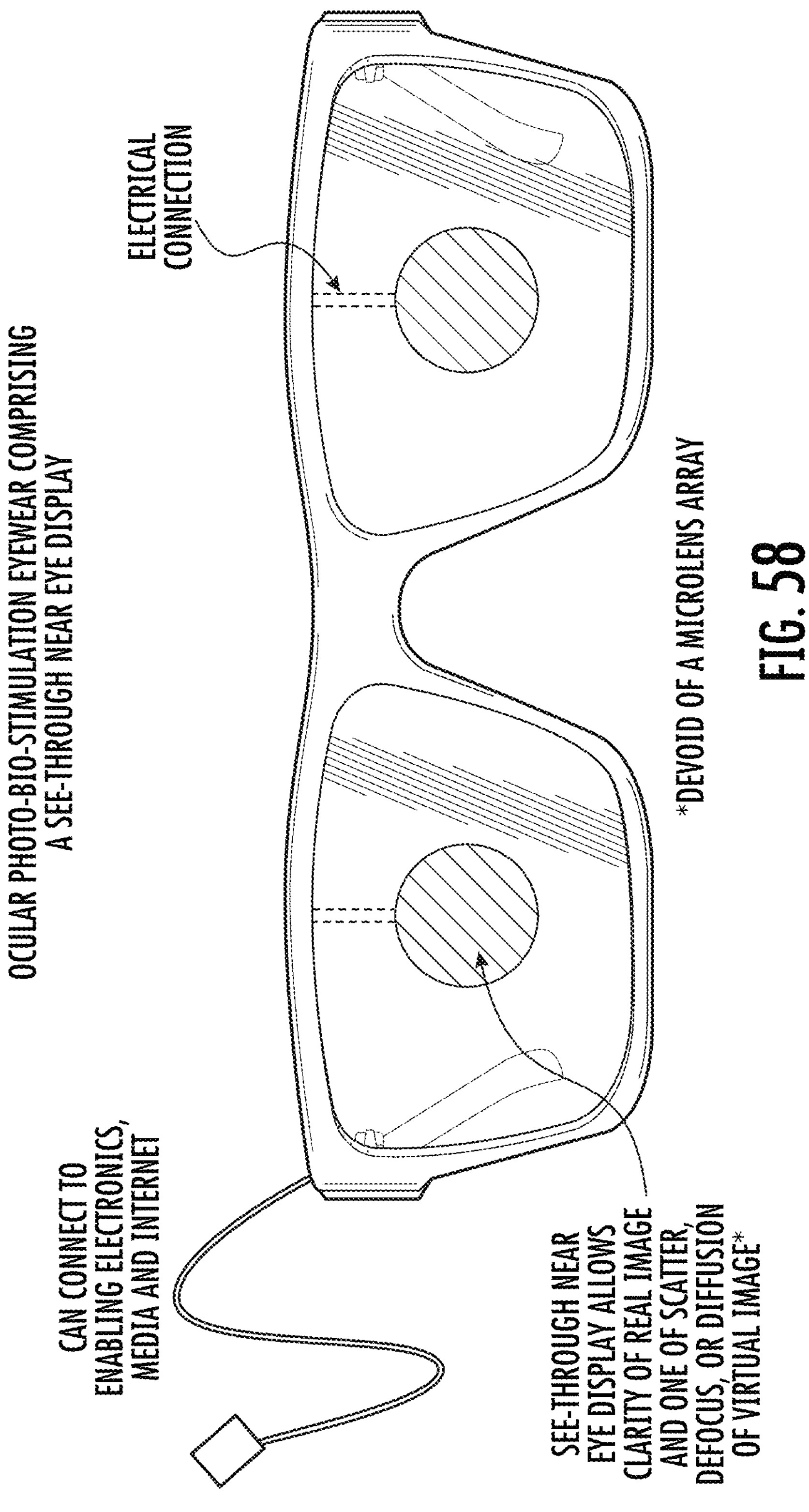
FIG. 58 shows an embodiment of the current invention as described herein.

In reference to FIGS. 56-58, the display diameter can be any dimension within the range of 10 mm to 50 mm in diameter. By way of example, the display can provide a focused or a non-focused virtual image. The view through this device is devoid of a real image. Illumination can be within the range of 300 lux to 20,000 lux. Display Pixels can be comprised by way of example one or more of: LEDs, OLEDs, TOLEDs, microOLEDs, iLeds, or quantum dots. In aspects, the device can transmit blue wavelengths within the range of 450 nm-500 nm, or 460 nm+/−20 nm, or 480 nm+/−30 nm; the device can transmit green wavelengths within the range of 520 nm+/−10 nm or 530 nm+/−20 nm; or the device can transmit red wavelengths within the range of 660 nm+/−20 nm, 630 nm+/−30 nm, or 700 nm+/−30 nm.

Such ocular photo-bio-stimulation treatments can be, by way of example only, for dry AMD. In still other embodiments of XR for the purposes of treating the fovea or macula, the light used for the treatment can be of a light wavelength to which the human eye is caused less pupil constriction, such as, by way of example only, 650 nm-700 nm. The second image can be that of black or dark grey. By using this combination, it is possible to have the pupil less constricted while the ocular photo-bio-stimulation stimulation treatment is taking place. Such treatments can be, by way of example only, for dry AMD.

In still other embodiments of XR for the purposes of treating a degenerative condition in the peripheral retina (including the far periphery), such as by way of example only, retinitis pigmentosa or diabetic retinopathy, a first moving image (which can be a black or dark grey image) being fixated on by the fovea which moves relative to the second image, while the second image which is used for the treatment can be of light wavelengths to which the human eye causes less pupil constriction, such as, by way of example only, 650 nm-700 nm. This allows for the second image or light to paint the peripheral retina as the eye moves. By using this combination, it is possible to have the pupil less constricted while the ocular photo-bio-stimulation treatment is taking place. It is worth noting that this inventive embodiment permits a light source or lighted image to treat the peripheral retina while not stimulating, treating, or harming the fovea or macula. To further enhance peripheral stimulation coverage the second image can comprise defocused light.

In still other embodiments of XR for the purposes of treating a degenerative condition in the peripheral retina, such as by way of example only, retinitis pigmentosa or diabetic retinopathy, a first moving image being fixated on by the fovea which moves relative to the second image can be a black or dark grey image, while the second image which is used for the treatment can be of light wavelengths to which the human eye does not see, such as, by way of example only, 830 nm+/−30 nm. This allows for the second image or light to paint the peripheral retina as the eye moves. By using this combination, it is possible to have the pupil mostly dilated while the ocular photo-bio-stimulation treatment is taking place. To further enhance peripheral stimulation coverage the second image can comprise defocused light.

As used herein a band is a band of light wavelengths that run concurrently with a beginning wavelength and ending wavelength. A transmission peak is the peak light wavelength or wavelengths having the highest light transmission that fall within a band of light wavelengths. As used herein, an image can be generated by light or by the absence of light (in the case of a black image). As used herein the term eyewear can be any eyewear that is used on, in, or about the eye of the user of the eyewear. By way of example only, eyewear can be any of dress eyewear, designer eyewear, safety eyewear, industrial eyewear, military eyewear, shooting eyewear, driving eyewear, sunglasses, googles, face shield, helmet with face shield, or contact lenses. The light can be that of 300 lux or more. The light can be that of 700 lux or more. The light can be that of 1000 lux of more.

As used herein, black can be a color. As used herein black can be generated by a plurality of colored pixels. As used herein black can be generated by a devoid of light or lack of light. The term paint as used herein means that light wavelengths strike and stimulate areas of the retina of one's eye as either the eye moves relative to a light, or the light moves relative to the eye. The use of the word target means to aim for the purposes of striking. Ocular photo-bio-stimulation as used herein comprises the use of light for the purposes of eliciting a neurological change or response, or a physiological change.

As used herein, an XR device can comprise lenses of optical power or no optical power. As used herein an XR device can comprise a wearer's best corrected optical prescription lens or lenses. Embodiments can stimulate or provide ocular photo-bio-stimulation treatment to one or more of the three photoreceptors as desired: Cones, Rod, Ganglion Cells, including melanopsin Ganglion cells. Embodiments can provide ocular photo-bio-stimulation treatment of amacrine cells. A real image light source can be that of a plasma display, TV display, tablet display, cell phone display, computer display, electronic display, or outdoor or indoor ambient lighting. In certain embodiments the user watches a distance separated electronic display through their XR eyewear. Such a display can give off the appropriate level of light intensity. The light can be that of 300 lux or more. The light can be that of 700 lux or more. The light can be that of 1000 lux of more. As used herein, light which stimulates any of the three photoreceptors of an eye first enters through the pupil of the eye. As used herein, light which stimulates the retina of an eye first enters through the pupil of the eye. As used herein an XR device can be that of one of AR, MR, VR, or Modified Reality eyewear, or one of AR, MR, VR, or Modified Reality contact lenses, or one of AR, MR, VR, or Modified Reality intra-ocular lens, or a combination of any of the three. In certain embodiments a prism can be added to the light or image that paints the retina prior to entering the pupil of the eye being ocular photo-bio-stimulation treated.

Embodiments of XR devices for providing ocular photo-bio-stimulation of the eye of the user can comprise appropriate safety guards. Such safety concerns can be addressed by one or more of: a timer, alarm, timed light switch, eye location sensor(s), retinal location sensor(s), cornea location sensor(s), and/or iris location sensor(s). A timer can be set by either the user, automatically by the software for the XR device, or by a remote professional monitoring the treatment approach of the user. An alarm being that of a light, sound, or vibration, can alert the user to turn off or take off the XR device. The light or lights which provide the ontogenetic stimulation can be timed to turn off after a set time. This set time can be set by either the user, automatically by the software for the XR device, or by a remote professional monitoring the treatment approach of the user. The location of retinal stimulation can be monitored by way of one or more of: cornea light reflex location sensor(s) or iris light reflex location sensor(s). The sensors can include a camera. The intensity of the light source and image can be monitored to ensure that the appropriate intensity of the ocular photo-bio-stimulation treatment is being provided.

Such monitoring can be checked by the user or remotely by a third party. The wavelengths of light being provided for the ocular photo-bio-stimulation treatment can be monitored by the user or by a remote third party. The ability to monitor a specific area of the retina being painted or stimulated can be confirmed and calibrated for the XR device in advance of being dispensed for a user to use remotely from that of the eye care professional, neurologist, physician or other technician or professional. Such calibration can be performed individually for each user of an XR device. The use of the XR device by the user can be communicated in real time to the monitoring professional or remote third party. The use of the XR device by the user can be communicated periodically to the monitoring professional. This allows for a remote third party to monitor the user's compliance with the ocular photo-bio-stimulation treatment. Messages can be communicated from the monitoring professional or remote third party to the user of the XR device by way of an image shown or displayed on the XR device. Messages can be communicated from the monitoring professional or remote third party to the user of the XR device by way of sound or audio heard from the XR device. The communication from the XR device to the professional or from the professional to the XR device can be provided by way of wired or wireless communication. Such communication can be in part or whole by way of the internet.

The XR device can comprise all required electronics for enabling the use of the XR device as well as any form of communication needed. Downloaded software can provide updated treatment programs. Such programs can affect the user experience, the treatment procedure or protocol, and/or the mechanical operation of the XR device. The XR device can comprise all required electronic components to accomplish any one or all the preceding XR device modalities of use or performance.

An embodiment of a biomarker (by way of example only) can be that of causing blue light (within the wavelengths of 480 nm+/−30 nm) to strike the eye's retina of a subject. If the subject's pupil enlarges this can be a biomarker that additional dopamine is being generated in the subject's brain. One of the embodiments of this invention is by monitoring the pupil diameter of the eye(s) of the subject being treated it is possible to objectively tell that the desired ocular photo-bio-stimulation effect is occurring either in one or more of the eye, the body or the brain of the individual being treated with light. By way of example only, an ocular photo-bio-stimulation treatment of the retina of eye of the subject being treated can be stopped when the pupil diameter shows an increase in size/diameter. Such monitoring can be accomplished, by way of example only, by a vision system, pupilometer, handheld measurement tool, corneal topographer that captures dimensions of pupil, or device comprising one or more IR sensors.

The method can first measure the patient pupils prior to or at the start of the ocular photo-bio-stimulation treatment and immediately either before or after ceasing the ocular photo-bio-stimulation treatment. In certain cases, the ocular photo-bio-stimulation treatment can be stopped within a period of time after the enlargement of the wearer's pupils first occurs. Such a measurement device or components can be built into, be attached to, or separately used to monitor the enlargement of the pupil of the subject. In certain cases, the device can automatically communicate an alarm once the pupil is enlarged. The alarm can be that of a sound, voice, vibration, or light signal. By way of example only, eyewear, smart eyewear, or XR eyewear can comprise a means to detect and measure the blink rate of a subject that wears such eyewear in response to ocular photo-bio-stimulation treatment.

Another bio-marker embodiment can be that of utilizing a subject's blink rate. If the subject's blink rate increases after (by way of example only) blue light (within the wavelength range of 480 nm+/−30 nm) is utilized to strike the subject's retina, the result can be that of a biomarker that dopamine is being generated in the subject's brain. Once again this can be monitored and measured objectively. Such measuring equipment for blink rate, by way of example only, includes computerized vision system that monitors the eye and lids, eyewear or equipment having light or lights that shine on the cornea to generate a corneal light reflection and sensors that measure the on off of the reflection coming from the cornea, or certain eye tracking instruments.

The method can first measure the subject's blink rate prior to or at the start of the ocular photo-bio-stimulation treatment and immediately either before or after ceasing the ocular photo-bio-stimulation treatment. In certain cases, the ocular photo-bio-stimulation treatment can be stopped within a period of time after the enlargement of the subject's blink rate first occurs. Such a measurement device or components can be built into, be attached to, or separately used to monitor the blink rate of the subject. In certain cases, the device can automatically communicate an alarm once the blink rate increases from the base line measured prior to the ocular photo-bio-stimulation treatment. The alarm can be that of a sound, voice, vibration, or light signal. By way of example only one of, eyewear, smart eyewear, or XR eyewear can comprise a means to detect and measure the blink rate of a subject that wears such eyewear in response to ocular photo-bio-stimulation treatment.

The XR ocular photo-bio-stimulation embodiments disclosed herein can utilize all required enabling components. By way of example only, eye tracking, vision measurement/monitoring system, see-through near eye display, near eye display, microlens array, filters, filter lens(es), lens(es) comprising the wearer's proper correction for his or her distance refractive error, chromatic aberration correcting lens comprising a power increase within the range of −0.35 D to −5.00 D additional increase in minus power peripheral to the central zone of the lens, timer, appropriate additional XR hardware (AR, MR, VR) such as by way of example only, controller, CPU, rechargeable battery, ability to be wired or wireless to one's cell phone or mobile phone. The embodiments disclosed herein can utilize all required software and communication components such as by way of example only, Wi-Fi and/or Bluetooth.

In certain ocular photo-bio-stimulation XR embodiments when looking at an electronic display screen (by way of example only, a large thin plasma screen, OLED screen, iLED screen, or LED screen), software can be downloaded to the AR or MR device and or the electronic display screen, or to a VR device. In certain embodiments software in the form of, by way of example only, one or more YouTube videos can be created so that when loaded or communicating to the remote electronic display screen it shows movement of an image or images to be in coordination with the AR or MR device. In certain embodiments software in the form of, by way of example only, one or more YouTube videos can be created so that when loaded or communicating to the AR or MR device that is worn, the AR or MR device shows movement of an image or images to be in coordination with the electronic display screen. And still in other cases software in the form of, by way of example only, YouTube videos can be downloaded or communicated to each the AR or MR device and the remote electronic display screen.

In certain ocular photo-bio-stimulation XR embodiments comprising a near eye display, the microarray can cause light to become defocused when it strikes the retina. This can occur by focusing in front of the retina or behind the retina.

In other XR embodiments comprising a near eye display, the microarray can cause light to focus within the retina. In certain XR embodiments the correcting lens for myopia can focus centrally for far vision, and peripheral to the central zone causing a defocus or light scatter. In certain XR embodiments the correcting lens for myopia can focus centrally for far vision and peripheral to the central zone causing the band of blue light wavelengths to strike the retina as opposed to conventional lenses having chromatic aberration where the blue light wavelength band focuses in front of the retina. As used herein when an image (virtual or real) is referred to, it is the light that forms the image that provides the ocular photo-bio-stimulation treatment. So, an image should be thought of as a light, or lack of a light when a black image.

Ocular photo-bio-stimulation XR eyewear can comprise a see-through near eye display without a microlens array, a non-see-through near eye display without a microlens array, see through near eye display with a microlens array, and/or a non-see-through near eye display with a microlens array. Such a microlens array permits with AR and MR the virtual image of a near eye display to be seen clearly. Without a microlens array the virtual image will be one or more of, out of focus, scattered, or dispersed. For the purposes of spreading light within a desired wavelength band across the retina, using the device with or without a micro lens array can work. The same is true with VR, however with VR both virtual images without a microlens array would appear out of focus, scattered, and/or dispersed. However, with a microlens array the virtual images will appear clear.

In reference to FIGS. 56-58, the see-through near eye display and the non-see-through near eye display can be comprised with a curved electronic display and a curved microlens array. A near eye display can be curved. The see-through near eye display and the non-see-through near eye display can be comprised with a flat electronic display and a flat microlens array. A near eye display can be flat. The eyewear can comprise a see-through near eye display. The eyewear can comprise a non-see-through near eye display. The display can comprise or be in optical alignment with a micro-lens array. The display can transmit the desired wavelengths of light through the micro-lens array and in focus for seeing a virtual image clearly. The display can be devoid of a microlens array. The microlens array can transmit the desired wavelengths of light and cause light defocus or light scatter. The display can transmit the desired wavelengths of light and cause light defocus or light scatter. The eyewear that supports AR, MR, VR, or Modified Reality components can be wrapped around eyewear. The eyewear that supports AR, MR, VR, or Modified Reality components can be conventional around eyewear. The eyewear that supports AR, MR, VR, or Modified Reality components can comprise side shields for the purposes of blocking peripheral light rays.

Figure 59A:
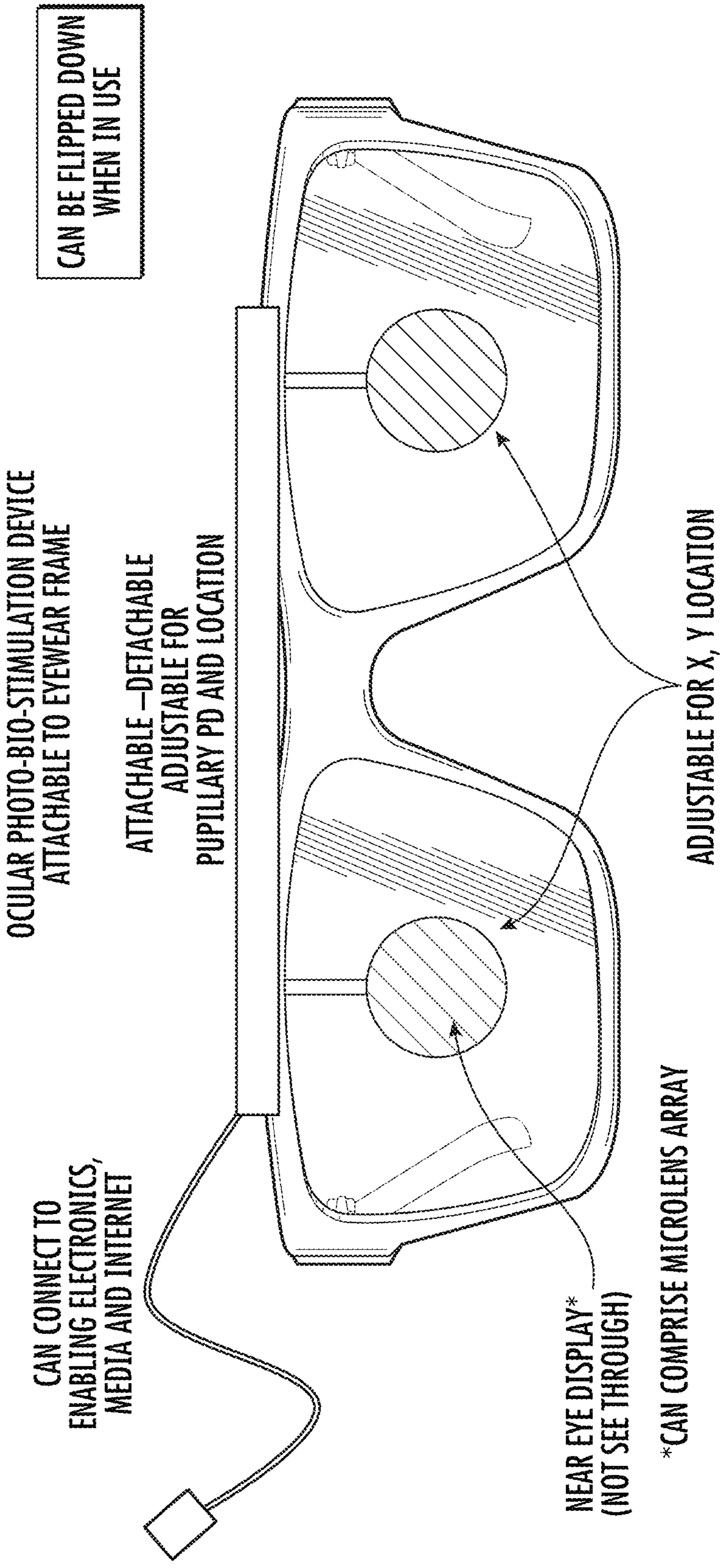
FIG. 59A-B shows an embodiment of the current invention as described herein.
Figure 59B:
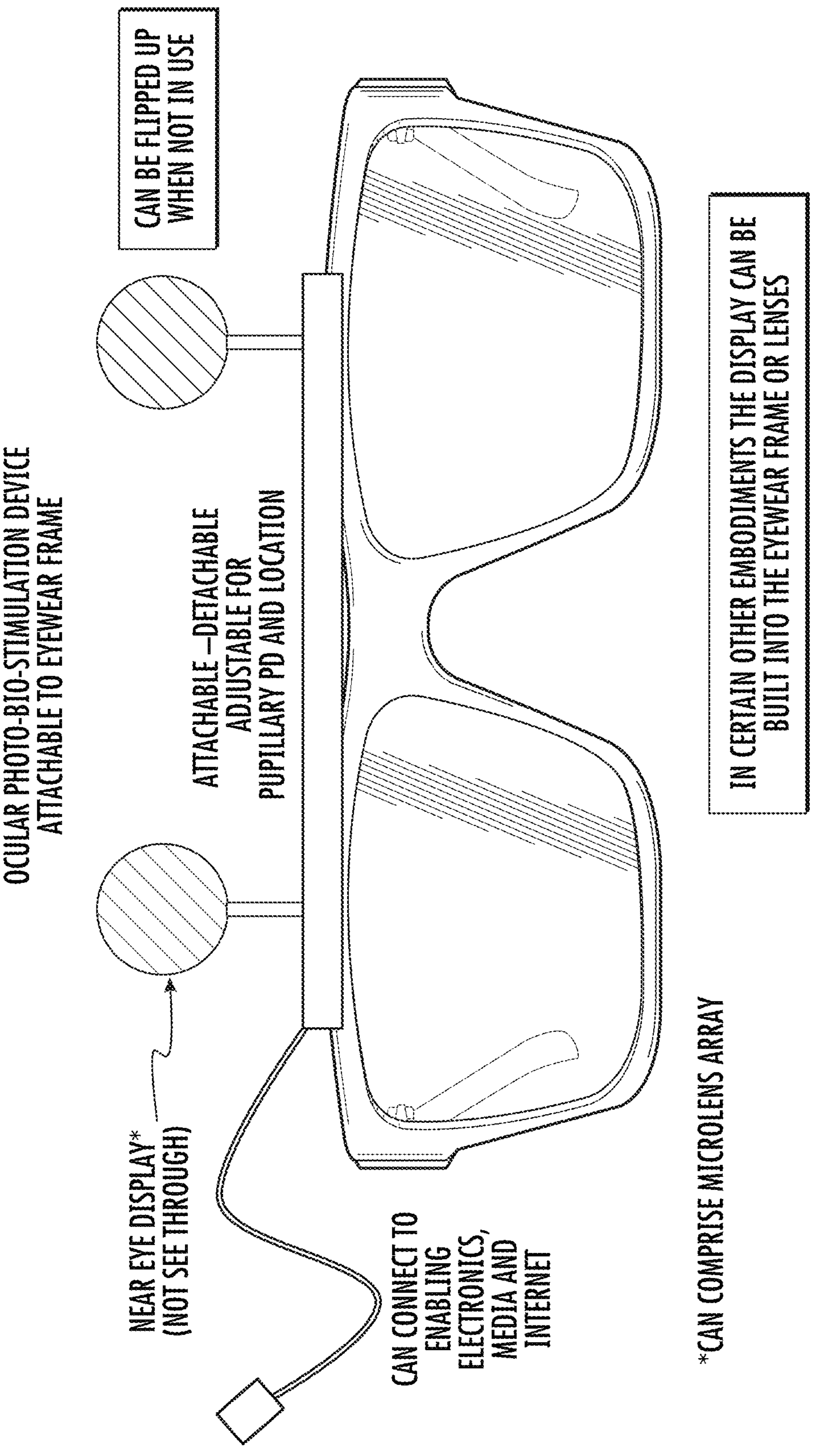
Figure 60A:
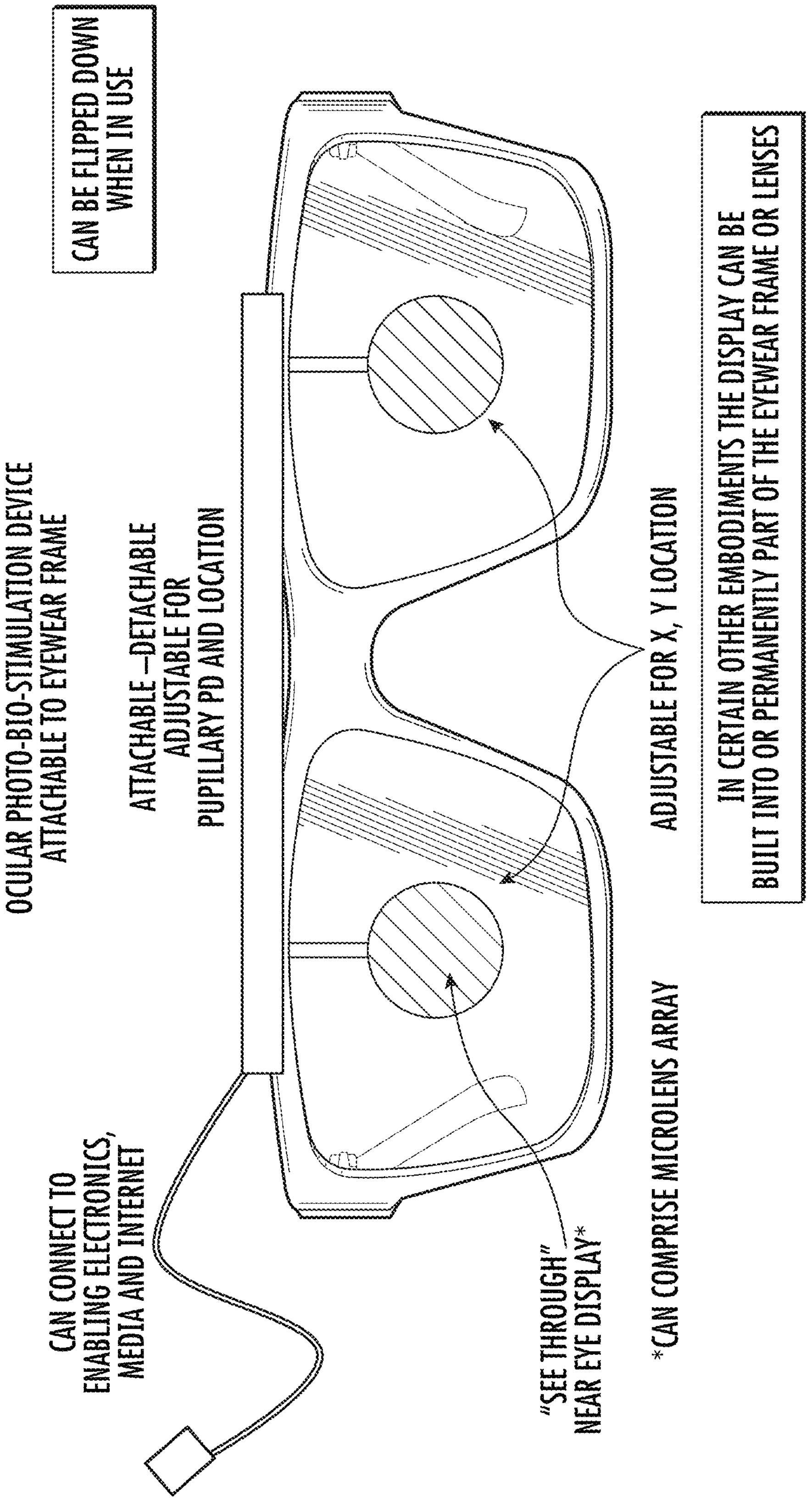
FIG. 60A-B shows an embodiment of the current invention as described herein.
Figure 60B:
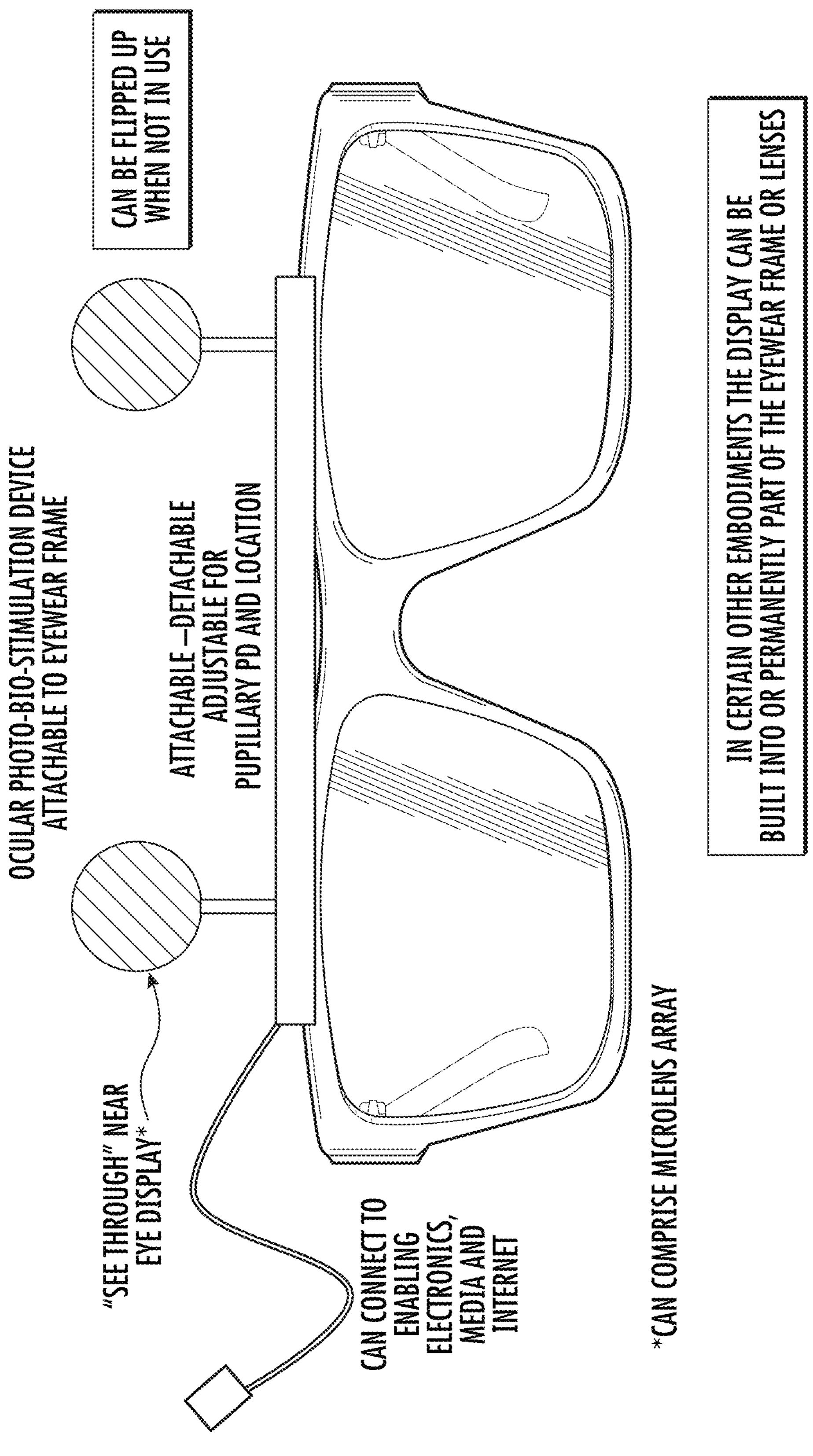

In reference to FIGS. 59A and 60A, the display diameter can be any dimension within the range of 10 mm to 50 mm in diameter. By way of example, the display can provide a focused or a non-focused virtual image. The view through this device is devoid of a real image. Illumination can be within the range of 300 lux to 20,000 lux. Display Pixels can be comprised by way of example, one of: OLEDs, TOLEDs, microOLEDs, iLeds, or quantum dots. In certain embodiments the XR device is attachable and detachable to one's conventional eyeglasses. Such an attachable XR device (one of AR, MR, VR, or Modified Reality) can be adjustable to align with the wearer's pupils. Such a device can comprise a means so that the near eye displays can be rotated out of position when not being used. The see-through near eye display and the non-see-through near eye display can be comprised with a flat electronic display and a flat microlens array. A near eye display can be flat. The XR device can comprise a see-through near eye display. The XR device can comprise a non-see-through near eye display. The display can comprise or be in optical alignment with a micro-lens array. The display can transmit the desired wavelengths of light through the micro-lens array and in focus for seeing a virtual image clearly. The display can be devoid of a microlens array. The microlens array can transmit the desired wavelengths of light and cause light defocus or light scatter. The display can transmit the desired wavelengths of light and cause light defocus or light scatter. (See, FIGS. 59B and 60B.) The see through near eye displays can be flipped out of position so not to be in the way of the wearer's line of sight when not XR ocular photo-bio-stimulation is not being used.

The moving fixation target can be that of a dot, circle or similar shape. In aspects, the size of the target is no larger than the size of the user's macula calculated and enlarged for the distance from the macula of the eye of the user to that of where the virtual image is located along the Z axis in space. The average size of the macula of the eye is approximately 5 mm in diameter.

With certain ocular photo-bio-stimulation VR or Modified Reality embodiments, when a central vision virtual fixation target moves, it will move across or within another virtual image comprising the wavelengths of light desired for painting the peripheral retina or retinas of the user. With certain AR, MR, or Modified Reality embodiments, the central vision fixation target could be a real image that moves, in which case it would be the virtual image that paints the desired wavelengths on the peripheral retina or retinas of the AR, MR, Mixed Reality wearer/user, or with AR, MR, Mixed Reality, the central vision fixation target could also be that of a virtual image that moves, in which case it would be the real image which paints the desired wavelengths on the peripheral retina or retinas of the wearer/user. Depending upon the ocular photo-bio-stimulation physiological effect desired, either the virtual image or the real image can paint the peripheral retina with light wavelengths within the wavelength range of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, while the eye of the wearer/user centrally fixates on a moving target. By way of example only, for increasing dopamine in the eye's retina and the brain, blue light wavelengths within the range of 480 nm+/−30 nm can be used to paint the peripheral retina while the central region of the wearer/user's eye is fixated on a moving black or grey dot.

As used herein the peripheral retina is retina that is peripheral to the outer edge of the central retina. As used herein the central retina would be that of the macula. Furthermore, the peripheral retina can be further subdivided into that of the mid peripheral zone and the far peripheral zone. For the purposes of this disclosure when stating periphery or peripheral to the central zone this would include all retina peripheral to the central zone thus the term peripheral retina can also include all or some of the mid periphery and or far periphery.

In embodiments where the ocular photo-bio-stimulation treatment is intended for treating the central region of the retina of an eye or that of the fovea and/or macula, the desired wavelengths can be applied whether the central image is that of a moving image or a fixed still image, so long as the eye of the wearer/user remains fixated at the target that is applying the light stimulation. By way of example only, when central fixation is fixed on either a moving target or that of a fixed stationary (fixation) target, 650 nm+/−30 nm can be applied for treating dry macular degeneration. For VR or Modified Reality, the fixation target would be one of the virtual images. For AR, MR, or Mixed Reality, the fixation target could be that of a real image or a virtual image. As used herein the peripheral retina is retina that is peripheral the outer edge of the central retina In certain XR ocular photo-bio-stimulation embodiments, the light/image that is painting the peripheral retina can be wavelengths within the wavelength range of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm. The light/image that acts as the fixation target can be preferably a color of black, grey, or red. While any colored fixation target can be used, by using black, grey or red as the fixation target (whether moving or stationary) the pupil of the wearer's eye can remain larger in size as compared to using yellow, blue, orange, or white, for the fixation target. It is also preferable in embodiments that the fixation target is a distance fixation target so it does not cause an accommodative pupil constriction, thus keeping the pupil diameter as large as possible.

In certain XR ocular photo-bio-stimulation embodiments, in addition to with VR or Modified Reality the two virtual images moving relative to one another, or with AR, MR or Modified Reality, the virtual image moving relative to the real image, the ocular photo-bio-stimulation XR (one of AR, MR, VR, or Modified Reality) embodiment can comprise a defocusing lens or a prism optic. In certain XR (one of AR, MR, VR, or Modified Reality) ocular photo-bio-stimulation embodiments, in addition to with VR, or Modified Reality, the two virtual images moving relative to one another, or with AR, MR or Modified Reality, the virtual image moving relative to the real image, the ocular photo-bio-stimulation XR embodiment can comprise a moving or rotating mirror that further enhances the painting of the peripheral retina of the user/wearer. Such a mirror can be a pin mirror. In certain embodiments multiple mirrors can be utilized. Still in other XR ocular photo-bio-modulation embodiments, in addition to with VR or Modified Reality, the two virtual images moving relative to one another, or with AR, MR or Modified Reality, the virtual image moving relative to the real image, the ocular photo-bio-stimulation XR embodiment can comprise a moving or rotating mirror and a defocusing lens or a prism optic that further enhances the painting of the peripheral retina for the user/wearer.

The average monocular visual field consists of central vision, which includes the inner 30 degrees of vision and central fixation, and the peripheral visual field, which extends to 100 degrees laterally, 60 degrees medially, 60 degrees upward, and 75 degrees downward. An estimated 20%-30%% of a monocular retina is not stimulated when fixated on a stationary distance object straight ahead. While binocular vision increases the size of the visual field, it does not increase the amount of light stimulation of the retina of each eye. Three different embodiments follow: move the eye relative to the light source, the light source relative to the eye, or the eye and the light source relative to each other.

The inventive embodiment which utilizes one light source being fixated while the other light source paints the retina permits approximately an additional 20%-30% of each retina to be stimulated or treated with light of the appropriate wavelength. In the case of treating myopia, it is light wavelengths within the range of 480 nm+/−30 nm, 450 nm-500 nm, or 650 nm+/−30 nm. In the case of treating retinitis pigmentosa or diabetic retinopathy it is wavelengths within the range of 650 nm+/−30 nm, 700 nm+/−30 nm or 830 nm+/−30 nm.

Different Inventive ocular photo-bio-stimulation XR embodiments disclosed herein permit stimulation or treatment with light of all regions of the retina including, fovea, macula, optic nerve head, mid periphery and most of the far-periphery. This allows for ocular photo-bio-stimulation light treatment for each of the three photoreceptors (as desired); Cones, Rods, and/or ipRGC Ganglion Cells.

In the case of treating myopia with ocular photo-bio-stimulation, the entire retina, or a portion of the retina, or the optic nerve head, can be stimulated or treated with light within the range of light wavelengths of 480 nm+/−30 nm, 650 nm+/−30 nm, or 700 nm+/−30 nm.

In the case of treating dry AMD with ocular photo-bio-stimulation, the fovea and a large portion of the macula can be treated with light within the range of light wavelength of 630 nm-700 nm, 650 nm+/−30 nm, or 830 nm+/−30 nm.

In the case of retina retinitis pigmentosa or diabetic retinopathy in the mid and far periphery any ocular photo-bio-stimulation treatment can be with light within the range of light wavelengths of 650 nm+/−30 nm, 700 nm+/−30 nm, or 830 nm+/−30 nm. In the case of retina retinitis pigmentosa or diabetic retinopathy in the mid and far periphery any ocular photo-bio-stimulation treatment can be with light within the range of light wavelengths of 650 nm+/−30 nm or 830 nm+/−30 nm. And in the case of treating myopia and additional dopamine deficient disorders with light, an embodiment can treat most of the retina (including the mid and far-peripheral region) or just the optic nerve head with light wavelengths within the range of 450 nm+/−30n or 650 nm+/−30 nm. Certain embodiments disclosed herein permit stimulating or treating the fovea and/or macula, but not the remainder of the retina.

In other embodiments disclosed herein the retina peripheral to the macula can be treated while the macula and fovea are not treated. In still other embodiments the most or all of the retina is treated. Treatment is that of ocular photo-bio-stimulation light treatment or therapy. The objective for treating dry AMD and/or retinitis pigmentosa and diabetic retinopathy with light is to increase the number of healthy mitochondria. The objective for treating myopia with light is to increase dopamine in the retina. This is also the case of many other dopamine disorders as by increasing dopamine in the retina, dopamine and/or serotonin can be increased in the brain.

In the case of treating dry eye with ocular photo-bio-stimulation, the use of one of the wavelength bands within the range of 630 nm-700 nm, 650 nm+/−30 nm, 700 nm+/−30 nm, or 830 nm+/−30 nm, targeting the eye lids meibomian glands can be utilized.

Figure 61:
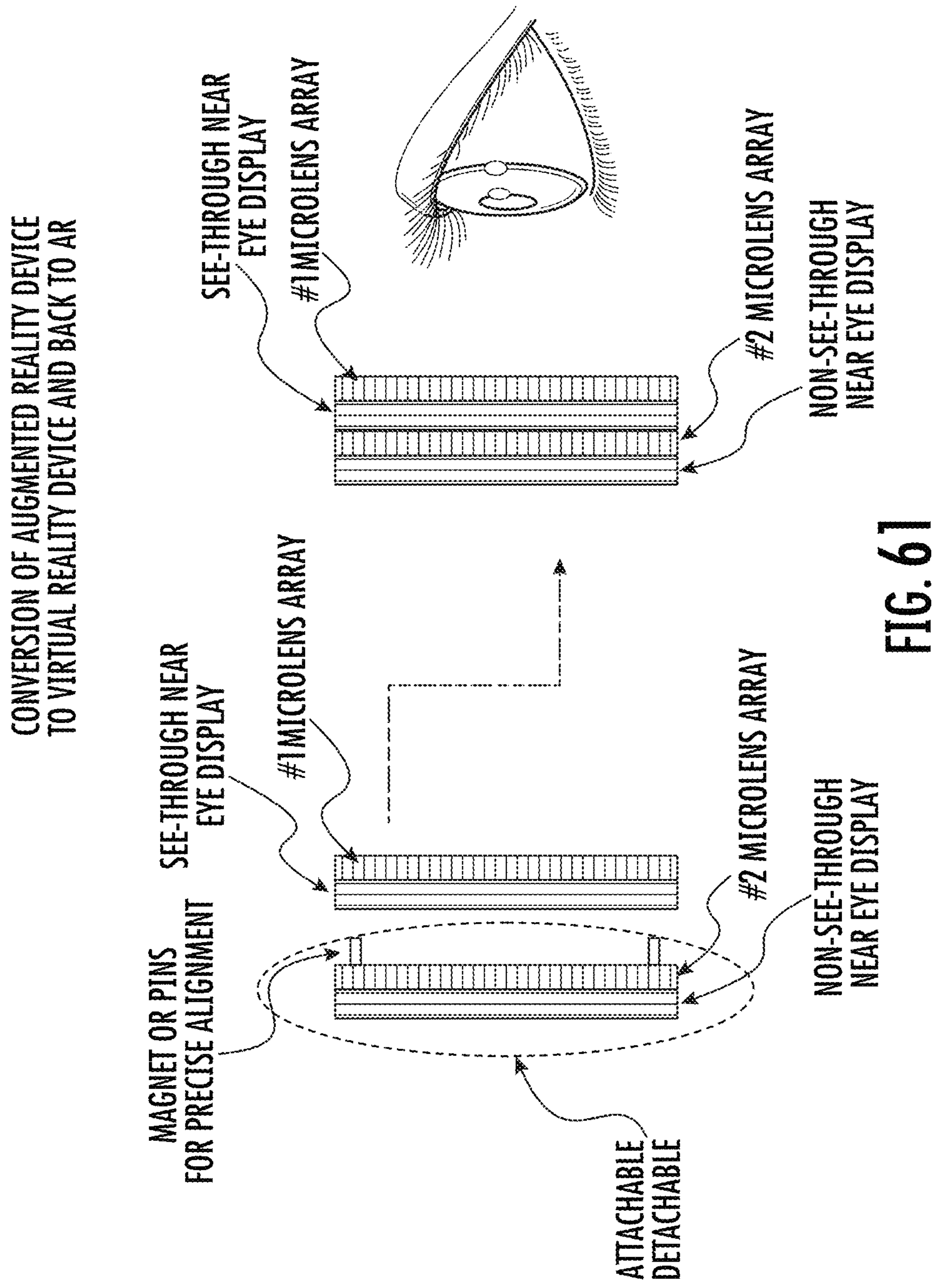
FIG. 61 shows an embodiment of the current invention as described herein.

In reference to FIG. 61, it shows a conversion of an AR device to a VR device, and back to AR. The non-see-through near eye display aligned with its microlens array can be slightly offset with the see-through near eye display and its aligned microlens array. The reason for the offset is to allow for the light generating the virtual image seen by the eye to pass between or through the pixels of the see-though near eye display. Even though there is an offset, the non-see-through near eye display, its aligned microlens array, and the see through near eye display, remain in optical communication, thus allowing light to be projected to the retina of the eye of a user.

Figure 62A:
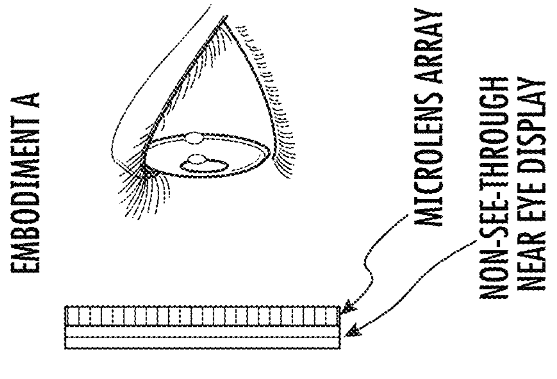
FIG. 62A-C shows an embodiment of the current invention as described herein.
Figure 62B:
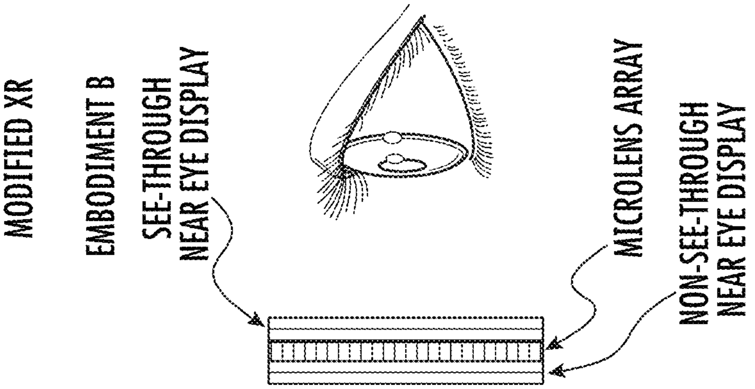
Figure 62C:
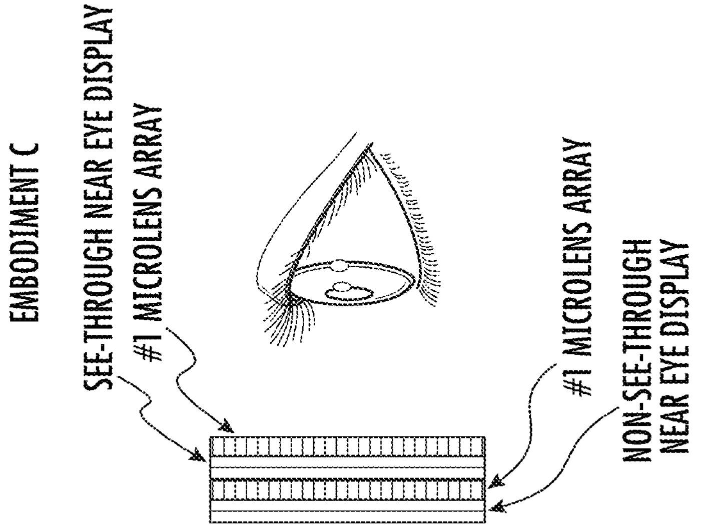
Figure 63:
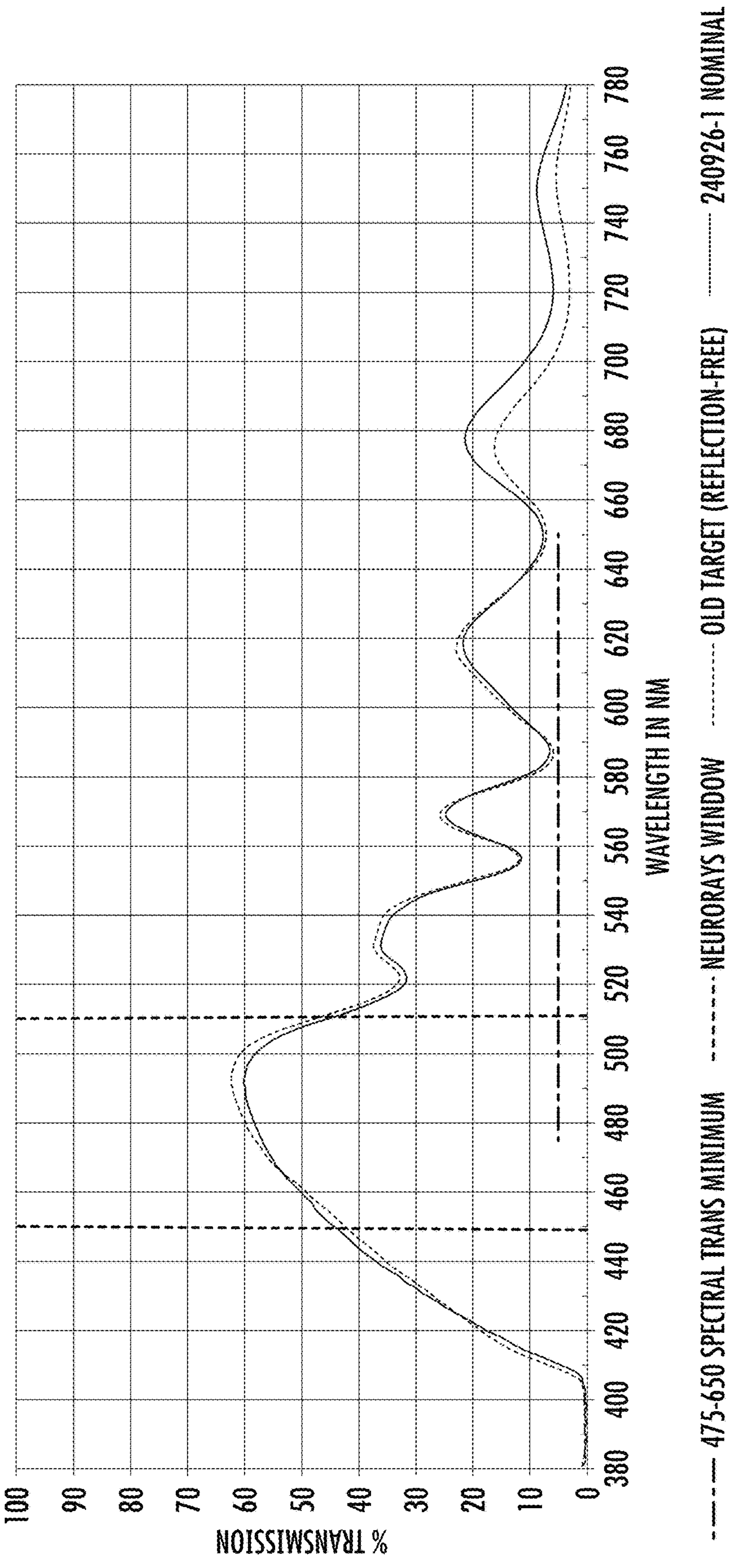
FIG. 63 is a graph showing functionality of the current invention as described herein.
Figure 64:
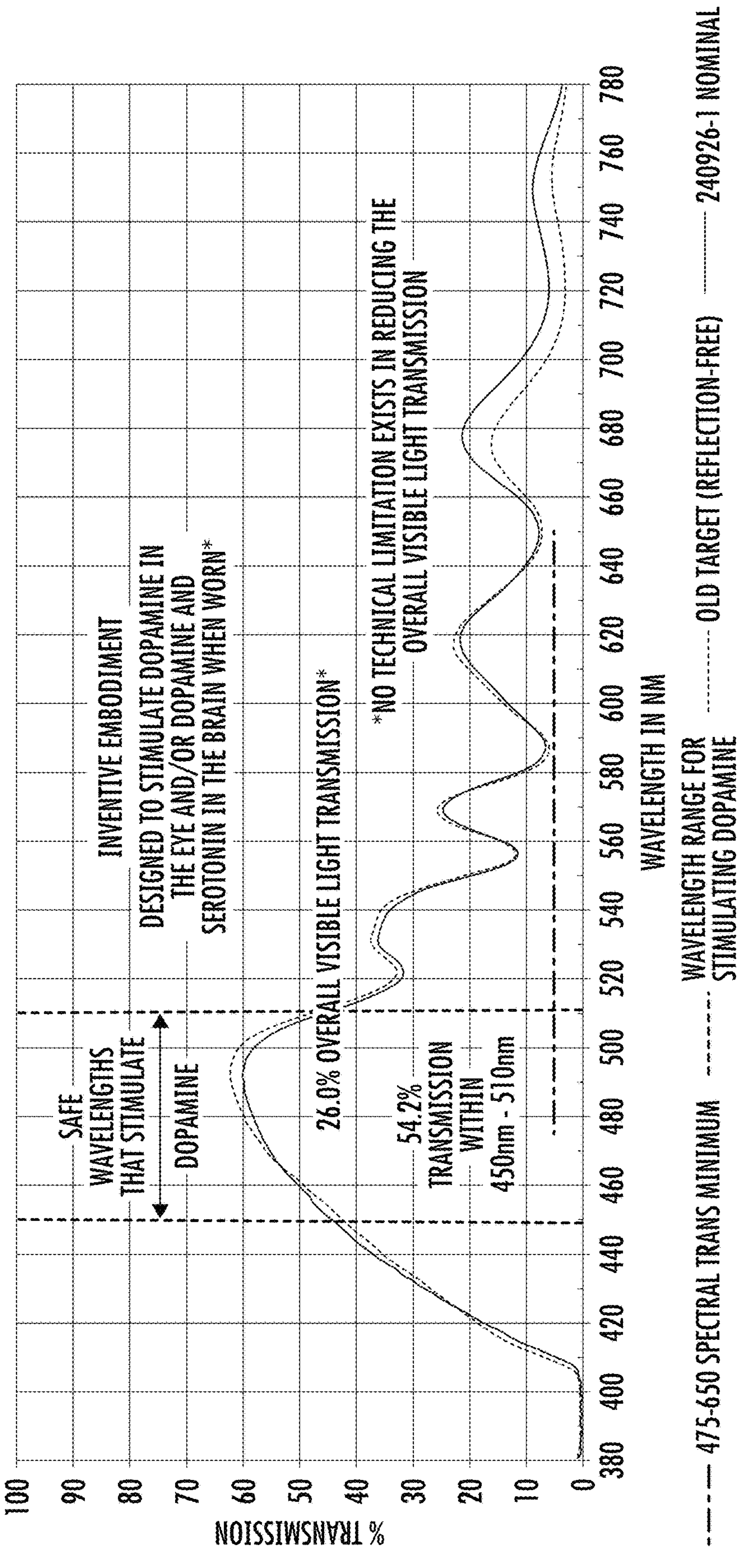
FIG. 64 is a graph showing functionality of the current invention as described herein.
Figure 65:
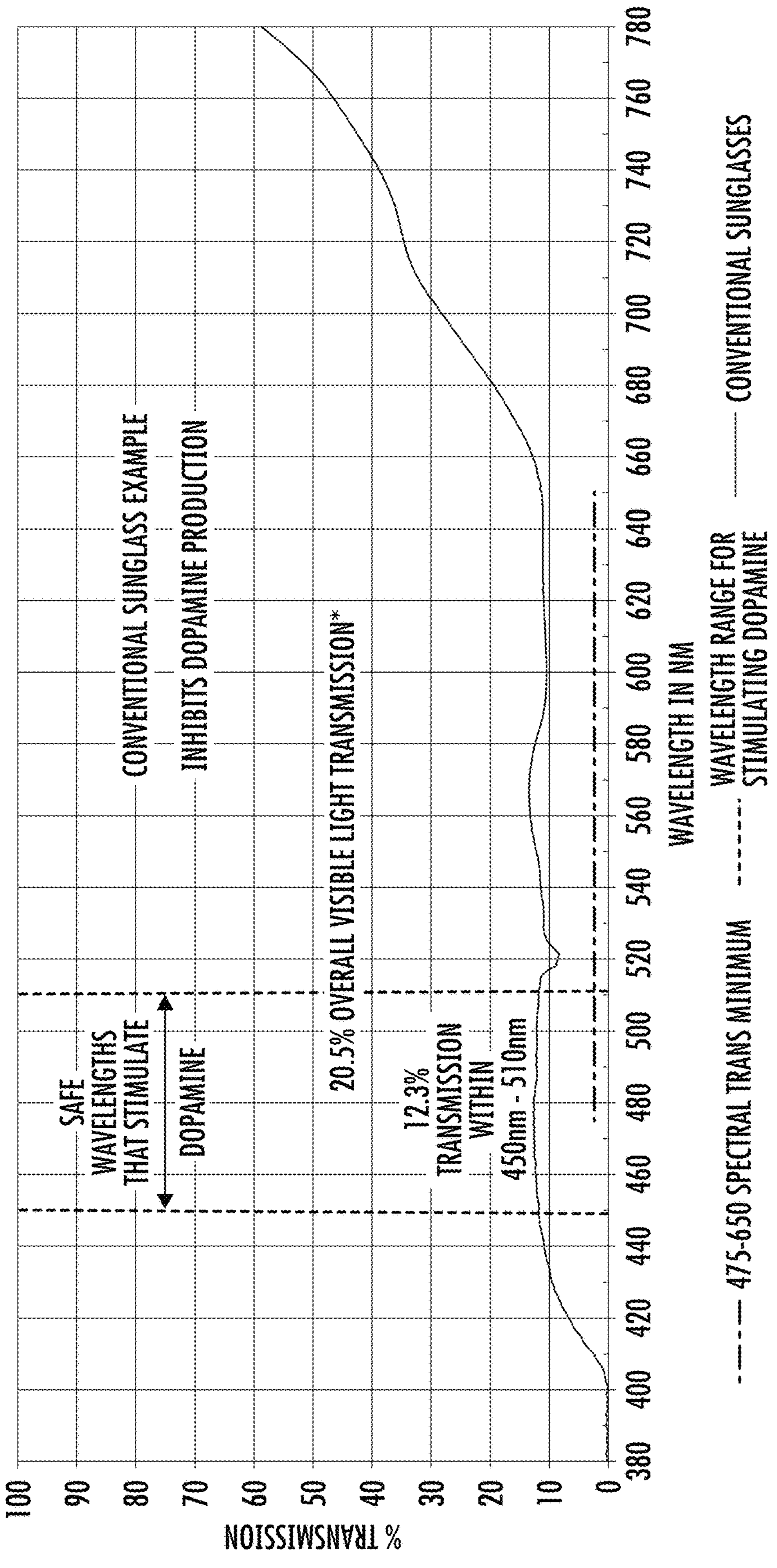
FIG. 65 is a graph showing functionality of the current invention as described herein.
Figure 66:
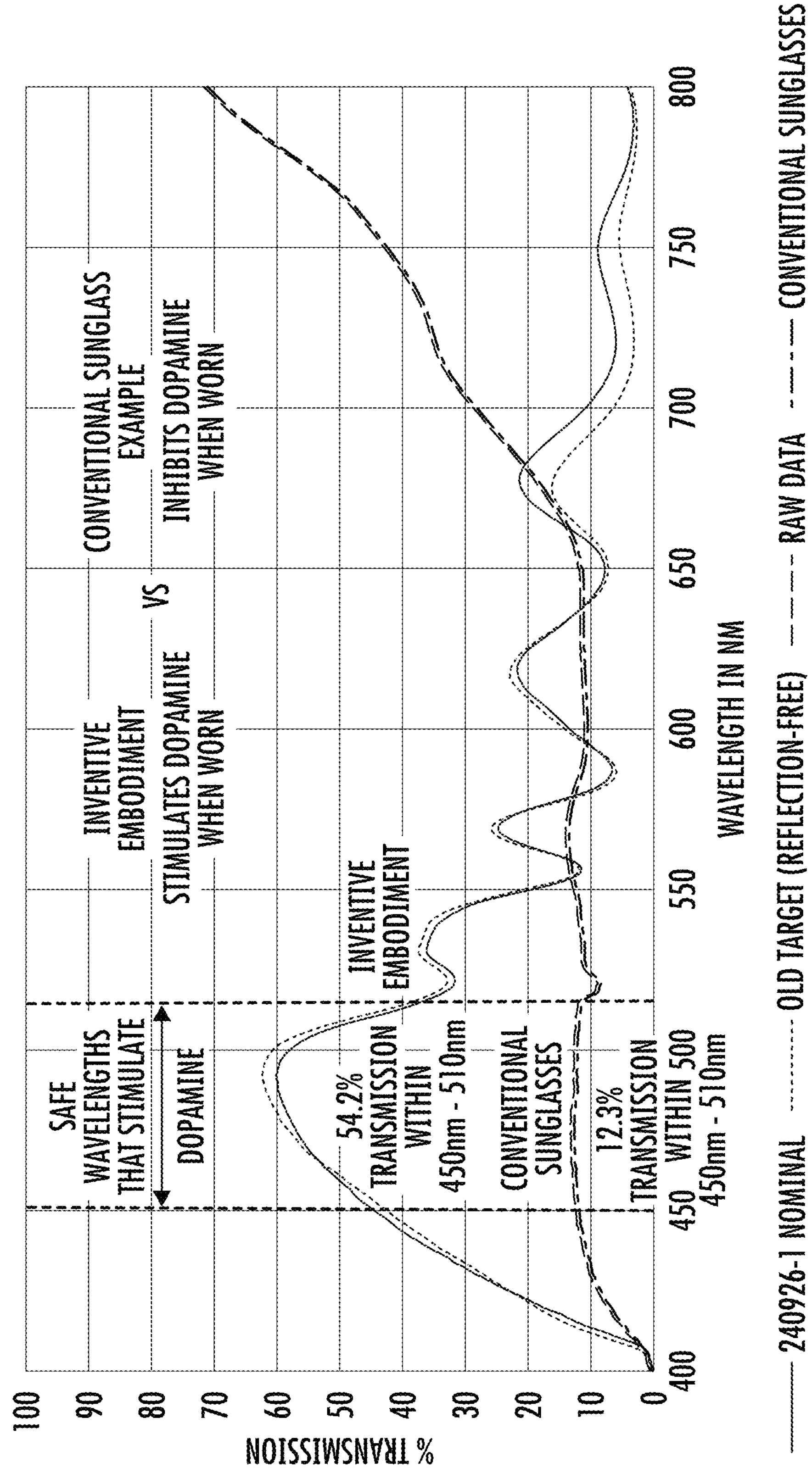
FIG. 66 is a graph showing functionality of the current invention as described herein.
Figure 67:
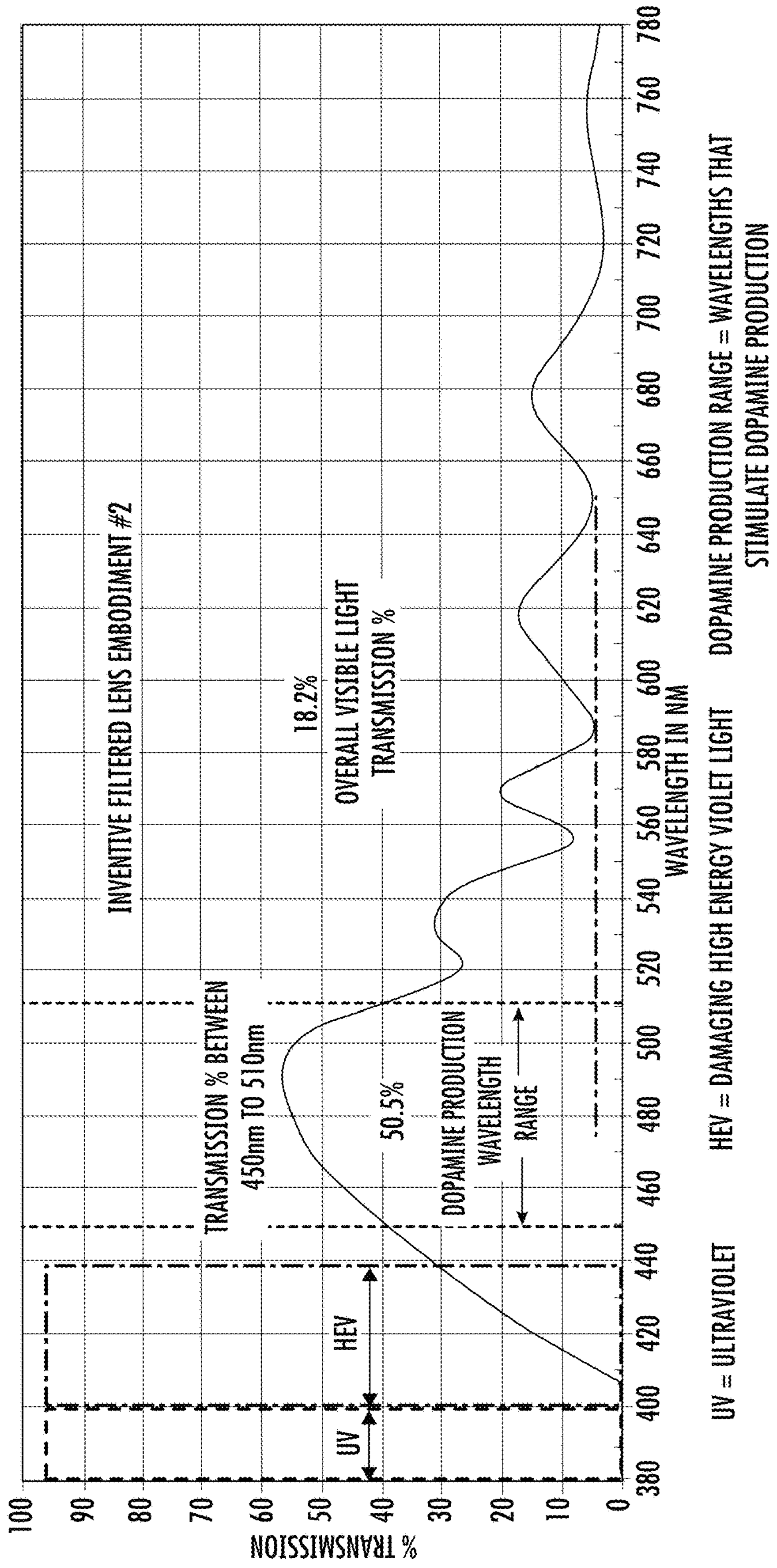
FIG. 67 is a chart showing improvements provided by the current invention over conventional eyewear.
Figure 70:
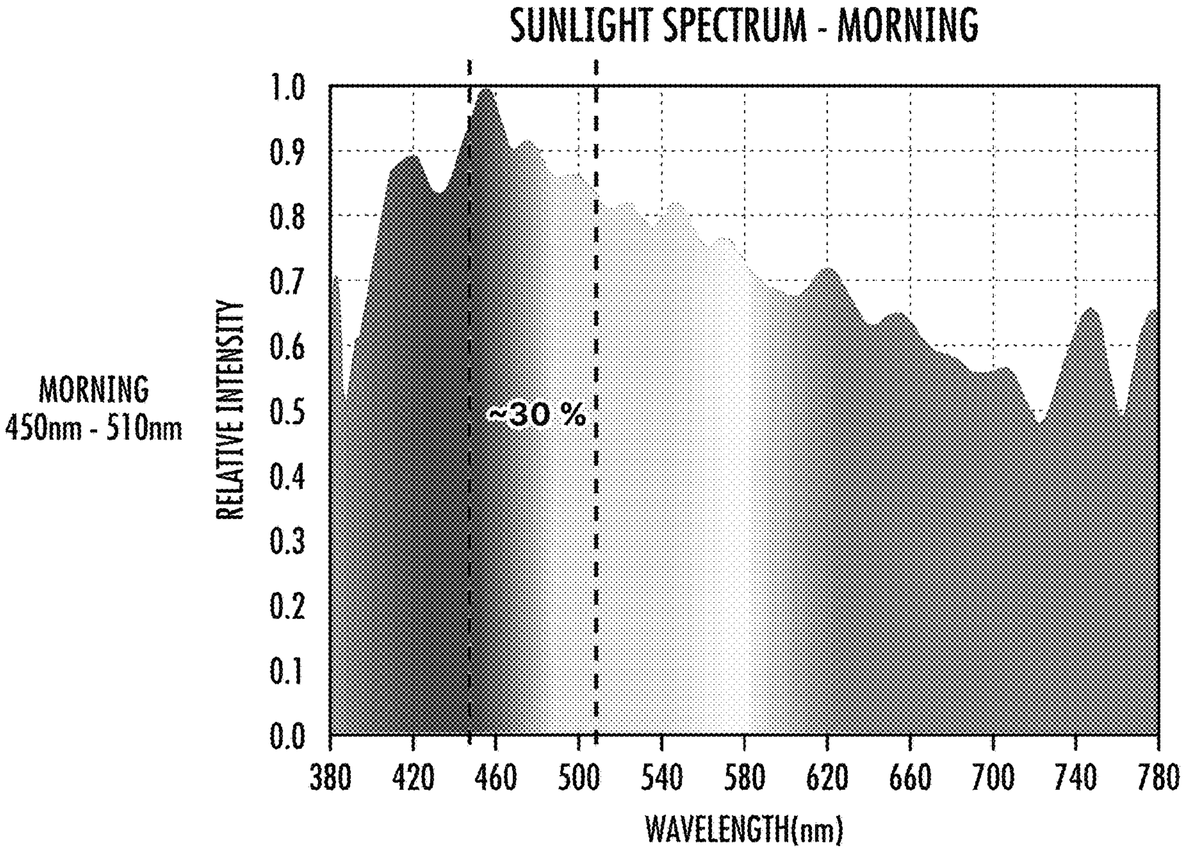
FIG. 70 shows sunlight spectrum at a point of time during the day.
Figure 71:
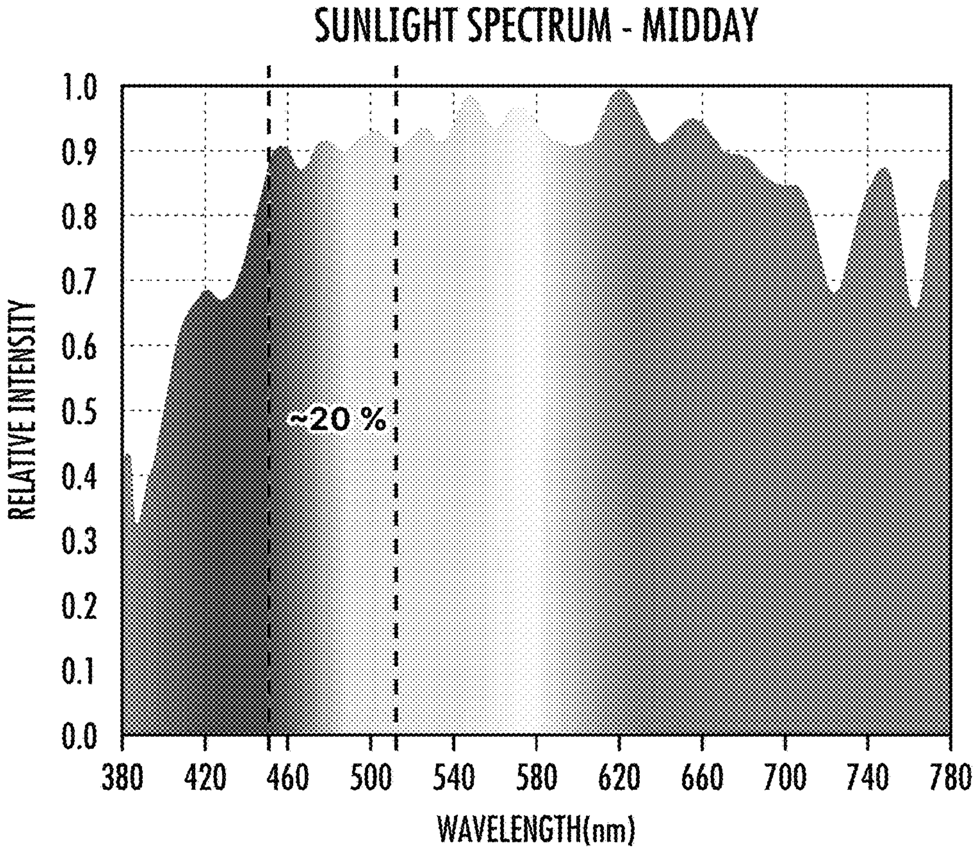
FIG. 71 shows sunlight spectrum at a point of time during the day.
Figure 72:
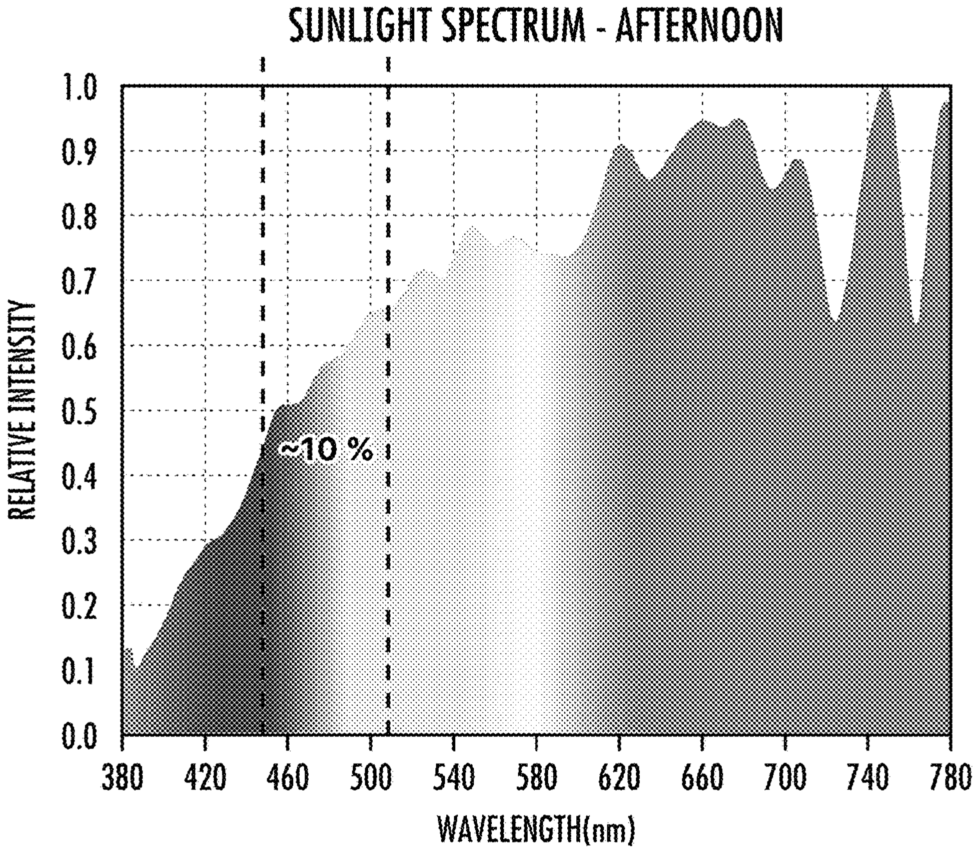
FIG. 72 shows sunlight spectrum at a point of time during the day.
Figure 73:
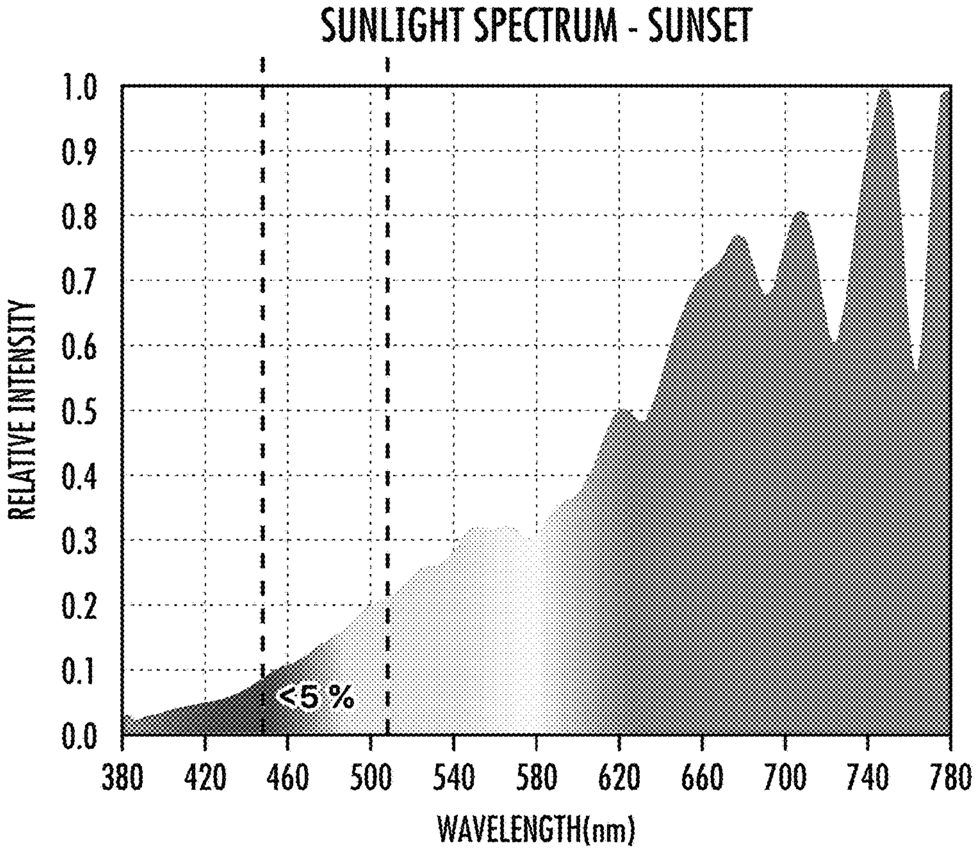
FIG. 73 shows sunlight spectrum at a point of time during the day.
Figure 77:
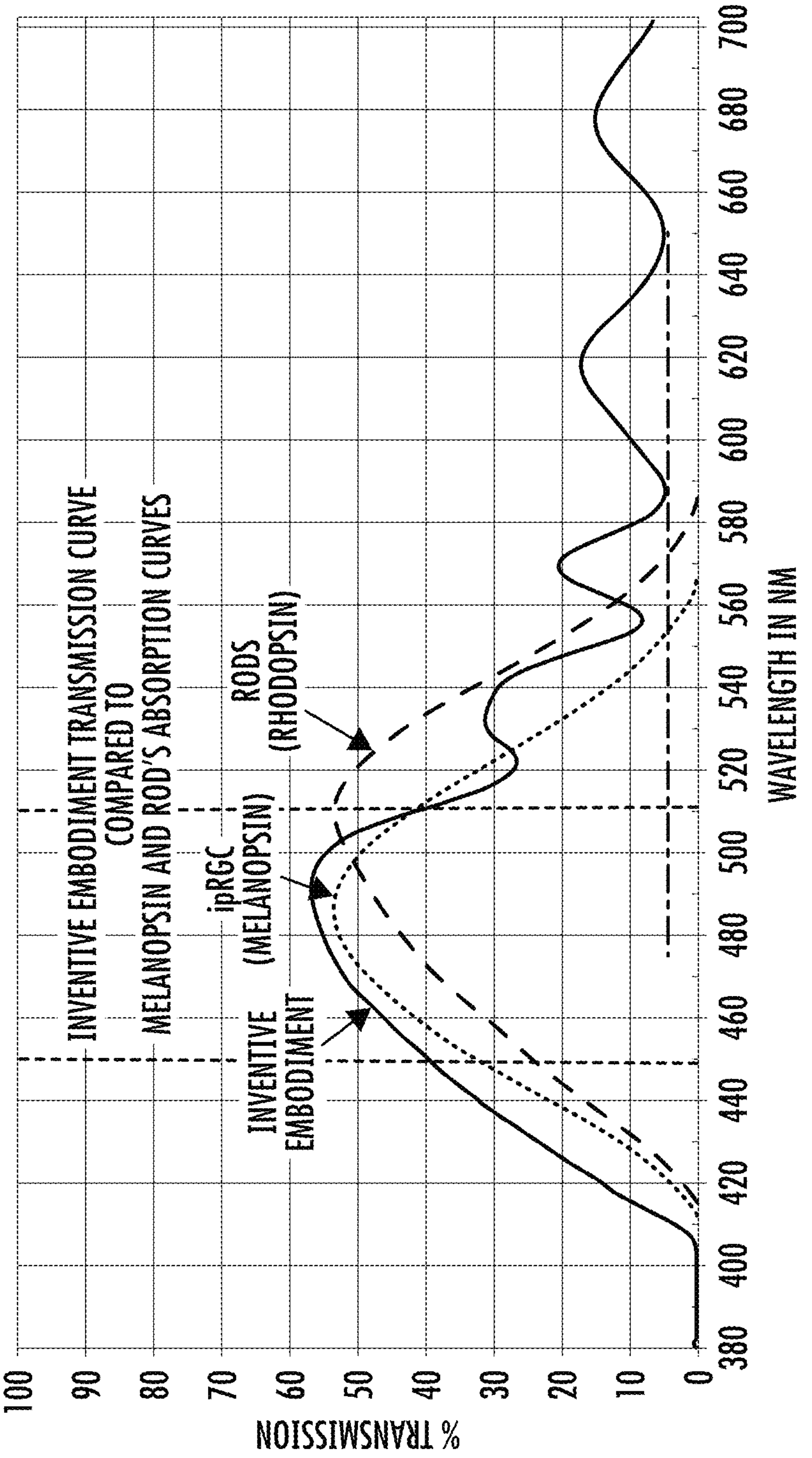
FIG. 77 is a graph showing improvements provided by the current invention over conventional eyewear.
Figure 78:
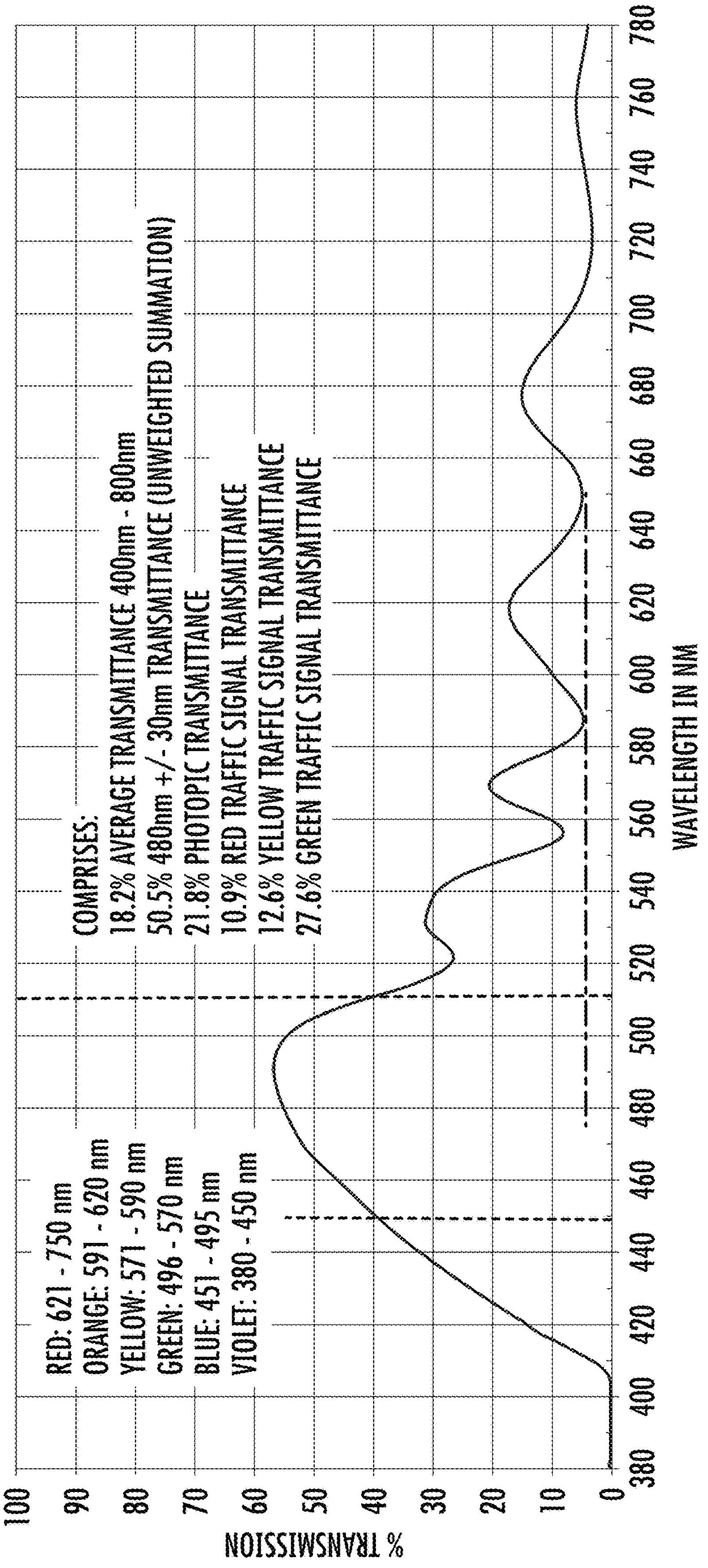
FIG. 78 is a graph showing improvements provided by the current invention over conventional eyewear, including an embodiment of the invention as described herein.
Figure 79:
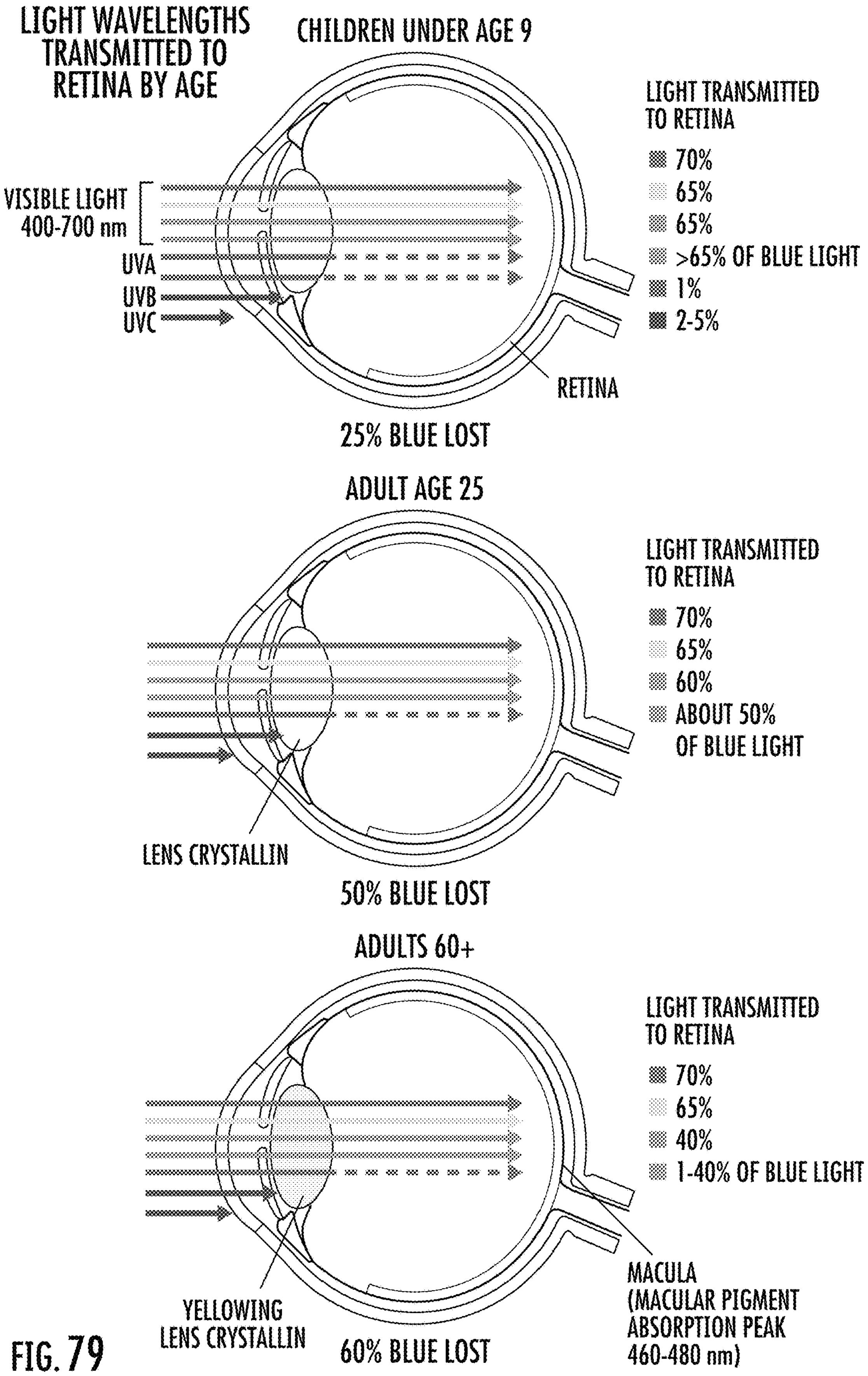
FIG. 79 shows how blue light transmission through the eye changes as a person ages.
Figure 80:
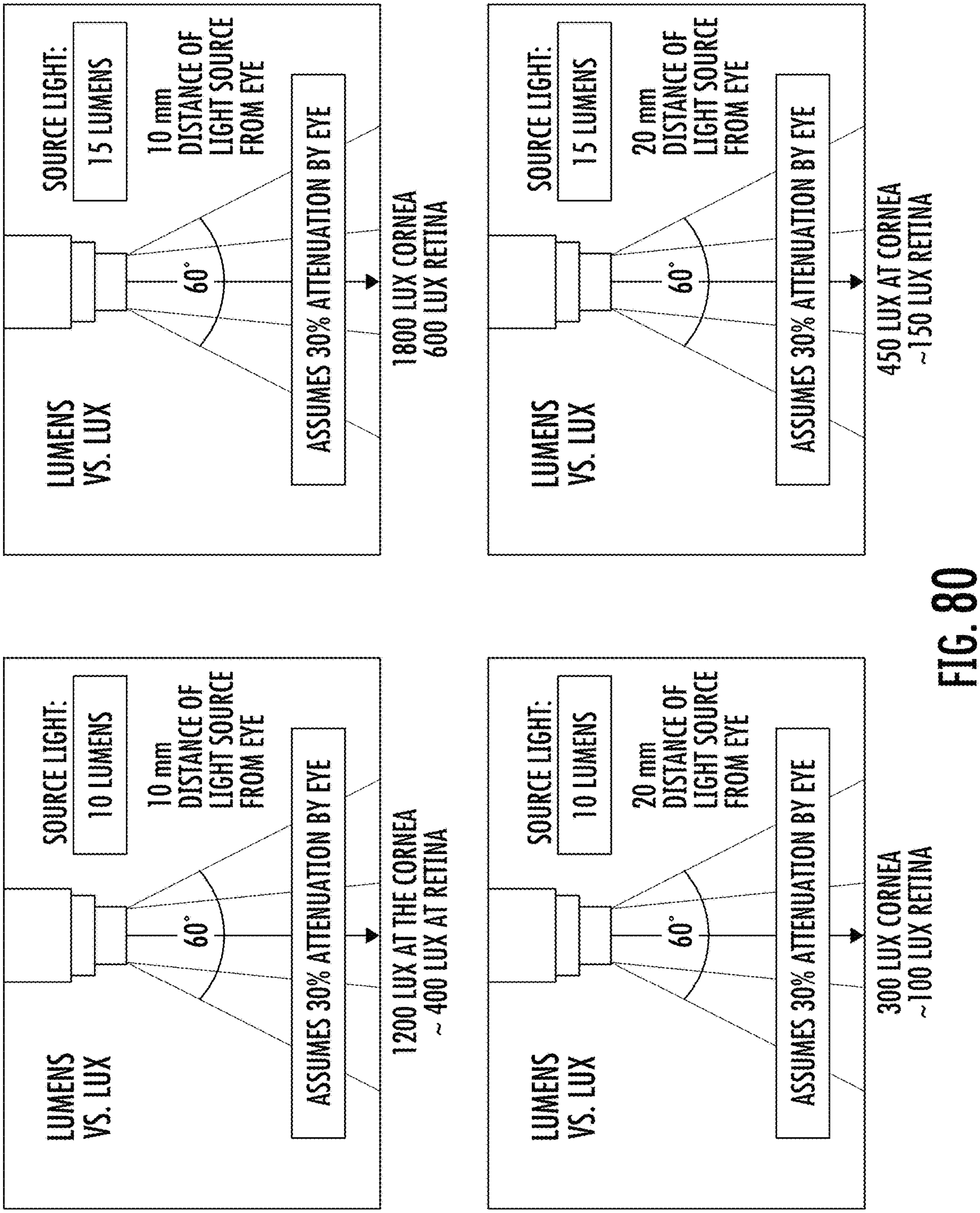
FIG. 80 shows how the power of the source light and/or distance of the light from the eye can affect the lux at the cornea and the retina.
Figure 81:
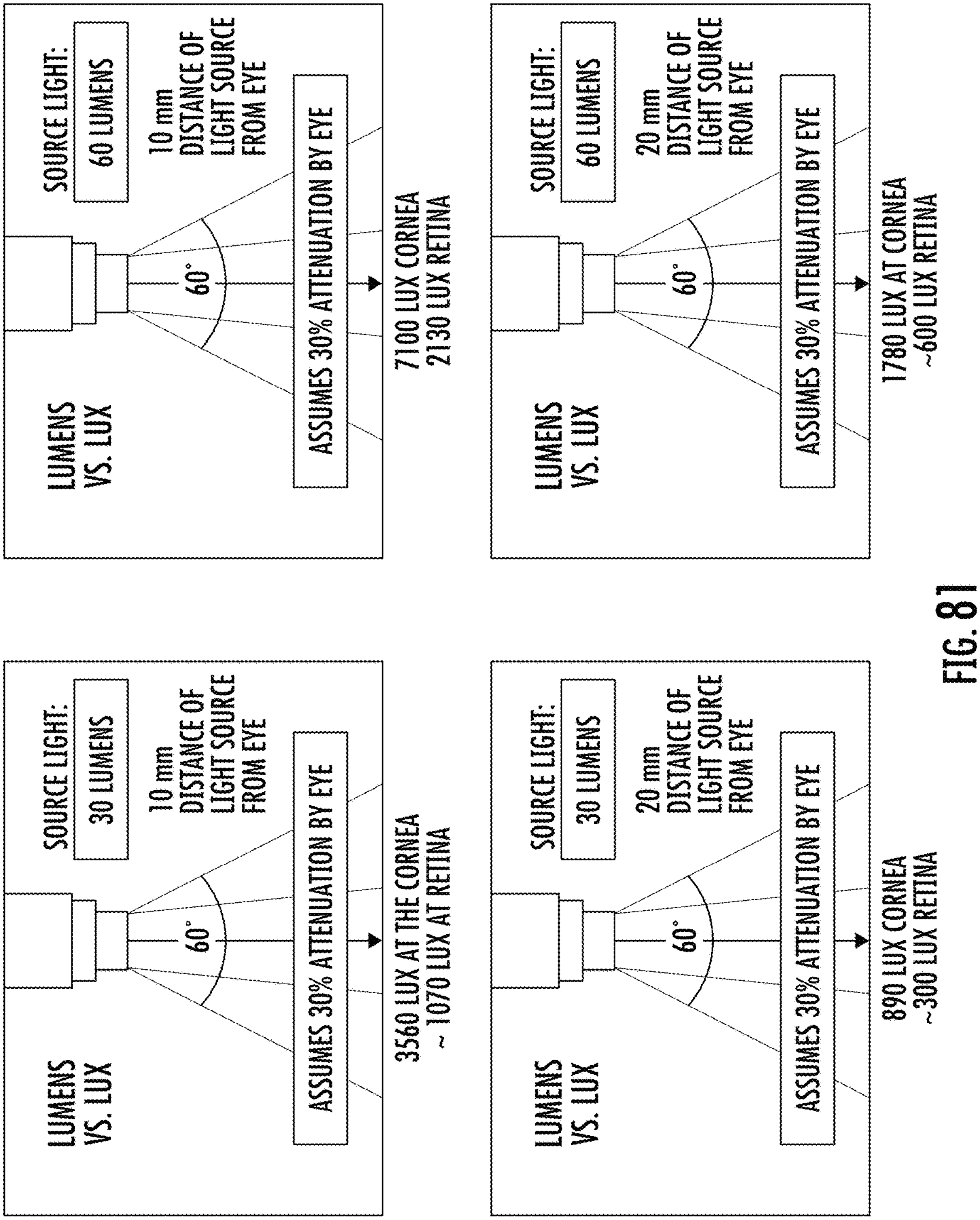
FIG. 81 shows how the power of the source light and/or distance of the light from the eye can affect the lux at the cornea and the retina.
Figure 82:
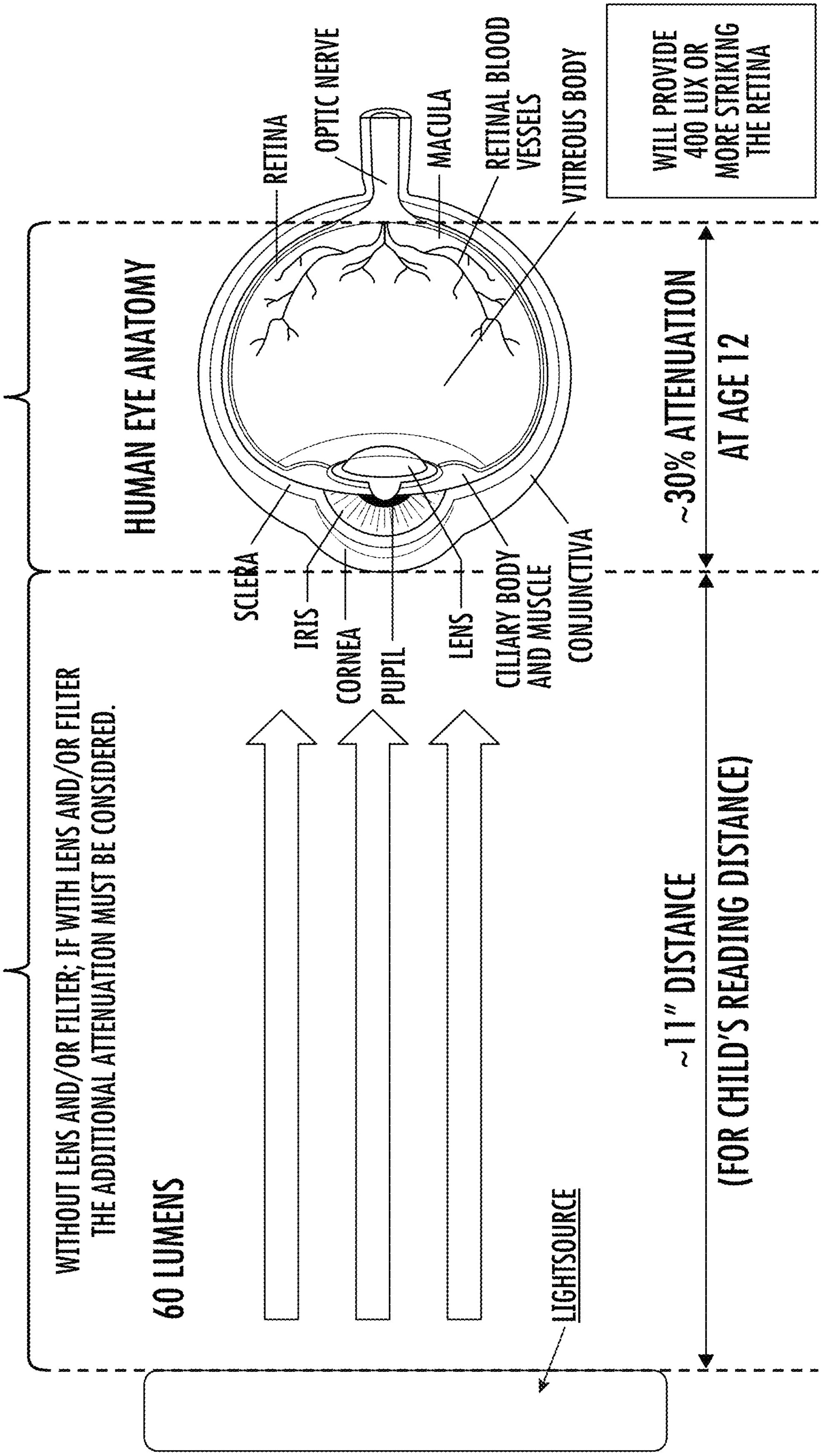
FIG. 82 shows how the power of the source light and/or distance of the light from the eye can affect the lux at the cornea and the retina.
Figure 83:
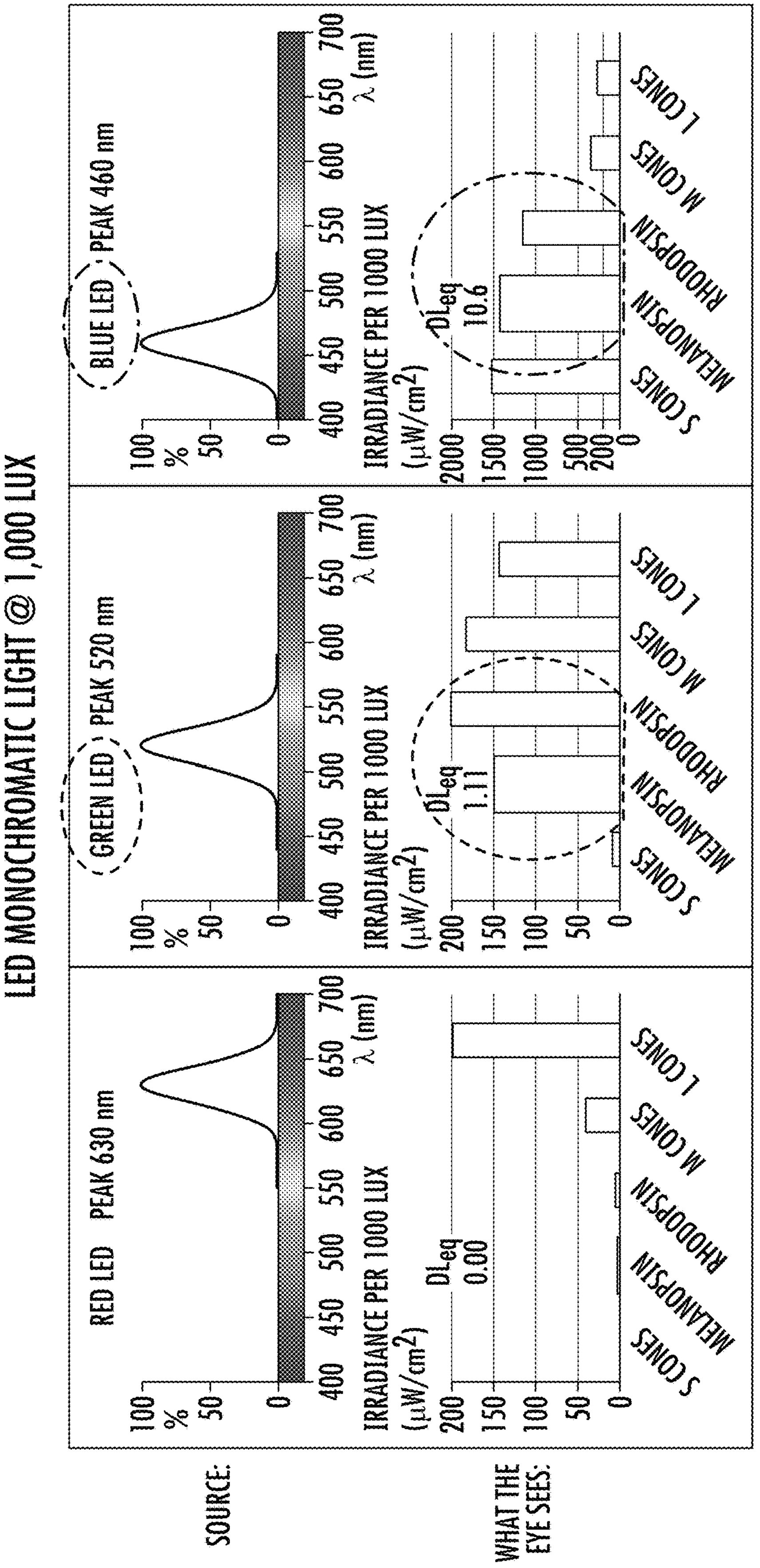
FIG. 83 shows how different light wavelengths can differently affect S Cones, Melanopsin, Rhodopsin, M Cones, and L Cones.
Figure 84:
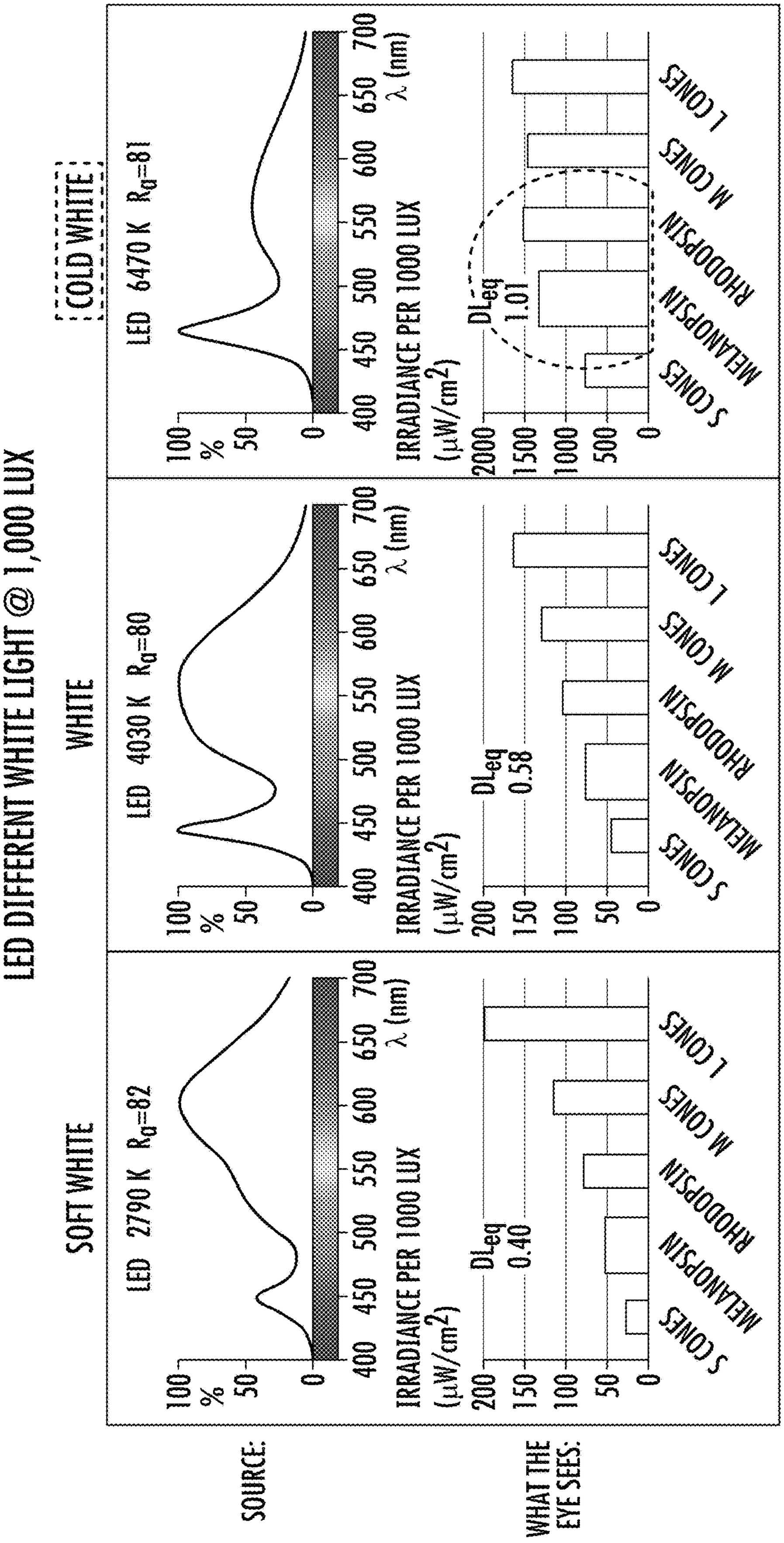
FIG. 84 shows how different light wavelengths can differently affect S Cones, Melanopsin, Rhodopsin, M Cones, and L Cones.
Figure 85:
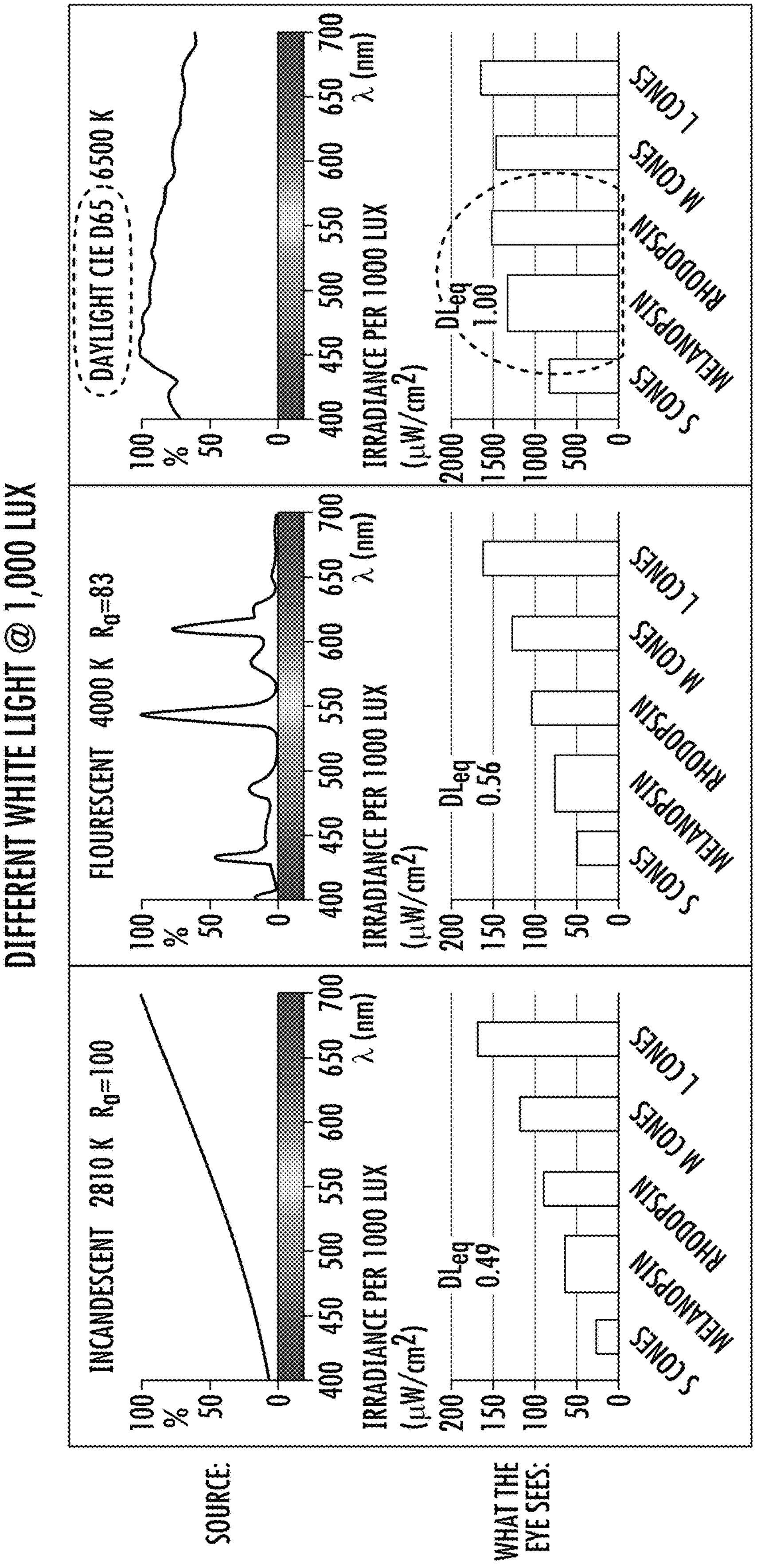
FIG. 85 shows how different light wavelengths can differently affect S Cones, Melanopsin, Rhodopsin, M Cones, and L Cones.
Figure 86:
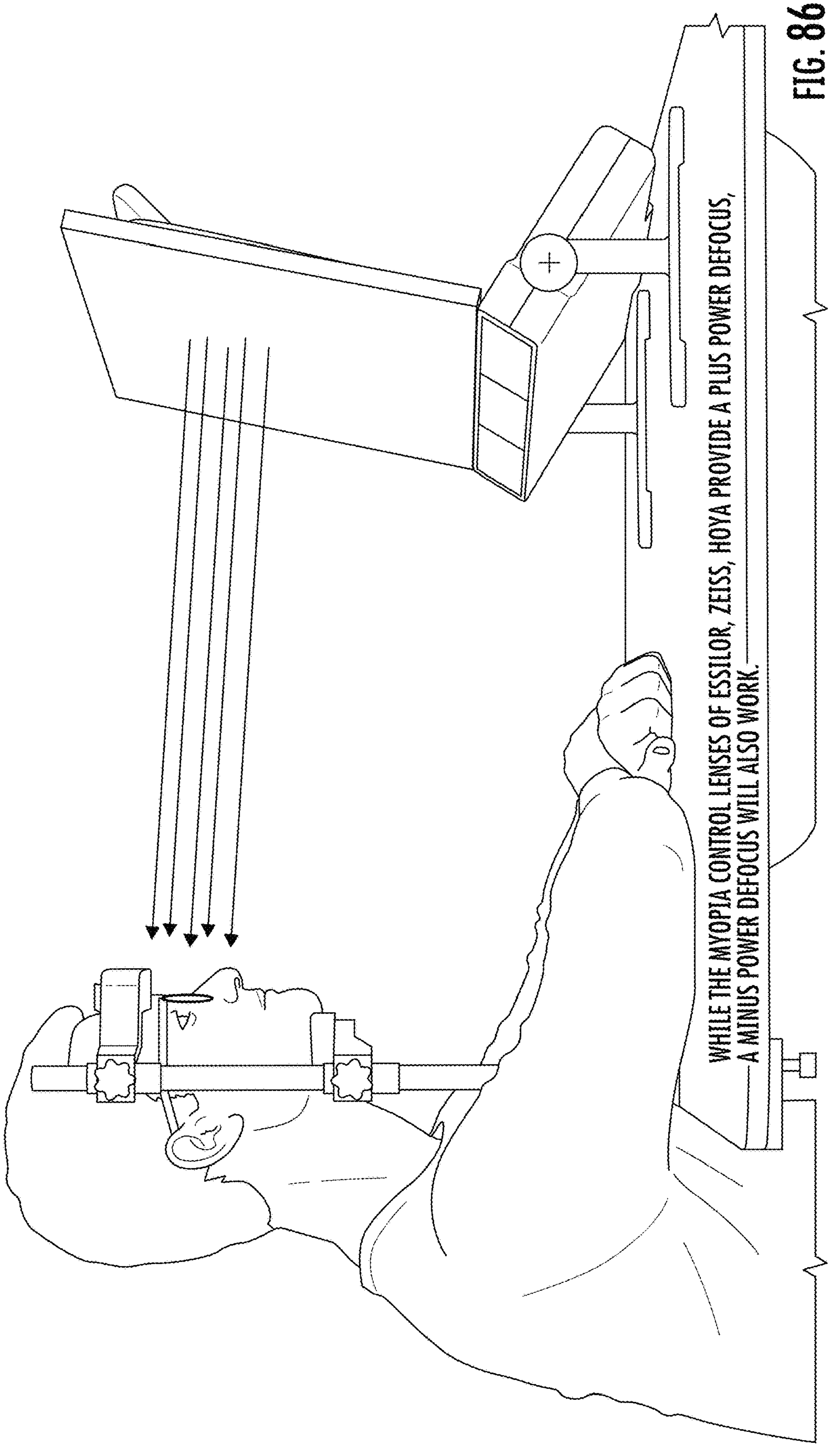
FIG. 86 shows ocular photo-bio-stimulation, wherein by way of example, any type of electronic display can provide light within the wavelength range of 450 nm-510 nm, having a light intensity of 400 lux or greater when striking the retina of the human eye. The time of treatment can be, by way of example only, 10 minutes or less, twice per day. The patient can play games (including with distance removed other people receiving treatment), use e-mail, or perform e-communication, while receiving ocular photo-bio-stimulation therapy. A computer application can be used to manage such light therapy. In aspects, the lenses being worn can be any type of myopia control lenses (e.g., Essilor Stellest Lens (H.A.L.T.), Zeiss Myocare, HoyaDims Miyosmart, Sightglass Vision (contrast reduction/diffusion), or chromatic aberration focused lenses or chromatic aberration refocused lenses. The lenses can be cleared or filtered.
Figure 87:
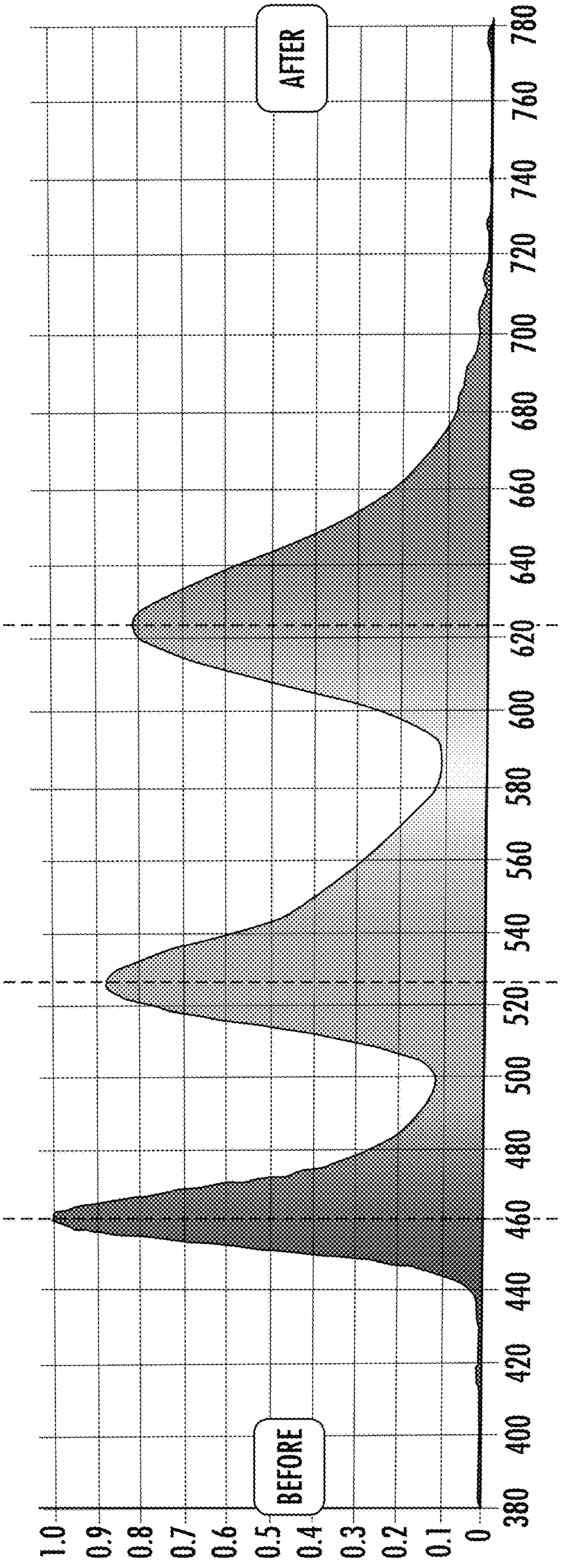
FIG. 87 shows that a combination can be used to stimulation the production of dopamine in the eye and/or brain of the user, the brightness level in lux is preferably turned up to display up 1,000 lux (or more ore less) or greater brightness intensity, such as up to 2,000 lux.
Figure 88:
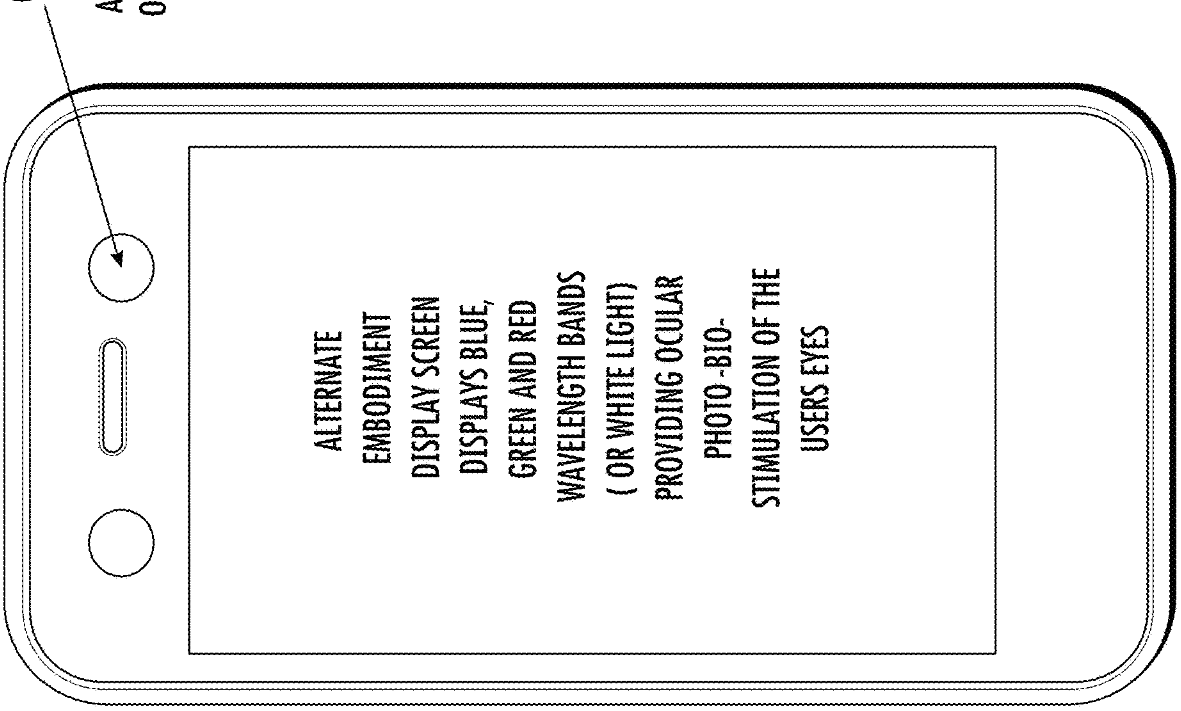
FIG. 88 shows an example of an embodiment described herein, such as a cell phone, tablet computer, laptop computer, desktop computer, electronic display, which can be used along with a computer application embodiment. It can be used for ocular photo-bio-stimulation for myopia control or prevention. It can also be used for treating neurological neurotransmitter deficiency disorder, such as deficiencies of one or more of: dopamine, serotonin, or norepinephrine in the brain. The device can include optional sensors that sense a distance from the screen compared to the user's face or eyes and can adjust the brightness of the screen up or down to maintain a preferred level of lux display light. It can be used with or without a lens or optic worn by the user receiving ocular photo-bio-stimulation light. The display can show blue, green, and red wavelength bands (or white light) providing ocular photo-bio-stimulation to the user.
Figure 89:
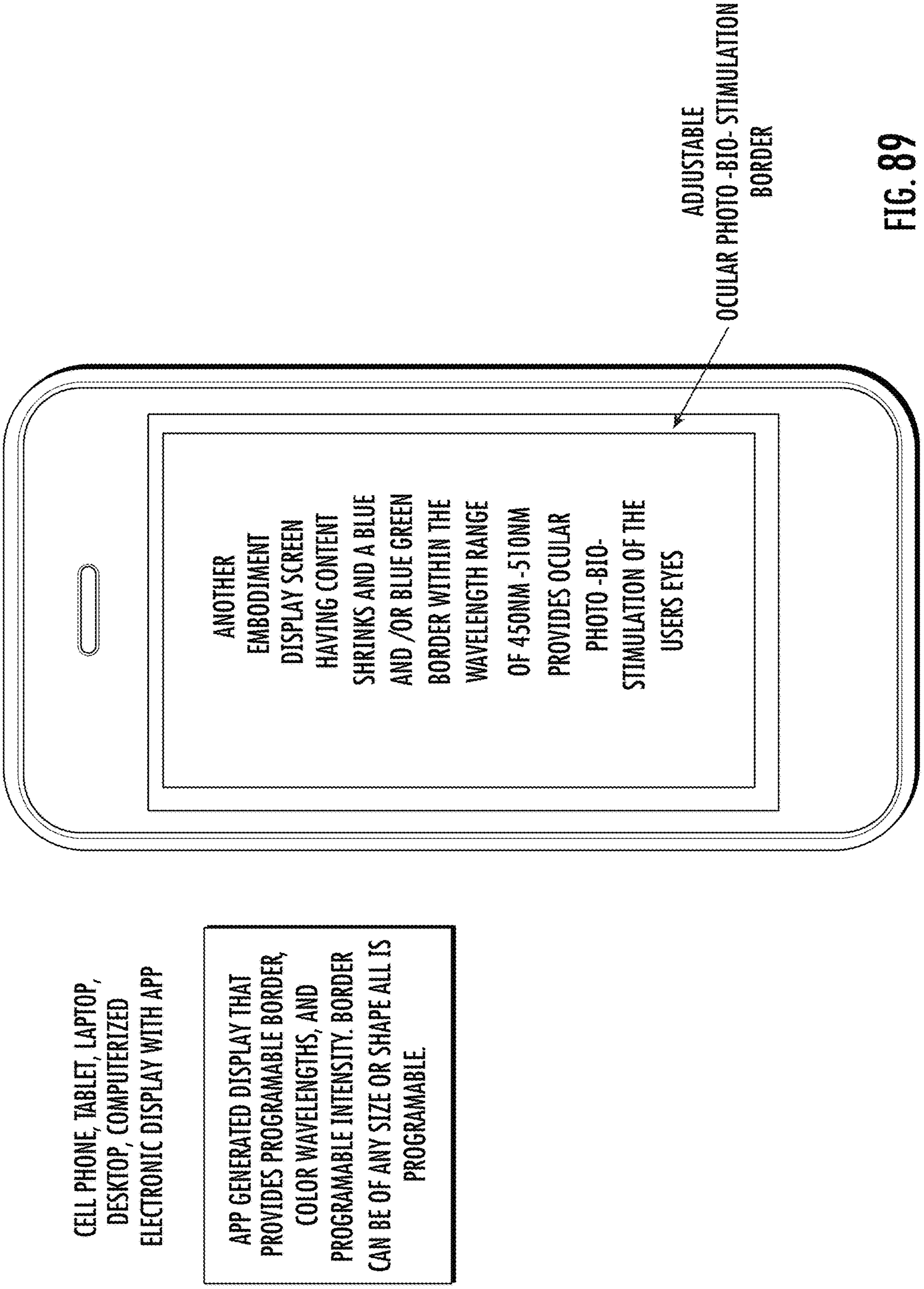
FIG. 89 shows an example of an embodiment described herein, such as a cell phone, tablet computer, laptop computer, desktop computer, electronic display, which can be used along with a computer application embodiment. It can be used for ocular photo-bio-stimulation for myopia control or prevention. It can also be used for treating neurological neurotransmitter deficiency disorder, such as deficiencies of one or more of: dopamine, serotonin, or norepinephrine in the brain. The device can include optional sensors that sense a distance from the screen compared to the user's face or eyes and can adjust the brightness of the screen up or down to maintain a preferred level of lux display light. It can be used with or without a lens or optic worn by the user receiving ocular photo-bio-stimulation light. In aspects, the computer application system generated display can provide a programmable border, color wavelengths, and programmable intensity. The border can be of any shape or size, and can all or partly be programmable. The display screen can have content that shrinks and a blue or blue green border within the wavelength range of 450 nm-510 nm provides ocular photo-bio-stimulation to the user.
Figure 90:
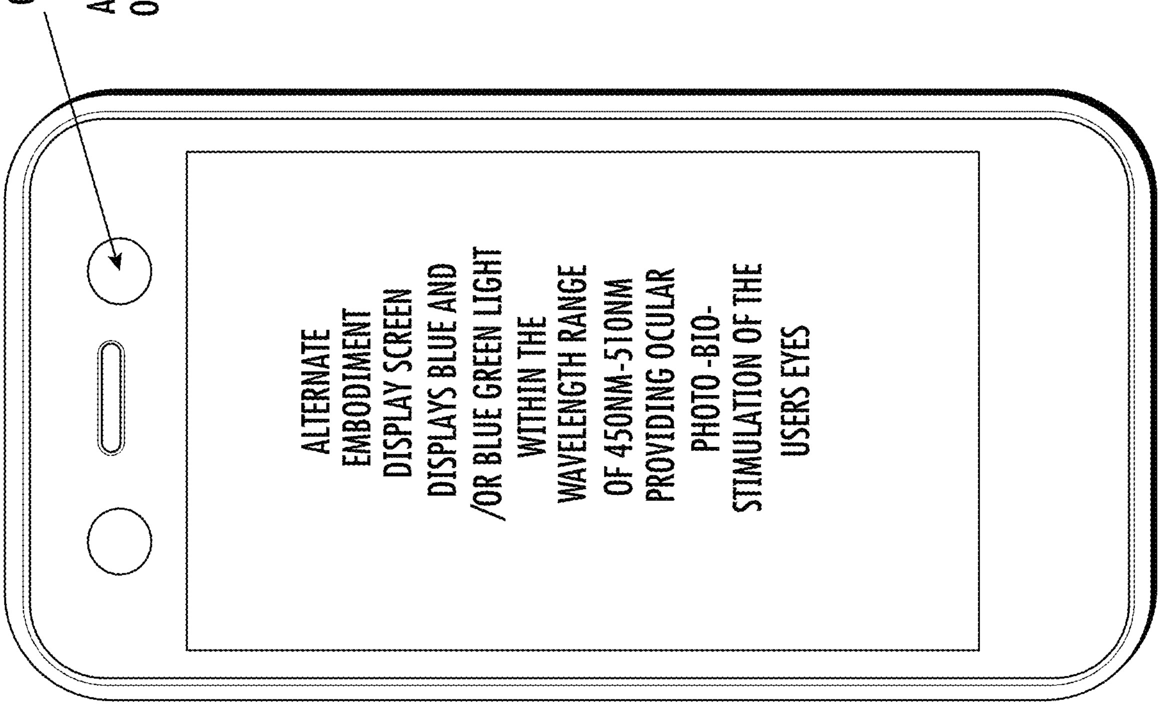
FIG. 90 shows an example of an embodiment described herein, such as a cell phone, tablet computer, laptop computer, desktop computer, electronic display, which can be used along with a computer application embodiment. It can be used for ocular photo-bio-stimulation for myopia control or prevention. It can also be used for treating neurological neurotransmitter deficiency disorder, such as deficiencies of one or more of: dopamine, serotonin, or norepinephrine in the brain. The device can include optional sensors that sense a distance from the screen compared to the user's face or eyes and can adjust the brightness of the screen up or down to maintain a preferred level of lux display light. It can be used with or without a lens or optic worn by the user receiving ocular photo-bio-stimulation light. In aspects, the computer application system generated display can provide a programmable border, color wavelengths, and programmable intensity. The border can be of any shape or size, and can all or partly be programmable. The display screen can have content that shrinks and a blue or blue green border within the wavelength range of 450 nm-510 nm provides ocular photo-bio-stimulation to the user.
Figure 91:
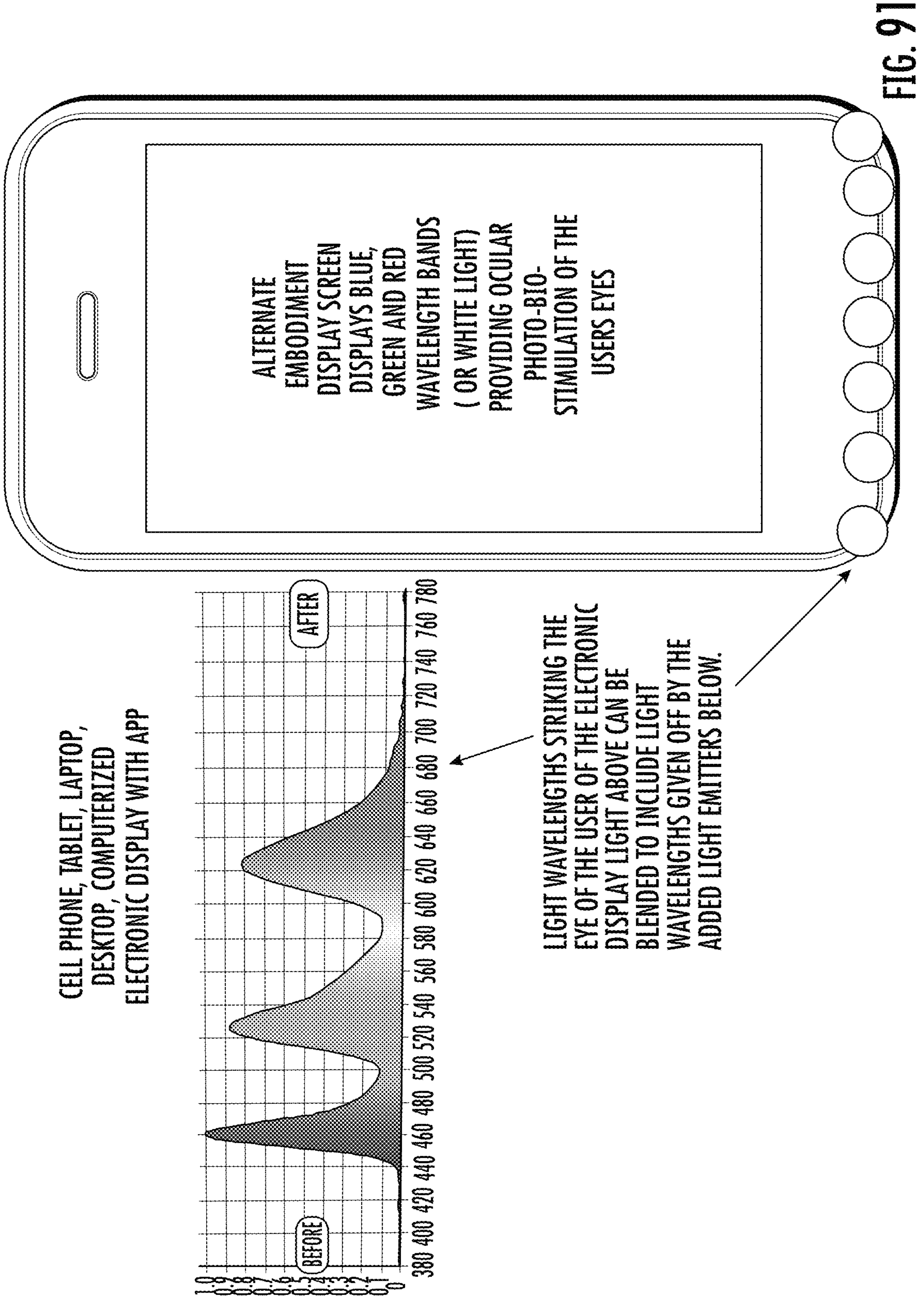
FIG. 91 shows an example of an embodiment described herein, such as a cell phone, tablet computer, laptop computer, desktop computer, electronic display, which can be used along with a computer application embodiment. It can be used for ocular photo-bio-stimulation for myopia control or prevention. It can also be used for treating neurological neurotransmitter deficiency disorder, such as deficiencies of one or more of: dopamine, serotonin, or norepinephrine in the brain. The device can include optional sensors that sense a distance from the screen compared to the user's face or eyes and can adjust the brightness of the screen up or down to maintain a preferred level of lux display light. It can be used with or without a lens or optic worn by the user receiving ocular photo-bio-stimulation light. In aspects, the computer application system generated display can provide a programmable border, color wavelengths, and programmable intensity. The border can be of any shape or size, and can all or partly be programmable. The display screen can have content that shrinks and a blue or blue green border within the wavelength range of 450 nm-510 nm provides ocular photo-bio-stimulation to the user. The light can be amplified by additional emitters. Thus, the light wavelengths striking the eye of the user of the electronic display can be blended to include light wavelengths given off by the added light emitters shown on the bottom of the phone pictured. This can affect the response as shown in the inset graph. Thus, in embodiments, blue and/or blue green light emitters (e.g., with the range of 450 nm-510 nm) can be attached to the display and controlled, for example, by a computer application. This can allow for adding additional light transmission within the range of 450 nm-510 nm to the light being transmitted by they display to the user, thus blending additional blue and/or blue green (cyan) light to the wavelengths of light being display on the display.
Figure 92:
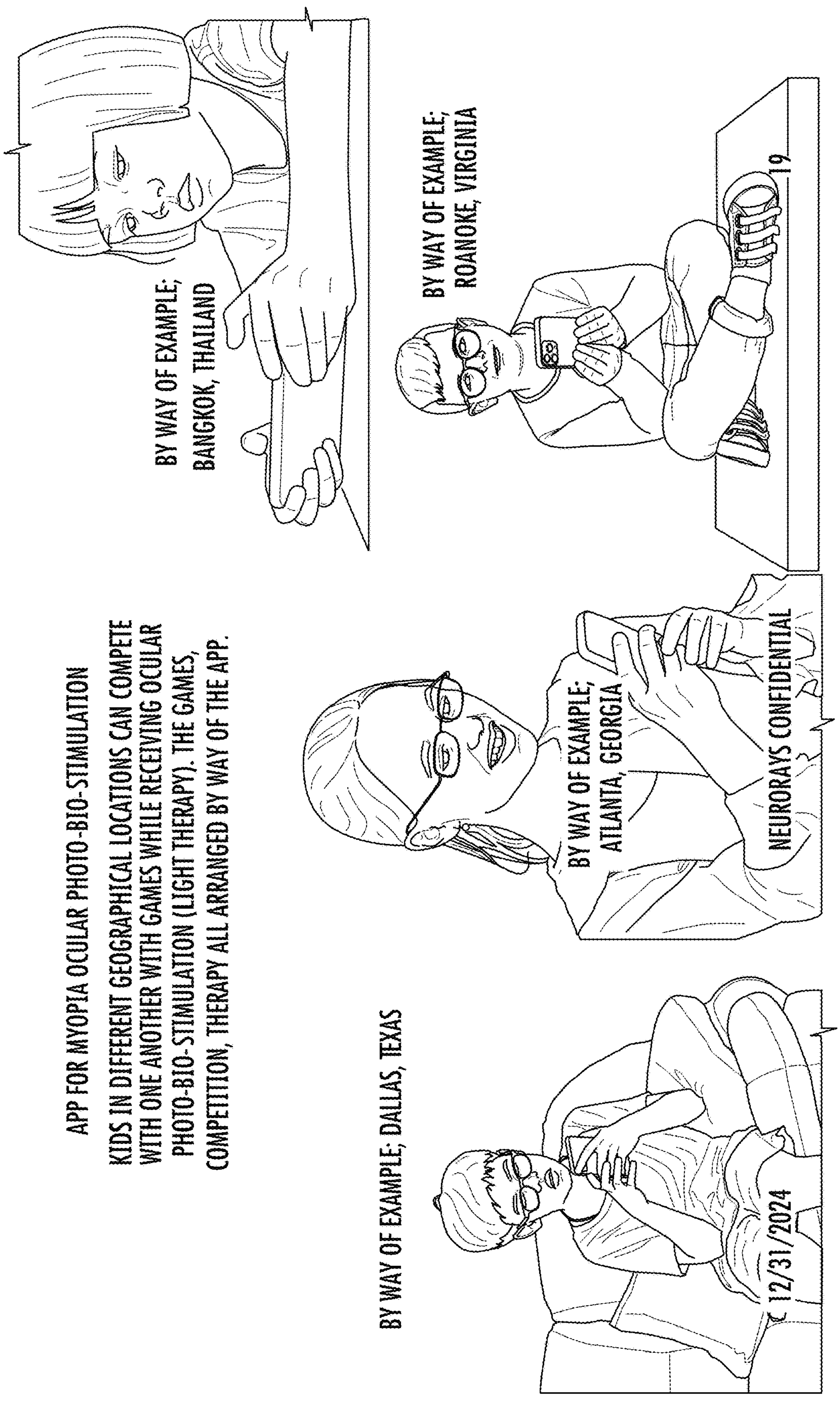
FIG. 92 shows that a computer application can be used to manage the device. In aspects, children (or people of any age) in different locations can compete with one another with games while receiving ocular photo-bio-stimulation light therapy.
Figure 94:
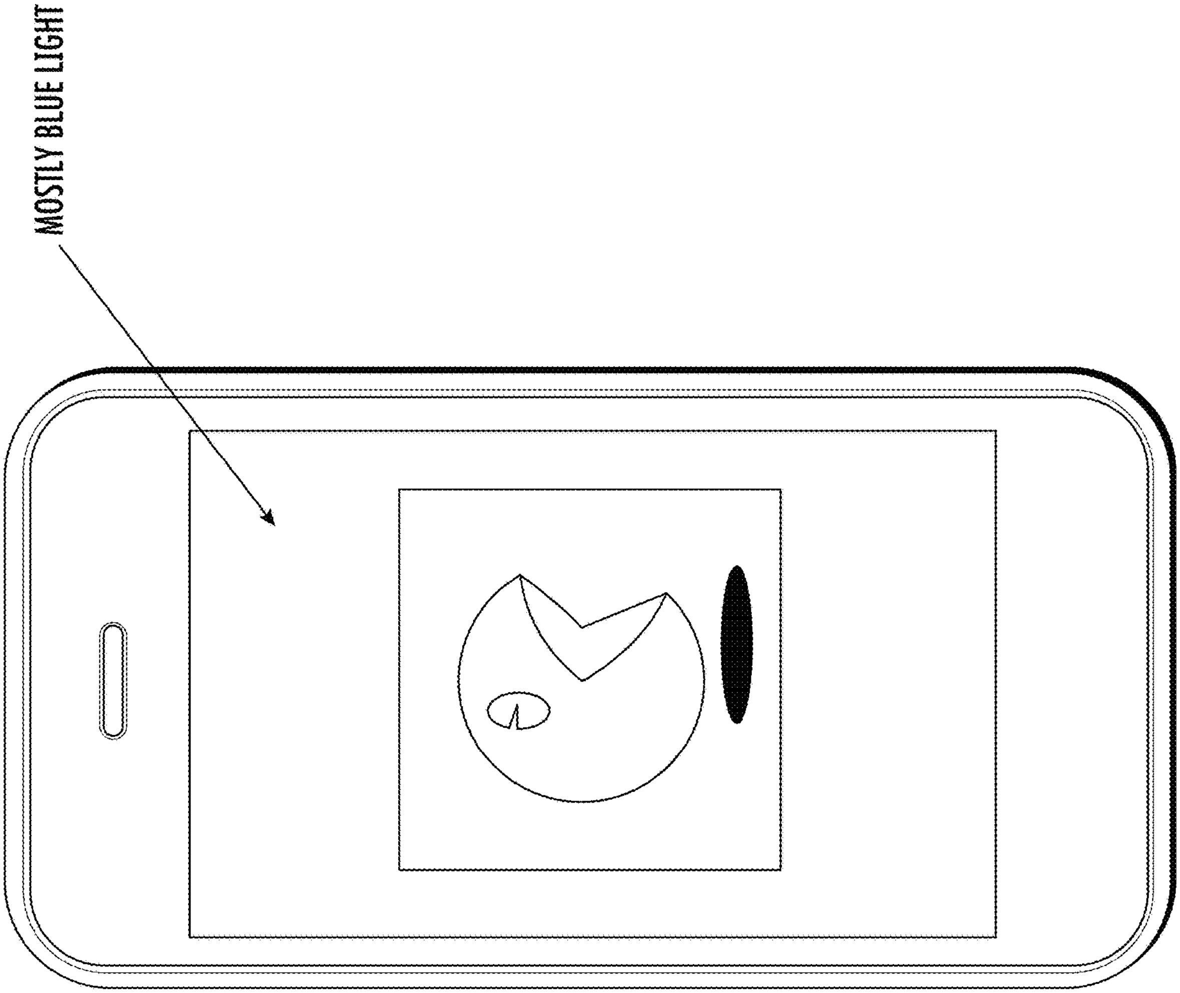
FIG. 94 shows that a computer application can be used to manage the device. In aspects, children (or people of any age) in different locations can compete with one another with games while receiving ocular photo-bio-stimulation light therapy. In aspects, as the eye follows the animated image around the display, blue light within the range of 450 nm to 520 nm strike different regions of the eye's retina. This photo-therapy can be performed monocularly or binocularly. The light can be mostly blue light, in examples.
Figure 95:
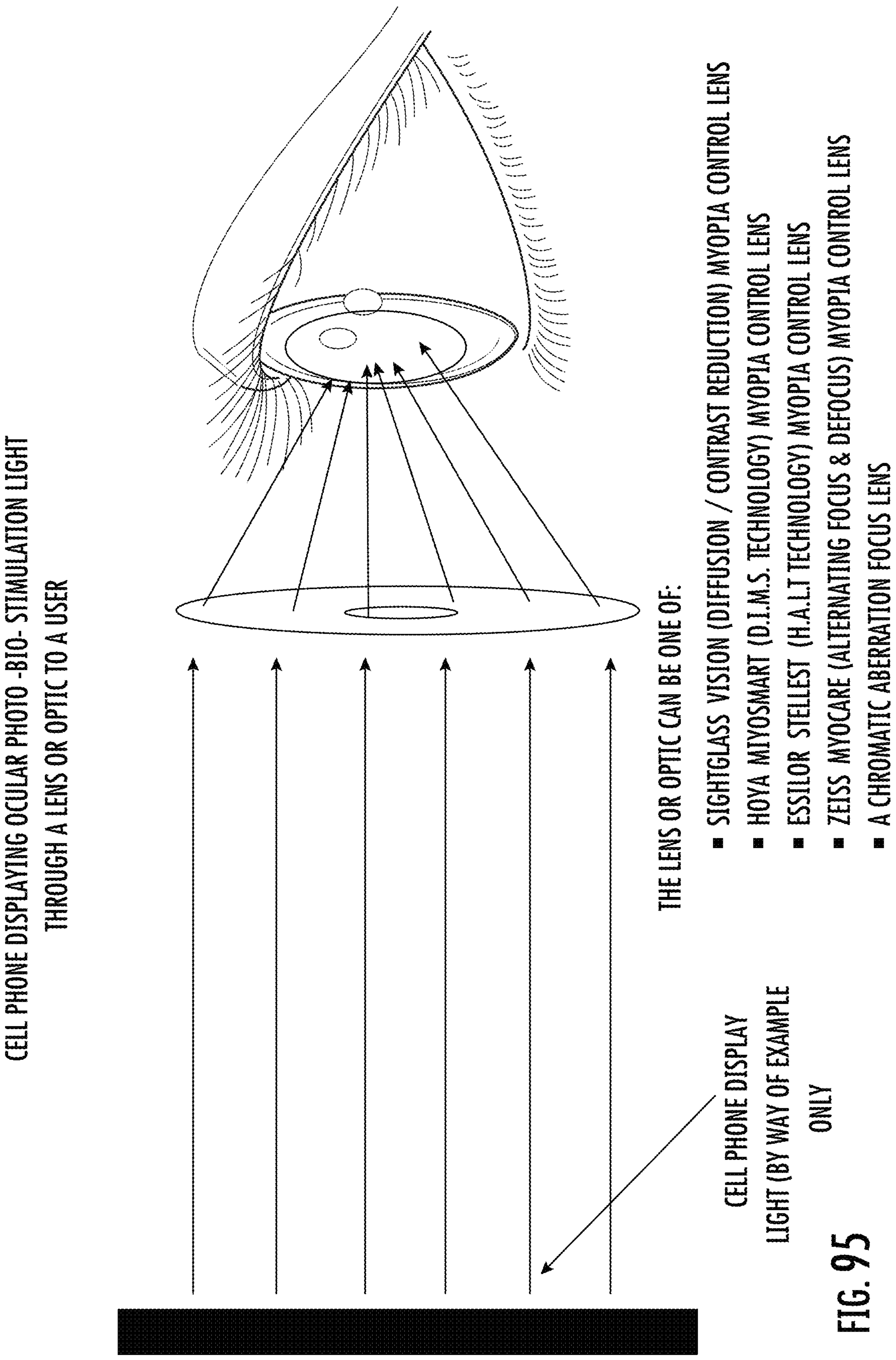
FIG. 95 shows an example of a cell phone display providing ocular photo-bio-stimulation light through a lens or optic to a user. The lens or optic can be any one of: Sightglass Vision (diffusion/contrast reduction) myopia control lens; Hoya Miyosmart (D.I.M.S. technology) myopia control lens; Essilor Stellest (H.A.L.T. technology) myopia control lens; Zeiss Myocare (alternating focus and defocus) myopia control lens; a chromatic aberration focus lens.
Figure 96:
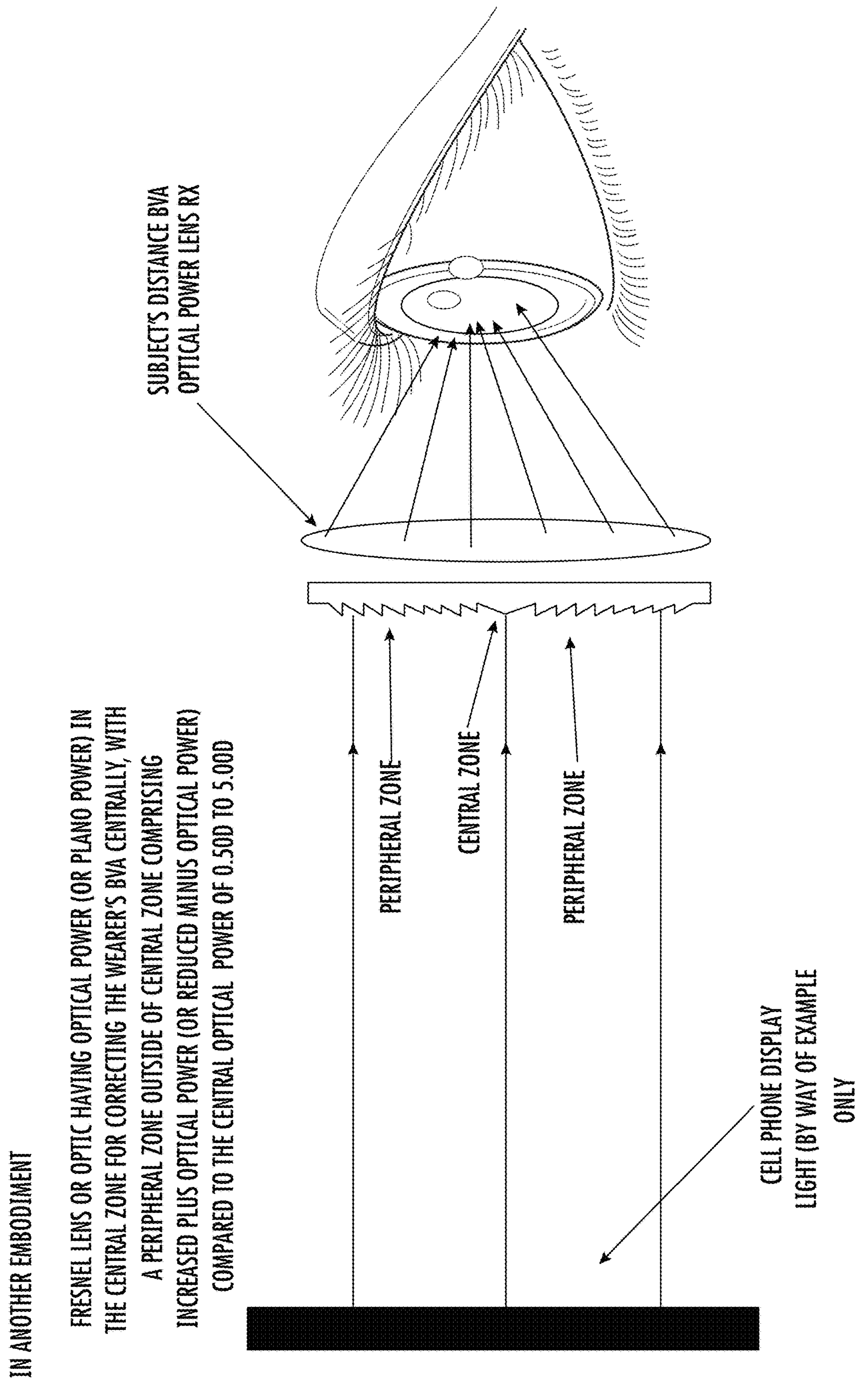
FIG. 96 shows an example of a cell phone display providing ocular photo-bio-stimulation light through a lens or optic to a user. In this embodiment, as shown, a Fresnel lens or optical having optical power (or plano power) is in a central zone for correcting the wearer's BVA centrally, with a peripheral zone outside of the central zone comprising increased plus optical power (or reduced minus optical power) compared to the central optical power of, for example, 0.50 D to 5.00 D. This optic can be housed or supported with fit-over eyewear, disposable eyewear, static cling that attached to the subject's lenses or held on its own, or supported by an eyeglass frame or other lens.
Figure 97:
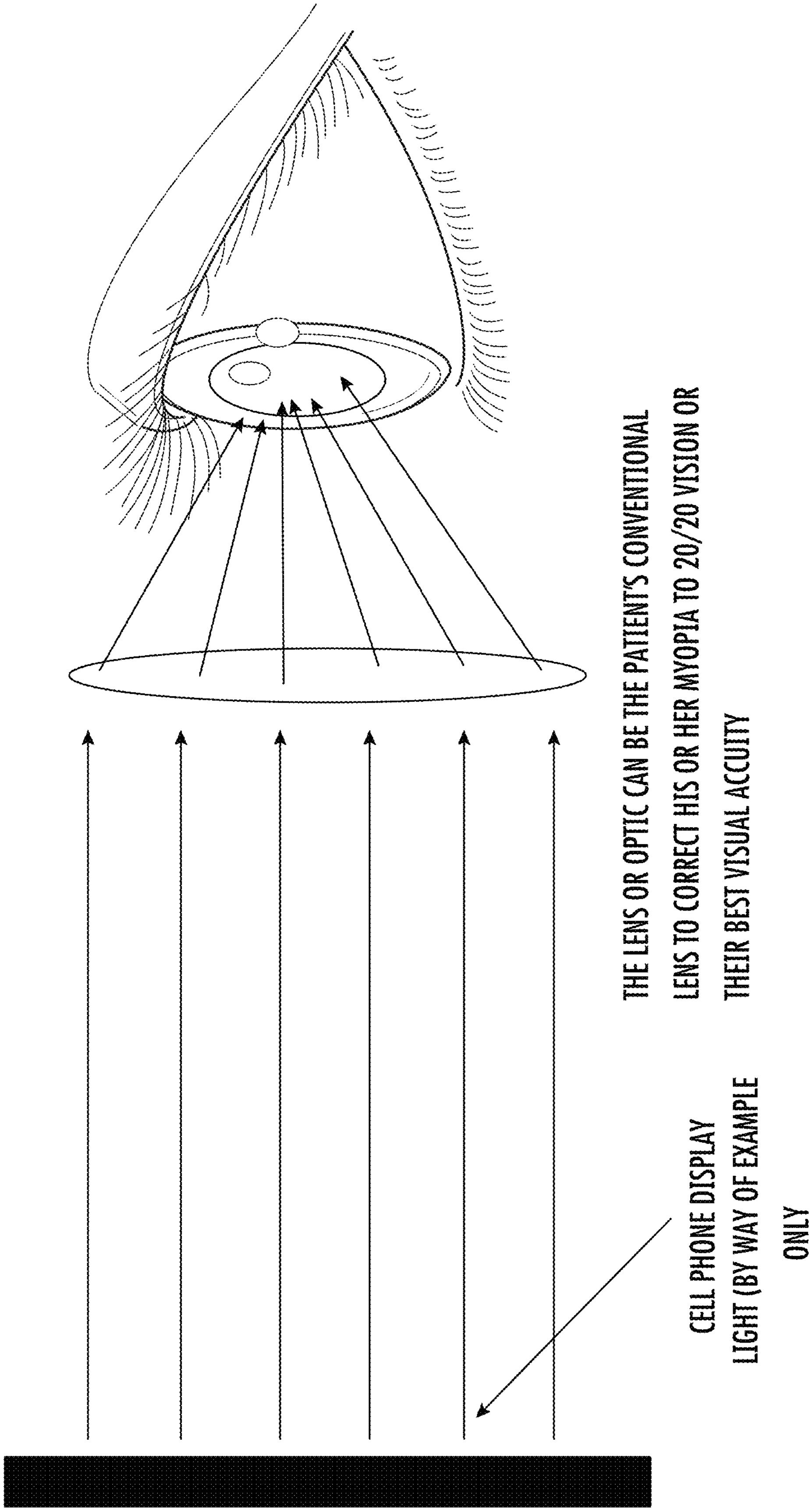
FIG. 97 shows an example of a cell phone display providing ocular photo-bio-stimulation light through a lens or optic to a user. The lens or optic can be the patient's conventional lens to correct his or her myopia to 20/20 vision or their best visual acuity.

In FIGS. 62B and 62C, the non-see-through near eye display aligned with its microlens array can be slightly offset with the see-through near eye display and its aligned microlens array. The reason for the offset is to allow for the light generating the virtual image seen by the eye to pass between or through the pixels of the see-though near eye display and its aligned microlens array. Even though there is an offset, the non-see-through near eye display, its aligned microlens array, and the see through near eye display, remain in optical communication, thus allowing light to be projected to the retina of the eye of a user. An embodiment can be that of an XR (one of AR, MR, VR, or Modified Reality) device wherein the XR device utilizes two light sources, wherein one light source generates a lighted real image and another light source generates a lighted virtual image, wherein the real image is that of a digital image or video and wherein the virtual image is that of a light that paints or stimulates areas of the retina of the eye of the wearer or user of the XR device. The virtual image can be generated by a see-through near eye display that allows the real image to be seen through the near eye display. In certain embodiments the virtual image can be generated by a non-see-through near eye display that comprises a see-through central zone devoid of pixels or electronic components so as to have peripheral pixels that can be formed as one of, a ring, partial ring, or series of separated pixels. Whether that of a non-see-through near eye display or a see-through near eye display, the central zone that allows the real image to be seen can be of a diameter within the range of 6 mm-12 mm in diameter. In certain embodiments the see-through near eye display can permit the real image to be seen without limitation to a central zone. The see-through central zone can be filtered to cause the pupil of the eye to enlarge. The virtual image can be generated by a filtered or non-filtered light source that projects wavelengths predominantly within the wavelengths range of one of, 480 nm+/−30 nm, 530 nm+/−20 nm, or 650 nm+/−30 nm. The light source for the real image can be one of, a computerized digital display device, television, computer electronic display, cell phone electronic display, tablet electronic display, and/or digital movie screen. This embodiment permits the user of the XR device to watch a video, movie or read text while the retina(s) of his or her eye can be being painted/treated with ocular photo-bio-stimulation. In certain embodiments, different pixels light for the purposes of painting the retina. In other embodiments the same pixels are lighted as the user's line of sight looks through the central clear zone. These pixels project light at various angles to the user's line of sight thus painting or stimulating non-central areas of the retina of the eye of the user.

An embodiment is that of a device for providing extended reality (one of AR, MR, VR, or Modified Reality), comprising a light source providing light to stimulate a retina of an eye of a user of the device, wherein the light is chosen to result in a physiological response in the user's eye or a body of the user, wherein the device causes the user to see a first lighted image and a second lighted image with a user's same eye, wherein the device projects the first lighted image having light wavelengths that are substantially within a wavelength range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, wherein at a same time as the user fixates on the second lighted image with the user's same eye, the first lighted image paints light wavelengths substantially within the wavelength range of at least one of 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, across or on different areas of the retina of the user's same eye. The first lighted image can be a virtual image. The second lighted image can be a real image. The first lighted image can be a real image. The second lighted image can be a virtual image. The second lighted images can be virtual images. The device is one of augmented reality eyewear, mixed reality eyewear, or virtual reality eyewear. The device can comprise a see-through near eye display. The device can comprise a non-see-through near eye display. The XR device can comprise an electronic display comprised of a plurality of pixels. The device can comprise a waveguide. The device can comprise a microlens array. The light of the first lighted image can be defocused light. The light of the first lighted image can be a diffused light. The light of the first lighted image can be focused light. The light of the first lighted image can be filtered light. The light of the second lighted image can be focused light. The light of the second lighted image can be defocused light. The light of the second lighted image can be diffused light. The light of the second lighted image can be filtered light. The first lighted image can be stationary/non-moving. The second lighted image can be moving. The first lighted image can be moving. The second lighted image can be stationary/non-moving. The second lighted image can be red, black, or grey. The first lighted image and/or the second lighted image can be generated with light from one or more of the following light emitters: light-emitting diodes (LEDs), organic light-emitting diodes (OLEDs), transparent organic light-emitting diodes, micro-OLEDs, micro-LEDs, ionic liquids for electrochemical devices (iLEDs), micro-iLEDS, quantum dots, florescent lights, ambient light, or incandescent lights. The light generating the first and/or second lighted images can be filtered by the filter or filters, and wherein the filter or filters can be one or more of: a bandpass filter, an interference filter, an absorption filter, a selective wavelengths filter, a notch filter, or a neutral density filter. The physiological response can be one or more of, a generation of additional dopamine, additional serotonin, improved mitochondria function, and/or reduction of age-related inflammation in the eye of the user. The physiological response can be a generation of additional dopamine or serotonin in the brain of the user. The first and second lighted images can modulate, by way of example only, within the range of 5 Hz and 15 Hz. The device can comprise one or more of a timer, a wireless communication component, or an alarm. The device can comprise one or more sensors for sensing and/or receiving biofeedback from the user. The device can be capable of delivering to the user sound, smell, vibration, or combinations thereof. The device can be capable of receiving biofeedback from the user. Biofeedback can include, increased blink rate, measuring blink rate, increased pupil size, and/or measuring pupil size.

Another embodiment is of an XR device (VR or Modified Reality) for providing light to stimulate a retina of a user's eye, the device comprising a non-see-through near eye display for providing the light and a microlens array for focusing or defocusing all or some of the light provided by the non-see-through near eye display, wherein the non-see-through near eye display produces a first lighted image, wherein a fixation target is seen within a perimeter of the first lighted image, wherein the first lighted image is substantially comprised of light wavelengths within the wavelength range of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, and wherein light wavelengths within the range of at least one of 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm, and can stimulate a portion of the user's retina or all of the retina as the user's eye fixates on the fixation target, and wherein such stimulation initiates a physiological response in the user. The device can be eyewear. The device can comprise a see-through near eye display located on the front-side of the non-see-through near eye display closest to the eye of the user. The non-see-through near eye display can produce a second lighted image. In front of the see-through near eye display on the side closest to the eye of the user, can be a second micro-lens array. The see-through near eye display provides a second light that generates a second lighted image. The first lighted image can be a virtual image. The second lighted image can be a virtual image. The light generating the first lighted image can be defocused light. The light generating the first lighted image can be diffused light. The light generating the first lighted image can be focused light. The light generating the first lighted image can be filtered light. The light generating the second lighted image can be defocused light. The light generating the second lighted image can be diffused light. The light generating the second lighted image can be focused light. The light generating the second lighted image can be filtered light. One or both of the first lighted image and/or the second lighted image can modulate between 5 Hz and 15 Hz. The fixation target can be stationery/non-moving. The fixation target can move. The fixation target can move relative to the first lighted image. The fixation target can move relative to a second lighted image. The fixation target color can be one of red, black, or grey. The fixation target can be the first lighted image. The fixation target can be the second lighted image. The fixation target can be a third lighted image. The second lighted image can be substantially comprised of light wavelengths within the wavelength range of one of: 480 nm+/−30 nm, 475 nm+/−20 nm, 530 nm+/−20 nm, or 650 nm+/−30 nm. One or both of the first lighted image and/or the second lighted image can be generated from one or more of the following light emitters: light-emitting diodes (LEDs), organic light-emitting diodes (OLEDs), transparent organic light-emitting diodes, micro-OLEDs, micro-LEDs, ionic liquids for electrochemical devices (iLEDs), micro-iLEDS, quantum dots, florescent lights, ambient light, or incandescent lights. One or both of the first lighted image and/or the second lighted image can be generated by light that has been filtered by one or more of: a bandpass filter, an interference filter, an absorption filter, a selective wavelengths filter, a notch filter, or a neutral density filter. The physiological response can be a generation of additional dopamine or serotonin in the eye of the user, in a brain of the user, or both. The physiological response can be one of, improved mitochondria function, or reduction of age-related inflammation in the eye of the user, the retina of the eye of the user, or both. The device can comprise one or more of a timer, a wireless communication component, or an alarm. The device can comprise one or more sensors for sensing and/or receiving biofeedback from the user. The device can be capable of delivering to the user in addition to light, one of, sound, smell, vibration, or combinations thereof. The device can be capable of receiving biofeedback from the user. Biofeedback can be increased blink rate, measuring blink rate, increased pupil size, and/or measuring pupil size. The light can modulate at a rate within the range of 5 Hz and 15 Hz.

A physiological response can be the generation of additional dopamine or serotonin in an eye of the user and/or in the brain of the user. Such additional dopamine in the retina of an eye of the user's eye can, one of, prevent, slow, or stop, myopia. Such additional dopamine or serotonin in the brain can help with many neurological dopamine deficiency disorders. The physiological response can also be the generation of improved mitochondria function or reduction of age-related inflammation in the eye in a section of the retina of the eye of the user. By way of example only, for dry AMD improved mitochondria function or reduction of age-related inflammation in the eye can occur around or within the macula area. For retinitis pigmentosa such improved mitochondria function or reduction of age-related inflammation in the eye can occur in the mid periphery or far periphery of the user's retina. For diabetic retinopathy such improved mitochondria function or reduction of age-related inflammation in the eye can occur in the mid periphery of the user's retina. Another physiological response can be the improvement of dry eye of a user of the devices taught herein, whereby the meibomian gland(s) are treated through the use of ocular photo-bio-stimulation therapy.

The device can comprise one or more of, a timer, wireless communication, or alarm. The ocular photo-bio-stimulation therapy can be timed not to exceed a certain amount of time. Should the time be exceeded an alarm can advise the user. The device can communicate with a remote third party so to keep the remote third party informed about the status of the ocular pho-bio-stimulation therapy. The device can receive biofeedback from the user. The biofeedback can be an enlarged pupil, or an increased blink rated, both of which can signal additional dopamine or serotonin being produced in the brain of the user. The device can deliver to the user one or more sounds, smell, or vibration, in addition to light.

The following are XR (can be one of AR, MR, VR, or Modified Reality) ocular photo-bio-stimulation embodiments taught herein.

Aspect 1: XR eyewear comprising a see-through near eye display comprising a micro-lens array, for ocular photo-bio-stimulation therapy (stimulating all or part of the retina for the purposes of obtaining a desired physiological response)

- Said ocular photo-bio-stimulation therapy or treatment for stimulating one or more of, the optic nerve head, macula/foveal area, or peripheral retina.
- Said XR eyewear can be one of, AR eyewear, MR eyewear, VR, or Modified Reality eyewear.
- Optionally comprising a means to identify or measure a biomarker, such as by way of example only, blink rate or pupil enlargement.
- Optionally comprising a filter or filters to reduce or block high energy blue wavelengths of light within the wavelength ranges of one or both: 449 nm-421 nm and 419 nm-400 nm.
- Optional timer.
- Optional alarm or component to alert the user; and
- Optional communication means for communicating to a third party.

Aspect 2: XR (can be one of AR, MR, VR, or Modified Reality) eyewear comprising a see-through near eye display, devoid of a microlens array, for ocular photo-bio-stimulation therapy (stimulating all or part of the retina for the purposes of obtaining a desired physiological response):

Said ocular photo-bio-stimulation therapy or treatment for stimulating one or more of, the optic nerve head, macula/foveal area, or peripheral retina;

Said XR eyewear can be one of AR eyewear, MR eyewear, VR, or Modified Reality eyewear;

Optionally comprising a means to identify or measure a biomarker, such as by way of example only, blink rate or pupil enlargement;

Optionally comprising a filter or filters to reduce or block blue light high energy wavelengths of light within the wavelength ranges of one or both: 449 nm-421 nm and 419 nm-400 nm;

Optional timer;

Optional alarm or component to alert the user; and

Optional communication means for communicating with a third party.

Aspect 3: XR (can be one of AR, MR, VR, or Modified Reality) eyewear comprising a non-see-through near eye display comprising a microlens array, for ocular photo-bio-stimulation therapy (stimulating all or part of the retina for the purposes of obtaining a desired physiological response):

Said ocular photo-bio-stimulation therapy or treatment for stimulating one or more of, the optic nerve head, macula/foveal area, or peripheral retina;

Said XR eyewear can be one of AR eyewear, MR eyewear, VR, or Modified Reality eyewear;

Optionally comprising a means to identify or measure a biomarker, such as by way of example only, blink rate or pupil enlargement;

Optionally comprising a filter or filters to reduce or block blue light high energy wavelengths of light within the wavelength ranges of one or both: 449 nm-421 nm and 419 nm-400 nm;

Optional timer;

Optional alarm or component to alert the user; and

Optional communication means for communicating with a third party.

Aspect 4: (Can be one of AR, MR, VR, or Modified Reality) XR eyewear comprising a non-see-through near eye display, devoid of a microlens array, for ocular photo-bio-stimulation therapy (stimulating all or part of the retina for the purposes of obtaining a desired physiological response):

Said ocular photo-bio-stimulation therapy or treatment for stimulating one or more of, the optic nerve head, macula/foveal area, or peripheral retina;

Said XR eyewear can be one of, AR eyewear, MR eyewear, VR, or Modified Reality eyewear;

Optionally comprising a means to identify or measure a biomarker, such as by way of example only, blink rate or pupil enlargement;

Optionally comprising a filter or filters to reduce or block certain blue light high energy wavelengths of light within the wavelength ranges of one or both: 449 nm-421 nm and 419 nm-400 nm;

Optional timer;

Optional alarm or component to alert the user; and

Optional communication means for communicating with a third party.

Aspect 5: (Can be one of AR, MR, VR, or Modified Reality) XR eyewear comprising a waveguide, for ocular photo-bio-stimulation therapy (stimulating all or part of the retina for the purposes of obtaining a desired physiological response):

Said ocular photo-bio-stimulation therapy or treatment for stimulating one or more of, the optic nerve head, macula/foveal area, or peripheral retina;

Said XR eyewear can be one of, AR eyewear, MR eyewear, VR, or Modified Reality eyewear;

Said XR eyewear comprising a means to identify or measure a biomarker, such as by way of example only, blink rate or pupil enlargement;

Optionally comprising a filter or filters to reduce or block blue light high energy wavelengths of light within the wavelength ranges of one or both: 449 nm-421 nm and 419 nm-400 nm;

Optional timer;

Optional alarm or component to alert the user; and

Optional communication means for communicating with a third party.

An XR (can be one of AR, MR, VR, or Modified Reality) eyewear near eye display diameter can be any dimension within the range of 10 mm to 70 mm in diameter. The near eye display can provide focused or a non-focused virtual image. For viewing a focused clear virtual image, a microlens array can be optically aligned with the near eye display and the combination is thus utilized. For viewing a non-focused virtual image such a micro-lens array, in certain embodiments a micro-lens array is not utilized. In other embodiments a defocused micro-lens array can be utilized and in still other embodiments a light scattering micro-lens array can be utilized. The illumination intensity from the near eye display can be within the range of 300 lux to 20,000 lux. Display Pixels can be comprised by way of example only, one of, OLEDs, TOLEDs, microOLEDs, iLeds, Quantum Dots, and/or LEDs. The near eye display can be see-through or non-see through (opaque). For VR the near eye display can be a non-see-through near eye display. For AR and MR, the near eye display can be a see-through near eye display. Artificial intelligence (AI) can be incorporated within the embodiment to optimize the desired physiological effect for the subject or user.

For viewing a real image with XR (AR, MR, or Modified Reality) while utilizing a near eye display, the near eye display needs to be see-through and thus is transparent or largely transparent. This permits, along with the proper alignment of a microlens array, the ability to see a real distance image through the see-through near eye display and also that of the micro-lens array. The illumination intensity from the near eye display can be within the range of 300 lux to 20,000 lux. Display Pixels can be comprised by way of example only, one of: OLEDs, TOLEDs, microOLEDs, iLeds, Quantum Dots, or LEDs. In certain see-through near eye display embodiments the wearer/user views the real image between the pixels and the microlenses of the microlens array. In other embodiments the viewer views the real image through transparent pixels. Artificial intelligence (AI) can be incorporated within the embodiment to optimize the desired physiological effect for the subject or user.

An embodiment includes an XR device (can be one of AR, MR, VR, or Modified Reality) comprising a first image and a second image, wherein the first image is generated by a first light, wherein the second image is generated by a second light, wherein one of the lights comprise a band of wavelengths of light having a transmission peak 2× or greater than any other transmission peak of visible light for that particular light, wherein the peak transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm or 830 nm+/−30 nm, and wherein the wavelengths of light that fall within the peak transmission band stimulates portions of the retina peripheral to macula of the user of the XR device as the user views an image with the XR device. Artificial intelligence (AI) can be incorporated within the embodiment to optimize the desired physiological effect for the subject or user.

An embodiment includes an XR device comprising a first image and a second image, wherein the first image is generated by a first light, wherein the second image is generated by a second light, wherein one of the lights comprise a band of wavelengths having a predominant transmission with at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm or 830 nm+/−30 nm, and wherein the wavelengths of light that fall within the predominant transmission band stimulates the macula or fovea of the user of the XR device as the user views an image with the XR device. Artificial intelligence (AI) can be incorporated within the embodiment to optimize the desired physiological effect for the subject or user.

An embodiment includes an XR device comprising a first image and a second image, wherein the first image is moved relative to the second image, wherein the first image is generated by a first light (or absence thereof), wherein the second image is generated by a second light (or absence thereof), wherein the predominant transmission wavelengths fall within at least one of the following light wavelength bands: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, or 650 nm+/−30 nm, or 700 nm+/−30 nm, and wherein the wavelengths of light that fall within the predominant transmission band paint portions of the retina peripheral to macula of the user of the XR device as the user views an image with the XR device. Artificial intelligence (AI) can be incorporated within the embodiment to optimize the desired physiological effect for the subject or user.

In aspects, the first image can move relative to a stationary second image. The first image and the second image can both-move. The first image can be a real image fixated on by the fovea of the user's eye. The second image can be a virtual image. The second image can paint portions of the far peripheral retina with light. The second image can move relative to a stationary first image. The first image can be a virtual image. The second image can be a real image fixated on by the fovea of the user's eye. The first image can paint portions of the far peripheral retina with light. Artificial intelligence (AI) can be incorporated within the embodiment to optimize the desired physiological effect for the subject or user.

The XR device can be a VR or Modified Reality device. The first and second images can be virtual images. The first light can form a real image. The first light can form a virtual image. The second light can form a real image. The second light can form a virtual image. Both the first and second light can form two virtual images. The first light can be focused light. The second light can be defocused light. The first light can be defocused light. The second light can be focused light. The first light can be filtered light. The second light can be filtered light. Wavelengths can be within the light wavelength band of at least one of: 480 nm+/−30 nm, 490 nm+/−5 nm, 490 nm+/−10 nm, 490 nm+/−20 nm, 490 nm+/−30 nm, 495 nm+/−5 nm, 495 nm+/−10 nm, 495 nm+/−20 nm, 495 nm+/−30 nm, 500 nm+/−5 nm, 500 nm+/−10 nm, 500 nm+/−20 nm, 500 nm+/−30 nm, 650 nm+/−30 nm, or 700 nm+/−30 nm or 830 nm+/−30 nm, and can be generated by way of the use one or more of: interference filter, absorption filter, neutral density filter, bandpass filter, notch filter, and/or selective wavelength filter. Artificial intelligence (AI) can be incorporated within the embodiment to optimize the desired physiological effect for the subject or user.

An image movement can be continuous. An image movement can be intermittent. An image movement can be periodic. The first light can be generated by one or more of: LEDs, OLEDs, TOLEDs, micro-OLEDs, micro-LEDs, micro-ileds, iLEDs, quantum dots, florescent lights, incandescent lights, sun, laser, plasma display, TV display, tablet display, cell phone display, computer display, or electronic display. The second light can be generated by one or more of: LEDs, OLEDs, TOLEDs, micro-OLEDs, micro-LEDs, micro-ileds, iLEDs, quantum dots, florescent lights, incandescent lights, sun, laser, plasma display, TV display, tablet display, cell phone display, computer display, or electronic display. The first image can modulate within the range, of one of 10 Hz+20 Hz or 40 Hz+/−10 Hz or 40 Hz+/−20 Hz. The second image can modulate within the range of 10 Hz+20 Hz or 40 Hz+/−10 Hz or 40 Hz+/−20 Hz. The first image can flicker. The second image can flicker. The first light can flicker. The second light can flicker. The first light can have an intensity of 300 lux or greater. The second light can have an intensity of 300 lux or greater. The XR device can provide two or more of the following, light, color, sound, smell. Artificial intelligence (AI) can be incorporated within the embodiment to optimize the desired physiological effect for the subject or user.

The time of stimulation of the retina can affect the retina sensitivity (which includes melanopsin, rhodopsin, and/or cones' opsin). The longer the time of ocular photo-bio-stimulation exposure the less sensitive the retina causes a shift of sensitivity to lower light wavelengths of light. By way of example, 1 second of exposure is most sensitive by the retina at 510 nm, 10 seconds of exposure at 500 nm, and 100 seconds of exposure at 480 nm. In certain embodiments the color of the ocular photo-bio-stimulation light can be alternated in a sequence. By way of example only green wavelengths, then blue green wavelengths, then blue wavelengths, can be shown, according to embodiments disclosed herein. In other embodiments, green wavelengths, then blue green wavelengths, then blue wavelengths, then white light, can be shown. This can be done to maximize the stimulation effect of light wavelength versus time on retinal excitation. Said another way, first (for a short period of time) have the green light wavelengths excite the retina, then have the bluish green wavelengths excite the retina, and then the longer the time period have the blue light wavelengths excite the retina. Thus, sequencing strong light intensity of green light wavelengths, then bluish green light wavelengths, and then blue light wavelengths, provides, in aspects of embodiment disclosed herein, for the maximum retinal stimulation. By way of example only, emit green for 1-5 seconds, emit bluish green for 10-60 seconds, then emit blue for 60 seconds, and so on, until the ocular photo-bio-stimulation is ceased. Age also affects the melanopsin absorption curves with at age 20 the peak sensitivity of melanopsin being 488 nm and by age 80 the peak sensitivity is 503 nm. So, while time of stimulation shifts the retinal sensitivity to the left and lower wavelengths, age shifts the sensitivity of melanopsin to the right.

In certain embodiments the ocular photo-bio-stimulation light can modulate within the range of: 5 Hz to 15 Hz, 10 Hz to 20 Hz, or 40 Hz+/−20 Hz. In other embodiments the ocular photo-bio-stimulation light source cannot modulate and thus has zero Hz. In certain embodiments an invisible white light spectral flickering can occur. In certain embodiments by using blue light within the wavelength range of 480 nm+/−30 nm and modulating at 40 Hz+/−10 Hz can result in a significant improvement of one or more of: depression, cognitive ability, alertness, and decision making of the user. However, visually 40 Hz+/−10 Hz can be annoying and distracting for a user. In certain embodiments an invisible spectral flickering can occur. In certain other embodiments which reduces visual unpleasantness for the user the ocular photo-bio-modulation light source can be modulated within the ranges between blue (450 nm-495 nm) and bluish green/cyan (495 nm-520 nm). In still other embodiments which reduces visual unpleasantness the ocular photo-bio-modulation light source can be modulated within the ranges between blue (450 nm-495 nm) and green (495 nm-570 nm). The ocular photo-bio-stimulation light can then stimulate, one or more of dopamine, serotonin, or norepinephrine in the brain. In certain embodiments by using blue light within the wavelength range of 480 nm+/−30 nm and modulation or flickering between 5 Hz and 15 Hz, or between 10 Hz and 12 Hz, the invention can be used to stimulate production or increase the production of dopamine in the eye's retina of the user.

A System and App (Computer Application) for a Computerized Device Comprising an Ocular Photo-Bio-Stimulation Light Source An embodiment can be that of a system with an computer application that can be communicated (wirelessly or wired) to an electronic display screen of a computerized device, wherein the application causes the display screen to shrink in overall size permitting a border partially or fully around the display screen. The computerized device can be that of a cell phone, tablet, laptop, desktop, or TV. The application can be purchased online. The border can be mostly comprised of light wavelengths within the range of 450 nm-510 nm. The border can be programed as to: size, shape, light intensity, and/or light wavelength range. In certain embodiments the full display is utilized to provide light. The light, whether from the border or the full display screen, can be of a light intensity providing 400 lux or more when striking the retina of the subject's eye. The electronic display and or border can be utilized to provide ocular photo-bio-stimulation to the eye of a subject. The electronic display can provide ocular photo-bio-stimulation that slows or stops the subject's eye from increasing in myopia. The electronic display can provide ocular photo-bio-stimulation that increases dopamine production in the subject's eye and/or brain.

The ocular photo-bio-stimulation can be provided to the subject for 15 minutes or less two times per day. The ocular photo-bio stimulation can be provided to the subject for 15 minutes or less one time per day. The subject can wear eyewear comprising a lens design of one of Essilor Stellest Lens (H.A.L.T), Zeiss Myocare, Hoya DIMS Miyosmart, Sightglass Vision (contrast reduction/diffusion), chromatic aberration focused lenses, or chromatic aberration refocused lenses, while the ocular photo-bio-stimulation therapy is being applied, and wherein the light from the ocular photo-bio-stimulation light source passes through the lenses of the eyewear prior to striking the retina of the subject. The eyewear supporting the lens(es) can be any eyewear, by way of example only, dress eyewear, fit-over or fit-around eyewear, disposable eyewear, safety eyewear, and/or sports eyewear.

An embodiment can be that of a computer application capable of being downloaded for an electronic display device to be used by a user, wherein the electronic display device is to be viewed by the user for providing photo-light therapy (ocular photo-bio-stimulation), wherein the photo-light therapy is for one or more of: preventing or controlling myopia progression, improving contrast sensitivity as seen by the user's eye, improving vision of a user's eye, reducing the depression effect of SAD of a user, reducing a depressed feeling of a user, reducing anxiety of a user, reducing ADHD of a user, reducing an addictive desire of a user, and/or increasing the happiness of a user, wherein the application automatically optimizes the light intensity (lux) given off by the electronic display, wherein the app automatically optimizes the peak light wavelength transmission of each blue and green wavelengths within the range of 450 nm-540 nm, and wherein the light intensity given off by the electronic display when indoors is 60 lumens or greater, and wherein the peak blue wavelength transmission when indoors is 50% or greater and the green wavelength transmission is 50% or greater. The peak blue wavelength transmission of the electronic display can be within the range of 450 nm to 480 nm. The peak blue wavelength transmission of the electronic display can be within the range of 470 nm to 490 nm. The green wavelength transmission can be within the range of 500 nm and 530 nm. The green wavelength transmission can be within the range of 495 nm and 530 nm.

The computer application can alter the visual effect of the electronic display screen. The computer application can alter an image effect of the electronic display screen. The computer application can adjust, turn off, and/or turn on, the photosensor associated with the electronic display screen. The computer application can turn night mode off or on. The computer application can turn the true tone on or off. The computer application can make an adjustment of the electronic display light intensity (lux). The computer application can adjust color temperature. The computer application can set a time of day for automatic turning on or notifying a user for manually turning on the electronic display. The computer application can set a time of day for automatic turn off or notify a user for manually turning off an electronic display. The computer application can make an adjustment of the electronic display light intensity. The computer application can adjust color temperature. The computer application can set a time of day for automatic turn on of an alarm (e.g., vibration, sound, or light) to notify user of a time to begin light therapy (ocular photo-bio-stimulation). The computer application can set a time of day for automatic turn on of an alarm (e.g., vibration, sound, or light) to notify a user of a time to stop light therapy (ocular photo-bio-stimulation). The computer application can communicate with a distance removed 3$^{rd}$ party device (e.g., remote electronic device) for, by way of example, compliance reporting.

The computer application can cause the electronic display to voice words, produce a sound, display an image, and/or vibrate. The computer application can cause the electronic display to display a game and/or animation. The computer application can cause the electronic display device to communicate with another distance removed 3rd party user of the computer application, using their own electronic display, who desires to compete or join in with the user of the electronic device regarding a game, animation, and/or video being shown to the user on the user's electronic display screen. The game, animation, or video can provide photo-light therapy (ocular photo-bio-stimulation) to a user as the game is being played, or the animation or video is being watched.

Information regarding the subject or patient who will be using the computer application for receiving ocular photo-bio-stimulation can be entered into the computer application by either the eye care professional or the subject or patient. The information can be that of age, birthdate, geolocation, where they live or receive their vision care, name of eye care provider, name of personal physician, gender or sex, and other information required.

The photo-light therapy (ocular photo-bio-stimulation) can stimulate the production of dopamine in the eye of the user and/or dopamine, serotonin, or norepinephrine in the brain of the user. The computer application, by way of sensors incorporated within the electronic display device, can provide biofeedback from the user and can be one or more of: pupil dimension of the user, blink rate of the user, and/or temperature of the user. The computer application can provide safeguards for the user by way of facial recognition of the user. The computer application can cause the electronic display device to note time of day when photo-light therapy (ocular photo-bio-stimulation) was utilized. The computer application can cause the electronic display device to note geolocation where photo-light therapy (ocular photo-bio-stimulation) was utilized. The computer application can cause a distance sensor of the electronic display device (when photo-light therapy is being provided to a user) to note the distance from the electronic display screen to the user's eye or face and adjust the light intensity level of the electronic display screen to account for such distance, thus maintaining the appropriate light intensity of the electronic display screen as the distance varies between the user and the electronic display screen. The computer application can adjust the light intensity of the electronic display screen to account for ambient room lighting. The photo-light therapy can be provided to a user while the user is wearing eyewear. The eyewear can comprise a lens or optic design of one of Essilor Stellest Lens (H.A.L.T), Zeiss Myocare, Hoya DIMS Miyosmart, Sightglass Vision (contrast reduction/diffusion), or chromatic aberration focused lenses, Fresnel lens or optic. The lens or optic can optically transmit light which is transmitted from the electronic display to the eye's retina of a user. The lens or optic can comprise a peripheral zone that comprises one or more of concentric groves that contain optics which act like tiny prisms, rings of optical defocus, Fresnel rings, chromatic aberration focused lens technology, aspheric lenslets, micro-lenslets, lenslet micro-array, nanoparticles or micro structured materials, and/or optical islands causing defocus or lack of focus. The lens or optic can comprise a light wavelength filter. Auxiliary light emitters can be attached to or used in association with the electronic display device. The wavelength of the auxiliary light emitter(s) can influence or alter the light being transmitted by the electronic display that strikes the eye's retina of a user. The computer application can keep track of measurements of the user's myopia, contrast sensitivity, depression, anxiety, addiction, ADHD, and happiness level. The app can keep track of improvements or lack thereof of the user's myopia, contrast sensitivity, depression, anxiety, addiction, ADHD, and/or happiness level. For myopia control, the measurements can be that of refractive error, accommodative amplitude, contrast sensitivity, and/or visual acuity. Lumens measure the total amount of light emitted by a light source (by way of example only, an iPhone), while lux measures how much light falls on a surface (in the case of the retina of an eye). The computer application can cause the electronic display screen to emit 40 lumens or more to cause 400 lux to strike the retina of the user's eye. The computer application can cause the electronic display screen to emit 40 lumens or more to generate dopamine in the retina of a user's eye. The computer application can cause the electronic display screen to emit 40 lumens or more to generate dopamine and/or serotonin in the user's brain.

The computer application can cause the electronic display screen to emit 10 lumens or more, 25 lumens or more, 50 lumens or more, 100 lumens or more, to cause 350 lux or more, or 400 lux or more, or 500 lux or more, to strike the retina of the user's eye. The computer application can cause the electronic display screen to emit a number of lumens of light, by way of example only, 25 lumens or more, or 50 lumens or more, to generate dopamine in the retina a user's eye. The computer application can cause the electronic display screen to emit a number of lumens of light, by way of example only, 10 lumens or more, 25 lumens or more, 50 lumens or more, 100 lumens or more, or 200 lumens or more, to generate dopamine and/or serotonin or a hormone in the brain that acts in a similar manner. The computer application can cause the electronic display screen, by way of example only, to emit 60 lumens or more to cause 400 lux of light intensity to strike the retina of the user's eye. The computer application can cause the electronic display screen, by way of example only, to emit 60 lumens or more to generate dopamine in the retain of a user's eye. The computer application can cause the electronic display screen, by way of example only, to emit 60 lumens or more to generate dopamine and/or serotonin in the user's brain. The computer application can cause the electronic display screen, by way of example only, to emit 60 lumens or more to generate dopamine in the retina of a user's eye. The computer application can cause the electronic display screen, by way of example only, to emit 60 lumens or more to generate dopamine and/or serotonin or a hormone that acts in a similar manner in the user's brain. The exact number of lumens or lux required to be given off by ocular photo-bio-stimulation light source depends upon the various light attenuation factors that occur from the light source to the retina of the subject or patient's eye. The electronic display can be, by way of example only, a cell phone, a mobile phone, a tablet computer, a laptop computer, a desktop computer, a television (TV), a computerized device comprising an electronic display, XR eyewear, or contact lens.

An aspect of the present invention includes: A system comprising a light, a timer and/or clock, a processor, and a storage having encoded thereon executable instructions that, when executed by the processor, cause the processor to carry out:

directly or indirectly causing the light to emit light and/or cease emitting light, wherein the emitted light comprises wavelengths of light capable of providing ocular photo-bio-stimulation to an eye of a user, wherein the light comprises wavelengths of light within the wavelength range of one or more of: 480 nm+/−30 nm, 530 nm+/−20 nm, or 650 nm+/−30 nm;

controlling a setting of the timer and/or clock to emit the ocular photo-bio-stimulation light for determined amounts of time, during chosen intervals of time, or both;

retaining in memory or reporting, one or more of, usage of the system, a setting of the timer and/or clock, usage of the ocular photo-bio-stimulation light, status of the system, status of the ocular photo-bio-stimulation light, or biofeedback of the user, to one or more of, the user, a technician, an eyecare professional, or a physician; and causing or allowing the system, the processor by way of electronic instructions from a remote eyecare professional or a physician, to start, stop, remove, terminate, change, or pause, emission of the ocular photo-bio-stimulation light.

The system can comprise a computerized device comprising the light, the timer and/or clock, and the processor, wherein the computerized device is one or more of: a cell phone, a laptop computer, a tablet computer, a desktop computer, a controller, a light box, eyewear, or a cell phone case, or a case electrically or optically connected to the computerized device.

The system can comprise one or more sensors for sensing or detecting the biofeedback of the user, wherein the biofeedback of the user sensed or detected is one of or more of: blink rate, pupil diameter, contrast sensitivity, heart rate, or eye refraction.

The system can comprises an ocular photo-bio-stimulation light that is generated by a light emitter or light emitters located on, within, attached to, housed in, or supported by, one or more of: the computerized device, an electronic display of the computerized device, a cell phone case for the computerized device, a laptop computer case for the computerized device, a tablet computer case for the electronic device, a case for housing or protecting an electronic display device, a television associated with the electronic device, a steering wheel, a steering device, a steering handle, an automobile dashboard, a light box, or eyewear.

The system can comprise a computerized device that includes or is associated with an electronic display, the system emits a border of the ocular photo-bio-stimulation light around part, or all, of a periphery of the electronic display.

The system can comprise an ocular photo-bio-stimulation light that emits a light intensity of one or more of: 10 lumens or more, 20 lumens or more, 50 lumens or more, 60 lumens or more, 100 lumens or more.

The system can comprise light intensity of the ocular photo-bio-stimulation light that strikes a retina of the user is one of or more of: 350 lux or greater, 400 lux or greater, or 500 lux or greater.

The system can comprise ocular photo-bio-stimulation light that comprises one or more of: blue and green light wavelengths, blue wavelengths, green wavelengths, or red wavelengths, having a transmission peak of 50% or more.

The system can comprise ocular photo-bio-stimulation light that emits from a light source comprising one or more of: light-emitting diodes ("LEDs"), organic LEDs, transparent organic LEDs, micro-organic LEDs, micro-LEDs, ionic liquids for electrochemical devices ("iLEDs"), micro-iLEDSs, quantum dots, fluorescent nanoparticles, incandescent lights, fluorescent lights, a laser, or plasma.

The system can comprise a transmission spectrum of the ocular photo-bio-stimulation light, when overlaid with one or more absorption spectrum of melanopsin and/or rhodopsin, covers a majority of the absorption spectrum of the melanopsin and/or rhodopsin.

The system can emit ocular photo-bio-stimulation light that improves in the user one or more of the following: vision, contrast sensitivity, visual acuity, alertness, concentration, focus, cognitive ability, mood, anxiety, depression, seasonal affective disorder, or attention deficit and hyperactivity disorder ("ADHD").

The system can emit ocular photo-bio-stimulation that: (a) increases the production of dopamine in the eye of the user, and/or (b) increases production of one or more of, dopamine, serotonin, or norepinephrine, in a brain of the user.

The system can comprise a processor, and storage, having encoded thereon executable instructions that, when executed by the processor, cause the processor to further carry out: identifying the user for security and/or compliance purposes.

The system can comprise a processor, and storage, having encoded thereon executable instructions that, when executed by the processor, cause the processor to further carry out: adjusting, turning off, or turning on, a photosensor associated with the system.

The system can comprise a processor, and storage, having encoded thereon executable instructions that, when executed by the processor, cause the processor to further carry out: turning on or off a night mode of the system or the light.

The system can comprise a processor, and storage, having encoded thereon executable instructions that, when executed by the processor, cause the processor to further carry out: turning on or off a true color tone of the system or the light.

The system can comprise a processor, and storage, having encoded thereon executable instructions that, when executed by the processor, cause the processor to further carry out: adjusting to a light intensity (lux or lumens) of the system or the light.

The system can comprise a processor, and the storage, having encoded thereon executable instructions that, when executed by the processor, cause the processor to further carry out: adjusting a color temperature of the system or the light.

The system can comprise a processor, and storage, having encoded thereon executable instructions that, when executed by the processor, cause the processor to further carry out: adjusting the system, the light, or a light intensity.

The system can comprise a processor, and storage, having encoded thereon executable instructions that, when executed by the processor, cause the processor to further carry out: causing a partial or full border of the ocular photo-bio-stimulation light to appear and disappear around text, images, numbers, or combinations thereof, that are being shown on an electronic display associated with the system.

The system can comprise an electronic display, wherein the processor, and the storage having encoded thereon executable instructions that, when executed by the processor, cause the processor to further carry out: causing text(s), image(s), number(s), or content, displayed on the electronic display to be in blue while a background on the electronic display appears in white, or wherein the text(s), the image(s), the number(s), or the content, displayed on the electronic display appears in white while the background appears in blue.

The system comprises a processor, and storage, having encoded thereon executable instructions that, when executed by the processor, cause the processor to further carry out: setting a time of day for automatic turn on or turn off of emission of the ocular photo-bio-stimulation light, or setting an alarm to notify the user of a time to begin or end emission of the ocular photo-bio-stimulation light.

The system comprises an electronic display, wherein the processor, and the storage having encoded thereon executable instructions that, when executed by the processor, cause the processor to further carry out: causing the electronic display to display a game and/or an animation, such that the electronic display provides ocular photo-bio-stimulation light therapy.

The system comprises a first electronic display for the user, wherein the processor, and the storage having encoded thereon executable instructions that, when executed by the processor, cause the processor to further carry out: causing the first electronic display, the processor, or the system, to communicate with a remote user of the system, wherein the remote user has a remote second electronic display, and wherein the remote user of the system can compete or join in with the user of the first electronic display to play a game, watch an animation, watch a video being shown to the user of the first electronic display, such that both electronic displays provide ocular photo-bio-stimulation light therapy.

The system comprises a processor, and the storage having encoded thereon executable instructions that, when executed by the processor, cause the processor to further carry out: causing a game, an animation, or a video, to start, that while being-played or watched, light from the game, the animation, or the video, provides the ocular photo-bio-stimulation therapy to the user.

The system comprises a processor, and the storage having encoded thereon executable instructions that, when executed by the processor, causes the processor to further carry out: adjusting the electronic display to provide ocular photo-bio-stimulation therapy to the viewer of the electronic display.

The system comprises a processor, and storage having encoded thereon executable instructions that, when executed by the processor, cause the processor to further carry out: notifying the user as to a time and a date of when to see the distance removed 3rd party for a follow up appointment.

The system of claim 1, wherein a distance removed third party is an eye care professional, an optometrist, an optometric assistant, an optician, an ophthalmologist, an ophthalmologist assistant, a physician, a physician assistant, a neurologist, a neurologist assistant, or a technician.

A remote third party can remotely control one or more settings of the system.

The system can comprise eyewear housing or supporting a clear or filtered lens, or a clear or filtered optic.

The system can comprise a clear or filtered lens, or clear or filtered optic, that spreads the ocular photo-bio-stimulation light across the retina of the user.

The system can further comprise a sensor for determining the distance between the ocular photo-bio-stimulation light source and the user's face or eye and wherein the system causes the light source to increase or decrease in light intensity partially based upon the distance between the light source and the user's face or eye.

The time of stimulation of the retina can affect the retina sensitivity (which includes melanopsin, rhodopsin, and cones' opsin). The longer the time of ocular photo-bio-stimulation exposure the less sensitive the retina, which causes a shift of sensitivity to lower light wavelengths of light. By way of example, 1 second of exposure is most sensitive by the retina at 510 nm, 10 seconds of exposure at 500 nm, and 100 seconds of exposure at 480 nm. In certain embodiments the color of the ocular photo-bio-stimulation light can be alternated in a sequence. By way of example only green wavelengths can be emitted, then blue green wavelengths, then blue wavelengths. In other embodiments, green wavelengths are emitted, then blue green wavelengths, then blue wavelengths, then white light, in that order. This can be done to maximize the stimulation effect of light wavelength versus time on retinal excitation. Said another way, first (for a short period of time) have the green light wavelengths excite the retina, then the bluish green wavelengths, and then the longer the time period have the blue light wavelengths excite the retina. Thus, sequencing strong light intensity of green light wavelengths, then bluish green light wavelengths, and then blue light wavelengths, can, in aspects, provide for the maximum retinal stimulation. By way of example only, emit green for 1-5 seconds, bluish green for 10-60 seconds, then blue for 60 seconds, until the ocular photo-bio-stimulation is ceased. Age also affects the melanopsin absorption curves, with at age 20 the peak sensitivity of melanopsin is 488 nm, and by age 80 the peak sensitivity is 503 nm. So, while time of stimulation shifts the retinal sensitivity to the left and lower wavelengths, age shifts the sensitivity of melanopsin to the right.

In certain embodiments the app can control or cause ocular photo-bio-stimulation light to modulate within the range of 5 Hz to 15 Hz, 10 Hz to 20 Hz, or 40 Hz+/−20 Hz. In other embodiments the ocular photo-bio-stimulation light source cannot modulate and thus has zero Hz. In certain embodiments an invisible white light spectral flickering can occur. In certain embodiments by using blue light within the wavelength range of 480 nm+/−30 nm and modulating at 40 Hz+/−10 Hz, the invention can result in a significant improvement of one or more of: depression, cognitive ability, alertness, and decision making of the user. However, visually 40 Hz+/−10 Hz can be annoying and distracting for a user. In certain embodiments an invisible spectral flickering can occur. In certain other embodiments which reduce visual unpleasantness for the user the ocular photo-bio-modulation light source can be modulated within the ranges between blue (450 nm-495 nm) and bluish green/cyan (495 nm-520 nm). In still other embodiments which reduces visual unpleasantness the ocular photo-bio-modulation light source can be modulated within the ranges between blue (450 nm-495 nm) and green (495 nm-570 nm). The ocular photo-bio-stimulation light can then stimulate, one or more of dopamine, serotonin, and/or norepinephrine in the brain. In certain embodiments by using blue light within the wavelength range of 480 nm+/−30 nm and modulation or flickering between 5 Hz and 15 Hz, or between 10 Hz and 12 Hz, the invention can be used to stimulate production or increase the production of dopamine in the eye's retina of the user.

The current invention includes several aspects:

Aspect 1: A system comprising a light, a timer and/or clock, a processor, and a storage having encoded thereon executable instructions that, when executed by the processor, cause the processor to carry out:

- directly or indirectly causing the light to emit light and/or cease emitting light, wherein the emitted light comprises wavelengths of light capable of providing ocular photo-bio-stimulation to an eye of a user, wherein the light comprises wavelengths of light within the wavelength range of one or more of: 480 nm+/−30 nm, 530 nm+/−20 nm, or 650 nm+/−30 nm;
- controlling a setting of the timer and/or clock to emit the ocular photo-bio-stimulation light for determined amounts of time, during chosen intervals of time, or both;
- retaining in memory or reporting, one or more of, usage of the system, a setting of the timer and/or clock, usage of the ocular photo-bio-stimulation light, status of the system, status of the ocular photo-bio-stimulation light, or biofeedback of the user, wherein, if reporting, the one or more of, the usage of the system, the setting of the timer and/or clock, the usage of the ocular photo-bio-stimulation light, the status of the system, the status of the ocular photo-bio-stimulation light, or the biofeedback of the user, is reported to one or more of, the user, a remote technician, an eyecare professional, or a physician; and causing or allowing the system, the processor, or both, by way of instructions from the user, the remote technician, the eyecare professional, or the physician, to start, stop, remove, terminate, change, or pause, emission of the ocular photo-bio-stimulation light.

Aspect 2: The system of Aspect 1, further comprising a computerized device comprising the light, the timer and/or clock, and the processor, wherein the computerized device is one or more of: a cell phone, a laptop computer, a tablet computer, a desktop computer, a controller, a light box, eyewear, or a cell phone case, or a case electrically or optically connected to the computerized device.

Aspect 3: The system of Aspect 1, further comprising one or more sensors for sensing or detecting the biofeedback of the user, wherein the biofeedback of the user sensed or detected is one of or more of: blink rate, pupil diameter, contrast sensitivity, heart rate, or eye refraction.

Aspect 4: The system of Aspect 2, wherein the ocular photo-bio-stimulation light is generated by a light emitter or light emitters located on, within, attached to, housed in, or supported by, one or more of: the computerized device, an electronic display of the computerized device, a cell phone case for the computerized device, a laptop computer case for the computerized device, a tablet computer case for the electronic device, a case for housing or protecting an electronic display device, a television associated with the electronic device, a steering wheel, a steering device, a steering handle, an automobile dashboard, a light box, or eyewear.

Aspect 5: The system of Aspect 4, wherein, when the computerized device includes or is associated with an electronic display, the system emits a border of the ocular photo-bio-stimulation light around part, or all, of a periphery of the electronic display.

Aspect 6: The system of Aspect 1, wherein the ocular photo-bio-stimulation light emits a light intensity of one or more of: 10 lumens or more, 20 lumens or more, 50 lumens or more, 60 lumens or more, or 100 lumens or more.

Aspect 7: The system of Aspect 1, wherein the light intensity of the ocular photo-bio-stimulation light that strikes a retina of the user is one of or more of: 350 lux or greater, 400 lux or greater, or 500 lux or greater.

Aspect 8: The system of Aspect 1, wherein the ocular photo-bio-stimulation light comprises one or more of: blue and green light wavelengths, blue wavelengths, green wavelengths, or red wavelengths, having a transmission peak of 50% or more.

Aspect 9: The system of Aspect 1, wherein the ocular photo-bio-stimulation light emits from a light source comprising one or more of: light-emitting diodes ("LEDs"), organic LEDs, transparent organic LEDs, micro-organic LEDs, micro-LEDs, ionic liquids for electrochemical devices ("iLEDs"), micro-iLEDSs, quantum dots, fluorescent nanoparticles, incandescent lights, fluorescent lights, a laser, or plasma.

Aspect 10: The system of Aspect 1, wherein a transmission spectrum of the ocular photo-bio-stimulation light, when overlaid with one or more absorption spectrum of melanopsin and/or rhodopsin, covers a majority of the absorption spectrum of the melanopsin and/or rhodopsin.

Aspect 11: The system of Aspect 1, wherein emitting the ocular photo-bio-stimulation improves in the user one or more of the following: vision, contrast sensitivity, visual acuity, alertness, concentration, focus, cognitive ability, mood, anxiety, depression, seasonal affective disorder, or attention deficit and hyperactivity disorder ("ADHD").

Aspect 12: The system of Aspect 1, wherein emitting the ocular photo-bio-stimulation: (a) increases a production of dopamine in the eye of the user, and/or (b) increases production of one or more of dopamine, serotonin, or norepinephrine, in a brain of the user.

Aspect 13: The system of Aspect 1, wherein the processor, and the storage having encoded thereon executable instructions that, when executed by the processor, cause the processor to further carry out: identifying the user for security and/or compliance purposes.

Aspect 14: The system of Aspect 1, wherein the processor, and the storage having encoded thereon executable instructions that, when executed by the processor, cause the processor to further carry out: adjusting, turning off, or turning on, a photosensor associated with the system.

Aspect 15: The system of Aspect 1, wherein the processor, and the storage having encoded thereon executable instructions that, when executed by the processor, cause the processor to further carry out: turning on or off a night mode of the system or the light.

Aspect 16: The system of Aspect, wherein the processor, and the storage having encoded thereon executable instructions that, when executed by the processor, cause the processor to further carry out: turning on or off a true color tone of the system or the light.

Aspect 17: The system of Aspect 1, wherein the processor, and the storage having encoded thereon executable instructions that, when executed by the processor, cause the processor to further carry out: adjusting to a light intensity (lux or lumens) of the system or the light.

Aspect 18: The system of Aspect 1, wherein the processor, and the storage having encoded thereon executable instructions that, when executed by the processor, cause the processor to further carry out: adjusting a color temperature of the system or the light.

Aspect 19: The system of Aspect 1, wherein the processor, and the storage having encoded thereon executable instructions that, when executed by the processor, cause the processor to further carry out: adjusting the system, the light, or a light intensity.

Aspect 20: The system of Aspect 1, further comprising an electronic display, wherein the processor, and the storage having encoded thereon executable instructions that, when executed by the processor, cause the processor to further carry out: causing a partial or full border of the ocular photo-bio-stimulation light to appear and disappear around text, images, numbers, or combinations thereof, that are being shown on the electronic display.

Aspect 21: The system of Aspect 1, further comprising an electronic display, wherein the processor, and the storage having encoded thereon executable instructions that, when executed by the processor, cause the processor to further carry out: causing text(s), image(s), number(s), or content, displayed on the electronic display to be in blue while a background on the electronic display appears in white, or wherein the text(s), the image(s), the number(s), or the content, displayed on the electronic display to appear in white while the background appears in blue.

Aspect 22: The system of Aspect 1, wherein the processor, and the storage having encoded thereon executable instructions that, when executed by the processor, cause the processor to further carry out: setting a time of day for automatic turn on or turn off of emission of the ocular photo-bio-stimulation light, or setting an alarm to notify the user of a time to begin or end emission of the ocular photo-bio-stimulation light.

Aspect 23: The system of Aspect 1, further comprising an electronic display, wherein the processor, and the storage having encoded thereon executable instructions that, when executed by the processor, cause the processor to further carry out: causing the electronic display to display a game and/or an animation, such that the electronic display provides ocular photo-bio-stimulation light therapy.

Aspect 24: The system of Aspect 1, further comprising a first electronic display for the user, wherein the processor, and the storage having encoded thereon executable instructions that, when executed by the processor, cause the processor to further carry out: causing the first electronic display, the processor, or the system, to communicate with a remote user of the system, wherein the remote user has a remote second electronic display, and wherein the remote user of the system can compete or join in with the user of the first electronic display to play a game, watch an animation, or watch a video being shown to the user of the first electronic display, and wherein both electronic displays provide ocular photo-bio-stimulation light therapy.

Aspect 25: The system of Aspect 1, wherein the processor, and the storage having encoded thereon executable instructions that, when executed by the processor, cause the processor to further carry out: causing a game, an animation, or a video, to start, that while being played or watched, light from the game, the animation, or the video, provides the ocular photo-bio-stimulation to the user.

Aspect 26: The system of Aspect 1, further comprising an electronic display, wherein the processor, and the storage having encoded thereon executable instructions that, when executed by the processor, cause the processor to further carry out: adjusting the electronic display to provide ocular photo-bio-stimulation therapy to the viewer of the electronic display.

Aspect 27: The system of Aspect 1, wherein a remote third party can remotely control one or more settings of the system.

Aspect 28: The system of Aspect 1, further comprising eyewear housing or supporting a clear or filtered lens, or a clear or filtered optic.

Aspect 29: The system of Aspect 28, wherein the clear or filtered lens or clear or filtered optic spreads the ocular photo-bio-stimulation light across the retina of the user.

Aspect 30: The system of Aspect 1, further comprising a sensor for determining a distance between the light and a user's face or eye, and wherein the system causes the ocular photo-bio-stimulation light to increase or decrease in light intensity partially based upon the distance between the light and the user's face or eye.

Aspect 31: A method of preventing myopia, the method comprising:

- identifying a child prone to myopia, likely to become myopic, or having a predisposition for myopia, before the child becomes myopic;
  - treating one or both retinas of one or both eyes of the child using ocular photo-bio-stimulation light;
  - providing a fixation target to the child located one or more of, within part of, adjacent to part of, or in front of part of, light radiation from the ocular photo-bio-stimulation light, and
- wherein the fixation target is sized and located to protect part or all of one or both maculas of the child during the ocular photo-bio-stimulation light treatment.

Aspect 32: The method of preventing myopia of Aspect 31, wherein the identified child is identified at one of, earlier than 6 years of age, 6 years of age, or after 6 years of age but before 25 years of age.

Aspect 33: The method of preventing myopia of Aspect 31, wherein a refractive status of the child comprises one of, +0.75 D or less hyperopia, plano (no refractive error), or a spherical equivalent that is less than −0.50 D.

Aspect 34: The method of preventing myopia of Aspect 31, wherein the fixation target viewed by the child is custom sized and positioned to protect part or all of the child's macula(s), fovea(s), or both.

Aspect 35: The method of preventing myopia of Aspect 31, wherein the fixation target: is opaque; is translucent; filters or attenuates certain of the ocular photo-bio-stimulation light; is one or more of, black, grey, or a contrasting color to that of the ocular photo-bio-stimulation light; is an optic that filters 50% or more of the ocular photo-bio-stimulation light; is a red lighted fixation target located within blue light radiation; is a red and black modulating fixation target; is a blue and black modulating fixation target; is a yellow filtered optic when used with blue ocular photo-bio-stimulation light; or is a cyan filtered optic when used with a red ocular photo-bio-stimulation light.

Aspect 36: The method of preventing myopia of Aspect 31, wherein the fixation target is closer to the eye of the child along a line of sight of the child than the ocular photo-bio-stimulation light, when the child is looking at or fixated on the fixation target.

Aspect 37: The method of preventing myopia of Aspect 31, further comprising using a sensor that turns the ocular photo-bio-stimulation light off if the child is not looking at or fixated on the fixation target.

Aspect 38: The method of preventing myopia of Aspect 31, further comprising using a lens or a micro lens array to keep the fixation target in focus.

Aspect 39: The method of preventing myopia of Aspect 31, wherein the fixation target is or comprises an image for the child to see.

Aspect 40: The method of preventing myopia of Aspect 31, wherein the fixation target covers part or all of one macula of the child's eye.

Aspect 41: The method of preventing myopia of Aspect 31, wherein the fixation target moves within the ocular photo-bio-stimulation light.

Aspect 42: The method of preventing myopia of Aspect 31, wherein when the fixation target moves, the ocular photo-bio-stimulation light paints the one or both retinas of the one or both eyes of the child.

Aspect 43: The method of preventing myopia of Aspect 31, wherein the fixation target is stationary and fixed when the child is being treated with the ocular photo-bio-stimulation light.

Aspect 44: The method of preventing myopia of Aspect 31, wherein the ocular photo-bio-stimulation light is provided by an ocular photo-bio-stimulation light source, and wherein the fixation target is located along a Z axis in front of the ocular photo-bio-stimulation light source closer to the one or both eyes of the child.

Aspect 45: The method of preventing myopia of Aspect 31, further comprising two or more of the following: measuring a refractive status of the child, measuring a choroidal thickness or scleral thickness of the one or both eyes of the child, measuring for an indication of low dopamine in the one or both eyes of the child, measuring for a B wave amplitude of an electroretinogram of the one or both eyes of the child, measuring contrast sensitivity of the child's vision, or measuring a best visual acuity of the child.

Aspect 46: The method of preventing myopia of Aspect 31, wherein the ocular photo-bio-stimulation light is configured to increase retinal dopamine of the child if the refractive status of the child is one or more of, +0.75 D or less hyperopia, plano (no optical power), a spherical equivalent being less than −0.50 D, and an ocular dopamine test of the child shows an indication of low dopamine.

Aspect 47: The method of preventing myopia of Aspect 31, further comprising two or more of the following: treating the child to increase a choroidal or scleral thickness of the one or both eyes of the child, treating the child to increase dopamine in the one or both eyes of the child, or treating the child to increase the B wave amplitude of an electroretinogram of the one or both eyes of the child.

Aspect 48: The method of preventing myopia of Aspect 31, wherein the one or both retinas of the one or both of the child's eyes are also treated with two or more of, one or more myopia control lenses, sunlight, or additional ocular photo-bio-stimulation light.

Aspect 49: The method of preventing myopia of Aspect 31, wherein the method offsets or prevents axial elongation or the myopia of the one or both eyes of the child.

Aspect 50: The method of preventing myopia of Aspect 31, wherein two or more of the following are utilized to determine if the child is prone to myopia, likely to become myopic, or having a predisposition for myopia: an autorefractor, a genetic test, an electroretinogram, a contrast sensitivity test, or a device to measure choroidal thickness or scleral thickness.

Aspect 51: The method of preventing myopia of Aspect 31, wherein ocular photo-bio-stimulation light that strikes the one or both retinas of the one or both eyes of the child is at least one of: 300 lux or greater, 500 lux or greater, 1,000 lux or greater, or 5,000 lux or greater.

Aspect 52: The method of preventing myopia of Aspect 31, wherein the ocular photo-bio-stimulation light comprises wavelengths within a range of one or more of, 480 nm+/−30 nm, 650 nm+/−30 nm, 700 nm+/−30 nm, or a combination of 480 nm+/−30 nm and 650 nm+/−30 nm.

Aspect 53: The method of preventing myopia of Aspect 31, wherein the ocular photo-bio-stimulation light modulates within a range of 5 Hz-15 Hz, 10 Hz to 20 Hz, or 40 Hz+/−20 Hz.

Aspect 54: The method of preventing myopia of Aspect 31, wherein a time of the ocular-photo-bio-stimulation treatment comprises one of, 1 minute to 5 minutes, 5 minutes to 30 minutes, or one hour or less, and wherein the ocular photo-bio-stimulation light treatment is repeated after a first ocular photo-bio-stimulation treatment.

Aspect 55: The method of preventing myopia of Aspect 31, wherein the ocular-photo-bio-stimulation light is timed and automatically stopped.

Aspect 56: The method of preventing myopia of Aspect 31, wherein the ocular photo-bio-stimulation light is provided by way of one or more of, defocused light to the one or both retinas of the one or both eyes of the child, through a myopia control lens or lenses, through a defocusing lens or lenses, or using a combination of red light and blue light.

Aspect 57: The method of preventing myopia of Aspect 31, wherein the ocular photo-bio-stimulation treatment is reported to an individual monitoring progress of the child's myopia.

Aspect 58: The method of preventing myopia of Aspect 31, further comprising using an instrument or eyewear that provides the ocular photo-bio-stimulation light to the one or both retinas of the one or both eyes of the child.

Aspect 59: A device for providing ocular photo-bio-stimulation, the device comprising an ocular photo-bio-stimulation light source providing ocular photo-bio-stimulation light and a fixation target, wherein the fixation target is sized and located to protect part or all of a macula of an eye of a user of the device while the ocular photo bio-stimulation light is applied to the eye of the user.

Aspect 60: The device of Aspect 59, wherein the ocular photo-bio-stimulation light comprises wavelengths within a range of one or more of, 480 nm+/−30 nm, 530 nm+/−20 nm, 650 nm+/−30 nm, 600 nm-700 nm, 700 nm+/−30 nm, or a combination of 480 nm+/−30 nm and 650 nm+/−30 nm.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

If a feature, parameter, aspect, or element, is described for particular embodiments herein, that feature, parameter, aspect, or element, can be used in or applied to other embodiments described herein.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purposes only.

It is to be understood that while certain illustrations and figures may be close to the right scale, most of the illustrations and figures are not intended to be of the correct scale.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. A method of preventing myopia, the method comprising:

identifying a child prone to myopia, likely to become myopic, or having a predisposition for myopia, before the child becomes myopic;

treating a retina of the child with ocular photo-bio-stimulation light; and casting or imparting one or more of, a black spot or area, a dark grey spot or area, or a dark color toned spot or area, over an entire fovea and part or all of a macula of the retina of the child, wherein the one or more of, the black spot or area, the dark grey spot or area, or the dark color toned spot or area, blocks, reduces, attenuates, eliminates, or filters, the ocular photo-bio-stimulation light, to operatively protect the entire fovea and the part or all of the macula of the retina of the child from the ocular photo-bio-stimulation light, and wherein a peripheral retina of the retina of the child receives a higher level of the ocular photo-bio-stimulation light than a central retina of the retina of the child.

2. The method of preventing myopia of claim 1, wherein the identified child is identified at one of, earlier than 6 years of age, 6 years of age, or after 6 years of age but before 25 years of age.

3. The method of preventing myopia of claim 1, wherein a refractive status of the child comprises one of, +0.75 D or less hyperopia, plano (no refractive error), or a spherical equivalent that is less than −0.50 D.

4. The method of preventing myopia of claim 1, further comprising: configuring a fixation target to cast or impart the one or more of, the black spot or area, the dark grey spot or area, or the dark color toned spot or area, over the entire fovea and the part or all of the macula of the retina of the child.

5. The method of preventing myopia of claim 4, wherein the fixation target is one or more of: opaque; translucent; configured to filter or attenuate some or all of the ocular photo-bio-stimulation light; black; grey; a contrasting color to that of the ocular photo-bio-stimulation light; or an optic that filters 50% or more of the ocular photo-bio-stimulation light.

6. The method of preventing myopia of claim 4, wherein the fixation target is closer to an eye of the child along a line of sight of the child than the ocular photo-bio-stimulation light or a source of the ocular photo-bio-stimulation light, when the child is looking at or fixated on the fixation target.

7. The method of preventing myopia of claim 4, further comprising using a sensor that turns the ocular photo-bio-stimulation light off if the child is not looking at or fixated on the fixation target.

8. The method of preventing myopia of claim 4, further comprising using a lens or a micro lens array to keep the fixation target in focus.

9. The method of preventing myopia of claim 4, wherein the fixation target moves within, or is in a stationary position within, the ocular photo-bio-stimulation light while treating the retina of the child with the ocular photo-bio-stimulation light.

10. The method of preventing myopia of claim 9, wherein when the fixation target moves, the ocular photo-bio-stimulation light paints the retina of the child.

11. The method of preventing myopia of claim 4, wherein the fixation target is stationary and fixed while treating the retina of the child with the ocular photo-bio-stimulation light.

12. The method of preventing myopia of claim 4, wherein the ocular photo-bio-stimulation light is provided by an ocular photo-bio-stimulation light source, and wherein the fixation target is located along a Z axis in front of the ocular photo-bio-stimulation light source and closer to the retina of the child.

13. The method of preventing myopia of claim 1, further comprising two or more of the following: measuring a refractive status of the child, measuring a choroidal thickness or scleral thickness of the retina of the child, measuring for an indication of low dopamine in the retina of the child, measuring for a B wave amplitude of an electroretinogram of the retina of the child, measuring contrast sensitivity of the child's vision, or measuring a best visual acuity of the child.

14. The method of preventing myopia of claim 1, wherein the ocular photo-bio-stimulation light is configured to increase retinal dopamine of the child if the refractive status of the child is one or more of, +0.75 D or less hyperopia, plano (no optical power), a spherical equivalent being less than −0.50 D, or an ocular dopamine test of the child shows an indication of low dopamine.

15. The method of preventing myopia of claim 1, further comprising two or more of the following: treating the retina of the child to increase a choroidal or scleral thickness of the retina of the child, treating the retina of the child to increase dopamine in the retina of the child, or treating the retina of the child to increase the B wave amplitude of an electroretinogram of the retina of the child.

16. The method of preventing myopia of claim 1, wherein the retina of the child is also treated with one or more of, one or more myopia control lenses, sunlight, or additional ocular photo-bio-stimulation light.

17. The method of preventing myopia of claim 1, wherein the method offsets or prevents axial elongation or myopia of the retina of the child.

18. The method of preventing myopia of claim 1, wherein two or more of the following are utilized to determine if the child is prone to myopia, likely to become myopic, or having a predisposition for myopia: an autorefractor, a genetic test, an electroretinogram, a contrast sensitivity test, or a device to measure choroidal thickness or scleral thickness.

19. The method of preventing myopia of claim 1, wherein ocular photo-bio-stimulation light that strikes the retina of the child is at least 300 lux or greater.

20. The method of preventing myopia of claim 1, wherein the ocular photo-bio-stimulation light comprises wavelengths within a range of one or more of, 480 nm+/−30 nm, 650 nm+/−30 nm, 700 nm+/−30 nm, 600 nm-700 nm, or 830 nm+/−30 nm.

21. The method of preventing myopia of claim 1, wherein the ocular photo-bio-stimulation light flickers, or wherein the ocular photo-bio-stimulation light modulates within a range of 5 Hz to 15 Hz, 10 Hz to 20 Hz, or 40 Hz+/−20 Hz.

22. The method of preventing myopia of claim 1, wherein a duration of a single ocular-photo-bio-stimulation light treatment session is one hour or less, and wherein the ocular photo-bio-stimulation light treatment is repeated after a first ocular photo-bio-stimulation light treatment.

23. The method of preventing myopia of claim 1, wherein the ocular-photo-bio-stimulation light is timed and automatically stopped.

24. The method of preventing myopia of claim 1, wherein the ocular photo-bio-stimulation light is provided by way of one or more of: an ocular photo-bio-stimulation light source; an annular ring comprising ocular photo-bio-stimulation light emitters on a periphery of the annular ring; an annular ring configured to emit, guide, or reflect the ocular photo-bio-stimulation light; an ocular photo-bio-stimulation light source transmitting the ocular photo-bio-stimulation light; defocused light to the retina of the child; through a myopia control lens or lenses; through a defocusing lens or lenses; or using a combination of red light and blue light.

25. The method of preventing myopia of claim 1, wherein information and/or data related to the ocular photo-bio-stimulation treatment is sent to a computing device, reported to one or more persons monitoring the prevention or progress of the child's myopia, or both.

26. The method of preventing myopia of claim 1, further comprising using an instrument or eyewear that provides the ocular photo-bio-stimulation light to the retina of the child.

* * * * *